United States Patent
Wherry et al.

(10) Patent No.: US 11,906,511 B2
(45) Date of Patent: Feb. 20, 2024

(54) METHODS AND COMPOSITIONS FOR TREATING DISEASES ASSOCIATED WITH EXHAUSTED T CELLS

(71) Applicant: THE TRUSTEES OF THE UNIVERSITY OF PENNSYLVANIA, Philadelphia, PA (US)

(72) Inventors: E. John Wherry, Havertown, PA (US); Bertram Bengsch, Freiburg (DE); Omar Khan, Philadelphia, PA (US); Jennifer Wu, Philadelphia, PA (US); Josephine Giles, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 362 days.

(21) Appl. No.: 16/759,676

(22) PCT Filed: Oct. 26, 2018

(86) PCT No.: PCT/US2018/057850
§ 371 (c)(1),
(2) Date: Apr. 27, 2020

(87) PCT Pub. No.: WO2019/084493
PCT Pub. Date: May 2, 2019

(65) Prior Publication Data
US 2021/0033595 A1 Feb. 4, 2021

Related U.S. Application Data

(60) Provisional application No. 62/661,467, filed on Apr. 23, 2018, provisional application No. 62/660,754, filed on Apr. 20, 2018, provisional application No. 62/578,212, filed on Oct. 27, 2017, provisional application No. 62/578,193, filed on Oct. 27, 2017.

(51) Int. Cl.
*C12Q 1/686* (2018.01)
*G01N 33/50* (2006.01)
*C12Q 1/6869* (2018.01)

(52) U.S. Cl.
CPC ........... *G01N 33/505* (2013.01); *C12Q 1/686* (2013.01); *C12Q 1/6869* (2013.01); *G01N 33/5091* (2013.01); *C12Q 2600/118* (2013.01); *G01N 2800/52* (2013.01)

(58) Field of Classification Search
None
See application file for complete search history.

(56) References Cited

U.S. PATENT DOCUMENTS

2016/0311890 A1 10/2016 Jones et al.

FOREIGN PATENT DOCUMENTS

| JP | 2011500730 | 1/2011 |
|---|---|---|
| WO | 2016/061456 A2 | 4/2016 |
| WO | 2017/075451 A1 | 5/2017 |
| WO | 2017/165412 A2 | 9/2017 |

OTHER PUBLICATIONS

Scott-Browne et al. Dynamic changes in chromatin accessibility occur in CD8+ T cells responding to viral infection. Immunity 45: 1327-1340. (Year: 2016).*
Zhang et al. Epigenetic manipulation restores functions of defective CD8+ T cells from chronic viral infection. Molecular Therapy 22: 1698-1706. (Year: 2014).*
Buenrostro et al. ATAC-seq: A method for assaying chromatin accessibility genome-wide. Curr. Protoc. Mol. Biol. 109:21.29.1-21.29.9. (Year: 2015).*
PCT/US2018/57850—International Search Report and Written Opinion dated Feb. 19, 2019.
Wherry, et al., "Molecular signature of CD8+ T cell exhaustion during chronic viral infection", Immunity 27:670-684, Oct. 2007.
Zajac et al., "Viral immune evasion due to persistence of activated T cells without effector function", J. Exp. Med. 188:2205-2213, Dec. 21, 1998.
Barber et al., "Restoring function in exhausted CD8 T cells during chronic viral infection", Nature 439:682-687, Feb. 9, 2006.
Topalian et al., "Safety, activity, and immune correlates of anti-PD-1 antibody in cancer", New Engl. J. Med. 366:2443-2454, Jun. 28, 2012.
Porter et al., "Chimeric antigen receptor-modified T cells in chronic lymphoid leukemia.", New Engl. J. Med. 365:725-733, Aug. 25, 2011.
Long et al., "4-1BB costimulation ameliorates T cell exhaustion induced by tonic signaling of chimeric antigen receptors", Nat. Med. 21:581-590, May 4, 2015.
Wherry, E.J., and Kurachi, M., "Molecular and cellular insights into T cell exhaustion", Nat Rev Immunol 15:486-499, Aug. 2015.
Callahan, M.K. et al., "Targeting T Cell Co-receptors for Cancer Therapy", Immunity 44:1069-1078, May 17, 2016.
Sharma P., and Allison, J.P., "The future of immune checkpoint therapy", Science 348:56-61, Apr. 3, 2015.
Pauken et al., "Epigenetic stability of exhausted T cells limits durability of reinvigoration by PD-1 blockade", Science 354(6316):1160-1165, Dec. 2, 2016.
Doering et al., "Network analysis reveals centrally connected genes and pathways involved in CD8T cell exhaustion versus memory", Immunity 37:1130-1144, Dec. 14, 2012.
Martinez, et al., "The transcription factor NFAT promotes exhaustion of activated CD8+ T cells", Immunity 42:265-278, Feb. 17, 2015.
Yi et al., "T-cell exhaustion: characteristics, causes and conversion", Immunol. 129:474-481, Mar. 10, 2010.

(Continued)

*Primary Examiner* — Samuel C Woolwine
(74) *Attorney, Agent, or Firm* — Saul Ewing LLP; Kathryn Doyle; Justin Crotty

(57) ABSTRACT

The present invention provides compositions and methods for detecting exhausted T cells in a subject. The present invention also provides methods for treating a subject having a disease characterized by the presence of exhausted T cells or certain subpopulations thereof.

2 Claims, 213 Drawing Sheets
Specification includes a Sequence Listing.

(56) References Cited

OTHER PUBLICATIONS

Wherry and Ahmed, "Memory CD8 T-cell differentiation during viral infection", J. Virol. 78:5535-5545, Jun. 2004.

Day et al., "PD-1 expression on HIV-specific T cells is associated with T-cell exhaustion and disease progression", Nature 443:350-4, Sep. 21, 2006.

Trautmann et al., "Upregulation of PD-1 expression on HIV-specific CD8+ T cells leads to reversible immune dysfunction", Nat. Med. 12:1198-202, Oct. 2006.

Urbani et al., "PD-1 expression in acute hepatitis C virus (HCV) infection is associated with HCV-specific CD8 exhaustion", J. Virol. 80:11398-403, Nov. 2006.

Paley et al., "Progenitor and terminal subsets of CD8+ T cells cooperate to contain chronic viral infection.", Science 338:1220-1225, Nov. 30, 2012.

Sen et al., "The epigenetic landscape of T cell exhaustion", Science 354(6316):1165-1169, Dec. 2, 2016.

Godec et al., "Compendium of Immune Signatures Identifies Conserved and Species-Specific Biology in Response to Inflammation", Immunity 44:194-206, Jan. 16, 2016.

Shin, et al., "Viral antigen and extensive division maintain virus-specific CD8 T cells during chronic infection", J. Exp. Med., 204: 941-94, Apr. 16, 2007.

Pellegrini, et al., "IL-7 engages multiple mechanisms to overcome chronic viral infection and limit organ pathology", Cell 144:601-613, Feb. 18, 2011.

Nanjappa, et al., "Immunotherapeutic effects of IL-7 during a chronic viral infection in mice", Blood 117:5123-5132, May 12, 2011.

Blackburn, et al., "Selective expansion of a subset of exhausted CD8 T cells by alphaPD-L1 blockade", Proc. Natl. Acad. Sci. U.S.A. 105:15016-15021, Sep. 30, 2008.

Quigley, M. et al., "Transcriptional analysis of HIV-specific CD8+ T cells shows that PD-1 inhibits T cell function by upregulating BATF", Nature Medicine, Oct. 1, 2010, vol. 16, No. 10, pp. 1147-1151.

Baitsch, L. et al., "Exhaustion of tumor-specific CD8+ T cells in metastases from melanoma patients", The Journal of Clinical Investigation, vol. 121, No. 6, May 9, 2011, pp. 2350-2360.

The Partial Supplementary European Search Report dated Jul. 13, 2021, of counterpart European Application No. 18870493.6.

The Extended European Search Report dated Oct. 14, 2021, of counterpart European Application No. 18870493.6.

\* cited by examiner

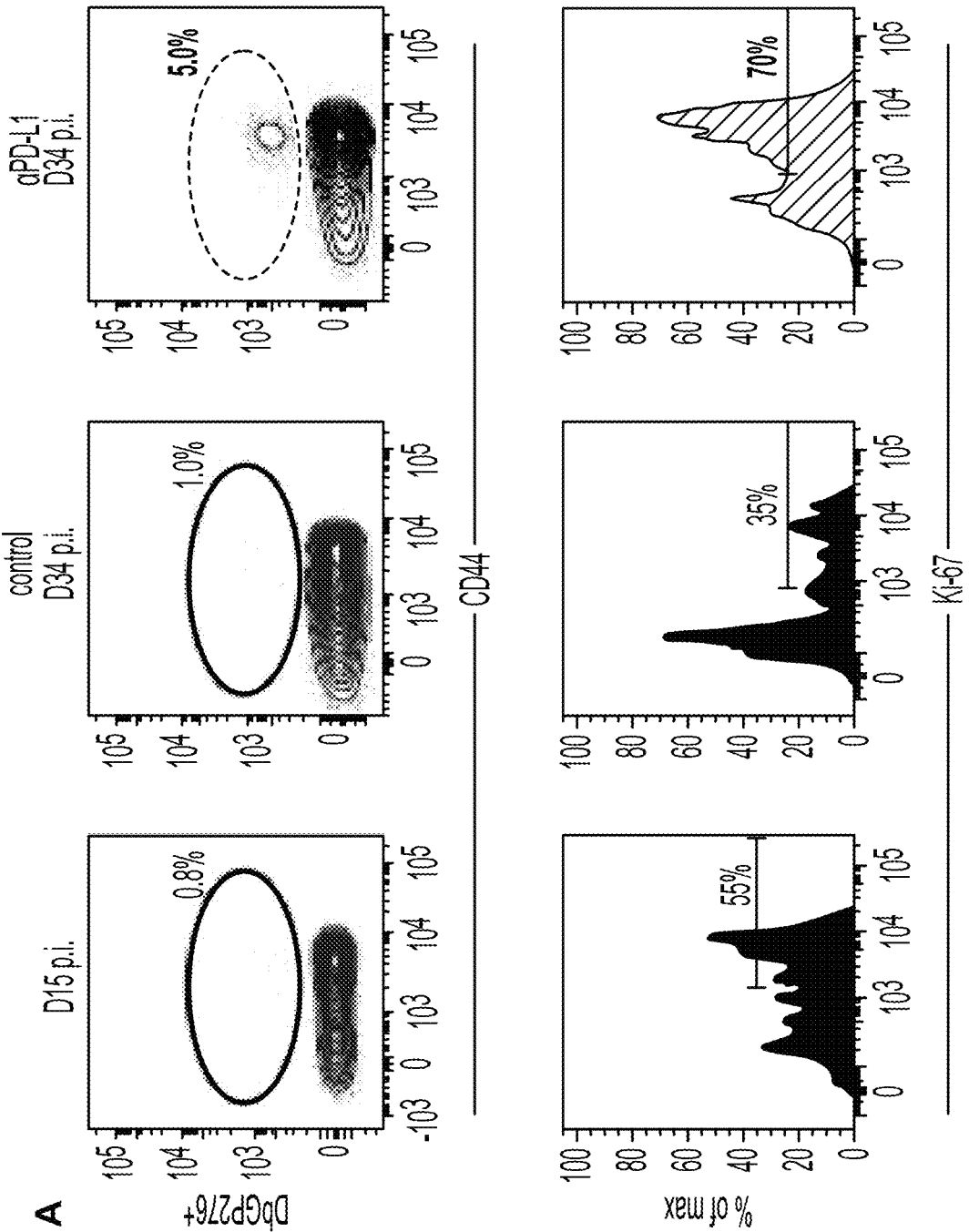

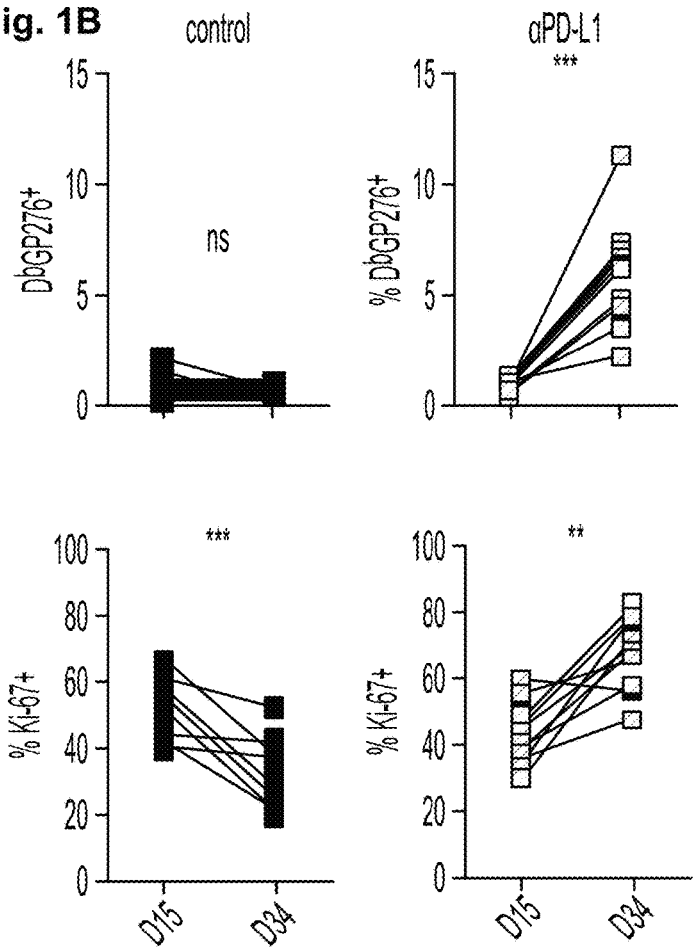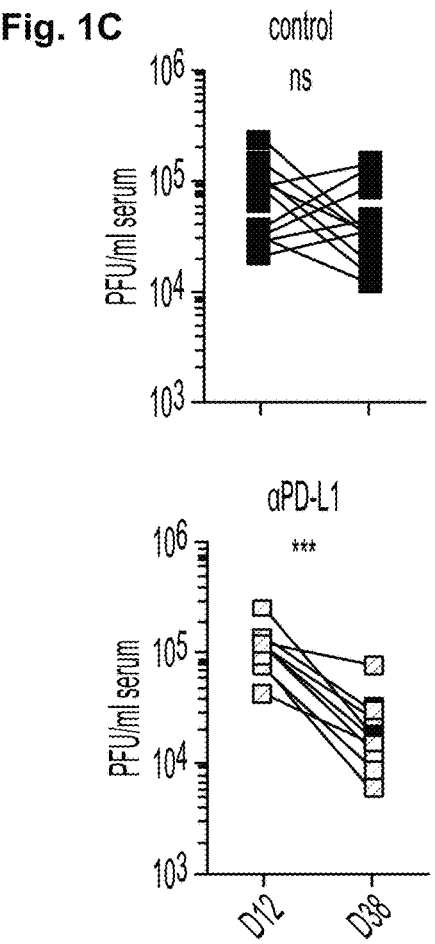

Fig. 1F

| LEM #: | Description | P value | FDR |
|---|---|---|---|
| TEFF vs TN 1 | Immune response<br>Response to wounding<br>Chemotaxis | 1.4E-9<br>1.3E-7<br>3E-6 | 2.2E-6<br>2.2E-4<br>4.9E-3 |
| TEFF vs TN 2 | Cell cycle phase<br>Cell cycle<br>Mitosis | 6.4E-74<br>8.7E-74<br>1.3E-60 | 5.3E-71<br>1.3E-70<br>1.9E-57 |
| TMEM vs TN 1 | Immune Response<br>Cellular defense response<br>Reg. of Protein Kinase cascade | 5.3E-8<br>3.3E-7<br>9.5E-4 | 8.4E-5<br>5.2E-4<br>1.5E0 |
| TMEM vs TN 2 | Leukocyte adhesion | 1.9E-2 | 2.6E1 |
| TMEM vs TN 3 | Immune Response<br>Neg. Reg. of Apoptosis<br>Reg. of Leukocyte Act. | 4.9E-14<br>2.7E-9<br>3.1E-9 | 8.1E-11<br>4.5E-6<br>5.2E-6 |
| TEX vs TN 1 | Immune response<br>Positive reg. of apoptosis<br>Reg. of lymphocyte proliferation | 9.1E-19<br>5.7E-9<br>9.6E-7 | 1.5E-15<br>9.3E-6<br>4.3E-4 |
| TEX vs TN 2 | Cell cycle phase<br>Cell cycle<br>Mitosis | 3.1E-64<br>5.2E-61<br>1.4E-51 | 4.7E-61<br>8E-58<br>2.1E-48 |
| TEX vs TN 3 | Immune response<br>Defense Response<br>Chemotaxis | 9.6E-9<br>1.3E-7<br>6.1E-4 | 1.6E-5<br>2.1E-4<br>9.9E-1 |
| αPD-L1 vs TEX 1 | Response to virus<br>Leukocyte activation<br>Defense response | 7.2E-19<br>4.1E-4<br>1.33E-6 | 1.1E-15<br>6.2E-1<br>2.0E-3 |
| αPD-L1 vs TEX 2 | Cell cycle phase<br>Cell cycle<br>Mitosis | 6.8E-51<br>1.4E-47<br>2E-44 | 1E-47<br>2.2E-44<br>3E-41 |

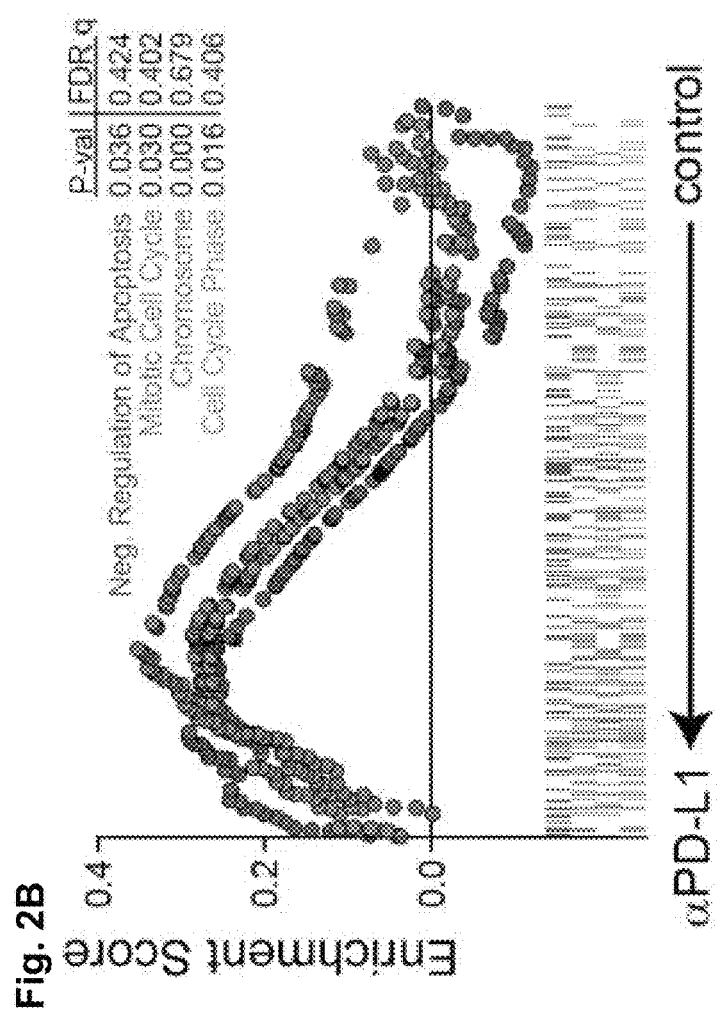
Fig. 2B
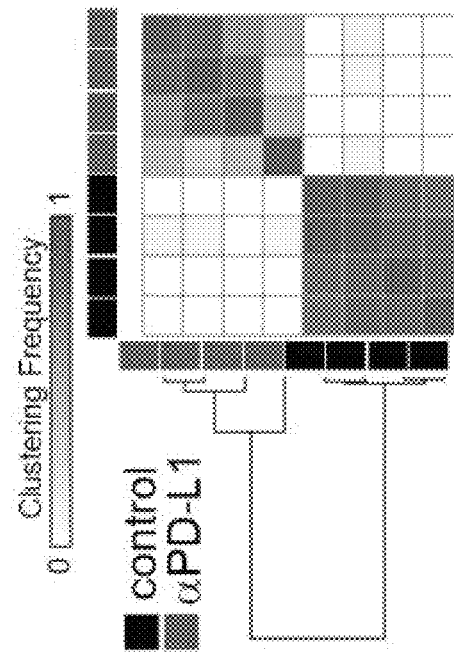
Fig. 2A Transcriptional Profiles +1 day post-tx

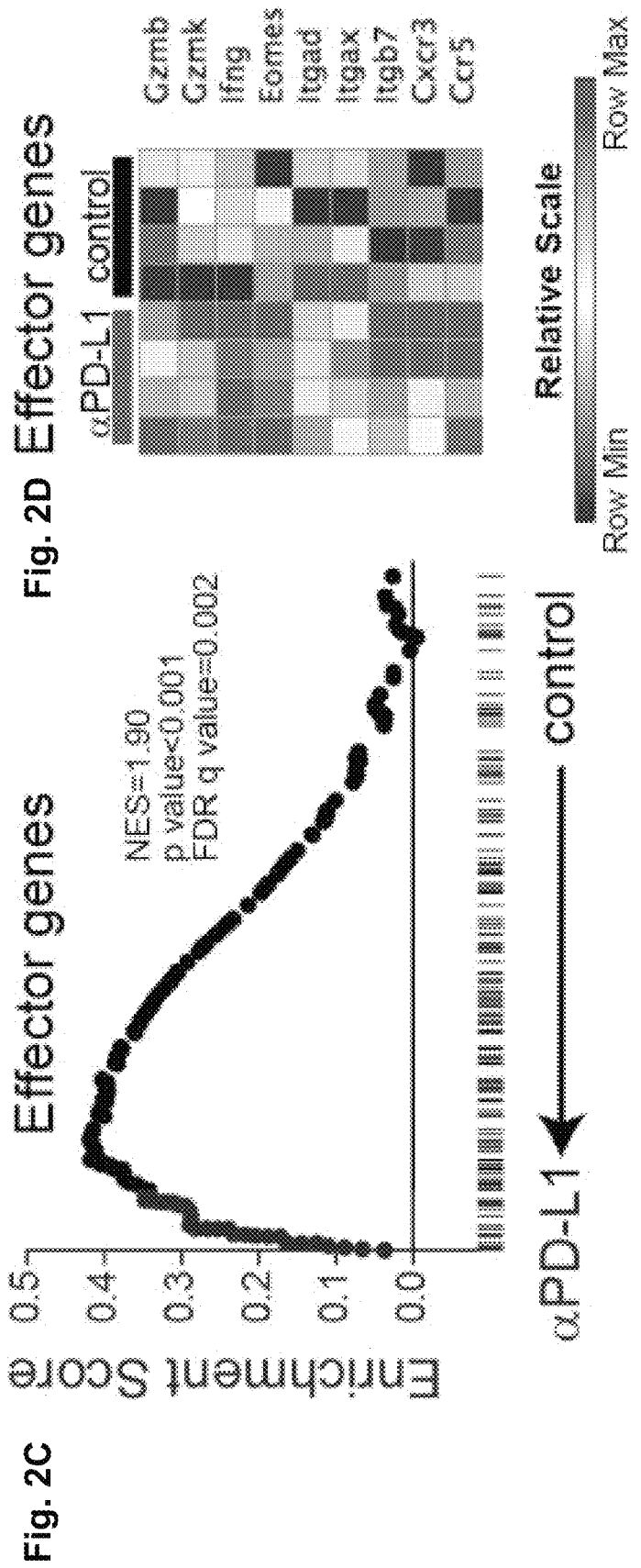

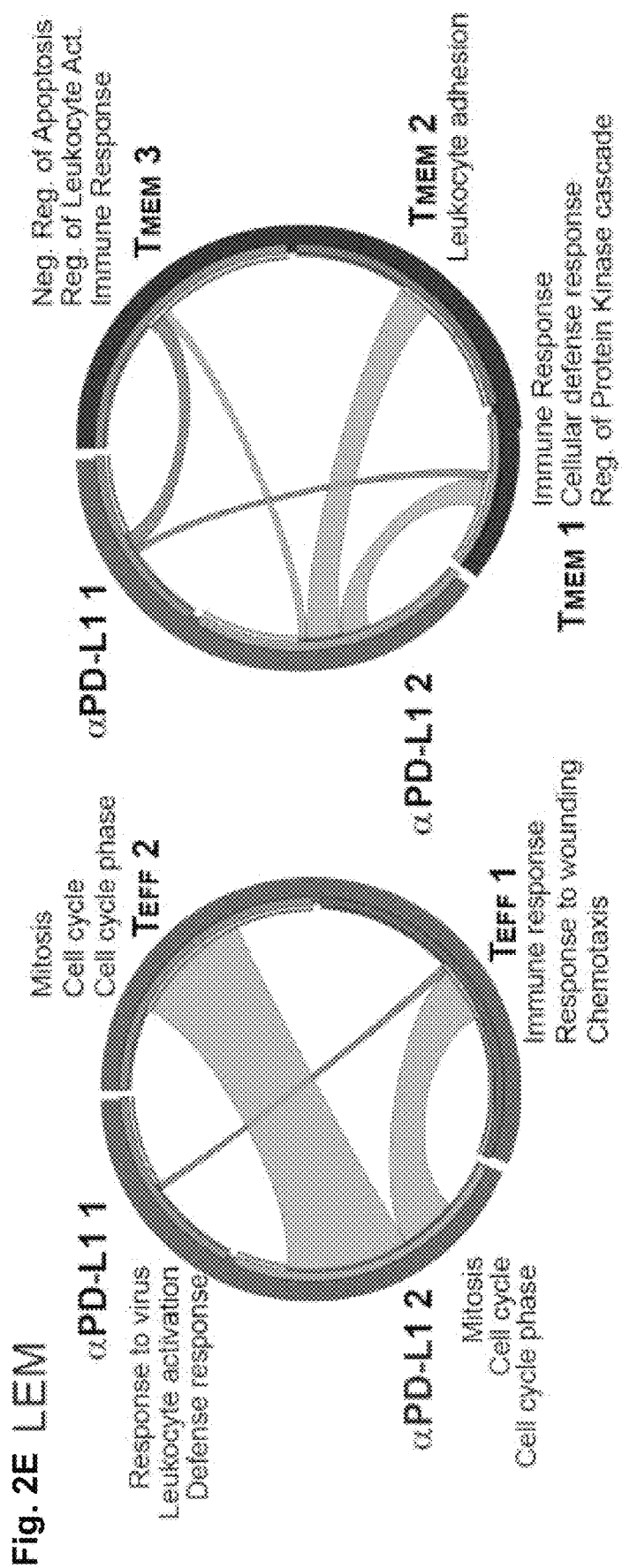
Fig. 2E LEM

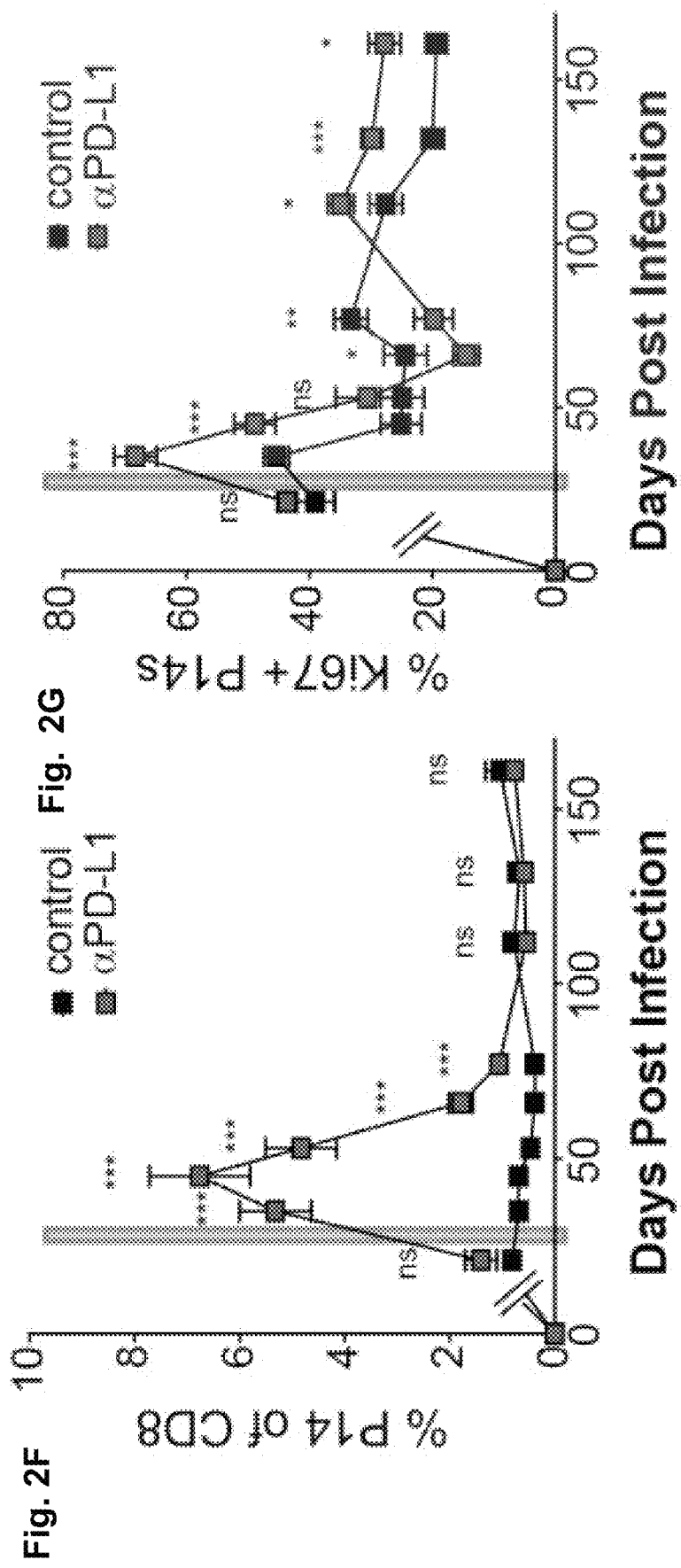

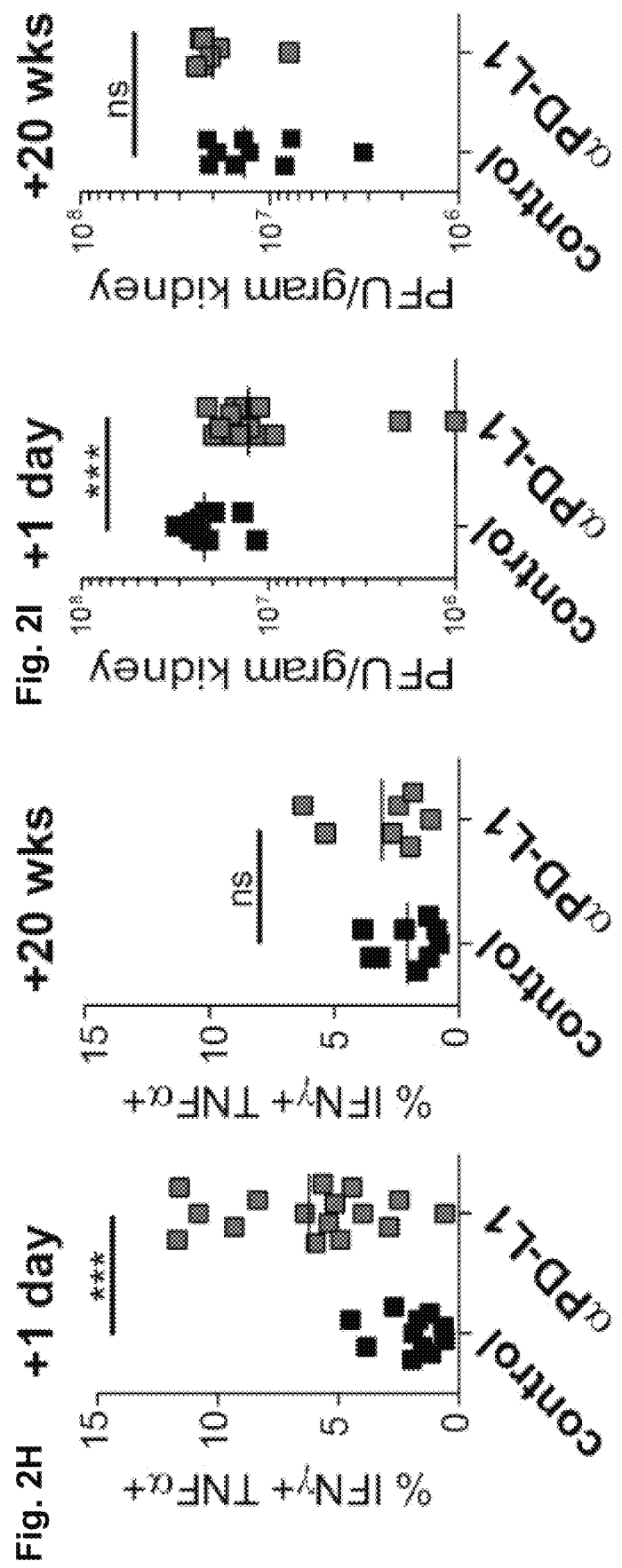

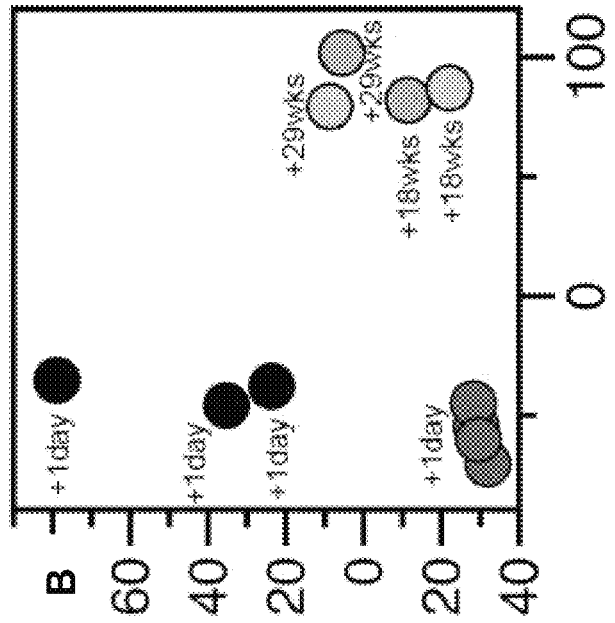
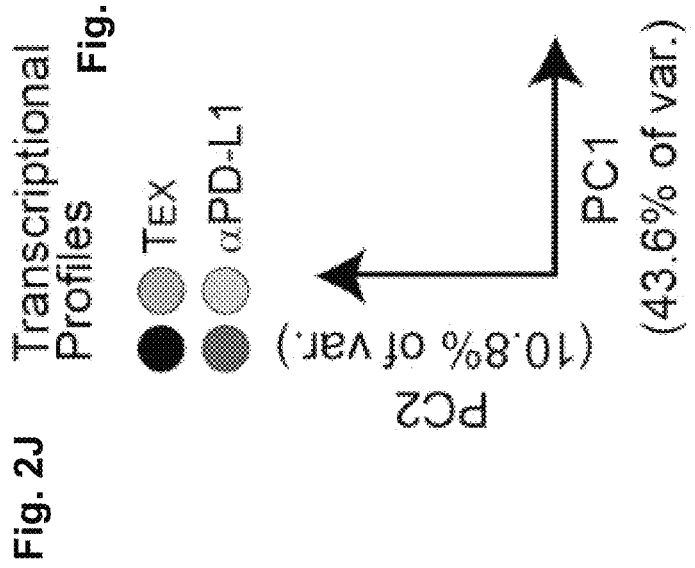
Fig. 2J
Fig. 2 B Transcriptional Profiles

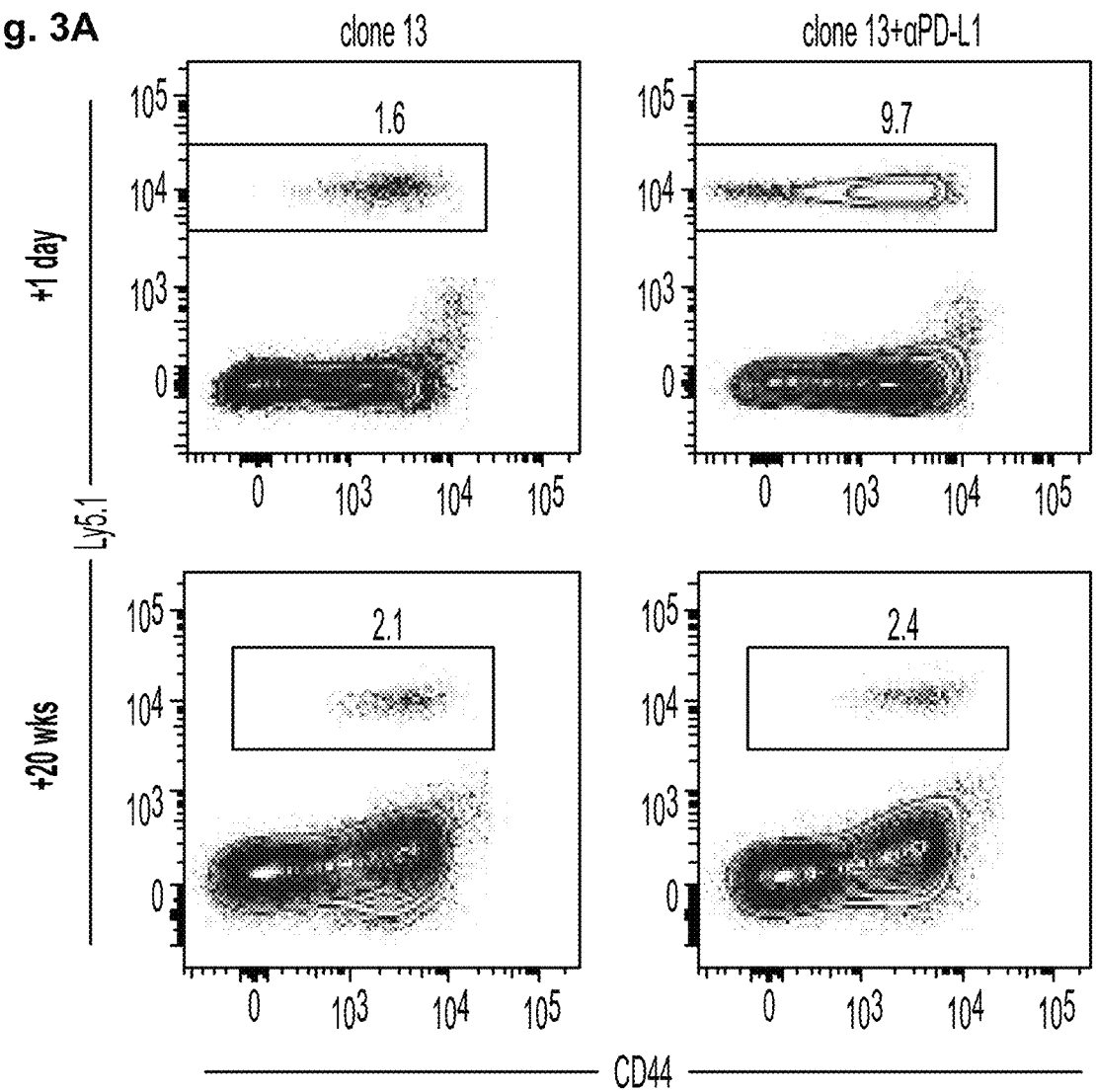

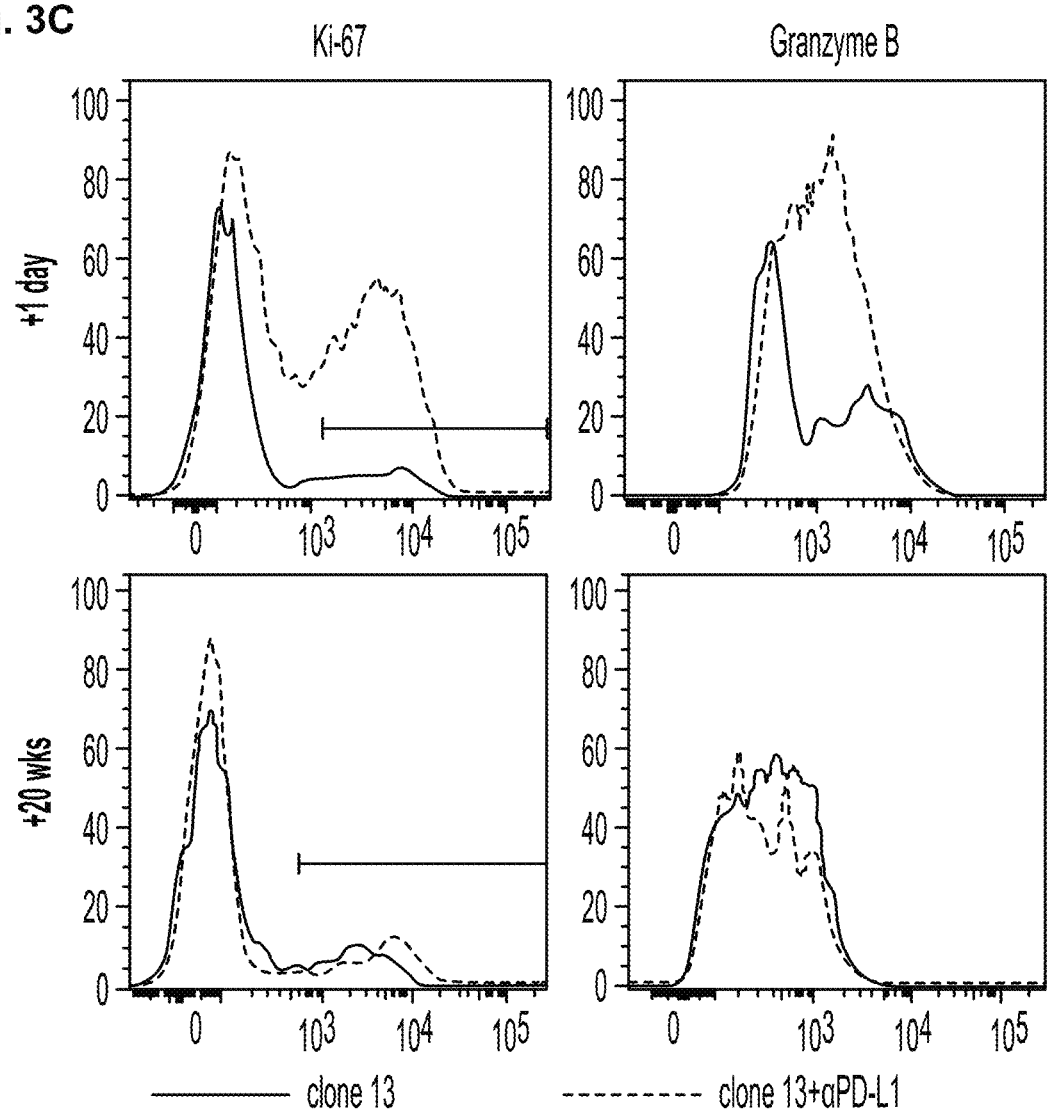

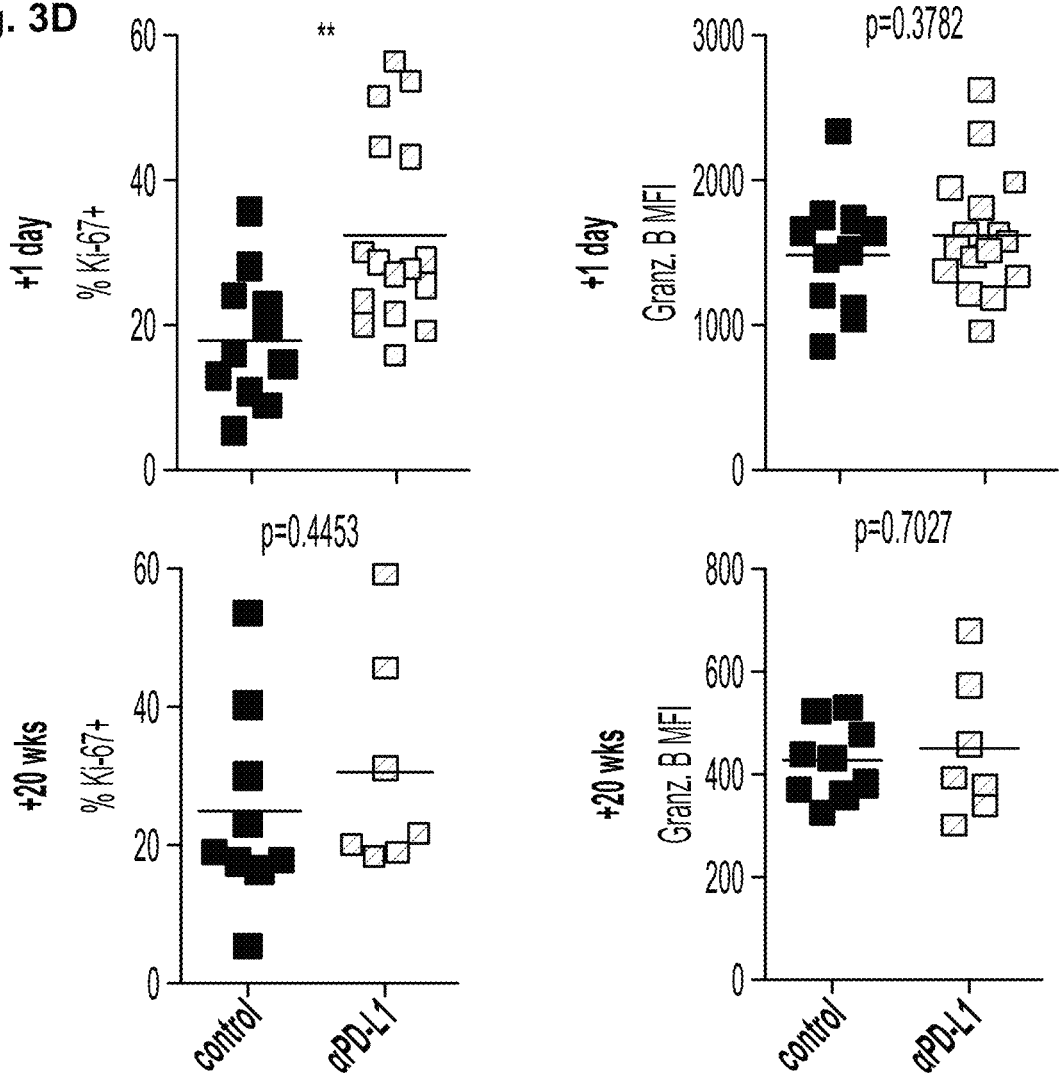

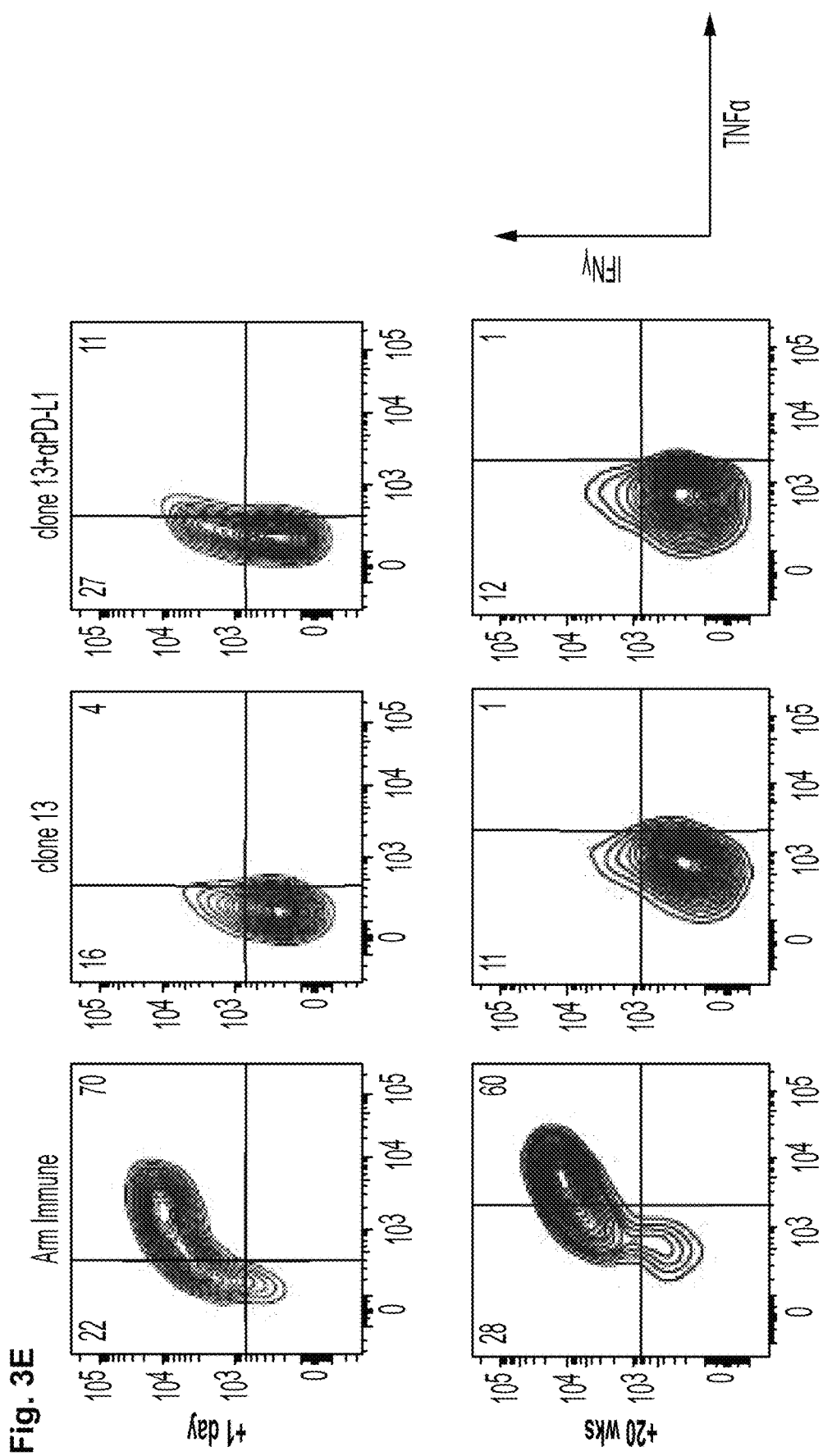

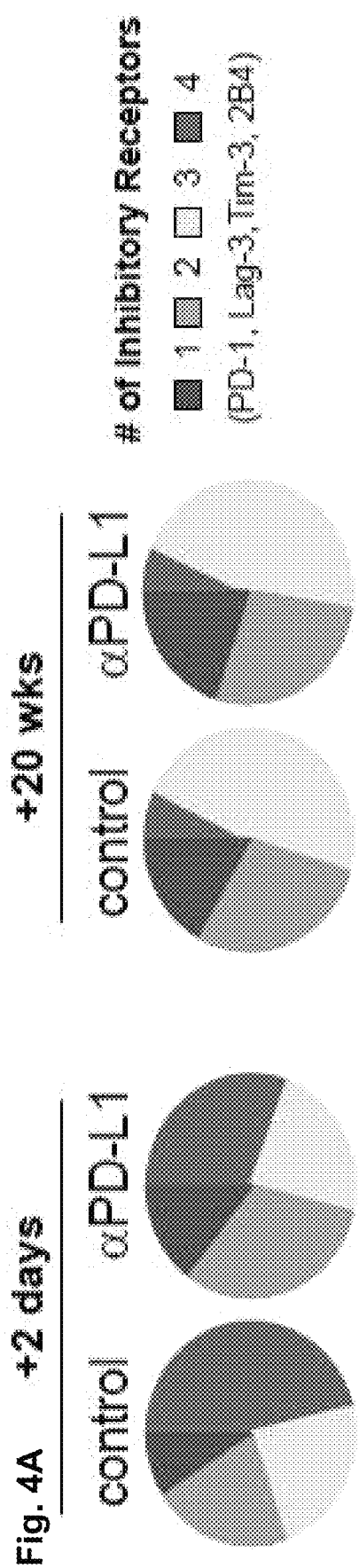

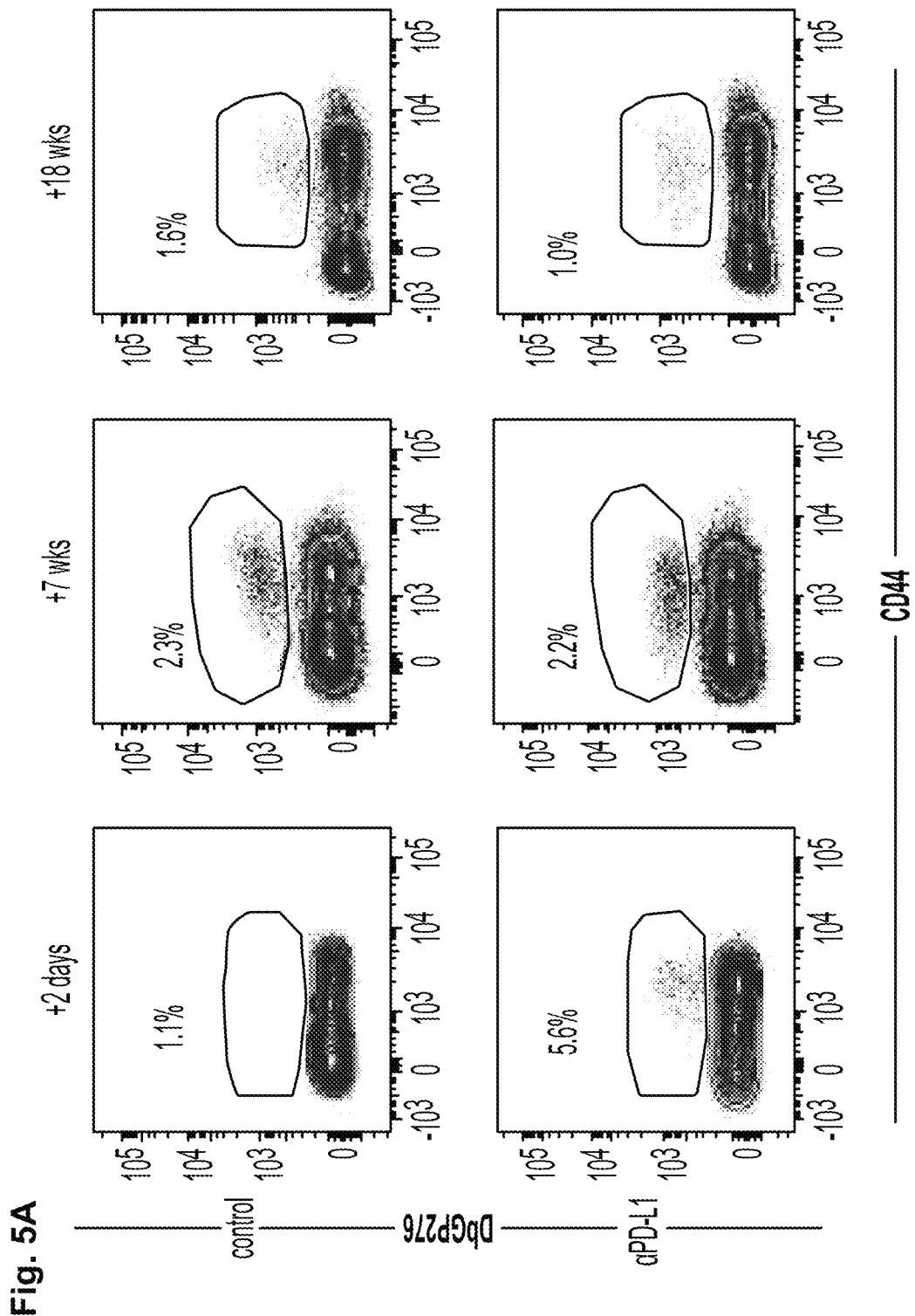

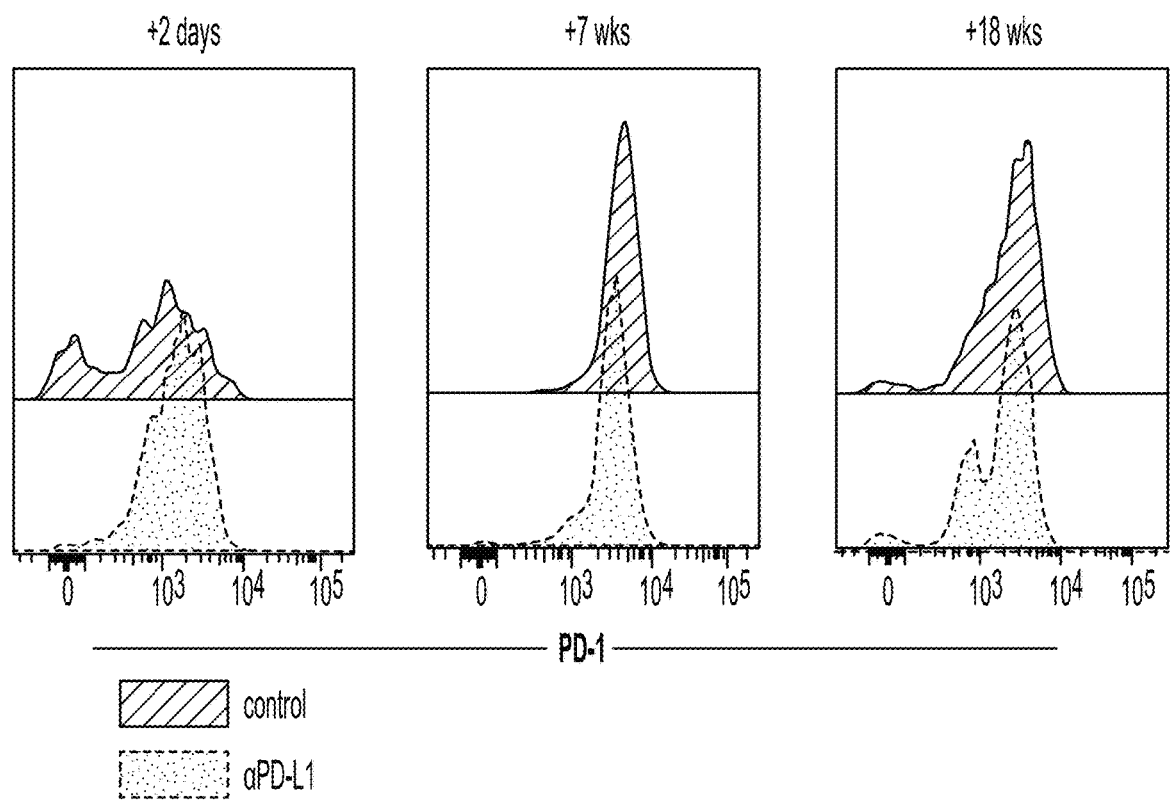

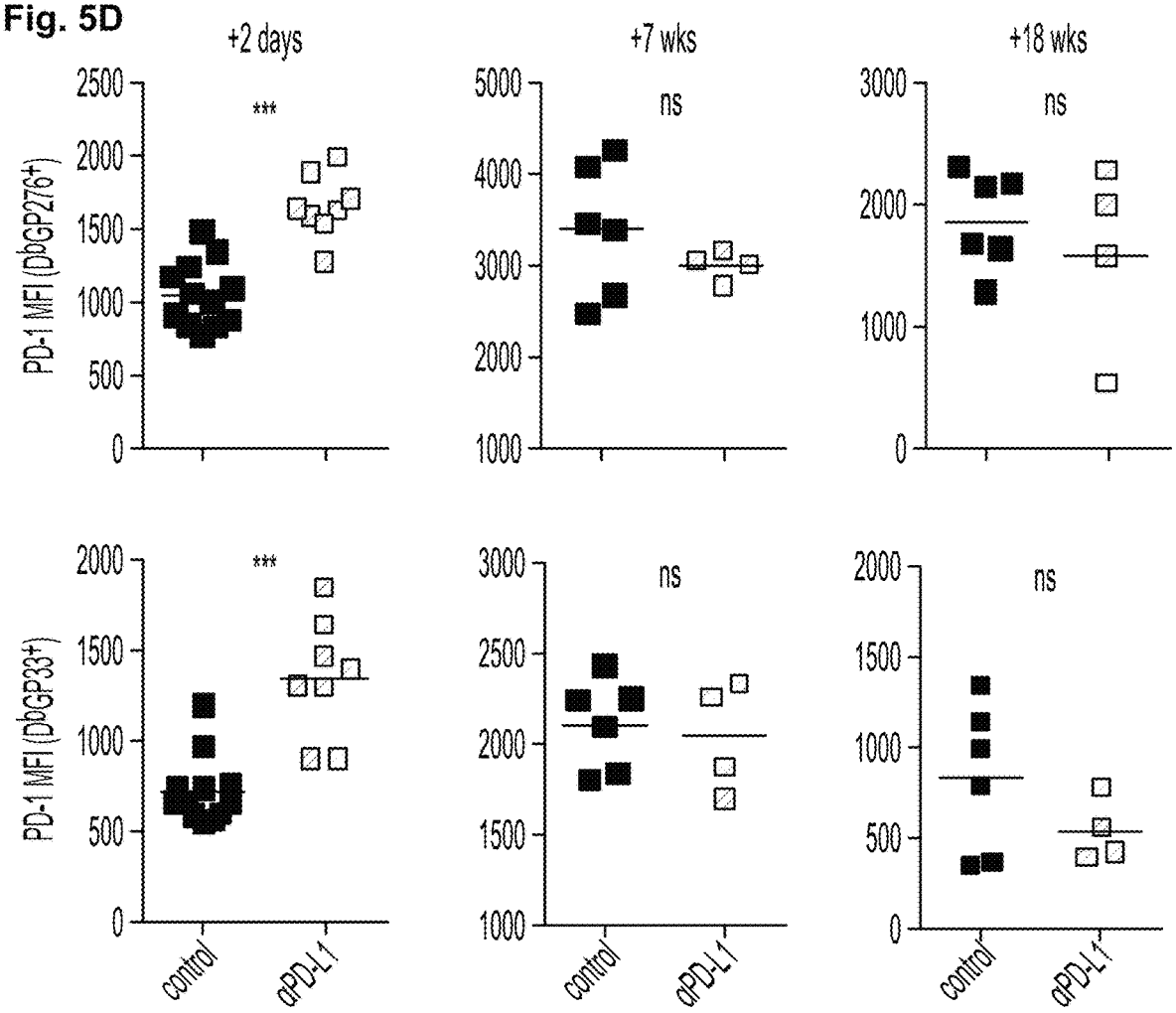

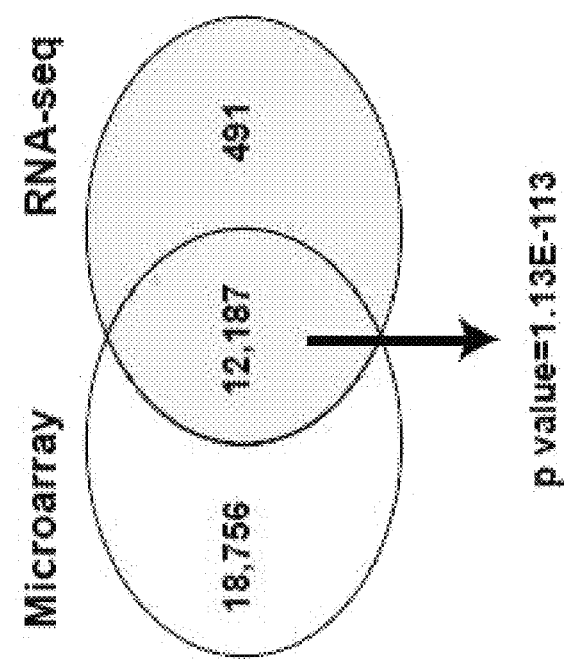
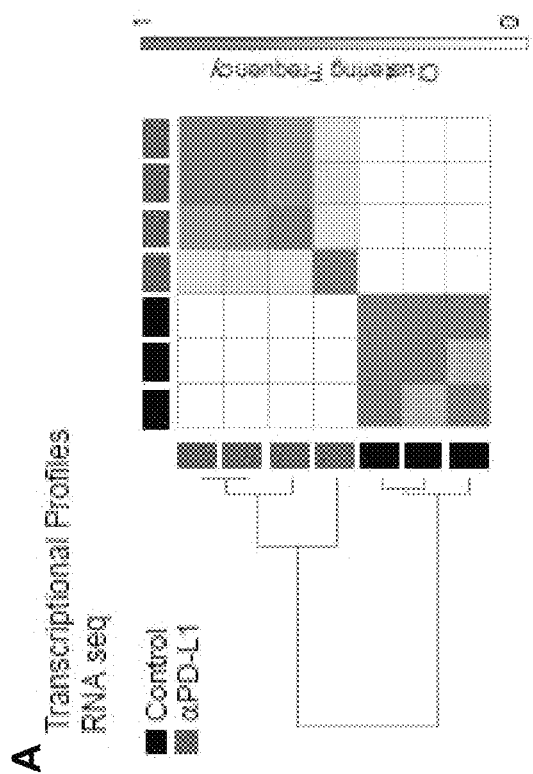
Fig. 6A
Fig. 6B

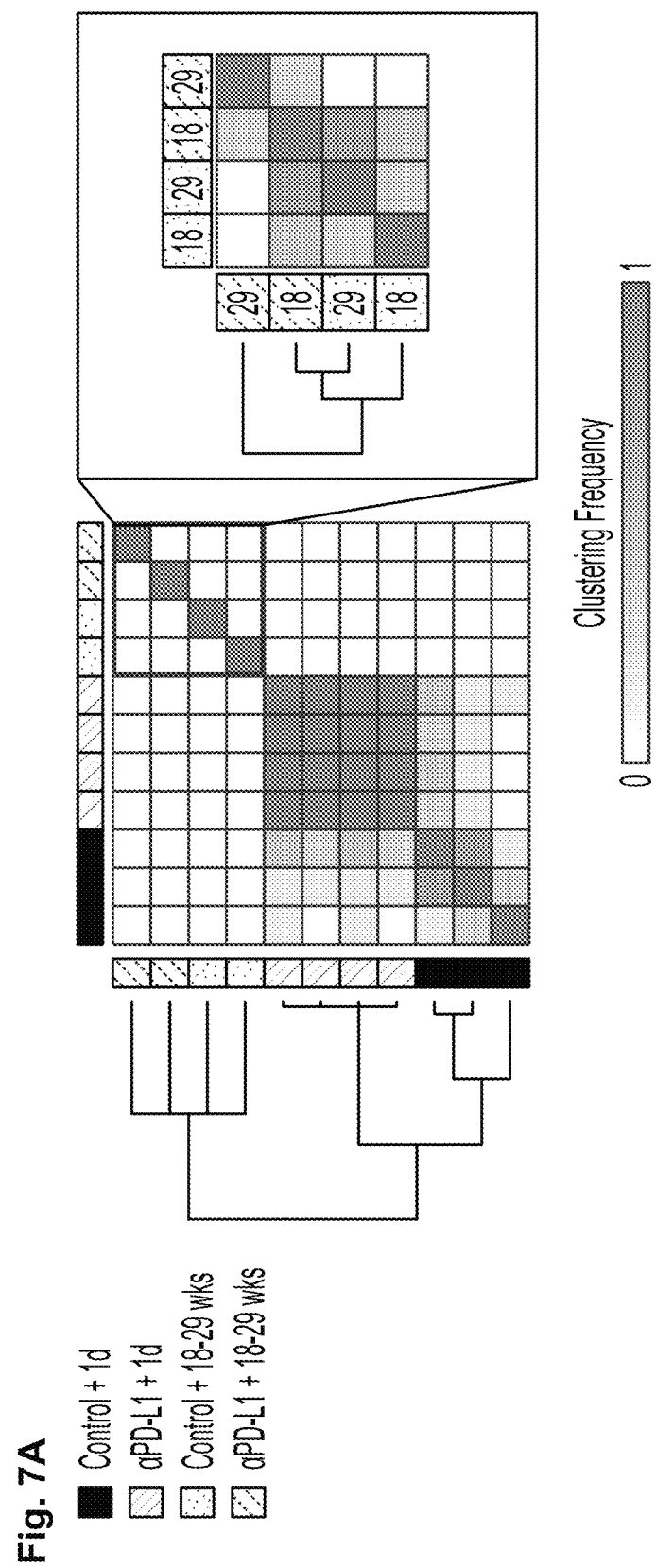

Fig. 7C

| Comparison | Total genes | Sig (p≤0.05) | LFC≥0.58 | LFC≥-0.58 |
|---|---|---|---|---|
| TEX vs αPD-L1 (+1d) | 12678 | 239 | 54 | 29 |
| TEX vs αPD-L1 (+18-29wks) | 12678 | 31 | 6 | 3 |
| TEX (+1d vs 18-29wks) | 12678 | 1008 | 168 | 346 |
| αPD-L1 (+1d vs 18-29wks) | 12678 | 1336 | 334 | 411 |

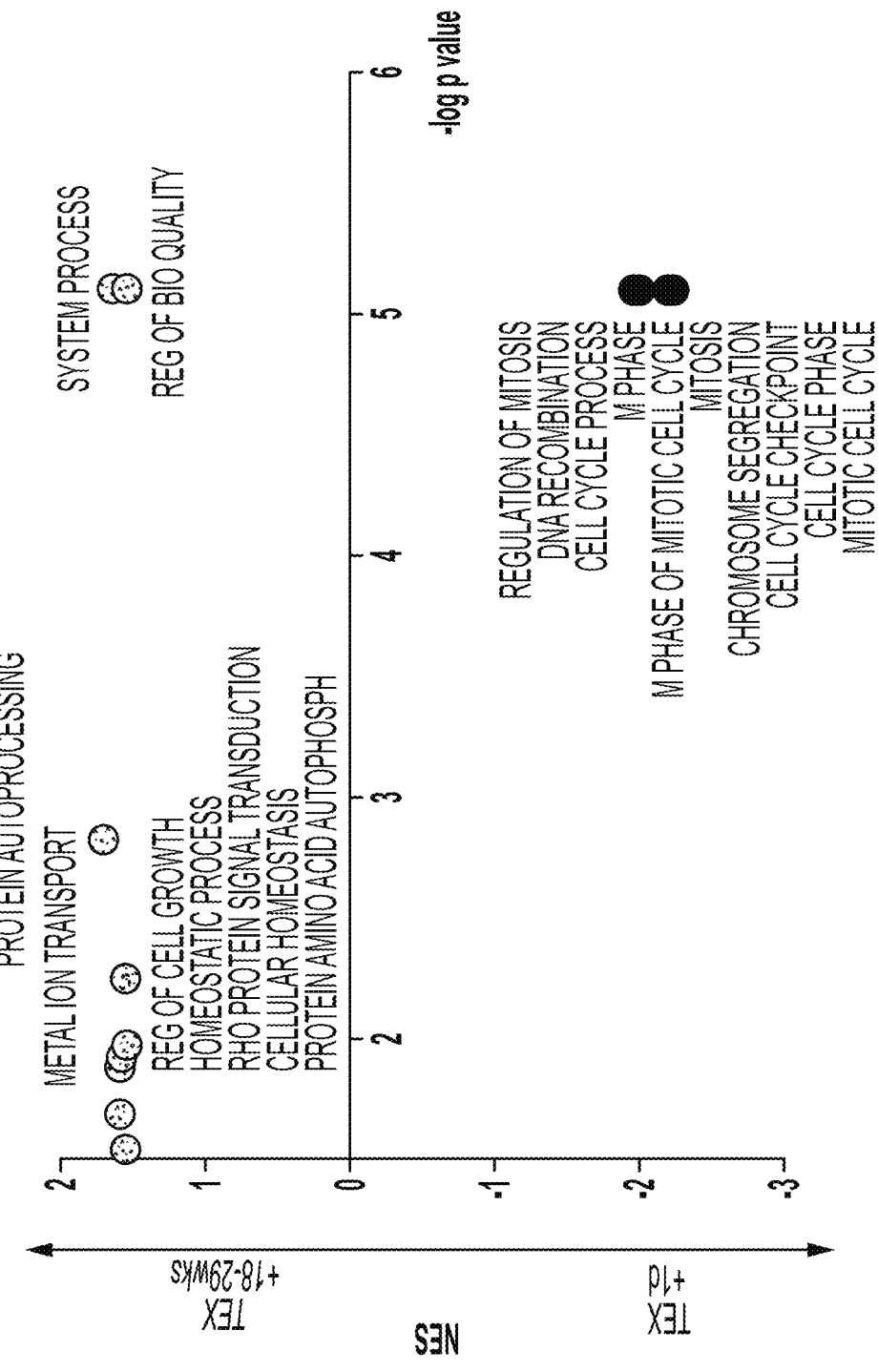

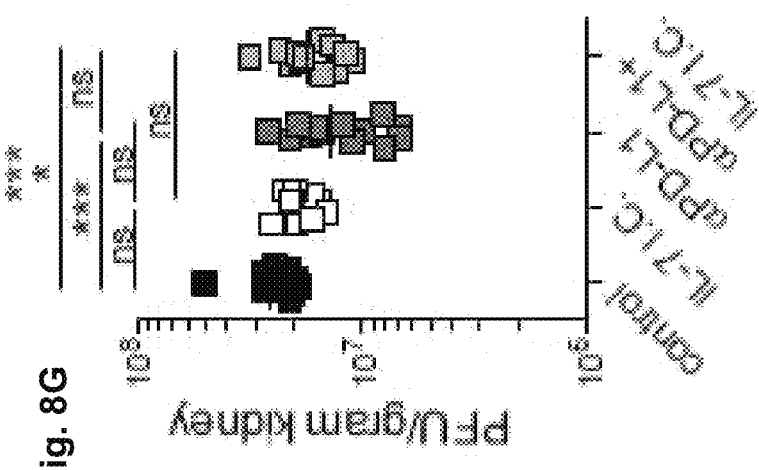
Fig. 8G
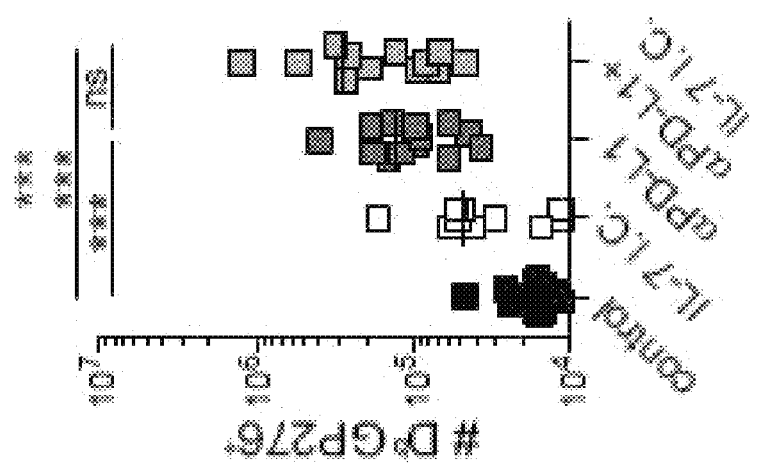
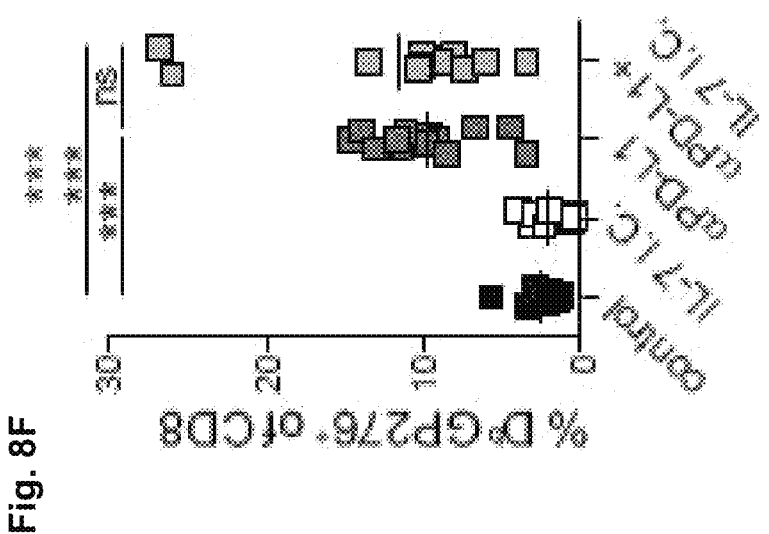
Fig. 8F

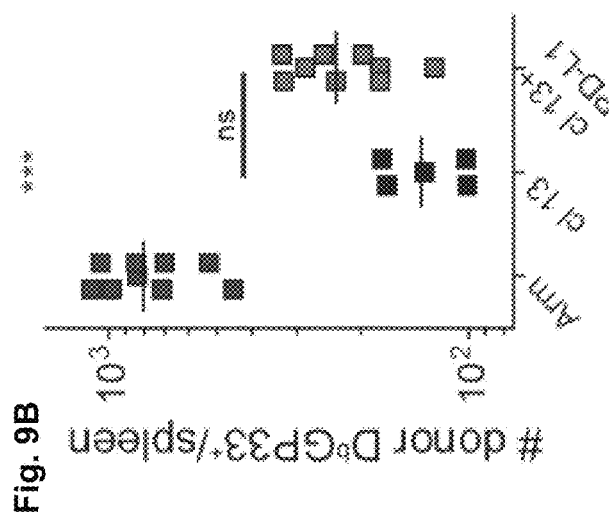
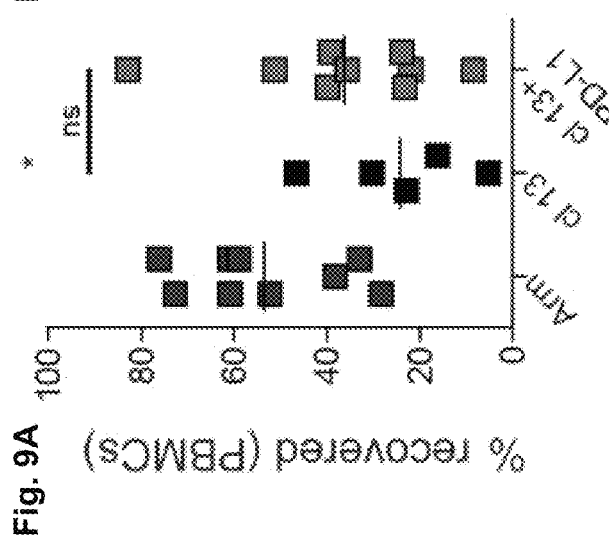
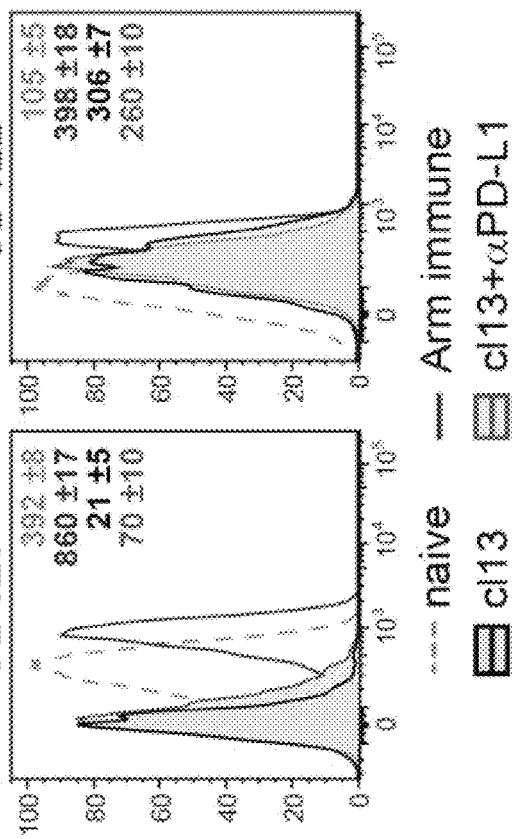

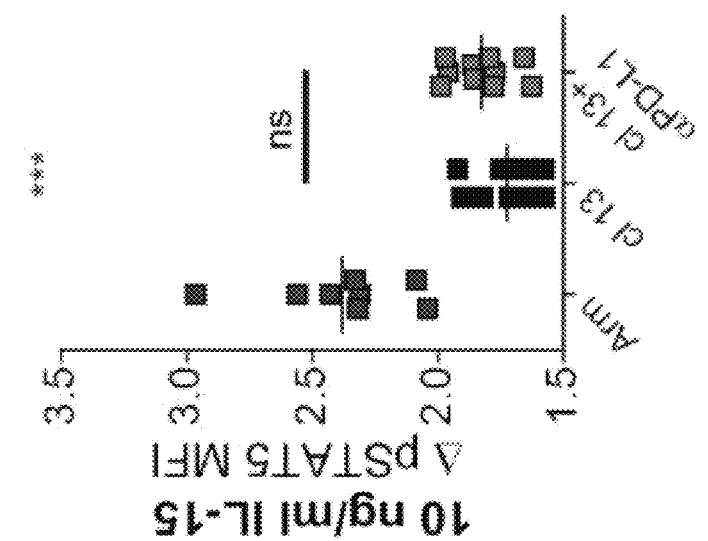
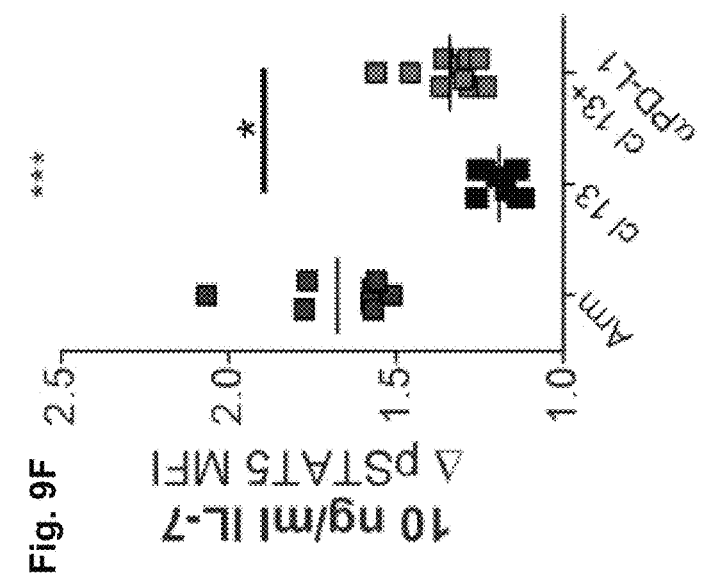
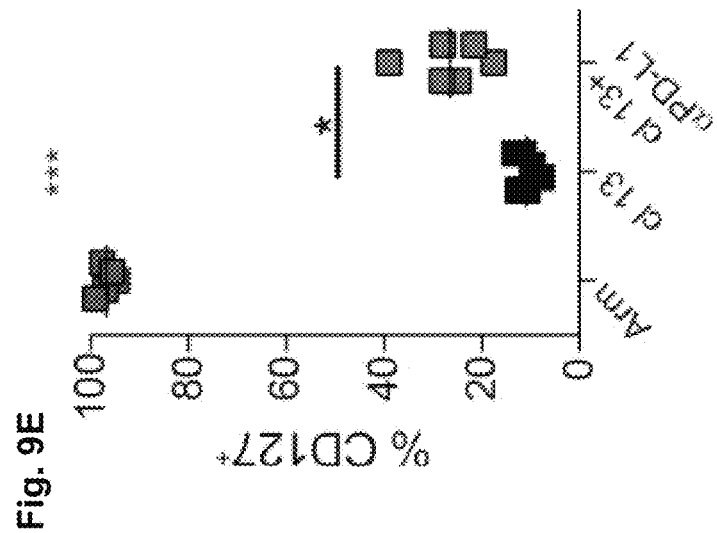
Fig. 9E
Fig. 9F

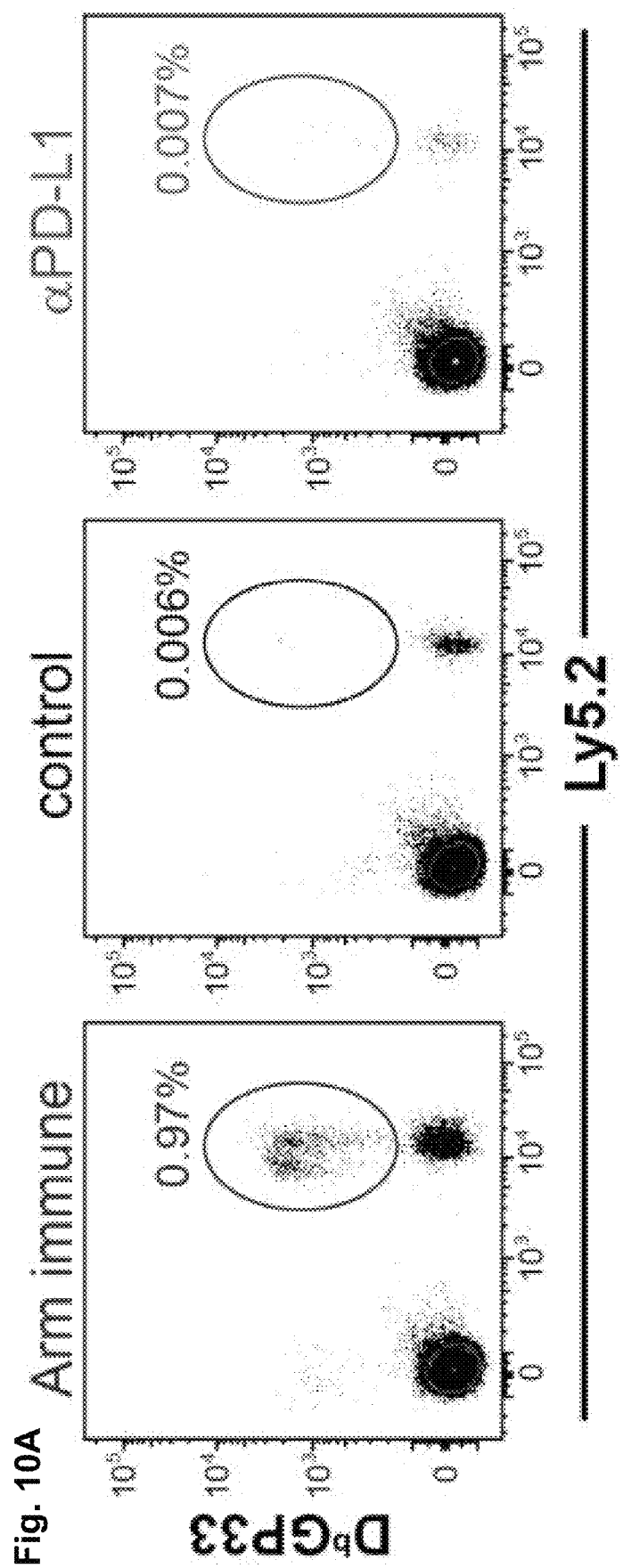

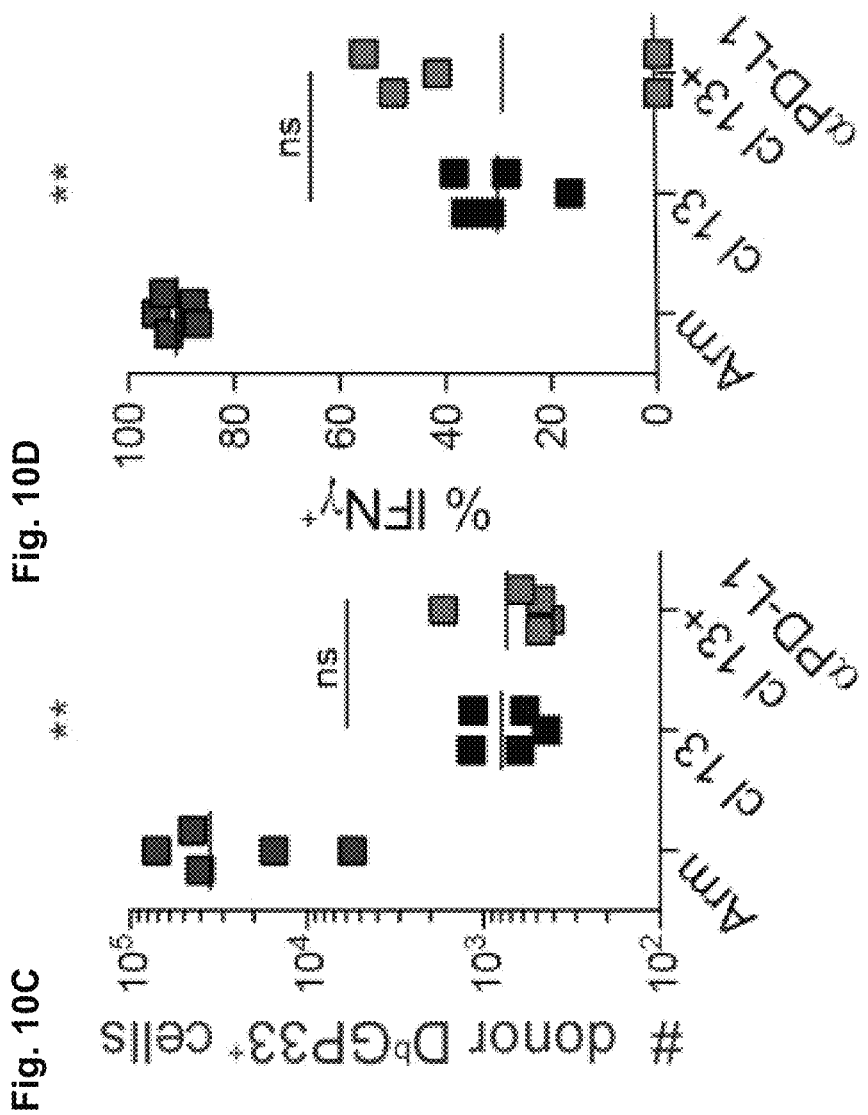

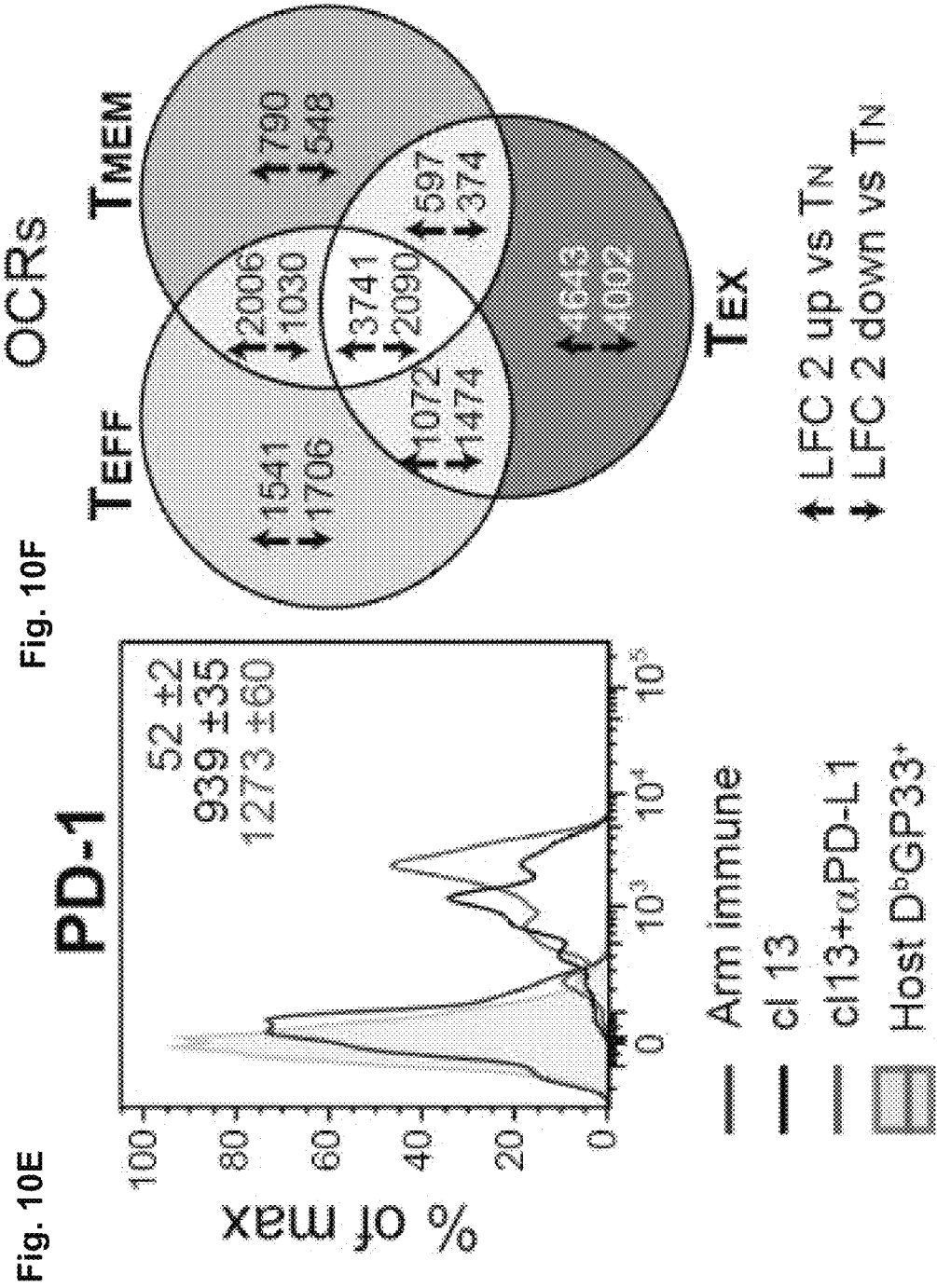

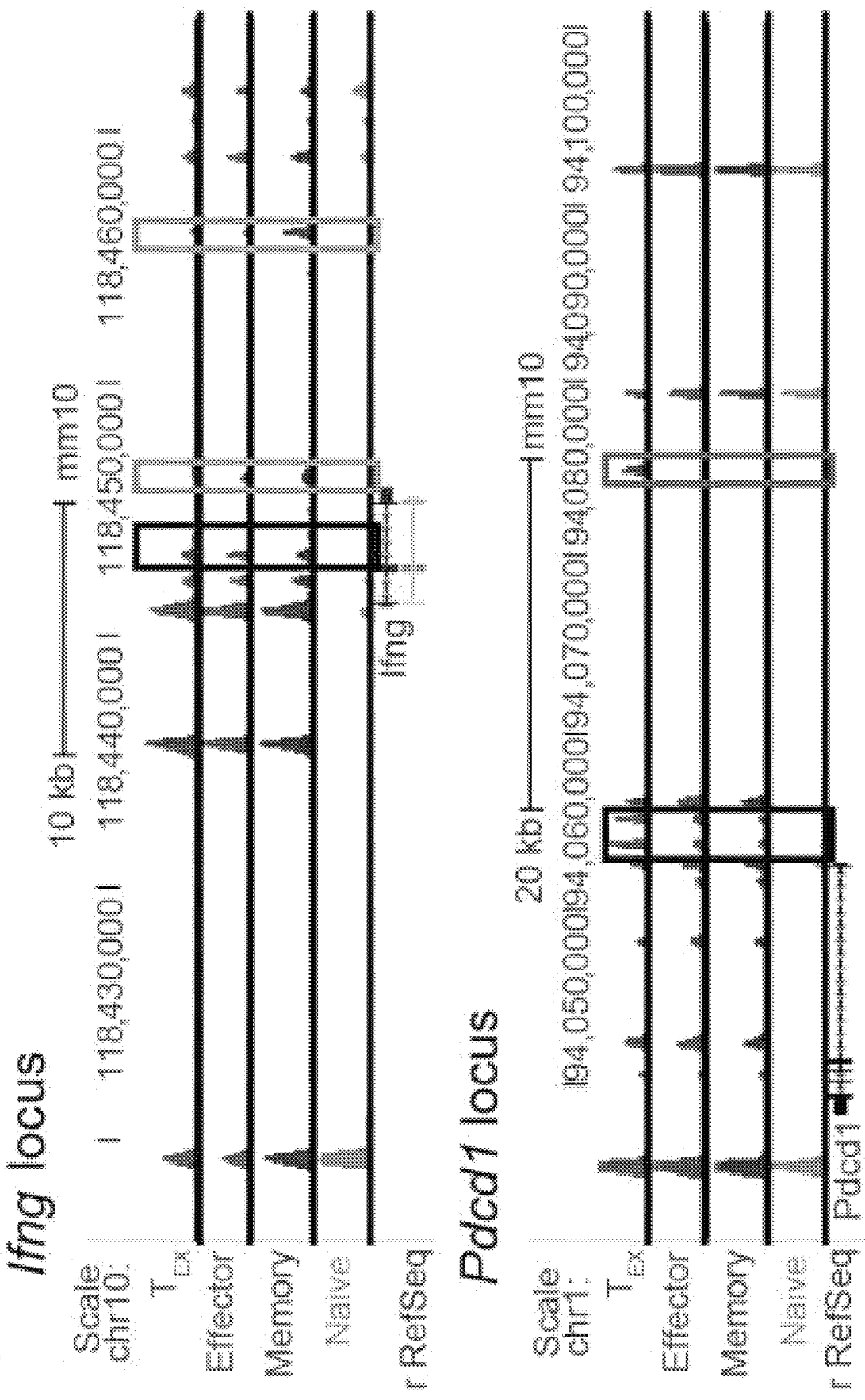

Fig. 11A

| | Total Paired Reads | Number Aligned | % Aligned | # of Peaks (MACS v1.4) |
|---|---|---|---|---|
| TN-1 | 21,580,793 | 19,895,761 | 92.19 | 47,245 |
| TN-2 | 37,179,087 | 34,405,396 | 92.54 | 52,242 |
| TEFF-1 | 52,854,827 | 47,732,769 | 90.31 | 64,351 |
| TEFF-2 | 51,028,317 | 46,145,040 | 90.43 | 60,124 |
| TMEM-1 | 61,364,436 | 42,757,634 | 89.68 | 58,448 |
| TMEM-2 | 60,666,170 | 55,654,432 | 91.74 | 58,676 |
| TEX-1 | 48,137,474 | 42,639,858 | 88.58 | 39,225 |
| TEX-2 | 66,496,181 | 60,252,069 | 90.61 | 59,910 |
| αPDL1-1 | 49,545,282 | 44,790,886 | 90.40 | 55,036 |
| αPDL1-2 | 59,567,799 | 53,608,743 | 90.00 | 56,564 |

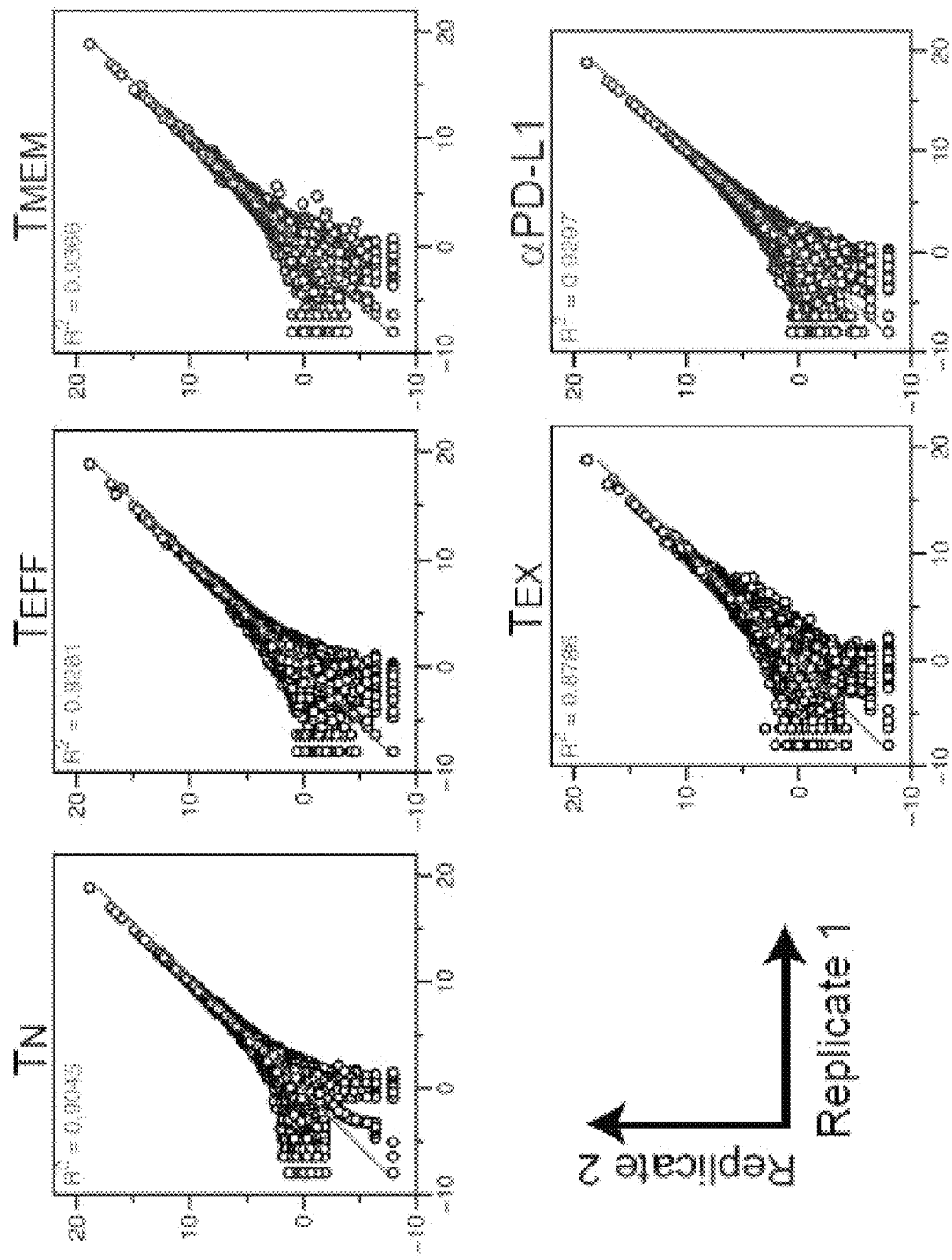
Fig. 11B Normalized ATAC peak enrichment

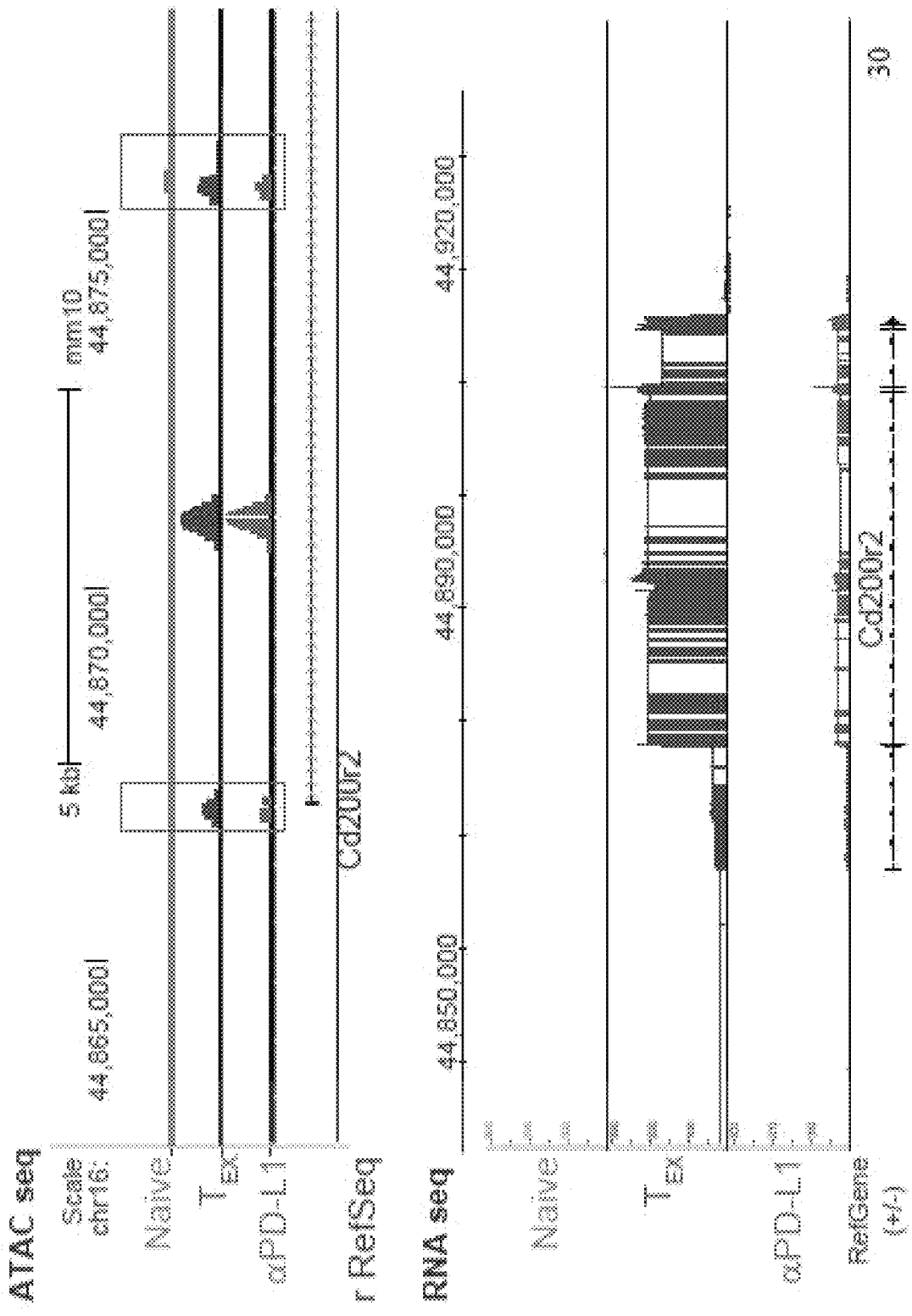

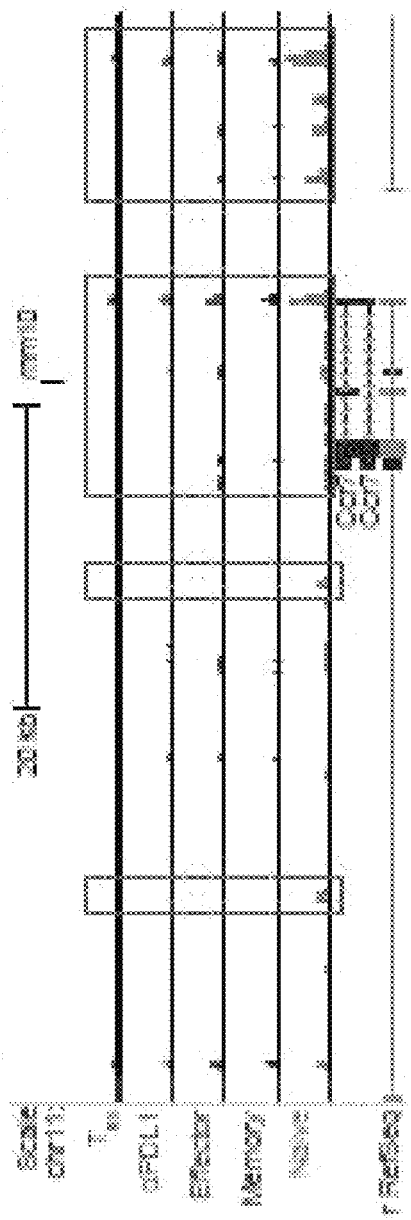
Fig. 15B *Ccr7*
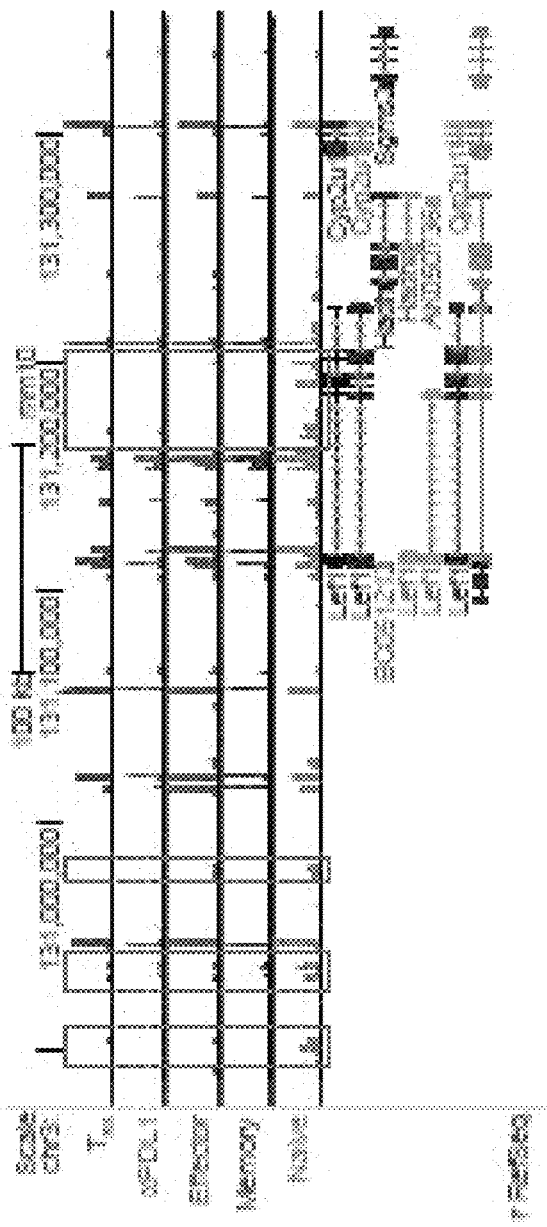
Fig. 15C *Lef1*

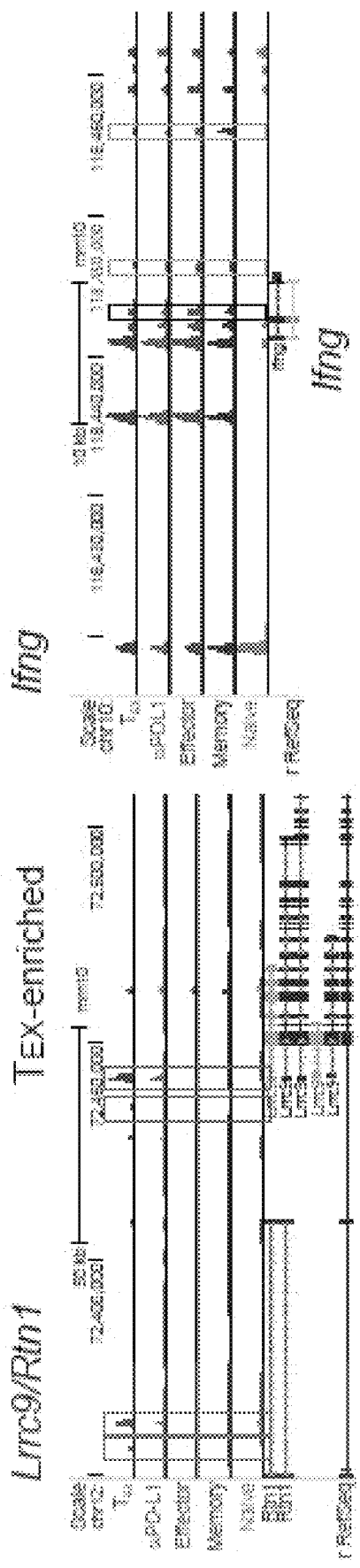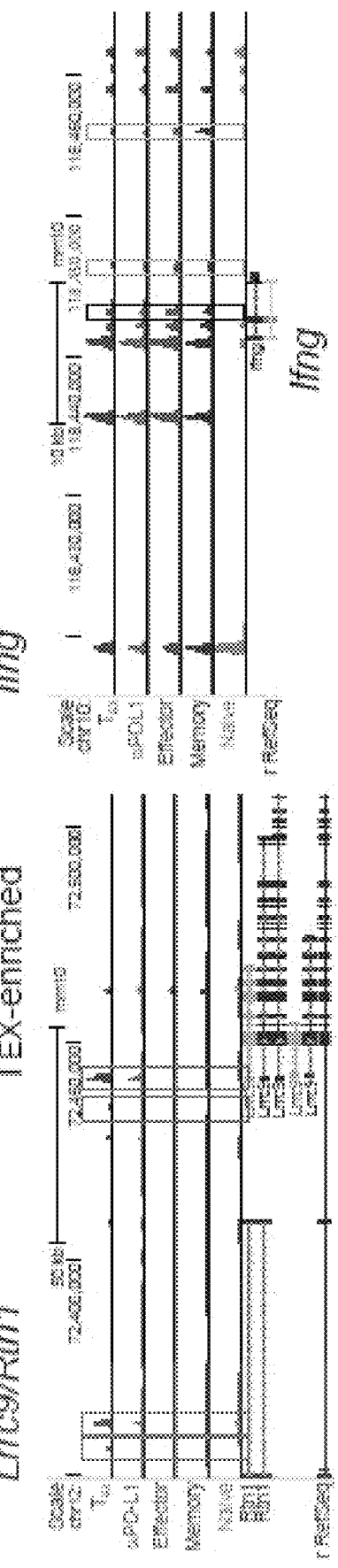

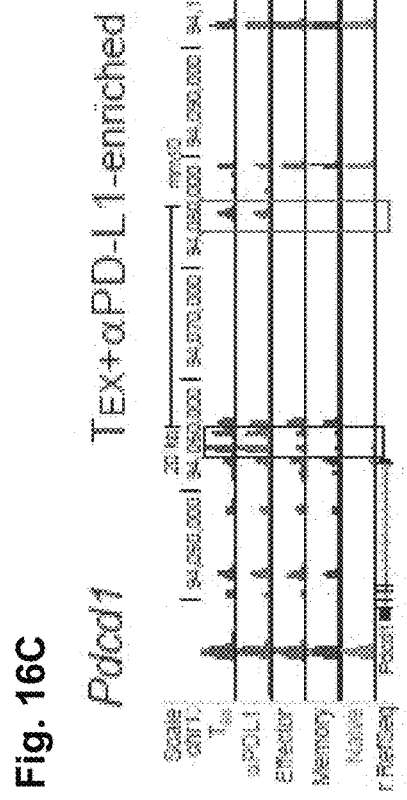
Fig. 16C  *Pdcd1*  TEx+αPD-L1-enriched
Fig. 16D  *Tbx21* (T-bet)

Cd200r

Nrc3

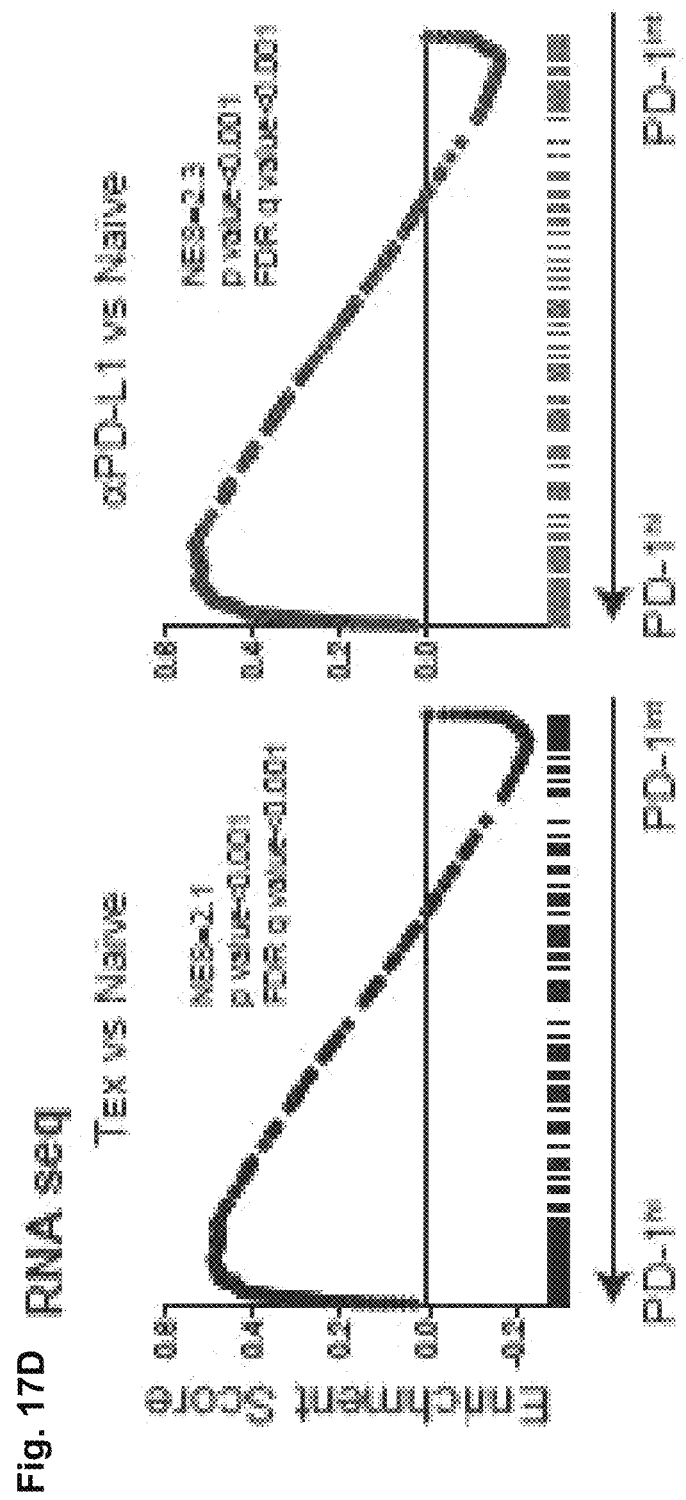
Fig. 17D RNA seq

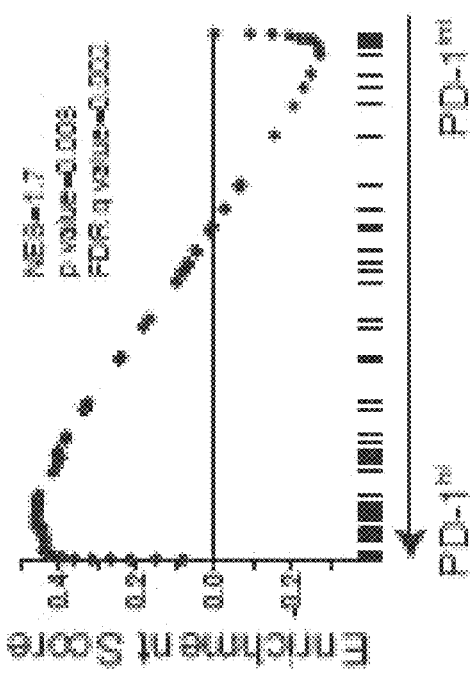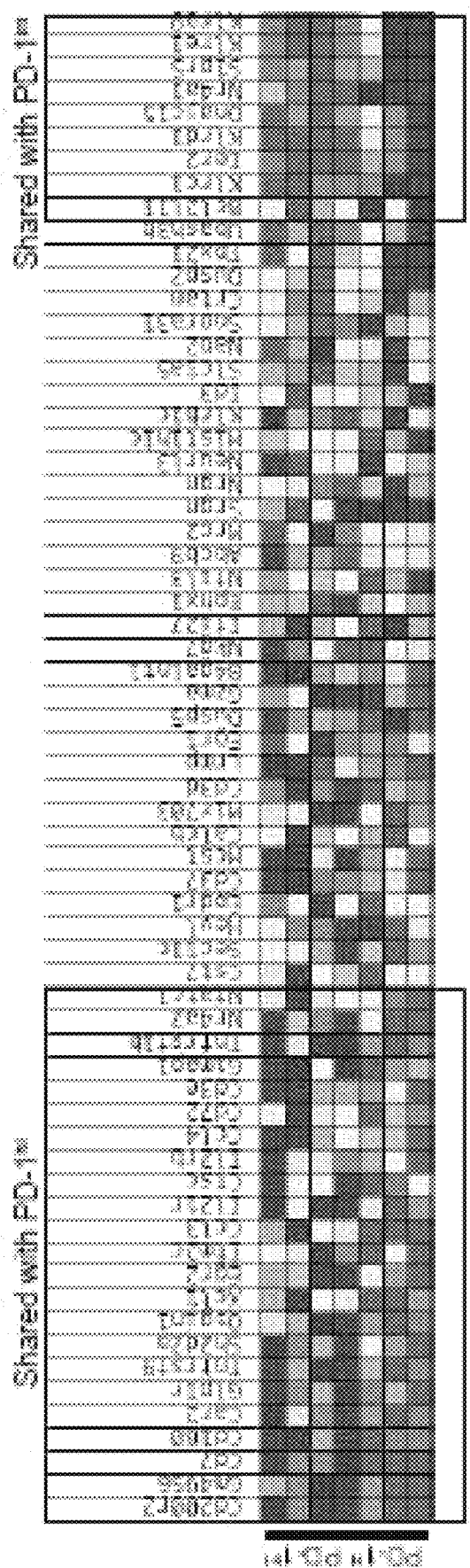
Fig. 17F

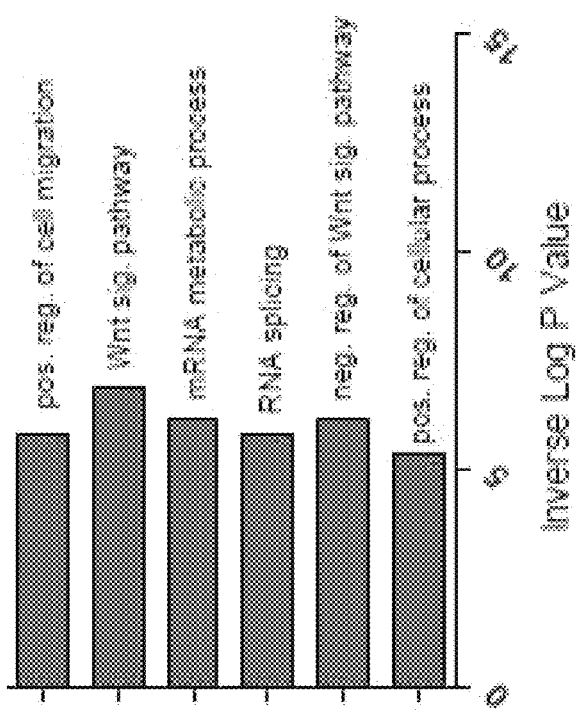
Fig. 18E αPD-L1-specific
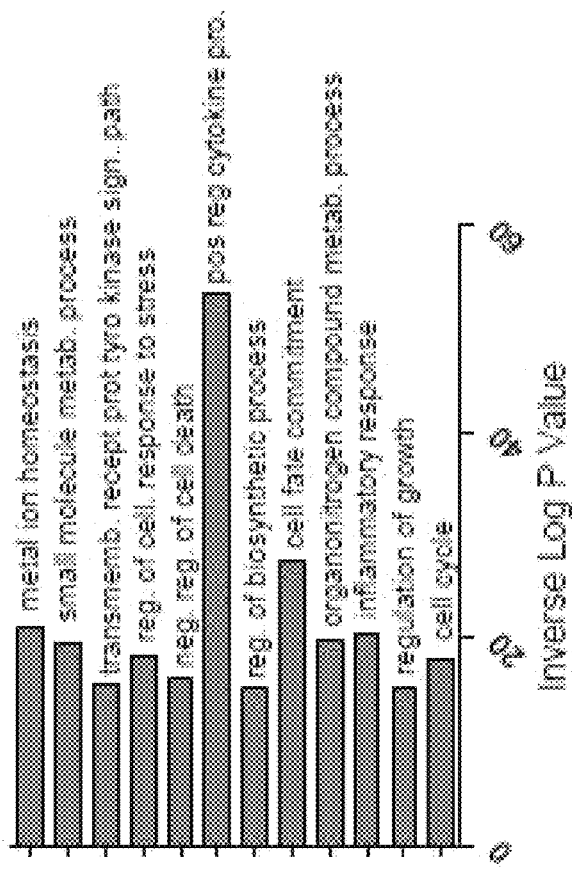
Fig. 18D Exhausted-specific

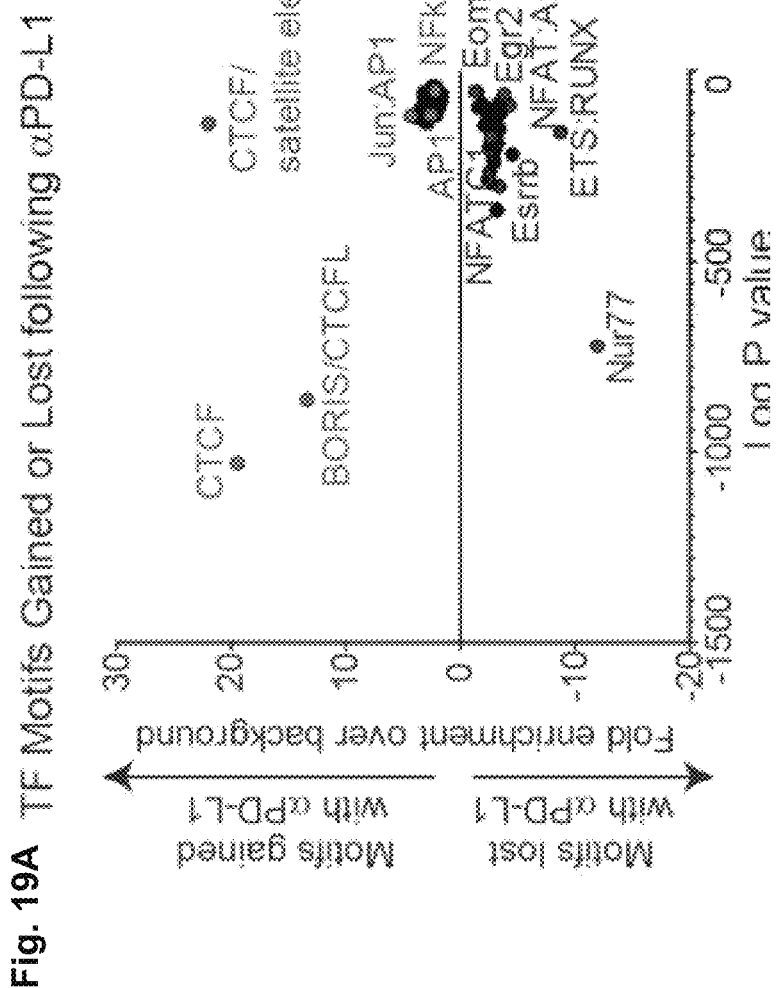
Fig. 19A  TF Motifs Gained or Lost following αPD-L1

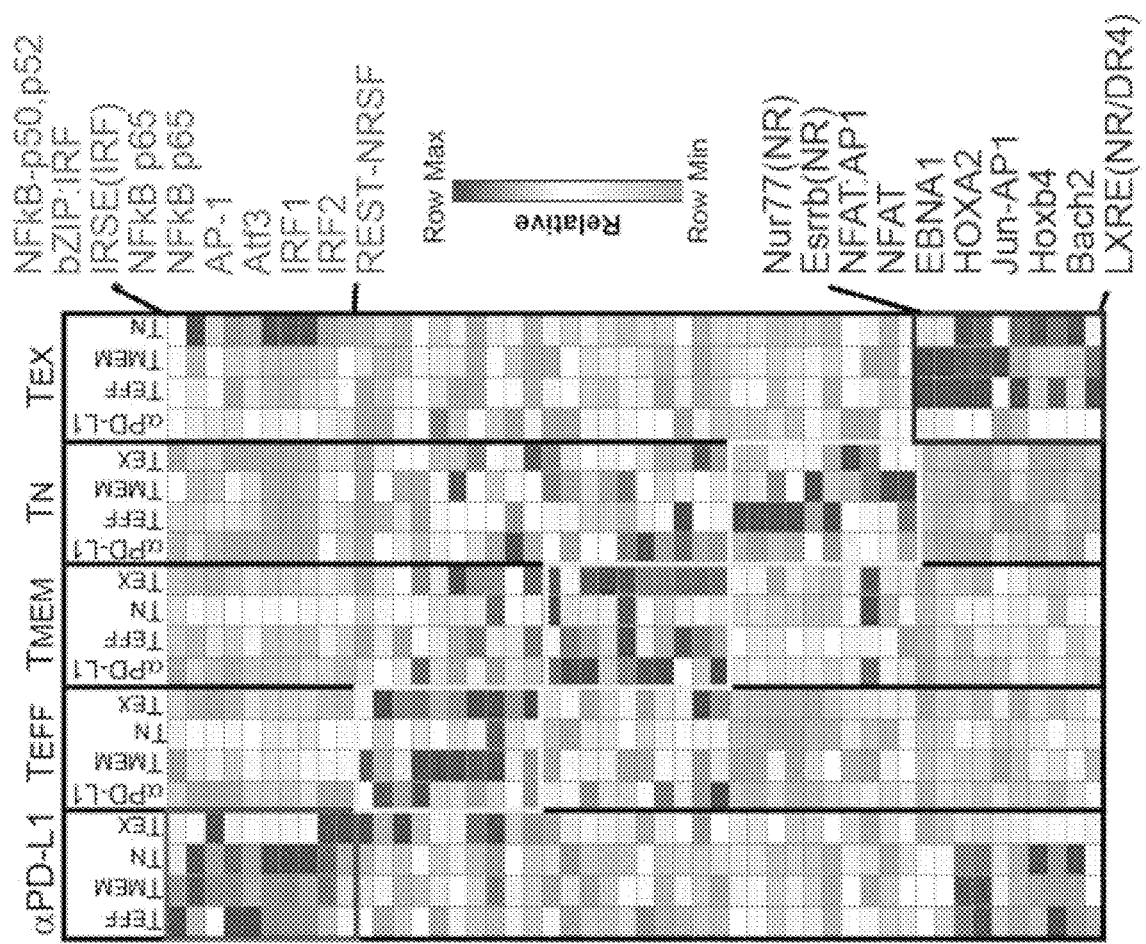
Fig. 19B TF Motif Enrichment in OCRs

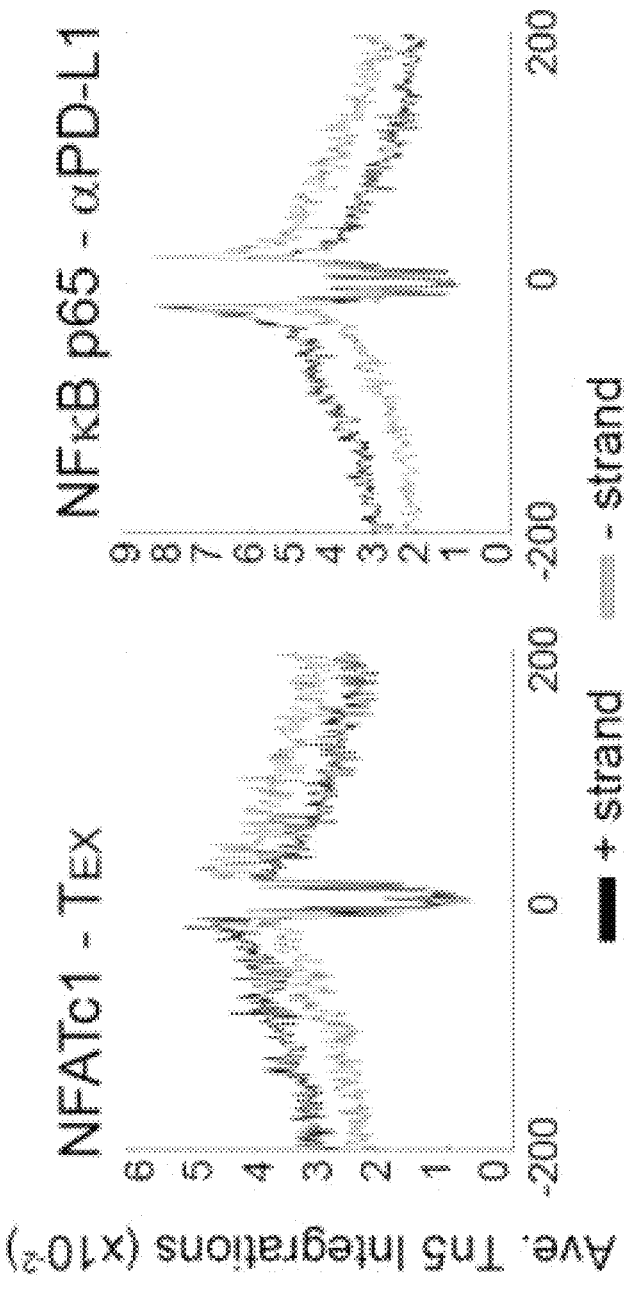
Fig. 19C TF Footprinting

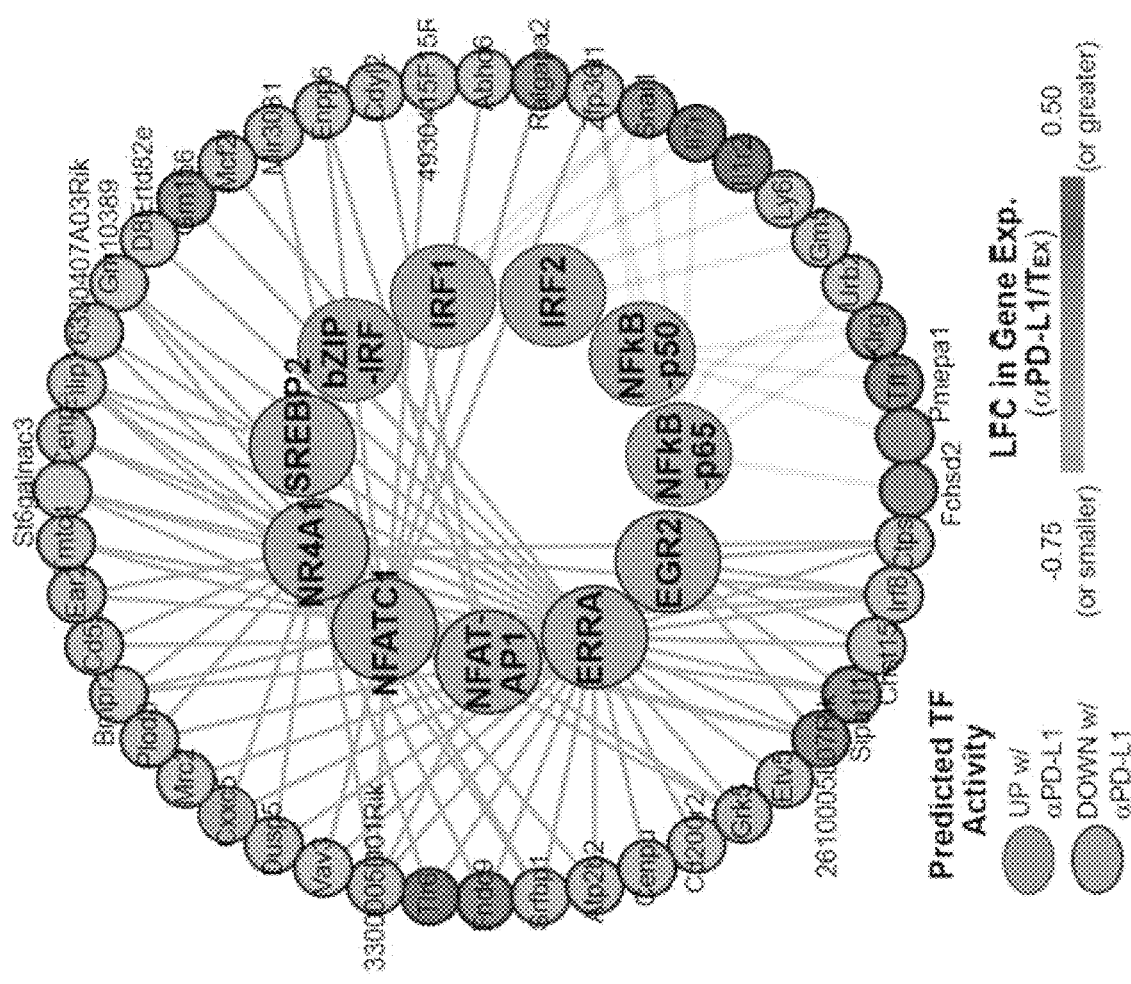
Fig. 19D Changes in integrated transcriptional network

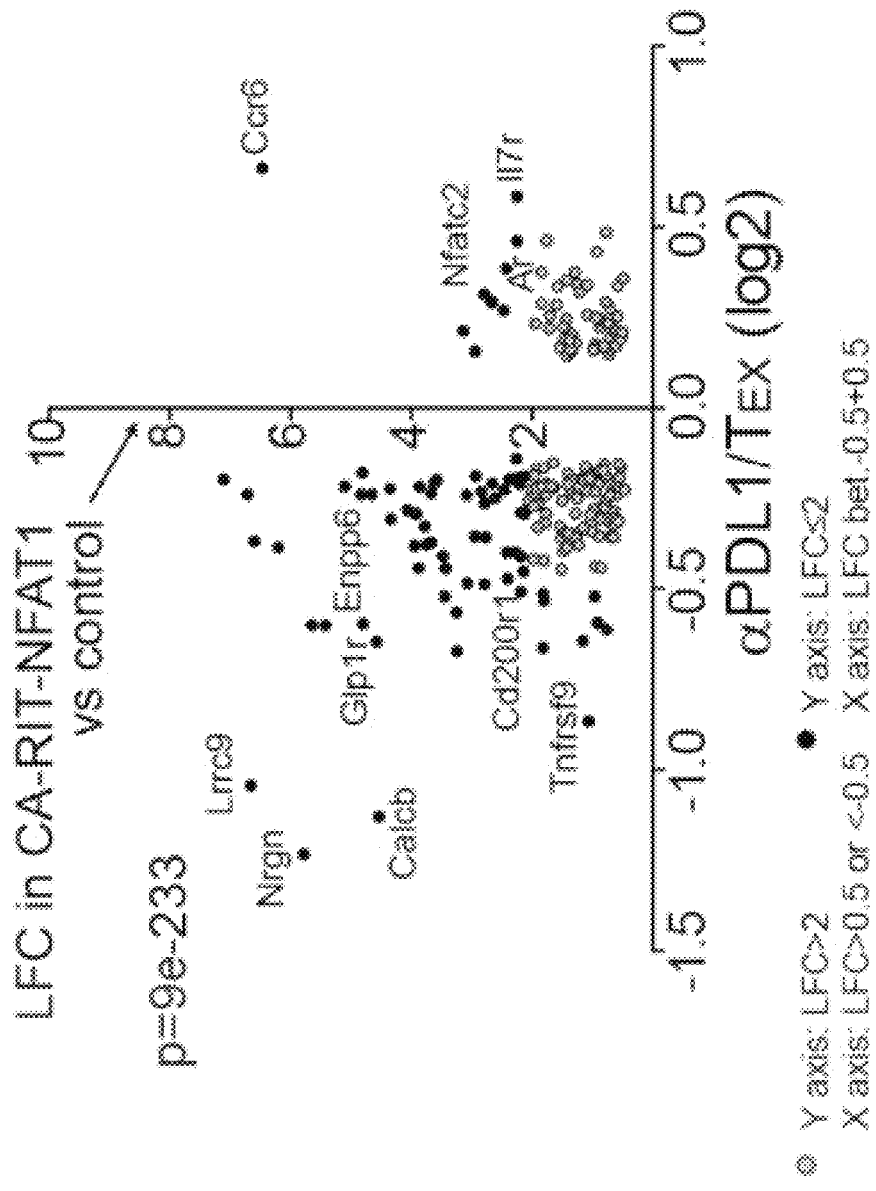
Fig. 19E  Transcript. changes in CA-RIT-NFAT1 target genes

Fig. 23A    Penn EAP

| Characteristics | n=29 | | RECIST Criteria | n=29 |
|---|---|---|---|---|
| Age, median years (range) | 57 (29-82) | | CR | 17% n=5 |
| ECOG PS 0/1 | 97% n=28 | | PR | 21% n=6 |
| Known Brain mets | 45% n=13 | | SD | 24% n=7 |
| LDH >ULN | 62% n=18 | | PD | 38% n=11 |
| BRAF mutated | 28% n=8 | | | |
| - BRAFi treated | 75% n=6 | | | |
| anti-CTLA4 treated | 100% n=29 | | | |

MSKCC Keynote-001

| Characteristics | n=18 | | RECIST Criteria | n=18 |
|---|---|---|---|---|
| Age, median years (range) | 63.5 (30-76) | | CR | 0% n=0 |
| ECOG PS 0/1 | 100% n=18 | | PR | 56% n=10 |
| Known Brain mets | 11% n=2 | | SD | 0% n=0 |
| LDH >ULN | 44% n=8 | | PD | 44% n=8 |
| BRAF mutated | 22% n=4 | | | |
| - BRAFi treated | 100% n=4 | | | |
| anti-CTLA4 treated | 89% n=16 | | | |

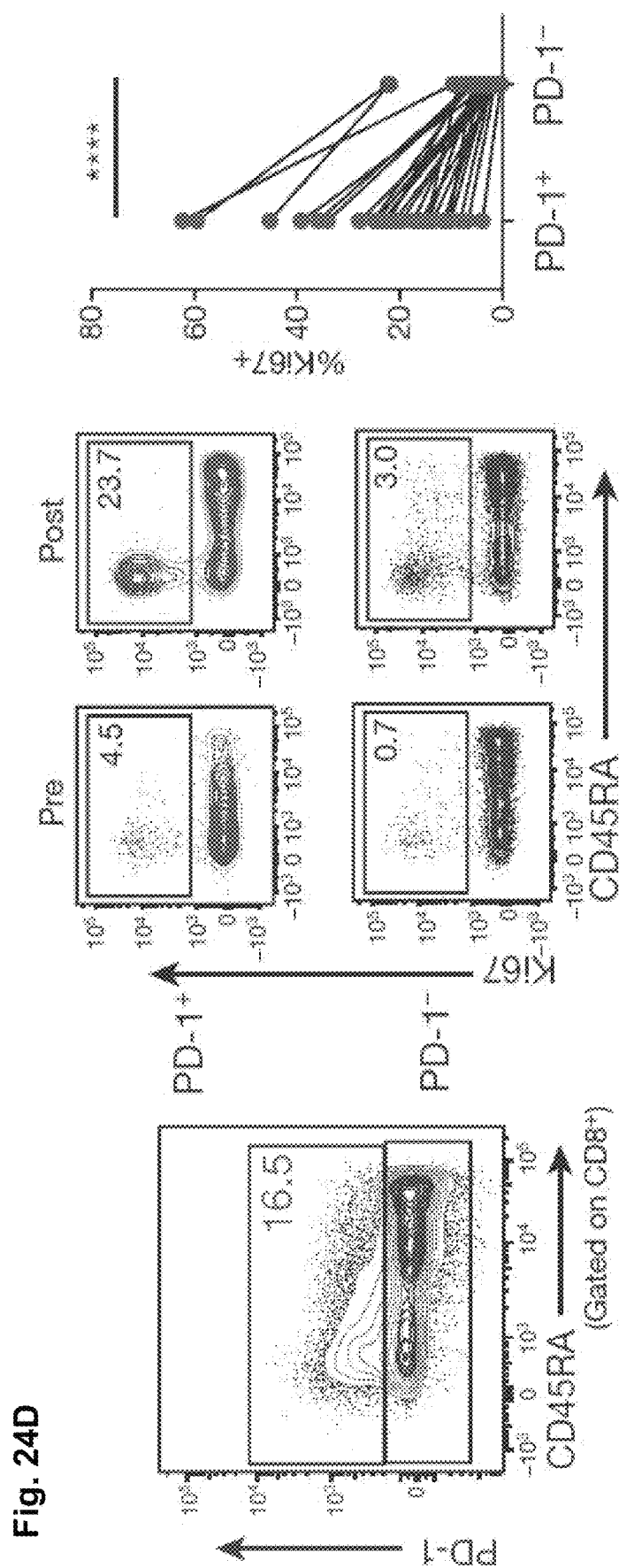

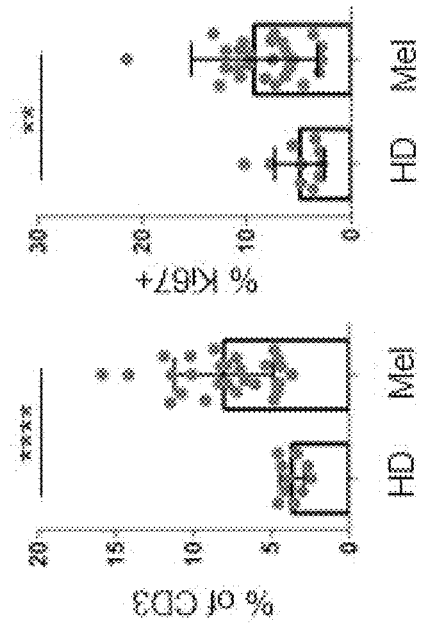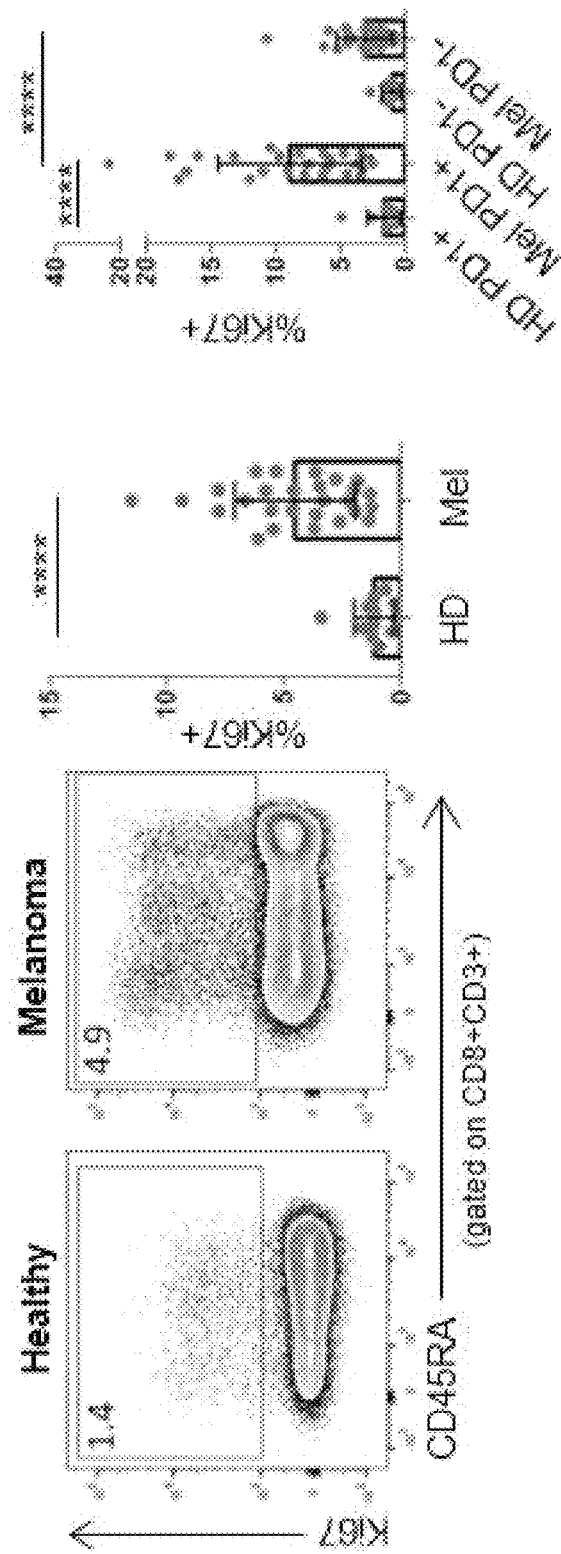
Fig. 25A  Fig. 25B  Fig. 25C

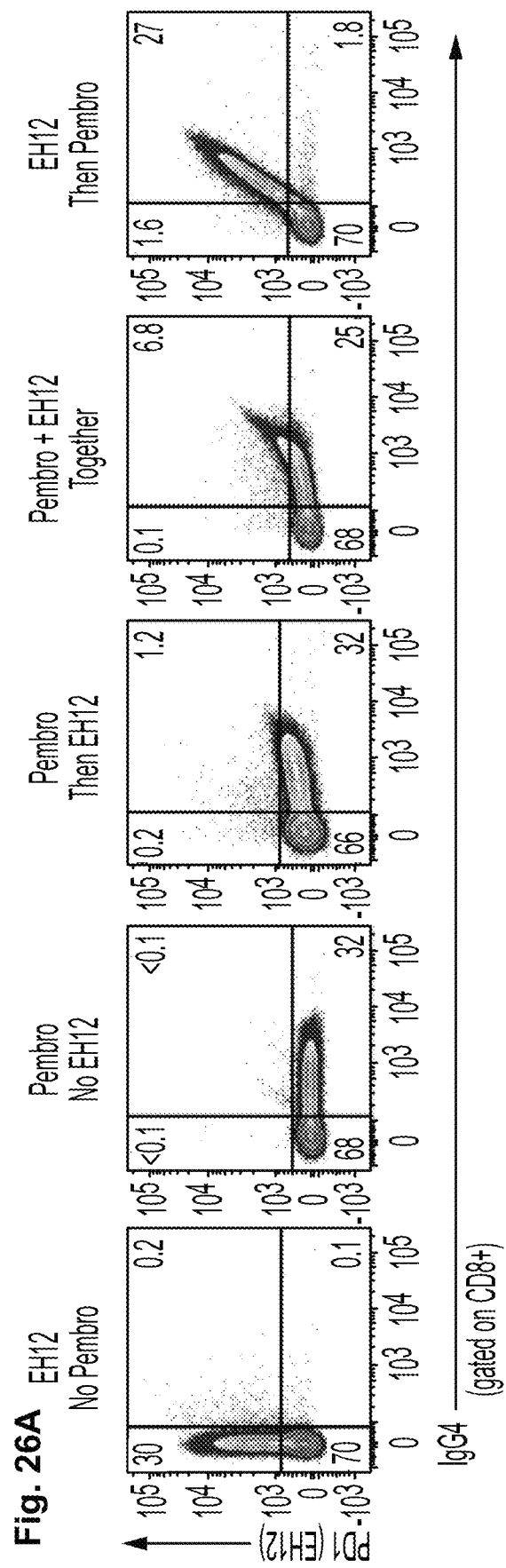

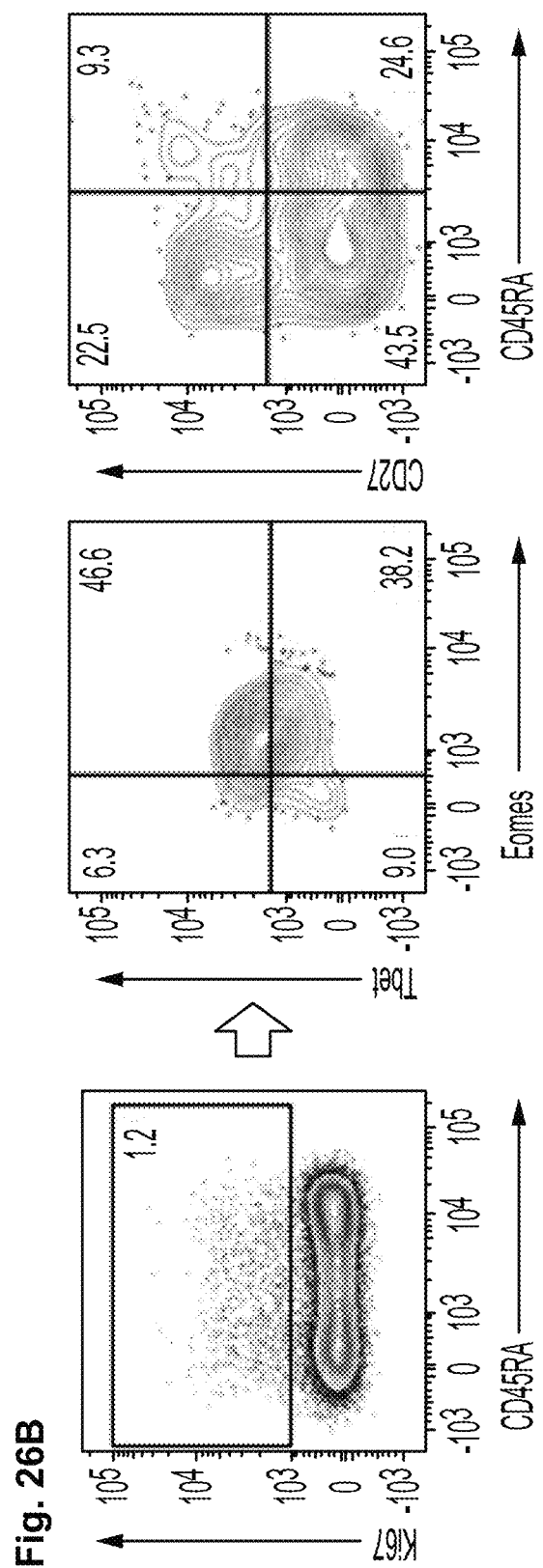

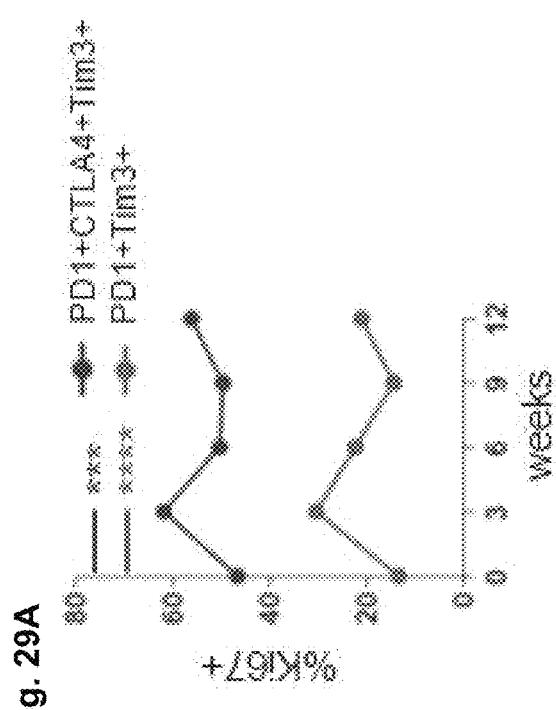
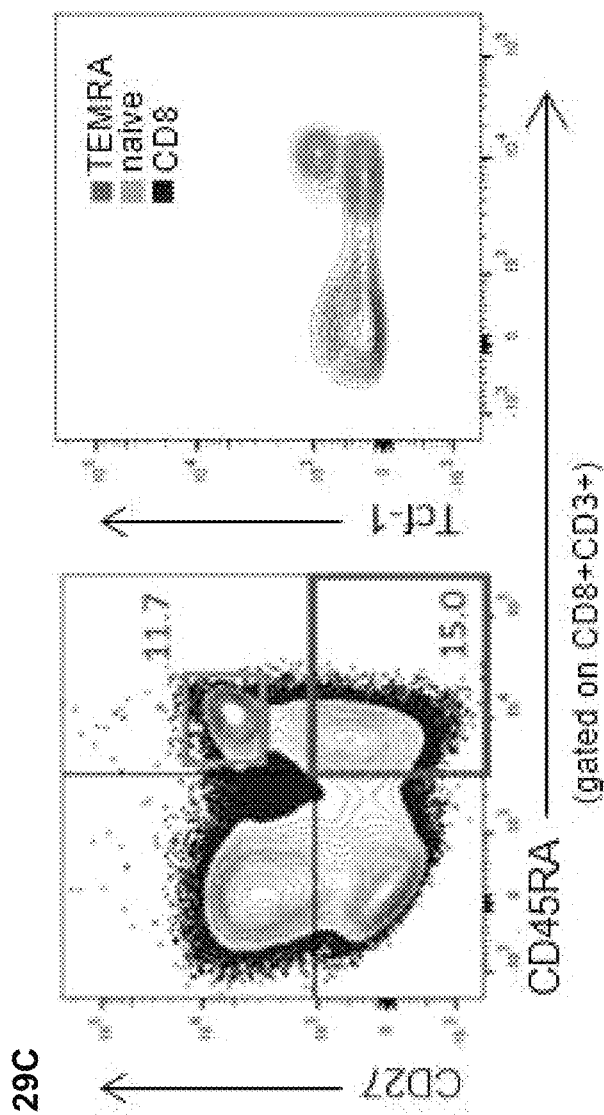
Fig. 29A  Fig. 29B  Fig. 29C

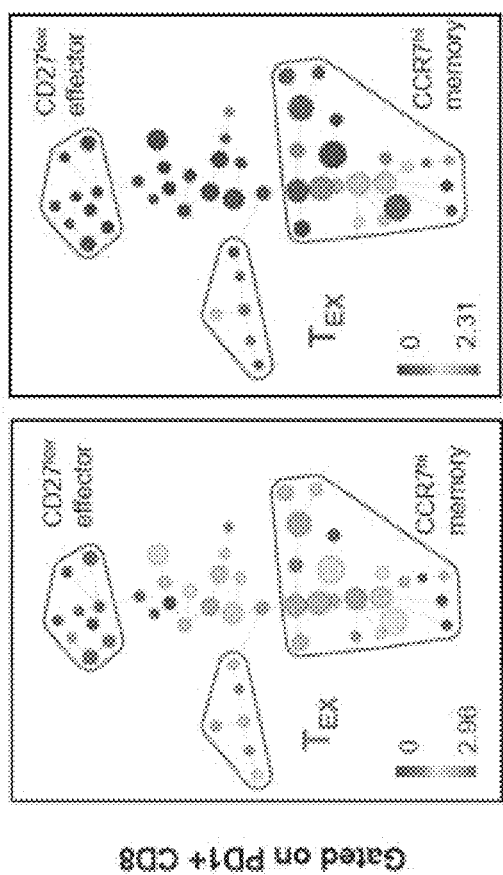
Fig. 30A
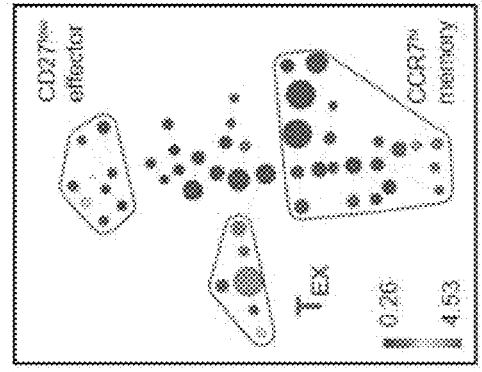
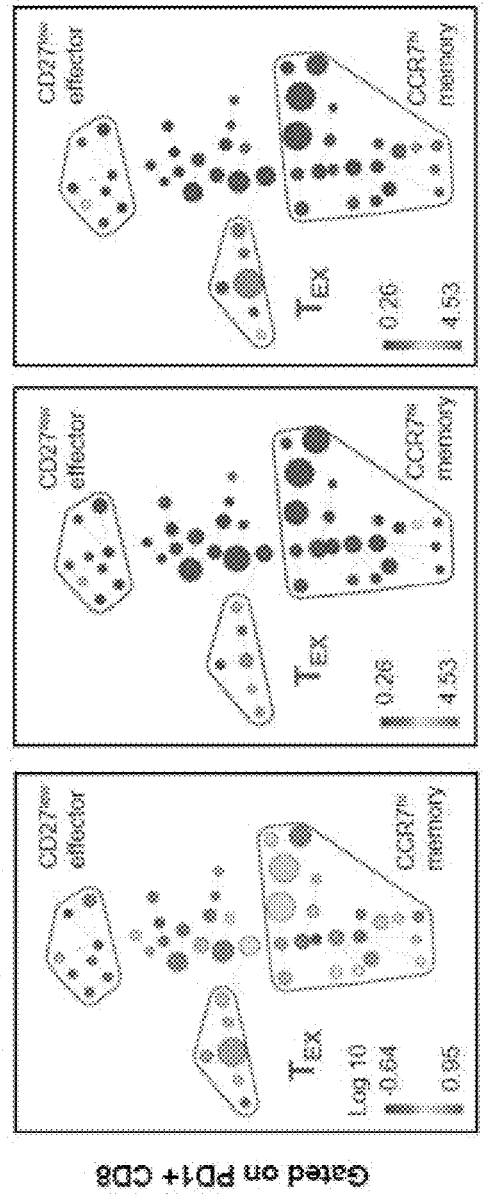
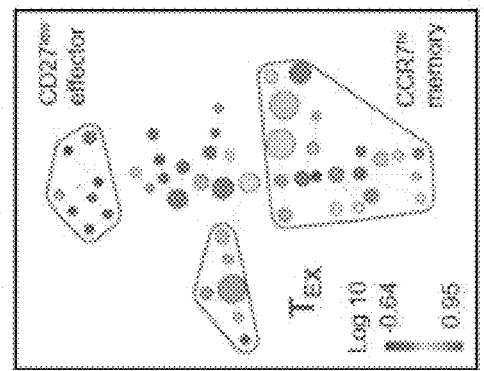
Fig. 30B

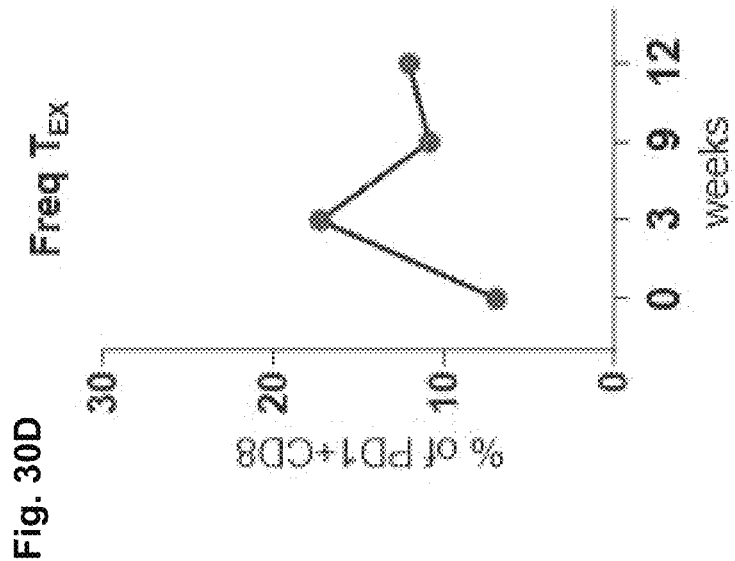
Fig. 30D
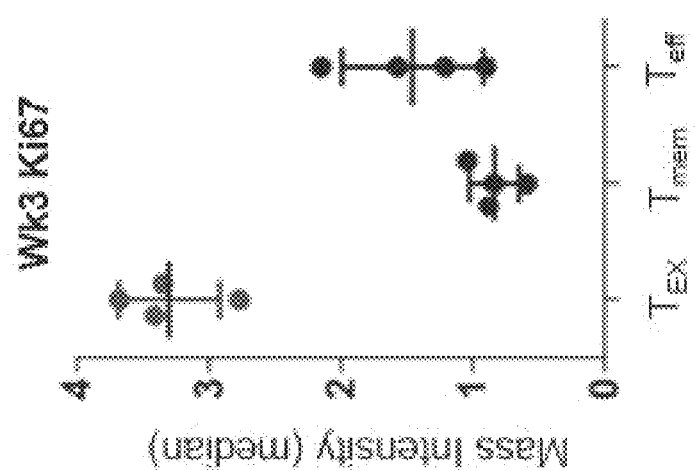
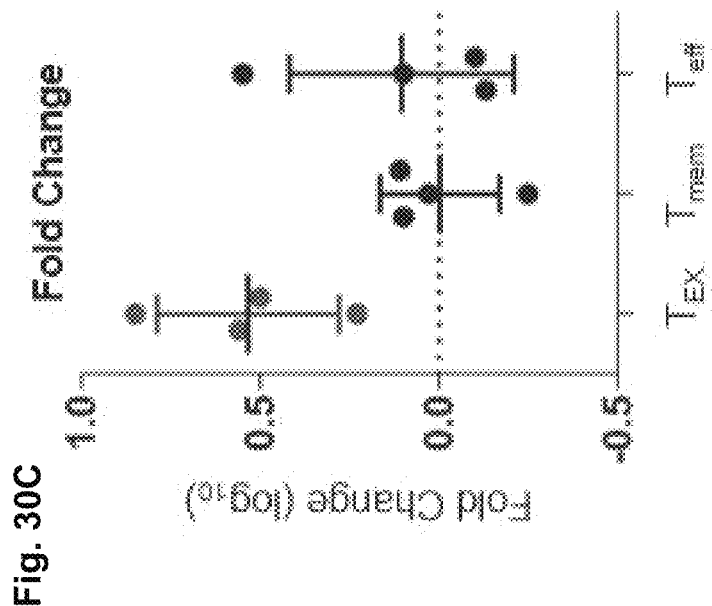
Fig. 30C

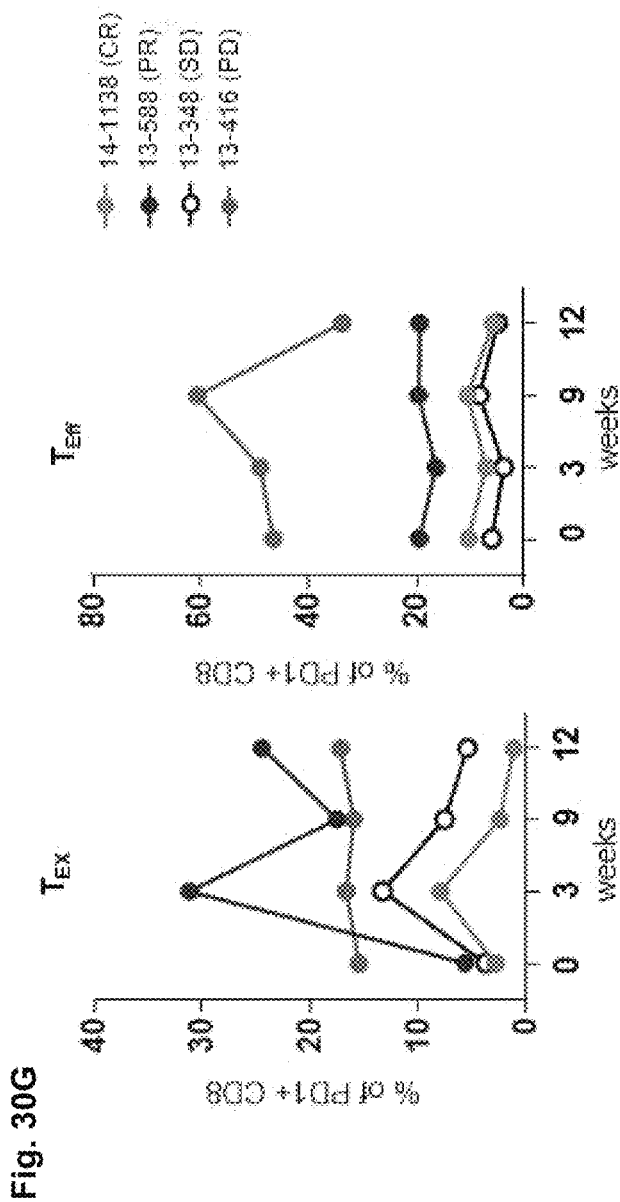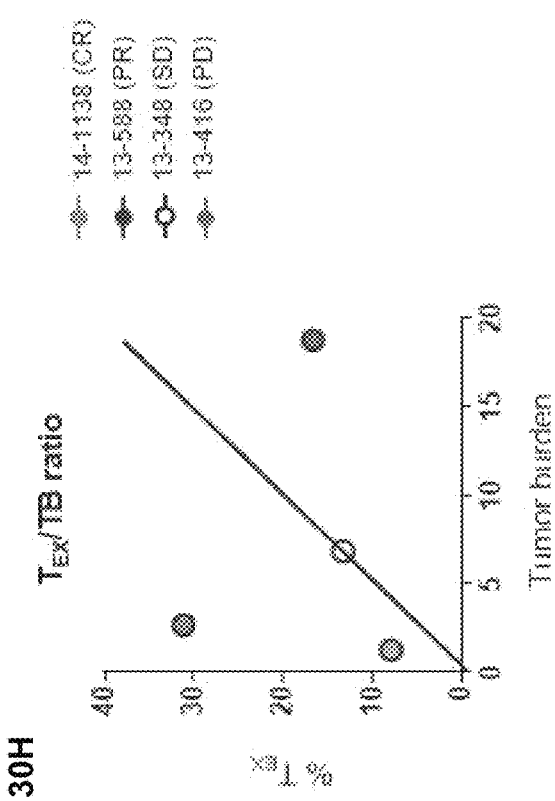

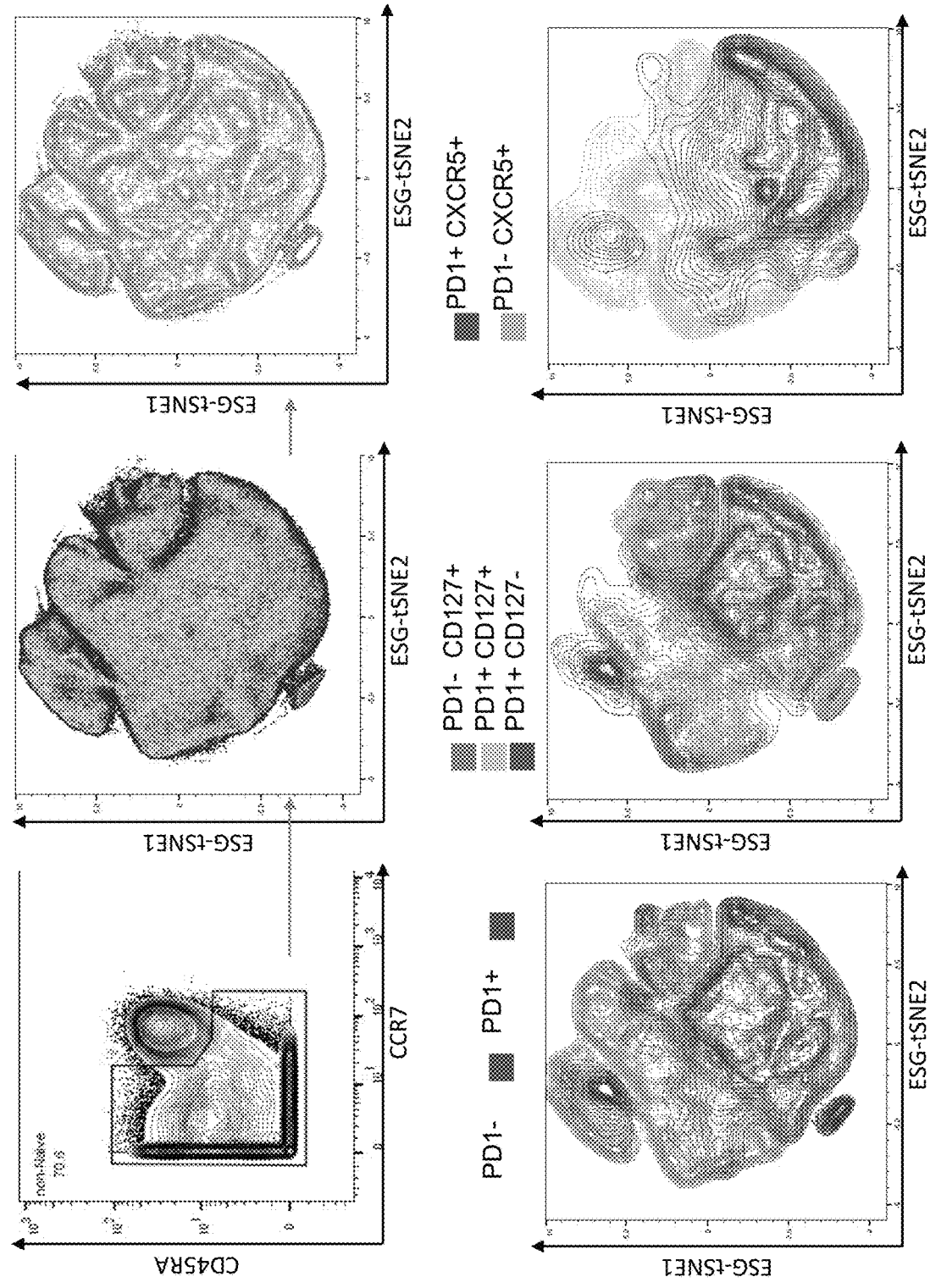

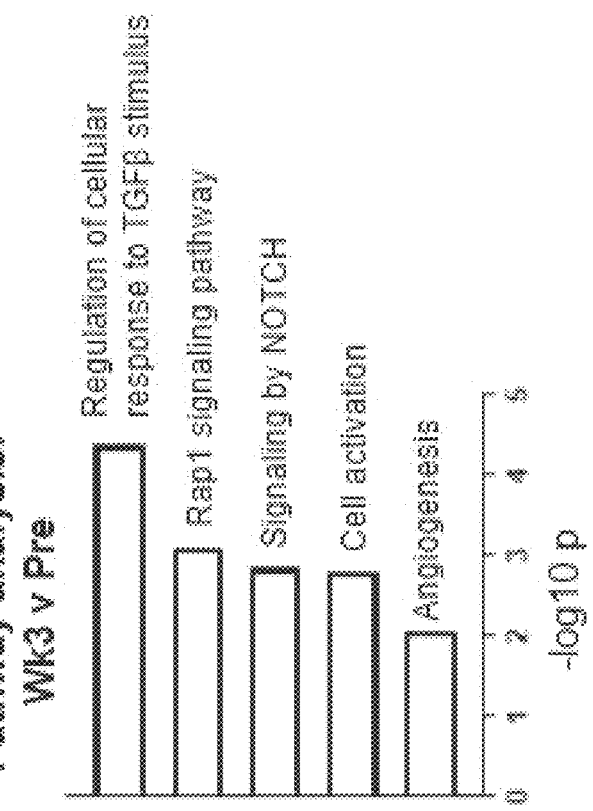
Fig. 31A
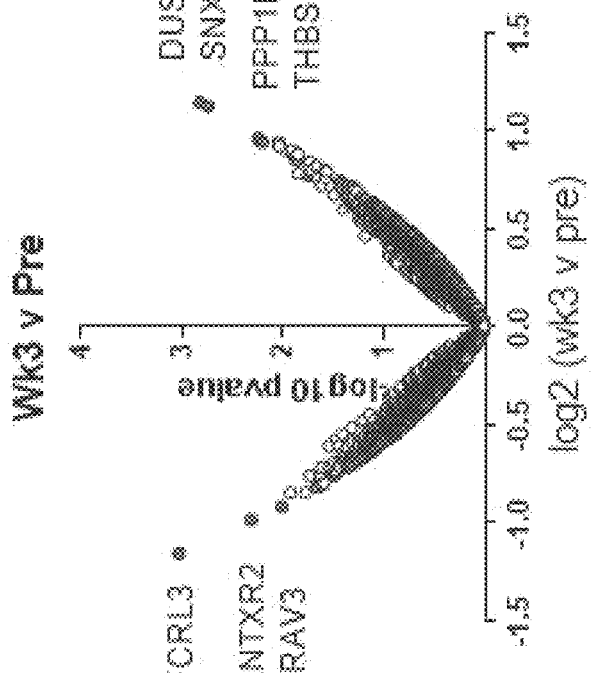
Fig. 31B Pathway analysis: Wk3 v Pre

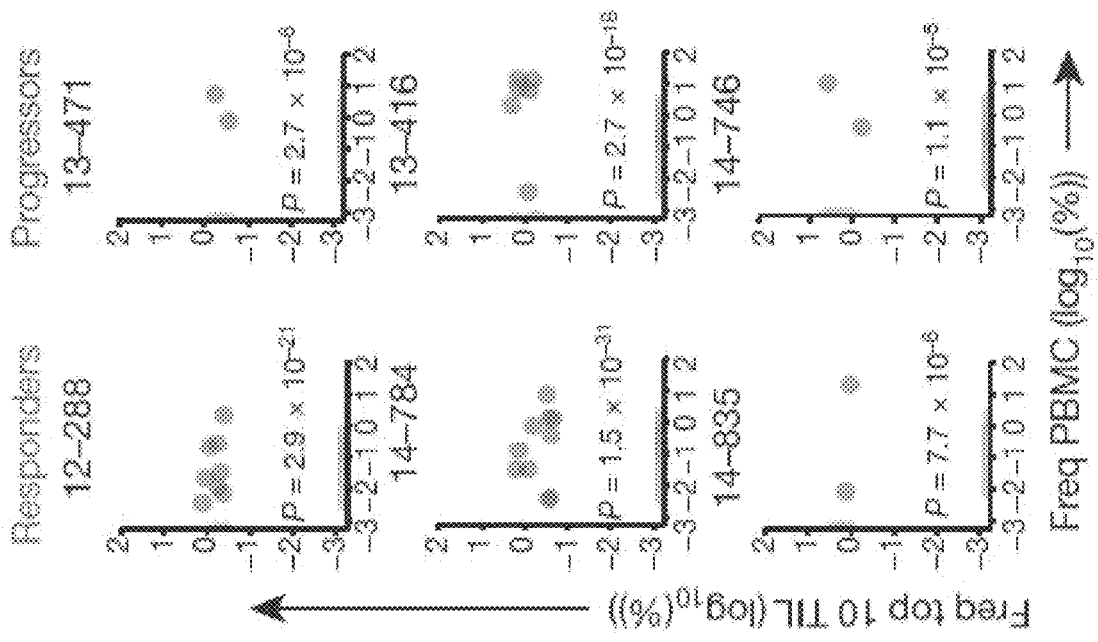
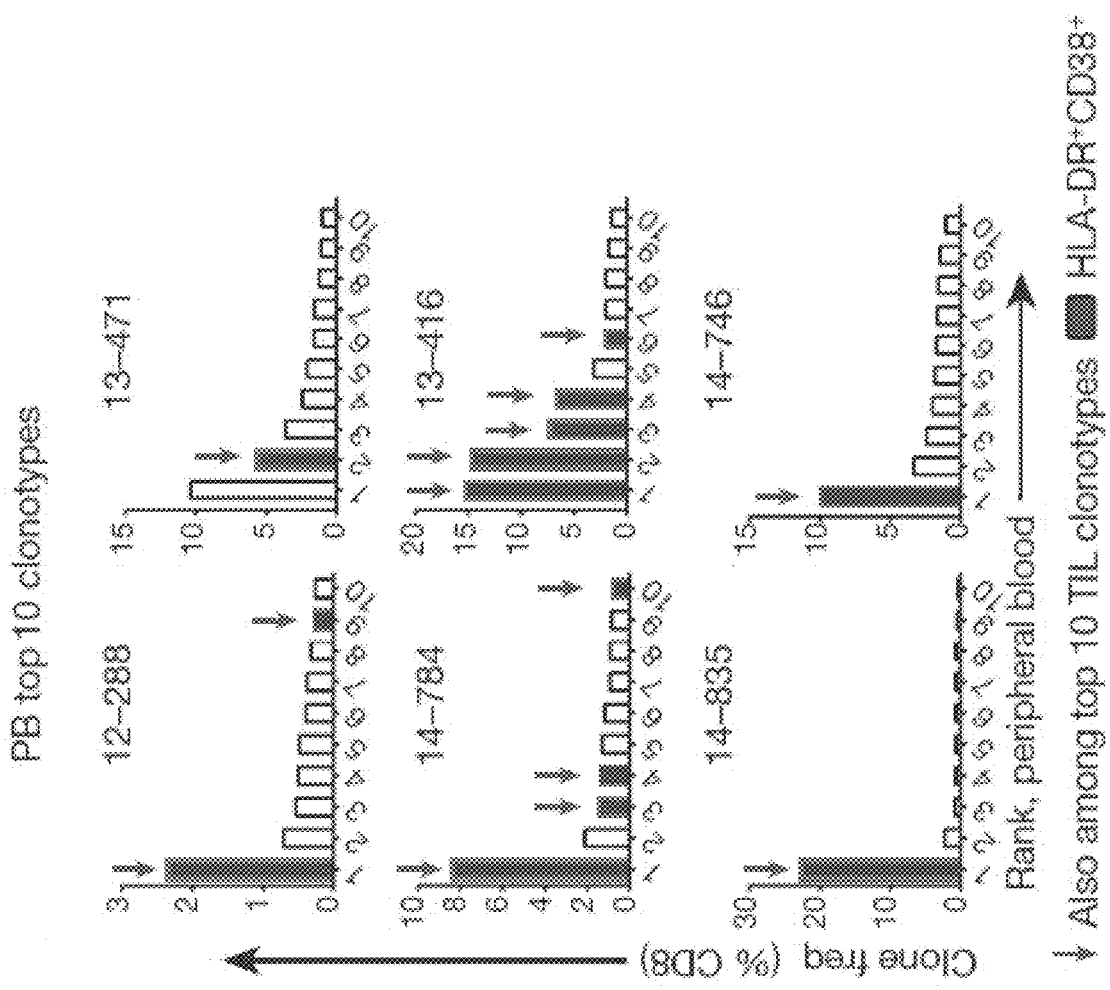
Fig. 32B
Fig. 32A

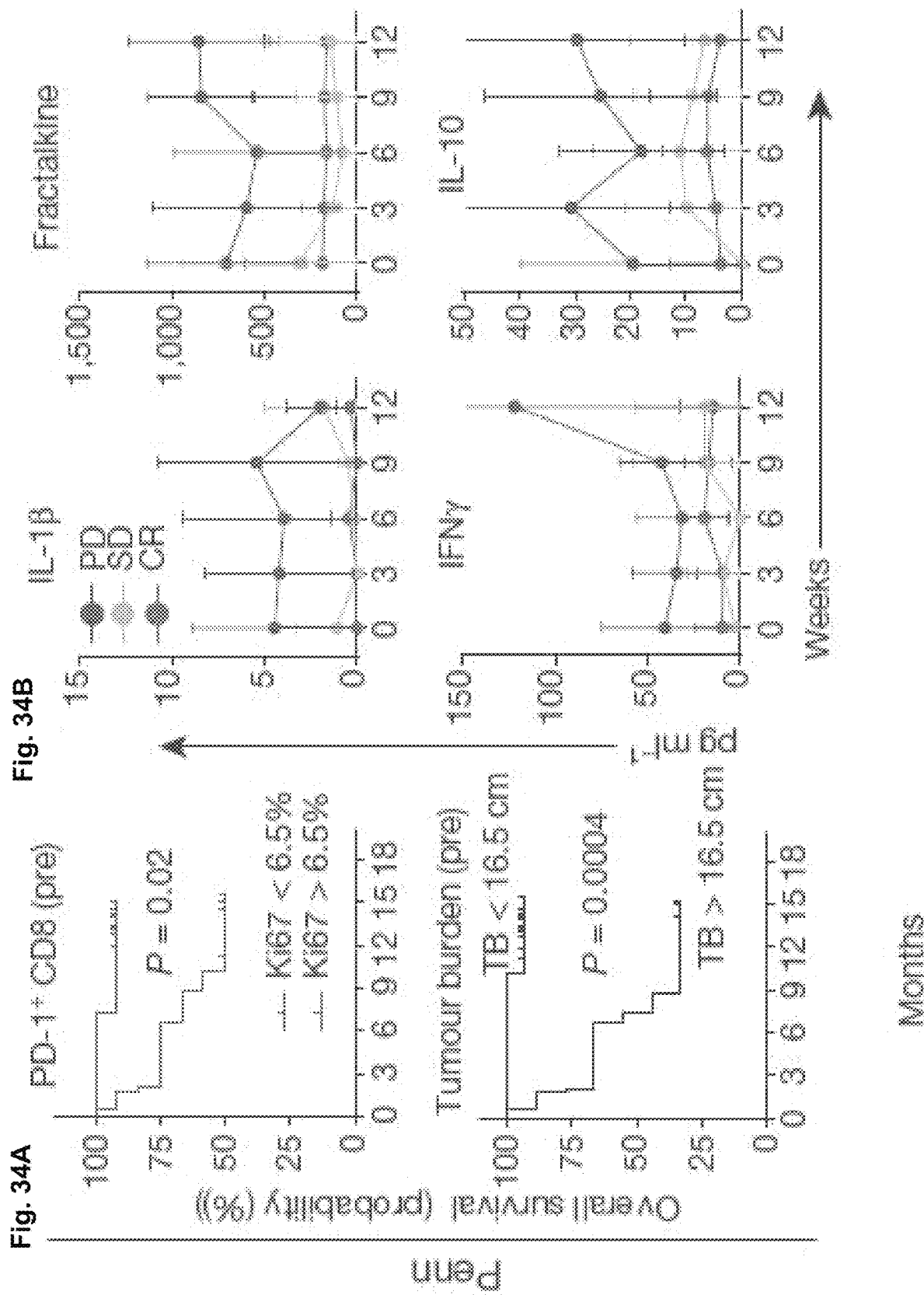

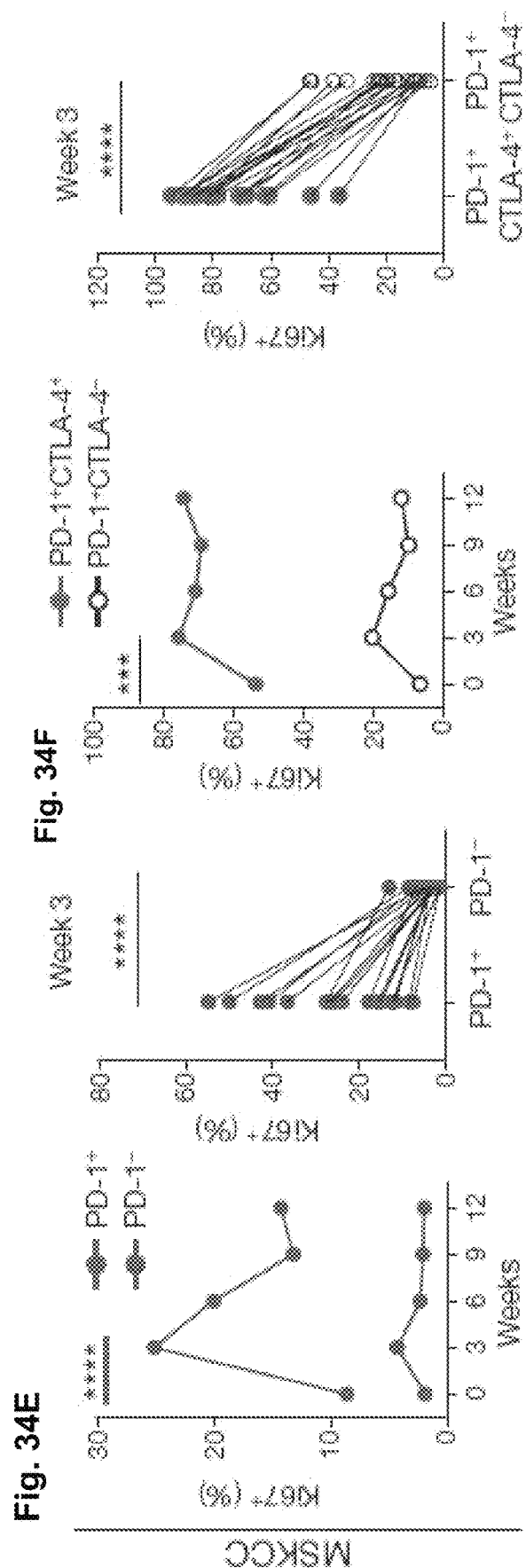

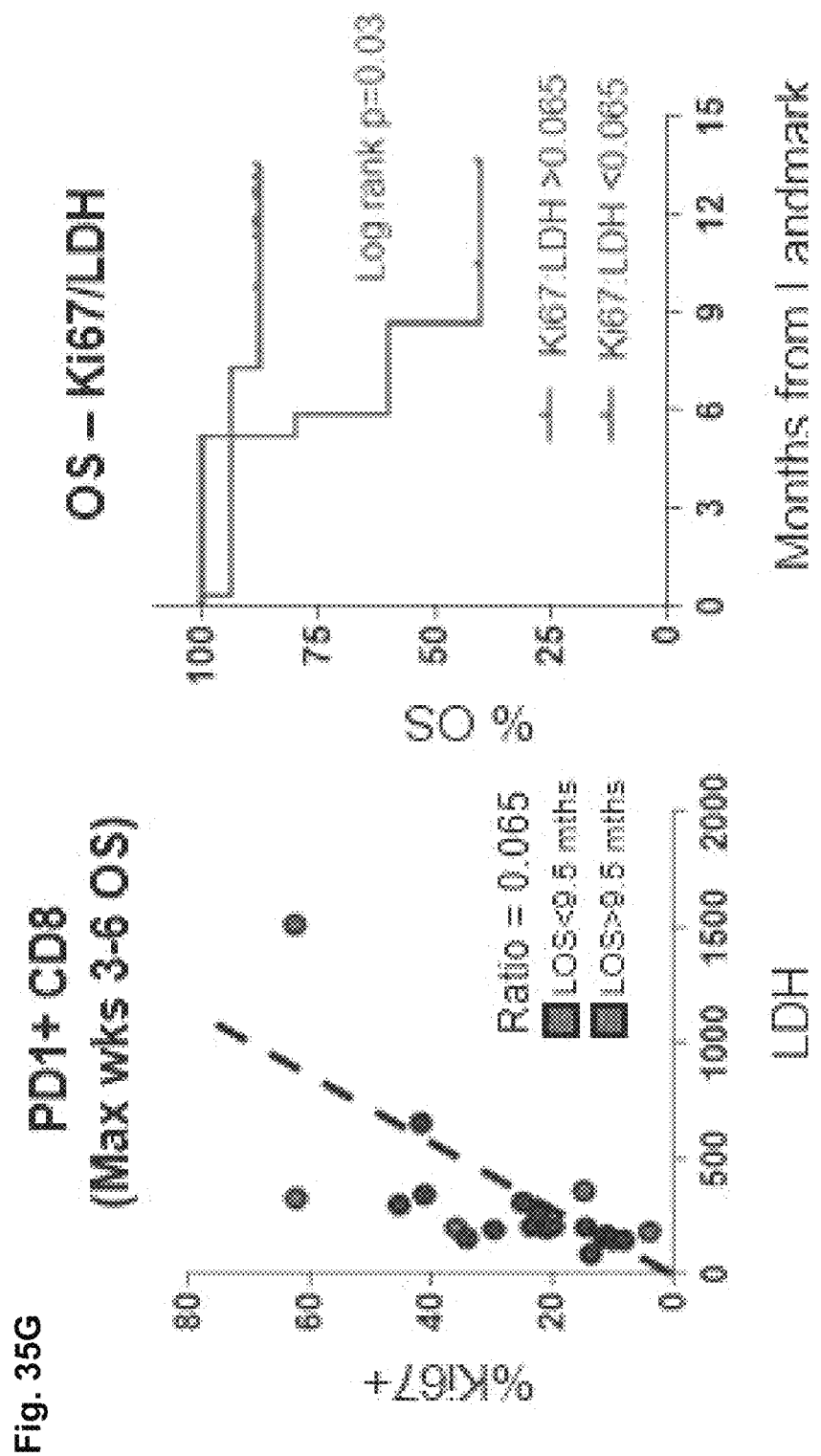

FIG. 48A
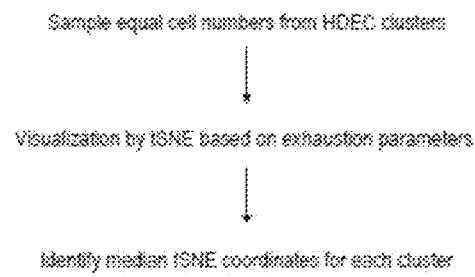
FIG. 48B  Sampled HDEC clusters arranged by tSNE
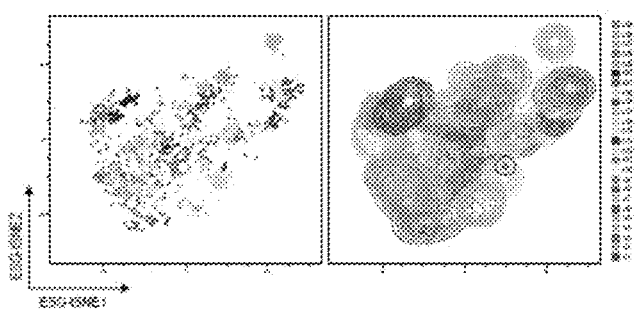
FIG. 48C  median cluster tSNE coordinates
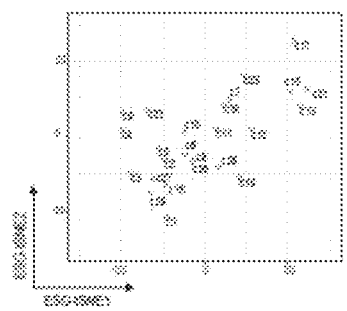

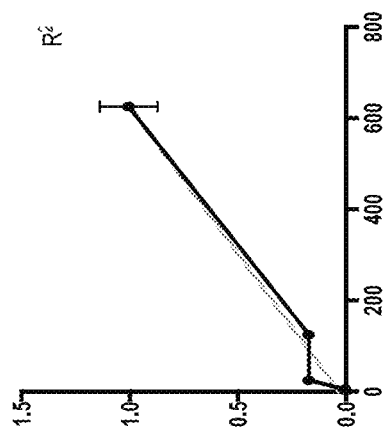
Fig. 51 ASSAY PERFORMANCE: PCR READOUT SCALES LINEARLY

Fig. 55B
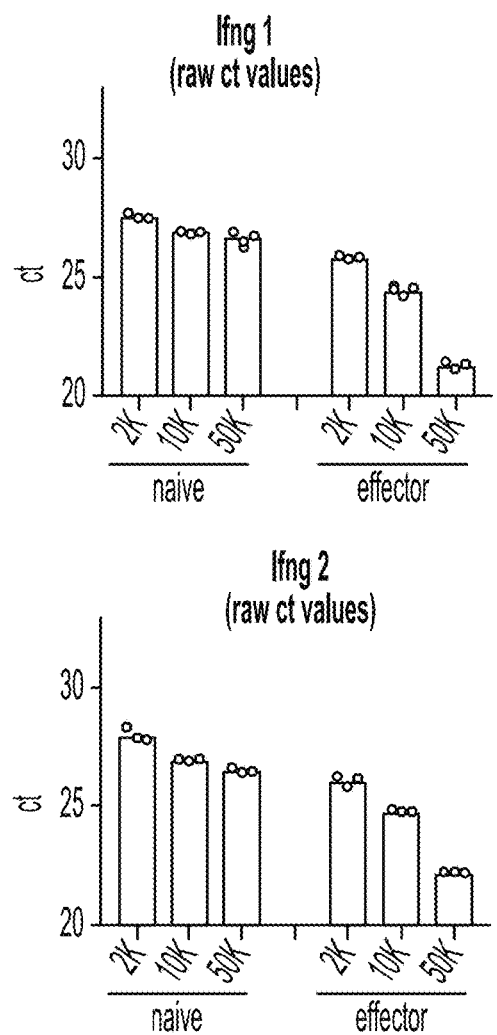
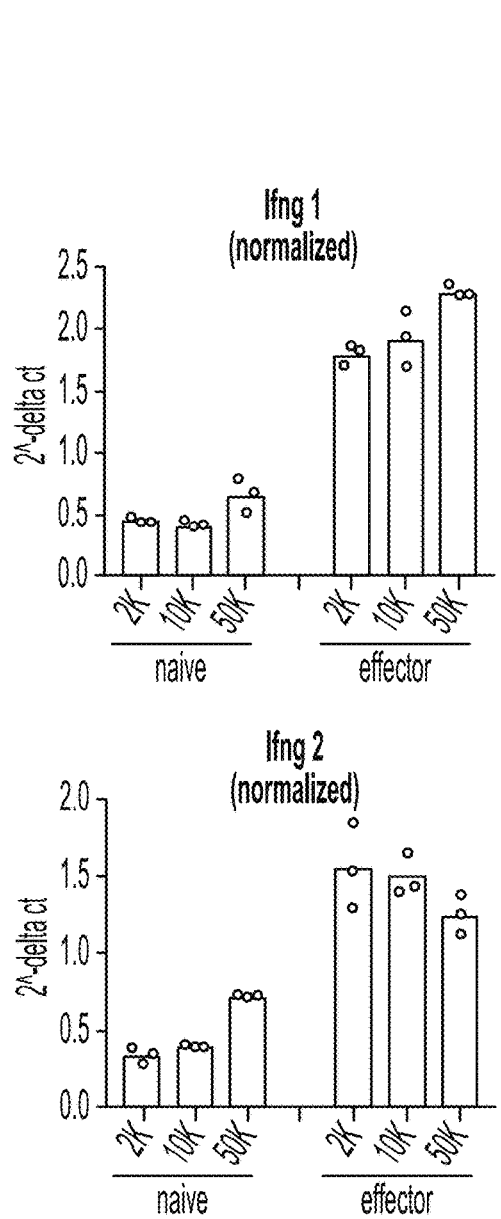
To FIG. 55B-1

METHODS AND COMPOSITIONS FOR TREATING DISEASES ASSOCIATED WITH EXHAUSTED T CELLS

CROSS-REFERENCE TO RELATED APPLICATIONS

The present application is a 35 U.S.C. § 371 national phase application from, and claims priority to, International Application No. PCT/US2018/057850, filed Oct. 26, 2018, and published under PCT Article 21(2) in English, which claims priority to U.S. Provisional Application No. 62/578,193, filed Oct. 27, 2017, U.S. Provisional Application No. 62/578,212, filed Oct. 27, 2017, U.S. Provisional Application No. 62/660,754, filed Apr. 20, 2018, and U.S. Provisional Application No. 62/661,467, filed Apr. 23, 2018, all of which applications are incorporated herein by reference in their entireties.

STATEMENT REGARDING FEDERALLY SPONSORED RESEARCH OR DEVELOPMENT

This invention was made with government support under Grant Nos. AI105343 and AI082630 awarded by the National Institutes of Health (NIH). The government has certain rights in the invention.

BACKGROUND

T cell exhaustion, which is an acquired state of T cell dysfunction, is a hallmark of cancer and chronic viral infection (Wherry et al. (2007) *Immunity* 27:670-684; Zajac et al. (1998) *J. Exp. Med.* 188:2205-2213). Recently, treatments to reverse T cell exhaustion in cancer have proven strikingly effective (Barber et al. (2006) *Nature* 439:682-687; Topalian et al. (2012) *New Engl. J. Med.* 366:2443-2454). Chimeric antigen receptor (CAR)-T cell therapy has also proven highly effective for hematologic malignancies (Porter et al. (2011) *New Engl. J. Med.* 365:725-733), but the development of exhaustion in engineered T cells to treat solid tumors remains a significant barrier to its broader use (Long et al. (2015) *Nat. Med.* 21:581-590). Identifying mechanisms that regulate T cell exhaustion could improve the efficacy of immune checkpoint blockade and adoptive T cell therapy for cancer immunotherapy (Barber et al. (2006) *Nature* 439:682-687; Topalian et al. (2012) *New Engl. J. Med.* 366:2443-2454; Porter et al. (2011) *New Engl. J. Med.* 365:725-733).

Current strategies for modulating T cell exhaustion rely on directly modulating expression of effector gene expression products, such as immune checkpoints, and such modulation produces undesired side effects since physiological levels of such effector gene expression products are often required for normal T cell function. In addition, such strategies are vulnerable to drug resistance and can lead to immunopathology. Accordingly, there is a great need in the art to identify compositions and methods useful for modulating expression of effector gene expression products in T cells or in cells that affect T cells that preserves physiologically relevant levels of such gene expression products.

Exhausted CD8 T cells ($T_{EX}$) often develop during chronic infections and cancer and prevent optimal control of disease. These cells have functional defects, co-express multiple inhibitory receptors (IRs) and develop an altered transcriptional, epigenetic, metabolic and differentiation program (Wherry, E. J., and Kurachi, M. (2015) *Nat Rev Immunol* 15:486-499). Novel immunotherapies target IRs expressed by $T_{EX}$ such as PD-1 or CTLA-4 and are having dramatic effects in cancer patients with potential applications in other settings (Callahan, M. K. et al. (2016) *Immunity* 44:1069-1078; Sharma P., and Allison, J. P. (2015) *Science* 348:56-61). Although $T_{EX}$ have been implicated in the response to checkpoint blockade in animal models, the underlying immunological mechanisms of therapeutic response or failure following IR targeting in humans remains poorly understood. $T_{EX}$ also play a prominent role in human chronic viral infections.

There remains a need for identifying and tracking T cells that are associated with a disease. There also remains a need for methods of treating and monitoring disease progression that utilize methods of identifying and tracking T cells and collections of T cells in a subject.

BRIEF SUMMARY

Provided is a method of identifying exhausted T cell ($T_{EX}$) populations characteristic of a disease state in a subject having a disease, the method comprising the steps of:
  (a) obtaining a sample comprising T cells from the subject;
  (b) measuring the expression of a panel of markers comprising one or more T cell lineage-specific markers or combinations of T cell lineage-specific markers and one or more T cell exhaustion-specific ($T_{EX}$) markers or combinations of $T_{EX}$-specific markers in the T cells from the subject having a disease;
  (c) comparing expression of the panel of markers to expression of the same panel of markers in a control sample comprising T cells; and
  (d) identifying one or more $T_{EX}$ populations characteristic of the disease, wherein a $T_{EX}$ population characteristic of the disease comprises a greater number of $T_{EX}$ cells in which expression of one or more markers in the panel of markers in the T cells from the subject having a disease is up-regulated or down-regulated compared to the number of $T_{EX}$ cells expressing the same one or more markers in the panel of markers in a control sample comprising T cells.

In some embodiments, the one or more T cell lineage-specific markers or combinations of T cell lineage-specific markers and the one or more $T_{EX}$-specific markers or combinations of markers is selected from the group consisting of CD45RA$^+$, PD-1$^-$/CD127$^-$, Tim-3$^{MMI}$, LAG-3$^{MMI}$, TCF1$^{MMI}$, CCR7$^+$, CD45RA$^+$/CD27$^+$, CD73$^+$, CD27$^+$, CD28$^+$, CD26$^+$, CD7$^{MMI}$, CD127$^+$, PD-1$^-$/CD127$^+$, Helios$^+$, CD16$^+$, Perforin$^+$, CD57$^+$, Granzyme B$^+$ (GzmB$^+$), T-bet$^+$, Granzyme K$^+$ (GzmK$^+$), PD-1$^+$/CXCR5$^+$, CXCR5$^+$, CD160$^+$, TIGIT$^+$, Eomesodermin$^+$ (Eomes$^+$), 2B4$^+$, KLRG1$^+$, Granzyme M$^+$ (GzmM$^+$), PD-1$^+$/2B4$^+$/CD160$^+$, PD-1$^+$/2B4$^+$, PD-1$^+$/Eomes$^+$, CD45RO$^+$, PD-1$^+$, PD-1$^+$/CD127$^-$, PD-1$^+$/CD127$^+$, CD200R$^{MMI}$, CD103$^+$, CTLA-4$^+$, PD-1$^+$/CTLA-4$^+$, CD38$^+$/CD39$^+$, Ki67$^+$, PD-1$^+$/CD39$^+$, HLA-DR$^{MMI}$, CD38$^+$, TOX$^{MMI}$, CD39$^+$, CD36$^+$, and Ptger2$^{MMI}$, wherein expression of the markers or combinations of markers is assessed by manual gating using (+) to indicate increased expression and (−) to indicate decreased expression, or by median metal intensity (MMI).

In some embodiments, the T cell lineage-specific markers or combinations of T cell lineage-specific markers and/or the one or more $T_{EX}$-specific markers or combinations of markers are those listed in Table 4. In some embodiments, the exhaustion-specific genes or sets of exhaustion-specific genes are those listed in FIG. 41C.

In some embodiments, the one or more T cell lineage-specific markers or combinations of T cell lineage-specific markers is selected from the group consisting of CD27$^+$, CD45RA$^+$, CCR7$^+$, and CD103$^+$, and wherein the one or more T$_{EX}$-specific markers or combinations of T$_{EX}$-specific markers is selected from the group consisting of CTLA-4$^+$, CD7$^+$, CD73$^-$, CD127$^-$, CD39$^+$, GzmK$^+$, XCL1$^+$, Helios$^+$, PD-1$^+$, CCR7$^-$, IL-21$^+$, TCF1$^-$, CXCL10$^+$, Eomes$^+$, Amphiregulin$^+$ (Areg$^+$), CD38$^+$, TOX$^+$, TIGIT$^+$, CXCR5$^+$, 2B4$^+$, IL-10$^+$, LAG-3$^+$, and Ptger2$^+$, wherein expression of the markers or combinations of markers is assessed by manual gating using (+) to indicate increased expression and (−) to indicate decreased expression.

In some embodiments, the panel of markers comprising one or more T cell lineage-specific markers or combinations of T cell lineage-specific markers and one or more T$_{EX}$-specific markers or combinations of T$_{EX}$-specific markers comprises a set of markers selected from the group consisting of:
(a) PD-1$^+$/CD39$^+$, CD38$^+$/CD39$^+$, GzmK$^+$, TIGIT$^+$, TCF1$^+$, 2B4$^+$, CD160$^+$, CD7, Helios, CD103, Ptger2$^+$, CTLA-4$^+$, Tim-3$^+$, LAG-3$^+$;
(b) PD-1$^+$, CD160$^+$, TIGIT$^+$, 2B4$^+$, CXCR5$^+$, GzmK$^+$, CD27$^+$, TCF1+;
(c) CD38$^+$/CD39$^+$, CD16$^+$, CXCR5$^+$, Helios$^+$, PD-1$^+$/CD39$^+$, CTLA-4$^-$, 2B4$^-$, TIGIT$^-$, CD160$^-$, CD7$^+$, Ptger2$^+$;
(d) PD-1$^+$/Eomes$^+$, 2B4$^+$/CD160$^+$/TIGIT$^+$, GzmB$^+$, CD16$^+$, Perforin$^+$, CD57$^+$, CD38$^+$/CD39$^-$, T-bet$^+$, GzmK$^-$;
(e) PD-1$^+$/Eomes$^+$, 2B4$^+$/CD160$^+$/TIGIT$^+$, GzmB$^+$, Tox+, GzmK$^+$;
(f) PD-1$^+$, PD-1$^+$/CD39$^+$, CD39$^+$, Ki67$^+$, CD38$^+$/CD39$^+$, CTLA-4$^+$, CD103$^+$, CD200R$^+$, Tim-3$^+$, Lag-3$^+$, CD28$^+$;
(g) PD-1$^+$/Eomes$^+$, 2B4$^+$/CD160$^+$/TIGIT$^+$, GzmB$^+$, Tox$^+$, CD38$^+$, GzmK$^+$, Ki67$^+$, HLA-DR$^+$, CXCR5$^+$, PD-1$^+$/CD39$^+$;
(h) PD-1$^+$/Eomes$^+$, 2B4$^+$/CD160$^+$/TIGIT$^+$, GzmB$^+$, Tox$^+$, GzmK$^-$;
(i) PD-1$^+$/Eomes$^+$, 2B4$^+$/CD160$^+$/TIGIT$^+$, GzmB$^+$, Helios$^+$, CD16$^+$, Perforin$^+$, CD57$^+$, PD-1$^{++}$, Ki67;
(j) TIGIT$^+$, Eomes$^+$, GzmB$^-$, CD160$^+$, 2B4$^+$, T-bet$^+$, Toxin$^{int}$; and
(k) TIGIT$^+$, Eomes$^+$, GzmB$^+$, CD160$^+$, 2B4$^+$, T-bet$^+$, Tox$^+$, CD16$^+$, CD57$^+$, Perforin$^+$;
wherein expression of the markers or combinations of markers is assessed by manual gating using (+), (++), or (+++) to indicate increased expression, (int) to indicate intermediate expression, and (−) to indicate decreased expression.

Also provided is a method of identifying T cell populations characteristic of a disease state in a subject having a disease, the method comprising the steps of:
(a) obtaining a sample comprising T cells from the subject;
(b) measuring the expression of a panel of markers comprising one or more T cell lineage-specific markers or combinations of T cell lineage-specific markers and one or more T$_{EX}$-specific markers or combinations of T$_{EX}$-specific markers in the T cells from the subject having a disease;
(c) comparing expression of the panel of markers to expression of the same panel of markers in a control sample comprising T cells; and
(d) identifying one or more T cell populations characteristic of the disease, wherein a T cell population characteristic of the disease comprises a greater number of T cells in which expression of one or more markers in the panel in the T cells from the subject having a disease is up-regulated or down-regulated compared to the number of T cells expressing the same one or more markers in a control sample comprising T cells.

In some embodiments, the panel comprises at least three markers or combinations of markers selected from the group consisting of 2B4, CCR7, CD103, CD127, CD16, CD160, CD200R, CD26, CD27, CD28, CD36, CD38, CD45RA, CD57, CD7, CD73, CTLA-4, CXCR5, Eomes, GzmB, GzmK, GzmM, Helios, HLA-DR, Ki67, KLRG1, LAG-3, PD-1, Perforin, PTGER2, T-bet, TCF-1, TIGIT, TIM-3, TOX, 2B4/CD160/TIGIT, CD160/TIGIT, CD38/39, CD45RA/CD27, PD-1/CD127, PD-1/CD39, and PD-1/Eomes.

In some embodiments, the panel of markers comprises a set of markers selected from the group consisting of:
(a) PD-1$^+$/CD39$^+$, CD38$^+$/CD39$^+$, GzmK$^+$, TIGIT$^+$, TCF1$^+$, 2B4$^+$, CD160$^+$, CD7, Helios, CD103, Ptger2$^+$, CTLA-4$^+$, Tim-3$^+$, LAG-3$^+$;
(b) PD-1$^+$, CD160$^+$, TIGIT$^+$, 2B4$^+$, CXCR5$^+$, GzmK$^+$, CD27$^+$, TCF1+;
(c) CD38$^+$/CD39$^+$, CD16$^+$, CXCR5$^+$, Helios$^+$, PD-1$^+$/CD39$^+$, CTLA-4$^-$, 2B4$^-$, TIGIT$^-$, CD160$^-$, CD7$^+$, Ptger2$^+$;
(d) PD-1$^+$/Eomes$^+$, 2B4$^+$/CD160$^+$/TIGIT$^+$, GzmB$^+$, CD16$^+$, Perforin$^+$, CD57$^+$, CD38$^+$/CD39$^-$, T-bet$^+$, GzmK$^-$;
(e) PD-1$^+$/Eomes$^+$, 2B4$^+$/CD160$^+$/TIGIT$^+$, GzmB$^+$, Tox+, GzmK$^+$;
(f) PD-1$^+$, PD-1$^+$/CD39$^+$, CD39$^+$, Ki67$^+$, CD38$^+$/CD39$^+$, CTLA-4$^+$, CD103$^+$, CD200R$^+$, Tim-3$^+$, Lag-3$^+$, CD28$^+$;
(g) PD-1$^+$/Eomes$^+$, 2B4$^+$/CD160$^+$/TIGIT$^+$, GzmB$^+$, Tox$^+$, CD38$^+$, GzmK$^+$, Ki67$^-$, HLA-DR$^+$, CXCR5$^+$, PD-1$^+$/CD39$^+$;
(h) PD-1$^+$/Eomes$^+$, 2B4$^+$/CD160$^+$/TIGIT$^+$, GzmB$^+$, Tox$^+$, GzmK$^-$;
(i) PD-1$^+$/Eomes$^+$, 2B4$^+$/CD160$^+$/TIGIT$^+$, GzmB$^+$, Helios$^+$, CD16$^+$, Perforin$^+$, CD57$^+$, PD-1$^{++}$, Ki67;
(j) TIGIT$^+$, Eomes$^+$, GzmB$^-$, CD160$^+$, 2B4$^+$, T-bet$^+$, Tox$^{int}$; and
(k) TIGIT$^+$, Eomes$^+$, GzmB$^+$, CD160$^+$, 2B4$^+$, T-bet$^+$, Tox$^+$, CD16$^+$, CD57$^+$, Perforin$^+$;
wherein expression of the markers or combinations of markers is assessed by manual gating using (+), (++), or (+++) to indicate increased expression, (int) to indicate intermediate expression, and (−) to indicate decreased expression.

Also provided is a method of monitoring disease progression in a subject having a disease, the method comprising the steps of:
(a) obtaining a sample comprising T cells from the subject;
(b) measuring the expression of a panel of markers comprising one or more T cell lineage-specific markers or combinations of T cell lineage-specific markers and one or more T cell exhaustion-specific (T$_{EX}$) markers or combinations of T$_{EX}$-specific markers in the T cells from the subject having a disease;
(c) comparing expression of the panel of markers to expression of the same panel of markers in a control sample comprising T cells;
(d) identifying one or more T$_{EX}$ populations characteristic of the disease, wherein a T$_{EX}$ population characteristic of the disease comprises a greater number of T$_{EX}$ cells in which expression of one or more markers in the panel of markers in the T cells from the subject having a disease is up-regulated or down-regulated compared to the number of $T_{EX}$ cells expressing the same one or more markers in the panel of markers in a control sample comprising T cells;

(e) repeating method steps (a), (b), (c), and (d) at one or more subsequent time points;

(f) determining the disease has progressed if a second or subsequent sample comprising T cells from the subject comprises a greater number of cells in the $T_{EX}$ population characteristic of the disease than the first or prior sample comprising T cells from the subject; or (g) determining the disease has not progressed if a second or subsequent sample comprising T cells from the subject comprises a lesser number of cells in the $T_{EX}$ population characteristic of the disease than the first or prior sample comprising T cells from the subject.

In some embodiments, the panel of markers comprises at least one set of T cell lineage-specific markers or combinations of T cell lineage-specific markers and $T_{EX}$-specific markers or combinations of $T_{EX}$-specific markers characteristic of one or more disease-associated populations of $T_{EX}$ cells (DATs) selected from the group consisting of:

(a) PD-1$^+$/CD39$^+$, CD38$^+$/CD39$^+$, GzmK$^+$, TIGIT$^+$, TCF1$^+$, 2B4$^+$, CD160$^+$, CD7$^+$, Helios$^+$, CD103$^+$, Ptger2$^+$, CTLA-4$^-$, Tim-3$^+$, and LAG-3$^+$;

(b) PD-1$^+$/Eomes$^+$, 2B4$^+$/CD160$^+$/TIGIT$^+$, GzmB$^+$, CD16$^+$, Perforin$^+$, CD57$^+$, CD38$^+$/CD39$^-$, T-bet$^+$, and GzmK$^-$;

(c) PD-1$^+$/Eomes$^+$, 2B4$^+$/CD160$^+$/TIGIT$^+$, GzmB$^+$, Helios$^+$, CD16$^+$, Perforin$^+$, CD57$^+$, PD-1$^{++}$, Ki67;

(d) PD-1$^+$/Eomes$^+$, 2B4$^+$/CD160$^+$/TIGIT$^+$, GzmB$^+$, Tox$^+$, CD38$^+$, GzmK$^+$, Ki67$^+$, HLA-DR$^+$, CXCR5$^+$, and PD-1$^+$/CD39$^+$; and wherein the panel of markers further comprises at least one set of T cell lineage-specific markers or combinations of T cell lineage-specific markers and $T_{EX}$-specific markers or combinations of $T_{EX}$-specific markers characteristic of one or more health-associated populations of $T_{EX}$ cells (HATs) selected from the group consisting of:

(e) TIGIT$^+$, Eomes$^+$, GzmB$^+$, CD160$^+$, 2B4$^+$, T-bet$^+$, Tox$^+$, CD16$^+$, CD57$^+$, Perforin$^+$;

(f) PD-1$^+$, CD160$^+$, TIGIT$^+$, 2B4$^+$, CXCR5$^+$, GzmK$^+$, CD27$^+$, TCF1$^-$; and PD-1$^+$/Eomes$^+$, 2B4$^+$/CD160$^-$/TIGIT$^+$, GzmB$^+$, Tox$^+$, GzmK$^+$.

In some embodiments, the method further comprises a step of calculating the ratio of DATs to HATs. In some embodiments, the disease has progressed if the ratio of CATs to HATs is increased in a second or subsequent sample comprising T cells from the subject, and the disease has not progressed if the ratio of DATs to HATs is decreased in a second or subsequent sample comprising T cells from the subject.

Also provided is a method of determining the exhaustion state of a subject's T cells, the method comprising the steps of:

(a) obtaining a sample comprising T cells from the subject;

(b) stimulating or activating the T cells;

(c) measuring production of one or more cytokines and one or more chemokines selected from the group consisting of IFNγ, TNFα, IL-2, IL-10, IL-21, CCL3, CCL4, XCL1, and Amphiregulin by the T cells;

(d) calculating a Functional Exhaustion Score (FES) as follows:

FES=[(2×(% IFN$^+$TNF$^-$)−(% IFN$^-$TNF$^+$)−(% IL-2$^+$))×(% CCL3/4$^+$)], wherein "% IFN$^+$TNF$^-$" refers to the percentage of T cells that produce IFNγ but not TNFα, wherein "% IFN$^-$TNF$^+$" refers to the percentage of T cells that produce TNFα but not IFNγ, wherein "% IL-2$^+$" refers to the percentage of T cells that produce IL-2, and wherein "% CCL3/4$^+$" refers to the percentage of cells that produce CCL3 and/or CCL4; and (e) determining the exhaustion state of the subject's T cells, wherein an FES>0 indicates that the subject's T cells are exhausted, and wherein a higher FES indicates an increasing degree of exhaustion in the subject's T cells.

Also provided is a method of monitoring disease progression in a subject having a disease, the method comprising the steps of:

(a) obtaining a sample comprising T cells from the subject;

(b) determining the exhaustion state of the subject's T cells by the method described above;

(c) repeating method steps (a) and (b) at one or more subsequent time points;

(d) determining the disease has progressed if a second or subsequent sample comprising T cells from the subject comprises an increased FES compared to the first or prior sample comprising T cells from the subject; or (e) determining the disease has not progressed if a second or subsequent sample comprising T cells from the subject comprises a decreased FES compared to the first or prior sample comprising T cells from the subject.

In any one of the preceding embodiments, the sample comprising T cells from the subject may comprise blood, ascites, pleural effusion, lymph, mucus, broncho-alveolar lavage or tissue. In some embodiments, the sample comprising T cells from the subject comprises CD8+ T cells, tumor-associated lymphocytes (TALs), or tumor-infiltrating lymphocytes (TILs).

Also provided is a method for identifying an epigenetic footprint characteristic of exhausted T cells, comprising the steps of: (a) obtaining a sample comprising exhausted T cells ($T_{EX}$) and a control sample comprising invigorated (i.e., normal, non-exhausted) T cells; (b) identifying open chromatin regions (OCRs) in both samples; and (c) comparing the OCRs identified in the $T_{EX}$ to the OCRs identified in the invigorated T cells; wherein the epigenetic footprint characteristic of $T_{EX}$ comprises one or more OCRs present in $T_{EX}$ and not present in the control T cells.

Also provided is a method for detecting exhausted T cells in a patient, wherein the method comprises detecting an OCR footprint, wherein the OCR footprint is correlated with exhausted T cells.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A illustrates representative flow cytometry plots gated on CD8+ cells (top) or histograms gated on $D^bGP276$ tetramer+ cells (bottom) on PBMCs isolated from mice before (day 15 p.i.) or after (day 34 p.i.) treatment with control or anti-PD-L1 antibody. FIG. 1B illustrates quantification of FIG. 1A showing frequency of $D^bGP276$ tetramer+ cells of CD8+ cells (top) and Ki-67+ of $D^bGP276$ tetramer+ cells (bottom) in PBMC. FIG. 1C illustrates viral load (plaque forming units/ml) in the serum pre- (day 12) and post- (day 38) treatment from mice shown in FIG. 1B. Lines connecting dots in FIG. 1B and FIG. 1C indicate data from the same mouse pre- and post-treatment. Asterisks indicating significance determined by paired t tests between groups are $p<0.01$ and *$p<0.001$. Data are representative of at least three independent experiments with at least 5 mice per group. FIG. 1D illustrates a row normalized heat map showing top genes significantly differentially expressed based on fold change in microarray data. Selected genes are indicated. Full list of genes with fold changes and p values available in Pauken et al. Table S1 (Pauken et al. Science 2016, 354(6316):1160-1165). FIG. 1E illustrates a Circos plot showing overlap in metagenes identified in control- versus anti-PD-L1 treated $T_{EX}$ compared to metagenes in $T_{EX}$ versus $T_N$. Transcriptional data for $T_{EX}$ versus $T_N$ was obtained from Doering et al. (Doering et al. Immunity 2012, 37:1130-1144). FIG. 1F illustrates P value and FDR q values for metagenes comparing $T_{EFF}$, $T_{MEM}$, or $T_{EX}$ to $T_N$ from Doering et al. (Doering et al. Immunity 2012, 37:1130-1144), and anti-PD-L1-treated $T_{EX}$ to control-treated $T_{EX}$ from FIGS. 2A-2J of the instant application. Details of metagene gene membership and overlaps can be found in Pauken et al. Table S4 (Pauken et al. Science 2016, 354 (6316):1160-1165).

FIGS. 2A-2J are a series of images depicting an effector-like transcriptional program in $T_{EX}$ cells induced by anti-PD-L1 that is not sustained after cessation of treatment. FIG. 2A illustrates consensus hierarchical clustering by 1-Pearson correlation from the microarray on control- or anti-PD-L1-treated $T_{EX}$. FIG. 2B illustrates Gene Set Enrichment Analysis (GSEA) of representative Gene Ontology (GO) terms. FIG. 2C illustrates GSEA of effector genes. FIG. 2D illustrates row normalized heat map of effector-associated genes. FIG. 2E illustrates Circos plots showing overlap in metagenes identified in anti-PD-L1-treated $T_{EX}$ compared to metagenes in $T_{EFF}$ (left) and $T_{MEM}$ cells (right). Ribbons connecting areas of the Circos plots indicate shared genes between groups. The microarray includes four independent experiments with 10-12 mice per group per experiment. FIG. 2F illustrates frequency of P14 cells among CD8 T cells and FIG. 2G illustrates Ki67+ P14 cells in the peripheral blood. Grey bar indicates antibody treatment period. FIG. 2H illustrates quantification of IFNγ+ TNFα+P14 cells. FIG. 2I illustrates viral load in the kidney. Data in FIGS. 2F-2G are one representative experiment. In FIGS. 2H-2I, the +1 day time point is combined from two representative experiments and the +20 week time point is from one representative experiment. Data in FIGS. 2F-2I are representative of at least two independent experiments with at least 4 mice per group per experiment. FIG. 2J illustrates principle component analysis of RNA-seq, % of variance (var.) indicated. The RNA-seq was performed on two to four independent experiments with 5-13 mice per group as indicated in the Methods. Each dot represents an independent experiment. Asterisks indicating significance determined by unpaired t tests between groups are * $p<0.05$, $p<0.01$, and *$p<0.001$.

FIGS. 3A-3E are a series of images depicting re-exhaustion of virus-specific CD8 T cells after cessation of anti-PD-L1 treatment. FIG. 3A illustrates representative flow cytometry plots gated on CD8+ T cells showing P14s (Ly5.1+ cells) in the spleen one day or 20 weeks after cessation of anti-PD-L1 treatment. FIG. 3B illustrates quantification of P14 frequency (left) and number (right) in the spleen from mice shown in FIG. 3A. FIG. 3C illustrates flow cytometry histograms of Ki-67 (left) and granzyme B (right) in the spleen. FIG. 3D illustrates quantification of FIG. 3C. FIG. 3E illustrates representative flow cytometry plots gated on P14 cells following ex vivo stimulation with gp33-41 peptide, showing IFNγ and TNFα production quantified in FIG. 2I. The mice depicted in FIG. 3A-FIG. 3E correspond to the mice depicted in FIGS. 2H and 2I. The +1 day time point is combined from two representative experiments and the +20 week time point is from one representative experiment. Data are representative of at least two independent experiments with at least 4 mice per group per experiment. Asterisks indicating significance determined by unpaired t tests between groups are * $p<0.05$, $p<0.01$, and *$p<0.001$.

FIGS. 4A-4C are a series of images depicting inhibitory receptor expression following anti-PD-L1 treatment. FIG. 4A illustrates co-expression of inhibitory receptors on P14 cells in the spleen 2 days (left) or 20 weeks (right) after cessation of treatment. Representative histograms (top) and quantification of geometric mean flouresence intensities (MFIs) from multiple mice (bottom) showing PD-1, Lag-3, Tim-3, and 2B4 in, as depicted in FIG. 4B, two days or, as depicted in FIG. 4C, 20 weeks after anti-PD-L1 treatment during clone 13 infection. Arm immune mice were day 30+ p.i. Gated on P14 cells. Data are representative of two independent experiments with at least three mice per Arm immune group and at least five mice per clone 13 group. Statistical significance was determined using non-parametric one-way ANOVA. Asterisk indicating significance between groups is * $p<0.05$, $p<0.01$, and *$p<0.001$. Blue asterisks indicate ANOVA p values, black asterisks indicate post-test p values.

FIGS. 5A-5F are a series of images depicting that re-invigoration of endogenous virus-specific CD8 T cells wanes over time when antigen remains high. Monitoring of endogenous virus-specific CD8 T cell responses at 2 days (in peripheral blood), 7 weeks (spleen), or 18 weeks (spleen) post-anti-PD-L1 treatment. FIG. 5A illustrates representative plots showing $D^bGP276$ tetramer and CD44. FIG. 5B illustrates quantification of the frequency of $D^bGP276$+(top) and $D^bGP33$+ (bottom) of the total CD8+ population. FIG. 5C illustrates representative histograms of PD-1 expression, gated on $D^bGP276$+ cells. FIG. 5D illustrates quantification of geometric MFI of PD-1, gated on $D^bGP276$+ cells (top) or $D^bGP33$+ cells (bottom). FIG. 5E illustrates representative histograms showing Ki-67 expression. FIG. 5F illustrates quantification of the frequency of Ki-67+ $D^bGP276$+ (top) or $D^bGP33$+ (bottom). Data are representative of two independent experiments with at least four mice per group. Asterisks indicating significance determined by unpaired t tests between groups are ***$p<0.001$.

FIGS. 6A-6E are a series of images depicting comparison of transcriptional profiles of control and anti-PD-L1-treated $T_{EX}$ cells generated by microarray or RNA-seq. FIG. 6A illustrates consensus hierarchical clustering of genes from the RNA-seq by variance (by 1-Pearson correlation) between $T_{EX}$ from control or anti-PD-L1-treated mice isolated 1 day after the two week treatment period. FIG. 6B illustrates overlap in genes assessed in microarray and RNA-seq data sets from mice 1 day after treatment. FIG. 6C illustrates comparison of log-fold changes (LFCs) of differentially expressed genes ($p<0.05$) after anti-PD-L1 treatment in the microarray and RNA-seq data sets. A complete list of differentially expressed genes is available in Pauken et al. Table S1 (Pauken et al. Science 2016, 354(6316):1160-1165) for the microarray and Pauken et al. Table S5 (Pauken et al. Science 2016, 354(6316):1160-1165) for the RNA seq. FIG. 6D illustrates GSEAs of representative significantly enriched GO terms. Complete list of GO terms for RNA-seq available in Pauken et al. Table S6 (Pauken et al. Science 2016, 354(6316):1160-1165). FIG. 6E illustrates the top 15 significantly enriched GO terms in anti-PD-L1 treated $T_{EX}$ compared to control $T_{EX}$ in the microarray (left) and RNA-seq (right). Complete list of GO terms available in Pauken et al. Table S2 (Pauken et al. Science 2016, 354(6316):1160-1165) for the microarray and Pauken et al. Table S6 (Pauken et al. Science 2016, 354(6316):1160-1165) for the RNA seq.

FIGS. 7A-7E are a series of images depicting temporal changes in the transcriptional profiles of $T_{EX}$ with or without anti-PD-L1 treatment using RNA-seq. FIG. 7A illustrates consensus hierarchical clustering of genes from the RNA-seq by variance (by 1-Pearson correlation) between $T_{EX}$ from control or anti-PD-L1-treated mice 1 day or 18-29 weeks after cessation of treatment. Clustering of all four groups shown to the left, pairwise comparison of control and anti-PD-L1-treated $T_{EX}$ 18-29 weeks post treatment shown boxed to the right. FIG. 7B illustrates a heat map of class neighbor analysis, showing the top genes differentially expressed in control or anti-PD-L1-treated $T_{EX}$ 1 day or 18-29 weeks after cessation of anti-PD-L1 treatment. The full list of genes is available in Pauken et al. Table S5 (Pauken et al. Science 2016, 354(6316):1160-1165). FIG. 7C depicts a table comparing the number of significantly changed genes in pairwise comparisons between the indicated treatments and time points. The full list of genes is available in Pauken et al. Table S5 (Pauken et al. Science 2016, 354(6316):1160-1165). FIG. 7D illustrates a heat map of RNA-seq showing top differentially expressed genes following anti-PD-L1 treatment one day after treatment, and corresponding expression of those genes 18-29 weeks after treatment. FIG. 7E illustrates the top GO terms associated with control $T_{EX}$ 1 day or 18-29 weeks after treatment. The full list of pairwise comparisons for short-term versus long-term, anti-PD-L1 versus control-treated $T_{EX}$ is available in Pauken et al. Table S6 (Pauken et al. Science 2016, 354 (6316):1160-1165).

FIGS. 8A-8H are a series of images depicting combination treatment with IL-7 i.c. and anti-PD-L1 augments virus-specific CD8 T cell responses in vivo. FIG. 8A illustrates the experimental design for FIGS. 2A and 2B. FIG. 8B illustrates representative flow cytometry histograms gated on P14 cells from spleens isolated at day 39 p.i. following ex vivo stimulation with IL-7 or IL-15 for 30 minutes. Shaded grey histograms are unstimulated controls, colored histograms are stimulated with cytokine. Quantification for multiple mice shown in FIG. 1F. FIG. 8C illustrates schematic for experimental design for combination therapy with anti-PD-L1 and IL-7 i.c. FIG. 8D illustrates representative flow cytometry plots gated on CD8+ T cells showing $D^bGP276+$ cells and P14 cells (Ly5.1+). Numbers next to gates indicate frequency of each population of CD8+ parent population. FIG. 8E illustrates the total number of viable cells in spleens following treatment with control, IL-7 i.c. anti-PD-L1, or both anti-PD-L1 and IL-7 i.c. Since data was normally distributed, significance was determined using a parametric one-way ANOVA and Bonferroni's multiple comparison test to compare groups. FIG. 8F illustrates frequency (left) and number (right) of $D^bGP276+$ CD8 T cells from mice shown in FIG. 8E. FIG. 8G illustrates viral load in the kidney following treatment for the mice in FIG. 8E. For FIG. 8F and FIG. 8G, significance was determined using a non-parametric one-way ANOVA (Kruskal-Wallis test) and Dunn's multiple test comparison to compare groups. For FIG. 8E-FIG. 8G, blue asterisks (top row) indicate ANOVA p values, black asterisks indicate post-test p values. FIG. 8H illustrates viral load in the serum pre- and post-treatment for the mice in FIG. 8E. Lines connect serial measurements from the same mouse. Significance determined using paired Student's t tests for each treatment group. Data from FIG. 8D-FIG. 8H are combined from two independent experiments with at least four mice per group. These data correspond to the mice shown in FIGS. 9G and 9H. Asterisks indicating significance are * $p<0.05$, $p<0.01$, and *$p<0.001$.

FIGS. 9A-9H are a series of images depicting that PD-1 pathway blockade moderately improves antigen-independent persistence and IL-7 signaling in $T_{EX}$. FIG. 9A illustrates the number of $D^bGP33+$ donor CD8 T cells per million PBMCs at day 27 (compared to day 1) post-transfer and FIG. 9B illustrates the number recovered from the spleen. FIG. 9C illustrates histograms of CD127 and CD122 expression on $T_{EX}$ P14 cells (Day 35 post clone 13) compared to $T_{MEM}$ P14 cells or bulk $CD44^{lo}$ $CD62L+T_N$ cells (Day 167 post LCMV Arm). Values indicate average geometric mean fluorescence intensity (MFI) and standard error of the mean (SEM). FIG. 9D illustrates contour plots of PD-1 versus CD127 from mice in FIG. 9C. FIG. 9E illustrates quantification of FIG. 9D. Data in FIG. 9A-FIG. 9E are representative of at least 2 independent experiments with at least 4 mice per group. FIG. 9F illustrates quantification of phospho-STAT5 induction by P14 cells at day 39 p.i. following ex vivo stimulation with IL-7 or IL-15 for 30 min. Values indicate fold change over unstimulated controls. (FIG. 9G) Frequency (of CD8+, left) and number (right) of P14 cells in the spleen after two weeks of treatment. FIG. 9H illustrates plots (left) and quantification (right) of IFNγ+ TNFα+ P14 cells from FIG. 9G following ex vivo peptide stimulation. Data in FIG. 9F-FIG. 9H are combined from 2 independent experiments with at least 4 mice per group. Asterisks indicating significance are * $p<0.05$, $p<0.01$, and *$p<0.001$ determined as described in Supplemental Methods of Pauken et al. (Pauken et al. Science 2016, 354(6316):1160-1165). Blue asterisks indicate ANOVA p values, black asterisks indicate post-test p values.

FIGS. 10A-10J are a series of images depicting that PD-1 pathway blockade fails to restore memory-like recall capacity or reprogram the epigenetic landscape of $T_{EX}$ into $T_{EFF}$ or $T_{MEM}$ cells. FIG. 10A-FIG. 10D depict the experimental design outlined in FIG. 8A that was used here except that recipient mice were rechallenged with Listeria-GP33 3.5 weeks post-transfer. FIG. 10A illustrates flow cytometry plots of responding $T_{MEM}$, $T_{EX}$ or anti-PD-L1 treated $T_{EX}$ at 6 days post rechallenge with Listeria-GP33. FIG. 10B illustrates concatenated flow cytometry plots gated on P14 cells from mice in FIG. 10A following ex vivo peptide stimulation. FIG. 10C illustrates quantification of donor (Ly5.2+) $D^bGP33+$ CD8 T cells in the spleens shown in FIG. 10A. FIG. 10D illustrates quantification of IFNγ+P14 cells shown in FIG. 10B. FIG. 10E illustrates histograms of PD-1 on donor $D^bGP33+$ cells from mice shown in FIG. 9B. Values indicate average geometric MFI and SEM. Data are representative of 2 independent experiments with at least 4 mice per group. Asterisks indicating significance are * $p<0.05$, $p<0.01$, and *$p<0.001$ determined as described in Supplemental Methods of Pauken et al. (Pauken et al.

Science 2016, 354(6316):1160-1165). Blue asterisks indicate ANOVA p values, black asterisks indicate post-test p values. FIG. 10F illustrates Venn diagrams of ATAC-seq open chromatin regions (OCRs) compared to $T_N$ cells (LFC≥2). Data from the two replicates are combined. FIG. 10G illustrates representative ATAC-seq tracks from one independent replicate per group shown at the Ifng and Pcdc1 loci. FIG. 10H illustrates co-cluster analysis of variance showing enrichment of OCRs in ATAC-seq data set. Solid lines separate cell types, replicates shown side-by-side. FIG. 10I illustrates box and whisker plots showing ATAC-seq enrichment from FIG. 10H. Whiskers represent the interquartile range. FIG. 10J illustrates principle component analysis of all OCRs. For FIG. 10I and FIG. 10J, each replicate is shown. ATAC seq data are from two independent experiments with 2-15 mice per group as described elsewhere herein.

FIGS. 11A-11B are a series of images depicting quality control analyses for ATAC-seq data. FIG. 11A depicts a table showing total paired reads, number aligned, % aligned, and number of peaks called for each biological replicate generated for ATAC-seq. FIG. 11B illustrates correlation of normalized ATAC-seq peak enrichment between replicate 1 and replicate 2 for each cell type. R2 indicates the degree of correlation between replicates.

FIG. 12A illustrates pie charts showing the distribution of ATAC-seq peaks in intergenic, intron, exon, and promoter/TSS regions by cell type. FIG. 12B illustrates pie charts comparing differential (LFC≥2 up (red) or down (blue)) or constant or non-differential (grey) regions of $T_{EFF}$, $T_{MEM}$, $T_{EX}$, or anti-PD-L1 $T_{EX}$ relative to $T_N$. FIG. 12C illustrates distribution of non-differential and differential ATAC-seq peaks compared to $T_N$ cells (LFC≥2 up or down). Data shown are on merged replicates for each cell type.

FIGS. 13A-13E are a series of images depicting that increased transcription for genes near regions of open chromatin correspond in each cell type. GSEA of gene sets corresponding to OCRs identified in ATAC-seq analysis, as illustrated in FIG. 13A, enriched in $T_{EFF}$ or $T_{MEM}$ compared to $T_N$ (LFC≥2), or, as illustrated in FIG. 13B, enriched in $T_N$ compared to $T_{EFF}$ or $T_{MEM}$ (LFC≥2) that were within 20 kb of transcription start sites (TSS). Data comparing transcription of the gene sets in FIG. 13A and FIG. 13B were obtained from Doering et al. (Doering et al. Immunity 2012, 37:1130-1144). FIGS. 13C and 13D illustrate GSEA of gene sets corresponding to peaks identified in ATAC-seq analysis enriched in (FIG. 13C) control- or anti-PD-L1-treated $T_{EX}$ compared to $T_N$ (LFC≥2) or (FIG. 13D) enriched in $T_N$ compared to control or anti-PD-L1-treated $T_{EX}$ (LFC≥2) that were within 20 kb of TSS. The RNA-seq data was used to compare transcription of the gene sets in FIG. 13C and FIG. 13D. FIG. 13E illustrates ATAC-seq and RNA-seq tracks showing the Cd200r2 locus in $T_N$, control $T_{EX}$, and anti-PD-L1-treated $T_{EX}$. Tracks from one representative replicate are displayed.

FIGS. 15A-15G are a series of images depicting co-cluster peak enrichment. FIG. 15A illustrates ATAC-seq enrichment of open chromatin regions (log 2) of $T_N$-enriched, $T_{EFF}$-enriched, and $T_{MEM}$-enriched groups from the co-cluster analysis shown in FIG. 10H, corresponding with FIG. 10I. Data for each replicate are shown separately. FIG. 15B-FIG. 15G illustrate representative tracks of loci enriched in $T_N$, $T_{EFF}$, or $T_{MEM}$. Red boxes indicate differential peaks between the designated group and the subsequent groups. Tracks from one representative replicate are displayed.

FIGS. 16A-16I are a series of images depicting representative ATAC-seq tracks. FIG. 16A illustrates representative tracks of different loci, enriched in control $T_{EX}$ or anti-PD-L1-treated $T_{EX}$ as indicated. Red boxes indicate differential peaks between the designated groups. In FIG. 16B, black boxes indicate shared peaks gained in $T_{EFF}$, $T_{MEM}$ and $T_{EX}$ compared to $T_N$, blue boxes indicate peaks lost in $T_{EX}$ compared to $T_{EFF}$ and $T_{MEM}$. In FIG. 16C, black boxes indicate peaks in the B and C regions of the Pdcd1 locus (Oestreich et al. J. Immunol. 2008, 181:4832-4839), and red box indicates a previously unidentified OCR. FIG. 16B and FIG. 16C are depicted in FIG. 10G, but here also include anti-PD-L1-treated $T_{EX}$. Tracks from one representative replicate are displayed. FIG. 16D shows Tbx21 (T-bet). FIG. 16E shows Cxcr5. FIG. 16F shows Il10. FIG. 16G shows Nlrc3. FIG. 16H shows Cd200r. FIG. 16I shows Atp8b4.

FIGS. 17A-17G are a series of images depicting that epigenetic and transcriptional profiles for control- and anti-PD-L1 treated $T_{EX}$ are enriched for features of the Eomes$^{hi}$ PD-1$^{hi}$ $T_{EX}$ subset. FIG. 17A illustrates representative flow cytometry plots gated on P14 cells showing T-bet and Eomes expression. Numbers indicate frequency of each population of the parent P14 population. FIG. 17B illustrates quantification of the frequency of T-bet$^{hi}$ and Eomes$^{hi}$ subsets shown in (FIG. 17A) following anti-PD-L1 treatment. FIG. 17C illustrates quantification of the geometric MFI of T-bet and Eomes in the mice shown in FIG. 17B. Data are representative of three independent experiments with at least four mice per group. Asterisks indicating significance determined by unpaired t tests between groups are *$p<0.05$, $p<0.01$, and *$p<0.001$. FIG. 17D illustrates GSEA comparing the genes enriched in $T_{EX}$ compared to $T_N$ or anti-PD-L1 versus $T_N$ (LFC≥2, $p<0.05$, top 200) to the transcriptional profiles of PD-line (T-bet$^{hi}$) or PD-1$^{hi}$ (Eomes$^{hi}$) cells. FIG. 17E illustrates GSEA comparing the genes near open chromatin regions enriched in $T_{EX}$ compared to $T_N$ or anti-PD-L1 versus $T_N$ (LFC≥4, $p<0.05$) to the transcriptional profiles of PD-1int or PD-1$^{hi}$ cells. GSEA (left) comparing the genes enriched in (FIG. 17F) $T_{EX}$ compared to anti-PD-L1 or (FIG. 17G) anti-PD-L1 compared to $T_{EX}$ (LFC≥2, $p<0.05$) to the transcriptional profiles of PD-1'n' (T-bet$^{hi}$) or PD-1$^{hi}$ (Eomes$^{hi}$) cells. Heat maps of individual genes shown to the right. Transcriptional profiles for PD-1$^{int}$ and PD-1$^{hi}$ cells obtained from Doering et al. (Doering et al. Immunity 2012, 37:1130-1144).

FIGS. 18A-18E are a series of images depicting co-cluster GO terms. FIG. 18A-FIG. 18E illustrate selected significantly enriched ($p<0.05$) GO terms associated with peaks from each cell type. Shown are terms that were associated with only one cell type identified using REVIGO (see materials & methods under Experimental Examples). A complete list of GO terms for each cell type can be found in Pauken et al. Table S8 (Pauken et al. Science 2016, 354 (6316):1160-1165). GO terms were identified on merged replicates.

FIGS. 19A-19F are a series of images depicting that differential transcription factor binding following PD-1 pathway blockade contributes to an altered transcriptional network during $T_{EX}$ re-invigoration. FIG. 19A illustrates enrichment of transcription factor (TF) binding motifs in OCRs lost or gained following anti-PD-L1 treatment. FIG.

19B illustrates Wellington bootstrap analysis of TF binding in pairwise comparisons for each cell type, the top 10 TFs (in boxes) enriched in all OCRs is shown. Full list in Pauken et al. Table S10 (Pauken et al. Science 2016, 354(6316):1160-1165). FIG. 19C illustrates TF footprint for NFATc1 in $T_{EX}$ and NFκB-p65 in anti-PD-L1-treated $T_{EX}$. FIG. 19D illustrates integrated network analysis of the transcriptional and epigenetic changes following anti-PD-L1. Lines connect TFs predicted to have altered activity to corresponding genes regulated. Details in Pauken et al. Table S11 (Pauken et al. Science 2016, 354(6316):1160-1165). FIG. 19E illustrates LFC of genes significantly changed by anti-PD-L1 treatment compared to genes significantly induced by the "partnerless" NFAT construct CA-RIT-NFAT1 (Martinez, et al. Immunity 2015, 42:265-278). FIG. 19F illustrates Venn diagram showing genes near OCRs containing given TF motifs in $T_{EFF}$, $T_{EX}$, or both (overlap) (top left). Percent difference in TF target genes changed (p<0.05, LFC≥0.3) with anti-PD-L1 in overlap compared to $T_{EX}$ only (bottom left). Sum of the absolute value of the LFC in expression in TF target genes following anti-PD-L1 (right). ATAC-seq data shown is combined replicates for each condition.

FIGS. 23A-23B are a series of images depicting clinical characteristics, response data, and immune data for cohorts analyzed. FIG. 23A illustrates samples obtained from the Penn pembro Expanded Access Program (left) and MSKCC Keynote-001 trial (right) that were included in analysis. FIG. 23B illustrates immune and clinical data from analyzed patients in Penn cohort stratified by fold change in Ki67 greater or less than 2.2 (blue, responder; red, non-responder).

FIGS. 24A-24F are a series of images depicting that CD8 T cells responding to anti-PD-1 therapy display an exhausted phenotype. FIG. 24A illustrates CR, clinical responder (response, complete response+partial response). NR, non-responder (stable disease+progressive disease). FIG. 24B illustrates Ki67 expression in CD8 T cells at indicated times (n=29). FIG. 24C illustrates expression of the indicated markers in Ki67+ (green) and Ki67− (blue) CD8 T cells at 3 weeks (n=27). FIG. 24D illustrates Ki67 expression in PD-1+ (red) and PD-1− (blue) CD8 T cells at 3 weeks (n=27). FIG. 24E illustrates Ki67 expression in PD-1+ (red) and PD-1− (blue) CD8 T cells at indicated times (n=29). FIG. 24F illustrates fold change of Ki67 expression at peak of immunologic response versus pretreatment. Dotted line denotes fold change of 2.21, which is the mean plus 3 s.d. in healthy donors (see FIG. 24D). *P<0.05, *P<0.001, **P<0.0001, Wilcoxon matched-pairs test. Error bars, s.d. Flow cytometry data in all panels are representative of 1-4 independent technical replicates of the stain indicated.

FIGS. 25A-25F are a series of images depicting that CD4+FOXP3−, CD4+FOXP3+ and CD8 T cells from patients with melanoma have increased Ki67 expression compared to healthy donors. FIG. 25A illustrates frequency and Ki67 expression in FOXP3+CD4 T cells in healthy donors and melanoma patients. Student's t-test. FIG. 25B illustrates Ki67 expression in CD8 T cells between healthy donors and melanoma patients. Mann-Whitney U-test. FIG. 25C illustrates Ki67 expression in PD-1+ and PD-1− CD8 T cells in healthy donors and patients with melanoma. Healthy donors versus patients, Mann-Whitney U-test; PD-1+ versus PD-1− CD8 T cells in patients with melanoma, Wilcoxon matched-pairs test. FIG. 25D illustrates Ki67 expression in FOXP3− CD4 T cells and FOXP3+ CD4 cells over time. Wilcoxon matched-pairs test. (FIG. 25E) Scatter plot of Ki67 expression in PD1+CD4+FOXP3− T cells versus tumor burden by PFS. FIG. 25F illustrates Ki67 expression in PD1+CD4+FOXP3+ cells versus tumor burden by PFS (pretreatment, n=29; post-treatment, n=27 (FIGS. 25E-25F)). For all panels, P<0.01, **P<0.0001. Error bars denote s.d. Flow cytometry data in all panels are representative of 1-4 independent technical replicates of the stain indicated.

FIGS. 26A-26D are a series of images depicting PD-1 detected after therapy using antihuman IgG4 and proliferating CD8 T cells in healthy donors. FIG. 26A illustrates healthy donor PBMCs were incubated with anti-PD-1 clone EH12 BV421 and/or pembro—alone, together or sequentially followed by anti-human IgG4− phycoerythrin. FIG. 26B illustrates plots of Eomes, T-bet, CD45RA, and CD27 expression in Ki67+ CD8 T cells from a representative healthy donor. (FIG. 26C) Comparison of Eomes versus T-bet and CD45RA versus CD27 phenotypes in patients with melanoma and healthy donors (melanoma, n=25; healthy donor, n=10). **P<0.01, Student's t-test. FIG. 26D illustrates mean fold change of Ki67 on PD-1+ CD8 T cells over 3 weeks in healthy donors (n=7). Error bars denote s.d.; center line denotes mean; dotted line denotes fold change of 2.21, which is equal to the mean+3 s.d. Flow cytometry data in all panels are representative of 1-2 independent technical replicates of the stain indicated.

FIG. 27A illustrates correlation of the percentage of PD-1+ CD8 T cells expressing Ki67 to months since last dose of anti-CTLA-4 (pretreatment, n=26; week 3, n=25). FIG. 27B illustrates correlation of the percentage of CTLA-4 in CD8 T cells and months since last dose of anti-CTLA-4 (pretreatment, n=26; week 3, n=25). FIG. 27C illustrates correlation of clinical parameters such as PFS, overall survival (OS), tumor burden, and Ki67 to tumor burden ratio with months since last dose of anti-CTLA-4 (pretreatment, n=23; week 3, n=22). r and P values, Pearson's correlations.

FIG. 28A illustrates marker expression in PD-1+CTLA-4+ CD8 T cells at 3 weeks (paired t-test; n=27). (FIG. 28B) Representative plots. FIG. 28C illustrates Ki67 expression in CD8 T cells expressing inhibitory receptors. Bars indicate differences (paired t-test and Wilcoxon matched-pairs test; n=27). FIG. 28D illustrates a heat map which shows effector, memory, and exhausted nodes from SPADE, hierarchically clustered. FIG. 28E illustrates SPADE for median mass intensities (MMI) of granzyme B (left) and perforin (right) at week 3 (n=4). FIG. 28F illustrates MMI of cytolytic markers in $T_{EFF}$, $T_{MEM}$, and $T_{EX}$ cells at 3 weeks (gated on PD-1+ CD8+). FIG. 28G illustrates MMI of cytolytic markers in $T_{EX}$ cells over time. GzmA, GzmB and GzmK indicate granzymes A, B and K, respectively. FIG. 28H illustrates RNA-seq of total CD8 T cells (n=3; see materials & methods under Experimental Examples). Gene set enrichment analysis of top 50 positive correlates of Ki67, and leading edge of positive (top) or negative (bottom) correlates of Ki67 that were enriched in anti-PD-L1-treated versus control $T_{EX}$-cell signatures from ref. 19 (bottom). NES, normalized enrichment score. *P<0.001, **P<0.0001. Error bars, s.d. Flow cytometry data (FIGS. 28A-28C) are representative of 1-4 independent technical replicates of the stain indicated. Mass cytometry data and RNA-seq data shown in FIGS. 28D-28H are representative of one technical replicate.

FIGS. 29A-29G are a series of images depicting that CD8 T cells with multiple inhibitory receptors and PD-1$^+$ CXCR5$^+$ CD8 T cells are reinvigorated by anti-PD-1 therapy. FIG. 29A illustrates Ki67 expression in CD8 T cells with multiple inhibitory receptors over time. Week 0 versus week 3 (n=27). Wilcoxon matched-pairs test. FIG. 29B illustrates the percentage of CD8 T cells positive for PD-1 during pembro treatment (n=27), Wilcoxon matched-pairs test. FIG. 29C illustrates back-gating of TEMRA and naive CD8 T cell populations onto CD45RA versus TCF-1 (right). FIG. 29D illustrates TCF-1 expression in PD-1+CXCR5+ CD8 T cells in blood at week 3 (n=11). Paired t-test. FIG. 29E illustrates Eomes/T-bet (red) and Eomes/TCF-1 (green) expression in PD-1+CXCR5+ (left) and PD-1+CTLA-4+ (right) subsets. FIG. 29F illustrates Ki67 expression in PD-1+CTLA-4+ and PD-1+CXCR5+ CD8 T cells over time (left) and fold change of Ki67 in PD-1+CXCR5+ and PD-1+CTLA-4+ subsets (right) (n=11). Wilcoxon matched-pairs test. FIG. 29G illustrates IFNγ production by PD-1+ CXCR5+ and PD-1+CTLA-4+ subsets over time; paired t-test. For all panels, *P<0.05, P<0.01, *P<0.001, ****P<0.0001. Error bars denote s.d. CXCR5 and TCF-1 stain is representative of one technical replicate. All other flow cytometry data are representative of 1-4 independent technical replicates of the stain indicated.

FIGS. 30A-30I are a series of images depicting that conventional differentiation state and clusters of $T_{EX}$ cells can be identified using CyTOF and high-dimensional visualization. FIGS. 30A-30C depict SPADE analysis applied to blood samples from patients with melanoma and analyzed by CyTOF. FIG. 30A illustrates SPADE tree showing MMI of CD27 (left) and CCR7 (right) (representative of 4 patients). FIG. 30B illustrates SPADE tree colored by median intensities of fold change frequency (left), and Ki67 expression (middle and right) before treatment and at 3 weeks. FIG. 30C illustrates fold change frequency (left) and MMI of Ki67 (right) of $T_{EX}$, $T_{MEM}$, and $T_{EFF}$ subsets. FIG. 30D illustrates frequency of $T_{EX}$ cluster in PD-1+CD8 T cells over time. FIG. 30E illustrates SPADE tree colored by MMI of Eomes (left) and CD39 (right) expression at 3 weeks (n=4). (FIG. 30F) MMI of Eomes (left) and CD39 (right) of $T_{EX}$, $T_{MEM}$, and $T_{EFF}$ subsets. FIG. 30G illustrates percentage of cells in $T_{EX}$ cluster (left) and $T_{EFF}$ cluster (right) in PD-1+ CD8 T cells over time based on CyTOF and SPADE analysis. FIG. 30H illustrates frequency of $T_{EX}$ versus tumor burden colored by response. Mass cytometry data in all panels are representative of one technical replicate. MMI shown in FIG. 30 represents arcsinh transformed data. FIG. 30I illustrates a dimensionality reduction (tSNE) representation of CD8 T cell differentiation in "exhaustion space." In other words, this dimensionality reduction represents that heterogeneity of CD8 T cells that is represented by the combination of traditional T cell lineage markers and epigenomically selected T cell exhaustion markers used in the cytometry panel described herein. On the background of this landscape three traditional ways of identifying population that may contain exhausted CD8 T cells are illustrated by showing where PD-1+, PD-1+CD127+ vs PD-1+ CD127− and PD-1+CXCR5+ CD8 T cells map. What these data illustrate is that even using these definitions, there is considerable heterogeneity in the exhausted T cell populations contained within the PD-1+, PD-1+CD127+, PD-1+ CD127− and PD-1+CXCR5+ subsets. This heterogeneity is further resolved by the additional markers in the epigenomically defined cytometry panel described herein.

FIGS. 31A-31D are a series of images depicting that RNA-seq of CD8 T cells reveals molecular pathways correlating with reinvigoration. FIGS. 31A-31D depict RNA-seq that was performed on total purified CD8 T cells from three patients at weeks 0, 3, 9, 12. FIG. 31A illustrates volcano plot of genes altered at 3 weeks compared to pretreatment. Volcano plot constructed using log 2 fold changes and their P values of all genes. FIG. 31B illustrates pathways identified by gene ontology analysis that were altered at week 3 compared to pretreatment using top 50 differentially expressed genes (all genes with fold change >1.5 and P<0.05). FIG. 31C illustrates correlation coefficients to Ki67 were used to generate a correlation network. Nodes colored by strength of correlation to Ki67 (Pearson r=1 (red), −1 (blue)); node size indicates degree of connectivity. FIG. 31D illustrates pathways identified by gene ontology analysis using top 100 correlated genes with Ki67 (positive and negatively correlated genes with correlation coefficients >0.67 and ≤0.67). RNA sequencing data in all panels are representative of one technical replicate.

FIGS. 32A-32F are a series of images depicting that tumor-infiltrating T-cell clones in responding peripheral blood CD8 T-cell population and blood Ki67+ CD8 T-cell response correlates with tumor burden. FIGS. 32A-32C depict TCR sequencing on CD8 T cells (see materials & methods under Experimental Examples, "Cell Sorting"). FIG. 32A illustrates frequency of clones in blood and among top 10 clones in tumor (red). Clones only in blood or tumor in grey (P value; Fisher's exact test). PBMCs, peripheral blood mononuclear cells. FIG. 32B illustrates frequencies of top 10 blood clones and those shared with top 10 tumor-infiltrating T-cell clones (red arrows). All shared clones were HLA-DR+CD38+ (maroon). FIG. 32C illustrates the proportion of HLA-DR+CD38+ clones among top 100 clones in blood shared versus not shared with top 10 TIL clones. FIG. 32D illustrates example CT scans of high (top) or low (bottom) tumor burden, and Ki67 expression in blood CD8 T cells. FIG. 32E illustrates the top 39 immune parameters correlated with tumor burden by random forest analysis at week 3 (top). Heat map of top five parameters (bottom). FIG. 32F illustrates Pearson correlation of tumor burden to Ki67 expression pretreatment and maximum post-treatment in indicated cells (n=25 pretreatment, 23 post-treatment). TCR sequencing data in FIGS. 32A-32C are representative of one technical replicate, r and P values, Pearson's correlations.

FIG. 33A illustrates TCR clones present at pretreatment and post-treatment that are also in the top 100 clones in the tumor. Clones that are among the top 10 in the peripheral blood post treatment highlighted in red. Patient 14-784 did not have an available pretreatment sample and was not included. FIG. 33B illustrates the percentage of CD8 T cells that are Ki67+ (red) and HLA-DR+CD38+ (blue) over time. FIG. 33C illustrates a representative plot of Ki67 expression in HLA DR+CD38+ CD8 T cells and CD8 T cells that were not CD38+HLA-DR+ (that is, CD38–HLA-DR–, CD38+HLA-DR–, and CD38–HLA-DR+). FIG. 33D illustrates a representative plot of HLA-DR and CD38 expression on Ki67+ and Ki67– CD8 T cells. FIG. 33E illustrates a representative plot of Eomes versus T-bet and PD-1 versus CTLA-4 in HLA-DR+CD38+ ('DR+ 38+') CD8 T-cell subsets and cells that were not CD38+ HLA-DR+. FIG. 33F illustrates the percentage of Eomes$^{hi}$T-bet$^{lo}$, PD-1, CTLA-4 and expression on CD8 T cells (n=5). TCR sequencing and flow cytometry data in all panels are representative of one technical replicate.

FIGS. 34A-34G are a series of images depicting that tracking CD8 T-cell reinvigoration in context of tumor burden predicts response to anti-PD-1 therapy. FIG. 34A illustrates overall survival of patients with high (n=11) and low (n=14) expression of Ki67 (top), or high (n=9) and low (n=16) tumor burden (bottom). Cut-points by CART analysis (see materials & methods under Experimental Examples). FIGS. 34B and 34C illustrate plasma cytokines by response and clinical benefit (Mann-Whitney U-test; progression n=8, clinical benefit n=9). CR, complete response; PD, progressive disease; SD, stable disease. (FIG. 34D) Objective response rate for high and low ratio of Ki67 to tumor burden (left), tumor burden versus Ki67 by LOS (landmark overall survival) (center), and Kaplan-Meier overall survival stratified by post-treatment Ki67 to tumor burden ratio (right). Objective response by Fischer's exact test (Ki67 to tumor burden ratio: high, n=13; low, n=10). Kaplan-Meier data (Ki67 to tumor burden ratio: high, n=13; low, n=12). FIGS. 34E-34G illustrate Independent Keynote 001 trial. FIGS. 34E, 34F illustrate Ki67 in indicated subsets (n=18; paired t-test (left), Wilcoxon matched-pairs test (right)). FIG. 34G illustrates the objective response rate for high and low Ki67 to tumor burden ratio (left), Ki67 versus tumor burden by LOS (center) (n=18), and Kaplan-Meier overall survival for high versus low post-treatment Ki67 expression to tumor burden (right). Objective response by Fischer's exact test (Ki67 to tumor burden ratio: high, n=11; low, n=7). Kaplan-Meier overall survival (Ki67 to tumor burden ratio: high, n=11; low, n=7). *$P<0.001$, **$P<0.0001$. Error bars, s.d. Cytokine data in FIGS. 34B, 34C are representative of two technical replicates. MSKCC flow data in FIGS. 34E-34G are representative of two technical replicates.

FIGS. 35A-35G are a series of images depicting that high Ki67 to tumor burden ratio correlates with improved clinical outcomes and model selection identifies BRAF and lactate dehydrogenase as correlates to Ki67. FIG. 35A illustrates a scatter plot of maximum fold change of Ki67 expression after treatment versus tumor burden stratified by PFS (n=23). FIG. 35B illustrates the maximum post-treatment Ki67 expression versus tumor burden by response (n=23). FIG. 35C illustrates Ki67 expression to tumor burden ratio stratified by landmark PFS (PFS starting from 6 weeks into therapy) (left; n=23). Kaplan-Meier analysis stratified by a Ki67 to tumor burden ratio of 1.94 (right; Ki67 to tumor burden ratio: high, n=13; low, n=10); log-rank test. FIG. 35D illustrates Baysean Information Criteria (BIC), used as a criterion for selection of multiple regression models that best predicted Ki67 (low BIC score produces a stronger model). FIG. 35E illustrates the percentage of Ki67 expression in CD8 T cells (left) and tumor burden (right) stratified by BRAF status. All BRAF+ patients had been treated with BRAF-targeted therapy (n=4, after removal of patients with unmeasurable tumor burden); Mann-Whitney U-test. (FIG. 35F) Correlation of percentage Ki67+ versus lactate dehydrogenase (LDH) (left) and tumor burden versus LDH (right); Pearson's correlation. (FIG. 35G) Ki67 to LDH ratio stratified by landmark overall survival (overall survival starting from 6 weeks into therapy) (left; n=23). Kaplan-Meier analysis stratified by a Ki67 to LDH ratio of 0.065 (right; Ki67 to LDH ratio: high, n=18; low, n=5); log-rank test.

FIG. 37A illustrates how genes that were up- or downregulated in virus-specific CD8 T cells isolated from d15 and d30 of chronic LCMV clone 13 infection ($T_{EX}$) were compared to $T_N$, $T_{EFF}$, $T_{MEM}$ isolated from acute LCMV Arm infection (GSE41867) and exhaustion-specific genes defined based on moderated Bayesian statistics in order to identify genes specifically regulated in exhaustion compared to canonical T cell populations. FIG. 37B is a heatmap of transcriptomic data indicating exhaustion-specific genes in $T_{EX}$ during LCMV infection. FIG. 37C illustrates that genesets that identified as up- or down-regulated in exhaustion were validated for enrichment in $T_{EX}$ compared to $T_N$, $T_{EFF}$, or $T_{MEM}$ in LCMV infection via GSEA. FIG. 37D illustrates enrichment of the up-regulated exhaustion gene signature in transcriptomic data from $T_{EX}$ subpopulations (PD-1$^{Hi}$ versus PD-1$^{Int}$, Tim-3+ versus CXCR5+) from LCMV clone 13 infection (GSE41869; GSE84105). FIG. 37E illustrates human T cells isolated from HIV-specific CD8 T cells from elite controllers versus progressors in HIV infection (GSE24081) or PBMC versus TIL in melanoma patients (GSE 24536). FDR and normalized enrichment score (NES) are indicated. The dashed lines in FIG. 37D and FIG. 37E indicate leading edge genes driving the NES. FIG. 37F illustrates that up-regulated exhaustion gene signature was analyzed in multiple mouse and human transcriptomic data-sets of $T_{EX}$ populations * and shows the NES plotted for each comparison. * indicates an FDR<0.001, <0.01, *<0.05. FIG. 37G shows a heatmap depicting leading edge genes driving the enrichment for the (upregulated) exhaustion signature in melanoma (PBMC versus TIL) (GSE 24536). FIG. 37H shows a heatmap depicting leading edge genes driving the enrichment for the (upregulated) exhaustion signature in HCV (CD39+ versus CD39– cells) (GSE 72752).

FIG. 38A shows a proportional Venn diagram that illustrates the fraction of transcriptionally identified genes with associated epigenetic changes (increased accessibility of open chromatin regions (OCR) in the vicinity of exhaustion genes for UP-, decreased accessibility of OCRs in the vicinity of DOWN-exhaustion genes). FIG. 38B shows exemplary ATAC-seq tracks indicating increased OCR (highlighted by grey bars) in the vicinity of exhaustion genes comparing $T_{EX}$, $T_N$, $T_{EFF}$ and $T_{MEM}$ from GSE86797. Shown are Pdcd1, Ctla4, Tigit, Eomes, Ikzf2, Tox, Cd38, Ptger2, Entpd1. FIG. 38C illustrates that exhaustion genes were analyzed for associated OCR changes and the role of these genes in driving the exhaustion geneset enrichment ("leading edge") in the comparisons of $T_{EX}$ versus other T cell transcriptomic datasets. Genes with an associated OCR accessibility change displayed higher leading edge involvement. *** p<0.001. FIG. 38D shows the leading edge contribution of exhaustion signature genes for exhaustion genes with an associated OCR change as a binary heatmap for genes up-regulated in exhaustion (rows indicate genes, columns individual GSEA comparisons, red denoting leading edge contribution. FIG. 38E shows the leading edge contribution of exhaustion signature genes for exhaustion genes with an associated OCR change as a binary heatmap for genes down-regulated in exhaustion (rows indicate genes, columns individual GSEA comparisons, red denoting leading edge contribution. FIG. 38F shows GO Term analysis of the exhaustion-specific genesets with associated OCR changes; the 20 GO terms with the lowest p values are shown.

FIG. 39A illustrates that exhaustion genesets defined in FIGS. 37A-37H and 38A-38F were used to design an exhaustion-focused mass cytometry panel. The leading edge contribution of genes chosen for CyTOF analysis is shown; rows indicate genes, columns individual GSEA comparisons. Cytokines and chemokines were analyzed in stimulation settings using a dedicated panel. FIG. 39B illustrates that genes selected for CyTOF had significantly higher leading edge contribution in $T_{EX}$ GSEA analyses compared to the remaining exhaustion genes from FIG. 37. *** p<0.001 and showed similar ability to discriminate $T_{EX}$ in single-cell transcriptomic data (see FIG. 44). FIG. 39C illustrates a heatmap depicting exhaustion marker expression by MMI (median metal intensity) on concatenated CD8 T cells from PBMC samples (n=35). $T_{EX}$ markers were analyzed on canonical CD8 T cell populations ($T_N$, $T_{CM}$, $T_{EM}$, $T_{EMRA}$) and total PD-1+ CD8 T cells in healthy subjects and patients with HIV and lung cancer. FIG. 39D illustrates that a reduced CD4/CD8 ratio is associated with more severe HIV infection and was used to interrogate links between exhaustion molecule expression and settings of known severe exhaustion. Linear regression analysis was performed for marker expression by peripheral CD8 T cells in patients with HIV infection and healthy donors. Samples were gated for percent positive or MMI as indicated. Each dot represents an individual patient CD8+ T cells expressing a given exhaustion maker plotted against the CD4/CD8 ratio. (n=75 samples from 48 HIV patients and healthy controls were analyzed, the higher sample number is due to inclusion of longitudinal samples when available). Positive correlations are depicted in green, negative correlations in red. Similar results were obtained in a repeat analysis on a subset of patients on a different mass cytometer (FIG. 45). FIG. 39E illustrates that these data were further analyzed for cross-correlation of exhaustion marker expression estimated by pairwise method (see also FIG. 46). FIG. 39F illustrates the expression of indicated exhaustion markers on CD8+ T cells plotted versus PD-1 in a representative healthy individual, an untreated HIV patient presenting with a CD4/CD8 ratio of 0.06 typical of AIDS, and tumor-infiltrating lymphocytes isolated from a lung cancer patient, highlighting complex non-linear context-depending co-expression patterns of exhaustion markers.

FIG. 40A illustrates an exhaustion map that was generated by tSNE-based dimensionality reduction on 48 samples using information about expression of 16 exhaustion markers on nonnaive (CD45RA–CCR7–) CD8 T cells. FIG. 40B illustrates expression of individual molecules (indicated in the upper left corner of each panel) on the exhaustion map that are visualized heatmap-style ("flame" color levels based on percentile of marker expression). FIG. 40C is a schematic illustrating that an exhaustion map was generated for HIV patients with varying severity of untreated disease based on CD4/CD8 ratio and ART-treated patients with suppressed viremia and compared to healthy subjects and patients with lung cancer. FIG. 40D shows that the exhaustion map was then examined by determining the location of bona fide HIV-, FLU-, and CMV-specific CD8 T cells identified by tetramer staining on the $T_{EX}$ landscape. FIG. 40E illustrates that total CD8 T cells from healthy subjects and viremic and ART HIV+ patients were also mapped onto the exhaustion landscape. FIG. 40F illustrates that a similar fingerprinting was applied to cells isolated from lung cancer patient samples: PBMC (left), macroscopically uninvolved lung tissue (middle) or tumor-infiltrating lymphocytes (right). FIG. 40G illustrates the differential overlay of TILs compared to CD8 T cells from uninvolved lung on the exhaustion map highlights TIL-enriched phenotypes. A TIL>LU cluster was gated as indicated by the arrow and validated on a per-sample basis (right).

FIG. 41A shows a schematic of the pipeline for high-dimensional CD8 $T_{EX}$ cluster identification by phenograph and assessment in disease. FIG. 41B illustrates that phenograph analysis of $T_{EX}$ markers was performed on live singlet CD45+CD3+CD8 T cells from 48 samples as detailed in. Canonical CD8 T cell populations and total PD-1+ T cells were analyzed for their composition based on the phenograph analysis. The top 5 phenograph clusters within $T_N$, $T_{CM}$, $T_{EM}$, $T_{EMRA}$ and PD-1+ CD8 T cells in the cohort are shown. FIG. 41C illustrates phenograph clusters that were tested for the expression of $T_{EX}$ genes and other markers using manual gating and intensity analysis. The heatmap indicates gated expression of markers or marker combinations (using (+) or (–), as in PD-1+CD39+) or median metal intensity (e.g., TOX). Row- and column-based clustering was performed using Pearson's correlation. The heatmap coloring reflects z scores after row normalization, as indicated. FIG. 41D illustrates changes in Phenograph cluster composition of HIV-specific T cells on or off antiretroviral therapy (ART). The contribution of phenograph clusters to virus-specific T cell responses from HIV patients and healthy controls detected via tetramer staining was analyzed, the top 5 clusters are shown (a total of 24 tetramer responses were identified, (CMV n=4, FLU n=5, HIV n=15). FIG. 41E illustrates a heatmap of mapped cytokine production of Phenograph clusters. Viremic HIV and control samples were stimulated with PMA/Ionomycin and were analyzed for cytokine expression by cluster mapping. Mapping was performed by Phenograph classify function. Heatmap indicates gated expression of markers or marker combinations and the functional exhaustion score (FES) computed as detailed in the STAR Methods section. Row-based clustering using Pearson's correlation metric was performed. Columns are arranged by increasing FES. Values displayed are row normalized. FIG. 41F illustrates the distribution of Phenograph clusters in healthy subjects, and treated and untreated HIV patients (total n=25) with differing disease states (CD4/CD8 ratio for viremic "Severe": <0.2, "Intermediate": 0.2-0.5, "Mild": >0.5), shown as stacked bar graph, the coloring reflects cluster assignment. The mean frequency of each cluster within each patient population is depicted by the size of the corresponding bar. FIG. 41G shows plots where the correlation of each phenograph cluster frequency with key parameters of HIV disease progression in viremic HIV patients (i.e. CD4/CD8 ratio and viral load) was plotted to highlight clusters linked to exhaustion-associated disease parameters (upper left panel). This coordinate system displays the relative frequency of each cluster in healthy subjects, HIV patients with untreated disease and patients on ART therapy (remaining panels). The dot size of each cluster corresponds linearly to its relative abundance, the color corresponds to the FES.

FIG. 42A shows a heatmap where the functional exhaustion score (FES) was calculated for in vitro differentiated T ($T_{EFF}$ generated from total PBMC, or sorted $T_N$, $T_{CM}$, $T_{EM}$, or $T_{EMRA}$ and activated using CD3/CD28 bead stimulation and IL-2) and compared to the cytokine expression profile of phenograph clusters as in the heatmap shown in FIG. 41E. $T_{CM}$ and $T_{EMRA}$-enriched clusters c7 and c10 are displayed for comparison in addition to phenograph clusters with high FES. FIG. 42B is a graph where phenograph clusters were plotted based on a tSNE analysis using exhaustion marker expression as outlined in FIG. 46 and colored by the FES, indicating concordance of high dimensional phenotypes and functional exhaustion. FIG. 42C is a heatmap illustrating that clusters were analyzed for transcription factor expression compared to FES. Heatmap is clustered by column using Pearson's correlation. Rows were arranged based on FES. Heatmap coloring reflects z scores after column normalization, as indicated. FIG. 42D illustrates $T_{EX}$ Clusters with high FES plotted versus correlation of cluster frequency with CD4/CD8 and viral load indicating HIV disease progression (as in FIG. 41G). FIG. 42E illustrates that virus-specific T cells identified in PBMCs from healthy subjects and HIV patients were analyzed for the prevalence of the top 2 (upper graph) and top 9 (middle graph) clusters with highest FES analyzed (sum of percentages for top 2 and top 9 clusters is displayed). Further, the $T_{EX}$ ratio (lower graph) is shown for the sum of clusters defined to be Disease Associated $T_{EX}$ (DAT; i.e. linked to severe HIV) divided by the sum of clusters defined to be Health Associated $T_{EX}$ (HAT; i.e., linked to mild HIV), as in FIG. 42D. FIG. 42F illustrates, as in FIG. 42E, Top2, Top9 and $T_{EX}$ ratios which were determined for CD8+ T cells from PBMC of healthy subjects and HIV patients and displayed by HIV disease stage.

FIG. 43A illustrates that the distribution of phenograph clusters in 7 lung cancer patients was analyzed in the peripheral blood, uninvolved lung tissue and the tumor microenvironment and compared to healthy controls, analogous to FIGS. 41A-41G. The mean frequency of each cluster in each patient population is indicated by the size of the corresponding bar. FIG. 43B shows a plot of high and low TIL functionality tumors. Tumors were evaluated based on CD8-TIL IFN-γ production following overnight anti-CD3+anti-CD28 stimulation, and stratified into high and low TIL functionality tumors. FIG. 43C illustrates the relative frequency of each phenograph cluster, which is shown on the same exhaustion coordinate system as in FIG. 42B and FIG. 58. The dot size corresponds linearly to relative abundance, the color corresponds to the FES. FIG. 43D illustrates that the sum of the frequencies for the Top2 and Top9 $T_{EX}$ clusters and $T_{EX}$ ratio were determined as defined in the HIV cohort in FIG. 42 and used to analyze $T_{EX}$ in the peripheral blood, unaffected lung and TIL of lung cancer patients. FIG. 43E shows phenograph clusters over-represented in low or high functionality TIL (for stacked bar analysis see FIG. 47). * indicates p<0.05. c8: pβ0.07; c29: pβ0.08. FIG. 43F illustrates bivariate plots that indicate expression of markers of exhaustion, activation, tissue residency and transcriptional programming for clusters differentially linked to tumor functionality. Plots display concatenated CD8+ T cell data from lung cancer patients and healthy subjects as assigned by phenograph clustering. FIG. 43G illustrates the sum of the frequencies of HAT or DAT clusters linked to mild or severe HIV as determined in the lung cancer cohort. TIL data was analyzed both as total aggregate data and separating the high and low functionality samples as shown in FIG. 43B. DAT clusters enrich in the dysfunctional tumor microenvironment in lung cancer.

FIG. 46A shows scatterplots of the data underlying the cross-correlation data. Each individual dot represents an individual patient sample data. FIG. 46B shows p values (left panel) and r values (right panel); data are arranged by clustering on the correlation value, as in FIG. 39E. (n=75 total samples analyzed)

FIG. 47A compares FLU-specific CD8 T cells derived from blood and lung. FIG. 47B shows HIV-specific CD8 T cells with indicated disease stage or therapy status. FIG. 47C shows TIL CD8 T cells split based on IFN-γ functionality. FIG. 47D shows CMV-specific CD8 T cells from the peripheral blood in a stacked bar graph display. The coloring reflects cluster assignment indicated by the panel on the right. Mean values were used for the stacked bar display.

FIGS. 48 A-48C illustrate tSNE analysis. FIG. 48A illustrates a schematic of the generation of a 2D exhaustion map of phenograph-defined exhaustion clusters using tSNE analysis of exhaustion markers. Equal numbers of cells (n=50) were sampled from each phenograph cluster to avoid tSNE distribution bias based on different cluster abundance. FIG. 48B illustrates tSNE coordinates calculated for cells sampled from every cluster using the exhaustion markers as input are shown by dot plot (left) and contour plot (right). The color panel on the right indicates the cluster assignment. FIG. 48C illustrates tSNE coordinates of median exhaustion map locations for exhaustion clusters as in FIG. 48B which were obtained and used to display a simplified view of the phenotypic relationship of phenograph clusters, as used in FIGS. 42B and 43C.

FIG. 49A shows a Box and Whiskers display of the 9 clusters with high FES (c1, c2, c3, c4, c5, c9, c16, c27, c29) indicating the abundance (expressed as % of CD8) of these clusters in patients with untreated mild, intermediate, severe and ART-treated HIV infection, and healthy subjects (total n=25). The grey horizontal line indicates the mean of all datapoints in each panel. FIG. 49B illustrates that a subgroup of 6 patients on ART therapy was further analyzed for correlations of clusters frequency and the CD4/CD8 ratio, as shown by dot plot with linear regression line (c1, c2, c3, c4, c29 for correlation with disease severity, c5, c9, c16, c27 for correlation with health).

FIG. 51 depicts a series of graphs showing linear regression (top row) and PCR efficiency (bottom row) for various primer pairs (Tcf7, CD8, and PD1) (Table 6), indicating assay performance and reliability of qPCR analysis on DNA generated from ATAC transposition and amplification. Data shown is representative of multiple samples.

FIG. 52A illustrates ATAC-seq tracks for different CD8 T cell subpopulations (naïve, effector, memory, exhausted, and anti-PDL1-treated exhausted) and EL4 cells (bottom two rows) at the Tcf7 locus (left), the CD8 locus (middle), and the exhaustion-specific ~–23 kb PD1 locus (right). FIG. 52B depicts summary data of raw $C_t$ (cycle threshold) values from naïve CD8, naïve CD4, and EL4 cells at various cell concentrations at the Tcf7 locus (top), the CD8 locus (middle), and the exhaustion-specific –23 kb PD1 locus (bottom). For the Tcf7 locus in the top row, 2 different primer sets (Tcf7 1 and Tcf7 2) were used (Table 6). Should be open in CD8 (left) and CD4 (middle) T cells but not EL4s (right). Lower $C_t$ values at 10K and 50K indicate strong signal in the assay. For the CD8 locus in the middle row, 2 different primer sets (CD8 1 and CD8 2) were used (Table 6). Should be open in CD8 (left) but not CD4 (middle) T cells or EL4s (right). Lower $C_t$ values at 10K and 50K indicate strong signal in the assay.

FIG. 54A illustrates known chromatin accessibility via ATAC-seq tracks for different CD8 T cell subpopulations (naïve, effector, memory, exhausted (NT-1 and NT-2), and anti-PDL1-treated exhausted) and EL4 cells (bottom two rows) at the positive control loci in the CD3gamma promoter and CD3epsilon 3' UTR. FIG. 54B depicts summary data of raw $C_t$ values generated from naïve and effector CD8 T cells at various cell concentrations at two positive control loci (Cd3gamma Promoter and Cd3epsilon 3' UTR) and one negative control locus (Col1alpha2).

FIG. 55A illustrates known chromatin accessibility via ATAC-seq tracks for different CD8 T cell subpopulations (naïve, effector, memory, exhausted (NT-1 and NT-2), and aPDL1-treated exhausted) and EL4 cells (bottom two rows) at the interferon gamma (IFNg) and interleukin-2 receptor alpha (IL-2Ra) loci. FIG. 55B depicts summary data of raw $C_t$ values (left column) and calculated and normalized accessibility fold change (right column) between naïve and effector CD8 T cells at varying cell concentrations.

DETAILED DESCRIPTION

Definitions

Figure 1D:
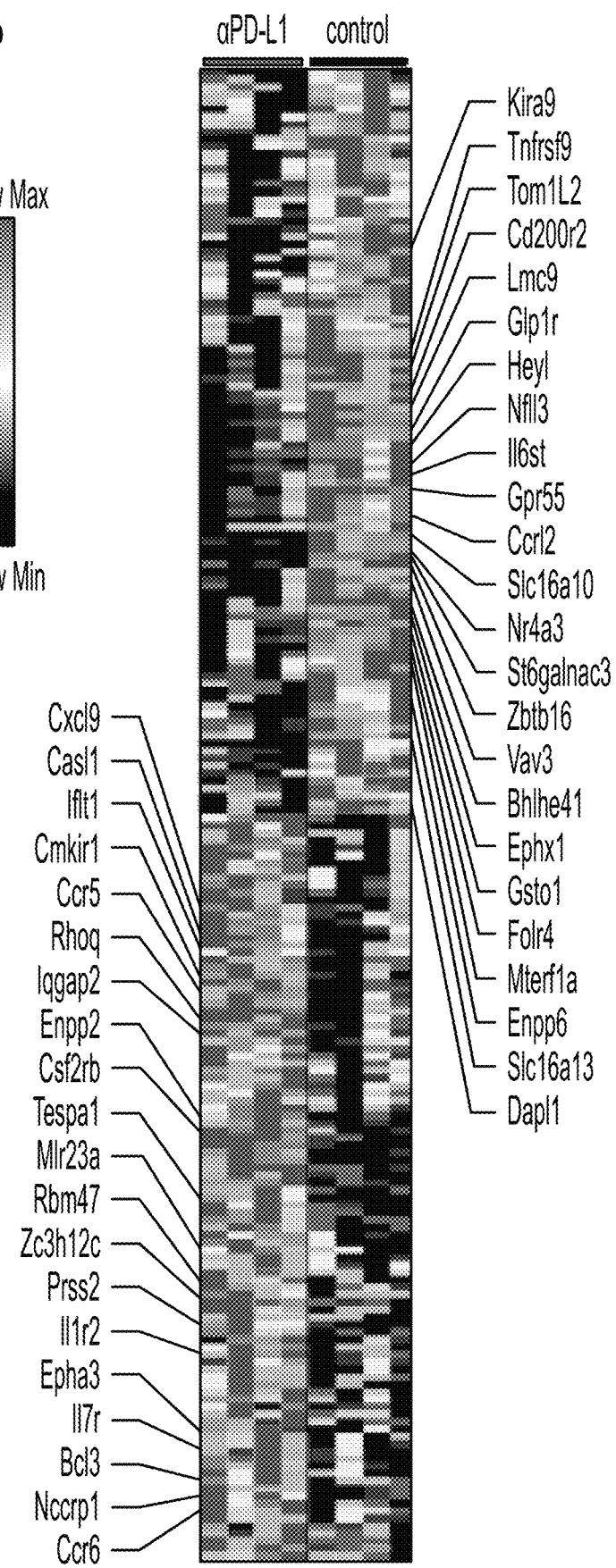
FIGS. 1A-1F are a series of images depicting the impact of anti-PD-L1 treatment on the transcriptional profile of $T_{EX}$.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instances ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

"Activators" or "agonists" of a soluble factor are used herein to refer to molecules of agents capable of activating or increasing the levels of the soluble factor. Activators are compounds that increase, promote, induce activation, activate, or upregulate the activity or expression of soluble factor, e.g., agonists. Assays for detecting activators include, e.g., expressing the soluble factor in vitro, in cells, or cell membranes, applying putative agonist compounds, and then determining the functional effects on activity of the soluble factor, as described elsewhere herein.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are often tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, and multispecific antibodies formed from antibody fragments.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multispecific antibodies, as well as fragments and derivatives of all of the foregoing, which fragments and derivatives have at least an antigenic binding site. Antibody derivatives may comprise a protein or chemical moiety conjugated to an antibody. The properties recited herein for antibodies and antibody fragments also apply to Fc fusion proteins described herein.

The term "antibody" as used herein also includes an "antigen-binding portion" of an antibody (or simply "antibody portion"). The term "antigen-binding portion," as used herein, refers to one or more fragments of an antibody that retain the ability to specifically bind to an antigen (e.g., PD-1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CHI domains; (ii) a F(ab')$_2$ fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) Science 242: 423-426; and Huston et al. (1988) Proc. Natl. Acad. Sci. USA 85:5879-5883; and Osbourn et al. (1998) Nat. Biotechnol. 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) Human Antibodies and Hybridomas 6:93-101) and use of a cysteine residue, a marker peptide and a C-terminal polyhistidine tag to make bivalent and biotinylated scFv polypeptides (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. In some embodiments, antibodies may bind specifically or substantially specifically to PD-1 polypeptides or fragments thereof. They may also be selective for such antigens such that they can distinguish such antigens from closely related antigens, such as other B7 family members. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

As used herein, a "blocking" agent or an "antagonist" is one which inhibits or reduces at least one biological activity of the antigen(s) it binds. For example, an anti-PD-1 antibody binds PD-1 and inhibits the ability of PD-1 to bind one or more ligands, for example, PD-L1 and/or PD-L2. In certain embodiments, the blocking antibodies or antagonist antibodies or fragments thereof described herein substantially or completely inhibit a given biological activity of the antigen(s). In certain embodiments, the term "inverse agonist" is used to refer to an agent that promotes the opposite action to normal. For example, a PD-1 inverse agonist can promote co-stimulation as opposed to co-inhibition of immune responses.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "auto-antigen" means, in accordance with the present invention, any self-antigen which is recognized by the immune system as if it were foreign. Auto-antigens comprise, but are not limited to, cellular proteins, phosphoproteins, cellular surface proteins, cellular lipids, nucleic acids, glycoproteins, including cell surface receptors.

The term "ATAC-seq" (Assay for Transposase-Accessible Chromatin using sequencing) is a technique used in molecular biology to study chromatin accessibility. ATAC-seq can be used as a rapid and sensitive method for epigenomic analysis. ATAC-seq captures open chromatin sites and can reveal the interplay between genomic locations of open chromatin, DNA-binding proteins, individual nucleosomes and chromatin compaction at nucleotide resolution. Chromatin undergoes various structural changes during a cell cycle. Histone proteins are the basic packer and arranger of chromatin and can be modified by various post-translational modifications to alter chromatin packing (histone modification). Most of the modifications occur on the histone tail. The consequences in terms of chromatin accessibility and compaction depend on, e.g., the amino-acid that is modified and the type of modification. For example, histone acetylation generally results in loosening and increased accessibility of chromatin for replication and transcription.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others. Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff man syndrome, systemic lupus erythematosus, Takayasu arteritis, temporal arteritis/giant cell arteritis, ulcerative colitis, uveitis, vitiligo and Wegener's granulomatosis.

As used herein, the term "autologous" is meant to refer to any material derived from the same individual to whom or to which it is later to be re-introduced into the individual.

"Allogeneic" refers to a graft derived from a different animal of the same species.

"Xenogeneic" refers to a graft derived from an animal of a different species.

As used herein, to "alleviate" a disease means reducing the severity of one or more symptoms of the disease.

The term "biomarker" or "marker" refers to a measurable entity of the present invention that has been determined to be indicative of T cell exhaustion. In some embodiments, markers or biomarkers include exhaustion-specific genes. For example, biomarkers described herein can be genomic regulatory regions that modulate the expression of at least one gene in a T cell. In some embodiments, biomarkers described herein can be effector genes or products thereof expressed by T cells and related to T cell activity and/or T cell exhaustion (e.g., high sustained PD-1 expression and/or activity in exhausted T cells). Biomarkers can also include, without limitation, cell types (e.g., engineered T cells), cell ratios (e.g., engineered T cells to exhausted T cell ratio), nucleic acids (e.g., genomic nucleic acids and/or transcribed nucleic acids) and proteins, particularly those provided in Pauken et al. Table S1 (Pauken et al. Science 2016, 354 (6316):1160-1165). Biomarkers can further include immunological targets or agents that downregulate unwanted immune reactions in order to treat the immune disorder of interest as described further herein. The modulation (e.g., increase or decrease) in biomarker activity can be measured in any number of ways (e.g., according to measures described herein, including using controls, ratios, comparisons to baselines, and the like). For example, a genomic regulatory region selectively chromatin accessible in exhausted CD8+ T cells that is engineered can decrease enhancer activity on at least one gene as measured by a reduction in gene expression (e.g., gene transcription and/or translation) of the at least one gene as compared to the transcription and/or translation of the at least one gene in the same T cell type from the same organism without the engineered genomic regulatory region. The modulation in gene expression can be assessed over time. A modulation can mean a change of at least 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 200%, 250%, 300%, 350%, 400%, 450%, 500%, 550%, 600%, 650%, 700%, 750%, 800%, 850%, 900%, 950%, 1000%, or more, or any range in between inclusive (e.g., 5% to 100%).

It is to be noted that the biomarkers described herein can be used to refer to any combination of features described herein regarding any individual or combination of such biomarkers. For example, any combination of ortholog across organisms, sequence composition, percentage identity, sequence length, domain structure, functional activity, mutation status, etc. can be used to describe a biomarker molecule of the present invention.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "bispecific antibody" or "multispecific antibody" refers to an antibody that recognizes more than one epitope. Such antibodies are useful for targeting different proteins using the same agent. Methods of making such antibodies are well-known in art (see, at least U.S. Pat. Nos. 5,798,229; 5,989,830; and Holliger et al. (2005) *Nat. Biotech.* 23:1126-1136).

The term "control" refers to any reference standard suitable to provide a comparison to the regulatory and/or expression products in the test sample. For efficiency, expression products are described, but the description applies equally to elements that regulate the expression products. In one embodiment, the control comprises obtaining a "control sample" from which expression product levels are detected and compared to the expression product levels from the test sample. Such a control sample may comprise any suitable sample, including but not limited to a sample from a control immune disorder patient (can be stored sample or previous sample measurement) with a known outcome; normal tissue or cells isolated from a subject, such as a normal patient or the immune disorder patient, cultured primary cells/tissues isolated from a subject such as a normal subject or the immune disorder patient, adjacent normal cells/tissues obtained from the same organ or body location of the immune disorder patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care immune disorder therapy). It will be understood by those of skill in the art that such control samples and reference standard expression product levels can be used in combination as controls in the methods of the present invention. In one embodiment, the control may comprise normal or non-immune disorder cell/tissue sample. In another preferred embodiment, the control may comprise an expression level for a set of patients, such as a set of immune disorder patients, or for a set of immune disorder patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having an immune disorder that has responded to a treatment of interest. In another embodiment, the control may also comprise a measured value for example, average level of expression of a particular gene in a population compared to the level of expression of a housekeeping gene in the same population. Such a population may comprise normal subjects, immune disorder patients who have not undergone any treatment (i.e., treatment naive), immune disorder patients undergoing standard of care therapy, or patients having an immune disorder that has responded to a treatment of interest. In another preferred embodiment, the control comprises a ratio transformation of expression product levels, including but not limited to determining a ratio of expression product levels of two cell types and/or genes in the test sample and comparing it to any suitable ratio of the same two cell types and/or genes in a reference standard; determining expression product levels of the two or more cell types and/or genes in the test sample and determining a difference in expression product levels in any suitable control; and determining expression product levels of the two or more cell types and/or genes in the test sample, normalizing their expression to expression of housekeeping cell types and/or genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with the immune disorder. In one embodiment a control expression product level is established wherein higher or lower levels of expression product relative to, for instance, a particular percentile, are used as the basis for predicting outcome. In another preferred embodiment, a control expression product level is established using expression product levels from immune disorder control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

As used herein, the term "helminth" means a parasitic worm that lives and feeds on a living host. In some embodiments, the helminth is a tapeworm, a fluke, or a roundworm. A tapeworm is a parasitic worm from the class Cestoda. It typically lives in the digestive tract of a vertebrate. A fluke is a flatworm from the class Trematoda. Flukes may cause disease in their host. Schistosomiasis is an example of a parasitic disease that is caused by a fluke. A roundworm constitutes the phylum Nematoda. Roundworms that are commonly parasitic on humans include ascarids, filarias, hookworms, pinworms and whipworms. Many roundworms cause disease in their hosts. For example, the species *Trichinella spiralis* is responsible for the disease trichinosis.

As used herein, the term "protozoan" means a single-celled eukaryotic organism. In some embodiments, the protozoan is *Acanthamoeba* spp., *Balamuthia mandrillaris*, *Blastocystis* spp., *Cryptosporidium* spp., *Dientamoeba fragilis*, *Entamoeba histolytica*, *Giardia lamblia*, *Leishmania* spp., *Naegleria fowleri*, *Plasmodium falciparum*, *Plasmodium vivax*, *Plasmodium ovale*, *Plasmodium malariae*, *Plasmodium knowlesi*, *Toxoplasma gondii*, *Trichomonas vaginalis*, *Trypanosoma bruceii* or *Trypanosoma cruzi*.

As used herein, the term "immune checkpoints" means a group of molecules on the cell surface of CD4+ and CD8+ T cells. These molecules fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Immunotherapeutic agents that can act as immune checkpoint inhibitors useful in the methods of the present invention, include, but are not limited to, Fc fusion proteins having effector function, such as certain classes of antibodies well-known in the art.

The term "anti-immune checkpoint therapy" refers to the use of agents that inhibit immune checkpoint nucleic acids and/or proteins. Inhibition of one or more immune checkpoints can block or otherwise neutralize inhibitory signaling to promote immunomodulation. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins that block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor (s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can bind to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "influenza virus," as used herein, refers to an RNA virus that is a member of the Orthomyxoviruses family. In some embodiments, the influenza virus is selected from the genera consisting of Influenza virus A, Influenza virus B, Influenza virus C and Influenza virus D. In further embodiments, the influenza A virus is of the subtype H1N1, H1N2, H2N2 or H3N2. In further embodiments, the influenza B virus of the B/Yamagata/16/88-like lineage or the B/Victoria/2/87-like lineage.

The term "polyoma virus," as used herein, refers to an unenveloped DNA virus that is a member of the Polyomaviridae family. A polyomavirus is a DNA virus with a circular genome. Some members of the family are oncoviruses, and may cause tumors. In some embodiments, the polyoma virus is BK virus (BKV), JC virus (JCV), KI polyoma virus (KIPyV), WU virus (WUPyV), Merkel cell polyomavirus (MCPyV), human polyoma virus 6 (HPyV6), human polyoma virus 7 (HPyV7), trichodysplasia spinulosa virus (TSPyV), human polyoma virus 9 (HPyV9), or MW virus (MWPyV).

"PD-1" is an immune checkpoint inhibitor that refers to a member of the immunoglobulin gene superfamily that functions as a co-inhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. Int. Immunol. 1996, 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 (see also Ishida et al. (1992) 20 *EMBO J*

11:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. *EMBO J.* 1992, 11:3887; Shinohara et al. (1994) *Genomics* 23:704; and U.S. Pat. No. 5,698,520). These features also define a larger family of polypeptides, called the immunoinhibitory receptors, which also includes gp49B, PIR-B, and the killer inhibitory receptors (KIRs) (Vivier and Daeron *Immunol. Today* 1997, 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6): 285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_00107697.5.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity" includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response. Agents that modulate PD-1 activity are well-known in the art. Representative examples include, without limitation, antibodies such as MDX-1106, Merck 3475, and CT-011. MDX-1106, also known as MDX-1106-04, ONO-4538 or BMS-936558, is a fully human IgG4 anti-PD-1 monoclonal antibody described in PCT Publ. No. WO 2006/121168 and U.S. Pat. No. 8,088,449. Merck 3475, also known as SCH-900475 and pembrolizumab, is a humanized IgG4 anti-PD-1 monoclonal antibody described in PCT Publ. No. WO 2009/114335; U.S. Pat. No. 8,354,509; and Hamid et al. (2013) *New Engl. J. Med.* 369:134-144. Pidilizumab (CT-011; CureTech) is a humanized IgG1 monoclonal antibody that binds to PD-1. Pidilizumab and other humanized anti-PD-1 monoclonal antibodies are disclosed in PCT Publ. No. WO 2009/101611. Similarly, AMP-224 (B7-DCIg; Amplimmune) is a PD-L2 Fc fusion soluble receptor that blocks the interaction between PD-1 and PD-L1 and is disclosed in PCT Publ. Nos. WO 2010/027827 and WO 2011/066342. Moreover, many other anti-PD-1 Fc fusion proteins are known in the art as described in U.S. Pat. No. 8,609,089; US Pat. Publ. No. 2010/028330; U.S. Pat. Publ. No. 2012-0114649; and PCT Publ. No. WO 2014/089113.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see, Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1 (CD80), B7-2 (CD86), inducible costimulatory ligand (ICOS-L), B7-H3, B7-H4, VISTA, B7-H6, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two B sheets, each consisting of anti-parallel B strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of B strands.

The term "immune disorders" refers to conditions characterized by an unwanted immune response. In some embodiments, the immune disorder is such that a desired anti-immune disorder response suppresses immune responses. Such conditions in which downregulation of an immune response is desired are well-known in the art and include, without limitation, situations of tissue, skin and organ transplantation, in graft-versus-host disease (GVHD), inflammation, or in autoimmune diseases, such as systemic lupus erythematosus, multiple sclerosis, allergy, hypersensitivity response, a disorder requiring improved vaccination efficiency, and a disorder requiring increased regulatory T cell production or function, as described further herein. In other embodiments, the immune disorder is such that a desired response is an increased immune response. Such conditions in which upregulation of an immune response is desired are well-known in the art and include, without limitation, disorders requiring increased CD4+ effector T cell production or function such as combating cancer, infections (e.g., parasitic, bacterial, helminthic, or viral infections), and the like.

The term "acute immune disorder" refers to conditions that can be resolved by an appropriate immune response that eradicates a targeted antigen and host comprising such a targeted antigen, such as a cancer or an infection agent like a virus, bacteria, parasite, *mycoplasma*, fungus, and the like. Such conditions are relatively brief and last on the order of a few days to a few weeks.

By contrast, the term "chronic immune disorders" refers to those conditions that are not effectively cleared or eliminated by the induction of a host immune response. In chronic immune disorders, a targeted antigen (and/or host comprising the targeted antigen), such as an infectious agent or cancer cell, and the immune response reach equilibrium such that the subject maintains the targeted antigen or host comprising the targeted antigen (e.g., remains infectious or afflicted with cancer) over a long period of time (i.e., a time period of months to years or even a lifetime) without necessarily expressing symptoms. Chronic immune disorders can involve stages of both silent and productive targeted antigen maintenance without rapidly killing or even producing excessive damage of the host cells. Detection of the targeted antigen or host comprising the targeted antigen can be made according to any one of many well-known methods in the art and described, for example, in U.S. Pat. Nos. 6,368,832, 6,579,854, and 6,808,710 and U.S. Patent Application Publication Nos. 20040137577, 20030232323, 20030166531, 20030064380, 20030044768, 20030039653, 20020164600, 20020160000, 20020110836, 20020107363, and 200201067.

In some embodiments, chronic immune disorders are the result of infection, such as an infection with a virus including, but not limited to, human immunodeficiency viruses (HIV), hepatitis C viruses (HCV), T-cell leukemia viruses, Epstein-Barr virus, cytomegalovirus, herpesviruses, varicella-zoster virus, measles, papovaviruses, prions, hepatitis viruses, adenoviruses, parvoviruses, papillomaviruses, prions, and the like. In some embodiments, chronic immune disorders are the result of infection, such as an infection with a virus including, but not limited to hepatitis B virus, noroviruses, and/or anelloviruses, In some embodiments, chronic immune disorders are the result of infection with non-viral chronic infections including, but not limited to malaria, *Mycobacterium tuberculosis*, *Trypanasoma cruzi*, *Toxoplasma gondii*, and/or *Leishmania major*. Chronic immune disorders include, for example, chronic conditions and latent conditions. As used herein, chronic immune disorders can be limited to chronic conditions, latent conditions, or both.

In a "chronic condition," the targeted antigen can be detected in the subject at all times regardless of whether the signs and symptoms of the disease are present or absent, even for an extended period of time. Non-limiting examples of chronic conditions resulting from infection include hepatitis B (caused by hepatitis B virus (HBV)) and hepatitis (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyoma virus BK, polyoma virus JC, measles virus, rubella virus, human immunodeficiency virus (HIV), human T cell leukemia virus I, and human T cell leukemia virus II. Parasitic persistent infections can arise as a result of infection by, for example, *Leishmania*, *Toxoplasma*, *Trypanosoma*, *Plasmodium*, *Schistosoma*, *Encephalitozoon*, norovirus, anellovirus, *mycobacterium* species, *malaria* species, *malaria*, *Mycobacterium tuberculosis*, *Trypanasoma cruzi*, *Toxoplasma gondii*, and/or *Leishmania major*.

A particular type of chronic condition involving infections is known as a "latent condition," where the infectious agent (such as a virus) is seemingly inactive and dormant such that the subject does not always exhibit signs or symptoms. In a latent viral infection, the virus remains in equilibrium with the host for long periods of time before symptoms again appear; however, the actual viruses cannot typically be detected until reactivation of the disease occurs. Infection latency is the ability of a pathogenic infection agent, such as a virus, to lie dormant within a cell. For example, a latent viral infection is a phase in the life cycle of certain viruses in which after initial infection, virus production ceases. However, the virus genome is not fully eradicated. The result of this is that the virus can reactivate and begin producing large amounts of viral progeny (the lytic part of the viral life cycle) without the host being infected by a new virus. The virus may stay within the host indefinitely. In one embodiment, virus latency is not identical to clinical latency, in which the virus is undergoing an incubation period but is not dormant. Non-limiting examples of latent infections include infections caused by herpes simplex virus (HSV)-1 (fever blisters), HSV-2 (genital herpes), and varicella zoster virus VZV (chickenpox-shingles).

As used herein, the term "immunotherapeutic agent" can include any molecule, peptide, antibody or other agent which can stimulate a host immune system to promote immunomodulation in the subject. Various immunotherapeutic agents are useful in the compositions and methods described herein.

The terms "inhibit" or "reverse" include the decrease, limitation, or blockage, of, for example a particular action, function, or interaction. In some embodiments, an immune disorder is "inhibited" or "reversed" if at least one symptom of the immune disorder is alleviated, terminated, slowed, or prevented. As used herein, an immune disorder is also "inhibited" or "reversed" if recurrence or spread of the immune disorder is reduced, slowed, delayed, or prevented.

An "isolated antibody" is intended to refer to an antibody that is substantially free of other antibodies having different antigenic specificities. Moreover, an isolated antibody may be substantially free of other cellular material and/or chemicals.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "$K_d$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancer cells can spread locally or through the bloodstream and lymphatic system to other parts of the body. The term "cancer" includes premalignant, as well as malignant, cancers. The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

By "chimeric protein" is meant any single polypeptide unit that comprises two distinct polypeptide domains, wherein the two domains are not naturally occurring within the same polypeptide unit. Typically, such chimeric proteins are made by expression of a cDNA construct but could be made by protein synthesis methods known in the art.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to ICOS, 4-1BB, CD28, CD226, CD27, OX40, CD30 and LIGHT.

A "co-stimulatory signal," as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "epigenetics" is defined as heritable changes in gene activity and expression that occur without alteration in DNA sequence. These non-genetic alternations are tightly regulated by two major epigenetic modifications: chemical modifications to the cytosine residues of DNA (DNA methylation) and chemical modifications of histone proteins associated with DNA (histone modifications). The term epigenetics may be used interchangeable to refer to the such changes in single genes or sets comprising multiple genes.

The term "epigenome" refers to the overall epigenetic state of a cell, and reflects global analyses of epigenetic markers across the entire genome. Mapping epigenetic modification patterns or profiling the epigenome in a given cell can identify epigenetic biomarkers for clinical prediction, diagnosis, and therapeutic development.

As used herein, the term "epigenetic pathway" comprises any component that contributes to the "epigenome" or epigenomic state of a cell.

As used herein "endogenous" refers to any material from or produced inside an organism, cell, tissue or system.

As used herein, the term "exogenous" refers to any material introduced to an organism, cell, tissue or system that was produced outside the organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

By the term "immune reaction," as used herein, is meant the detectable result of stimulating and/or activating an immune cell, for example cytokine secretion, antibody secretion, cytolytic activity or antibody dependent cell cytotoxicity (ADCC).

"Immune response" or "immunological response," as the term is used herein, means a process that results in the activation and/or invocation of an effector function in either the T cells, B cells, natural killer (NK) cells, and/or antigen-presenting cells. Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like. As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Immune cell," as used herein includes any cell that is involved in the generation, regulation or effect of the acquired or innate immune system. Immune cells include T cells such as CD4+ cells, CD8+ cells and various other T cell subsets, B cells, natural killer cells, macrophages, monocytes and dendritic cells, and neutrophils.

The term "immune related disease" means a disease in which a component of the immune system of a mammal causes, mediates or otherwise contributes to morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

The term "infectious disease" refers to a disorder caused by pathogenic (micro)organisms such as bacteria, viruses, fungi, or parasites. Infectious diseases of the present disclosure include, but are not limited to a bacterium, virus, protozoan, *mycoplasma*, fungus, yeast, parasite, or prion. For example, but not by way of limitation, the immunogen may be a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, and *Trypanosoma cruzi*.

"Inhibitors" or "antagonists" of a soluble factor are used herein to refer to molecules of agents capable of inhibiting, inactivating or reducing the levels of the soluble factor. Inhibitors are compounds that, e.g., bind to, partially or totally block activity, decrease, prevent, delay activation, inactivate, desensitize, or down regulate the activity or expression of soluble factor, e.g., antagonists. Inhibitors include polypeptide inhibitors, such as antibodies, soluble receptors and the like, as well as nucleic acid inhibitors such as siRNA or antisense RNA, genetically modified versions of the soluble factor, e.g., versions with altered activity, as well as naturally occurring and synthetic soluble factor antagonists, small chemical molecules and the like. Assays for detecting inhibitors include, e.g., expressing the soluble factor in vitro, in cells, or cell membranes, applying putative antagonist compounds, and then determining the functional effects on activity of the soluble factor, as described elsewhere herein.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The phrase "level of a soluble factor" in a biological sample as used herein typically refers to the amount of protein, protein fragment or peptide levels of the soluble factor that is present in a biological sample. A "level of a soluble factor" need not be quantified, but can simply be detected, e.g., a subjective, visual detection by a human, with or without comparison to a level from a control sample or a level expected of a control sample.

"Mass cytometry", or "CyTOF", is a variation of flow cytometry in which antibodies are labeled with heavy metal ion tags rather than fluorochromes. Readout is by time-of-flight mass spectrometry. This allows for the combination of many more antibody specificities in a single sample, without significant spillover between channels.

By the term "modulating" an immune response, as used herein, is meant mediating a detectable increase or decrease in the level of an immune response in a mammal compared with the level of an immune response in the mammal in the absence of a treatment or compound, and/or compared with the level of an immune response in an otherwise identical but untreated mammal. The term encompasses perturbing and/or affecting a native signal or response thereby mediating a beneficial therapeutic response in a mammal, preferably, a human.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "retrovirus," as used herein, is a member of the Retroviridae. A retrovirus is a single-stranded positive-sense RNA virus. In some embodiments, the retrovirus is an alpha-retrovirus, a beta-retrovirus, a gamma-retrovirus, a delta-retrovirus, an epsilon-retrovirus, a lentivirus or a spumavirus. In some embodiments, the retrovirus is a lentivirus selected from the group consisting of human immunodeficiency virus (HIV) and equine infectious anemia virus (EIAV).

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Exemplary subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "T cell", also known as T-lymphocyte, or thymocyte is known in the art. It is a type of white blood cell which is primarily produced in the thymus. T cells are part of the immune system and develop from stem cells in the bone marrow. They help protect the body from infection and may help fight cancer. T cells can be distinguished from other lymphocytes, such as B cells and natural killer cells, by the presence of a T-cell receptor on the cell surface. There are several subsets of T cells, of which each have a distinct function. In some embodiments, the T cell is a CD8+ T cell. The term CD8+ T cell is used interchangeably with the term CD8 T cell, herein.

Antigen-naïve T cells (naïve T cells, $T_N$) expand and differentiate into memory T cells ($T_{MEM}$) and effector T cells ($T_{EFF}$) after they encounter their cognate antigen within the context of an MHC molecule on the surface of a professional antigen presenting cell (e.g. a dendritic cell).

"Memory T cells" ($T_{MEM}$) are a subset of infection—as well as potentially cancer-fighting T cells (also known as a T lymphocyte) that have previously encountered and responded to their cognate antigen; thus, the term antigen-experienced T cell is often applied. Such T cells can recognize foreign invaders, such as bacteria or viruses, as well as cancer cells. Memory T cells have become "experienced" by having encountered antigen during a prior infection, encounter with cancer, or previous vaccination. At a second encounter with the invader, memory T cells can reproduce to mount a faster and stronger immune response than the first time the immune system responded to the invader. This behavior is utilized in T lymphocyte proliferation assays, which can reveal exposure to specific antigens.

"Effector T cells" ($T_{EFF}$) describes a broad group of cells that includes several T cell types that actively respond to a stimulus, such as co-stimulation. This includes CD4+, CD8+, cytotoxic, helper, killer, regulatory, and potentially other T cell types.

An "exhausted T cell" ($T_{EX}$) is a T cell that instead of clearing an infection, tumor, or cancer becomes "exhausted" and has an impaired ability to clear, alleviate, or reduce the infection, tumor, or cancer. An exhausted T cell can be a CD8+ T cell. An exhausted T cell can be a CD4+ T cell. Exhausted T cells have progressively lost T-cell function. "Exhaustion" or "unresponsiveness" refers to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation or cell division, entrance into the cell cycle, cytokine production, cytotoxicity, trafficking, phagocytotic activity, or any combination thereof. Normal input signals can include, but are not limited to, stimulation via a receptor (e.g., T cell receptor, B cell receptor, co-stimulatory receptor, and the like).

An "exhausted T cell population" ($T_{EX}$ population) is a population of exhausted T cells. A $T_{EX}$ population may be characteristic of a disease state in a subject having a disease. Provided herein are methods for identifying $T_{EX}$ populations that are characteristic of a disease state in a subject having a disease.

"T-cell exhaustion", a type of immunosuppression, is characterized by deprived effector function, sustained expression of inhibitory receptors, and a distinct transcriptional state (Wherry. Nat Immunol. 2011, 12(6):492-9). T cell exhaustion comprises a state of impaired effector functions, high inhibitory receptor expression including Programmed Death-1 (PD-1, or CD279), transcriptional reprogramming, and defective immune memory (Pauken et al. Science 2016, 354(6316):1160-1165).

In some embodiments, for example when detecting or measuring T cell exhaustion, a "control T cell" refers to a T cell that is not an exhausted T cell. In said embodiments, the control T cell can be, e.g., a $T_N$, $T_{EFF}$, and/or $T_{MEM}$. A population of control T cells refers to any combination of control T cell types. In some embodiments, for example when detecting or measuring the degree of reinvigoration of a formerly exhausted T cell, a "control T cell" refers to an exhausted T cell.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "transplant," as used herein, refers to cells, tissue, or an organ that is introduced into an individual. The source of the transplanted material can be cultured cells, cells from another individual, or cells from the same individual (e.g., after the cells are cultured in vitro). Exemplary organ transplants are kidney, liver, heart, lung, and pancreas.

To "treat" a disease as the term is used herein, means to reduce the frequency or severity of at least one sign or symptom of a disease or disorder experienced by a subject. In some embodiments, to "treat" includes reduction of symptoms of the disease and administration of a prophylactic treatment such as, for example, a prophylactic vaccine.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present disclosure provides methods for detecting and tracking exhausted T cells in a patient having a disease. The present disclosure also provides methods for treating a patient having a disease. The present disclosure also provides methods for determining a modification in treatment for a patient having a disease. In some embodiments, the disease is a tumor. In some embodiments, the disease is a cancer. In some embodiments, the disease is an infectious disease.

In some embodiments, the method for detecting and tracking exhausted T cells in a patient having a disease comprises using an epigenomic assay comprising a high parameter mass cytometry panel to identify an epigenomic signature unique to the exhausted T cells as compared with naïve, effector, and/or memory T cells, wherein the assay allows single-cell proteomic identification and evaluation of the exhausted T cells. In some embodiments, the method for treating a patient having a disease comprises detecting exhausted T cells in the patient before and after a first treatment by using an epigenomic assay to identify an epigenomic signature unique to the exhausted T cells as compared with naïve, effector, and/or memory T cells, wherein if exhausted T cell numbers decrease in said patient after said first treatment, then a second treatment is administered to the patient that increases an immunological response in the patient, and wherein if exhausted T cell numbers do not decrease in the patient after the first treatment, then either a second treatment is administered that increases an immunological response or a second treatment is administered that modulates an immunological response in the patient. In some embodiments, the method for determining a modification of a treatment in a patient having a disease comprises tracking exhausted T cells in the patient before and after the treatment and using a cytometry assay to identify an epigenomic signature unique to the exhausted T cells as compared with naïve, effector, and/or memory T cells, wherein when the epigenomic signature is identified, the modification of the treatment is determined which will increase the patient's immunological response.

Also provided is a method of identifying exhausted T cell ($T_{EX}$) populations characteristic of a disease state in a subject having a disease, the method comprising the steps of:
(d) obtaining a sample comprising T cells from the subject;
(e) measuring the expression of a panel of markers comprising one or more T cell lineage-specific markers or combinations of T cell lineage-specific markers and one or more T cell exhaustion-specific ($T_{EX}$) markers or combinations of $T_{EX}$-specific markers in the T cells from the subject having a disease;
(f) comparing expression of the panel of markers to expression of the same panel of markers in a control sample comprising T cells; and
(d) identifying one or more $T_{EX}$ populations characteristic of the disease, wherein a $T_{EX}$ population characteristic of the disease comprises a greater number of $T_{EX}$ cells in which expression of one or more markers in the panel of markers in the T cells from the subject having a disease is up-regulated or down-regulated compared to the number of $T_{EX}$ cells expressing the same one or more markers in the panel of markers in a control sample comprising T cells.

In some embodiments, the one or more T cell lineage-specific markers or combinations of T cell lineage-specific markers and the one or more $T_{EX}$-specific markers or combinations of markers is selected from the group consisting of CD45RA$^+$, PD-1$^-$/CD127$^-$, Tim-3$^{MMI}$, LAG-3$^{MMI}$, TCF1$^{MMI}$, CCR7$^+$, CD45RA$^+$/CD27$^+$, CD73$^+$, CD27$^+$, CD28$^+$, CD26$^+$, CD7$^{MMI}$, CD127$^+$, PD-1$^-$/CD127$^+$, Helios$^+$, CD16$^+$, Perforin$^+$, CD57$^+$, Granzyme B$^+$ (GzmB$^+$), T-bet$^+$, Granzyme K$^+$ (GzmK$^+$), PD-1$^+$/CXCR5$^+$, CXCR5$^+$, CD160$^+$, TIGIT$^+$, Eomesodermin$^+$ (Eomes$^+$), 2B4$^+$, KLRG1$^+$, Granzyme M$^+$ (GzmM$^+$), PD-1$^+$/2B4$^+$/CD160$^+$, PD-1$^+$/2B4$^+$, PD-1$^+$/Eomes$^+$, CD45RO$^+$, PD-1$^+$, PD-1$^+$/CD127$^-$, PD-1$^+$/CD127$^+$, CD200R$^{MMI}$, CD103$^+$, CTLA-4$^+$, PD-1$^+$/CTLA-4$^+$, CD38$^+$/CD39$^+$, Ki67$^+$, PD-1$^+$/CD39$^+$, HLA-DR$^{MMI}$, CD38$^+$, TOX$^{MMI}$, CD39$^+$, CD36$^+$, and Ptger2$^{MMI}$, wherein expression of the markers or combinations of markers is assessed by manual gating using (+) to indicate increased expression and (−) to indicate decreased expression, or by median metal intensity (MMI).

In some embodiments, the T cell lineage-specific markers or combinations of T cell lineage-specific markers and/or the one or more $T_{EX}$-specific markers or combinations of markers are those listed in Table 4. In some embodiments, the exhaustion-specific genes or sets of exhaustion-specific genes are those listed in FIG. 41C.

In some embodiments, the one or more T cell lineage-specific markers or combinations of T cell lineage-specific markers is selected from the group consisting of CD27$^+$, CD45RA$^+$, CCR7$^+$, and CD103$^+$, and wherein the one or more $T_{EX}$-specific markers or combinations of $T_{EX}$-specific markers is selected from the group consisting of CTLA-4$^+$, CD7$^+$, CD73$^-$, CD127$^-$, CD39$^+$, GzmK$^+$, XCL1$^+$, Helios$^+$, PD-1$^+$, CCR7$^-$, IL-21$^+$, TCF1$^-$, CXCL10$^+$, Eomes$^+$, Amphiregulin$^+$ (Areg$^+$), CD38$^+$, TOX$^+$, TIGIT$^+$, CXCR5$^+$, 2B4$^+$, IL-10$^+$, LAG-3$^+$, and Ptger2$^+$, wherein expression of the markers or combinations of markers is assessed by manual gating using (+) to indicate increased expression and (−) to indicate decreased expression.

In some embodiments, the panel of markers comprising one or more T cell lineage-specific markers or combinations of T cell lineage-specific markers and one or more $T_{EX}$-specific markers or combinations of $T_{EX}$-specific markers comprises a set of markers selected from the group consisting of:

(l) PD-1$^+$/CD39$^+$, CD38$^+$/CD39$^+$, GzmK$^+$, TIGIT$^+$, TCF1$^+$, 2B4$^+$, CD160$^+$, CD7, Helios, CD103, Ptger2$^+$, CTLA-4$^+$, Tim-3$^+$, LAG-3$^+$;

(m) PD-1$^+$, CD160$^+$, TIGIT$^+$, 2B4$^+$, CXCR5$^+$, GzmK$^+$, CD27$^+$, TCF1+;

(n) CD38$^+$/CD39$^+$, CD16$^+$, CXCR5$^+$, Helios$^+$, PD-1$^+$/CD39$^+$, CTLA-4$^-$, 2B4$^-$, TIGIT$^-$, CD160$^-$, CD7$^+$, Ptger2$^+$;

(o) PD-1$^+$/Eomes$^+$, 2B4$^+$/CD160$^+$/TIGIT$^+$, GzmB$^+$, CD16$^+$, Perforin$^+$, CD57$^+$, CD38$^+$/CD39$^-$, T-bet$^+$, GzmK$^-$;

(p) PD-1$^+$/Eomes$^+$, 2B4$^+$/CD160$^+$/TIGIT$^+$, GzmB$^+$, Tox+, GzmK$^+$;

(q) PD-1$^+$, PD-1$^+$/CD39$^+$, CD39$^+$, Ki67$^+$, CD38$^+$/CD39$^+$, CTLA-4$^+$, CD103$^+$, CD200R$^+$, Tim-3$^+$, Lag-3$^+$, CD28$^+$;

(r) PD-1$^+$/Eomes$^+$, 2B4$^+$/CD160$^+$/TIGIT$^+$, GzmB$^+$, Tox$^+$, CD38$^+$, GzmK$^+$, Ki67$^-$, HLA-DR$^+$, CXCR5$^+$, PD-1$^+$/CD39$^+$;

(s) PD-1$^+$/Eomes$^+$, 2B4$^+$/CD160$^+$/TIGIT$^+$, GzmB$^+$, Tox$^+$, GzmK$^-$;

(t) PD-1$^+$/Eomes$^+$, 2B4$^+$/CD160$^+$/TIGIT$^+$, GzmB$^+$, Helios$^+$, CD16$^+$, Perforin$^+$, CD57$^+$, PD-1$^{++}$, Ki67;

(u) TIGIT$^+$, Eomes$^+$, GzmB$^-$, CD160$^+$, 2B4$^+$, T-bet$^+$, Tox$^{int}$; and (v) TIGIT$^+$, Eomes$^+$, GzmB$^+$, CD160$^+$, 2B4$^+$, T-bet$^+$, Tox$^+$, CD16$^+$, CD57$^+$, Perforin$^+$;

wherein expression of the markers or combinations of markers is assessed by manual gating using (+), (++), or (+++) to indicate increased expression, (int) to indicate intermediate expression, and (−) to indicate decreased expression.

Also provided is a method of identifying T cell populations characteristic of a disease state in a subject having a disease, the method comprising the steps of:

(d) obtaining a sample comprising T cells from the subject;

(e) measuring the expression of a panel of markers comprising one or more T cell lineage-specific markers or combinations of T cell lineage-specific markers and one or more $T_{EX}$-specific markers or combinations of $T_{EX}$-specific markers in the T cells from the subject having a disease;

(f) comparing expression of the panel of markers to expression of the same panel of markers in a control sample comprising T cells; and (d) identifying one or more T cell populations characteristic of the disease, wherein a T cell population characteristic of the disease comprises a greater number of T cells in which expression of one or more markers in the panel in the T cells from the subject having a disease is up-regulated or down-regulated compared to the number of T cells expressing the same one or more markers in a control sample comprising T cells.

In some embodiments, the panel comprises at least three markers or combinations of markers selected from the group consisting of 2B4, CCR7, CD103, CD127, CD16, CD160, CD200R, CD26, CD27, CD28, CD36, CD38, CD45RA, CD57, CD7, CD73, CTLA-4, CXCR5, Eomes, GzmB, GzmK, GzmM, Helios, HLA-DR, Ki67, KLRG1, LAG-3, PD-1, Perforin, PTGER2, T-bet, TCF-1, TIGIT, TIM-3, TOX, 2B4/CD160/TIGIT, CD160/TIGIT, CD38/39, CD45RA/CD27, PD-1/CD127, PD-1/CD39, and PD-1/Eomes.

In some embodiments, the panel of markers comprises a set of markers selected from the group consisting of:

(l) PD-1$^+$/CD39$^+$, CD38$^+$/CD39$^+$, GzmK$^+$, TIGIT$^+$, TCF1$^+$, 2B4$^+$, CD160$^+$, CD7, Helios, CD103, Ptger2$^+$, CTLA-4$^+$, Tim-3$^+$, LAG-3$^+$;

(m) PD-1$^+$, CD160$^+$, TIGIT$^+$, 2B4$^+$, CXCR5$^+$, GzmK$^+$, CD27$^+$, TCF1+;

(n) CD38$^+$/CD39$^+$, CD16$^+$, CXCR5$^+$, Helios$^+$, PD-1$^+$/CD39$^+$, CTLA-4$^-$, 2B4$^-$, TIGIT$^-$, CD160$^-$, CD7$^+$, Ptger2$^+$;

(o) PD-1$^+$/Eomes$^+$, 2B4$^+$/CD160$^+$/TIGIT$^+$, GzmB$^+$, CD16$^+$, Perforin$^+$, CD57$^+$, CD38$^+$/CD39$^-$, T-bet$^+$, GzmK$^-$;

(P) PD-1$^+$/Eomes$^+$, 2B4$^+$/CD160$^+$/TIGIT$^+$, GzmB$^+$, Tox+, GzmK$^+$;

(q) PD-1$^+$, PD-1$^+$/CD39$^+$, CD39$^+$, Ki67$^+$, CD38$^+$/CD39$^+$, CTLA-4$^+$, CD103$^+$, CD200R$^+$, Tim-3$^+$, Lag-3$^+$, CD28$^+$;

(r) PD-1$^+$/Eomes$^+$, 2B4$^+$/CD160$^+$/TIGIT$^+$, GzmB$^+$, Tox$^+$, CD38$^+$, GzmK$^+$, Ki67$^+$, HLA-DR$^+$, CXCR5$^+$, PD-1$^+$/CD39$^+$;

(s) PD-1$^+$/Eomes$^+$, 2B4$^+$/CD160$^+$/TIGIT$^+$, GzmB$^+$, Tox$^+$, GzmK$^-$;

(t) PD-1$^+$/Eomes$^+$, 2B4$^+$/CD160$^+$/TIGIT$^+$, GzmB$^+$, Helios$^+$, CD16$^+$, Perforin$^+$, CD57$^+$, PD-1$^+$, Ki67;

(u) TIGIT$^+$, Eomes$^+$, GzmB$^-$, CD160$^+$, 2B4$^+$, T-bet$^+$, Tox$^{int}$; and (v) TIGIT$^+$, Eomes$^+$, GzmB$^+$, CD160$^+$, 2B4$^+$, T-bet$^+$, Tox$^+$, CD16$^+$, CD57$^+$, Perforin$^+$;

wherein expression of the markers or combinations of markers is assessed by manual gating using (+), (++), or (+++) to indicate increased expression, (int) to indicate intermediate expression, and (−) to indicate decreased expression.

Also provided is a method of monitoring disease progression in a subject having a disease, the method comprising the steps of:

(g) obtaining a sample comprising T cells from the subject;

(h) measuring the expression of a panel of markers comprising one or more T cell lineage-specific markers or combinations of T cell lineage-specific markers and one or more T cell exhaustion-specific ($T_{EX}$) markers or combinations of $T_{EX}$-specific markers in the T cells from the subject having a disease;

(i) comparing expression of the panel of markers to expression of the same panel of markers in a control sample comprising T cells;

(j) identifying one or more $T_{EX}$ populations characteristic of the disease, wherein a $T_{EX}$ population characteristic of the disease comprises a greater number of $T_{EX}$ cells in which expression of one or more markers in the panel of markers in the T cells from the subject having a disease is up-regulated or down-regulated compared to the number of $T_{EX}$ cells expressing the same one or more markers in the panel of markers in a control sample comprising T cells;

(k) repeating method steps (a), (b), (c), and (d) at one or more subsequent time points;

(l) determining the disease has progressed if a second or subsequent sample comprising T cells from the subject comprises a greater number of cells in the $T_{EX}$ population characteristic of the disease than the first or prior sample comprising T cells from the subject; or (g) determining the disease has not progressed if a second or subsequent sample comprising T cells from the subject comprises a lesser number of cells in the $T_{EX}$ population characteristic of the disease than the first or prior sample comprising T cells from the subject.

In some embodiments, the panel of markers comprises at least one set of T cell lineage-specific markers or combinations of T cell lineage-specific markers and $T_{EX}$-specific markers or combinations of $T_{EX}$-specific markers characteristic of one or more disease-associated populations of $T_{EX}$ cells (DATs) selected from the group consisting of:

(g) PD-1$^+$/CD39$^+$, CD38$^+$/CD39$^+$, GzmK$^+$, TIGIT$^+$, TCF1$^+$, 2B4$^+$, CD160$^+$, CD7$^+$, Helios$^+$, CD103$^+$, Ptger2$^+$, CTLA-4$^+$, Tim-3$^+$, and LAG-3$^+$;

(h) PD-1$^+$/Eomes$^+$, 2B4$^+$/CD160$^+$/TIGIT$^+$, GzmB$^+$, CD16$^+$, Perforin$^+$, CD57$^+$, CD38$^+$/CD39$^-$, T-bet$^+$, and GzmK$^-$;

(i) PD-1$^+$/Eomes$^+$, 2B4$^+$/CD160$^+$/TIGIT$^+$, GzmB$^+$, Helios$^+$, CD16$^+$, Perforin$^+$, CD57$^+$, PD-1$^{++}$, Ki67;

(j) PD-1$^+$/Eomes$^+$, 2B4$^+$/CD160$^+$/TIGIT$^+$, GzmB$^+$, Tox$^-$, CD38$^+$, GzmK$^+$, Ki67$^+$, HLA-DR$^+$, CXCR5$^+$, and PD-1$^+$/CD39$^+$; and wherein the panel of markers further comprises at least one set of T cell lineage-specific markers or combinations of T cell lineage-specific markers and $T_{EX}$-specific markers or combinations of $T_{EX}$-specific markers characteristic of one or more health-associated populations of Teat cells (HATs) selected from the group consisting of:

(k) TIGIT$^+$, Eomes$^+$, GzmB$^+$, CD160$^+$, 2B4$^+$, T-bet$^+$, Tox$^+$, CD16$^+$, CD57$^+$, Perforin$^+$;

(l) PD-1$^+$, CD160$^+$, TIGIT$^+$, 2B4$^+$, CXCR5$^+$, GzmK$^+$, CD27$^+$, TCF1$^+$; and PD-1$^+$/Eomes$^+$, 2B4$^+$/CD160$^+$/TIGIT$^+$, GzmB$^+$, Tox$^+$, GzmK$^+$.

In some embodiments, the method further comprises a step of calculating the ratio of DATs to HATs. In some embodiments, the disease has progressed if the ratio of CATs to HATs is increased in a second or subsequent sample comprising T cells from the subject, and the disease has not progressed if the ratio of DATs to HATs is decreased in a second or subsequent sample comprising T cells from the subject.

Also provided is a method of determining the exhaustion state of a subject's T cells, the method comprising the steps of:

(e) obtaining a sample comprising T cells from the subject;

(f) stimulating or activating the T cells;

(g) measuring production of one or more cytokines and one or more chemokines selected from the group consisting of IFNγ, TNFα, IL-2, IL-10, IL-21, CCL3, CCL4, XCL1, and Amphiregulin by the T cells;

(h) calculating a Functional Exhaustion Score (FES) as follows:

$$FES=[(2\times(\% \text{ IFN}^+\text{TNF}^-)-(\% \text{ IFN}^-\text{TNF}^+)-(\% \text{ IL-2}^+))\times(\% \text{ CCL3/4}^+)],$$

wherein "% IFN$^+$TNF$^-$" refers to the percentage of T cells that produce IFNγ but not TNFα, wherein "% IFN$^-$TNF$^+$" refers to the percentage of T cells that produce TNFα but not IFNγ, wherein "% IL-2$^+$" refers to the percentage of T cells that produce IL-2, and wherein "% CCL3/4$^+$" refers to the percentage of cells that produce CCL3 and/or CCL4; and (e) determining the exhaustion state of the subject's T cells, wherein an FES>0 indicates that the subject's T cells are exhausted, and wherein a higher FES indicates an increasing degree of exhaustion in the subject's T cells.

Also provided is a method of monitoring disease progression in a subject having a disease, the method comprising the steps of:

(f) obtaining a sample comprising T cells from the subject;

(g) determining the exhaustion state of the subject's T cells by the method described above;

(h) repeating method steps (a) and (b) at one or more subsequent time points;

(i) determining the disease has progressed if a second or subsequent sample comprising T cells from the subject comprises an increased FES compared to the first or prior sample comprising T cells from the subject; or (j) determining the disease has not progressed if a second or subsequent sample comprising T cells from the subject comprises a decreased FES compared to the first or prior sample comprising T cells from the subject.

In any one of the preceding embodiments, the sample comprising T cells from the subject may comprise blood, ascites, pleural effusion, lymph, mucus, broncho-alveolar lavage or tissue. In some embodiments, the sample comprising T cells from the subject comprises CD8+ T cells, tumor-associated lymphocytes (TALs), or tumor-infiltrating lymphocytes (TILs).

Disease

In some embodiments, the disease is selected from the group consisting of cancer, viral infection, bacterial infection, and parasite infection. In further embodiments, the viral infection is with a virus selected from the group consisting of hepatitis viruses, herpesviruses, polyoma viruses, anelloviruses, adenoviruses, retroviruses, and influenza viruses. In some embodiments, the disease is a bacterial infection selected from the group consisting of *Mycobacterium tuberculosis* (MTB), *Staphylococcus aureus*, *Streptococcus pyogenes*, *Clostridium botulinum*, *Campylobacter jejuni*, *Escherichia coli*, *Listeria monocytogenes*, *Salmonella enterica*, *Salmonella bongori*, and *Vibrio cholera*. In some embodiments, the cancer is responsive to treatment with an immune checkpoint inhibitor. In further embodiments, the cancer responsive to treatment with immune checkpoint inhibitors is selected from the group consisting of unresectable melanoma, metastatic melanoma, Stage III melanoma, metastatic non-small cell lung cancer (NSCLC), NSCLC, recurrent squamous cell cancer of the head and neck (SCCHN), metastatic renal cell carcinoma (RCC), urothelial carcinoma, hepatocellular carcinoma (HCC), bladder cancer, colorectal cancer, ovarian cancer, and endothelial cancer.

Stimulating and/or Activating T Cells

In some embodiments, the T cells may be stimulated and/or activated with phorbol 12-myristate 13-acetate (PMA) and ionomycin. In further embodiments, the T cells are stimulated and/or activated with PMA and ionomycin in the presence of monensin and Brefeldin A (BFA). Methods of stimulating and/or activating T cells are known in the art. By performing the activation step in the presence of brefeldin A ("BFA") and/or monensin, which inhibit protein transport through the cellular secretion pathway, cytokine proteins accumulate in the cells and may be detected.

In some embodiments, the T cells may be stimulated and/or activated with anti-CD3 antibodies, anti-CD28 antibodies, or anti-CD2 antibodies (or combinations thereof). In further embodiments the anti-CD3 antibodies, anti-CD28 antibodies, or anti-CD2 antibodies (or combinations thereof) may be attached to a solid substrate, such as a bead.

Enhancer States

The present disclosure provides methods for identifying enhancers' states in populations of T cells. The present disclosure also provides methods for treating a patient having a disease comprising identifying an enhancer state in a population of T cells from the patient and administering an engineered T cell of the disclosure to the patient. The enhancer state of the cell refers to identifying which enhancer(s) within the epigenome of the cell are in open chromatin region(s) (OCR), and therefore potentially active. In some embodiments, the enhancer state of the cell refers to a specific pattern of open and closed chromatin regions that define an exhausted, naïve, effector or memory T cell.

Epigenetic Pathway

As described herein, an epigenetic pathway comprises any combination of components that contributes to the "epigenome" or epigenomic state of a cell.

The term "epigenetic pathway" refers to a combination of signals or biological components that transmit such signals that together establish and maintain a stably heritable epigenetic state. In certain embodiments, an epigenetic pathway comprises a signal originating from the environment that triggers the start of the epigenetic pathway, an epigenetic initiator that receives this signal and is capable of determining the precise chromatin location and or DNA environment for establishing a particular epigenomic state, and an epigenetic maintainer that sustains that particular epigenetic state in the initial and succeeding generations.

High Priority Epigenetic Pathway

The disclosure provides methods of treating a disease in a patient, the method comprising administering an engineered T cell to the patient, the engineered T cell comprising one or more alterations in one or more high priority epigenetic pathways. In some embodiments, the alterations comprise genetic modifications introduced via genome engineering approaches or epigenetic modifications using inhibitors or activators of epigenetic regulators. In some embodiments, the high priority epigenetic pathway is or has been targeted to reverse or prevent exhaustion of the T cell. In some embodiments, the high priority epigenetic pathway has been targeted by genome engineering, e.g. by knocking out/in genes in the epigenetic pathway, or by modifying the function of protein encoding genes in epigenetic pathways. In some embodiments, the high priority epigenetic pathway is targeted by administering to the patient a drug that modifies an epigenetic pathway. In some embodiments, the high priority epigenetic pathway is targeted by genetic engineering of the non-coding genome in locations that control expression of epigenetic regulators. For example, there are exhaustion specific enhancers that are open in a locus for an epigenetic regulator of exhaustion that may be deleted or modified that would change the expression pattern of the gene. In some embodiments, the gene is Tox, a key epigenetic regulator of exhaustion, and the locus is the Tox locus.

High priority epigenetic pathways are genes, loci, or proteins that fulfill one of the following criteria: a) are genes/proteins with a known or potential role in generating or changing epigenetic marks; or b) genes with known roles in T cell exhaustion based on transcriptional profiling studies that also have distinct epigenetic modifications in exhausted T cells. In some embodiments, the high priority epigenetic pathway comprises epigenetic changes in at least one of Tox, SET protein, RuvBl1 protein, RuvBl2 protein, DPY30 protein, Tox2, Suv39h2, Csprs, Sfinbt1, Hmgn3, Chd9, Rnf2, Ikzf3, Kmt2e, Satb1, Tet1, Tet2, Tet3, Kdm5b, Sfmbt2, Actr6, Prmt7, genes encoding inhibitory receptors and/or T cell transcription factors, and other relevant T cell genes including PD-1, CTLA-4, LAG-3, Tim3, CD200/CD200R, Ptger2, Ptger4, T-bet, Eomes, Tox, Blimp1, BATF, AP-1 family members, IRF4, and other genes described in Wherry et al., Doering et al., and/or Crawford et al. (Wherry et al. Immunity 2007, 27:670-684, incorporated herein by reference in its entirety; Doering et al. Immunity 2012, 37:1130-1144, incorporated herein by reference in its entirety; Crawford et al. Immunity 2014, 40(2):289-302, incorporated herein by reference in its entirety).

Epigenetic Targets

In some embodiments, a target associated with an epigenetic pathway, or as used herein an "epigenetic target", is targeted within a cell with a drug or with genome engineering via CRISPR/Cas9 targeting, as further described below. In some embodiments, the epigenetic target is a Tet enzyme (e.g., Tet1, Tet2), an HDAC, Tox, Tox2, Csprs, Drud1, Sfmbt1, Chd9, Suv39h2, Sap30L, Hmgn3, BAZ2b, Prmt6, SET, Ruvbl1/2, DPY30, MLL proteins, Ezh1/2, PRC complex, CBP, BET, and/or p300. In some embodiments, the epigenetic target can be any histone acetyl transferase, deacetylase, methylase, or demethylase, or any other epigenetic modifying enzyme or chromatin modifying enzyme. In some embodiments, the epigenetic target is an enzyme or intracellular protein capable of regulating epigenetic patterns. In some embodiments, the epigenetic target is a cell surface protein that regulates a downstream epigenetic pathway. In some embodiments, the epigenetic target is at least one of EHMT2, KDM4A, RAD54L2, PHF8, SIRT2, ATF2, KDM3B, TET2, BRD4, KDM2B, BRD9, MINA, SMARCAD1, HDAC2, TRIM28, KDM5C, CARM1, EHMT1, JMJD8, CHD1L, BRPF1, SETD1A, CHD4, SETDB1, NAT10, SIRT7, BRD8, HLTF, PBRM1, SETDB2, SUV39H2, EZH2, HELLS, ATAD2, RAD54L, SETD8, HAT1, RPA3, SMYD2, TAF1, BRD7, HDAC3, TTF2, BAZ1B, SUV39H1, HDAC1, SMARCA4, BRD3, FEV, JMJD6, ACAT1, SETD6, SETD4, CLOCK, SMYD3, KDM6B, KDM6A, SIRT1, SMARCAL1, HDAC5, SP100, ELP3, KAT2A, INO80, CHD3, KDM4B, HDAC8, SETD1B, HDAC7, SETD7, TET1, ZMYND11, CHD8, CREBBP, SHPRH, TET3, HDAC4, NSD1, TRIM33, ERCC6, PHIP, BRD1, KAT2B, CHD1, EP400, NCOA2, BAZ2A, JARID2, SETD5, SUV420H2, ATRX, ZMYND8, HIF1AN, BRPF3, KDM5A, TRIM24, KDM4C, BRD2, CHD9, EZH1, BRWD1, SMARCA2, KDM5B, PRDM2, CHD2, SUV420H1, ASH1L, BPTF, CHD6, KDM3A, EP300, SETD2, JMJD1C, ATAD2B, BAZ2B, BRWD3, JMJD4, CHD5, PHF2. In some embodiments, the cell is a T cell. In some embodiments, the cell is an exhausted T cell.

Transcriptional Targets

The epigenome provides the context in which transcription factors function. Although global epigenetic landscape information did not previously exist for exhausted T cells, studies of the Pdcd1 locus (which encodes PD1) have been informative. Analysis of the Pdcd1 promoter region in acutely resolved LCMV infection demonstrated that these regions were largely demethylated in the effector phase and then became remethylated as infection resolved and CD8+ T cell memory formed. By contrast, the Pdcd1 locus became completely demethylated in chronic LCMV infection and no remethylation was observed, even when viral titers and PD1 protein expression by exhausted CD8+ T cells decreased (Youngblood et al. Immunity. 2011, 35(3):400-12). Similar data were obtained in studies examining well-controlled HIV infection (Youngblood et al. J Immunol. 2013, 191(2): 540-4133). The present disclosure teaches that epigenetic regulation of gene expression in CD8+ T cell exhaustion can prevent or reverse exhaustion and provides evidence for a durable imprint of exhaustion in the epigenome.

In some embodiments, a transcriptional target associated with an epigenetic pathway, or as used herein a "transcriptional target" is targeted within a cell. In some embodiments, the transcriptional target is at least one of Tox, SET protein, RuvBl1 protein, RuvBl2 protein, DPY30 protein, Tox2, Suv39h2, Csprs, Sfmbt1, Hmgn3, Chd9, Rnf2, Ikzf3, Kmt2e, Satb1, Tet1, Tet2, Tet3, Kdm5b, Sfmbt2, Actr6, and Prmt7. In some embodiments, the transcriptional target is at least one of Pdcd1, Ccr7, Gzmb, Lef1, Itgam, Itgax, Itgad, Cd44, Kcnj8, Lrrc9/Rtn1, Ifng, Tbx21, Cxcr5, Il10, Nlrc3, Cd200r, and/or Atp8b4. In some embodiments, the transcriptional target is A330093E20Rik, Rnf19a, 2010010A06Rik, Cdh23, Abtb2, Dync2li1, Lrrc1, Scn1b, Man1a, Gimap3, Lef1, Col26a1, Gpr180, Fam126a, Wdyhv1, Mir6395, Gpr34, Fcgr1, Rpia, A430107P09Rik, Hbs1l, Slc35b3, Tmem248, Cox7a2l, BB019430, Pde5a, Sept7, Lrrc3b, Cd101, Znrf3, Znrf1, Gm6260, Prpf40a, Ets1, Scn3a, Kremen1, Fam210a, Trpm1, Pip4k2a, Trnp1, Sell, Nfia, Lipa, Zc3hc1, Msgn1, Yeats4, Abcd2, Tbc1d1, Kcnh8, Zfp407, Capg, Gm7538, Rgcc, Sh3bp5, S1pr1, Zfp957, Mcur1, D16Ertd472e, Trat1, Fam107b, Mbtps1, Egr3, Palm3, 9030624G23Rik, Ppp6r1, Ckap4, Rngtt, Crtc3, Peak1, Lhx2, Btg1, Serbp1, Cd2, Acoxl, Hormad2, Gm10684, Smo, A630075F10Rik, Ndst1, E030018B13Rik, Skp1a, Kcnh8, Nck2, Frmd7, Cldn10, Peli1, 2010300C02Rik, Insl5, Supt20, Slc4a4, Rph3al, Dip2c, Pm20d2, Nsg2, Rbm26, Tpk1, Stambpl1, AF357399, Car2, Mir145b, Zfp592, Galnt4, Gm5083, Thnsl1, Dhx40, Gm20098, Ly6i, Sugt1, Ywhaz, Rad23b, Bcor, Gm12159, Vegfa, Cacna1b, Arhgef11, 2210408F21Rik, Mettl8, Wdr73, Usp12, Art4, Clvs1, Mir6388, Diap2, Gm10532, Msi2, 4930546C10Rik, Mbnl1, Tm6sf1, Ppp2r5a, Mageb16-ps1, Neurl1b, Sspn, Suv420h1, 2410088K16Rik, Rgl2, Timm8a2, Aebp2, Mam12, Ldhal6b, Peak1, Parp2, Apbb2, Tctex1d1, Dtnb, Tspan3, 4930578N18Rik, Pced1b, Commd9, Lrrc3b, Rras2, Gm10638, 1600002D24Rik, Arsb, Ube2e2, 1700009P17Rik, P4ha2, Susd1, Cdkal1, Efcc1, Malat1, 4931403G20Rik, Tox, Arpc3, Atg10, Gpbp1, Gm5148, AI317395, Abhd2, Celsr1, Tsen2, Pfkfb3, Cyc1, Mir378c, Slamf6, Btg1, Phf2, Cxcr4, Gm10789, Atl2, 6030407O03Rik, Ggnbp1, Angpt1, 9530077C05Rik, Basp1, Rapgef6, H2-Ea-ps, Fam214a, Ppfia4, Lta4h, Ets2, Slc29a1, Xpo4, Gramd3, Itfg3, Fli1, Frmd6, Rbp1, Olfml3, Peli1, Srpk1, Hmgcs1, Irf2bp2, Cxxc5, Ccdc171, Cntnap2, Fance, Cblb, Cubn, Sfmbt2, Srsf3, Pepd, Dgkd, Osbpl6, Trib2, Zfand3, Dchs1, 5430421F17Rik, Fpr3, Dapl1, Trat1, 0610040J01Rik, Gm14005, BC051019, Tank, Tnfsf11, Rara, Pik3c2a, Elmo1, Nck2, Bcl2l11, Fam78a, Gm10638, Prkcq, Gpr126, Bach2, Ttc30b, Nlk, Ube2e2, Usp3, 4932441J04Rik, Larp4b, Serbp1, Dbn1, Vav3, Derl1, H2-T23, C130021I20Rik, Fbxl14, Ets1, Fgf8, Abl2, Acvr1b, Upk1b, Efcab10, Uchl3, Cd302, Cdc40, Nsg2, Tmem222, P2ry10, Klrb1b, Mc1r, Car8, BC048403, Taf8, Atp1b1, Mir30c-2, Luc7l2, Erbb4, Arhgdib, Ube2h, Itpr2, Vav3, Ptgfrn, D630010B17Rik, Eif2s3x, Vav3, Nfe2l3, Ccdc171, Fignl1, 4930519F09Rik, 1700123O12Rik, Acsf2, Ndufb9, Atp7a, Upp2, Ptpla, Man1a, Rgs3, Zbtb2, Trib2, Npr1, Fez2, Tle4, Fuca1, Cmip, Bcap29, Syne1, Dmbt1, Ell, Blnk, Sepw1, Gltscr1, Erdr1, Med13l, Moxd1, Btg1, Akap6, 1810053B23Rik, Rsu1, Gprasp2, Art4, Gpd2, Tmlhe, A430107P09Rik, Kcnj9, Atp8a1, Adam6b, 2010109I03Rik, Spred2, Raver2, Ap1m2, Dclre1a, Rbp7, Gcc1, Traf4, Satb1, Gm5538, Il12a, Fam60a, Thrb, Elk3, Vps45, Tle4, Akap13, Gprin3, Sox21, Emp1, Wfdc2, Slc45a1, Lnpep, Rapgef6, Txn2, Frmd4b, Myoz3, Zfp870, Bcl6, Mvb12b, Ntrk3, Spaca1, Mir701, Cdca7, Gm5083, S1pr1, Spry4, Cck, Il6st, Hebp2, Slc43a2, Tdrd5, Gm5833, Mir7-2, Mir1931, Pdgfb, 1700052N19Rik, Nfkbiz, Gm20753, Hapln1, Rras2, Diap2, Manba, Cers6, Rasgrp1, Lnpep, Apln, Ephb2, Arpp21, Mical3, Chic2, E130114P18Rik, Ipcef1, Dyrk2, Bach2, Mir122a, B230206H07Rik, Ceacam9, A730006G06Rik, 4930542C21Rik, A430107P09Rik, Trat1, Ccr2, H2-Ob, Adm, Yeats4, Ccne1, Gpc5, Spsb1, Jrk1, Orc4, Camkmt, Nfia, Celf2, Gadd45a, Gtf2a1, Nrde2, Nipa2, Rmi2, Lcor, Btg1, Atg10, D6Ertd527e, Ccm2, Dpysl2, Dirc2, Cpm, Arhgap15, A730043L09Rik, Raph1, Cst10, Slc7a13, Ramp1, Atp1b1, Zfp120, Slc39a13, Zfp706, Agr2, Tagap, Mir3110, Ubash3b, Dnmt3aos, H2-B1, Agbl1, Smc6, 1700060C20Rik, Trib2, A930005H10Rik, Btg1, Scml4, Mir196b, Efna5, Tmem14a, Kcnj15, Snrpd3, Nnmt, Ryr1, Ptk2, P2rx4, 5830428M24Rik, Commd3, Cd28, Hspb11, BC021785, Tcf7, Cstb, Art4, Tet3, Map3k13, Camkv, Ralbp1, 9330175M20Rik, Tgtp1, Selt, Irgc1, Tcf7, Tet1, Bnip3l, Nrbf2, Nim1k, Rfx8, Tlr6, Grik1, Tox, 1700061G19Rik, Dhrs3, 4930519G04Rik, Mid1, Ap1ar, Basp1, Aqp4, 4930415F15Rik, Aif1, Rnf125, Fam134b, Atp13a3, Dmbt1, Mbnl1, Nfam1, Lmo4, Znrf1, Ambp, 4930523C07Rik, Bfsp2, Zfp592, Gm2447, Gm16157, Gjd3, Tgtp1, Ston2, Lypd6b, Rnf7, Zbtb2, BC051537, 4930417O13Rik, Arntl, Ttc9b, Foxp1, Mir7219, Mrgprb5, Tnik, Dhrsx, Foxp1, Tubb2a, Cyb5r2, Itga4, Snx9, Fam65b, C78339, Mir7212, Ldlrap1, H2-Oa, Snx12, Tdrp, Mnd1-ps, Foxp1, Gucy2c, Creb1, Scn4b, Irf4, Rftn2, Gpr125, Dpf1, Fam134b, Akap13, Tmem108, Suclg1, Mn1, Sema4b, Gm6682, Slc46a2, Dennd3, Bach2, Sytl2, Grhl3, Smad3, 1600014C10Rik, 4930455C13Rik, 3200001D21Rik, Nup153, Grk6, Zfhx3, Fhit, Hmg20b, 4930564D02Rik, Bach2, Slc39a3, Urad, Smc1a, Maml1, Zadh2, 8030462N17Rik, Fsbp, Tmem243, Srp14, Lix1, Tmc1, Tspan11, Tns1, Serpinb5, 1810026B05Rik, Smad7, Mir3108, Phxr4, Tmem131, Olfr1507, Kidins220, Mir378c, Afap1, Rere, Sin3b, Efemp2, Neto2, Mir7669, Tgtp1, Gramd3, Map7d2, Chst2, Sp110, Ccdc162, Igf1r, Mir3110, Dcdc2b, Dse, Dlgap2, Armc9, E230029C05Rik, Gm11944, Tnik, Kat6b, Nkiras1, Tbcel, B4galt1, Cd2ap, Tnks, Icos, Tanc1, Sik1, Tor1aip2, 4930453N24Rik, Bnip1, Gm6313, 4930415F15Rik, Inpp5a, Atoh7, 2210417A02Rik, Pdss2, Lamtor3, Ptbp2, Ostm1, Nrarp, Fry1, Mir1907, Gm10638, Sumo1, Zfp60, 1600014C10Rik, Haao, Syde2, Ep300, Ndrg3, Tex2, Cdx2, Eefsec, Tmem131, Mir6959, Fyn, Prkcq, Mical3, Snhg7, Ambra1, Rag2, Vdac1, Ptpla, Tram1, Aak1, Pebp4, Sgpp1, 2410007B07Rik, Itpr2, Tulp2, Mir6395, Elovl6, Ppp1r3b, Zc3h4, Sptbn4, Rap1b, Vgll4, Kcna2, Cnot6, Tbc1d1, Pde4d, Rapgef4, Fbxo47, Proca1, Aim, 2310001H17Rik, Tmem131, Sh2d3c, Gtpbp8, 1700030C10Rik, Polr3b, Fam69a, Bcan, 4930465M20Rik, Sbp1, Emg1, Aaed1, LOC102633315, 5930430L01Rik, Adsl, Foxp1, Gm20337, Trdmt1, Gm9920, Foxo1, Olfml3, Fyb, Pgpep11, Nsg2, Tex26, Fancc, Cngb1, Rapgef2, 2010010A06Rik, 2410007B07Rik, Lbh, Pnrc1, Lad1, Mycn, Abad15, Cd1d2, 4930428G15Rik, Hnrnpll, Dnaja2, Ccr7, Mmp15, Neto2, Bach2os, Efr3a, Rnf41, Mir7656, Znrf3, Rtkn2, Sesn1, Zp3r, Glrp1, Kdm7a, 3200001D21Rik, Pdss1, 5730403I07Rik, Mmp15, Thrb, Zbtb16, Vkorc1, E330009J07Rik, Dntt, 4933406J10Rik, Sim2, Lgals9, Gm12216, Grb10, Ednra, Fam3c, Birc6, Bace1, Sfrp2, 2010107G12Rik, Zfp184, Ctso, Zfp462, Abcb1a, Gm6639, Mir1258, Dyrk1b, Ralb, Thrb, S100a6, Gm590, Dnajc1, Zfand3, Blm, Ikzf2, Lrrc32, Nsg2, Foxp1, Tnpo1, Zfat, Specc1, Snora75, Vps45, Acp6, Syde1, Ext13, Fbxl14, Cdh26, Celf2, Cd2, Tshz2, Cntln, Fam65c, Dad1, Akap6, Gm15880, E330011O21Rik, Kdf1, Gstt1, 2700046G09Rik, Sort1, Nyap2, 1700063O14Rik, Cog6, Extl1, Vmn2r96, Il12b, Lclat1, A430107P09Rik, Zkscan16, Chl1, Nck2, Cdy1, St6gal1, Mir21c, 2810428I15Rik, Cnr2, Rab44, 1700064J06Rik, Zfp191, Peli1, Als2cl, Gnas, 2300005B03Rik, BC033916, Cd226, 1700049E22Rik, Nipal1, Gimap6, Gm5086, 8430436N08Rik, Ift80, Zfp697, Svs1, 4930459C07Rik, Epcam, Zfp706, Pde11a, Slc43a1, Slc9a9, Tshz2, Fbxw11, Mir7046, Zpbp, 1700123O12Rik, Slc16a1, Gm7457, Tcf4, Fbxl12, Il9r, Galnt6, Gm5868, Panx1, Hs3st5, Jarid2, Phxr4, Dock2, Nrip1, Lasp1, 1700066B19Rik, Marcks, Plekha7, Wdr41, Pdss2, Gpr83, Rapgef4, Gm15910, Colq, Olfr1507, Vgll4, Fgfr1op, Fanc1, Capn1, Lonp2, Rnf38, Gpaa1, 1700016G22Rik, Vmn2r98, Gm7325, Gm826, Rpl31, Klrc1, Ikzf1, Crlf3, Cd44, Gypc, AU019990, Fbxl13, Tsc22d3, Tgm2, Ptpn14, Fancc, Arhgap26, Tgfbr2, Klf2, Sept7, Ptprc, Btn2a2, 4921511I17Rik, Ppp2r5a, C78339, Arhgap39, Ism1, Mpzl2, 2810459M11Rik, Dyrk2, Tspan13, Fbxl14, Plat, Celf5, Susd3, Rps6ka2, Gtf2ird1, Naif1, Rsph3a, Tssc1, Ext1, Snora7a, Bcl2l11, Pip4k2a, Npl, Tmem236, Cox7a2l, A530013C23Rik, Rgl1, Pgk1, Ift80, Emid1, Inpp4b, Cldn10, Gls, Tnni1, Folr4, Gm5766, Olfr1507, Hpcal1, Cyth4, St8sia6, 5430434I15Rik, Ropn1l, Serinc1, Mad2l1, 4921525O09Rik, A430107P09Rik, Gm11127, Tra2a, Urb2, Pgpep1l, Cacna1d, 5730403I07Rik, Fam49a, 1700025F24Rik, Stat1, Calm1, Kcna7, Eif1, Mir669m-2, Kdr, 1700123O12Rik, Mir8099-2, Hspa8, 2010010A06Rik, Zfp53, 4930524O05Rik, Abl1, Uvrag, Slc16a1, Dnah7b, Golph3, Ipcef1, Usp3, Jun, Snord89, Tcf7, Rbpms, Folr4, Papss2, Spred2, Stpg1, Mgat5, Lpin1, D8Ertd82e, Dhx40, Slit3, 4933405E24Rik, Nsun6, A430107P09Rik, Apol7e, Raly, Celf2, Ndufs7, Mir6921, Kbtbd11, Gc, Haao, Gm9054, Slc44a3, Tnfrsf19, Lef1, Ankrd11, Plxdc1, A430107P09Rik, Zcchc2, Zmat4, Jun, Adamts14, Slamf6, Adamts17, A430107P09Rik, Alox5ap, Mir6368, Ncor2, Ets1, Pmpcb, Mvk, 4922502D21Rik, 1700025G04Rik, Rgmb, Gpnmb, Stk17b, Ceacam9, Ttc1, E130006D01Rik, Camkmt, Ankrd63, Agtr1b, Khdrbs1, Zfp706, Cux1, 4922502D21Rik, Btbd1, Timm8a2, Itga4, Reep2, Uvrag, Cyfip2, Elovl6, Tfeb, Spag16, Tbcel, Lmo2, Rasgrp1, Fam86, Ktn1, Fbxo32, Gata3, Ly86, Ptgs2os2, Fam111a, Lrrc16a, B430306N03Rik, Tff3, Kcnn4, Mtif3, Ldlrap1, Tmem260, Pla2r1, Basp1, Ncoa3, Ngly1, Ccdc162, Nhsl2, Cdc123, Hnrnpu, Arhgap18, Zfl2, Gm6498, Bex6, B630005N14Rik, Dynlt1b, Lypd6b, Clec2e, Rbm17, Pstpip1, Lrp12, Akap2, Camk2d, Igf1r, Atp1a1, Gsn, Rragd, Actn1, Odf3b, Nudt4, Vmn2r99, Parp11, Adipoq, Fam221a, Il6ra, Kif23, Fabp5, Srpk2, Ikzf1, Fbxw7, Slamf9, St6gal1, Vav1, Serbp1, Reep1, Agr3, Plc12, Kcnj15, Aebp2, Gm20139, Mtx2, Sel1l, Mbnl2, A430078G23Rik, Krr1, Lclat1, Zfp438, 4930487H11Rik, B4galt1, Ifngr2, Olfr221, Asb4, Gm6793, Ap1m1, Pdlim5, Gltscr1, 1110032F04Rik, Ankrd13a, Abcd2, Iqsec1, Inpp5a, Pdzrn3, Akirin2, Pip4k2a, Dyrk2, Jun, 4930465M20Rik, Osbpl9, Ttc30a1, Ctnnbl1, Tmem243, Olig3, Ubtd2, 4930540M03Rik, Dnajc5b, Dennd1a, Gadd45a, Rpl8, Dapl1, Cd2ap, 6430710C18Rik, Slc16a5, Rcbtb2, Hmgxb3, A630075F10Rik, Ankrd2, St8sia1, Ptk2b, Paqr8, Tox, Wdr37, Stat4, Rplp1, Ccnj, Hspbp1, Mthfd1l, Zcchc9, Gm13293, Camk4, Htt, Usp10, Plekha6, Gm5617, Cnksr3, Mir7218, Lcp2, Cd28, Lbp, Ncoa3, Skil, Hey1, Mir6368, Akap6, Spin1, Ccdc174, Stambpl1, Ggta1, Pifo, Stim2, Rras2, Tomm20l, Gm5538, Skap2, H2-Ob, Zfp3612, Clec2d, Erdr1, Dapl1, Vasp, Cytip, B4galnt3, Hamp, Mex3b, Tcf712, Vps13d, Alox5ap, Mtss1, Gm7457, Fam46a, Taf3, 2810408I11Rik, Ms4a7, Mad2l1, Selt, Snrpf, Hcn2, Frmd4b, Hivep1, Tspan13, Nfia, Asap1, Nt5e, Misp, Mam12, Sh3pxd2a, Ccdc162, Setd7, Etohi1, Acvr11, Fntb, Shank3, Rhoh, Prok2, Marcks, A830010M20Rik, Ywhaz, Mtss1, Gm8369, Fam188b, Atp2a2, 4933405E24Rik, 4932443I19Rik, Notch2, Zc3h12b, Numb, Neb, Ramp1, Zfp831, Impdh2, Grk1, 4930459C07Rik, Mir7035, Setd3, Cdc42se2, Spo11, Fam166b, Mir6419, Atp10d, C2cd5, 4933412E24Rik, Boll, Calr4, Il22ra2, Slc22a16, Syde2, Fyn, Slc27a6, Stx3, Gm6313, Rbm18, Gm13293, Tbc1d8, Fabp5, 4930546C10Rik, Slc16a1, Cnr2, Kcnip2, Trim69, Agbl1, Plvap, Ms4a6c, Usp38, Atl2, Sh3kbp1, Ppfibp2, Pim1, Pmis2, Sh3pxd2a, Ms4a4c, Klf3, Cblb, Mir701, Dmwd, Mtss1, Cdk13, Cabp2, Chdh, Pde4b, Ston2, Cmah, Fbxl14, Syk, Trio, Btg1, Ski, Cnot2, Stk38, Tm9sf3, 4930482G09Rik, Parp11, Jarid2, Mam13, 6430710C18Rik, Commd9, Fhit, Scamp1, Tcf7, Ncf1, Ric8b, Gm3716, Scml2, Nr2f2, Ssr1, Il6st, Ankrd50, Pnmal2, Foxp1, Raver2, Ccdc64, 8430436N08Rik, Klf13, Itga5, Commd3, Mro, Ms4a7, Rock2, Enc1, Rab3gap1, Nav2, Tlr1, Gm7457, Elfn1, Rpl34, Agfg1, 1700020N01Rik, Irf4, Gm8369, Olfr1507, Grik4, Akap6, Mir6387, Thrb, Gm20110, Mir7670, Bag4, Gm15441, LOC101055769, Pak1, Mbd2, Ralgps2, Lipg, Gpnmb, Ubash3b, Kntc1, Aqp9, Znrf2, Cmah, Peli1, Chd7, Tmsb4x, Copb1, Gimap1, Bcas1os2, Ppapdc1b, Cdc14a, Ier5, Susd3, Birc2, Sun2, Itga5, Rlbp1, St8sia1, Hectd1, Chn2, Bcas1os2, Slc39a11, Cdc7, Me3, Stk17b, Ccr4, Peli1, Cd226, 2510009E07Rik, Sh2d1a, Zfp2, Mei4, Chst2, Nipal1, Tbcel, Itgb6, Tmed10, Gm4489, Tmcc1, A430107P09Rik, Abtb2, Tgfbr3, Zfp704, Reep5, Apcdd1, Pik3r1, Ms12, Gm20098, Eif4e3, 5430402O13Rik, Tssc1, Lphn2, Kcnh8, 4921525O09Rik, Fam46c, Pum2, Itsn2, Slc11a2, Usp6nl, Gimap6, A430107P09Rik, Nipb1, Nrxn3, 1700042O10Rik, Capn3, 4930526I15Rik, Plat, Gm15850, Dock10, Shisa2, Wbscr16, Egfl7, Zfp957, Gm20110, Slc4a8, Ago2, Pnp2, Tgfbr3, Hmga2, Pdlim7, Dip2c, Atp1b1, Pxk, Snora26, Gm6498, Sema3d, 3300002I08Rik, 9330175E14Rik, BB123696, Fibcd1, Slc6a19, S100a6, Commd9, Lpar4, Cntn5, Nr1i2, Panx1, Dock2, Ptov1, 5330411J11Rik, Sec24d, Ms4a4b, Eif3g, Rsbn1l, Plxnc1, Jarid2, 1810041L15Rik, Diap2, A630075F10Rik, Klf13, Tlk1, Lef1, Slc4a4, 2610020H08Rik, Tbce, 9430014N10Rik, Slc16a10, 2310042E22Rik, Lrrc3b, St6gal1, Tnfrsf1a, U90926, Fam134b, Grxcr2, Dok5, Aldh8a1, Cybrd1, Smarcb1, Jmy, Zfp608, Cdkn2aipnl, Aire, Prps2, Gm839, 4933412E24Rik, St6gal1, Ube2d2b, Mab21l1, Slc23a2, Keap1, Brdt, Piwil2, A930005H10Rik, Fyb, Ncald, Lgals9, Zfp704, Dguok, Gm15706, Nr3c1, Med13, Rictor, Paxbp1, Mir1903, Sv2a, Slx1b, Tbc1d24, Wnt5b, Ccr7, Ptk2, Mir21c, Aox4, Slc35b4, Mgat5, Zfp281, Mycn, 1700016G22Rik, Odc1, Prkcb, Ate1, Ncbp1, 3300002I08Rik, Ly6d, Spag16, Clk1, Atg10, 1700030L20Rik, Nsg2, Agps, Goltla, Cntn5, Cadm4, Malsu1, Frmd4b, Gm6607, Cdh23, Gramd4, Slc44a2, Limd2, Lphn2, 1700010K23Rik, Lrrc66, Akap7, Pea15b, D030024E09Rik, Zscan10, Lsm2, Kcnj13, Cdhr3, Fbxl17, Lhx2, Olfm2, Cyp2r1, Wisp3, BB123696, Nlrc4, 2010010A06Rik, Elovl6, Eea1, Mir1907, Gls, B4galnt3, Epb4.1, Tshz1, Gpr126, Rgmb, Ncs1, Tet1, Hoxa1, 4930515G16Rik, Usp33, Stk10, Klh16, Ccdc109b, Manba, Gm5111, Chst15, Runx1, Rgs3, Gm4759, Ldlrad4, 4933400F21Rik, 4933406C10Rik, Diap2, Mir6403, Plin2, Zmiz1, Mam13, Fam86, Hbs1l, Inpp4b, Gm14405, Mgat5, Cntn5, Ramp3, Ifnk, Pgm1, Mfsd6, Armcx1, Mir5127, Gimap6, Mir6387, Slc38a2, Gsdmcl-ps, Cd24a, Kmt2e, Csrp1, 9530052E02Rik, Stk17b, Fyb, Lhfpl5, Atp8a2, Amn1, Sertad2, Epb4.1l2, Stk24, Cdk17, Camk4, Rpa1, Zmynd11, Efcab11, Mir491, Zc3hc1, Vps45, Rgs3, Ube2m, Tspan5, Insr, Snapc1, Btg1, Cox10, Znrf1, Camk4, Ddr1, Gm11981, Sesn1, Commd8, Nrip1, Polr3k, Eya3, Ppp1r1b, Pcdh7, A430107P09Rik, Efcc1, Mtss1, Hpn, Armcx1, Gm20139, Alg14, Sec11a, Cyb5d1, Trpm1, Fam65b, 5730508B09Rik, Frmd4b, Gm10584, Gm5069, Pmepa1, Sell, Mir6413, Klf12, Rhoq, Plc12, Prrc1, Emp1, D030024E09Rik, Rnf145, Bach2, Prkcq, Hic1, Msmo1, Map3k7cl, A1854517, 4922502D21Rik, Vti1a, Zcchc9, Spats2, Mir7681, Wdr89, Bcl6, Cytip, Gm13293, Creb314, Peli1, Pak1, Efcab11, Usp7, 4931403G20Rik, 1700030A11Rik, Mvb12b, Ampd3, Cubn, Baiap3, Med30, Actbl2, Kat6b, Peli1, Tmevpg1, Nsf, Hpcal1, Ube4b, Fam110b, C330011F03Rik, Inadl, Sesn3, Tmem30c, Itgb6, Dlg1, Srp14, 3300005D01Rik, Ggact, Mir21c, Cyp2s1, Mir7061, Bach1, Insr, 2410114N07Rik, H2-Eb1, Tasp1, Tusc3, Irf2bp2, 1700056E22Rik, Ppp6c, Slain2, Cnn3, 6030407O03Rik, Acbd6, Hmgb1, P2rx4, Cdk19, 1700061G19Rik, Tesk2, Plxnc1, Ercc3, 2010010A06Rik, Stk17b, Tspan9, Kcnj16, Ddx10, Wnt16, Sp4, Hilpda, Slc38a6, Tgfbr2, Fggy, Sugct, Begain, Mnd1-ps, Ksr2, Eif2d, Ms4a4d, Stim1, Cst10, Nfatc1, Ppifos, Gng7, Mir211, Txk, 4930415F15Rik, Tmem64, Stim1, Pip5k1b, Kcnj15, Commd8, Mir3108, Atp11b, Stk17b, Emc3, Cldn10, Akap13, Abcb1a, Mthfd1l, Foxk1, Rgs3, Gdnf, Micu1, Il7r, Arhgap35, Olfr1364, Ms4a4b, Rgs10, Flt3, Sfrp2, Il9r, Sf1, Gm1604b, Galnt4, Dtnb, Supt20, Fntb, Zmynd11, Tulp3, 2410007B07Rik, Tsen15, Abhd2, Dgcr6, Filip1l, Ift81, 4933401D09Rik, Gtdc1, Ano6, Mir1928, Peli1, Jak1, Cdk19, Syne1, 1123r, Tpm2, Fam65b, Kidins220, Vav1, 9030617O03Rik, C1ql3, Ceacam9, Ehd2, Vtcn1, Dusp7, Pik3ip1, Ostm1, Ppard, Olfr372, Mir7032, Npy, Phxr4, Grap2, Thrb, Wipi1, Dock4, Mfsd6, Zmynd8, Mylip, Setx, Ccdc146, Il12a, Sall3, Mir7048, Hapln1, Casp3, Bbs9, Syne1, Tdrd3, 4930565D16Rik, Gm20098, Tcf4, Haao, Snd1, Zfp706, Agfg1, Gm8709, Syne1, 4933406J10Rik, Pik3c2b, Manba, Olfr1033, Aurkb, 9330175E14Rik, Foxo1, Sfmbt2, Bach2, Pogz, 4930459C07Rik, Phxr4, Map7d2, Gm20750, Il12b, Sesn3, Psen2, Suco, Mad2l1, E030030I06Rik, Gadd45a, Abca1, Boll, 4930430F21Rik, Cstad, Lyst, Rasgrp4, 4833427F10Rik, Ehd2, 4930445N18Rik, Ppm1h, Gltscr1, Irf8, Lgi1, Gm10432, H2-M10.1, Crtc3, 4930453N24Rik, Irs2, 1700042O10Rik, Rabgap1l, Rnf144a, Csk, Rpia, A430090L17Rik, Mir8097, Serbp1, Mir684-1, Tcf4, Commd8, Tet3, Nr1i2, Gm10190, Prkcq, Orai2, Dpy30, Sbk2, Tssc1, Cd5, Sipa1l2, Dcp1a, 1810006J02Rik, Itgae, D030025E07Rik, Wibg, Bach2, Irf4, Ctnnd1, Usp7, Rftn1, Themis, 4930440I19Rik, Thrb, Nr1d2, Tgtp1, Ccdc162, Atp8b2, Speer4f, Stra8, Gm4906, Fam46c, Pag1, Etv3, Erdr1, Dhrsx, Fam65b, Gosr1, Trem2, Fbln1, Sp3, Mef2a, Bcor, Map4k4, Magi2, Pak2, Rph3al, Lgi4, Pja2, Tceal3, Efcab11, Arhgap5, Ext1, Smyd3, Prim2, Satb1, Stag2, Themis2, Pim1, Apol8, Lrrc6, Shb, Magi2, Commd8, Zfp879, Trp53i11, Rgl1, Abcd3, Diap2, Zbtb2, C030016D13Rik, Arhgdib, A630075F10Rik, C730036E19Rik, Phc2, Adamts10, Inpp4b, Cd200, Itpr2, Fgfr1, Gm5434, Scn2b, D8Ertd82e, Gm2a, Ube2v1, Bend4, Lpp, Mir181a-2, Gm13293, P2ry1, Klf7, E030018B13Rik, Rhobtb2, Ddr1, Ggnbp1, Gimap7, Mamstr, Cmip, Setbp1, Fcgr4, Slc1a3, Zfp608, 2810403A07Rik, Gm7538, Mir378a, Hoxa13, 2610301B20Rik, Ngly1, Sergef, Tpp2, Slc35b3, Mam13, Nav1, Txk, Fam195a, Scml4, Tlr12, Gpr125, Zfp3612, Suclg2, Tec, Akap2, Rab38, C030018K13Rik, 4933433H22Rik, Osbpl11, Capn13, Ankrd50, Mir1928, Mir3108, Slc39a10, Dock2, Dip2c, Aebp2, A530046M15Rik, Gm6251, Mtx2, Exoc4, Olig3, Dph6, Emb, Xpc, Gm7538, Tnfsf8, Afap1l2, Cenpv, Gsn, Rbms2, E2f3, Smarce1, Foxp1, Slc37a3, Apbb1ip, Tex10, Bend4, Pcgf5, Trio, Klf5, Gja8, E130006D01Rik, Ncor2, Acbd6, Alg14, Scmh1, D830013O20Rik, Galnt4, Ndufa6, Timm8a2, 2210010C04Rik, 4931403E22Rik, Gys2, G630090E17Rik, Dapl1, Nup160, Fxyd7, Zscan18, Bid, Serh1, Cdk17, Lrtm2, 3930402G23Rik, Tm2d1, Snora7a, C8g, Nkap, 2410007B07Rik, Ilf3, Mir7017, Gpr83, Thada, Ambra1, Fancc, B3galt4, Thnsl1, Etv5, Aox2, Tgm2, Man1a, Edem1, Hnrnph1, Atp6v0e2, Clec4f, Hey1, Fam3c, Stat4, Slc46a1, Rps15a-ps6, Kdm4c, Upb1, Sik1, Nceh1, Prkcq, Btg1, Galnt2, 2010010A06Rik, Neu3, Cubn, Mir1928, Rapgef2, Nedd41, Egfl7, B3gnt2, Tgtp2, Gm13546, Ext1, Pold4, Ggact, B3gnt7, Gm5868, Tlr7, Lefty2, Npff, Tcf712, D130058E03, Pag1, 4930578N18Rik, 6430710C18Rik, Fam43a, Snora81, Cyp20a1, 4922502D21Rik, Lsm1, Gm10791, Kcnh2, 1700109K24Rik, Nol6, 4922502D21Rik, Trib2, Nrf1, Rgag4, 4930426L09Rik, Ppil3, Vmn2r96, Ngly1, 1810046K07Rik, Hid1, Olfr1510, Nrip1, Dhtkd1, Ms4a6b, 4930583K01Rik, Atp1b3, Mir7046, St8sia1, Pcdh7, Micalcl, D030024E09Rik, Pold4, Coro2b, Adamts14, Auh, Fus, Hc1s1, Prkcq, Nim1k, Zdhhc14, Kcnh2, Cd37, Ttc27, Olfm2, Ubac2, Mir6387, Zfp619, Zbtb9, Gpr125, Ppp2r5a, Adgb, Pard3, Ctrl, Ddr1, Ckmt2, Lpar6, Sspn, Gm4792, 9430008C03Rik, Ngly1, Tbx19, Heatr1, Cdc14a, Nabp1, 8430436N08Rik, Cd247, Llph, Pex10, Eea1, Lef1, Ly75, Dock11, Haao, Rgs3, Mnd1-ps, Maml1, Stxbp1, Parp11, G530011O06Rik, Mgrn1, Ift57, Mef2a, AI427809, Ldhb, Cdk19, Lrrc3b, Osm, Dnajc15, Mirlet7i, Stk38, Cep170, Rcn3, Gramd1a, Mfng, Vgll4, 1700017N19Rik, Atp1a3, Ptpla, Mir6962, Jun, Cdk19, Gm10638, Zfp3612, Slc39a10, Tpd52, Mthfd11, Agbl1, 4922502D21Rik, Ceacam2, Drosha, Fut8, Cox10, Dnajb12, Thns12, Eefsec, Pgpep11, 4932441J04Rik, Fndc7, Clip1, 2700046G09Rik, Itpkb, Kremen1, Mpp6, Ccr9, Tbcb, Rictor, Gm3716, Icosl, Cpeb4, Mir7681, Kmt2c, Mak16, Gi1, Actl9, Gpatch2, Sept14, Aebp2, Phlpp1, Zfp957, Ap3m2, Zcchc2, C030018K13Rik, Cdk17, Tmem217, Cog6, Dock2, Il7r, Crybb2, Slc16a10, Ppp1r1b, E430016F16Rik, Fbxo17, Akr1d1, D10Jhu81e, Irgc1, Klf7, Pcdh7, Nipb1, Rrn3, Mir7681, Arhgef33, Rhoq, Dusp5, Itga4, Palm2, Map10, Tigd2, Mfge8, Zfp580, Peli1, Trim59, F730035M05Rik, Gpr110, Lyst, Slc10a4, C230029M16, Gpnmb, Rgs3, Rab3ip, Vps54, Cox7a2l, Slc7a15, Serbp1, Slc22a16, Prkch, 4933433H22Rik, Arap2, Mkl1, Slc22a16, Fli1, Stk24, Stard8, Arhgap29, Pcca, Treml2, Tssc1, Pgpep11, Syde2, A430107P09Rik, Foxo1, 8430436N08Rik, D030024E09Rik, Tcf7, Ifitm6, Ctso, Capzb, Lypd3, Lix1, Ccdc170, Tasp1, Dnah7a, Sugt1, Pde7a, Pcnp, Klf5, Olfr1357, Ldha16b, Kctd12b, Cxxc5, Pkn2, Mboat2, Angpt1, N6amt2, Gm839, Bach1, Il2ra, Ankrd12, Ccdc64, Pptc7, Ikzf2, Svil, Tlr1, Rell1, Tma16, Mbnl1, Cyfip2, Rps6ka2, Elovl6, Dapl1, Zfand3, Unc5cl, Zfp619, Sytl3, BC031361, Fam26e, Gm2799, Chst15, LOC101055769, Sepp1, a, Ccdc171, Hemgn, Pik3c3, Lrp12, Capn11, Pvr, Prkcq, 4932702P03Rik, 2300002M23Rik, Tef, Foxp1, Lypd6b, 4933412E24Rik, Wnt4, Marco, Elfn2, Smim9, Dip2b, March2, Frs2, Olfr1507, Mir7219, Fbxl22, Vim, 4933432G23Rik, L3mbtl1, Mad1l1, Calr4, Lrrc3b, Strada, Mir363, Tspan9, Esrp1, Panx1, Tgfbr2, Emb, Spata3, Ext1, Calm2, AY512915, C530008M17Rik, Mitf, Wdr11, Mir5127, Selt, Gm6623, Gm684, Gm3716, Tgtp2, Sptb, Hamp2, Itgb6, Cd2ap, Prnp, Ift80, Slamf6, Pou2af1, Snx29, G530011O06Rik, Wipf2, Fam134b, 4930428G15Rik, Igll1, Phxr4, Sgms2, Gm12159, Igf2bp3, Haao, Bai2, Sh3pxd2a, Scn4b, Eif4e3, Snx29, Tmem194b, Ifngr2, Gm5766, Zcchc24, Sox5os3, Efna5, Tecta, Mir7687, Mir6367, Itga4, Tns4, Ccm2, Wipf1, Cerk, Znrf1, Elovl5, Phtf2, 1300002E11Rik, 2210417A02Rik, Mir7061, Grhpr, Mark4, 4930564C03Rik, Svopl, Pja2, Tfdp2, Rbm11, Usp6nl, Mir6368, A430107P09Rik, Bcl2, Cdc42se2, 4933433H22Rik, Apol8, Xpnpep2, Dach2, Mir205, Stard5, Fsbp, Rph3al, Vav3, Gm10125, Lpcat1, Cd2ap, Bank1, Smurf1, Aox2, C230029M16, Sgms1, Eci3, Xpnpep2, Pfkfb2, Utrn, Ldlrad3, Gabrr1, Kcna2, Ywhaz, Stard13, Atp10a, Slc39a10, Whsc1l1, Gm12522, Trio, Man1cl, Hmha1, Gm10791, Kidins220, Lad1, Mir1928, Gm13710, Mir1963, Lama4, Pard3, Susd3, Taok3, Skor2, Matn2, Tet2, Mir7674, Ccdc64b, Fam49b, 4933412E24Rik, Thsd1, Sall3, Papss2, Tceal3, Rreb1, Klrd1, Rgs3, Cst10, Itga4, Gm20098, Smarca4, Cyp2d22, Kdm6b, Cntn5, Dyrk2, Dusp10, Srpk2, Etv5, Slc25a25, Cfl2, Micu1, Ets1, Gm6559, Zfr, Mrp152, Cerk, D630010B17Rik, Ext1, Cblb, Gnai2, Apol7e, Manba, Dusp10, Smim8, Mir6907, Pard3, Tmem35, Ric8b, Gm14124, Pik3r1, Gm11981, Dip2c, Plin2, Fam228a, Tlr1, Lypd6b, Zc3h12b, Abcg1, Ext1, Camk2g, Ptgr2, Mnd1-ps, Rftn1, Sox8, Sdc3, Mab21l3, Arid1b, Tdrp, 4921525O09Rik, Arid4b, Micu2, Ly86, Afp, Grap2, Ist1, Sh2d4b, Rad52, Mir1668, Rpgrip1l, Gramd1a, Sgk1, Fos, Smad4, Hdac4, B3gnt3, Nr4a3, St8sia1, Psg-ps1, Actl9, Pdk1, Il2ra, Irf2, Fasl, Hsdl1, Galnt5, Itk, Mam12, Erdr1, Ndufa6, Tbc1d23, Slc43a2, Iqgap1, Klf7, Bend5, Klf4, Lif, Calr4, Cnst, Ifnk, G3bp2, Tbc1d2, C030034L19Rik, Zfhx3, Bcl11a, Retnlb, Ap3m1, Hlcs, Serpinf1, Gm16390, Wdr37, St8sia1, Cenpu, Gm10638, Tfpi, Fabp7, Wisp3, Psma1, Tet2, AI854703, Lmo4, Ppp1r1b, Mgat5, Foxp1, Gm3716, Mir6349, Tle4, Itgb8, Rab11fip4, Tbcel, Npepps, 1300002E11Rik, Celf2, 4933412E24Rik, 4930415F15Rik, Olfr1507, Itgb3, Bace1, 2010015L04Rik, Mir7656, Esrp1, Spred2, Myo10, A930001A20Rik, BC048403, Lincpint, Mturn, Shisa2, Mef2d, Rac2, Dusp6, Lef1, Tmem64, Lrig1, Atp6v1g1, 1700017N19Rik, Dfna5, Zfp286, Gimap9, Gbe1, Cdc37, Pard6g, Serp2, Pid1, 4930465M20Rik, P2rx4, Opalin, Mir684-1, Ngly1, Ndufa4, Mir16-2, Trib2, Slc17a9, Itpripl1, Uri1, Rnf32, Prlr, Lyrm7, Fbln1, Nenf, Atl2, Slfn1, Supt20, Ski, Pno1, Foxo1, Olig3, 5330411J11Rik, Eci3, Clic4, Naa30, Abca1, Mpp1, Adcy6, Ptprc, Fbxo27, Ahcyl2, 1700016K19Rik, Gm14405, Drosha, Lrrc1, Mir7014, Cdk19, Ldlrap1, Pgpep1l, Fgl2, Nck2, Acvr2a, Myo10, Cblb, Gm590, Kcnq5, Col6a1, 4930480M12Rik, Rad23b, Tram2, Pygo1, Mir6368, A430107P09Rik, Afap1, Pip4k2a, Slc46a2, Mgat5, Slc27a6, Ntper, Cuedc1, Ramp1, Enthd1, Mir6374, Stmn1-rs1, Gm684, Fbin1, Lef1, Chd7, Ppp1r3fos, Abi1, Plau, Aif1l, Tesc, Edem3, Tbcel, Prdm5, Lnpep, Dyrk2, Gm6260, 4930428G15Rik, Carns1, 8430436N08Rik, Plekha5, Hexim2, Ccr7, Foxp1, Satb1, Rpgrip1, Dnm3os, Retnlb, Tram1, Tmppe, Car12, Snord14c, Ets1, Crtc3, Kcnh8, Hey1, Slc44a2, Dip2c, Ankrd44, C230029M16, Nwd1, Mrps11, Cpb1, 4930567H12Rik, Mir378c, Dnaja2, Fnbp1l, Tab3, Zap70, Cenpk, Bcar3, Usp6nl, Ppp4r2, Has1, Tbc1d22a, Dync2li1, BC055111, Sepw1, Ap1s3, Ass1, Metrnl, Rsph3a, Dpysl2, Rapgef6, Cxcr4, Mir8095, Sgsm3, Actn1, Grb10, S1pr1, Rasgrp1, Dnajc6, Agfg1, Map3k15, 4930465M20Rik, Csnk1g3, Trpv5, Klf3, Zfp3612, Mir181a-1, Slc30a9, Taf3, Eml2, Tssc1, 1190002N15Rik, Cdh26, Sav1, Ghsr, Msra, Fam134b, Tusc3, Itpkb, Dtwd2, Frmd7, Gm20750, 4933440M02Rik, St8sia1, Mir8105, Mir7681, Sntg1, Hipk2, Cd8b1, Stk24, Zmat4, Pnoc, Creb1, Trps1, Gls, Gm15706, Ubtd2, Kif1b, Pex3, Ect2l, 4732490B19Rik, Calm2, Syne1, Ap1b1, Ldha, Mmp15, Tnks, Gm20098, Spred2, Igf2bp3, Atp1a3, Pdzrn3, Qser1, Ppm1l, D930032P07Rik, Vmn2r98, G530011O06Rik, Ikzf1, D630010B17Rik, Mettl8, Gm590, Enthd1, Ccdc152, Ywhaq, Atp8a2, Thra, Ildr1, Rpap3, Ltb, Rev3l, Med13l, Dner, Ralgps2, 4930428G15Rik, Dnajc1, Arhgap6, Fam101b, Nfam1, Ccr7, Psma6, Gm1631, Hadh, 3425401B19Rik, Irf4, Zak, Brdt, Fam71f2, Slc25a12, Ippk, Fnbp1l, Rps16, 4930540M03Rik, Cd5, Ube2e1, A430107P09Rik, Rapgef4, Olfr1507, Rmdn2, Lhfp, Mir1893, Lgals3, Gn13l, Whsc1l1, Sh2d1a, BC061194, Mbnl2, Zbtb38, Golph3, 4930430F21Rik, H2-Q1, Ntrk3, Ninj2, Cd3e, Statsb, Lbx1, 4933412E24Rik, Pten, Gm2447, Mtx2, Tmcc3, Lin28a, Cyb5a, Znrf1, Fancc, 1500015O10Rik, Plekho1, Prss32, Gjd2, Gphbs, Ccr7, 4931403G20Rik, Mboat1, Dyrk2, Il9r, Sos1, Etv2, Txnip, Fam110b, Rph3al, Mboat4, Plekhh2, Irf6, Thoc7, Yeats4, A430107P09Rik, Ms4a7, 4930567H12Rik, Zfp930, Zap70, Uaca, Nsg2, Myo10, Ctf1, AU015836, Mir7681, 9830132P13Rik, 1700021F07Rik, Ipo4, Icosl, Smad5, Cyp26b1, Mgarp, A430078G23Rik, Kdm6a, I730028E13Rik, Hs2st1, Tox, Akr1d1, 1810010D01Rik, Rp134, Ramp1, Hcls1, Rab3ip, 4930445N18Rik, Ext13, Sox4, Gjd3, Gm14305, 1700061F12Rik, Lnpep, Wnt5b, Mark4, Stmnd1, Olfr1507, A430107P09Rik, Commd8, AI427809, Mir6979, Cdc42se2, Gpr125, Tcf25, Taf8, Lclat1, Wdr89, Ptk2b, Pitpnb, Ttf2, St6gal1, Mam12, Lrch3, 5430427M07Rik, Bach1, Exoc4, Mef2d, Vps37b, Wdr37, Ccr7, Fam221a, Mif, Vmn1r157, Mpp6, Chd2, Sept6, She, Prg4, Snord83b, Gm7616, 2410114N07Rik, Wdr37, Gdpd4, Vdac1, Mir5104, Rsrc1, 4930523C07Rik, Akap2, Lyst, G6pc2, Klh14, Slc35b4, Setbp1, Akap2, 1700072005Rik, Gm1604b, Kcna10, Stambpl1, Npas2, Dnajc1, Ddx25, 4933433H22Rik, Plcg2, 4930562F07Rik, Armc4, Foxo1, Samd91, Gm16157, Gpnmb, Tmem141, Mir6413, Gabbr2, Fgf8, Prdm2, Ikzf3, Diexf, Ccdc8, Esd, Macrod1, Tm2d1, 4930572O13Rik, A130077B15Rik, Lck, Kdm2a, Rbbp8, Cd47, Gm6578, Klf2, Zfp536, Ube2e3, Aff3, Man1a, 4930413G21Rik, Crtam, Rpa1, Kcnh3, 2900008C10Rik, Tbc1d31, Snn, Malat1, Bambi-ps1, Wisp3, Mrgprb5, Gch1, Nabp1, Mettl9, Zfp3612, Mir7669, 4933401H06Rik, Prkrir, Erdr1, Olfr630, Tmem168, Gbp11, Mbnl1, Plin2, Scn2b, Car8, Ngly1, Kcna2, Dpp6, BC027231, Gosr1, 1700016L21Rik, Ccdc170, Manba, Osbpl9, Purb, Rftn2, Klf3, Cdca71, Supt71, Rgs3, Rbpms, Mir6349, 5830418P13Rik, Pkn2, Basp1, Btg2, Ifnk, 5730403I07Rik, Srsf1, Kif3a, Fbxo27, Gipr, Colq, 4930540M03Rik, Pard6g, Bcl11a, Ezh1, Cd2, Foxq1, Rybp, Pgap1, Usp10, Sh3bp5, Pmp22, Sdc3, Rnf145, Ankrd44, Tacc2, Sh3bp4, 4930465M20Rik, Slc19a3, Gm10791, Map4k4, Bhmt, Gm10190, Zdhhc18, Mroh2b, Gpr3, Tgfbr2, Reck, Atxn7l3b, Ngly1, Il12rb1, Gucy2c, Gpr83, 1700025G04Rik, Arap1, Chrm3, 8430436N08Rik, Postn, Lonp2, Ly6d, Zfp516, Fam102b, Psap, Rere, Fam217a, Cox4i1, Slc7a1, C9, Mir6374, Mdm1, 2310043L19Rik, Fbxl17, Gm5468, Panx1, Sct, Racgap1, Ppm1b, Samd12, E330009J07Rik, Cd101, Zcchc2, Gadl1, Rapgef6, Steap3, Fgfr1op, Setd7, 3110056K07Rik, Gm5538, Ino80e, St6gal1, Nsmce1, Ccdc64, Cxcr4, Gata3, Cerk, Chst15, Mir3089, Map4k4, Akap13, Slc30a9, Gm10790, Npffr1, Tdrp, Gm20098, Ddhd2, St8sia6, Lhx2, Syt6, Dtl, Themis, Mam12, Sh3bgrl2, Sptbn1, Fam207a, Lmna, Nfatc2, Gm12185, Arhgap6, Atg14, Macrod2, Mir3110, Fam46c, Wdr63, Ppp2r1b, Prdm9, Lphn2, Mir574, 119, Elovl6, Chd7, Pitpna, Atoh7, Mc2r, Celf2, Tdrd3, Rassf2, Gm10640, Ncoa3, Lyst, Fyb, Gm2447, Ap1ar, Stag2, Foxp1, Rock2, Pdlim1, Bin1, Gm10125, Bach2, Fbxl22, 2900015J15Rik, Rgs2, Cldn10, Lrrc8d, Rad23b, Supt20, Dgkd, Atn1, Agtr1a, Pias2, Gm10791, Tmem60, Prkag2, P4ha2, Trat1, March5, Tcf7, Wbscr27, Gm6498, Hist1h2bn, Zfp120, Trub1, Mir1936, Ms4a7, Nfatc4, Lrrn3, Trat1, Sox4, Nhsl1, Lincenc1, Tmem243, St6gal1, Dpysl2, Cntln, Il7r, Olfr9, Erbb2ip, Rpl10l, Mir211, Srbd1, Lphn2, Fam3c, Sorcs2, Thrb, Katnal1, Mir199a-1, Fbxo32, Rpap3, Arfip1, Rp119, Itm2a, Trim56, Ier51, Btg1, Plekhb1, Rp134, Pik3r1, Mir6349, Ikbkb, Cntn5, Sh3kbp1, Btg1, Cd101, 4930523C07Rik, Qsox2, Serh1, Rfc1, Cga, Bmyc, Sla, Rev31, Fam134b, Ggact, Mir466o, 28-Feb, Akr1d1, Tnfsfl1, 2310040G24Rik, Gclc, Pde4b, Dgkz, Hsbp1, Eif3k, Gipc3, Mthfd1l, P2ry1, Ets1, Cxcr4, Pja1, Treml2, Ccr7, C230024C17Rik, Rps6ka5, Klf4, Cx3cr1, Echdc3, Hspa8, Lama4, Mgll, Ophn1, Thnsl1, Disci, Pdzrn3, Sms, Zfp704, Zfp3612, Fam105a, Mad2l1, Dazap2, Fbxl14, Vapb, Ifnab, Zgrf1, Rtkn2, Ppp2r3c, Vmn2r96, Bbs9, Ifnlr1, 1700064J06Rik, Ppp1r37, Tgfbr2, Slc2a2, Lef1, Ccr7, Foxq1, Gan, D6Ertd527e, Snx9, Hes7, Fbxo47, Cox10, Bend3, Sgms1, Slc30a9, Gm3716, Foxo1, Rsbn1l, Tmc1, Fam120a, Gpr18, Efhc1, Ramp3, She, Akap7, Vezf1, Dnajc3, Tnpo1, Nudt1611, Gm19589, Ankrd60, Txk, Lix1, Dnajc6, Serinc5, Lef1, Tars, Gm3336, Bace1, Nedd41, Trib2, Gm6994, Bcl11a, Mir5127, Klrb1b, Nfix, Tigd2, Map4k2, Uxs1, Bach2, 4930583K01Rik, Klhdc9, Eepd1, Als2cl, Pard3, Wdr27, Ikzf1, Btg1, Ly6e, Prm1, Taco1, Itpr2, Limk2, Bend4, Gtf3c3, Kcnh8, Cd96, Fam229b, Adamts14, Lyrm7, Fhit, Sqrd1, Fpr-rs4, Tmem260, Cd55, Mir214, Mir3093, Amigo2, Dapp1, C030018K13Rik, A230028O05Rik, Shf, Lef1, Nrp1, Efr3a, Tmem30b, Mynn, Tgfbr2, Nfia, Ipcef1, Atl2, Thpo, Fam49a, Mir6387, Rtkn2, Gucy1a3, Chrna9, Rassf2, Clip4, Wnt10a, Opalin, Llph, Mir6995, Sorcs2, Slc2a2, Gm20110, Syne1, 2810001G20Rik, 5430434I15Rik, Ppp1r37, Itgb6, Hspa8, Il9r, Glrp1, 5430421F17Rik, Tstd2, Zswim2, Ext1, Slc16a10, Zfp957, Slfn5, Lrch1, Scin, Card11, Ext1, Tet1, Scml4, Diap2, 4933433H22Rik, Zfp629, Tspan13, Prkcq, Zcchc13, Cd74, E330017L17Rik, Tm2d1, Gpr126, Nrn1, Fam124b, Tubb2a, Tdrp, Tnfrsf1a, Foxp1, Fam107b, Epb4.115, Fam78a, Rasal2, Mapk9, Creb3l2, 4930539M17Rik, Kcmf1, Ctage5, Ankrd12, Manba, Tmc1, Lman1l, Nacad, Agr3, 4933433H22Rik, Matk, H2bfin, Kcnh2, Pgr15l, Inpp4b, Kcmf1, 4933430N04Rik, Vmn2r92, Stk17b, Foxp1, Cep571l, Lix1, Kcna10, Vangl2, Treh, Enthd1, Gm6559, Brf2, 4921525O09Rik, Prkcq, Igsf3, Fut8, Limk2, 5730508B09Rik, Clasp2, Twsg1, Tmem126b, Hoxa7, Cd28, Sh3bp5, Furin, 1700001P01Rik, Diap2, Tecta, Icosl, F11r, Mir7023, Fes, Map3k5, Spry4, Cd44, Ralgps1, Gm16793, Alox5ap, Mir5098, Arid1b, Ugcg, Ctla4, Snx9, Mir8095, Isl2, Osbpl6, Dyrk1a, Cd300a, A930011G23Rik, Fam26e, Ikzf2, Enpp6, Mir181a-1, Lyst, Grhl2, Aldh1a7, Hmgb1-rs17, 2410004B18Rik, Dnm2, Nabp1, Foxp1, Tnfrsf10b, Prkcq, Sgsm3, Agr3, 1700017N19Rik, Tle3, 4933406K04Rik, Insr, Whrn, Ets1, Lefl, Mir5618, Soat1, Ccr7, Cmss1, Ahcyl2, Mgat1, Hspa13, Znrf2, Kcnh8, Tdrp, Gm1604b, Vmn2r95, Akap6, Tbc1d22a, Lbp, Mkl1, Rsu1, Sstr2, Slc37a3, Ube2d2a, Itpka, Rnf220, Hnrnph2, Gm2933, Akap2, Pdzk1ip1, Wwp1, Vapb, Dyrk1a, Dynlt1b, Zfp365, Ssh2, R3hdm1, Nek10, Zswim2, Ccdc90b, Znrf1, Ms4a5, 4933406K04Rik, Actr2, Rgmb, Ston2, Gnas, Stk17b, Pim1, Mtr, K1h12, Cdk15, H2-Ob, Il23r, Slain2, Tssc1, Sbk1, Ube4a, H2-T3, Gtf2ird1, Tyw5, Hbs11, Efhc1, Rpe, March6, Itga4, Fam13a, Lst1, Ankrd55, Nif3l1, Fam69b, Mir7674, 2810001G20Rik, Gpr19, 4930567H12Rik, Foxp1, Dgkz, Cenpf, Amigo2, Panx1, B4galt2, Pag1, Ubl3, 1110059E24Rik, Hs1bp3, Slc6a19os, Mdm1, Limd2, Slc6a19, Bank1, Alg13, Wisp3, Sult5a1, Fam86, Dennd2d, Cacnb2, Tesc, Mdm1, Adipoq, 1810026B05Rik, Mir325, 1700096J18Rik, D030024E09Rik, G0s2, Mir7219, S1pr1, Cxcr1, Ext1, Chd1, Ly86, Dhx40, 4930564D02Rik, Dctn6, Il7r, E230025N22Rik, Sgk3, Bach2, Ramp1, Syt6, Gsap, Ccdc152, Jakmip1, Atp8a1, Grap2, Dynlt1f, 4921513I03Rik, Gpc6, Kcna10, Ipcef1, Mir7061, Btg1, Stoml1, Zfand3, Aqp4, Zfp281, Ccr2, Nrip3, C230029M16, Tcf4, Hadh, Mthfd1l, Lhfp, Gpr114, Plbd1, 1110034G24Rik, Cd79a, Gse1, Churc1, Map3k7cl, Filip1l, Galnt7, Appl2, March5, Zswim6, Skap1, Tgfbr3, Slc16a2, Palld, Atg10, Cap2, Dfna5, Tlr7, Slc24a1, Hivep2, Dock4, Cd300a, Igf2bp2, A430107P09Rik, Lrrn3, March2, Gm21057, Apbb1ip, Piga, Zbp1, A430107P09Rik, Trappc8, Zdhhc14, Stk17b, Sh3pxd2a, Ppifos, Chd1, Socs1, Kdr, Gramd3, Urad, Sipa1l1, Gm20098, P2ry2, Gas8, Sox5os3, Ccdc117, A130077B15Rik, Basp1, Zfp365, Syde2, Laptm4b, Sik1, 4933433H22Rik, Npff, Arntl, Alb, Zmynd11, Gm20098, Il9, Hadh, Sstr2, Emp1, Lefl, Galnt10, 5430434I15Rik, Cmah, 4631405J19Rik, Hesx1, Gm16793, Rp1p0, Sall3, Xdh, St8sia1, Folr4, Sp3, Rassf3, Aox2, Emp1, Rragc, Proser2, Gm8817, D030028A08Rik, Btg1, Mad2l1, Upb1, 1810006J02Rik, 4932702P03Rik, Rhoh, Gm10790, Dock10, Fam166b, Pcdh1, Zbtb24, Camk1g, 4933407L21Rik, Pde7a, A430093F15Rik, Pmepa1, Ropn1l, Grap2, Rims3, Rps6ka1, Eps15, 4930445N18Rik, 6430710C18Rik, Ppp1r13b, Il21r, Mtmr2, Prex2, Atp6v0d2, Ablim1, Hnrnpd, Syde1, Slc16a1, Mbnl1, Sgms1, H2-DMb1, Ly6a, Tlr1, gm20098, Galnt5, Edem1, Fam173b, Gpr126, Nbeal1, Prlr, Tmc1, Csrnp1, Atp10a, Dusp4, Lpar6, Pitpnb, Actr2, Ago2, Lphn2, Gm2447, Myo18a, Cd101, Cngb1, 1700027J07Rik, Vmn2r91, Folr4, Satb1, Man2a2, Smim14, 3300005D01Rik, D130058E03, Angptl2, Ercc3, Tmem87a, Syne1, Ptrf, Gm2447, Zscan2, Bend4, Endod1, Tgfb3, Mir6962, Rragd, 4931403G20Rik, Ddr1, Map4k3, Fabp4, Stk17b, Gm5122, Rapgef4, Neurl1b, Pdgfrb, Cirh1a, Fnip1, E030002003Rik, Fam65b, H2-DMa, Btg1, Zc3h12b, Prkch, Sipa1l1, Tdrp, Adtrp, Fam129c, Runx3, Ilvbl, Tbx19, Filip1l, A430107P09Rik, Ccdc11, Lphn2, Spg11, Mir6395, Foxp1, Dtnb, Mrpl13, Egln3, Fpr1, Rapgef4, A130077B15Rik, Tlr7, Rbpms, Gm1966, Tmem150b, Rev31, Mad2l1, Gm1604b, Tasp1, Sic 19a3, Trappc10, Ralgps2, Npas1, Ptprs, Slc36a1os, Maf, Wdr12, Polr3k, Gm20750, D14Ertd670e, Fam46c, Fam46c, Ptger1, Lclat1, Nina, Actn2, Tspan11, Zfp879, Spred2, Satb1, Nabp1, 4930486L24Rik, Ugcg, Txk, A430107P09Rik, Hadh, Abtb2, Rbm33, Fli1, Fyn, Mgat4a, Snd1, Glt8d2, H2bfm, 9130401M01Rik, Snd1, Mir3079, Pcdh7, Cnga1, Tldc1, Ugdh, Aven, Mir8104, Rgl1, Sox6, Map3k14, Akirin2, Mir684-2, Rfx2, Fyb, Ccdc711, Ece1, Gm8884, 4921507P07Rik, Mir6933, Slc6a7, Cox7b2, Rfx4, Gm5617, Sh3kbp1, Pds5a, 9030617O03Rik, Gpr126, Ctnnbl1, Prpf40a, Gpr22, Cldn10, Cdk19, Sgk3, Rgs3, Mir6995, Cdon, Stk17b, Samhd1, Gm16793, Lag3, Olfm2, Cyb5a, Zfp438, Akap2, Dpf1, 3110052M02Rik, Lrp6, Haao, Camk2a, Tspan9, 5430434I15Rik, Stk24, Tlr12, A930005H10Rik, Slc4a4, U2af1, Fbxl21, Opalin, Rybp, Igsf3, Aim1, Wasf2, Rgs3, Frs2, Smok4a, Pak4, Zscan22, A430107P09Rik, Slc35b3, Serpinb5, Med30, Cdc16, Agfg1, Tmem261, Plxna1, Myo5c, Gpr183, Suclg1, Cdk19, 4930556N09Rik, Lpp, Tmem260, Ubgln2, Mir378b, Btla, Gm19589, Ano6, Clint1, Ube4b, Olfr1507, Rab33a, 4930523C07Rik, St6gal1, 1600014K23Rik, Nnmt, Ift80, Htr3b, Rp134, Ipcef1, Psma6, Dnmt3a, Hpgds, Stxbp3a, Mir6907, 1700056E22Rik, Smad7, Mir7078, Mir181b-2, Il27ra, Stat1, C030018K13Rik, Foxg1, Hpcal1, Msra, Zc3hav1, Tdrd6, Tnfrsf4, 4921517T22Rik, Rubie, Plekhg6, Brd4, Sort1, U90926, 4930519F09Rik, Il4ra, Smyd2, Prkch, March9, Ghsr, Rps6ka2, Rpp21, Vps13c, 1600002D24Rik, Fam136a, 4921511I17Rik, Spef1, Mam13, St8sia1, Ssbp2, Stk4, Tnfrsf19, Snord104, Olfr1507, Dysf, Cntn5, Cd2, Raver2, Gm10790, Pja1, Tmprss9, Klf5, Ubash3b, Tle3, Scml4, Snx4, Tert, Sptbn1, Mir326, Aff1, Gm8298, Ephb2, Tec, F3, Exoc6, Sema4f, Dennd1a, Gmcl1, Gm10532, St3gal1, Chd7, Gm6268, Tox, Pja2, K1h13, Dnajc10, Foxp1, Trp53inp1, Gtf3c3, Scd2, Atl2, Dach2, Lynx1, Cand1, Cxcr4, Gm20098, Fscn3, Il9r, Dph5, Sh3bp5, St6gal1, Fli1, Mir5127, Ubac1, Gm16793, Nsmaf, Sp6, Rnf145, Ccr7, Orai1, Serbp1, St6galnac5, Tox, Cacna1b, A430035B10Rik, Alpl, H2-DMb2, Etnk1, Olfr1507, Mtr, Rgmb, Pmp22, Dctn6, Fli1, Mir326, Slc17a7, Sepp1, Slc6a19, Cngb1, Mir7681, Ccr9, K1h14, Atp6v1g3, Clec16a, Speer2, Gsn, Umps, Unc5cl, Aox2, Dcaf8, Igf2bp3, Car2, Rnf43, Kdm7a, Tgfbr3, Eldr, BC094916, Unc80, Zmynd11, Nabp1, Adamts14, Gm20139, Fgfr1, Tmem141, C130026L21Rik, D630039A03Rik, Mturn, Herc3, Gm5468, Mir6398, Fam86, Nsg2, Cblb, Erbb4, Mir7-2, Smurf1, Clec16a, Lhx2, Tomm20, Ifngr2, Acacb, Gm10791, Bach1, Epb4.1l2, Tmem154, Tssc1, Vdac1, Itgae, Raph1, Klf3, Pnrc1, Sell, Tdrp, Ptk2, A630072M18Rik, Slc41a3, Rab11b, Tnfrsf10b, Lrp12, Ptger3, Aggf1, 1700029F12Rik, Dpf1, Gm14295, Ubqln2, Coq2, Txndc8, P2ry1, 4933430H16Rik, Tctex1d1, Sfmbt2, Alg14, Tha1, Ets1, Cd101, Neu3, Mob3b, Kcna2, Irs2, Mbnl1, Fntb, Nipb1, Slc16a5, Ccdc174, Ncs1, BC037032, Fry1, Lipa, Hs1bp3, Cd101, Chd1, Atad1, Ppp1r3fos, Pde4b, Lamtor3, Klf2, Ttc27, Dntt, 5830454E08Rik, Panx1, Cyp2r1, Rhou, Mir701, Ccr7, Arhgap26, Ankrd36, Retnlb, Themis, Med13l, Slc6a19os, Znrf2, Mettl8, Mir3108, D030025E07Rik, Mir145b, Igsec1, Cd8b1, Clic1, 1810026B05Rik, Ptprs, Med7, Mthfd11, Dnali1, Bach1, Mgmt, Ppm1b, 4933430H16Rik, Cd40lg, Txk, Cdc14a, Il9r, Slc7a15, Prkch, Srpk2, Tmbim7, Rcor1, Vti1a, B3gnt2, Tmem261, Gria3, Tusc3, Rgs3, Satb1, Sept6, Setbp1, Cep68, Ric8b, Il6ra, Znrf2, Lypd6b, Tmem29, Myh9, 4921511I17Rik, Dlx1, Lhx2, and/or Chst15. In some embodiments, the transcriptional target is Irf8, Ctps, Chst15, Sipa1l1, 2610005L07Rik, Irf8, Etv5, Ctps, Grk5, Cd200r2, Cenpu, Atp2b2, Srfbp1, Fndc9, Tlr6, 3300005D01Rik, Vav3, Dusp5, Sipa1l1, Chst15, 2610005L07Rik, Cxxc5, Mrc2, Plod3, Bmpr2, Cd55, Ear2, Tmtc4, St6galnac3, Cenpa, Filip1, 6330407A03Rik, Gm10389, D8Ertd82e, Gm156, Mcf21, Enpp6, 2610005L07Rik, Cdy12, 3300005D01Rik, Gm10389, Irf8, Mir3081, Grk5, Enpp6, Srfbp1, 3300005D01Rik, Vav3, Chst15, Sipa1l1, Filip1, 2610005L07Rik, Bmpr2, 4930415F15Rik, St6galnac3, Ralgapa2, Tmtc4, Abhd6, Gm10389, Zfp3611, Ctps, Atp2b2, Fndc9, Tlr6, 3300005D01Rik, Dusp5, Cxxc5, Irf8, Plod3, Bmpr2, Cd55, Ear2, St6galnac3, Cenpa, Grk5, Filip1, 6330407A03Rik, Srfbp1, Filip1, Snai1, Il7r, Il1r2, Ly6i, Gm5, Snai1, Snai1, Klrg1, Tff1, Zfp3611, Pmepa1, Urb2, Snai1, Klrg1, Fchsd2, Il7r, Zfp3611, and/or Klrg1.

Engineered T Cell

In some embodiments, the invention provides a cell (e.g., T cell) engineered to have an altered epigenome that contributes to increased immunological response in a patient having a disease such as cancer or an infectious disease. In some embodiments, the engineered T cell of the present disclosure comprises an alteration in a high priority epigenetic pathway. In some embodiments, the T cell is an exhausted T cell ($T_{EX}$). In some embodiments, the high priority epigenetic pathway is targeted. In some embodiments, the targeting of the high priority epigenetic pathway prevents or reverses exhaustion of the T cell. Targeting of the epigenetic pathway can result in one or more changes in expression of at least one of Tox, SET protein, RuvBl1 protein, RuvBl2 protein, DPY30 protein, Tox2, Suv39h2, Csprs, Sfmbt1, Hmgn3, Chd9, Rnf2, Ikzf3, Kmt2e, Satb1, Tet1, Tet2, Tet3, Kdm5b, Sfmbt2, Actr6, and Prmt7. In some embodiments, the epigenetic pathway is targeted with a drug or with genome engineering via CRISPR/Cas9 targeting.

In some embodiments, the drug is 5-Azacytidine (Aza), Zebularine, a DNMT1 inhibitor, e.g. RG108, a BET family protein inhibitor, e.g. I-BET726 (inhibitor of BET726), a histone acetylase (HAT) inhibitor e.g. curcumin, garcinol, anacardiac acid. In some embodiments, the drug is an isothiozolone that inhibits PCAF and p300 (Heerboth et al. Use of Epigenetic Drugs in Disease: An Overview. *Genetics & Epigenetics* 2014:6 9-19). In further embodiments, the drug is Lys-CoA, C464, a histone methylation inhibitor e.g. 3-deazepanoclin A (DZNep), an HDAC inhibitor e.g. an aminosuberoyl hydroxamic acid, including suberanilohydroxamic acid (SAHA; market name Vorinostat), or ACY-1215 (an inhibitor of HDAC6).

Epigenomic Signature

Exhausted T cells have a unique epigenome in comparison to naïve, effector, and/or memory T cells. This unique epigenome is referred to herein as an "epigenomic signature." The epigenomic signature comprises a signature of genes uniquely expressed in $T_{EX}$.

An approach that could not only identify and enumerate, but also interrogate changes in activation state and relation to disease status could be of considerable value in monitoring patients on immunotherapies and be used to guide choices of immunotherapeutic approaches and help track immunological treatment response.

A signature of genes uniquely expressed in $T_{EX}$ is identified herein. In some embodiments, the signature of genes uniquely expressed in $T_{EX}$ comprises at least one of A330093E20Rik, Rnf19a, 2010010A06Rik, Cdh23, Abtb2, Dync2li1, Lrrc1, Scn1b, Man1a, Gimap3, Lef1, Col26a1, Gpr180, Fam126a, Wdyhv1, Mir6395, Gpr34, Fcgr1, Rpia, A430107P09Rik, Hbs1l, Slc35b3, Tmem248, Cox7a2l, BB019430, Pde5a, Sept7, Lrrc3b, Cd101, Znrf3, Znrf1, Gm6260, Prpf40a, Ets1, Scn3a, Kremen1, Fam210a, Trpm1, Pip4k2a, Trnp1, Sell, Nfia, Lipa, Zc3hc1, Msgn1, Yeats4, Abcd2, Tbc1d1, Kcnh8, Zfp407, Capg, Gm7538, Rgcc, Sh3bp5, S1pr1, Zfp957, Mcur1, D16Ertd472e, Trat1, Fam107b, Mbtps1, Egr3, Palm3, 9030624G23Rik, Ppp6r1, Ckap4, Rngtt, Crtc3, Peak1, Lhx2, Btg1, Serbp1, Cd2, Acoxl, Hormad2, Gm10684, Smo, A630075F10Rik, Ndst1, E030018B13Rik, Skp1a, Kcnh8, Nck2, Frmd7, Cldn10, Peli1, 2010300C02Rik, Insl5, Supt20, Slc4a4, Rph3al, Dip2c, Pm20d2, Nsg2, Rbm26, Tpk1, Stambpl1, AF357399, Car2, Mir145b, Zfp592, Galnt4, Gm5083, Thnsl1, Dhx40, Gm20098, Ly6i, Sugt1, Ywhaz, Rad23b, Bcor, Gm12159, Vegfa, Cacna1b, Arhgef11, 2210408F21Rik, Mettl8, Wdr73, Usp12, Art4, Clvs1, Mir6388, Diap2, Gm10532, Msi2, 4930546C10Rik, Mbnl1, Tm6sf1, Ppp2r5a, Mageb16-ps1, Neurl1b, Sspn, Suv420h1, 2410088K16Rik, Rgl2, Timm8a2, Aebp2, Mam12, Ldhal6b, Peak1, Parp2, Apbb2, Tctex1d1, Dtnb, Tspan3, 4930578N18Rik, Pced1b, Commd9, Lrrc3b, Rras2, Gm10638, 1600002D24Rik, Arsb, Ube2e2, 1700009P17Rik, P4ha2, Susd1, Cdkal1, Efcc1, Malat1, 4931403G20Rik, Tox, Arpc3, Atg10, Gpbp1, Gm5148, AI317395, Abhd2, Celsr1, Tsen2, Pfkfb3, Cyc1, Mir378c, Slamf6, Btg1, Phf2, Cxcr4, Gm10789, Atl2, 6030407O03Rik, Ggnbp1, Angpt1, 9530077C05Rik, Basp1, Rapgef6, H2-Ea-ps, Fam214a, Ppfia4, Lta4h, Ets2, Slc29a1, Xpo4, Gramd3, Itfg3, Fli1, Frmd6, Rbp1, Olfml3, Peli1, Srpk1, Hmgcs1, Irf2bp2, Cxxc5, Ccdc171, Cntnap2, Fance, Cblb, Cubn, Sfmbt2, Srsf3, Pepd, Dgkd, Osbpl6, Trib2, Zfand3, Dchs1, 5430421F17Rik, Fpr3, Dapl1, Trat1, 0610040J01Rik, Gm14005, BC051019, Tank, Tnfsf11, Rara, Pik3c2a, Elmo1, Nck2, Bcl2l11, Fam78a, Gm10638, Prkcq, Gpr126, Bach2, Ttc30b, Nlk, Ube2e2, Usp3, 4932441J04Rik, Larp4b, Serbp1, Dbn1, Vav3, Derl1, H2-T23, C130021I20Rik, Fbxl14, Ets1, Fgf8, Abl2, Acvr1b, Upk1b, Efcab10, Uchl3, Cd302, Cdc40, Nsg2, Tmem222, P2ry10, Klrb1b, Mc1r, Car8, BC048403, Taf8, Atp1b1, Mir30c-2, Luc7l2, Erbb4, Arhgdib, Ube2h, Itpr2, Vav3, Ptgfrn, D630010B17Rik, Eif2s3x, Vav3, Nfe2l3, Ccdc171, Fignl1, 4930519F09Rik, 1700123O12Rik, Acsf2, Ndufb9, Atp7a, Upp2, Ptpla, Man1a, Rgs3, Zbtb2, Trib2, Npr1, Fez2, Tle4, Fuca1, Cmip, Bcap29, Syne1, Dmbt1, Ell, Blnk, Sepw1, Gltscr1, Erdr1, Med13l, Moxd1, Btg1, Akap6, 1810053B23Rik, Rsu1, Gprasp2, Art4, Gpd2, Tmlhe, A430107P09Rik, Kcnj9, Atp8a1, Adam6b, 2010109I03Rik, Spred2, Raver2, Ap1m2, Dclre1a, Rbp7, Gcc1, Traf4, Satb1, Gm5538, Il12a, Fam60a, Thrb, Elk3, Vps45, Tle4, Akap13, Gprin3, Sox21, Emp1, Wfdc2, Slc45a1, Lnpep, Rapgef6, Txn2, Frmd4b, Myoz3, Zfp870, Bcl6, Mvb12b, Ntrk3, Spaca1, Mir701, Cdca7, Gm5083, S1pr1, Spry4, Cck, Il6st, Hebp2, Slc43a2, Tdrd5, Gm5833, Mir7-2, Mir1931, Pdgfb, 1700052N19Rik, Nfkbiz, Gm20753, Hapln1, Rras2, Diap2, Manba, Cers6, Rasgrp1, Lnpep, Apln, Ephb2, Arpp21, Mical3, Chic2, E130114P18Rik, Ipcef1, Dyrk2, Bach2, Mir122a, B230206H07Rik, Ceacam9, A730006G06Rik, 4930542C21Rik, A430107P09Rik, Trat1, Ccr2, H2-Ob, Adm, Yeats4, Ccne1, Gpc5, Spsb1, Jrkl, Orc4, Camkmt, Nfia, Celf2, Gadd45a, Gtf2a1, Nrde2, Nipa2, Rmi2, Lcor, Btg1, Atg10, D6Ertd527e, Ccm2, Dpysl2, Dirc2, Cpm, Arhgap15, A730043L09Rik, Raph1, Cst10, Slc7a13, Ramp1, Atp1b1, Zfp120, Slc39a13, Zfp706, Agr2, Tagap, Mir3110, Ubash3b, Dnmt3aos, H2-B1, Agbl1, Smc6, 1700060C20Rik, Trib2, A930005H10Rik, Btg1, Scml4, Mir196b, Efna5, Tmem14a, Kcnj15, Snrpd3, Nnmt, Ryr1, Ptk2, P2rx4, 5830428M24Rik, Commd3, Cd28, Hspb11, BC021785, Tcf7, Cstb, Art4, Tet3, Map3k13, Camkv, Ralbp1, 9330175M20Rik, Tgtp1, Selt, Irgc1, Tcf7, Tet1, Bnip31, Nrbf2, Nim1k, Rfx8, Tlr6, Grik1, Tox, 1700061G19Rik, Dhrs3, 4930519G04Rik, Mid1, Ap1ar, Basp1, Aqp4, 4930415F15Rik, Aif1, Rnf125, Fam134b, Atp13a3, Dmbt1, Mbnl1, Nfam1, Lmo4, Znrf1, Ambp, 4930523C07Rik, Bfsp2, Zfp592, Gm2447, Gm16157, Gjd3, Tgtp1, Ston2, Lypd6b, Rnf7, Zbtb2, BC051537, 4930417O13Rik, Arntl, Ttc9b, Foxp1, Mir7219, Mrgprb5, Tnik, Dhrsx, Foxp1, Tubb2a, Cyb5r2, Itga4, Snx9, Fam65b, C78339, Mir7212, Ldlrap1, H2-Oa, Snx12, Tdrp, Mndl-ps, Foxp1, Gucy2c, Creb1, Scn4b, Irf4, Rftn2, Gpr125, Dpf1, Fam134b, Akap13, Tmem108, Suclg1, Mn1, Sema4b, Gm6682, Slc46a2, Dennd3, Bach2, Sytl2, Grhl3, Smad3, 1600014C10Rik, 4930455C13Rik, 3200001D21Rik, Nup153, Grk6, Zfhx3, Fhit, Hmg20b, 4930564D02Rik, Bach2, Slc39a3, Urad, Smc1a, Maml1, Zadh2, 8030462N17Rik, Fsbp, Tmem243, Srp14, Lix1, Tmc1, Tspan11, Tns1, Serpinb5, 1810026B05Rik, Smad7, Mir3108, Phxr4, Tmem131, Olfr1507, Kidins220, Mir378c, Afap1, Rere, Sin3b, Efemp2, Neto2, Mir7669, Tgtp1, Gramd3, Map7d2, Chst2, Sp110, Ccdc162, Igf1r, Mir3110, Dcdc2b, Dse, Dlgap2, Armc9, E230029C05Rik, Gm11944, Tnik, Kat6b, Nkiras1, Tbcel, B4galt1, Cd2ap, Tnks, Icos, Tanc1, Sik1, Tor1aip2, 4930453N24Rik, Bnip1, Gm6313, 4930415F15Rik, Inpp5a, Atoh7, 2210417A02Rik, Pdss2, Lamtor3, Ptbp2, Ostm1, Nrarp, Fry1, Mir1907, Gm10638, Sumo1, Zfp60, 1600014C10Rik, Haao, Syde2, Ep300, Ndrg3, Tex2, Cdx2, Eefsec, Tmem131, Mir6959, Fyn, Prkcq, Mical3, Snhg7, Ambra1, Rag2, Vdac1, Ptpla, Tram1, Aak1, Pebp4, Sgpp1, 2410007B07Rik, Itpr2, Tulp2, Mir6395, Elovl6, Ppp1r3b, Zc3h4, Sptbn4, Rap1b, Vgll4, Kcna2, Cnot6, Tbc1d1, Pde4d, Rapgef4, Fbxo47, Proca1, Aim, 2310001H17Rik, Tmem131, Sh2d3c, Gtpbp8, 1700030C10Rik, Polr3b, Fam69a, Bcan, 4930465M20Rik, Sbp1, Emg1, Aaed1, LOC102633315, 5930430L01Rik, Adsl, Foxp1, Gm20337, Trdmt1, Gm9920, Foxo1, Olfml3, Fyb, Pgpep1l, Nsg2, Tex26, Fancc, Cngb1, Rapgef2, 2010010A06Rik, 2410007B07Rik, Lbh, Pnrc1, Lad1, Mycn, Abad15, Cd1d2, 4930428G15Rik, Hnrnp11, Dnaja2, Ccr7, Mmp15, Neto2, Bach2os, Efr3a, Rnf41, Mir7656, Znrf3, Rtkn2, Sesn1, Zp3r, Glrp1, Kdm7a, 3200001D21Rik, Pdss1, 5730403I07Rik, Mmp15, Thrb, Zbtb16, Vkorc1, E330009J07Rik, Dntt, 4933406J10Rik, Sim2, Lgals9, Gm12216, Grb10, Ednra, Fam3c, Birc6, Bace1, Sfrp2, 2010107G12Rik, Zfp184, Ctso, Zfp462, Abcb1a, Gm6639, Mir1258, Dyrk1b, Ralb, Thrb, S100a6, Gm590, Dnajc1, Zfand3, Blm, Ikzf2, Lrrc32, Nsg2, Foxp1, Tnpo1, Zfat, Specc1, Snora75, Vps45, Acp6, Syde1, Ext13, Fbxl14, Cdh26, Celf2, Cd2, Tshz2, Cntln, Fam65c, Dad1, Akap6, Gm15880, E330011O21Rik, Kdf1, Gstt1, 2700046G09Rik, Sort1, Nyap2, 1700063O14Rik, Cog6, Extl1, Vmn2r96, Il12b, Lclat1, A430107P09Rik, Zkscan16, Chl1, Nck2, Cdyl, St6gal1, Mir21c, 2810428I15Rik, Cnr2, Rab44, 1700064J06Rik, Zfp191, Peli1, Als2c1, Gnas, 2300005B03Rik, BC033916, Cd226, 1700049E22Rik, Nipal1, Gimap6, Gm5086, 8430436N08Rik, Ift80, Zfp697, Svs1, 4930459C07Rik, Epcam, Zfp706, Pde11a, Slc43a1, Slc9a9, Tshz2, Fbxw11, Mir7046, Zpbp, 1700123O12Rik, Slc16a1, Gm7457, Tcf4, Fbxl12, Il9r, Galnt6, Gm5868, Panx1, Hs3st5, Jarid2, Phxr4, Dock2, Nrip1, Lasp1, 1700066B19Rik, Marcks, Plekha7, Wdr41, Pdss2, Gpr83, Rapgef4, Gm15910, Colq, Olfr1507, Vgll4, Fgfr1op, Fanc1, Capn1, Lonp2, Rnf38, Gpaa1, 1700016G22Rik, Vmn2r98, Gm7325, Gm826, Rp131, Klrc1, Ikzf1, Crlf3, Cd44, Gypc, AU019990, Fbxl13, Tsc22d3, Tgm2, Ptpn14, Fancc, Arhgap26, Tgfbr2, Klf2, Sept7, Ptprc, Btn2a2, 4921511I17Rik, Ppp2r5a, C78339, Arhgap39, Ism1, Mpzl2, 2810459M11Rik, Dyrk2, Tspan13, Fbxl14, Plat, Celf5, Susd3, Rps6ka2, Gtf2ird1, Naif1, Rsph3a, Tssc1, Extl1, Snora7a, Bcl2l11, Pip4k2a, Npl, Tmem236, Cox7a2l, A530013C23Rik, Rgl1, Pgk1, Ift80, Emid1, Inpp4b, Cldn10, Gls, Tnni1, Folr4, Gm5766, Olfr1507, Hpcal1, Cyth4, St8sia6, 5430434I15Rik, Ropn1l, Serinc1, Mad2l1, 4921525O09Rik, A430107P09Rik, Gm11127, Tra2a, Urb2, Pgpep1l, Cacna1d, 5730403I07Rik, Fam49a, 1700025F24Rik, Stat1, Calm1, Kcna7, Eif1, Mir669m-2, Kdr, 1700123O12Rik, Mir8099-2, Hspa8, 2010010A06Rik, Zfp53, 4930524O05Rik, Abl1, Uvrag, Slc16a1, Dnah7b, Golph3, Ipcef1, Usp3, Jun, Snord89, Tcf7, Rbpms, Folr4, Papss2, Spred2, Stpg1, Mgat5, Lpin1, D8Ertd82e, Dhx40, Slit3, 4933405E24Rik, Nsun6, A430107P09Rik, Apol7e, Raly, Celf2, Ndufs7, Mir6921, Kbtbd11, Gc, Haao, Gm9054, Slc44a3, Tnfrsf19, Lefl, Ankrd11, Plxdc1, A430107P09Rik, Zcchc2, Zmat4, Jun, Adamts14, Slamf6, Adamts17, A430107P09Rik, Alox5ap, Mir6368, Ncor2, Ets1, Pmpcb, Mvk, 4922502D21Rik, 1700025G04Rik, Rgmb, Gpnmb, Stk17b, Ceacam9, Ttc1, E130006D01Rik, Camkmt, Ankrd63, Agtr1b, Khdrbs1, Zfp706, Cux1, 4922502D21Rik, Btbd1, Timm8a2, Itga4, Reep2, Uvrag, Cyfip2, Elovl6, Tfeb, Spag16, Tbcel, Lmo2, Rasgrp1, Fam86, Ktn1, Fbxo32, Gata3, Ly86, Ptgs2os2, Fam111a, Lrrc16a, B430306N03Rik, Tff3, Kcnn4, Mtif3, Ldlrap1, Tmem260, Pla2r1, Basp1, Ncoa3, Ngly1, Ccdc162, Nhsl2, Cdc123, Hnrnpu, Arhgap18, Zfl2, Gm6498, Bex6, B630005N14Rik, Dynlt1b, Lypd6b, Clec2e, Rbm17, Pstpip1, Lrp12, Akap2, Camk2d, Igf1r, Atp1a1, Gsn, Rragd, Actn1, Odf3b, Nudt4, Vmn2r99, Parp11, Adipoq, Fam221a, Il6ra, Kif23, Fabp5, Srpk2, Ikzf1, Fbxw7, Slamf9, St6gal1, Vav1, Serbp1, Reep1, Agr3, Plc12, Kcnj15, Aebp2, Gm20139, Mtx2, Sel11, Mbnl2, A430078G23Rik, Krr1, Lclat1, Zfp438, 4930487H11Rik, B4galt1, Ifngr2, Olfr221, Asb4, Gm6793, Ap1m1, Pdlim5, Gltscr1, 1110032F04Rik, Ankrd13a, Abcd2, Iqsec1, Inpp5a, Pdzrn3, Akirin2, Pip4k2a, Dyrk2, Jun, 4930465M20Rik, Osbpl9, Ttc30a1, Ctnnbl1, Tmem243, Olig3, Ubtd2, 4930540M03Rik, Dnajc5b, Dennd1a, Gadd45a, Rpl8, Dapl1, Cd2ap, 6430710C18Rik, Slc16a5, Rcbtb2, Hmgxb3, A630075F10Rik, Ankrd2, St8sia1, Ptk2b, Paqr8, Tox, Wdr37, Stat4, Rplp1, Ccnj, Hspbp1, Mthfd1l, Zcchc9, Gm13293, Camk4, Htt, Usp10, Plekha6, Gm5617, Cnksr3, Mir7218, Lcp2, Cd28, Lbp, Ncoa3, Skil, Hey1, Mir6368, Akap6, Spin1, Ccdc174, Stambpl1, Ggta1, Pifo, Stim2, Rras2, Tomm20l, Gm5538, Skap2, H2-Ob, Zfp3612, Clec2d, Erdr1, Dapl1, Vasp, Cytip, B4galnt3, Hamp, Mex3b, Tcf712, Vps13d, Alox5ap, Mtss1, Gm7457, Fam46a, Taf3, 2810408I11Rik, Ms4a7, Mad2l1, Selt, Snrpf, Hcn2, Frmd4b, Hivep1, Tspan13, Nfia, Asap1, Nt5e, Misp, Mam12, Sh3pxd2a, Ccdc162, Setd7, Etohi1, Acvrl1, Fntb, Shank3, Rhoh, Prok2, Marcks, A830010M20Rik, Ywhaz, Mtss1, Gm8369, Fam188b, Atp2a2, 4933405E24Rik, 4932443I19Rik, Notch2, Zc3h12b, Numb, Neb, Ramp1, Zfp831, Impdh2, Grk1, 4930459C07Rik, Mir7035, Setd3, Cdc42se2, Spo11, Fam166b, Mir6419, Atp10d, C2cd5, 4933412E24Rik, Bol1, Calr4, Il22ra2, Slc22a16, Syde2, Fyn, Slc27a6, Stx3, Gm6313, Rbm18, Gm13293, Tbc1d8, Fabp5, 4930546C10Rik, Slc16a1, Cnr2, Kcnip2, Trim69, Agbl1, Plvap, Ms4a6c, Usp38, Atl2, Sh3kbp1, Ppfibp2, Pim1, Pmis2, Sh3pxd2a, Ms4a4c, Klf3, Cblb, Mir701, Dmwd, Mtss1, Cdk13, Cabp2, Chdh, Pde4b, Ston2, Cmah, Fbxl14, Syk, Trio, Btg1, Ski, Cnot2, Stk38, Tm9sf3, 4930482G09Rik, Parp11, Jarid2, Mam13, 6430710C18Rik, Commd9, Fhit, Scampi, Tcf7, Ncf1, Ric8b, Gm3716, Scml2, Nr2f2, Ssr1, Il6st, Ankrd50, Pnmal2, Foxp1, Raver2, Ccdc64, 8430436N08Rik, Klf13, Itga5, Commd3, Mro, Ms4a7, Rock2, Enc1, Rab3gap1, Nav2, Tlr1, Gm7457, Elfn1, Rpl34, Agfg1, 1700020N01Rik, Irf4, Gm8369, Olfr1507, Grik4, Akap6, Mir6387, Thrb, Gm20110, Mir7670, Bag4, Gm15441, LOC101055769, Pak1, Mbd2, Ralgps2, Lipg, Gpnmb, Ubash3b, Kntc1, Aqp9, Znrf2, Cmah, Peli1, Chd7, Tmsb4x, Copb1, Gimap1, Bcas1os2, Ppapdc1b, Cdc14a, Ier5, Susd3, Birc2, Sun2, Itga5, Rlbp1, St8sia1, Hectd1, Chn2, Bcas1os2, Slc39a11, Cdc7, Me3, Stk17b, Ccr4, Peli1, Cd226, 2510009E07Rik, Sh2d1a, Zfp2, Mei4, Chst2, Nipa11, Tbcel, Itgb6, Tmed10, Gm44899, Tmcc1, A430107P09Rik, Abtb2, Tgfbr3, Zfp704, Reep5, Apcdd1, Pik3r1, Ms12, Gm20098, Eif4e3, 5430402O13Rik, Tssc1, Lphn2, Kcnh8, 4921525O09Rik, Fam46c, Pum2, Itsn2, Slc11a2, Usp6nl, Gimap6, A430107P09Rik, Nipbl, Nrxn3, 1700042O10Rik, Capn3, 4930526I15Rik, Plat, Gm15850, Dock10, Shisa2, Wbscr16, Egfl7, Zfp957, Gm20110, Slc4a8, Ago2, Pnp2, Tgfbr3, Hmga2, Pdlim7, Dip2c, Atp1b1, Pxk, Snora26, Gm6498, Sema3d, 3300002I08Rik, 9330175E14Rik, BB123696, Fibcd1, Slc6a19, S100a6, Commd9, Lpar4, Cntn5, Nr1i2, Panx1, Dock2, Ptov1, 5330411J11Rik, Sec24d, Ms4a4b, Eif3g, Rsbn1l, Plxnc1, Jarid2, 1810041L15Rik, Diap2, A630075F10Rik, Klf13, Tlk1, Lef1, Slc4a4, 2610020H08Rik, Tbce, 9430014N10Rik, Slc16a10, 2310042E22Rik, Lrrc3b, St6gal1, Tnfrsf1a, U90926, Fam134b, Grxcr2, Dok5, Aldh8a1, Cybrd1, Smarcb1, Jmy, Zfp608, Cdkn2aipnl, Aire, Prps2, Gm839, 4933412E24Rik, St6gal1, Ube2d2b, Mab21l1, Slc23a2, Keap1, Brdt, Piwil2, A930005H10Rik, Fyb, Ncald, Lgals9, Zfp704, Dguok, Gm15706, Nr3c1, Med13, Rictor, Paxbp1, Mir1903, Sv2a, Slx1b, Tbc1d24, Wnt5b, Ccr7, Ptk2, Mir21c, Aox4, Slc35b4, Mgat5, Zfp281, Mycn, 1700016G22Rik, Odc1, Prkcb, Ate1, Ncbp1, 3300002I08Rik, Ly6d, Spag16, Clk1, Atg10, 1700030L20Rik, Nsg2, Agps, Golt1a, Cntn5, Cadm4, Malsu1, Frmd4b, Gm6607, Cdh23, Gramd4, Slc44a2, Limd2, Lphn2, 1700010K23Rik, Lrrc66, Akap7, Pea15b, D030024E09Rik, Zscan10, Lsm2, Kcnj13, Cdhr3, Fbxl17, Lhx2, Olfm2, Cyp2r1, Wisp3, BB123696, Nlrc4, 2010010A06Rik, Elovl6, Eea1, Mir1907, Gls, B4galnt3, Epb4.1, Tshz1, Gpr126, Rgmb, Ncs1, Tet1, Hoxa1, 4930515G16Rik, Usp33, Stk10, Klh16, Ccdc109b, Manba, Gm5111, Chst15, Runx1, Rgs3, Gm4759, Ldlrad4, 4933400F21Rik, 4933406C10Rik, Diap2, Mir6403, Plin2, Zmiz1, Mam13, Fam86, Hbs1l, Inpp4b, Gm14405, Mgat5, Cntn5, Ramp3, Ifnk, Pgm1, Mfsd6, Armcx1, Mir5127, Gimap6, Mir6387, Slc38a2, Gsdmcl-ps, Cd24a, Kmt2e, Csrp1, 9530052E02Rik, Stk17b, Fyb, Lhfpl5, Atp8a2, Amn1, Sertad2, Epb4.1l2, Stk24, Cdk17, Camk4, Rpa1, Zmynd11, Efcab11, Mir491, Zc3hc1, Vps45, Rgs3, Ube2m, Tspan5, Insr, Snapc1, Btg1, Cox10, Znrf1, Camk4, Ddr1, Gm11981, Sesn1, Commd8, Nrip1, Polr3k, Eya3, Ppp1r1b, Pcdh7, A430107P09Rik, Efcc1, Mtss1, Hpn, Armcx1, Gm20139, Alg14, Sec11a, Cyb5d1, Trpm1, Fam65b, 5730508B09Rik, Frmd4b, Gm10584, Gm5069, Pmepa1, Sell, Mir6413, Klf12, Rhoq, Plc12, Prrc1, Emp1, D030024E09Rik, Rnf145, Bach2, Prkcq, Hic1, Msmo1, Map3k7c1, A1854517, 4922502D21Rik, Vti1a, Zcchc9, Spats2, Mir7681, Wdr89, Bcl6, Cytip, Gm13293, Creb314, Peli1, Pak1, Efcab11, Usp7, 4931403G20Rik, 1700030A11Rik, Mvb12b, Ampd3, Cubn, Baiap3, Med30, Actbl2, Kat6b, Peli1, Tmevpg1, Nsf, Hpcal1, Ube4b, Fam110b, C330011F03Rik, Inadl, Sesn3, Tmem30c, Itgb6, Dlg1, Srp14, 3300005D01Rik, Ggact, Mir21c, Cyp2s1, Mir7061, Bach1, Insr, 2410114N07Rik, H2-Eb1, Tasp1, Tusc3, Irf2bp2, 1700056E22Rik, Ppp6c, Slain2, Cnn3, 6030407O03Rik, Acbd6, Hmgb1, P2rx4, Cdk19, 1700061G19Rik, Tesk2, Plxnc1, Ercc3, 2010010A06Rik, Stk17b, Tspan9, Kcnj16, Ddx10, Wnt16, Sp4, Hilpda, Slc38a6, Tgfbr2, Fggy, Sugct, Begain, Mnd1-ps, Ksr2, Eif2d, Ms4a4d, Stim1, Cst10, Nfatc1, Ppifos, Gng7, Mir211, Txk, 4930415F15Rik, Tmem64, Stim1, Pip5k1b, Kcnj15, Commd8, Mir3108, Atp11b, Stk17b, Emc3, Cldn10, Akap13, Abcb1a, Mthfd1l, Foxk1, Rgs3, Gdnf, Micu1, Il7r, Arhgap35, Olfr1364, Ms4a4b, Rgs10, Flt3, Sfrp2, Il9r, Sf1, Gm1604b, Galnt4, Dtnb, Supt20, Fntb, Zmynd11, Tulp3, 2410007B07Rik, Tsen15, Abhd2, Dgcr6, Filip1l, Ift81, 4933401D09Rik, Gtdc1, Ano6, Mir1928, Peli1, Jak1, Cdk19, Syne1, 1123r, Tpm2, Fam65b, Kidins220, Vav1, 9030617O03Rik, C1ql3, Ceacam9, Ehd2, Vtcn1, Dusp7, Pik3ip1, Ostm1, Ppard, Olfr372, Mir7032, Npy, Phxr4, Grap2, Thrb, Wipi1, Dock4, Mfsd6, Zmynd8, Mylip, Setx, Ccdc146, Il12a, Sall3, Mir7048, Hapln1, Casp3, Bbs9, Syne1, Tdrd3, 4930565D16Rik, Gm20098, Tcf4, Haao, Snd1, Zfp706, Agfg1, Gm8709, Syne1, 4933406J10Rik, Pik3c2b, Manba, Olfr1033, Aurkb, 9330175E14Rik, Foxo1, Sfmbt2, Bach2, Pogz, 4930459C07Rik, Phxr4, Map7d2, Gm20750, Il12b, Sesn3, Psen2, Suco, Mad2l1, E030030I06Rik, Gadd45a, Abca1, Boll, 4930430F21Rik, Cstad, Lyst, Rasgrp4, 4833427F10Rik, Ehd2, 4930445N18Rik, Ppm1h, Gltscr1, Irf8, Lgi1, Gm10432, H2-M10.1, Crtc3, 4930453N24Rik, Irs2, 1700042O10Rik, Rabgap1l, Rnf144a, Csk, Rpia, A430090L17Rik, Mir8097, Serbp1, Mir684-1, Tcf4, Commd8, Tet3, Nr1i2, Gm10190, Prkcq, Orai2, Dpy30, Sbk2, Tssc1, Cd5, Sipa1l2, Dcp1a, 1810006J02Rik, Itgae, D030025E07Rik, Wibg, Bach2, Irf4, Ctnnd1, Usp7, Rftn1, Themis, 4930440I19Rik, Thrb, Nrl d2, Tgtp1, Ccdc162, Atp8b2, Speer4f, Stra8, Gm4906, Fam46c, Pag1, Etv3, Erdr1, Dhrsx, Fam65b, Gosr1, Trem2, Fbln1, Sp3, Mef2a, Bcor, Map4k4, Magi2, Pak2, Rph3al, Lgi4, Pja2, Tceal3, Efcab11, Arhgap5, Ext1, Smyd3, Prim2, Satb1, Stag2, Themis2, Pim1, Apol8, Lrrc6, Shb, Magi2, Commd8, Zfp879, Trp53i11, Rgl1, Abcd3, Diap2, Zbtb2, C030016D13Rik, Arhgdib, A630075F10Rik, C730036E19Rik, Phc2, Adamts10, Inpp4b, Cd200, Itpr2, Fgfr1, Gm5434, Scn2b, D8Ertd82e, Gm2a, Ube2v1, Bend4, Lpp, Mir181a-2, Gm13293, P2ry1, Klf7, E030018B13Rik, Rhobtb2, Ddr1, Ggnbp1, Gimap7, Mamstr, Cmip, Setbp1, Fcgr4, Slc1a3, Zfp608, 2810403A07Rik, Gm7538, Mir378a, Hoxa13, 2610301B20Rik, Ngly1, Sergef, Tpp2, Slc35b3, Mam13, Nav1, Txk, Fam195a, Scml4, Tlr12, Gpr125, Zfp3612, Suclg2, Tec, Akap2, Rab38, C030018K13Rik, 4933433H22Rik, Osbpl11, Capn13, Ankrd50, Mir1928, Mir3108, Slc39a10, Dock2, Dip2c, Aebp2, A530046M15Rik, Gm6251, Mtx2, Exoc4, Olig3, Dph6, Emb, Xpc, Gm7538, Tnfsf8, Afap112, Cenpv, Gsn, Rbms2, E2f3, Smarce1, Foxp1, Slc37a3, Apbb1ip, Tex10, Bend4, Pcgf5, Trio, Klf5, Gja8, E130006D01Rik, Ncor2, Acbd6, Alg14, Scmh1, D830013O20Rik, Galnt4, Ndufa6, Timm8a2, 2210010C04Rik, 4931403E22Rik, Gys2, G630090E17Rik, Dapl1, Nup160, Fxyd7, Zscan18, Bid, Serh1, Cdk17, Lrtm2, 3930402G23Rik, Tm2d1, Snora7a, C8g, Nkap, 2410007B07Rik, Ilf3, Mir7017, Gpr83, Thada, Ambra1, Fancc, B3galt4, Thnsl1, Etv5, Aox2, Tgm2, Man1a, Edem1, Hnrnph1, Atp6v0e2, Clec4f, Hey1, Fam3c, Stat4, Slc46a1, Rps15a-ps6, Kdm4c, Upb1, Sik1, Nceh1, Prkcq, Btg1, Galnt2, 2010010A06Rik, Neu3, Cubn, Mir1928, Rapgef2, Nedd41, Egfl7, B3gnt2, Tgtp2, Gm13546, Ext1, Pold4, Ggact, B3gnt7, Gm5868, Tlr7, Lefty2, Npff, Tcf712, D130058E03, Pag1, 4930578N18Rik, 6430710C18Rik, Fam43a, Snora81, Cyp20a1, 4922502D21Rik, Lsm1, Gm10791, Kcnh2, 1700109K24Rik, Nol6, 4922502D21Rik, Trib2, Nrf1, Rgag4, 4930426L09Rik, Ppil3, Vmn2r96, Ngly1, 1810046K07Rik, Hid1, Olfr1510, Nrip1, Dhtkd1, Ms4a6b, 4930583K01Rik, Atp1b3, Mir7046, St8sia1, Pcdh7, Micalcl, D030024E09Rik, Pold4, Coro2b, Adamts14, Auh, Fus, Hc1s1, Prkcq, Nim1k, Zdhhc14, Kcnh2, Cd37, Ttc27, Olfm2, Ubac2, Mir6387, Zfp619, Zbtb9, Gpr125, Ppp2r5a, Adgb, Pard3, Ctrl, Ddr1, Ckmt2, Lpar6, Sspn, Gm4792, 9430008C03Rik, Ngly1, Tbx19, Heatr1, Cdc14a, Nabp1, 8430436N08Rik, Cd247, Llph, Pex10, Eea1, Lef1, Ly75, Dock11, Haao, Rgs3, Mnd1-ps, Maml1, Stxbp1, Parp11, G530011O06Rik, Mgrn1, Ift57, Mef2a, AI427809, Ldhb, Cdk19, Lrrc3b, Osm, Dnajc15, Mirlet7i, Stk38, Cep170, Rcn3, Gramd1a, Mfng, Vgll4, 1700017N19Rik, Atp1a3, Ptpla, Mir6962, Jun, Cdk19, Gm10638, Zfp3612, Slc39a10, Tpd52, Mthfd11, Agbl1, 4922502D21Rik, Ceacam2, Drosha, Fut8, Cox10, Dnajb12, Thns12, Eefsec, Pgpep11, 4932441J04Rik, Fndc7, Clip1, 2700046G09Rik, Itpkb, Kremen1, Mpp6, Ccr9, Tbcb, Rictor, Gm3716, Icosl, Cpeb4, Mir7681, Kmt2c, Mak16, Gi1, Actl9, Gpatch2, Sept14, Aebp2, Phlpp1, Zfp957, Ap3m2, Zcchc2, C030018K13Rik, Cdk17, Tmem217, Cog6, Dock2, Il7r, Crybb2, Slc16a10, Ppp1r1b, E430016F16Rik, Fbxo17, Akr1d1, D10Jhu81e, Irgc1, Klf7, Pcdh7, Nipb1, Rrn3, Mir7681, Arhgef33, Rhoq, Dusp5, Itga4, Palm2, Map10, Tigd2, Mfge8, Zfp580, Peli1, Trim59, F730035M05Rik, Gpr110, Lyst, Slc10a4, C230029M16, Gpnmb, Rgs3, Rab3ip, Vps54, Cox7a2l, Slc7a15, Serbp1, Slc22a16, Prkch, 4933433H22Rik, Arap2, Mkl1, Slc22a16, Fli1, Stk24, Stard8, Arhgap29, Pcca, Treml2, Tssc1, Pgpep11, Syde2, A430107P09Rik, Foxo1, 8430436N08Rik, D030024E09Rik, Tcf7, Ifitm6, Ctso, Capzb, Lypd3, Lix1, Ccdc170, Tasp1, Dnah7a, Sugt1, Pde7a, Pcnp, Klf5, Olfr1357, Ldhal6b, Kctd12b, Cxxc5, Pkn2, Mboat2, Angpt1, N6amt2, Gm839, Bach1, Il2ra, Ankrd12, Ccdc64, Pptc7, Ikzf2, Svil, Tlr1, Rell1, Tma16, Mbnl1, Cyfip2, Rps6ka2, Elovl6, Dapl1, Zfand3, Unc5c1, Zfp619, Sytl3, BC031361, Fam26e, Gm2799, Chst15, LOC101055769, Sepp1, a, Ccdc171, Hemgn, Pik3c3, Lrp12, Capn11, Pvr, Prkcq, 4932702P03Rik, 2300002M23Rik, Tef, Foxp1, Lypd6b, 4933412E24Rik, Wnt4, Marco, Elfn2, Smim9, Dip2b, March2, Frs2, Olfr1507, Mir7219, Fbxl22, Vim, 4933432G23Rik, L3mbtl1, Madl11, Calr4, Lrrc3b, Strada, Mir363, Tspan9, Esrp1, Panx1, Tgfbr2, Emb, Spata3, Ext1, Calm2, AY512915, C530008M17Rik, Mitf, Wdr11, Mir5127, Selt, Gm6623, Gm684, Gm3716, Tgtp2, Sptb, Hamp2, Itgb6, Cd2ap, Prnp, Ift80, Slamf6, Pou2af1, Snx29, G530011O06Rik, Wipf2, Fam134b, 4930428G15Rik, Igll1, Phxr4, Sgms2, Gm12159, Igf2bp3, Haao, Bai2, Sh3pxd2a, Scn4b, Eif4e3, Snx29, Tmem194b, Ifngr2, Gm5766, Zcchc24, Sox5os3, Efna5, Tecta, Mir7687, Mir6367, Itga4, Tns4, Ccm2, Wipf1, Cerk, Znrf1, Elovl5, Phtf2, 1300002E11Rik, 2210417A02Rik, Mir7061, Grhpr, Mark4, 4930564C03Rik, Svopl, Pja2, Tfdp2, Rbm11, Usp6nl, Mir6368, A430107P09Rik, Bcl2, Cdc42se2, 4933433H22Rik, Apol8, Xpnpep2, Dach2, Mir205, Stard5, Fsbp, Rph3al, Vav3, Gm10125, Lpcat1, Cd2ap, Bank1, Smurf1, Aox2, C230029M16, Sgms1, Eci3, Xpnpep2, Pfkfb2, Utrn, Ldlrad3, Gabrr1, Kcna2, Ywhaz, Stard13, Atp10a, Slc39a10, Whsc1l1, Gm12522, Trio, Man1c1, Hmha1, Gm10791, Kidins220, Lad1, Mir1928, Gm13710, Mir1963, Lama4, Pard3, Susd3, Taok3, Skor2, Matn2, Tet2, Mir7674, Ccdc64b, Fam49b, 4933412E24Rik, Thsd1, Sall3, Papss2, Tceal3, Rreb1, Klrd1, Rgs3, Cst10, Itga4, Gm20098, Smarca4, Cyp2d22, Kdm6b, Cntn5, Dyrk2, Dusp10, Srpk2, Etv5, Slc25a25, Cfl2, Micu1, Ets1, Gm6559, Zfr, Mrp152, Cerk, D630010B17Rik, Ext1, Cblb, Gnai2, Apol7e, Manba, Dusp10, Smim8, Mir6907, Pard3, Tmem35, Ric8b, Gm14124, Pik3r1, Gm11981, Dip2c, Plin2, Fam228a, Tlr1, Lypd6b, Zc3h12b, Abcg1, Ext1, Camk2g, Ptgr2, Mnd1-ps, Rftn1, Sox8, Sdc3, Mab2113, Arid1b, Tdrp, 4921525009Rik, Arid4b, Micu2, Ly86, Afp, Grap2, Ist1, Sh2d4b, Rad52, Mir1668, Rpgrip11, Gramd1a, Sgk1, Fos, Smad4, Hdac4, B3gnt3, Nr4a3, St8sia1, Psg-ps1, Actl9, Pdk1, Il2ra, Irf2, Fasl, Hsdl1, Galnt5, Itk, Mam12, Erdr1, Ndufa6, Tbc1d23, Slc43a2, Iqgap1, Klf7, Bend5, Klf4, Lif, Calr4, Cnst, Ifnk, G3bp2, Tbc1d2, C030034L19Rik, Zfhx3, Bcl11a, Retnlb, Ap3m1, Hlcs, Serpinf1, Gm16390, Wdr37, St8sia1, Cenpu, Gm10638, Tfpi, Fabp7, Wisp3, Psma1, Tet2, AI854703, Lmo4, Ppp1r1b, Mgat5, Foxp1, Gm3716, Mir6349, Tl e4, Itgb8, Rab11fip4, Tbcel, Npepps, 1300002E11Rik, Celf2, 4933412E24Rik, 4930415F15Rik, Olfr1507, Itgb3, Bace1, 2010015L04Rik, Mir7656, Esrp1, Spred2, Myo10, A930001A20Rik, BC048403, Lincpint, Mturn, Shisa2, Mef2d, Rac2, Dusp6, Lef1, Tmem64, Lrig1, Atp6v1g1, 1700017N19Rik, Dfna5, Zfp286, Gimap9, Gbe1, Cdc37, Pard6g, Serp2, Pid1, 4930465M20Rik, P2rx4, Opalin, Mir684-1, Ngly1, Ndufa4, Mir16-2, Trib2, Slc17a9, Itpripl1, Uri1, Rnf32, Prlr, Lyrm7, Fbln1, Nenf, Atl2, Slfn1, Supt20, Ski, Pno1, Foxo1, Olig3, 5330411J11Rik, Eci3, Clic4, Naa30, Abca1, Mpp1, Adcy6, Ptprc, Fbxo27, Ahcyl2, 1700016K19Rik, Gm14405, Drosha, Lrrc1, Mir7014, Cdk19, Ldlrap1, Pgpep11, Fgl2, Nck2, Acvr2a, Myo10, Cblb, Gm590, Kcng5, Col6a1, 4930480M12Rik, Rad23b, Tram2, Pygo1, Mir6368, A430107P09Rik, Afap1, Pip4k2a, Slc46a2, Mgat5, Slc27a6, Ntper, Cuedc1, Rampl, Enthd1, Mir6374, Stmn1-rs1, Gm684, Fbin1, Lef1, Chd7, Ppp1r3fos, Abi1, Plau, Aif11, Tesc, Edem3, Tbcel, Prdm5, Lnpep, Dyrk2, Gm6260, 4930428G15Rik, Carns1, 8430436N08Rik, Plekha5, Hexim2, Ccr7, Foxp1, Satb1, Rpgrip1, Dnm3os, Retnlb, Tram1, Tmppe, Car12, Snord14c, Ets1, Crtc3, Kcnh8, Hey1, Slc44a2, Dip2c, Ankrd44, C230029M16, Nwd1, Mrps11, Cpb1, 4930567H12Rik, Mir378c, Dnaja2, Fnbp1l, Tab3, Zap70, Cenpk, Bcar3, Usp6nl, Ppp4r2, Has1, Tbc1d22a, Dync2li1, BC055111, Sepw1, Ap1s3, Ass1, Metrnl, Rsph3a, Dpysl2, Rapgef6, Cxcr4, Mir8095, Sgsm3, Actn1, Grb10, S1pr1, Rasgrp1, Dnajc6, Agfg1, Map3k15, 4930465M20Rik, Csnk1g3, Trpv5, Klf3, Zfp3612, Mir181a-1, Slc30a9, Taf3, Eml2, Tssc1, 1190002N15Rik, Cdh26, Sav1, Ghsr, Msra, Fam134b, Tusc3, Itpkb, Dtwd2, Frmd7, Gm20750, 4933440M02Rik, St8sia1, Mir8105, Mir7681, Sntg1, Hipk2, Cd8b1, Stk24, Zmat4, Pnoc, Creb1, Trps1, Gls, Gm15706, Ubtd2, Kif1b, Pex3, Ect2l, 4732490B19Rik, Calm2, Syne1, Ap1b1, Ldha, Mmp15, Tnks, Gm20098, Spred2, Igf2bp3, Atp1a3, Pdzrn3, Qser1, Ppm1l, D930032P07Rik, Vmn2r98, G530011O06Rik, Ikzf1, D630010B17Rik, Mettl8, Gm590, Enthd1, Ccdc152, Ywhaq, Atp8a2, Thra, Ildr1, Rpap3, Ltb, Rev31, Med13l, Dner, Ralgps2, 4930428G15Rik, Dnajc1, Arhgap6, Fam101b, Nfam1, Ccr7, Psma6, Gm1631, Hadh, 3425401B19Rik, Irf4, Zak, Brdt, Fam71f2, Slc25a12, Ippk, Fnbp1l, Rps16, 4930540M03Rik, Cd5, Ube2e1, A430107P09Rik, Rapgef4, Olfr1507, Rmdn2, Lhfp, Mir1893, Lgals3, Gn131, Whsc111, Sh2d1a, BC061194, Mbnl2, Zbtb38, Golph3, 4930430F21Rik, H2-Q1, Ntrk3, Ninj2, Cd3e, Statsb, Lbx1, 4933412E24Rik, Pten, Gm2447, Mtx2, Tmcc3, Lin28a, Cyb5a, Znrf1, Fancc, 1500015O10Rik, Plekho1, Prss32, Gjd2, Gphbs, Ccr7, 4931403G20Rik, Mboat1, Dyrk2, Il9r, Sos1, Etv2, Txnip, Fam110b, Rph3al, Mboat4, Plekhh2, Irf6, Thoc7, Yeats4, A430107P09Rik, Ms4a7, 4930567H12Rik, Zfp930, Zap70, Uaca, Nsg2, Myo10, Ctf1, AU015836, Mir7681, 9830132P13Rik, 1700021F07Rik, Ipo4, Icosl, Smad5, Cyp26b1, Mgarp, A430078G23Rik, Kdm6a, I730028E13Rik, Hs2st1, Tox, Akr1d1, 1810010D01Rik, Rp134, Ramp1, Hc1s1, Rab3ip, 4930445N18Rik, Ext13, Sox4, Gjd3, Gm14305, 1700061F12Rik, Lnpep, Wnt5b, Mark4, Stmnd1, Olfr1507, A430107P09Rik, Commd8, AI427809, Mir6979, Cdc42se2, Gpr125, Tcf25, Taf8, Lclat1, Wdr89, Ptk2b, Pitpnb, Ttf2, St6gal1, Maml2, Lrch3, 5430427M07Rik, Bach1, Exoc4, Mef2d, Vps37b, Wdr37, Ccr7, Fam221a, Mif, Vmn1r157, Mpp6, Chd2, Sept6, She, Prg4, Snord83b, Gm7616, 2410114N07Rik, Wdr37, Gdpd4, Vdac1, Mir5104, Rsrc1, 4930523C07Rik, Akap2, Lyst, G6pc2, K1h14, Slc35b4, Setbp1, Akap2, 1700072O05Rik, Gm1604b, Kcna10, Stambpl1, Npas2, Dnajc1, Ddx25, 4933433H22Rik, Plcg2, 4930562F07Rik, Armc4, Foxo1, Samd91, Gm16157, Gpnmb, Tmem141, Mir6413, Gabbr2, Fgf8, Prdm2, Ikzf3, Diexf, Ccdc8, Esd, Macrod1, Tm2d1, 4930572O13Rik, A130077B15Rik, Lck, Kdm2a, Rbbp8, Cd47, Gm6578, Klf2, Zfp536, Ube2e3, Aff3, Man1a, 4930413G21Rik, Crtam, Rpa1, Kcnh3, 2900008C10Rik, Tbc1d31, Snn, Malat1, Bambi-ps1, Wisp3, Mrgprb5, Gch1, Nabp1, Mettl9, Zfp3612, Mir7669, 4933401H06Rik, Prkrir, Erdr1, Olfr630, Tmem168, Gbp11, Mbnl1, Plin2, Scn2b, Car8, Ngly1, Kcna2, Dpp6, BC027231, Gosr1, 1700016L21Rik, Ccdc170, Manba, Osbpl9, Purb, Rftn2, Klf3, Cdca71, Supt71, Rgs3, Rbpms, Mir6349, 5830418P13Rik, Pkn2, Basp1, Btg2, Ifnk, 5730403I07Rik, Srsf1, Kif3a, Fbxo27, Gipr, Colq, 4930540M03Rik, Pard6g, Bcl11a, Ezh1, Cd2, Foxq1, Rybp, Pgap1, Usp10, Sh3bp5, Pmp22, Sdc3, Rnf145, Ankrd44, Tacc2, Sh3bp4, 4930465M20Rik, Slc19a3, Gm10791, Map4k4, Bhmt, Gm10190, Zdhhc18, Mroh2b, Gpr3, Tgfbr2, Reck, Atxn713b, Ngly1, Il12rb1, Gucy2c, Gpr83, 1700025G04Rik, Arap1, Chrm3, 8430436N08Rik, Postn, Lonp2, Ly6d, Zfp516, Fam102b, Psap, Rere, Fam217a, Cox4i1, Slc7a1, C9, Mir6374, Mdm1, 2310043L19Rik, Fbxl17, Gm5468, Panx1, Sct, Racgap1, Ppm1b, Samd12, E330009J07Rik, Cd101, Zcchc2, Gadl1, Rapgef6, Steap3, Fgfr1op, Setd7, 3110056K07Rik, Gm5538, Ino80e, St6gal1, Nsmce1, Ccdc64, Cxcr4, Gata3, Cerk, Chst15, Mir3089, Map4k4, Akap13, Slc30a9, Gm10790, Npffr1, Tdrp, Gm20098, Ddhd2, St8sia6, Lhx2, Syt6, Dtl, Themis, Mam12, Sh3bgrl2, Sptbn1, Fam207a, Lmna, Nfatc2, Gm12185, Arhgap6, Atg14, Macrod2, Mir3110, Fam46c, Wdr63, Ppp2r1b, Prdm9, Lphn2, Mir574, 119, Elovl6, Chd7, Pitpna, Atoh7, Mc2r, Celf2, Tdrd3, Rassf2, Gm10640, Ncoa3, Lyst, Fyb, Gm2447, Ap1ar, Stag2, Foxp1, Rock2, Pdlim1, Bin1, Gm10125, Bach2, Fbxl22, 2900005J15Rik, Rgs2, Cldn10, Lrrc8d, Rad23b, Supt20, Dgkd, Atn1, Agtr1a, Pias2, Gm10791, Tmem60, Prkag2, P4ha2, Trat1, March5, Tcf7, Wbscr27, Gm6498, Hist1h2bn, Zfp120, Trub1, Mir1936, Ms4a7, Nfatc4, Lrrn3, Trat1, Sox4, Nhsl1, Lincenc1, Tmem243, St6gal1, Dpysl2, Cntln, Il7r, Olfr9, Erbb2ip, Rpl10l, Mir211, Srbd1, Lphn2, Fam3c, Sorcs2, Thrb, Katnal1, Mir199a-1, Fbxo32, Rpap3, Arfip1, Rpl19, Itm2a, Trim56, Ier51, Btg1, Plekhb1, Rp134, Pik3r1, Mir6349, Ikbkb, Cntn5, Sh3kbp1, Btg1, Cd101, 4930523C07Rik, Qsox2, Serh1, Rfc1, Cga, Bmyc, Sla, Rev31, Fam134b, Ggact, Mir466o, 28-Feb, Alai d1, Tnfsf11, 2310040G24Rik, Gclc, Pde4b, Dgkz, Hsbp1, Eif3k, Gipc3, Mthfd1l, P2ry1, Ets1, Cxcr4, Pja1, Treml2, Ccr7, C230024C17Rik, Rps6ka5, Klf4, Cx3cr1, Echdc3, Hspa8, Lama4, Mgll, Ophn1, Thnsl1, Disci, Pdzrn3, Sms, Zfp704, Zfp3612, Fam105a, Mad2l1, Dazap2, Fbxl14, Vapb, Ifnab, Zgrf1, Rtkn2, Ppp2r3c, Vmn2r96, Bbs9, Ifnlr1, 1700064J06Rik, Ppp1r37, Tgfbr2, Slc2a2, Lef1, Ccr7, Foxq1, Gan, D6Ertd527e, Snx9, Hes7, Fbxo47, Cox10, Bend3, Sgms1, Slc30a9, Gm3716, Foxo1, Rsbn1l, Tmc1, Fam120a, Gpr18, Efhc1, Ramp3, She, Akap7, Vezf1, Dnajc3, Tnpo1, Nudt1611, Gm19589, Ankrd60, Txk, Lix1, Dnajc6, Serinc5, Lef1, Tars, Gm3336, Bace1, Nedd41, Trib2, Gm6994, Bcl11a, Mir5127, Klrb1b, Nfix, Tigd2, Map4k2, Uxs1, Bach2, 4930583K01Rik, Klhdc9, Eepd1, Als2c1, Pard3, Wdr27, Ikzf1, Btg1, Ly6e, Prm1, Taco1, Itpr2, Limk2, Bend4, Gtf3c3, Kcnh8, Cd96, Fam229b, Adamts14, Lyrm7, Fhit, Sqrd1, Fpr-rs4, Tmem260, Cd55, Mir214, Mir3093, Amigo2, Dapp1, C030018K13Rik, A230028O05Rik, Shf, Lef1, Nrp1, Efr3a, Tmem30b, Mynn, Tgfbr2, Nfia, Ipcef1, Atl2, Thpo, Fam49a, Mir6387, Rtkn2, Gucy1a3, Chrna9, Rassf2, Clip4, Wnt10a, Opalin, Llph, Mir6995, Sorcs2, Slc2a2, Gm20110, Syne1, 2810001G20Rik, 5430434I15Rik, Ppp1r37, Itgb6, Hspa8, Il9r, Glrp1, 5430421F17Rik, Tstd2, Zswim2, Ext1, Slc16a10, Zfp957, Slfn5, Lrch1, Scin, Card11, Ext1, Tet1, Scml4, Diap2, 4933433H22Rik, Zfp629, Tspan13, Prkcq, Zcchc13, Cd74, E330017L17Rik, Tm2d1, Gpr126, Nrn1, Fam124b, Tubb2a, Tdrp, Tnfrsf1a, Foxp1, Fam107b, Epb4.115, Fam78a, Rasal2, Mapk9, Creb3l2, 4930539M17Rik, Kcmf1, Ctage5, Ankrd12, Manba, Tmc1, Lman1l, Nacad, Agr3, 4933433H22Rik, Matk, H2bfin, Kcnh2, Pgr151, Inpp4b, Kcmf1, 4933430N04Rik, Vmn2r92, Stk17b, Foxp1, Cep5711, Lix1, Kcna10, Vangl2, Treh, Enthd1, Gm6559, Brf2, 4921525O09Rik, Prkcq, Igsf3, Fut8, Limk2, 5730508B09Rik, Clasp2, Twsg1, Tmem126b, Hoxa7, Cd28, Sh3bp5, Furin, 1700001P01Rik, Diap2, Tecta, Icosl, F11r, Mir7023, Fes, Map3k5, Spry4, Cd44, Ralgps1, Gm16793, Alox5ap, Mir5098, Arid1b, Ucg, Ctla4, Snx9, Mir8095, Isl2, Osbpl6, Dyrk1a, Cd300a, A930011G23Rik, Fam26e, Ikzf2, Enpp6, Mir181a-1, Lyst, Grhl1, Aldh1a7, Hmgb1-rs17, 2410004B18Rik, Dnm2, Nabp1, Foxp1, Tnfrsf10b, Prkcq, Sgsm3, Agr3, 1700017N19Rik, Tle3, 4933406K04Rik, Insr, Whrn, Ets1, Lef1, Mir5618, Soat1, Ccr7, Cmss1, Ahcyl2, Mgat1, Hspa13, Znrf2, Kcnh8, Tdrp, Gm1604b, Vmn2r95, Akap6, Tbc1d22a, Lbp, Mkl1, Rsu1, Sstr2, Slc37a3, Ube2d2a, Itpka, Rnf220, Hnrnph2, Gm2933, Akap2, Pdzk1ip1, Wwp1, Vapb, Dyrk1a, Dynlt1b, Zfp365, Ssh2, R3hdm1, Nek10, Zswim2, Ccdc90b, Znrf1, Ms4a5, 4933406K04Rik, Actr2, Rgmb, Ston2, Gnas, Stk17b, Pim1, Mtr, Klh12, Cdk15, H2-Ob, Il23r, Slain2, Tssc1, Sbk1, Ube4a, H2-T3, Gtf2ird1, Tyw5, Hbs1l, Efhc1, Rpe, March6, Itga4, Fam13a, Lst1, Ankrd55, Nif3l1, Fam69b, Mir7674, 2810001G20Rik, Gpr19, 4930567H12Rik, Foxp1, Dgkz, Cenpf, Amigo2, Panx1, B4galt3, Pag1, Ubl3, 1110059E24Rik, Hs1bp3, Slc6a19os, Mdm1, Limd2, Slc6a19, Bank1, Alg13, Wisp3, Sult5a1, Fam86, Dennd2d, Cacnb2, Tesc, Mdm1, Adipoq, 1810026B05Rik, Mir325, 1700096J18Rik, D030024E09Rik, G0s2, Mir7219, S1pr1, Cxcr1, Ext1, Chd1, Ly86, Dhx40, 4930564D02Rik, Dctn6, Il7r, E230025N22Rik, Sgk3, Bach2, Ramp1, Syt6, Gsap, Ccdc152, Jakmip1, Atp8a1, Grap2, Dynlt1f, 4921513I03Rik, Gpc6, Kcna10, Ipcef1, Mir7061, Btg1, Stoml1, Zfand3, Aqp4, Zfp281, Ccr2, Nrip3, C230029M16, Tcf4, Hadh, Mthfd1l, Lhfp, Gpr114, Plbd1, 1110034G24Rik, Cd79a, Gse1, Churc1, Map3k7c1, Filip1l, Galnt7, Appl2, March5, Zswim6, Skap1, Tgfbr3, Slc16a2, Palld, Atg10, Cap2, Dfna5, Tlr7, Slc24a1, Hivep2, Dock4, Cd300a, Igf2bp2, A430107P09Rik, Lrrn3, March2, Gm21057, Apbb1ip, Piga, Zbp1, A430107P09Rik, Trappc8, Zdhhc14, Stk17b, Sh3pxd2a, Ppifos, Chd1, Socs1, Kdr, Gramd3, Urad, Sipa1l1, Gm20098, P2ry2, Gas8, Sox5os3, Ccdc117, A130077B15Rik, Basp1, Zfp365, Syde2, Laptm4b, Sik1, 4933433H22Rik, Npff, Arntl, Alb, Zmynd11, Gm20098, Il9, Hadh, Sstr2, Emp1, Lef1, Galnt10, 5430434I15Rik, Cmah, 4631405J19Rik, Hesx1, Gm16793, Rp1p0, Sall3, Xdh, St8sia1, Folr4, Sp3, Rassf3, Aox2, Emp1, Rragc, Proser2, Gm8817, D030028A08Rik, Btg1, Mad2l1, Upb1, 1810006J02Rik, 4932702P03Rik, Rhoh, Gm10790, Dock10, Fam166b, Pcdh1, Zbtb24, Camk1g, 4933407L21Rik, Pde7a, A430093F15Rik, Pmepa1, Ropn1l, Grap2, Rims3, Rps6ka1, Eps15, 4930445N18Rik, 6430710C18Rik, Ppp1r13b, Il21r, Mtmr2, Prex2, Atp6v0d2, Ablim1, Hnrnpd, Syde1, Slc16a1, Mbnl1, Sgms1, H2-DMb1, Ly6a, Tlr1, Gm20098, Galnt5, Edem1, Fam173b, Gpr126, Nbeal1, Prlr, Tmc1, Csrnp1, Atp10a, Dusp4, Lpar6, Pitpnb, Actr2, Ago2, Lphn2, Gm2447, Myo18a, Cd101, Cngb1, 1700027J07Rik, Vmn2r91, Folr4, Satb1, Man2a2, Smim14, 3300005D01Rik, D130058E03, Angptl2, Ercc3, Tmem87a, Syne1, Ptrf, Gm2447, Zscan2, Bend4, Endod1, Tgfb3, Mir6962, Rragd, 4931403G20Rik, Ddr1, Map4k3, Fabp4, Stk17b, Gm5122, Rapgef4, Neurl1b, Pdgfrb, Cirh1a, Fnip1, E030002O03Rik, Fam65b, H2-DMa, Btg1, Zc3h12b, Prkch, Sipa1l1, Tdrp, Adtrp, Fam129c, Runx3, Ilvbl, Tbx19, Filip1l, A430107P09Rik, Ccdc11, Lphn2, Spg11, Mir6395, Foxp1, Dtnb, Mrpl13, Egln3, Fpr1, Rapgef4, A130077B15Rik, Tlr7, Rbpms, Gm1966, Tmem150b, Rev31, Mad2l1, Gm1604b, Tasp1, Sic 19a3, Trappc10, Ralgps2, Npas1, Ptprs, Slc36a1os, Maf, Wdr12, Polr3k, Gm20750, D14Ertd670e, Fam46c, Fam46c, Ptger1, Lclat1, Nina, Actn2, Tspan11, Zfp879, Spred2, Satb1, Nabp1, 4930486L24Rik, Ugcg, Txk, A430107P09Rik, Hadh, Abtb2, Rbm33, Fli1, Fyn, Mgat4a, Snd1, Glt8d2, H2bfm, 9130401M01Rik, Snd1, Mir3079, Pcdh7, Cnga1, Tldc1, Ugdh, Aven, Mir8104, Rgl1, Sox6, Map3k14, Akirin2, Mir684-2, Rfx2, Fyb, Ccdc711, Ece1, Gm8884, 4921507P07Rik, Mir6933, Slc6a7, Cox7b2, Rfx4, Gm5617, Sh3kbp1, Pds5a, 9030617O03Rik, Gpr126, Ctnnbl1, Prpf40a, Gpr22, Cldn10, Cdk19, Sgk3, Rgs3, Mir6995, Cdon, Stk17b, Samhd1, Gm16793, Lag3, Olfm2, Cyb5a, Zfp438, Akap2, Dpf1, 3110052M02Rik, Lrp6, Haao, Camk2a, Tspan9, 5430434I15Rik, Stk24, Tlr12, A930005H10Rik, Slc4a4, U2af1, Fbxl21, Opalin, Rybp, Igsf3, Aim1, Wasf2, Rgs3, Frs2, Smok4a, Pak4, Zscan22, A430107P09Rik, Slc35b3, Serpinb5, Med30, Cdc16, Agfg1, Tmem261, Plxna1, Myo5c, Gpr183, Suclg1, Cdk19, 4930556N09Rik, Lpp, Tmem260, Ubgln2, Mir378b, Btla, Gm19589, Ano6, Clint1, Ube4b, Olfr1507, Rab33a, 4930523C07Rik, St6gal1, 1600014K23Rik, Nnmt, Ift80, Htr3b, Rpl34, Ipcef1, Psma6, Dnmt3a, Hpgds, Stxbp3a, Mir6907, 1700056E22Rik, Smad7, Mir7078, Mir181b-2, Il27ra, Stat1, C030018K13Rik, Foxg1, Hpcal1, Msra, Zc3hav1, Tdrd6, Tnfrsf4, 4921517D22Rik, Rubie, Plekhg6, Brd4, Sort1, U90926, 4930519F09Rik, Il4ra, Smyd2, Prkch, March9, Ghsr, Rps6ka2, Rpp21, Vps13c, 1600002D24Rik, Fam136a, 4921511I17Rik, Spef1, Mam13, St8sia1, Ssbp2, Stk4, Tnfrsf19, Snord104, Olfr1507, Dysf, Cntn5, Cd2, Raver2, Gm10790, Pja1, Tmprss9, Klf5, Ubash3b, T1e3, Scml4, Snx4, Tert, Sptbn1, Mir326, Affl, Gm8298, Ephb2, Tec, F3, Exoc6, Sema4f, Dennd1a, Gmcl1, Gm10532, St3gal1, Chd7, Gm6268, Tox, Pja2, Klh13, Dnajc10, Foxp1, Trp53inp1, Gtf3c3, Scd2, Atl2, Dach2, Lynx1, Cand1, Cxcr4, Gm20098, Fscn3, Il9r, Dph5, Sh3bp5, St6gall, Fli1, Mir5127, Ubac1, Gm16793, Nsmaf, Sp6, Rnf145, Ccr7, Orai1, Serbp1, St6galnac5, Tox, Cacna1b, A430035B10Rik, Alpl, H2-DMb2, Etnk1, Olfr1507, Mtr, Rgmb, Pmp22, Dctn6, Fli1, Mir326, Slc17a7, Sepp1, Slc6a19, Cngb1, Mir7681, Ccr9, Klh14, Atp6v1g3, Clec16a, Speer2, Gsn, Umps, Unc5c1, Aox2, Dcaf8, Igf2bp3, Car2, Rnf43, Kdm7a, Tgfbr3, Eldr, BC094916, Unc80, Zmynd11, Nabp1, Adamts14, Gm20139, Fgfr1, Tmem141, C130026L21Rik, D630039A03Rik, Mturn, Herc3, Gm5468, Mir6398, Fam86, Nsg2, Cblb, Erbb4, Mir7-2, Smurf1, Clec16a, Lhx2, Tomm20, Ifngr2, Acacb, Gm10791, Bach1, Epb4.1l2, Tmem154, Tssc1, Vdac1, Itgae, Raph1, Klf3, Pnrc1, Sell, Tdrp, Ptk2, A630072M18Rik, Slc41a3, Rab11b, Tnfrsf10b, Lrp12, Ptger3, Aggf1, 1700029F12Rik, Dpf1, Gm14295, Ubgln2, Coq2, Txndc8, P2ry1, 4933430H16Rik, Tctex1d1, Sfmbt2, Alg14, Tha1, Ets1, Cd101, Neu3, Mob3b, Kcna2, Irs2, Mbnl1, Fntb, Nipb1, Slc16a5, Ccdc174, Ncs1, BC037032, Fry1, Lipa, Hs1bp3, Cd101, Chd1, Atad1, Ppp1r3fos, Pde4b, Lamtor3, Klf2, Ttc27, Dntt, 5830454E08Rik, Panx1, Cyp2r1, Rhou, Mir701, Ccr7, Arhgap26, Ankrd36, Retnlb, Themis, Med13l, Slc6a19os, Znrf2, Mettl8, Mir3108, D030025E07Rik, Mir145b, Igsec1, Cd8b1, Clic1, 1810026B05Rik, Ptprs, Med7, Mthfd1l, Dnali1, Bach1, Mgmt, Ppm1b, 4933430H16Rik, Cd40lg, Txk, Cdc14a, Il9r, Slc7a15, Prkch, Srpk2, Tmbim7, Rcor1, Vti1a, B3gnt2, Tmem261, Gria3, Tusc3, Rgs3, Satb1, Sept6, Setbp1, Cep68, Ric8b, Il6ra, Znrf2, Lypd6b, Tmem29, Myh9, 4921511I17Rik, Dlx1, Lhx2, and Chst15. A signature of genes uniquely expressed in $T_{EX}$ is identified herein. In some embodiments, the signature of genes uniquely expressed in $T_{EX}$ comprises at least one of EHMT2, KDM4A, RAD54L2, PHF8, SIRT2, ATF2, KDM3B, TET2, BRD4, KDM2B, BRD9, MINA, SMARCAD1, HDAC2, TRIM28, KDM5C, CARM1, EHMT1, JMJD8, CHD1L, BRPF1, SETD1A, CHD4, SETDB1, NAT10, SIRT7, BRD8, HLTF, PBRM1, SETDB2, SUV39H2, EZH2, HELLS, ATAD2, RAD54L, SETD8, HAT1, RPA3, SMYD2, TAF1, BRD7, HDAC3, TTF2, BAZ1B, SUV39H1, HDAC1, SMARCA4, BRD3, FEV, JMJD6, ACAT1, SETD6, SETD4, CLOCK, SMYD3, KDM6B, KDM6A, SIRT1, SMARCAL1, HDAC5, SP100, ELP3, KAT2A, INO80, CHD3, KDM4B, HDAC8, SETD1B, HDAC7, SETD7, TET1, ZMYND11, CHD8, CREBBP, SHPRH, TET3, HDAC4, NSD1, TRIM33, ERCC6, PHIP, BRD1, KAT2B, CHD1, EP400, NCOA2, BAZ2A, JARID2, SETD5, SUV420H2, ATRX, ZMYND8, HIF1AN, BRPF3, KDM5A, TRIM24, KDM4C, BRD2, CHD9, EZH1, BRWD1, SMARCA2, KDM5B, PRDM2, CHD2, SUV420H1, ASH1L, BPTF, CHD6, KDM3A, EP300, SETD2, JMJD1C, ATAD2B, BAZ2B, BRWD3, JMJD4, CHD5, and PHF2. A novel approach was used that combined cross-species identification of $T_{EX}$ specific transcriptional and epigenetic changes. Genes were identified that are specifically up-regulated in $T_{EX}$ compared to canonical T cell populations (naïve, effector, memory T cells) in the lymphocytic choriomeningitis virus (LCMV) model in mice. Among this set of genes the subset that had unique $T_{EX}$ specific epigenetic changes in open chromatin regions was further selected based on ATAC-seq analyses (Pauken et al 2016 Science). This signature outperforms previous exhaustion signatures because the epigenetically selected genes drive the enrichment with other datasets typically accumulating at the leading edge of signature enrichment.

Epigenomic Assay

As used herein, an "epigenomic assay" is one which can identify an epigenomic signature of the epigenome of a cell, e.g., a T cell, for example, an exhausted T cell. As used herein, "epigenomically selected" is when a combination of comparative transcriptomics is used to derive a highly specific transcriptional signature of exhausted T cells and then that gene set is filtered through the epigenetic data to select genes that are specifically expressed by exhausted T cells and have exhaustion specific epigenetic changes. The epigenomically selected gene set is used to generate an epigenomic assay comprising a high parameter mass cytometry panel. In some embodiments, the epigenomic assay is a cytometry assay, for example a mass cytometry assay. In some embodiments, the cytometry assay is a high parameter (e.g., 20, 25, 30, 35, 40, 45, 50, 55, 60, 65, 70, 75, 80, 85, 90, 95, 100, 105, 110, 115, 120, 125, or 130 parameter) cytometry assay. In some embodiments, the high parameter cytometry assay is a 45 parameter cytometry assay. In some embodiments, the high parameter cytometry assay is a 30 parameter cytometry assay.

$T_{EX}$ are a major target of checkpoint blockade and other immunotherapies for cancer and will likely also play a role in therapeutics for chronic infections and autoimmunity. Despite their therapeutic importance a major problem in the field is the inability to specifically identify, track these cells and monitor changes in their behavior and functional potential. This disclosure provides the methods for identifying and tracking these cells. The present invention is superior to previous approaches that focused on only 1-2 markers because those approaches do not distinguish $T_{EX}$ from other kinds of cells and the current approach provides substantially more information about the behavior of these cells based on the high dimensionality. This latter feature allowed changes in $T_{EX}$ to be connected to disease status and therapeutic responsiveness. Use of this signature and cytometric approach should be of interest for blood based immune profiling for exhaustion ranging from check-up visits to cancer monitoring. In particular, any company conducting immunotherapy trials, as well as companies seeking to develop novel immunotherapy approaches should be interested in dissecting the heterogeneity of $T_{EX}$ as surrogates and targets of immunotherapies.

Proteomics and Proteomic Identification

Proteomics is the large-scale study of proteins. The proteome is the entire set of proteins that are produced or modified by an organism or system. While proteomics generally refers to the large-scale experimental analysis of proteins, it is often specifically used for protein purification and mass spectrometry. The term "proteomic identification" refers to the identification of proteins. The proteins can be identified using various techniques, e.g., mass cytometry.

Open Chromatin Region (OCR) Library and OCR Footprinting

A chromatin-accessible region is a region of chromatin within a cell that is accessible to molecules and regulatory elements such as transcription factors, enzymes including chromatin modifying enzymes, etc. Within chromatin accessible regions are chromatin accessible genomic gene regulatory regions, for example enhancers and/or suppressors.

A strategy of the invention is to identify open chromatin regions (OCRs) that are unique to $T_{EX}$ in comparison to $T_N$, $T_{EFF}$, and/or $T_{MEM}$, thereby generating an OCR library for a population of cells, e.g., $T_N$, $T_{EFF}$, and/or $T_{MEM}$, $T_{EX}$. The OCR library consists of open chromatin regions within a population of T cells. A PCR method is used to assess the "state of openness" at specific enhancer regions in a population of T cells, e.g., $T_N$, $T_{EFF}$, and/or $T_{MEM}$, $T_{EX}$. The method allows one to identify enhancers that are present in open chromatin regions in a population of cells. An OCR footprint is generated by the identifying enhancers within the OCR library of a population of cells. Comparing an OCR footprint of a population of $T_{EX}$ to an OCR footprint of a population of control T cells identifies an enhancer state that is unique to the $T_{EX}$ population. The enhancer state of a cell, e.g., a T cell, is essentially an enhancer-specific epigenomic signature or an enhancer profile of the cell.

Enhancer State

Open chromatin regions were interrogated to determine the enhancer state of the T cell. The enhancer state of the cell refers to which enhancer(s) within the epigenome of the cell are in open chromatin region(s) (OCR), and therefore accessible to other proteins.

Quantitative PCR

An enhancer openness PCR assay is used herein to interrogate epigenetic/epigenomic state, enhancer state, and therapeutic modulation. The assay comprises the steps of: peripheral blood isolation; CD8+ T cell enrichment; cell lysis; chromatin release; transposition reaction and library generation; compilation of the relevant OCR library for testing and selection of primers; qPCR readout of sample OCRs; and high throughput testing by multiple parallel qPCR or array-based platform for: OCR state of open or closed that relate to CD8+ T cell changes associated with disease presence/absence, disease severity, and/or response to therapy.

Disease

T cell exhaustion usually manifests with several characteristic features, such as progressive and hierarchical loss of effector functions, sustained upregulation and co-expression of multiple inhibitory receptors, altered expression and use of key transcription factors, metabolic derangements, and a failure to transition to quiescence and acquire antigen-independent memory T cell homeostatic responsiveness. Although T cell exhaustion was first described in chronic viral infection in mice, it has also been observed in humans during infections such as HIV and hepatitis C virus (HCV), as well as in cancer. Importantly, while T cell exhaustion prevents optimal control of infections and tumors, modulating pathways overexpressed in exhaustion—for example, by targeting programmed cell death protein 1 (PD1) and cytotoxic T lymphocyte antigen 4 (CTLA4)—can reverse this dysfunctional state and reinvigorate immune responses. However, these immune responses are rarely durable in patients. In some embodiments, the patient has a disease and is treated with an engineered T cell of the disclosure. In some embodiments, the T cell is engineered as described above, for example via CRISPR/Cas9 targeting. In some embodiments, the T cell is engineered by exposure to a drug that effects an epigenetic change in the T cell. In some embodiments, the T cell is engineered to express a chimeric antigen receptor (CAR). In some embodiments, the disease is cancer. In some embodiments, the disease is an infectious disease.

Treatments

In some embodiments, the patient is administered an engineered T cell of the disclosure wherein the T cell has been engineered to prevent, reverse or increases exhaustion of the T cell. In further embodiments, the patient is administered an engineered T cell of the disclosure that has been engineered to prevent or reverse exhaustion of the T cell. In some embodiments, the T cell has been engineered by targeting a high priority epigenetic pathway in the T cell, as described herein. In some embodiments, administering the engineered T cell increases an immunological response in the patient. In some embodiments, the patient having a disease is treated for the disease with one or more immune checkpoint inhibitors before being administered the engineered T cell. In some embodiments, the patient was treated with one or more immune checkpoint inhibitors before administering the engineered T cell. In some embodiments, the engineered T cell is administered simultaneously or concurrently with an immune checkpoint inhibitor. The immune checkpoint inhibitor, without limitation, can be an antagonist of or an antibody against PD-1, PD-L1, CTLA-4, TIM3, B7-H3, BTLA, VISTA, CD40, CEACAM1/CD66a, CD80B7-1, CD86/B7-2, OX40/CD134, CD40 Ligand, ICOS Ligand/B7-H2, 4-1BBL/CD137L, or B7-DC/PD-L2/CD273. In some embodiments, the immune checkpoint inhibitor is targeted with an anti-immune checkpoint inhibitor antibody. In some embodiments, the anti-immune checkpoint inhibitor antibody is an anti-PD-1, PD-L1, CTLA-4, TIM3, B7-H3, BTLA, VISTA, CD40, CEACAM1/CD66a, CD80B7-1, CD86/B7-2, OX40/CD134, CD40 Ligand, ICOS Ligand/B7-H2, 4-1BBL/CD137L, B7-DC/PD-L2/CD273, CD39/CD73, CD200/CD200R, LAG-3, TNFR2, KIRs, IDO, IL-10, IL-27, or TIGIT/CD226/CD112/CD122R/CD94 antibody. In some embodiments, the patient is simultaneously or concurrently treated with an anti-immune checkpoint inhibitor and an engineered T cell of the disclosure.

Humanized Antibodies

In some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein by its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13 (5): 353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences.

Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

T Cells

During acute infections or vaccinations, naive T cells are activated and differentiate into effector T cells over the course of 1-2 weeks. This differentiation is accompanied by robust proliferation, transcriptional, epigenetic and metabolic reprogramming, and the acquisition of cardinal features of effector T cells such as effector function, altered tissue homing and dramatic numerical expansion. Following the peak of effector expansion, the resolution of inflammation and the clearance of antigen, most activated T cells die, but a subset persists and transitions into the memory T cell pool. These memory T cells downregulate much of the activation program of effector T cells, yet they maintain the ability to rapidly reactivate effector functions upon restimulation. In addition, memory T cells develop a key memory property of antigen-independent self-renewal, which is a type of stem cell-like, slow division that is driven by interleukin-7 (IL-7) and IL-15. There is considerable diversity and complexity of memory T cell subsets and differentiation following acute infections or vaccinations (for example, effector memory T cells versus central memory T cells). However, a key aspect of the development of functional, persisting memory T cells is that after the effector phase, memory development occurs in the absence of ongoing antigen stimulation and high levels of persisting inflammation. (Wherry and Kurachi. Nat Rev Immunol. 2015, 15(8):486-499)

By contrast, during chronic infections and cancer—which involve persistent antigen exposure and/or inflammation—this program of memory T cell differentiation is markedly altered. An altered differentiation state, termed T cell exhaustion, usually manifests with several characteristic features, such as progressive and hierarchical loss of effector functions, sustained upregulation and co-expression of multiple inhibitory receptors, altered expression and use of key transcription factors, metabolic derangements, and a failure to transition to quiescence and acquire antigen-independent memory T cell homeostatic responsiveness. Although T cell exhaustion was first described in chronic viral infection in mice, it has also been observed in humans during infections such as HIV and hepatitis C virus (HCV), as well as in cancer. Importantly, while T cell exhaustion prevents optimal control of infections and tumors, modulating pathways overexpressed in exhaustion—for example, by targeting programmed cell death protein 1 (PD1) and cytotoxic T lymphocyte antigen 4 (CTLA4)—can reverse this dysfunctional state and reinvigorate immune responses. However, a durable clinical response often does not occur because of failure to fully reinvigorate $T_{EX}$.

Exhausted T Cells

Exhausted T cells are not inert. They retain suboptimal but crucial functions that limit ongoing pathogen replication or tumor progression. Despite this host—pathogen stalemate mediated by exhausted T cells, these cells are not effective in eradicating pathogens or tumors, and there has been considerable interest in avoiding or reversing exhaustion. The demonstration that T cell exhaustion is reversible (at least at the population level) rather than a terminal or irreversible fate provides a substantial clinical opportunity to use immunotherapy to improve immunity. Although the immunological effects of these human treatments remain to be fully defined, emerging results support the notion that reversal of T cell exhaustion in humans is a causative mechanism for the marked antitumor effect that is seen in many patients receiving agents that block the PD1 pathway.

Exhausted immune cells can have a reduction of at least 10%, 15%, 20%, 25%, 30%, 35%, 40%, 45%, 50%, 55%, 60%, 65%, 70%, 75%, 80%, 85%, 90%, 95%, 99% or more in cytotoxic activity, cytokine production, proliferation, trafficking, phagocytotic activity, or any combination thereof, relative to a corresponding control immune cell of the same type. In one embodiment, a cell that is exhausted is a CD8+ T cell (e.g., an effector CD8+ T cell that is antigen-specific). CD8 cells normally proliferate (e.g., clonally expand) in response to T cell receptor and/or co-stimulatory receptor stimulation, as well as in response to cytokines such as IL-2. Thus, an exhausted CD8 T cell is one which does not proliferate and/or produce cytokines in response to normal input signals. It is well known that the exhaustion of effector functions can be delineated according to several stages, which eventually lead to terminal or full exhaustion and, ultimately, deletion (Yi et al. (2010) *Immunol.* 129:474-481; Wherry and Ahmed (2004) *J. Virol.* 78:5535-5545). In the first stage, functional T cells enter a "partial exhaustion I" phase characterized by the loss of a subset of effector functions, including loss of IL-2 production, reduced TNFα production, and reduced capacity for proliferation and/or ex vivo lysis ability. In the second stage, partially exhausted T cells enter a "partial exhaustion II" phase when both IL-2 and TNFα production ceases following antigenic stimulation and IFNγ production is reduced. "Full exhaustion" or "terminal exhaustion" occurs when CD8+ T cells lose all effector functions, including the lack of production of IL-2, TNFα, and IFNγ and loss of ex vivo lytic ability and proliferative potential, following antigenic stimulation. A fully exhausted CD8+ T cell is one which does not proliferate, does not lyse target cells (cytotoxicity), and/or does not produce appropriate cytokines, such as IL-2, TNFα, or IFNγ, in response to normal input signals. Such lack of effector functions can occur when the antigen load is high and/or CD4 help is low. This hierarchical loss of function is also associated with the expression of co-inhibitor immune receptors, such as PD-1, TIM-3, LAG-3, and the like (Day et al. (2006) Nature 443:350-4; Trautmann et al. (2006) Nat. Med. 12:1198-202; and Urbani et al. (2006) J. Virol. 80:1398-1403). Other molecular markers distinguish the hierarchical stages of immune cell exhaustion, such as high eomesodermin (EOMES) and low TBET expression as a marker of terminally exhausted T cells (Paley et al. (2012) Science 338:1220-1225). Additional markers of exhausted T cells, such as the reduction of Bcl-b and the increased production of BLIMP-1 (Pdrm1).

In some embodiments, the exhausted CD8+ T cell expresses a T cell exhaustion biomarker selected from the group consisting of a checkpoint inhibitor, PD-1 (Pdcd1), TIM-3 (Havcr2), LAG-3 (Lag3), CTLA-4 (Ctla4), 2B4 (CD244), CD39 (Entpo1), CD160, eomesodermin (Eomes), T-BET (Tbx21), BATF, BLIMP-1 (Prdm1), NFATC1, NR4A2, MAFB, OCT-2 (Pou2f2), Foxp1, retinoic acid receptor alpha (Rara), and combinations thereof. In still another embodiment, the T cell is a CD8+ T cell. In yet another embodiment, the CD8+ T cell is a non-exhausted T cell or an exhausted T cell. In another embodiment, the non-exhausted CD8+ T cell is a naïve, functional effector, or memory cell. In another embodiment, the exhausted CD8+ T cell expresses a T cell exhaustion biomarker selected from the group consisting of a checkpoint inhibitor, PD-1 (Pdcd1), TIM-3 (Havcr2), LAG-3 (Lag3), CTLA-4 (Ctla4), 2B4 (CD244), CD39 (Entpd1), CD160, eomesodermin (Eomes), T-BET (Tbx21), BATF, BLIMP-1 (Prdm1), NFATC1, NR4A2, MAFB, OCT-2 (Pou2f2), Foxp1, retinoic acid receptor alpha (Rara), and combinations thereof. In still another embodiment, the T cell is a primary T cell isolated from the mammal, engineered, and returned ex vivo to the mammal. In yet another embodiment, the T cell is present in vivo within the mammal or is cultured in vitro.

Inhibitory Receptors and Treatment with Immune Checkpoint Blockade

Inhibitory receptors are crucial negative regulatory pathways that control autoreactivity and immunopathology. Although inhibitory receptors are transiently expressed in functional effector T cells during activation, higher and sustained expression of inhibitory receptors is a hallmark of exhausted T cells. The inhibitory signaling pathway mediated by PD1 in response to binding of PD1 ligand 1 (PDL1) and/or PDL2 offers an illustrative example. Whereas our understanding of the molecular mechanisms by which the inhibitory receptor PD1 controls T cell exhaustion remains incomplete, and without wishing to be bound by any theory, there are several mechanisms by which inhibitory receptors such as PD1 might regulate T cell function: first, by ectodomain competition, which refers to inhibitory receptors sequestering target receptors or ligands and/or preventing the optimal formation of microclusters and lipid rafts (for example, CTLA4); second, through modulation of intracellular mediators, which can cause local and transient intracellular attenuation of positive signals from activating receptors such as the TCR and co-stimulatory receptors; and third, through the induction of inhibitory genes.

Whereas there is some knowledge about PD1, understanding of the intracellular mechanisms of action of inhibitory receptors—including those of PD1—is incomplete. The intracellular domain of PD1 contains an immunoreceptor tyrosine-based inhibitory motif (ITIM) and an immunoreceptor tyrosine-based switch motif (ITSM)35. In vitro studies suggest a role for the ITSM in recruiting the tyrosine-protein phosphatase SHP1 (also known as PTPN6) and/or SHP2 (also known as PTPN11). The role of the ITIM in PD1 function remains poorly understood. Other evidence implicates a role for PD1 signaling in modulating the phosphoinositide 3-kinase (PI3K), AKT and RAS pathways, and also links PD1 to cell cycle control. Notably, much of our information about how PD1 controls T cell signaling is derived from in vitro studies of acutely activated T cells. In vivo studies of the role of PD1 during acute T cell activation and expansion suggest a possible role for PD1 signaling in either increasing mobility paralysis or decreasing migratory arrest, depending on the context. Finally, signaling downstream of PD1 may in fact induce the expression of genes that could negatively regulate the expression of effector genes, such as BATF, which encodes the activator protein 1 (AP-1) family member basic leucine zipper transcription factor ATF-like. Despite this elegant work, it is unclear how these observations relate to exhausted T cells exposed to chronic infection in vivo.

PD1 expression is rapidly upregulated upon T cell activation, and it may persist at moderate levels in healthy humans, indicating that PD1 expression alone is not a unique feature of exhausted T cells. However, during chronic infections PD1 expression can be substantially higher than observed on functional effector or memory CD8+ T cells. During chronic infection, sustained upregulation of PD1 is usually dependent on continued epitope recognition, although examples exist of residual PD1 expression even after removal of persisting antigen signaling.

In addition to PD1, exhausted T cells express a range of other cell surface inhibitory molecules. Exhausted T cells can co-express PD1 together with lymphocyte activation gene 3 protein (LAG3), 2B4 (also known as CD244), CD160, T cell immunoglobulin domain and mucin domain-containing protein 3 (TIM3; also known as HAVCR2), CTLA4 and many other inhibitory receptors. Typically, the higher the number of inhibitory receptors co-expressed by exhausted T cells, the more severe the exhaustion. Indeed, although individual expression of PD1 or other inhibitory receptors is not indicative of exhaustion, co-expression of multiple inhibitory receptors is a cardinal feature. These co-expression patterns are mechanistically relevant, as simultaneous blockade of multiple inhibitory receptors results in synergistic reversal of T cell exhaustion. This concept was demonstrated for PD1 and LAG3 in chronic LCMV infection, and for PD1 and CTLA4 in HIV infection, other infections and cancer. Many other combinations of inhibitory receptors such as PD1 and TIM3 can also co-regulate exhausted T cells. PD1 and CTLA4 blockade in patients with melanoma demonstrated impressive tumor control, and clinical trials of other combinations of agents blocking inhibitory receptors are underway (for example, ClinicalTrials.gov identifiers NCT01968109, NCT02210117 and NCT02408861, which are among >120 other trials involving the PD1 pathway). Overall, these data on the role of inhibitory receptors in co-regulation of T cell exhaustion suggest that these pathways are non-redundant. These molecules come from diverse structural families, bind ligands with distinct expression patterns and have distinct intracellular signaling domains. Thus, there is the potential to tailor or tune the type and magnitude of exhausted T cell reinvigoration.

In addition to inhibitory receptors, it has become clear that co-stimulatory receptors are involved in T cell exhaustion. For example, desensitization of co-stimulatory pathway signaling through the loss of adaptor molecules can serve as a mechanism of T cell dysfunction during chronic infection.

The signaling adaptor tumor necrosis factor receptor (TNFR)-associated factor 1 (TRAF1) is downregulated in dysfunctional T cells in HIV progressors, as well as in chronic LCMV infection. Adoptive transfer of CD8+ T cells expressing TRAF1 enhanced control of chronic LCMV infection compared with transfer of TRAF1-deficient CD8+ T cells, which indicates a crucial role for TRAF1-dependent co-stimulatory pathways in this setting. It has also been possible to exploit the potential beneficial role of co-stimulation to reverse exhaustion by combining agonistic antibodies to positive co-stimulatory pathways with blockade of inhibitory pathways. 4-1BB (also known as CD137 and TNFRSF9) is a TNFR family member and positive co-stimulatory molecule that is expressed on activated T cells. Combining PD1 blockade and treatment with an agonistic antibody to 4-1BB dramatically improved exhausted T cell function and viral control. Although a simple model of positive versus negative co-stimulation during T cell exhaustion probably has mechanistic validity, the diversity of pathways and much of the experimental data suggest that specific qualitative signals may be imparted by distinct co-stimulatory and co-inhibitory pathways (Wherry and Kurachi. Nat Rev Immunol. 2015, 15(8):486-499).

In some embodiments, an inhibitory receptor is targeted in the patient. In some embodiments, the inhibitory receptor is targeted with an immune checkpoint inhibitor. The immune checkpoint inhibitor, without limitation, can be an antagonist of PD-1, PD-L1, CTLA-4, TIM3, B7-H3, BTLA, VISTA, CD40, CEACAM1/CD66a, CD80B7-1, CD86/B7-2, OX40/CD134, CD40 Ligand, ICOS Ligand/B7-H2, 4-1BBL/CD137L, or B7-DC/PD-L2/CD273. In some embodiments, the immune checkpoint inhibitor is targeted with one or more antibodies against one or more immune checkpoint inhibitors. The immune checkpoint inhibitor, without limitation, can be an anti-PD-1, PD-L1, CTLA-4, TIM3, B7-H3, BTLA, VISTA, CD40, CEACAM1/CD66a, CD80B7-1, CD86/B7-2, OX40/CD134, CD40 Ligand, ICOS Ligand/B7-H2, 4-1BBL/CD137L, or B7-DC/PD-L2/CD273 antibody. In some embodiments, the immune checkpoint inhibitor is targeted with an anti-immune checkpoint inhibitor antibody. In some embodiments, the patient is simultaneously or concurrently treated with an anti-immune checkpoint inhibitor and an engineered T cell of the disclosure. In some embodiments, the patient is treated with an engineered T cell of the disclosure after the patient has been treated with an anti-immune checkpoint inhibitor, e.g., 1 minute, 5 minutes, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days after treatment with an immune checkpoint inhibitor.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the assays of the present invention and practice the claimed methods. The following working examples therefore, specifically point out some embodiments of the present invention, and are not to be construed as limiting in any way the remainder of the disclosure.

The materials and methods employed in these experiments are now described.

Mice, Infections, and Antibody Treatment

Five to six week old female C57BL/6 and B6-Ly5.2CR (B6 mice expressing Ly5.1) were purchased from Charles River (NCI strains). C57BL/6 P14 mice were bred to B6-Ly5.2CR mice to generate P14 Ly5.1$^+$ mice as described (Odorizzi et al. J. Exp. Med. 2015, 212:1125-1137). LCMV strains (Armstrong (Arm) and clone 13) were propagated and titers were determined as described (Odorizzi et al. J. Exp. Med. 2015, 212:1125-1137). B6 mice were infected intraperitoneally (i.p.) with $2\times10^5$ PFU LCMV Arm or intravenously (i.v.) with $4\times10^6$ PFU LCMV clone 13 to establish acute or persistent infection, respectively. For all clone 13 infections, CD4 T cells were depleted by i.p. injection of 200 µg of anti-CD4 (clone GK1.5, Bio X Cell) on days $^-1$ and $^+1$ p.i. with LCMV clone 13. Anti-PD-L1 (clone 10F.9G2, Bio X Cell) or an isotype control antibody (Rat IgG2b, Bio X Cell) was administered i.p. starting between day 22-25 p.i., 200 µg/injection for five injections every third day for 5 total treatments as described (Barber et al. Nature 2006, 439, 682-687). For some experiments vehicle (PBS) was injected as a control. For experiments where IL-7 was administered in vivo, the cytokine was complexed to anti-IL-7 to increase stability. For these experiments, IL-7/anti-IL-7 immune complexes (i.c.) were prepared as described (Boyman et al. J. Immunol. 2008, 180:7265-7275). Briefly, 1.5 µg of recombinant human IL-7 (NCI Preclinical Repository or Biolegend) and 7.5 µg of anti-human/anti-mouse IL-7 (clone m25, provided by Charlie Surh) per mouse per injection were mixed and allowed to complex for 30 min prior to diluting with PBS for injection. Complexes were administered i.p. simultaneously with anti-PD-L1 (every third day for 5 injections). All mice were maintained under specific pathogen free conditions at the University of Pennsylvania, and all protocols were approved by the Institutional Animal Care and Use Committee.

Lymphocyte Isolation and Adoptive Transfer

For experiments where P14 cells were monitored, P14 cells were isolated from the peripheral blood of P14 transgenic mice using histopaque gradients, and P14 cells (500 for clone 13 experiments, and 500-2000 for Arm experiments) were adoptively transferred i.v. into 5-6 weeks old recipient B6 mice at least one day prior to infection. Similar results were obtained when comparing P14 cells to endogenous $D^bGP33^+$ and $D^bGP276^+$ cells (FIG. 5), and previous reports have shown that the number of P14 cells transferred for clone 13 experiments (500) did not impact viral load (Odorizzi et al. J. Exp. Med. 2015, 212:1125-1137; Blattman et al. J. Virol. 2009, 83:4386-4394). For experiments where $T_{MEM}$, $T_{EX}$, or anti-PD-L1-treated $T_{EX}$ were adoptively transferred, CD8 T cells were isolated one day post the antibody treatment period from spleens, and were enriched using CD8 T cell EasySep negative selection kits (Stem Cell Technologies) according to the manufacturer's instructions. Numbers were normalized between groups based on $D^bGP33$ tetramer staining prior to i.v. adoptive transfer into antigen free recipient mice. LCMV immune mice (day 30$^+$ p.i.) were used as antigen free recipients so endogenous LCMV-specific memory could eliminate any transferred virus as described (Angelosanto et al. J. Virol. 2012, 86:8161-8170). For experiments testing antigen-independent persistence, recipient mice were immune to LCMV Arm (day 30+ pi). For rechallenge experiments, recipient mice had previously cleared low dose (200 PFU) infection with LCMV clone 13 V35A lacking the GP33 epitope as described (Shin, et al. J. Exp. Med. 2007, 204: 941-949). V35A immune mice were used for recall experiments to prevent direct competition with endogenous $D^bGP33$-specific memory CD8 T cells.

Flow Cytometry

MHC class I peptide tetramers ($D^bGP276$ and $D^bGP33$) were made as described (Qiu et al. Nat. Biotechnol. 2011, 29:886-891) or obtained from the NIH tetramer core. Antibodies were purchased from eBioscience, BD, Biolegend, Life Technologies, R&D Systems and AbD Serotec, and included antibodies against CD8, CD4, B220, CD45.1, CD45.2, CD44, CD122, CD127, PD-1, 2B4, Tim-3, Lag-3, Ki-67, granzyme B, IFNγ, TNFα, and phospho-STAT5. Single cell suspensions were stained with Live/Dead Aqua (Life Technologies) according to the manufacturer's instructions prior to staining for surface antigens. Intracellular staining for Ki-67 and granzyme B was performed using the eBioscience Foxp3 fixation/permeabilization kit according to the manufacturer's instructions (eBioscience). Intracellular staining for IFNγ and TNFα was performed using the BD cytofix/cytoperm kit according to manufacturer's instructions (BD) following a 5 hour in vitro restimulation with 0.2 µg/ml gp33-41 peptide (KAVYNFA™, GenScript) in the presence of brefeldin A and monensin (BD). For phosho-STAT5 detection, splenocytes were rested for 1-2 hours at 37° C. prior to stimulation. Cells were stimulated for 30 minutes with 10 ng/ml recombinant murine IL-7 or IL-15 (Peprotech). Cells were then fixed with paraformaldehyde for 15 minutes at 37° C., washed once, and immediately resuspended in Phospho Perm Buffer III (BD) and incubated for 30 minutes on ice. Cells were subsequently washed and stained according to manufacturer's instructions. Cells were collected on an LSR II flow cytometer (BD), and data were analyzed using FlowJo software (Tree Star). Sorting was conducted on a FACSAria (BD), and post-sort purities were obtained to determine sort quality.

Gene Expression by Microarray and RNA-Seq

For transcriptional profiling by microarray, CD8 T cells from spleens 1-2 days after the final treatment (after receiving 5 total treatments as described above) were enriched using magnetic beads (CD8 negative selection kit, Stem Cell Technologies) and $D^bGP276^+$ CD8 T cells were sorted on a FACSAria (BD). Four independent experiments were performed for each treatment group with 10-12 mice pooled per group per experiment. RNA was isolated with TRIzol (Life Technologies) according to manufacturer's instructions. RNA was processed, amplified, labeled, and hybridized to Affymetrix GeneChip MoGene 2.0 ST microarrays at the University of Pennsylvania Microarray Facility. Microarray data were processed and analyzed as previously described (Doering et al. Immunity 2012, 37:1130-1144). The heat map module in Gene Pattern was used to identify and display differentially expressed genes. Gene set enrichment analyses and leading edge metagene analyses were performed as described (Godec et al. Immunity 2016, 44:194-206). Metagenes for anti-PD-L1 were identified using the microarray data set comparing anti-PD-L1 to control $T_{EX}$. Metagenes for T (Day 8 post-LCMV Arm infection), $T_{MEM}$ (Day 30 post-LCMV Arm infection), and $T_{EX}$ (Day 30 post-LCMV clone 13 infection) cells were generated by comparing to naïve T cells using previously published transcriptional profiles (Doering et al. Immunity 2012, 37:1130-1144). Details of the metagene composition and comparisons can be found in Pauken et al. Table S4 (Pauken et al. Science 2016, 354(6316):1160-1165). To generate the effector gene list shown in FIG. 2C, we started with the top 300 genes up-regulated at Day 6 post Arm compared to naïve in (Doering et al. Immunity 2012, 37:1130-1144). Genes that had GO membership for six of the major cell cycle terms (cell cycle, mitosis, spindle, DNA replication, mitotic cell cycle, and cell cycle) were then removed. This list is shown in Pauken et al. Table S3 (Pauken et al. Science 2016, 354(6316):1160-1165).

For transcriptional profiling by RNA-seq, CD8 T cells from spleens were enriched using magnetic beads (CD8 negative selection kit, Stem Cell Technologies) and P14 cells were sorted on a FACSAria (BD). P14 cells were sorted either 1 day post final treatment (with 5 doses of anti-PD-L1 or control as described above; three independent experiments for control (5-7 mice each pooled), four independent experiments for anti-PD-L1 (5-6 mice each pooled)), or long-term (two independent experiments, at 18 (5 control-treated and 7 anti-PD-L1-treated mice pooled) and 29 weeks (13 control-treated and 12 anti-PD-L1-treated mice pooled)) after the final treatment. Naïve CD8+ T cells were sorted from pooled spleens from 2-3 uninfected C57BL/6 mice from two independent experiments. Cells were lysed and frozen in buffer RLT plus (RNeasy Plus Lysis Buffer, Qiagen) with 1% 2-mercaptoethanol (Sigma). Total RNA from sorted cells was extracted using the Applied Biosystems Arcturus PicoPure RNA isolation kit. Double stranded cDNA was generated using the Clontech SMRT-seq v4 method and was fragmented using the Covaris S220 in microTubes. Indexed Illumina-compatible sequencing libraries were generated from fragmented cDNA using the NEBNext Ultra II methodology. Libraries were quantified using Kapa Library QC kit for Illumina, pooled, and sequenced on an Illumina NextSeq 500 for 75 cycles (single end). Sequenced libraries were aligned to the mm10 reference genome using STAR and gene expression from RefSeq genes was quantified using Cufflinks and reported as FPKM values.

Epigenetic Profiling by ATAC-Seq

CD8 T cells were enriched using magnetic beads (CD8 negative selection kit, Stem Cell Technologies) and P14 CD8 T cells (day 8 p.i. Arm (5 spleens per experiment pooled), day 33 p.i. Arm (12-13 spleens per experiment pooled), day 35 p.i. clone 13 (15 spleens per experiment for control-treated pooled, 7 mice per experiment for anti-PD-L1-treated pooled)) or naïve CD8 T cells (from 2-3 spleens pooled) were sorted on a FACSAria (BD). Control- and anti-PD-L1 treated $T_{EX}$ cells were sorted one day after the final treatment (5 total treatments, every third day) as described above. Two independent experiments per condition were performed. ATAC-seq was performed as described in Buenrostro et al. Nat. Methods 2013, 10:1213-1218. Briefly, nuclei were isolated from 50,000-150,000 sorted cells per replicate using a solution of 10 mM Tris-HCl, 10 mM NaCl, 3 mM $MgCl_2$, and 0.1% IGEPAL CA-630. Immediately following nuclei isolation, the transposition reaction was conducted using Tn5 transposase and TD buffer (Illumina) for 45 minutes at 37° C. Transposed DNA fragments were purified using a Qiagen MinElute Kit, barcoded with dual indexes (Illumina Nextera) and PCR amplified using NEBNext High Fidelity 2×PCR master mix (New England Labs). The size distribution and molarity of the sequencing library were determined by using an Agilent Bioanalyzer and KAPA quantitative RT-PCR (KAPA Biosystems). Sequencing was performed using a high output, 150 cycle kit with V2 chemistry on a NextSeq 500 (Illumina). Paired-end reads were mapped to the mm10 reference genome using Bowtie2. Only concordantly mapped pairs were kept for further analysis. Peak calling was performed using MACS v1.4 to identify areas of sequence tag enrichment. BedTools was used to find common intersection between identified peaks (lbp minimum overlap) and to create a merged peak list. ATAC-seq tag enrichment, DNA motif analysis across the merged peak list, and GO term assessment were computed using HOMER (homer-.salk.edu). Principal component analysis, spectral co-clustering, and hierarchical clustering were performed using scipy, matplotlib, and scikit-learn. REVIGO was used to identify unique GO terms across different cell types. The list of peaks was filtered for some downstream analysis to remove peaks that had low enrichment across all five cell types (third quartile).

Transcription Factor Footprinting and Network Analysis

To build the integrated transcriptional network based on the unique epigenetic landscape of $T_{EX}$ (FIG. 19D), Wellington bootstrap (Piper et al. BMC Genomics 2015, 16:1000) was first used to identify transcription factor (TF) binding motifs enriched in either control- or anti-PD-L1-treated $T_{EX}$ in all OCRs compared to the other cell types probed by computing 20 sets of differential footprints for all ordered pairs of the 5 cell types ($T_N$, $T_{EFF}$, $T_{MEM}$, $T_{EX}$, anti-PD-L1-treated $T_{EX}$). To analyze motif frequencies in differential footprints, a motif search was done within these footprint coordinates using annotatePeaks.pl script from HOMER (Heinz et al. Mol. Cell 2010, 38:576-589) and relative motif frequencies were calculated as described in (Piper et al. BMC Genomics 2015, 16:1000). A matrix was generated and motif scores were displayed as a heat map (FIG. 19B) using the ClassNeighbors module of GenePattern (Reich et al. Nat. Genet. 2006, 38:500-501) to show cell-type specific TFs.

Significantly enriched TF binding motifs were subsequently validated to be included in the downstream network. TFs that were not detectable transcriptionally in the RNA-seq and/or TFs that had minimal evidence of binding to their consensus sequence with TF footprint analysis were excluded. For TF footprint validation, average profiles of the Tn5 cuts within a 200 bp window around different TF motifs were estimated and plotted using Wellington dnase_average_footprinting.py (Piper et al. Nucleic Acids Res. 2013, 41, e201). A network was then built with these validated TFs and the differentially expressed genes in $T_{EX}$ cells following anti-PD-L1 treatment from the microarray data set. Genes were included that had a LFC≥0.3. Lines connecting a TF with a target gene were based on that gene having a consensus binding motif for that TF in the region. The full list of TFs and target genes is available in Pauken et al. Table S11 (Pauken et al. Science 2016, 354(6316):1160-1165).

Figure 22A:
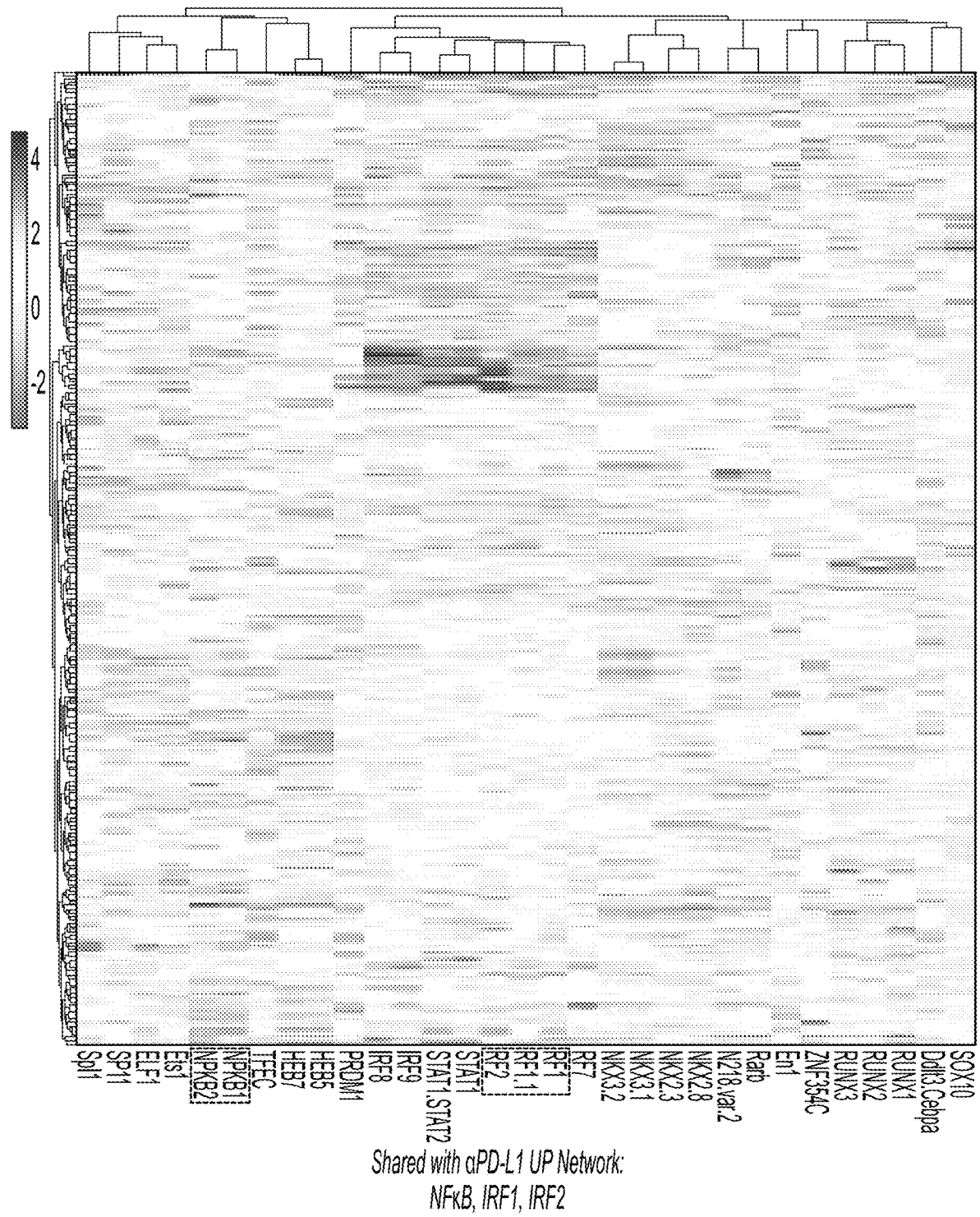
FIGS. 22A-22B are a series of images depicting predicted transcription factors involved in regulating differentially expressed genes in re-invigorated $T_{EX}$ following anti-PD-L1 treatment. The differentially expressed genes up, as illustrated in FIG. 22A, or down, as illustrated in FIG. 22B, by microarray after 2 weeks of anti-PD-L1 treatment (p<0.05, LFC≥0.3) (y-axis) and the transcription factors predicted to bind the promoter regions of these genes (x-axis) identified using PSCAN analysis. Transcription factors identified using this analysis that are shared with the transcription factors identified in FIG. 19B-FIG. 19D are listed underneath each heat map. Complete list of genes corresponding to different transcription factors is available in Pauken et al. Table S12 (Pauken et al. Science 2016, 354(6316):1160-1165).
Figure 22B:
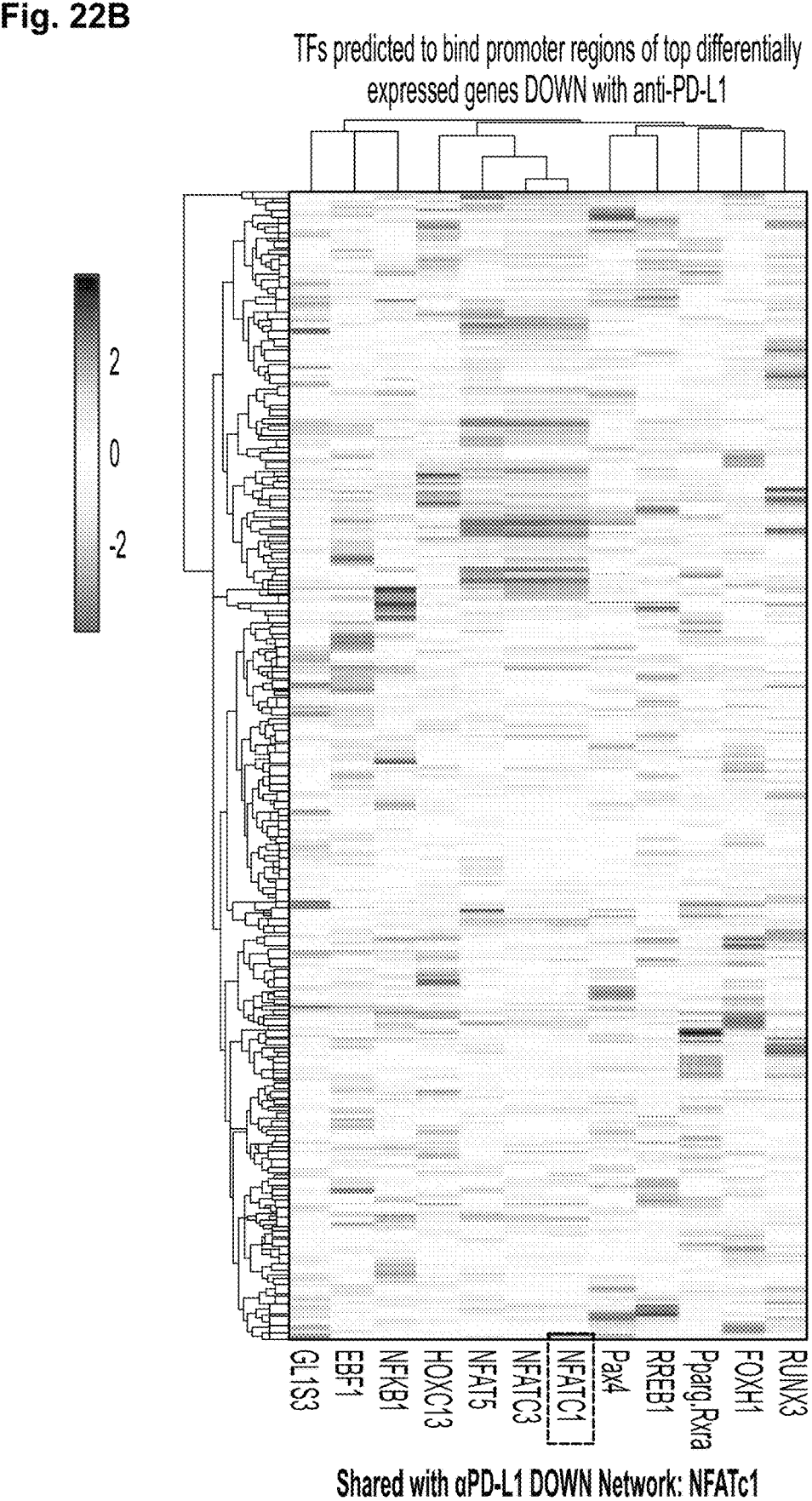

To validate TFs identified in this integrated network analysis correlating the epigenetic landscape and transcriptional changes, we constructed a second network using the differentially expressed genes from the microarray following anti-PD-L1 treatment (LFC≥0.3 up or down, p<0.05) and used PSCAN to identify the TFs predicted to contain consensus binding motifs in the promoter regions of those genes (available in Pauken et al. Table S12 (Pauken et al. Science 2016, 354(6316):1160-1165)). The enrichment for each TF for the differentially expressed genes was plotted as a heat map (FIG. 22). To test the prediction that anti-PD-L1 caused a re-engagement of effector-like circuitry in $T_{EX}$, we determined genes near all OCRs in $T_{EFF}$ or $T_{EX}$ cells that contained consensus binding motifs for TFs identified in the integrated network analysis (FIG. 19D) and selected additional TFs of interest including T-bet, Eomes, Prdm1 (Blimp1), and Runx1-3. We excluded genes near OCRs for which there was no transcriptional data in the microarray. The percentage of genes changed following anti-PD-L1 that contained membership in the list for the overlap between $T_{EFF}$ and $T_{EX}$ or $T_{EX}$ alone was then calculated, and the percent difference in the overlap compared to $T_{EX}$ alone was plotted.

Statistical Analysis

Statistics for flow cytometry and viral load data were analyzed using GraphPad Prism software. For comparisons between two independent conditions when only two conditions were being compared, significance was determined using unpaired Student's t tests. Paired Student's t tests were used when samples from the same mouse were being compared at two different time points as indicated in the Brief Description of the Drawings. One way ANOVA tests were used when more than two groups were being compared. We first tested for normality using the D'Agostino and Pearson normality test. If all groups were determined to be normally distributed, a parametric one way ANOVA was performed, and post-test analyses of groups of interest were performed using Bonferroni's multiple comparison test. If not all groups were determined to be normally distributed, a non-parametric ANOVA (Kruskal-Wallis test) was performed, and post test analyses of groups of interest were performed using Dunn's multiple test comparisons. P values for the ANOVA are indicated in blue next to the Y axis in each figure, and the p values for post-tests between indicated pairs are in black. P values were considered significant if less than 0.05. Asterisks used to indicate significance correspond with: $p<0.05^*$, $p<0.01^{}$, $p<0.001^{*}$.

Patients and Specimen Collection

Patients with stage N melanoma were enrolled for treatment with pembrolizumab (2 mg kg$^{-1}$ by infusion every 3 weeks) under an Expanded Access Program at Penn (www.clinicaltrials.gov identifier NCT02083484) or on NCT01295827 at Memorial Sloan Kettering Cancer Center ('MSKCC'). Patients consented for blood collection under the University of Pennsylvania Abramson Cancer Center's ('Penn') melanoma research program tissue collection protocol UPCC 08607 and under protocol 00-144 at MSKCC, in accordance with the Institutional Review Boards of both institutions. Peripheral blood was obtained in sodium heparin tubes before treatment and before each pembro infusion every 3 weeks for 12 weeks. Peripheral blood mononuclear cells (PBMCs) were isolated using ficoll gradient and stored using standard protocols.

Assessment of Response and Tumor Burden

Tumor burden. Total measurable tumor burden was defined as the sum of the long axis of all measurable lesions reported on the pre-therapy imaging reports. Patients with only non-measurable lesions or active brain metastasis were excluded from analysis involving clinical response and tumor burden. Assessment of clinical response and tumor burden was performed independently in a blinded fashion.

Clinical response, Penn cohort. Clinical response to anti-PD-1 therapy for the Penn cohort was determined as best response based on immune related RECIST (irRECIST) using unidimensional measurements (Nishino et al. Clin. Cancer Res. 2013, 19:3936-3943). In addition, the following modifications were used. (1) Lymph node lesions with a short axis between 10 and 15 mm with a standard uptake value (SUV) of greater than 5 on PET scan were included as measurable lesions. (2) Lesions greater than 5 mm confirmed to be melanoma by biopsy were included as measurable lesions.

Clinical response, MSKCC cohort. Clinical response for the MSKCC cohort was assessed based on immune-related response criteria (Wolchok et al. Clin. Cancer Res. 2009, 15:7412-7420) using bidimensional measurements at the 12 week time point.

Flow Cytometry

Penn cohort. Cryopreserved PBMC samples from pre-treatment, cycles 1-4 (weeks 3-12) were thawed and stained with master mix of antibodies for surface stains including CD4 (Biolegend, OKT4), CD8 (ebioscience, RPA-T8), 2B4 (Beckman Coulter, 1M2658), CD45RA (Biolegend, HI100), TIM-3 (F38-2E2), LAG-3 (Enzo, ALX-804-806B-C100), CXCR5-BV421 (BD, RF8B2) and CD27 (BD, L128) and intracellular stains for FOXP3 (BD, 259D/C7), CTLA-4 (BD, BNI3), Eomes (ebioscience, WD1928), T-bet (Biolegend, 4B10), GzmB (Life Tech, GB11), TCF-1-AlexaFluor647 (Biolegend, 7F11A10) and Ki67 (BD, B56). Permeabilization was performed using the FOXP3 Fixation/Permeabilization Concentrate and Diluent kit (eBioscience). PD-1 on post pembro specimens was detected using anti-human IgG4 PE (Southern Biotec). Pretreatment samples were pretreated with 25 µg ml$^{-1}$ pembro in vitro for 30 min at 37° C., washed twice and stained with standard antibody mix. Cells were resuspended in 1% paraformaldehyde until acquisition on a BD Biosciences LSR II cytometer and analyzed using FlowJo (Tree Star).

MSKCC cohort. PBMC samples at the indicated visits pre- and post-pembrolizumab treatment were thawed and stained with a fixable Aqua viability dye (Invitrogen) and a cocktail of antibodies to the following surface markers: CD8-Qdot605 (Invitrogen, 3B5), CD4-Qdot655 (Invitrogen, S3.5), PD-1-PE (BD, MIH4), LAG-3-FITC (Enzo, 17B4), ICOS-PE-Cy7 (eBioscience, ISA-3), TIM-3-APC (R&D Systems, 344823). Cells were next fixed and permeabilized with the FOXP3/Ki67 Fixation/Permeabilization Concentrate and Diluent (eBioscience), and subsequently stained intracellularly with CD3-BV570 (Biolegend, UCHT1), Ki67-AlexaFluor700 (BD), FOXP3-eFluor450 (eBioscience), and CTLA-4-PerCP-eFluor710 (eBioscience). Stained cells were acquired on a BD Biosciences LSR-Fortessa and analyzed using FlowJo software (FlowJo, LLC).

Cell Sorting

Cryopreserved PBMC samples were thawed and stained as per flow cytometry protocol (above). For RNA sequencing experiments, total CD8 T cells were sorted, using a dump/dead-CD3$^+$CD8$^+$ gating strategy. For TCR sequencing experiments, CD8 T cells were gated as above, and CD38$^+$HLA-DR$^+$ and cells that were not CD38$^+$HLA-DR$^+$ (that is, CD38$^-$HLA-DR$^-$, CD38$^+$HLA-DR$^-$, and CD38$^-$HLA-DR$^+$) were sorted. Cell sorting was performed on BD Aria Sorter.

Cytokine Analysis

Concentration of circulating plasma cytokines was analyzed using Luminex technology (EMD Millipore).

Stimulation with PMA and Ionomycin

Thawed cells were stimulated with phorbol 12-myristate 13-acetate (PMA) (Sigma) at 0.25 µg ml$^{-1}$ and ionomycin (Sigma) at 2.5 µg ml$^{-1}$ for 2-5 h in 37° C. and stained. Cytokine production was analyzed with intracellular staining using antibodies to IFNγ (Biolegend, B27) and TNF-α (Biolegend, Mab11).

Random Forest for Classification and Regression

Random forest regression and classification (RF-RC) is a multivariable non-parametric ensemble partitioning tree method that can be used to model the effect of all interactions between genes and proteins as predictors on a response variable (Breiman Mach. Learn. 2001, 45:5-32). Each model is constructed using approximately two-thirds of randomly selected samples and cross-validated on the one-third of the samples left out of the model building process ('out-of-bag' samples). After many iterations, results of all models are averaged to provide unbiased estimates of predicted values, error rates, and measures of variable importance. Performance of an RF-RC model is measured by the mean square error for regression and by misclassification error rate for classification. Flow cytometry subsets were used as possible predictors of clinical response variables. For each predictor, an importance score is determined, that measures the contribution of the variable to the error rate (higher scores are more predictive). We used the 'randomForest' R package version 4.6-12 implementation and the following parameters: 5,000 trees, node size of 1, mtry value (that is, number of variables available for splitting at each node) equal to the square root of the number of variables in the model, and the Breiman-Cutler permutation method for importance score determination. The mean decrease in accuracy is used as the importance score measure.

Mass Cytometry and CyTOF Analysis

Mass cytometry reagents were obtained from Fluidigm or generated by custom conjugation of unlabelled mAbs to isotope-loaded polymers using the MAXPAR kit (Fluidigm). Mass cytometry antibodies used are shown in Table 5. Mass cytometry staining was performed as described (Bengsch et al. J Immunol Methods. 2017, pii:S0022-1759 (17)30132-1). Briefly, single-cell suspensions were pelleted, and incubated with 20 µM Lanthanum-139 (Trace Sciences)-loaded maleimido-mono-amine-DOTA (Macrocyclics) in PBS and incubated for 10 min at room temperature (RT) for live/dead discrimination (LD). Cells were washed in staining buffer and resuspended in surface antibody cocktail, incubated for 30 min at room temperature, washed twice in staining buffer, fixed, and permeabilized using FOXP3 staining buffer set (eBioscience), and stained intracellularly for 60 min at RT. Cells were further washed twice before fixation in 1.6% PFA (Electron Microscopy Sciences) solution containing 125 nM iridium overnight at 4° C. Prior to data acquisition on CyTOF2 (Fluidigm), cells were washed twice in PBS and once in dH$_2$O. Data analysis was performed with FlowJo v10 (TreeStar) and SPADE (Cytobank) as outlined previously (Breiman. Mach. Learn. 2001, 45:5-32). Analysis of fold change frequency was performed using the 'percenttotalratiolog' parameter for SPADE that performs the calculation log$_{10}$[percentage of total (week 3)/(percentage of total (pretreatment)]. Summary statistics for T$_{EX}$, T$_{MEM}$, and T$_{EFF}$ cells were calculated as the median fold change or mass intensity of each cluster by taking into account the proportion contributed by each node. R package 'pheatmap' was used for creating heat maps.

Mass Cytometry (CyTOF) Assay and Tracking T$_{EX}$

Transcriptional profiling available through the Gene Expression Omnibus (GEO) database (www.ncbi.nlm.nih.gov/gds) under the accession number GSE41867 described in (Doering et al. Immunity 2012, 37:1130-1144) was used together with ATAC-Seq data described in Pauken et al. and/or Sen et al. (Pauken et al. Science 2016, 354 (6316):1160-1165; Sen et al. Science. 2016, 354(6316): 1165-1169) (GSE97646, GSE86881). Transcriptional profiling data was downloaded from GEO and annotated using R 3.3.1 and GEOquery package. ATAC-Seq open chromatin region (OCR) analysis was done as in Pauken et al. and/or Sen et al. (Pauken et al. Science 2016, 354(6316):1160-1165; Sen et al. Science. 2016, 354(6316):1165-1169) (GSE97646, GSE86881). Identification of exhaustion-specific transciptomic and epigenomic expression patterns was performed using moderated Bayesian statistics calculated in limma package. Specifically, genes up- or down-regulated in exhausted CD8 T cells were selected if their moderated T statistic was (>=2.9) compared to control T cell populations.

The epigenomically selected gene set was used to generate a high-parameter mass cytometry panel (45 parameter) that allows the single-cell proteomic identification and evaluation of exhausted T cells in humans. The high-dimensional nature of mass cytometry data allows substantial resolution in evaluating the activation/differentiation state of exhausted T cells in "exhaustion space" defined by the parameters in the mass cytometry panel. Bioinformatic analysis using tSNE- and Phenograph-based algorithms identified distinct cellular exhaustion phenotypes in HIV patients, lung cancer and melanoma patients and healthy individuals. Analysis indicated: distinct $T_{EX}$ populations linked to disease severity or therapy in HIV and cancer; ability to use the composition of the $T_{EX}$ pool as a fingerprint of disease state; ability to approximate the extent of an individual's pool of exhaustion by blood profiling, which allows discrimination of healthy individuals from patients with chronic disease (viral/tumor); and high convergence between phenotypic and functional definitions of exhaustion using a newly invented exhaustion score metric for functional profiling. Specifically, bead-based normalization of CyTOF data was performed using www.github.com/nolan-lab/bead-normalization/releases. FCS files were further analyzed by commercial software FlowJo v10 (TreeStar), FCS-Express 6 (DeNovo Software) and ViSNE (Cytobank). R based tSNE analysis was performed using Rtsne package. Phenograph analysis was performed using RPhenograph package implemented via cytofkit package, described in (Chen et al. PLoS Comput Biol. 2016, 12(9):e1005112; Levine et al. Cell. 2015, 162(1):184-97). For visualization, 10000 nodes were sampled from the graph following clustering (i.e. the clustering was performed on the full dataset, but only a subsample is displayed for readability). The resulting subgraph was then laid out using the ForceAtlas2 force-directed layout algorithm (Jacomy et al. PLoS One. 2014, 9(6): e98679). Analysis of exhaustion data space using Visne or Phenograph was performed on mass channels corresponding to exhaustion-specific molecules. Phenograph analysis of exhaustion data space on Iridium intercalator positive, singlet LD negative CD45+CD3+CD8 T cells identified 30 high-dimensional clusters, of which 5 (c14, c20, c22, c24, c30) represented cell frequencies <0.01% of CD8 T cells after quality control gating and were excluded from downstream analysis. To develop an "exhaustion score" samples were split for direct phenotypic analysis or stimulation with PMA/Ionomycin in complete media for 5 h at 37 C in the presence of Monensin and Brefeldin A and stained for mass cytometry analysis. Exhaustion-specific markers shared between the phenotyping and stimulation panel were used to construct a shared tSNE-based exhaustion map. Gates reflecting the Phenograph clusters were identified on this shared exhaustion map, and cytokine expression in the corresponding gates from stimulated samples was mapped to the Phenograph clusters. For validation, a second mapping method was used as implemented by the "classify" mode of Phenograph (Levine et al. Cell. 2015, 162(1):184-97). The training data was constructed by sampling 50,000 cells from each of the samples with a stimulus. The exhaustion markers common to both the unstimulated and post stim data, CTLA4, CD7, CD127, Helios, PD-1, CCR7, Eomes, CD38, TOX, TIGIT, CXCR5, 2B4, LAG3, CD36 were used for this analysis. For each stimulated sample, a nearest neighbor graph using the Jaccard metric was constructed using the training data and cells from the stimulated sample. Random walk probabilities through the graph were used to assign clusters to each of the stimulated cells. These findings provide a framework for the assessment of exhausted T cell populations in the blood and additional insights into the severity of exhaustion, relation to disease and changes with disease progression or intervention. The invention allows assessing key disease-relevant $T_{EX}$ populations that are key to the diagnostics, monitoring, and target identification in cancer immunotherapies.

T-Cell Receptor Sequencing

Manual macrodissection was performed on FFPE slides, if necessary, using a scalpel and a slide stained with haematoxylin and eosin (H&E) as a guide. Tissue deparaffinization and DNA extraction were performed using standard methods. DNA was quantified using Qubit dsDNA BR Assay (Invitrogen). Peripheral blood CD8 T cells were purified and isolated from PBMCs using BD Aria Sorter. DNA extraction, amplification, library preparation, sequencing, and preliminary bioinformatics analysis was performed by Adaptive Biotechnologies. Amplification and sequencing of TCRB CDR3 was performed at a survey level resolution using the immunoSEQ Platform (Adaptive Biotechnologies).

Immunohistochemistry for PD-L1 and CD8, and Analysis

Formalin-fixed, paraffin-embedded tumors were collected at the time of surgical resection or from a biopsy. For anti-PD-L1 staining, after heat-induced antigen retrieval (Bond ER2, 20 min), the tumor slides were stained with an anti-PD-L1 antibody (E1L3N, Cell Signaling) at 1:50 dilution. To confirm specificity, the anti-PD-L1 antibody was validated by staining Hodgkin's lymphoma cells and placenta. For anti-CD8 staining, after heat-induced antigen retrieval (Bond ER1, 20 min), the tumor slides were stained with an anti-CD8 antibody (M7103, Dako) at 1:40 dilution. Tumor infiltrating CD8-positive T cells was scored as absent, minimal, mild, moderate and brisk by a blinded expert melanoma pathologist. Tumor-infiltrating CD8 T cells were also analyzed by image recognition analysis using ImageJ2. Digital slides were acquired by a Leica microscope. RGB stack images of CD8 staining were converted to greyscale, and particles (positive stain) counted using a threshold value of 100 with a size between 10 and 625 $\mu m^2$. Total area of the tumor was calculated using a tumor mask.

RNA Sequencing and Analysis

After sorting, the cells were resuspended and frozen in RLT buffer (Qiagen). RNA was isolated using the Qiagen RNeasy micro kit (Cat. No. 74034) according to the manufacturer's protocol. RNA-seq libraries were prepared using the SMARTer Stranded Total RNA-Seq Kit for Pico Input Mammalian from Clonetech according to the manufacturer's protocol (Cat. No. 635007). The libraries were sequenced on an Illumina NextSeq machine using a 300-cycle high-output flow cell (Cat. No. 15057929), with a read depth between 9 million and 20.6 million paired mapped reads. The Fastq files were aligned using STAR 2.5.2a and hg19. The aligned files were processed using PORT gene-based normalization (www.github.com/itmat/Normalization). The differential gene expression was performed with Limma. Limma-voom was used to identify significantly different transcripts between groups using P value <0.05. For patients with a Ki67 peak at cycle 1 (three patients), the top 40 genes highly correlated with MK167 were taken to create a correlative network including the top 5 genes correlating with the MK167-correlated genes. The final network had nodes with highly correlated (absolutely value of the correlation coefficient>0.7 (abs(corr)>0.7)) values with MK167. Cytoscape 3.4.0 was used for creation of correlation network, and metascape.org was used to enrich genes for GO biological processes. The data discussed in this publication have been deposited in NCBI Gene Expression Omnibus and are accessible through GEO Series accession number GSE96578 (www.ncbi.nlm.nih.gov/geo/query/acc.cgi?acc=GSE96578), incorporated by reference herein in its entirety.

Whole-Exome Sequencing, Mutational Burden Analysis and Neoepitope Prediction

Manual macrodissection was performed on FFPE slides, if necessary, using a scalpel and H&E-stained slide as a guide. Tissue deparaffinization and DNA extraction were performed using standard methods. DNA was quantified using Qubit dsDNA BR Assay (Invitrogen). DNA libraries were created using NEBNext Ultra DNA Library Prep Kit for Illumina (New England BioLabs) and targets were captured with SureSelect Human All Exon V6$^+$ COSMIC (Agilent). HLA with OptiType and neoepitope predictions were made using Ccons 1.1 Server.

Statistical Methods and Classification and Regression Tree (CART) Analysis

Figure 27A:
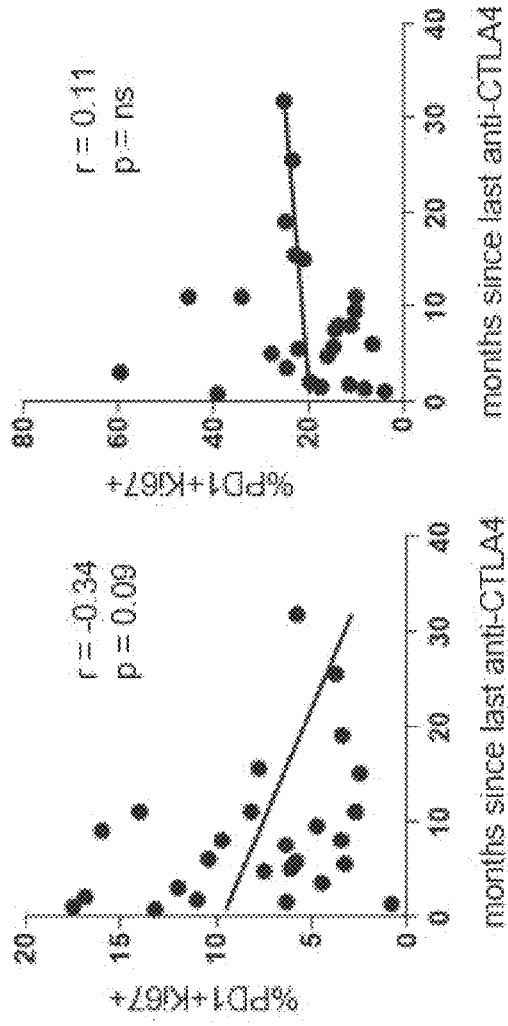
FIGS. 27A-27C are a series of images depicting that effect of anti-CTLA-4 therapy on Ki67 expression is restricted to the pretreatment time point.
Figure 27B:
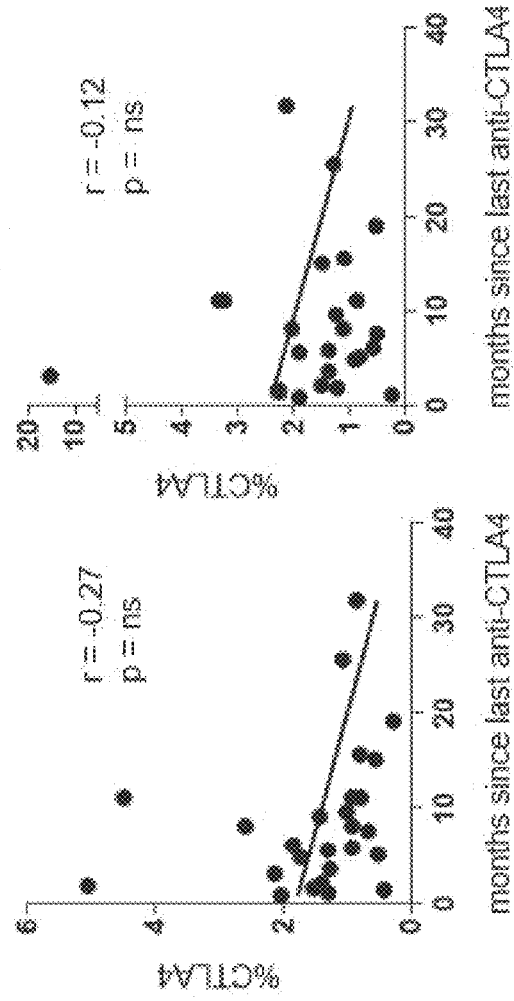
Figure 27C:
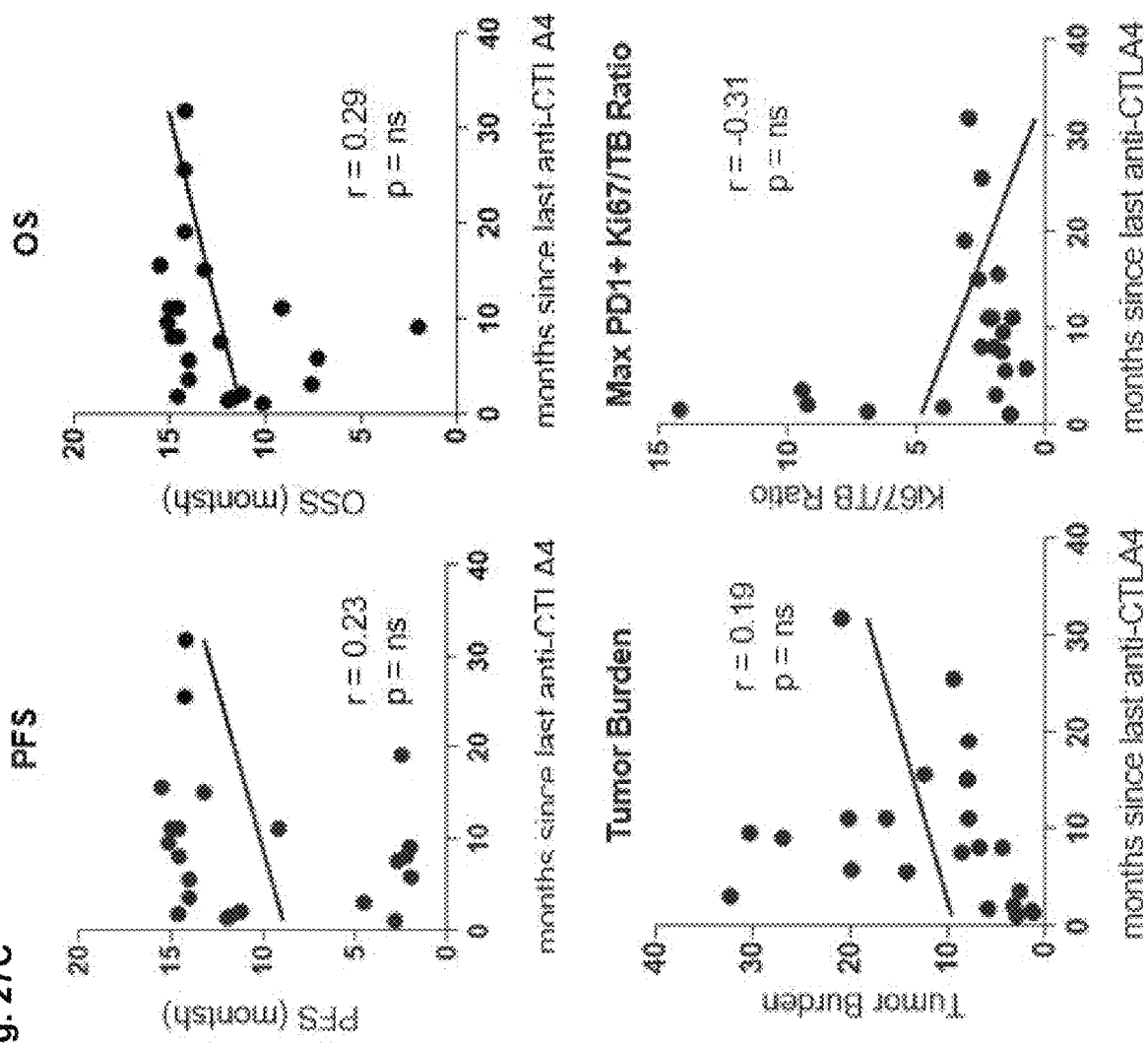
Figure 34C:
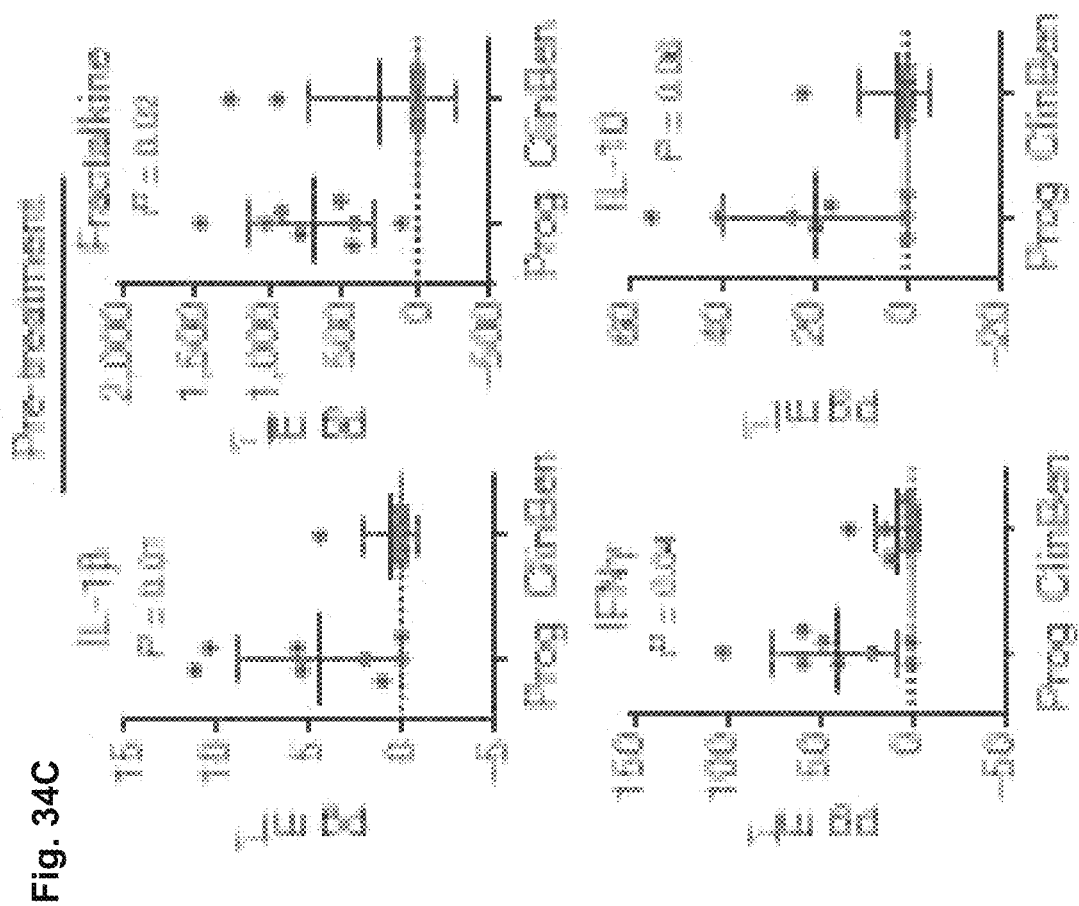
Figure 34D:
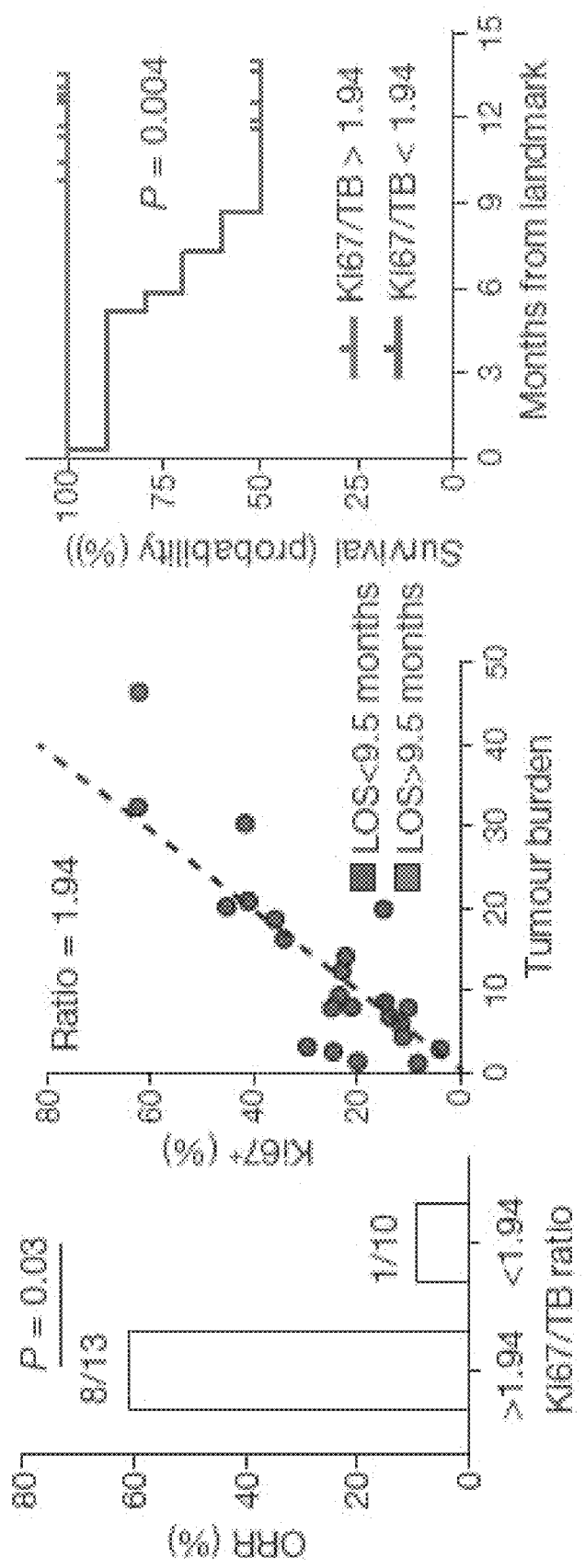
Figure 34G:
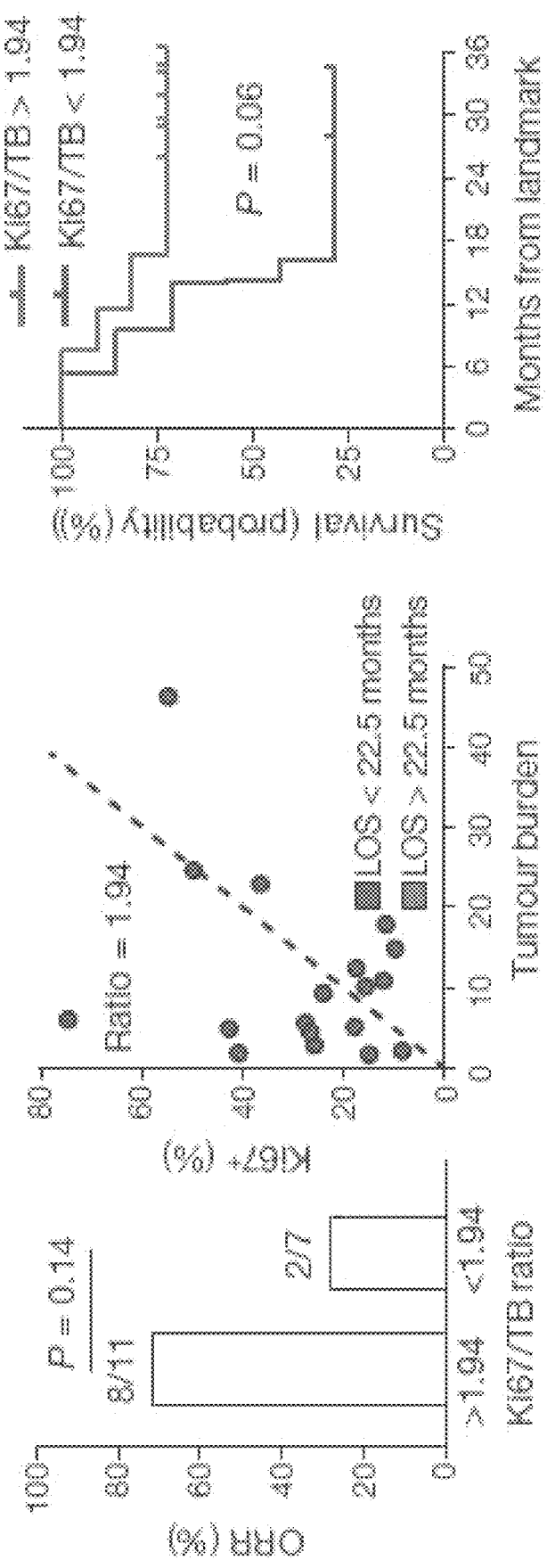

For group comparisons and correlation analyses, testing was performed using PRISM 6.0. Normality of distributions was assessed using D'Agostino-Pearson omnibus normality test and variance between groups of data was assessed using the F-test. For normally distributed data, significance of mean differences was determined using two-sided paired or unpaired Student's t-tests, and for groups that differed in variance, unpaired t-test with Welch's correction was used. For non-normal data, non-parametric Mann-Whitney U-tests or Wilcoxon matched-pairs signed rank tests were used for unpaired and paired analyses, respectively. Descriptive statistics included mean, median, standard deviation and range for continuous variables and frequency and proportion for categorical variables. Correlations between continuous variables were determined by Pearson's r coefficient, whereas correlations between ordinal-scaled categorical variables were determined by Spearman's r coefficient. Overall survival was defined from the initiation of treatment to date of death or last patient contact alive and estimated by the Kaplan-Meier method. Landmark overall survival and PFS analysis was defined as overall survival and PFS starting from 6 weeks after therapy. To visually inspect the relationships between Ki67 (week 6 maximum), baseline tumor burden and clinical outcomes, we constructed simple scatter plots of Ki67 by baseline tumor burden and employed color-coded symbols for clinical outcome such as overall survival, PFS, and clinical response. In general, the mean was used for dichotomization of clinical outcomes. This included PFS and landmark PFS in the Penn dataset (FIG. 27, FIG. 35) and landmark overall survival for MSKCC dataset (FIG. 34G). In the Penn dataset, landmark overall survival was dichotomized using a cutoff of 9.5 months, as it represented the longest complete survival time (that is, no patient with LOS<9.5 months was alive and censored for survival) (FIG. 34D, FIG. 35). The log rank test was employed to compare overall survival between patient subgroups. The ratio of Ki67 to tumor burden was associated with overall survival and was further examined by CART analysis. CART identified the optimal cut point to split this continuous variable into two homogenous subgroups according to overall survival. By this method, the optimal cut point is selected from all possible cut points. Survival and CART statistical analyses were performed using either IBM SPSS v23 or STATA v14. Similar analysis was performed for landmark PFS.

Model Selection, Principal Component Analysis and Fisher's Exact Calculation

Model selection is a method of selecting models among a set of candidate models. The R package 'leaps' version 2.9 with parameters 'nvmax=3', and 'nbest=10' was used to select the ten best models on the basis of linear regression for predicting CD8 and Ki67 expression.

Clinical parameters were used as predictor variables and Ki67 as the dependent variable. This method evaluates all one-variable, two-variable, and three-variable models and ranks best-fitting models using the Bayesian information criterion (BIC), penalized by number of variables. Lower BIC score signals a better model.

Principle component analysis was used to visualize three variables: tumor burden, Ki67, and mutational burden in two-dimensional space. R package factoMiner was used to calculate and extract the percentage of variance explained by principal components and the variables contained in each PCA variable.

Fisher's exact test was used to test the hypothesis that the probability of finding shared TCR CDR3 clonotypes (between top 10 tumor-infiltrating T-cell clones and peripheral blood, FIG. 32A) among all unique sequenced peripheral blood clones was different than the probability of finding a clone in the tumor by random chance, with an theoretical estimate of $10^7$ possible peripheral blood clonotypes. P value was calculated using the R function 'ftsher.test( )'.

High Dimensional Data Analysis

Bead-based normalization of CyTOF data was performed using Nolan lab normalizer available through www.github.com/nolanlab/bead-normalization/releases. FCS files were further analyzed by commercial software FlowJo v10 (TreeStar), FCSExpress 6 (DeNovo Software) and ViSNE (Cytobank). R based tSNE analysis was performed using Rtsne package. Phenograph analysis was performed using RPhenograph package implemented via cytofkit package, described in (Chen et al. PLoS Comput Biol. 2016, 12(9): e1005112; Levine et al. Cell. 2015, 162(1):184-97). For visualization, 10000 nodes were sampled from the graph following clustering (i.e. the clustering was performed on the full dataset, but only a subsample is displayed for readability). The resulting subgraph was then laid out using the ForceAtlas2 force-directed layout algorithm (Jacomy et al. PLoS One. 2014, 9(6): e98679). Analysis of exhaustion data space using Visne or Phenograph was performed on mass channels corresponding to exhaustion-specific molecules as defined through FIGS. 24 and 28. Phenograph analysis of exhaustion data space on Iridium intercalator positive, singlet LD negative CD45+CD3+CD8 T cells identified 30 high-dimensional clusters, of which 5 (c14, c20, c22, c24, c30) represented cell frequencies <0.01% of CD8 T cells after quality control gating and were excluded from downstream analysis.

Exhaustion Function Mapping

Samples were split for direct phenotypic analysis or stimulation with PMA/Ionomycin in complete media for 5 h at 37 C in the presence of Monensin and Brefeldin A and stained for mass cytometry analysis. Exhaustion-specific markers shared between the phenotyping and stimulation panel were used to construct a shared tSNE-based exhaustion map. Gates reflecting the Phenograph clusters were identified on this shared exhaustion map, and cytokine expression in the corresponding gates from stimulated samples was mapped to the Phenograph clusters (see also FIG. 26). For validation, a second mapping method was used as implemented by the "classify" mode of Phenograph (Levine et al. Cell. 2015, 162(1):184-97). The training data was constructed by sampling 50 k cells from each of the samples with a stimulus. The exhaustion markers common to both the unstimulated and post stim data, CTLA4, CD7, CD127, Helios, PD-1, CCR7, Eomes, CD38, TOX, TIGIT, CXCR5, 2B4, LAG3, CD36 were used for this analysis. For each stimulated sample, a nearest neighbor graph using the Jaccard metric was constructed using the training data and cells from the stimulated sample. Random walk probabilities through the graph were used to assign clusters to each of the stimulated cells. See (Levine et al. Cell. 2015, 162(1):184-97) for a more detailed description.

Heatmap Display

Heatmaps were generated using the Pheatmap R package (v. 1.0.8). Color representation is based on the z-score and indicated by a color palette in the figures next to the heatmaps.

Statistical Analysis and Data Visualization

Statistical analysis was performed using JMP 12.2.0 (SAS), GraphPad Prism 7.02 and R 3.3.1 limma package. In FIGS. 29-31, simple regression analysis of Phenograph cluster frequencies in patient samples was performed and the respective pearson correlation was plotted using R ggplot2 package.

Data Availability

RNA sequencing data that support the findings have been deposited in NCBI Gene Expression Omnibus and are accessible through GEO Series accession number GSE96578 (www.ncbi.nlm.nih.gov/geo/query/acc.cgi?acc=GSE96578). Flow cytometry, TCR sequencing, and clinical data are included in Huang et al. (Huang et al. Nature 2017, 4; 545(7652):60-65, doi:10.1038/nature22079) and its Extended Data and Supplementary Information, incorporated herein by reference, in its entirety.

Materials and Methods for Examples 10 to 18

Patient Populations and Specimen Collection

Blood was acquired with the written informed consent of all study participants and with the approval of the University of Pennsylvania Institutional Review Board. HIV samples were obtained through the Penn Center for AIDS Research (CFAR) (IRB #815056), for lung cancer blood and tissue samples were obtained (IRB #813004) and for healthy controls blood was obtained (IRB #820151). PBMC and TIL were extracted as described (Huang et al. (2017) Nature 545:60-65; Quatromoni et al. (2015) J Leukoc Biol 97:201-209).

Transcriptomic and Epigenomic Data Analysis

Transcriptional profiling of LCMV-specific T cells available through the Gene Expression Omnibus (GEO) database (www.ncbi.nlm.nih.gov/gds) under the accession number GSE41867 was described in Doering et al. (Doering et al. (2012) Immunity 37:1130-1144). ATAC-Seq data was described in Pauken et al. Science (2016) 354(6316):1160-1165 and Sen et al. (2016) Science 354(6316):1165-1169 (GSE97646, GSE86881). Transcriptional profiling data was downloaded from GEO and annotated using R 3.3.1 and GEOquery package. ATAC-Seq open chromatin region (OCR) analysis was done as in Pauken et al. Science (2016) 354(6316):1160-1165 and Sen et al. (2016) Science 354 (6316):1165-1169 (GSE97646, GSE86881). Identification of exhaustion-specific transcriptomic and epigenomic expression patterns was performed using moderated Bayesian statistics calculated in limma package. Specifically, genes up- or down-regulated in virus-specific $T_{EX}$ were selected if their moderated T statistic was (>=2.9) compared to $T_N$, $T_{EFF}$ and $T_{MEM}$.

Gene Enrichment and Variation Analysis

Gene set enrichment analysis (GSEA) using Broad Institute software (www.broadinstitute.org/gsea/index.jsp) was performed on microarray data from GEO. Exhaustion-specific gene signatures were tested by GSEA. Normalized Enrichment scores (NES) and leading edge (LE) genes obtained by GSEA were used for comparison across different datasets in FIGS. 1, 2 and 3. In FIG. 8, Gene set variation analysis (GSVA) using GSVA R package (Hanzelmann et al. (2013) BMC Bioinformatics 14:7) was performed to interrogate single cell transcriptomic data from Tirosh et al. (2016) Science 352:189-196) and assess different exhaustion gene sets in the tumor microenvironment. Briefly, CD8 T cell single-cell data was obtained from NIH GEO (GSE72056; available at www.ncbi.nlm.nih.gov/geo/query/acc.cgi?acc=GSE72056), and GSVA of single-cell data was performed using the full epigenomically—and transcriptomically defined exhaustion gene list or a subset of genes later analyzed by CyTOF. The results of the GSVA analysis using the UP- and DOWN-regulated gene lists were used to calculate a GSVA exhaustion score (GSVA_score_UP–GSVA_score_DN).

Cell Sorting and In Vitro Culture for $T_{EFF}$ Activation

PBMC or sorted T cell populations were stimulated with anti-CD3/CD28 beads (Miltenyi Biotec) in the presence of 20 U/ml IL-2 (Stemcell) for 72 hours in supplemented culture media (RPMI 1640 (Gibco) supplemented with L-glutamin, 10% FCS and Penicillin/Streptomycin). Sorting was performed on a FACS Aria II (BD Biosciences) after staining for $T_N$ (CCR7+CD45RA+CD27+), $T_{CM}$ (CD27+CD45RA–CCR7+), $T_{EM}$ (CD27–CCR7–CD45RA–), T (CD27–CCR7–CD45RA+) and PD-1+ populations using anti-CD27-BV785 (clone 0323), anti-CD45RA-BV605 (clone HI100), anti-PD-1-BV421 (clone E12.2.H7), anti-CD8 APC-Fire (clone RPA-T8) (Biolegend), anti-CCR7-FITC (clone 150503) (BD Biosciences), and after staining with life/dead reagent Ghost Violet (Tonbo).

Mass Cytometry

Figure 45:
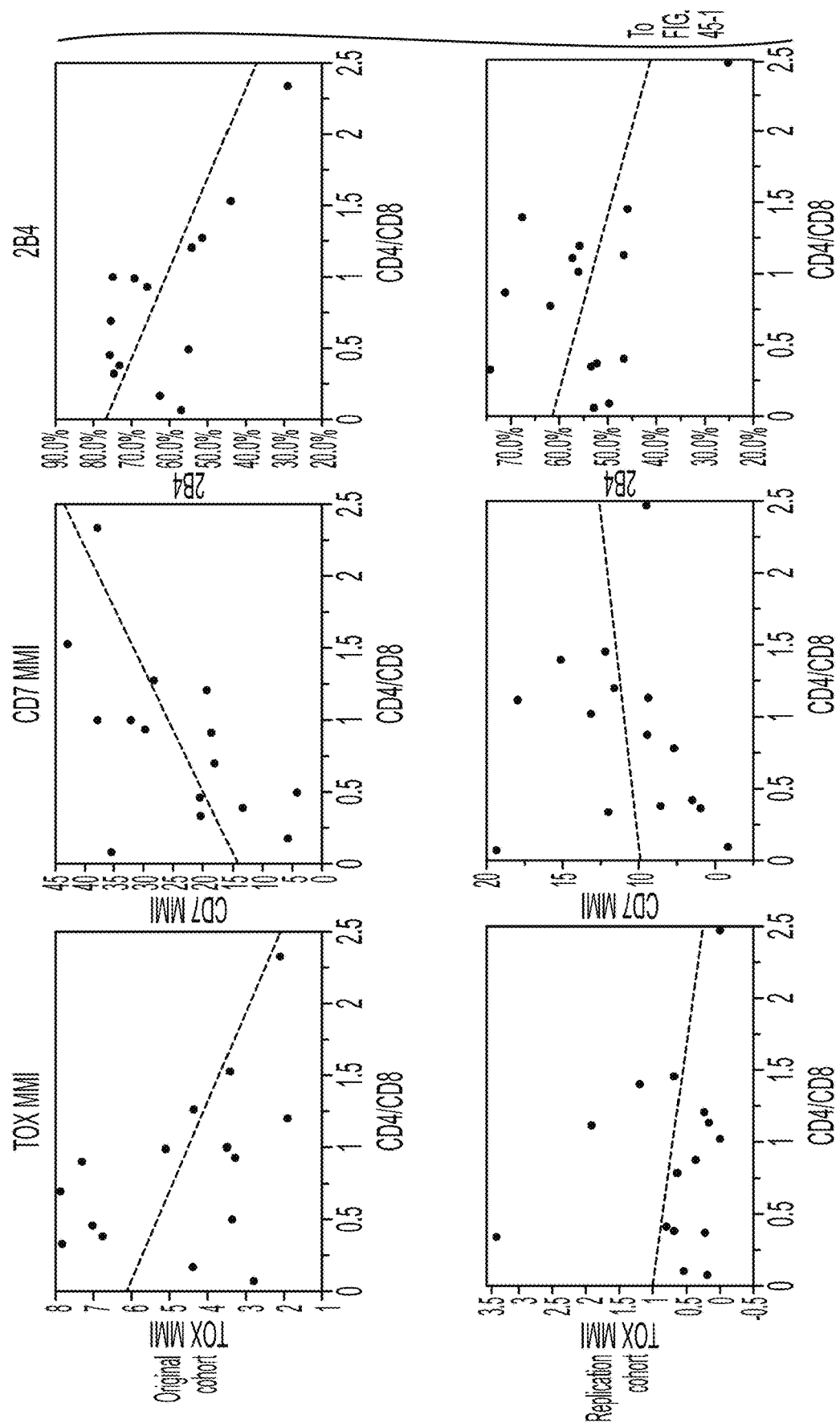
FIG. 45 illustrates that 15 patient PBMC samples from the same time point that had been analyzed in FIG. 39D were tested for reproducibility of results, stained and acquired on a different mass cytometer (Fluidigm Helios system). Linear regression analysis of marker expression by peripheral CD8 T cells in patients and healthy donors is shown. Samples were gated for positivity of exhaustion marker expression. Each dot represents the frequency per sample/individual patient of CD8+ T cells expressing the indicated maker (except where MMI was used as indicated) plotted against the CD4/CD8 for that patient Results are arranged in rows alternating between the original data obtained on a Fluidigm CyTOF2 ("original analysis") and the repeat cohort data obtained later ("replication data"). Positive correlations are depicted in green, negative correlations in red.
Figures 1, 45:
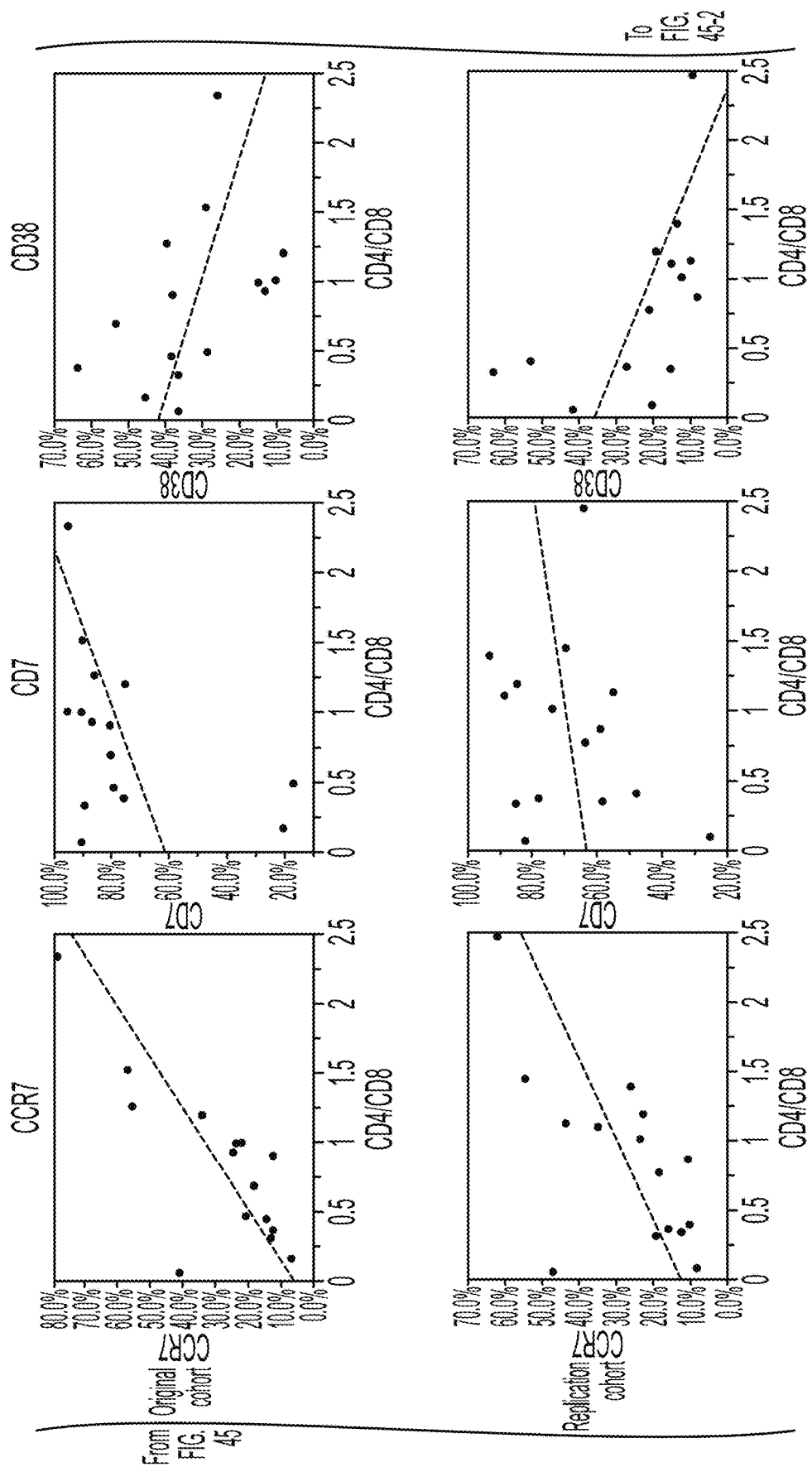
Figures 2, 45:
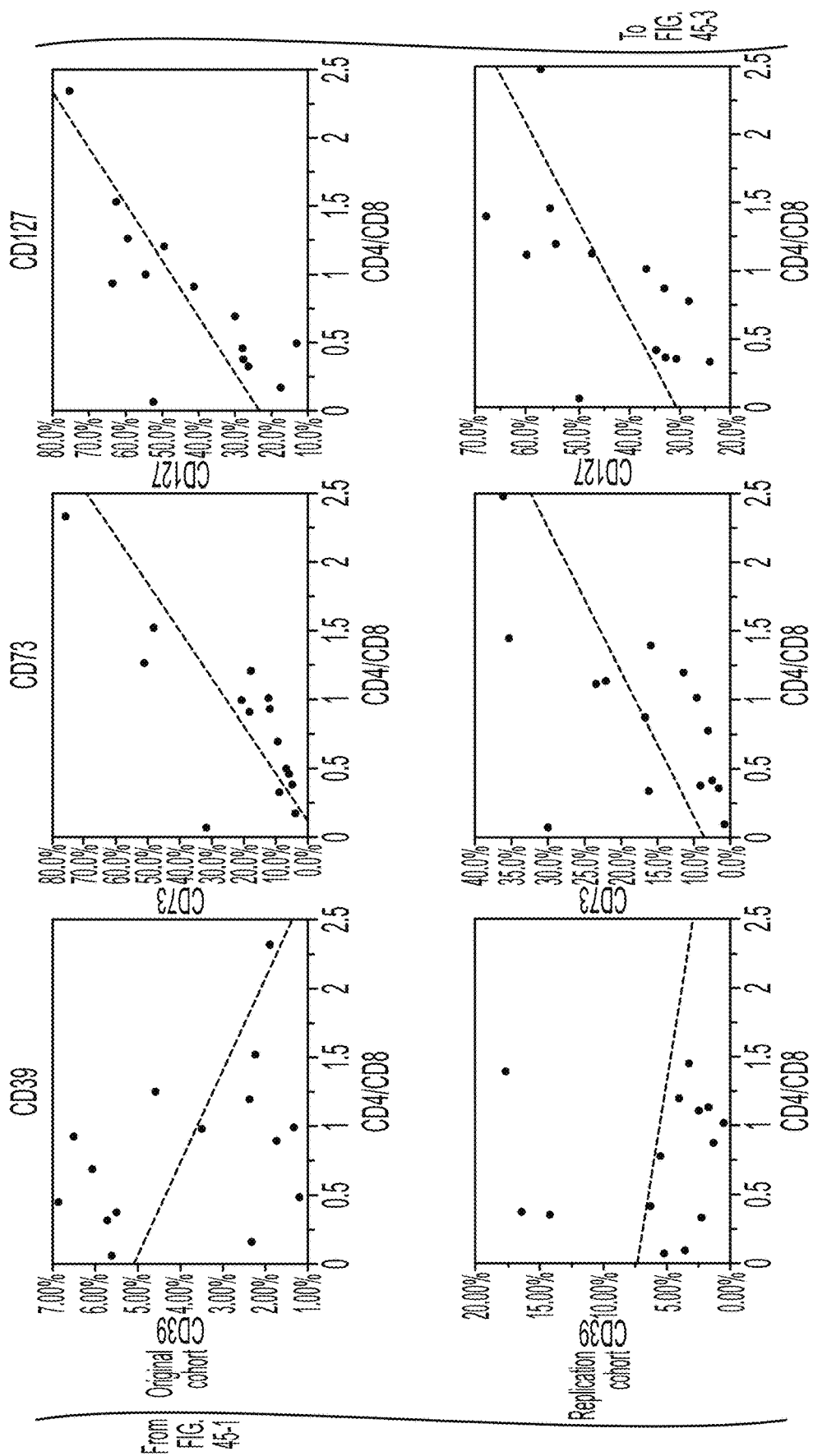
Figures 3, 45:
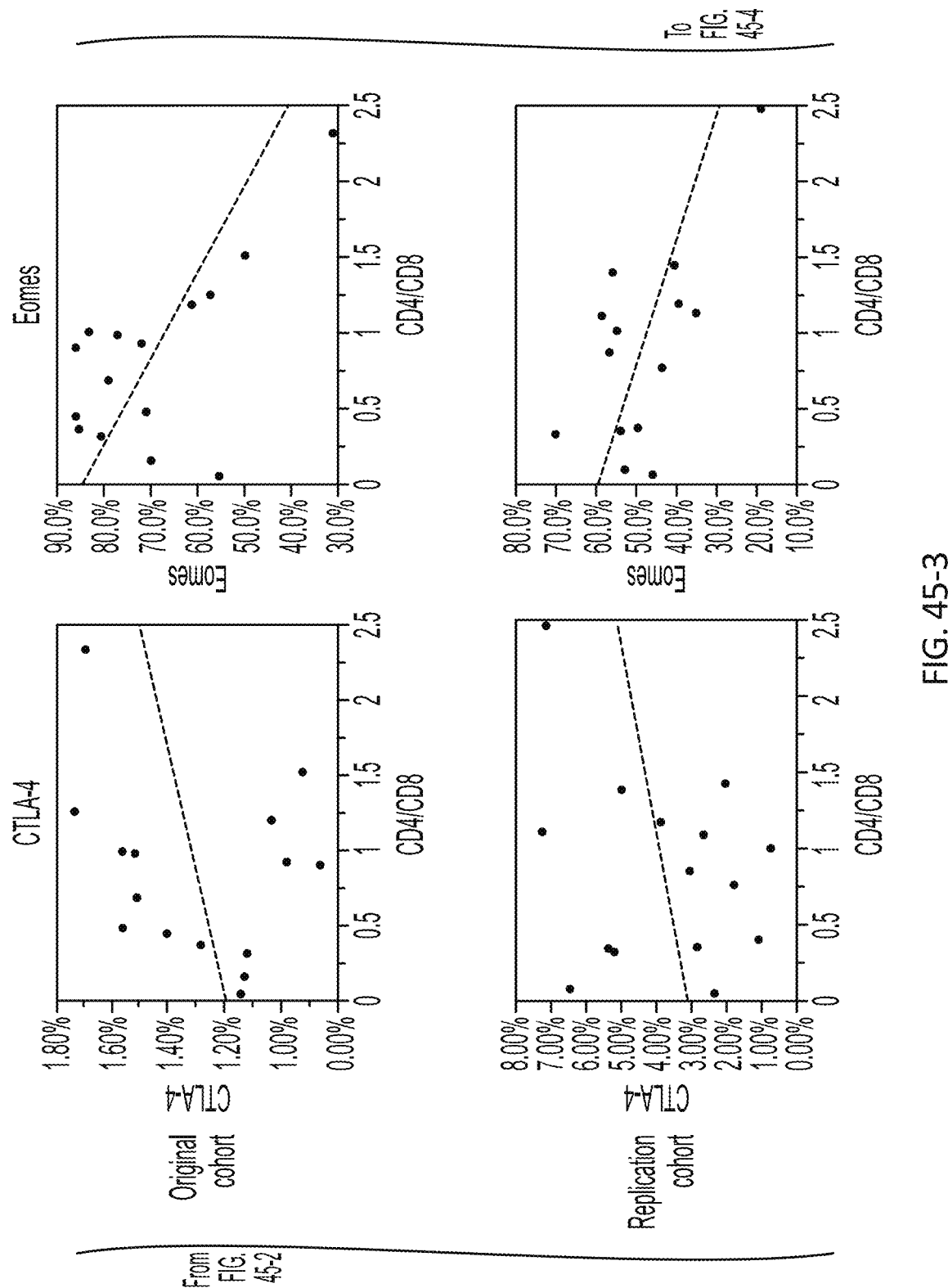
Figures 4, 45:
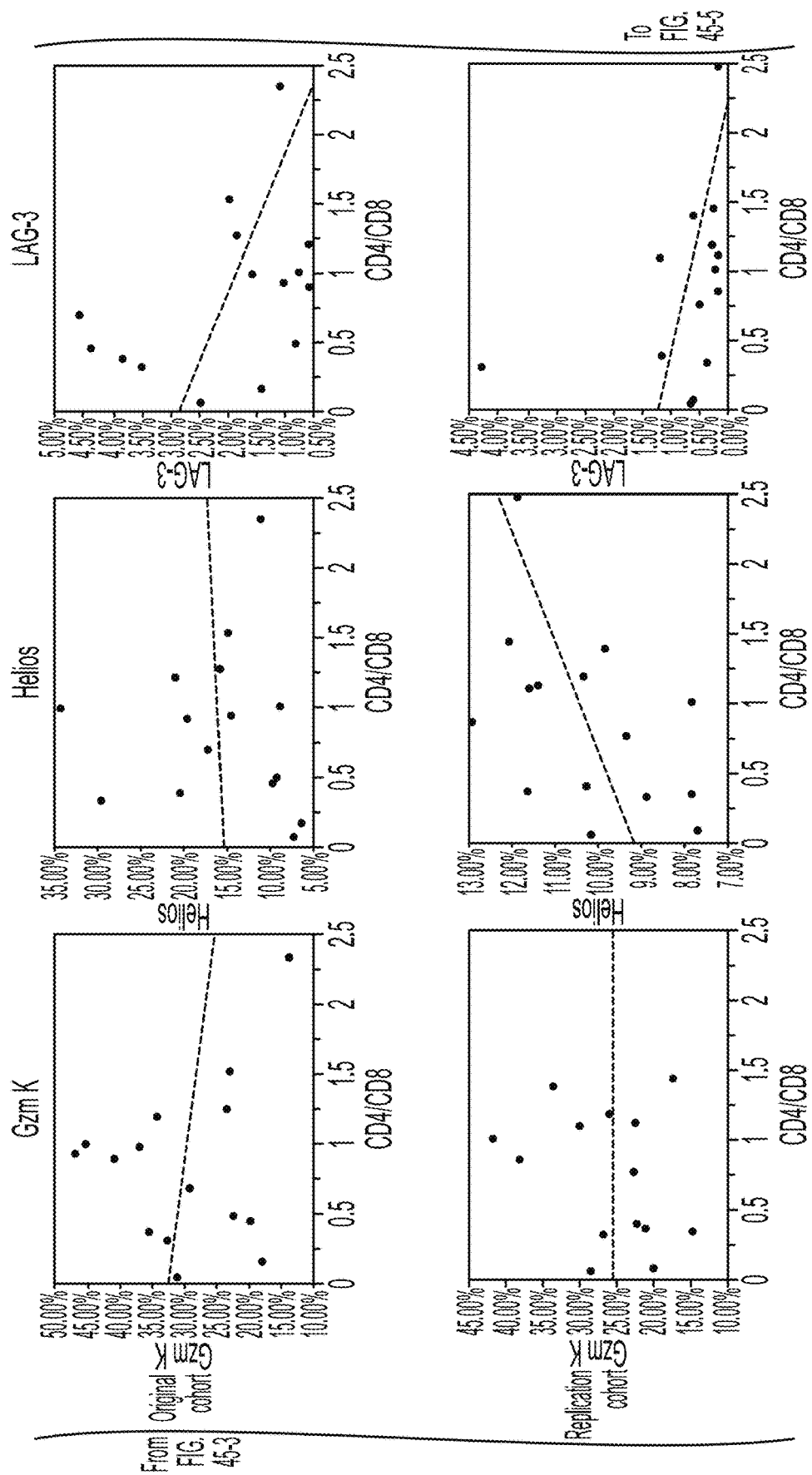
Figures 5, 45:
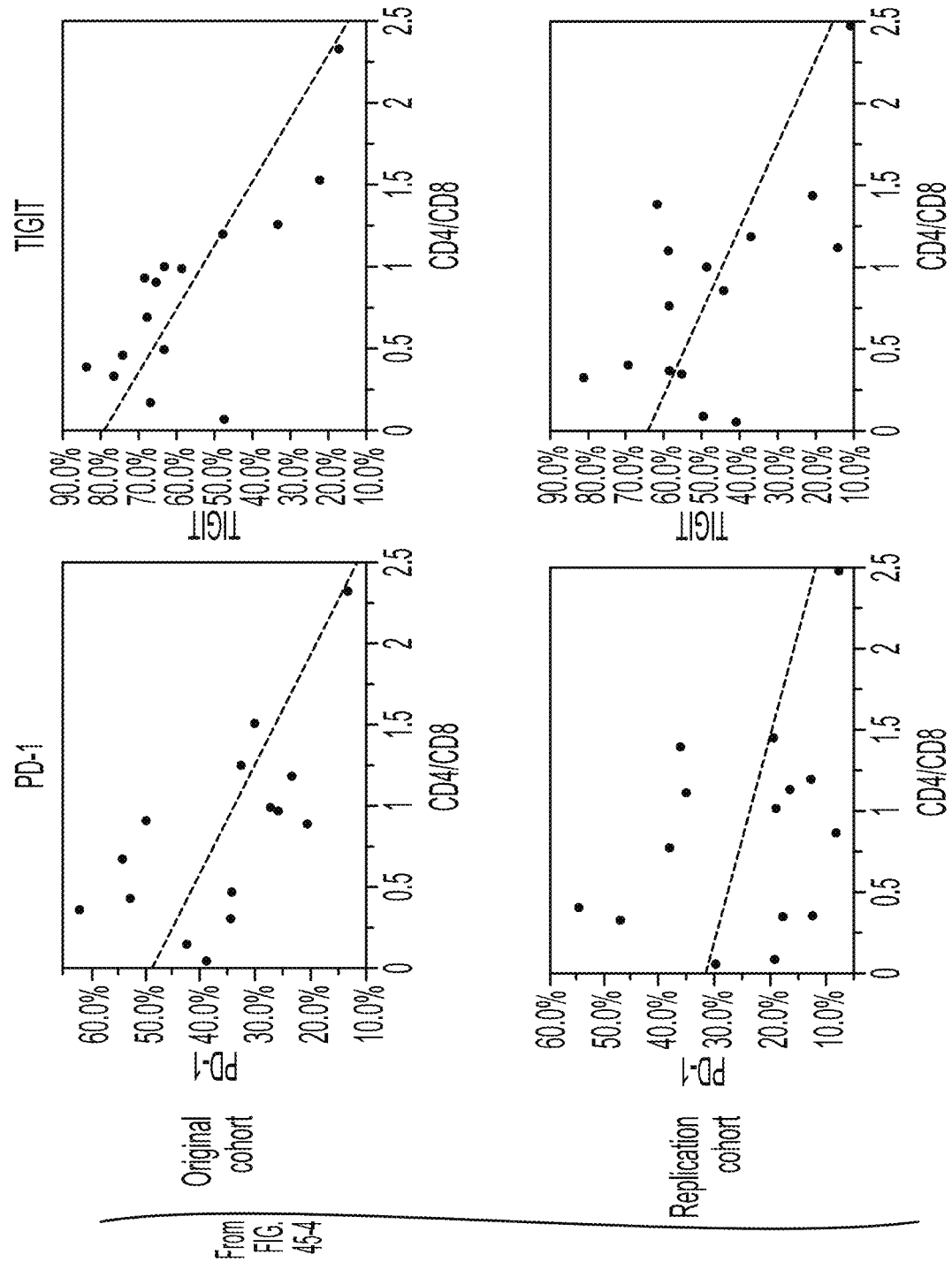

Mass cytometry reagents were obtained from Fluidigm or generated by custom conjugation to isotope-loaded polymers using MAXPAR kit (Fluidigm). Mass cytometry antibodies used are shown in Table 5. Exhaustion-specific markers were chosen for mass cytometry based on: 1) presence in the transcriptional signature of $T_{EX}$ (either uniquely up or downregulated); 2) the presence of unique $T_{EX}$ specific epigenetic changes in the gene locus (either gained or lost); and 3) the availability of suitable antibodies for CyTOF, either pre-conjugated or after in-house conjugation and validation. Staining was performed as described (Bengsch et al. (2017) J Immunol Methods 453:3-10). Briefly, single-cell suspensions were pelleted, incubated with 20 μM Lanthanum-139 (Trace Sciences)-loaded maleimido-mono-amine-DOTA (Macrocyclics) in PBS for 10 min at RT for live/dead discrimination (LD). Cells were washed in staining buffer and resuspended in surface antibody cocktail, incubated for 30 min at RT, washed twice in staining buffer, fixed and permeabilized using FoxP3 staining buffer set (eBioscience), and stained intracellularly for 60 min at RT. Cells were further washed twice before fixation in 1.6% PFA (Electron Microscopy Sciences) solution containing 125 nM Iridium overnight at 4C. Prior to data acquisition on CyTOF2 (Fluidigm), and in a repeat cohort experiment on a CyTOF Helios (Fluidigm), cells were washed twice in PBS and once in $dH_2O$. Mass cytometry data on samples from 57 patients were acquired in different batches. In particular, samples analyzed in FIGS. 40-43 were obtained in three batches using the same core antibodies, with similar CyTOF instrument performance. For batch control, we also used bead-based normalization and analyzed PBMC from a single control donor in every batch, displaying similar results in the high-dimensional analysis (data not shown). Later, repeat cohort analyses were performed by reanalysis of patient samples from the same original bleed date stained at a later time point and acquired on a different mass cytometer and resulted in similar conclusions as the original analysis (FIG. 39, FIG. 45)

High Dimensional Data Analysis

Bead-based normalization of CyTOF data was performed using the Nolan lab normalizer available through github-.com/nolanlab/bead-normalization/releases. FCS files were further analyzed by commercial software FlowJo v10 (TreeStar), FCSExpress 6 (DeNovo Software) and ViSNE (Cytobank). R based tSNE analysis was performed using Rtsne package. Phenograph was performed using RPhenograph package implemented via cytofkit package, described in (Chen et al. (2016) *PLoS Comput Biol* 12, e1005112; Levine et al. (2015) *Cell* 162:184-197). Analysis of exhaustion data space using ViSNE or Phenograph was performed on mass channels corresponding to exhaustion-specific molecules as defined through FIGS. 37 and 38. Phenograph analysis of exhaustion data space on Iridium intercalator positive, singlet LD negative CD45+CD3+CD8 T cells identified 30 high-dimensional clusters, of which 5 (c14, c20, c22, c24, c30) represented cell frequencies <0.01% of CD8 T cells after quality control gating and were excluded from downstream analyses. After Phenograph and Visne analysis, data was integrated into fcs files and further processed by FlowJo or FCSExpress.

Exhaustion Function Mapping

Samples were split for direct phenotypic analysis or stimulation with PMA/Ionomycin in complete media for 5 h at 37 C in the presence of Monensin and Brefeldin A and stained for mass cytometry analysis. Exhaustion-specific markers shared between the phenotyping and stimulation panel ("scaffold") were used to map post-stimulation samples to pre-stimulation clusters by the "classify" mode of Phenograph (Levine et al. (2015) Cell 162:184-197). The training data was constructed by sampling equal amounts of cells (50000) from each of the samples with a stimulus. The exhaustion markers common to both the unstimulated and post stimulation data, CTLA4, CD7, CD127, Helios, PD-1, CCR7, Eomes, CD39, TOX, TIGIT, CXCR5, 2B4, LAG3 were used for these analyses. For each stimulated sample, a nearest neighbor graph using the Jaccard metric was constructed using the training data and cells from the stimulated sample. Random walk probabilities through the graph were used to assign clusters to each of the stimulated cells. See Levine et al. (2015) Cell 162:184-197, for a more detailed description. A functional exhaustion score (FES) was then calculated using the production of IL-2 and CCL3, as well as IFN-7 and TNF coproduction $(2*(\% \text{ IFN}^+\text{TNF}^-)-(\% \text{ IFN}^-\text{TNF}^+)-(\% \text{ IL-2}^+))\times(\% \text{ CCL3/4}^+)$.

Heatmap Display

Heatmaps were generated using the Pheatmap R package (v. 1.0.8). Color representation is based on the z-score and indicated by a color palette in the figures next to the heatmaps.

Statistical Analysis and Data Visualization

Statistical analysis was performed using JMP 12.2.0 (SAS), GraphPad Prism 7.02 and R 3.3.1 limma package. Group comparisons in FIGS. 41-43 were performed using unpaired t test with Welch's correction. In FIGS. 41 and 42, simple regression analysis of phenograph cluster frequencies in viremic HIV patient samples was performed versus viral load and the CD4/CD8 ratio. The respective Pearson correlation was plotted using R ggplot2 package. The cluster dot size displayed in FIGS. 41G and 43C was scaled proportionally to the abundance of individual clusters (% of CD8). In FIGS. 42 and 43, sum of the percentage of phenograph clusters per sample was calculated for the top2 and top9 clusters with highest FES shown in FIGS. 41 and 42, the Disease- or Health Associated $T_{EX}$ clusters in HIV (DAT/HAT) indicated in FIG. 42. In addition a $T_{EX}$ ratio was calculated using the sum of the frequency of DAT divided by the sum of the frequency of HAT to assess a skewing of the composition of different qualities of $T_{EX}$ across diseases.

Results of the experiments are now described.

Figure 1E:
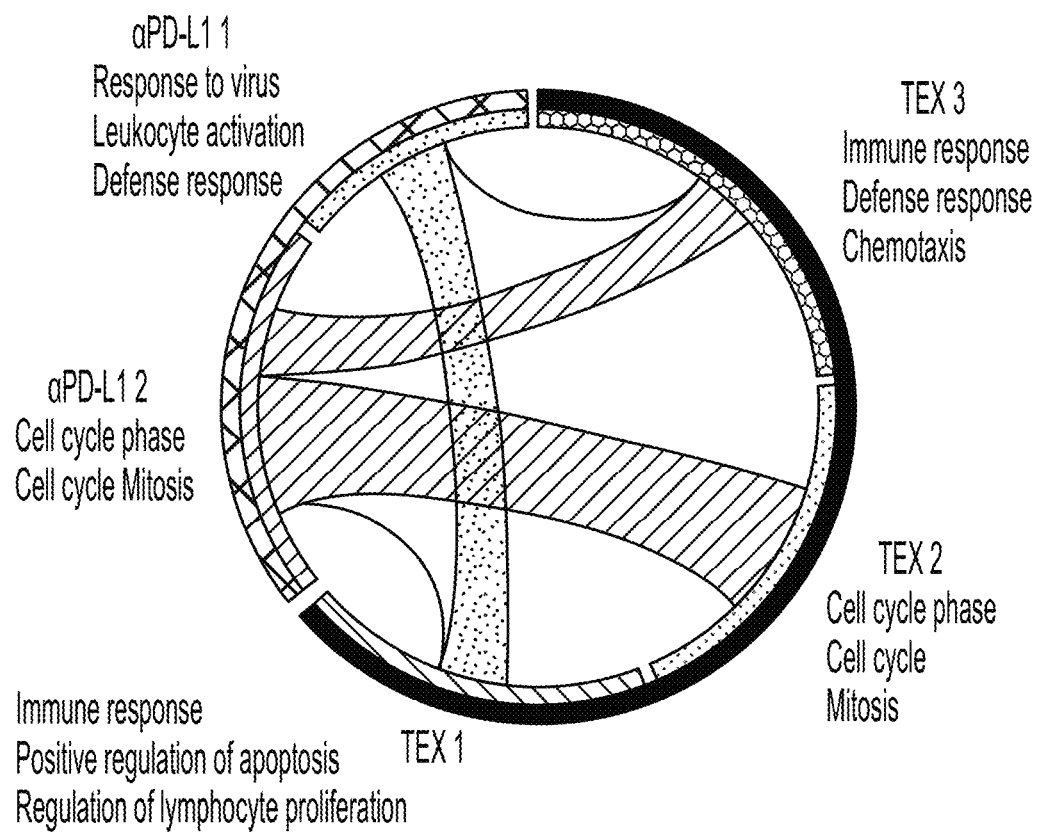

Example 1. Anti-PD-L1 Induces an Effector-Like Transcriptional Program in $T_{EX}$ Cells that is not Sustained after Cessation of Treatment Cellular, transcriptional, and epigenetic changes associated with PD-1 pathway blockade were interrogated using the mouse model of chronic lymphocytic choriomeningitis virus (LCMV) infection (FIG. 1A-FIG. 1C) (Barber et al. Nature. 2006, 439(7077):682-7; Pauken et al. Science 2016, 354(6316):1160-1165—Supplemental Information on Science online). Following anti-PD-L1 treatment, 1080 genes were up-regulated and 1686 genes were down-regulated (p<0.05, LFC≥0.2) (FIG. 2A, FIG. 1D, and Pauken et al. Table S1 (Pauken et al. Science 2016, 354(6316):1160-1165)). Previous studies identified transcriptional (Gubin et al. Nature. 2014, 515:577-581) or cellular (Bengsch et al. 2016, Immunity 45, 358-373; Staron et al. 2014, Immunity 41, 802-814) changes in metabolic pathways following PD-1 pathway blockade. Indeed, several metabolic genes were altered following PD-L1 blockade (Pauken et al. Table S1 (Pauken et al. Science 2016, 354(6316):1160-1165)). Gene Set Enrichment Analysis (GSEA), however, identified more prominent changes in cell division pathways (FIG. 2B, Pauken et al. Table S2 (Pauken et al. Science 2016, 354 (6316):1160-1165)) (Barber et al. Nature 2006, 439, 682-687; Patsoukis et al. Sci. Signal. 2012, 5, ra46). In addition, many effector-related genes were biased toward the anti-PD-L1 group (FIGS. 2C-2D, Pauken et al. Table S3 (Pauken et al. Science 2016, 354(6316):1160-1165)). Other genes of interest included Cxcl9, Il1r2 and Il7r (up) and Klra9, Tnfrsf9, and Cd200r2 (down) (FIG. 1D and Pauken et al. Table S1 (Pauken et al. Science 2016, 354(6316):1160-1165)). Using Leading Edge Metagene (LEM) analysis (Godec. Immunity. 2016, 44:194-206) two metagenes were identified in anti-PD-L1-treated $T_{EX}$ compared to control $T_{EX}$; one corresponding to leukocyte activation and one to cell cycle (FIG. 2E; FIGS. 1E, and 1F; and Pauken et al. Table S4 (Pauken et al. Science 2016, 354(6316):1160-1165)). The anti-PD-L1-treated $T_{EX}$ metagenes displayed some overlap with $T_{EFF}$, largely driven by cell cycle pathways, but minimal overlap with $T_{MEM}$ (FIG. 2E and Pauken et al. Table S4 (Pauken et al. Science 2016, 354(6316):1160-1165)) suggesting limited acquisition of memory potential upon $T_{EX}$ re-invigoration.

Figures 6C, 6D:
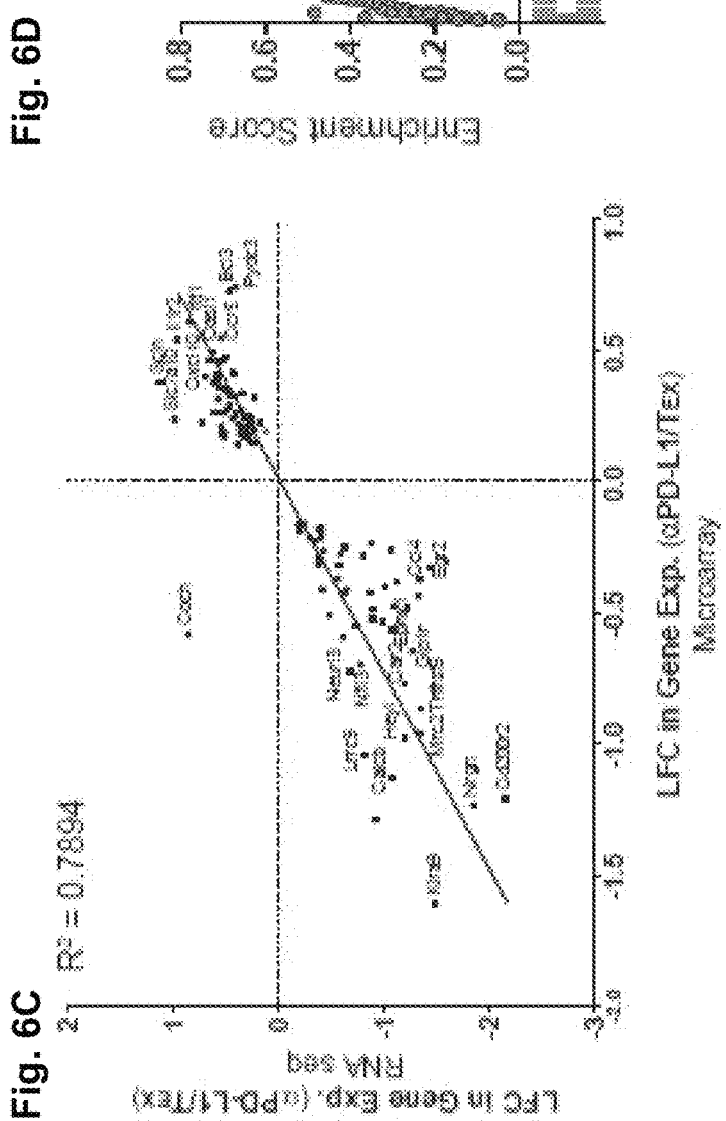
Figure 6E:
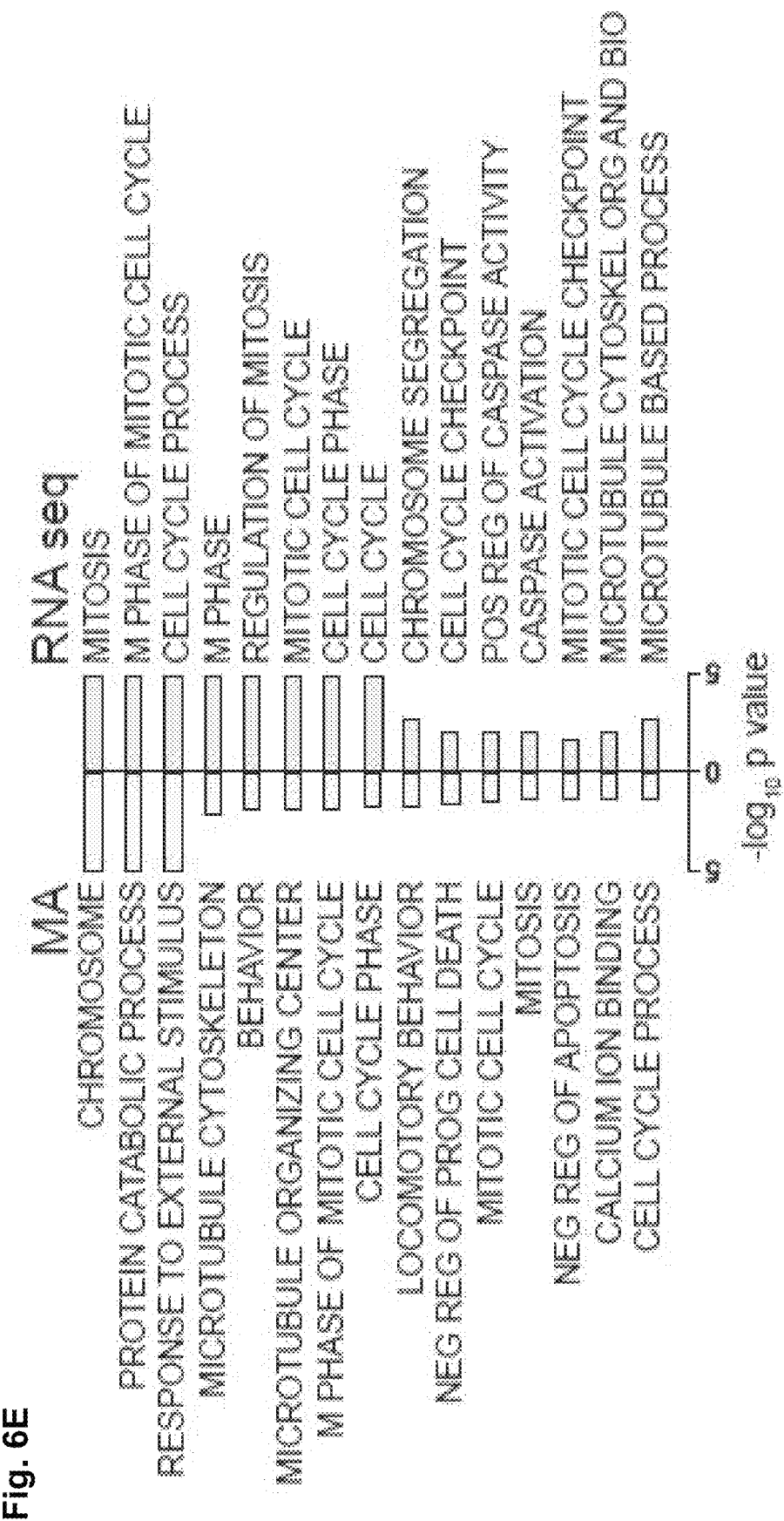
Figure 7B:
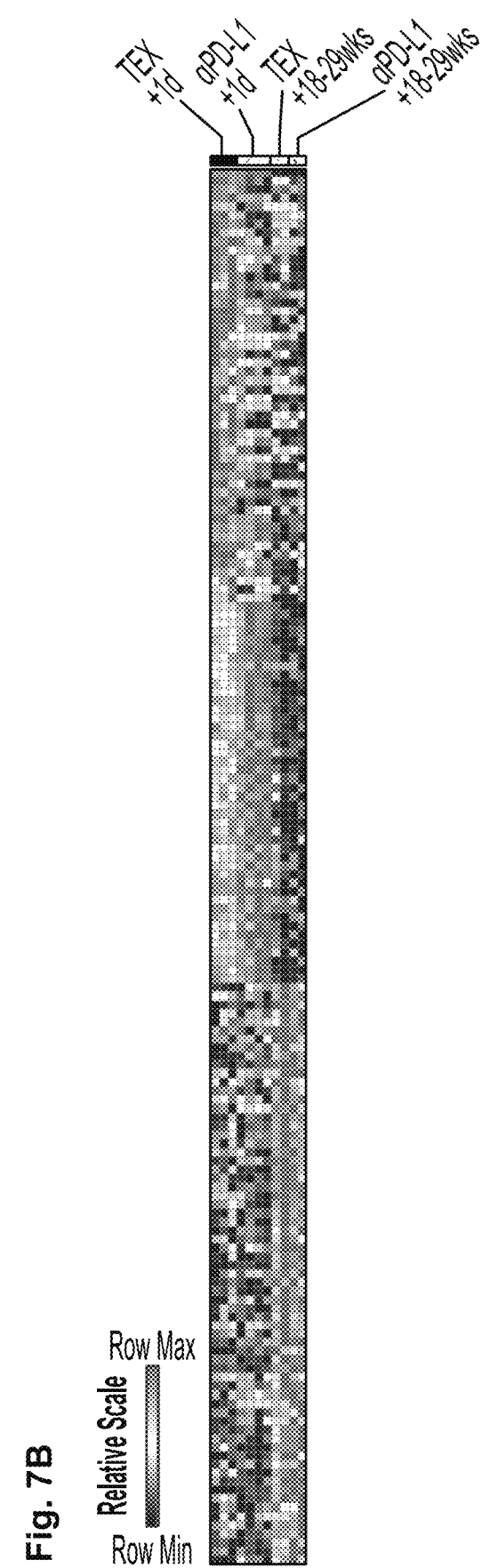
Figure 7D:
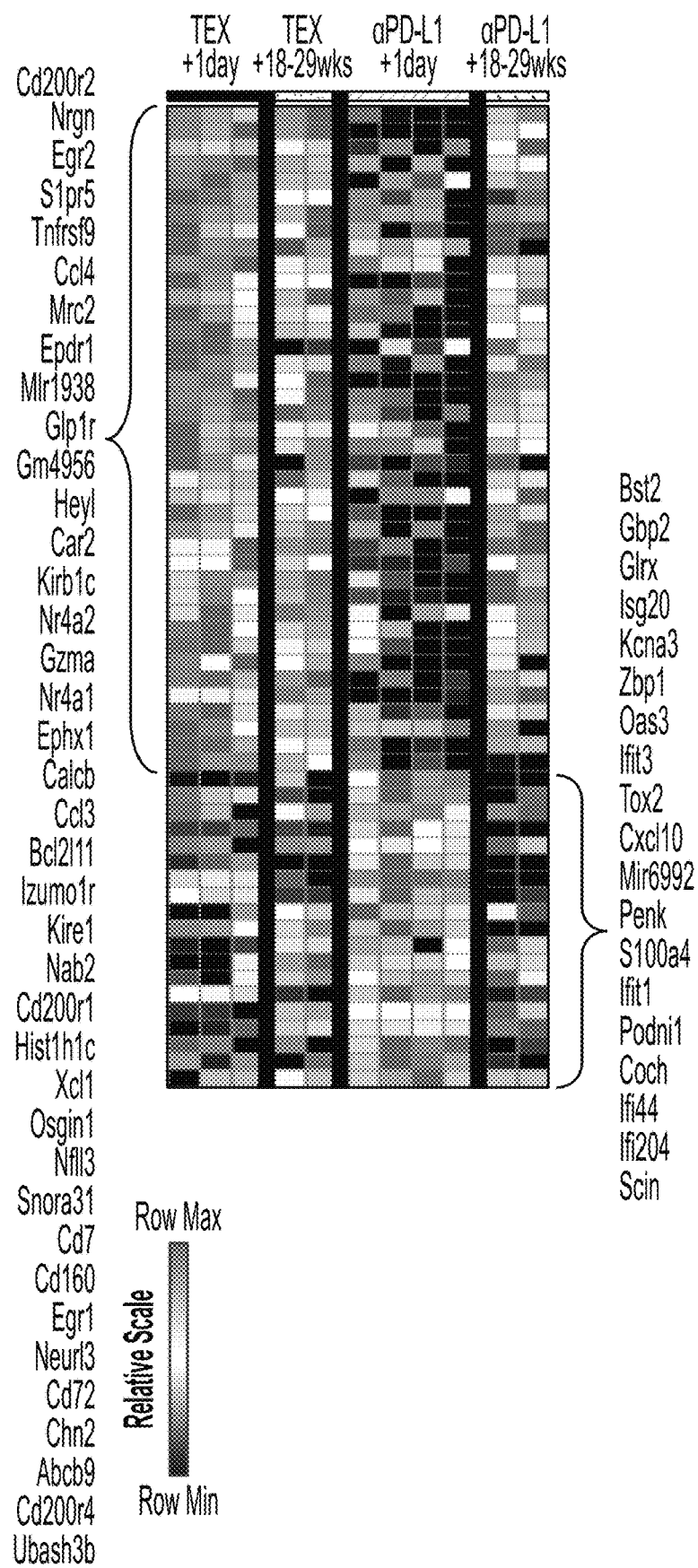

PD-1 pathway blockade can re-activate functions in $T_{EX}$, but whether re-invigoration is sustained is unclear. Here, there was a robust re-invigoration of $T_{EX}$ as expected (FIGS. 2F, 2G, 1A, 1B, and 3) (Barber et al. Nature 2006, 439, 682-687), and expansion peaked ~3 weeks after initiation of blockade. By 8-11 weeks post-treatment, however, this re-invigoration was lost and the quantity, proliferation, effector function and inhibitory receptor expression of LCMV-specific CD8 T cells in the anti-PD-L1-treated mice were comparable to control-treated mice (FIGS. 2F to 2H, and FIGS. 3 to 5). Moreover, although anti-PD-L1 treatment reduced viral load immediately after treatment, 4 months later viral load was similar to control-treated mice (FIG. 2I). Lastly, 18-29 weeks after cessation of blockade, the transcriptional profiles of control- and anti-PD-L1-treated groups were similar (FIG. 2J, FIGS. 6 and 7, and Pauken et al. Tables S5 and S6 (Pauken et al. Science 2016, 354(6316): 1160-1165)). Collectively, these data indicate that when antigen remains high, $T_{EX}$ re-invigorated by PD-1 pathway blockade become "re-exhausted."

Figure 8B:
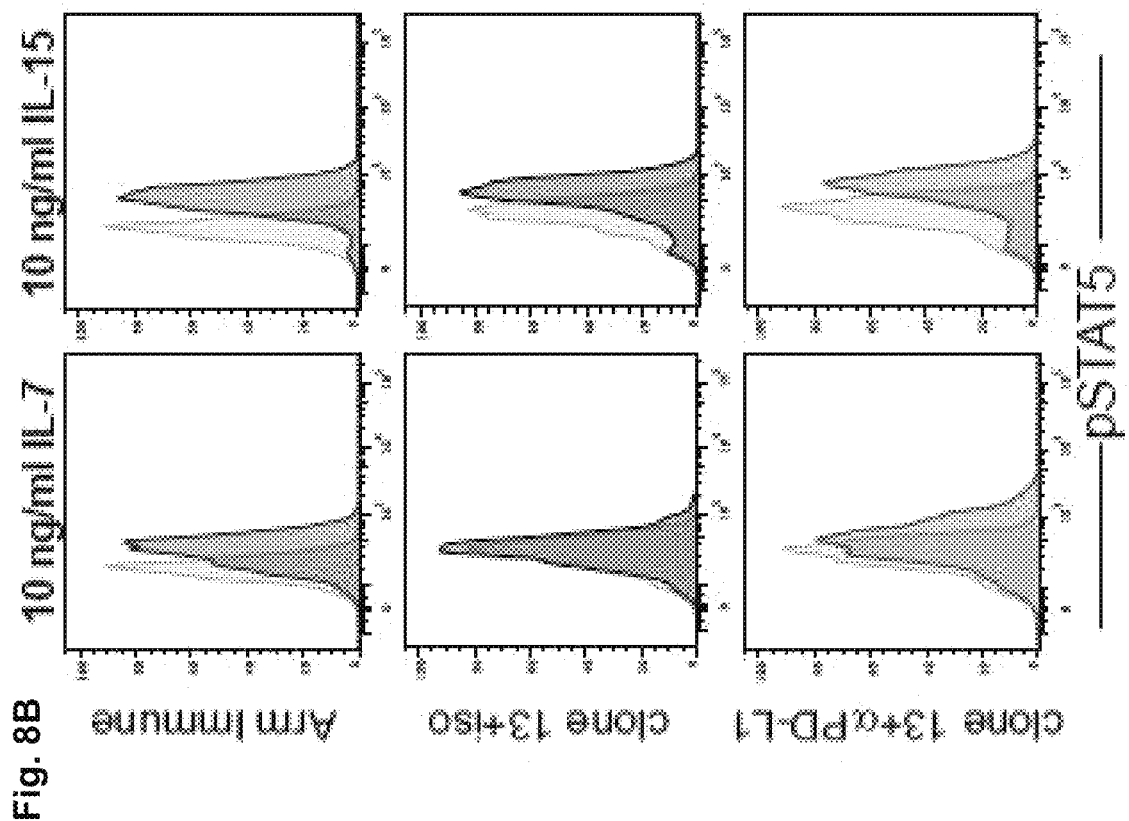
Figure 8A:
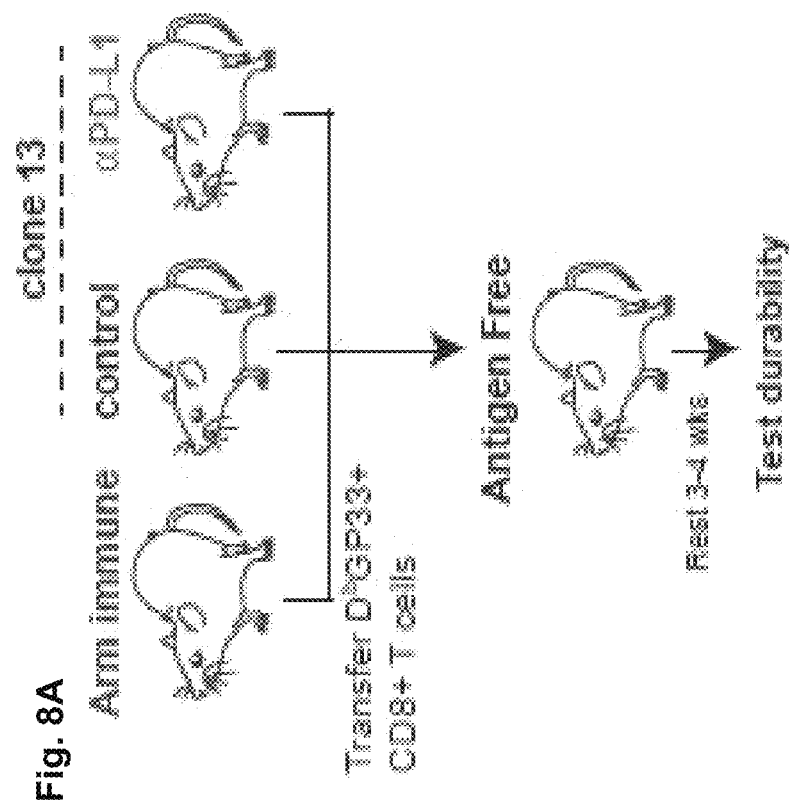
Figure 9D:
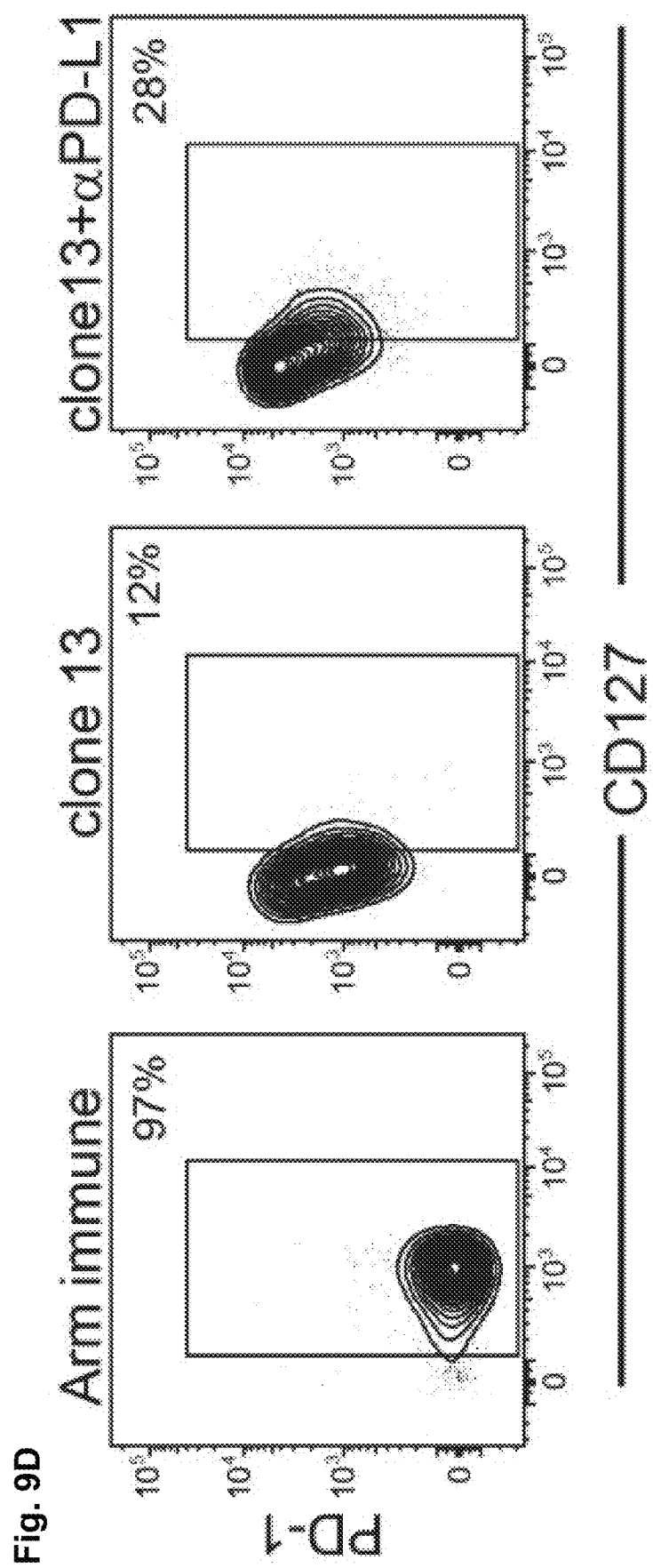
Figure 9G:
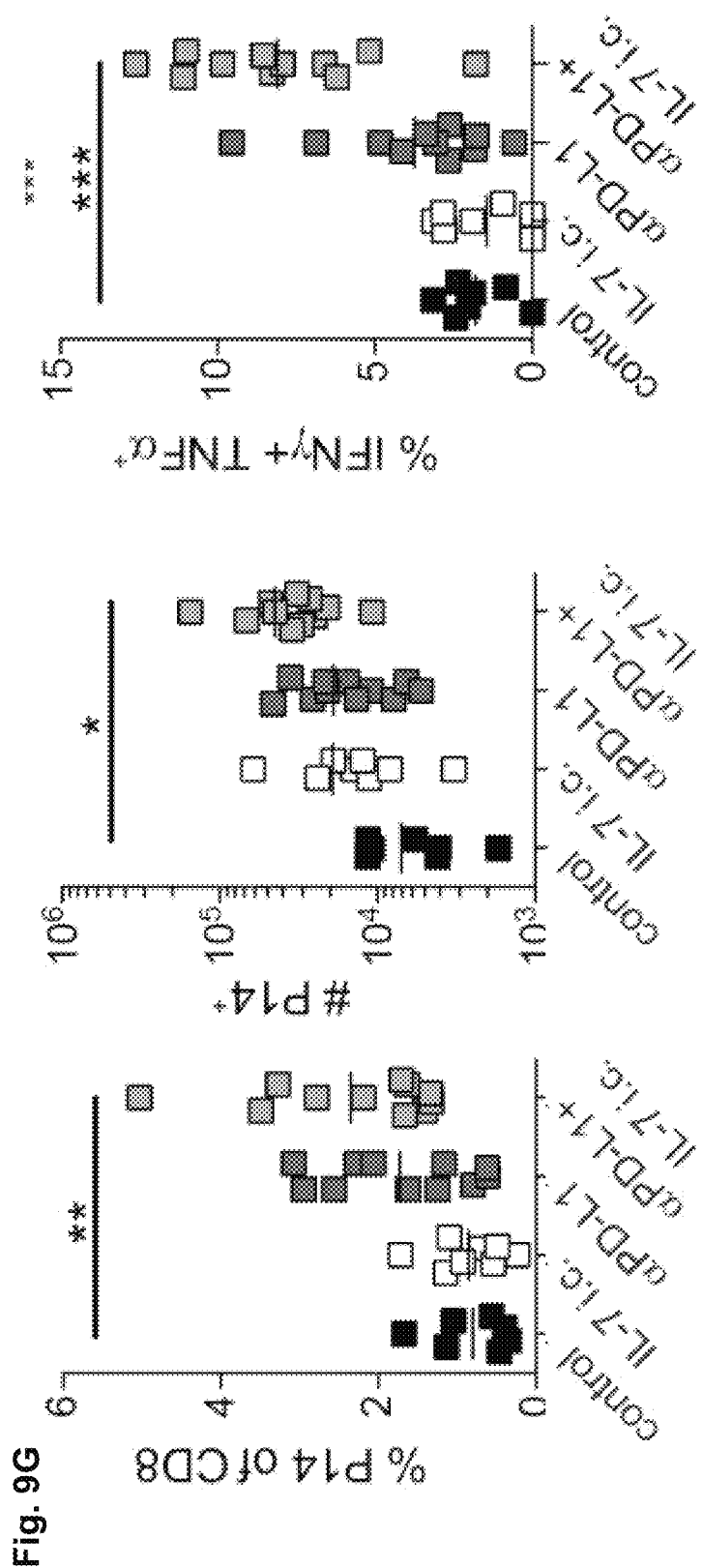
Figure 9H:
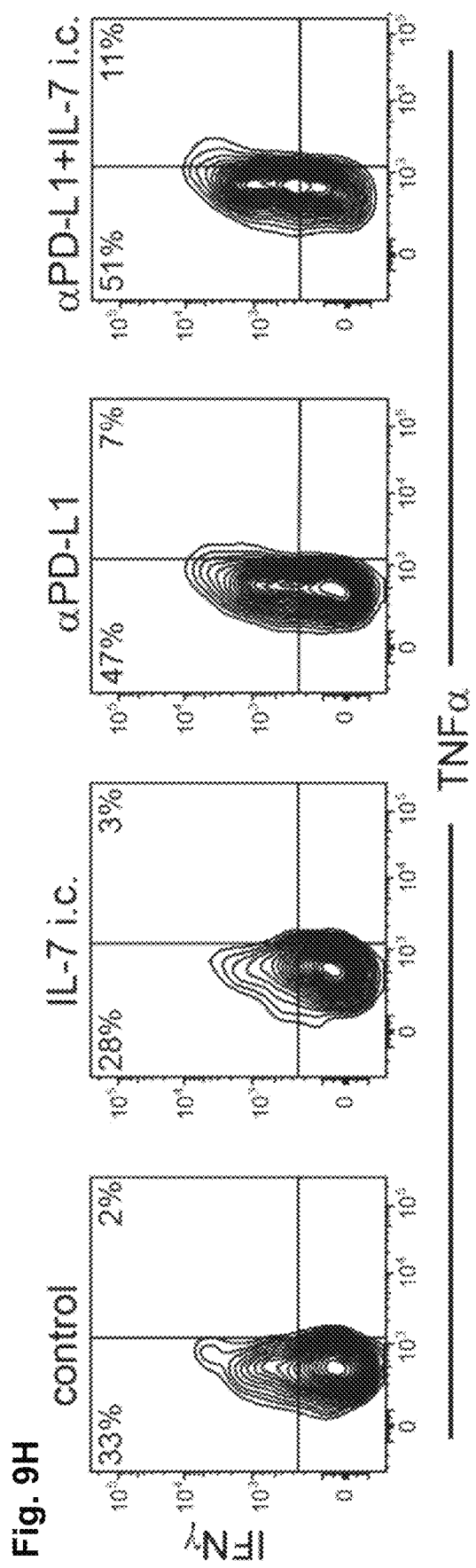
Figure 10B:
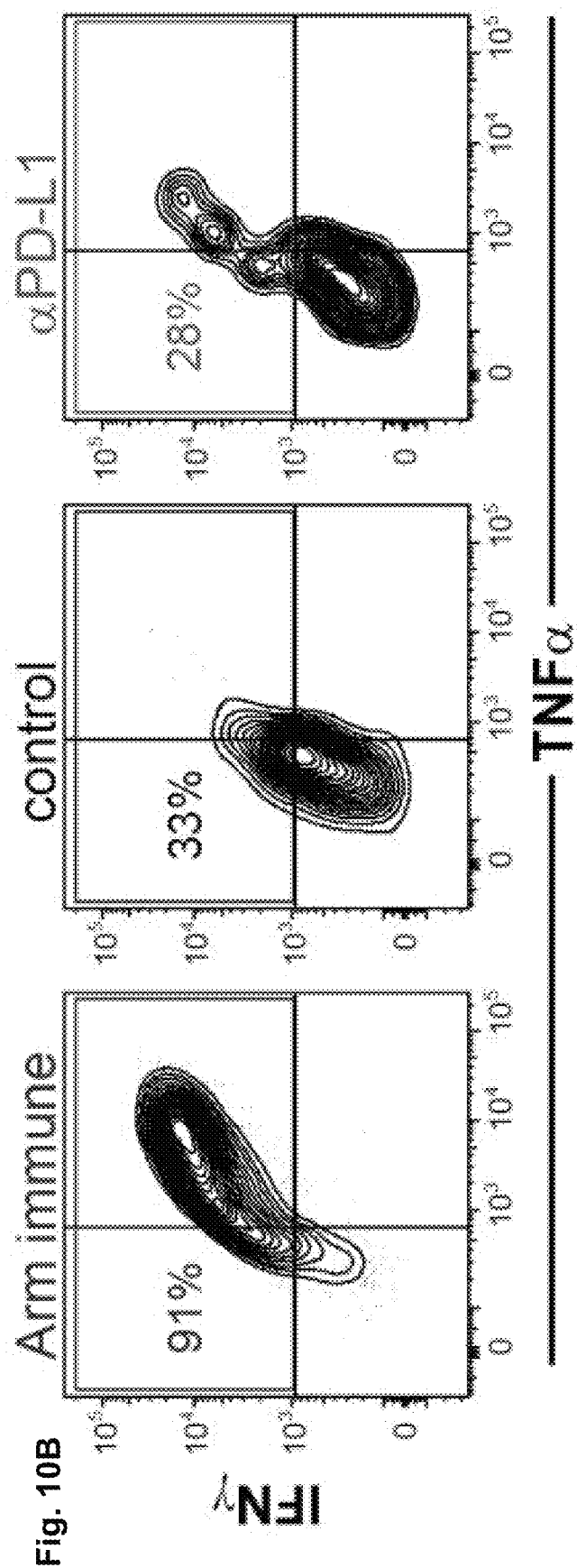
Figure 10H:
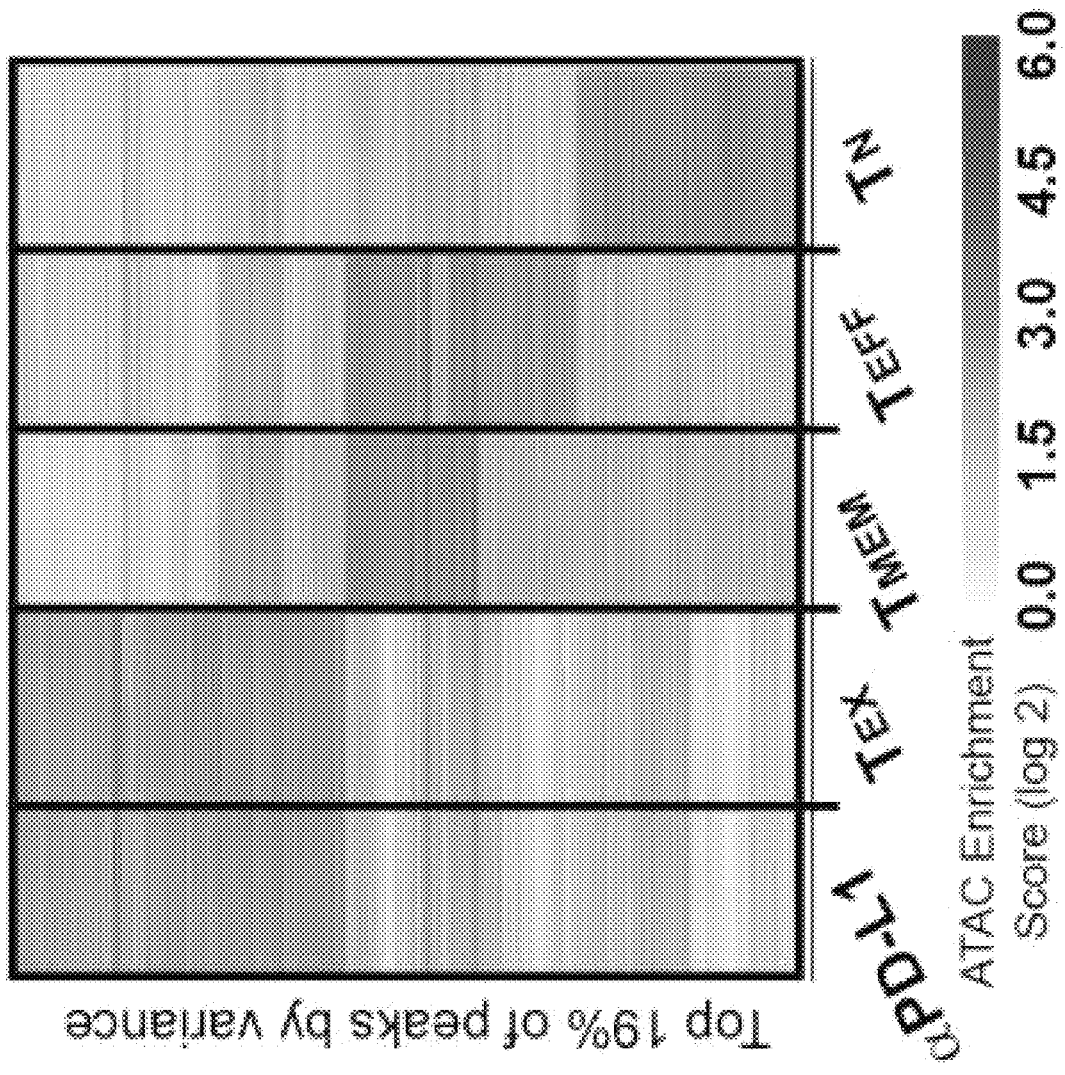
Figure 10I:
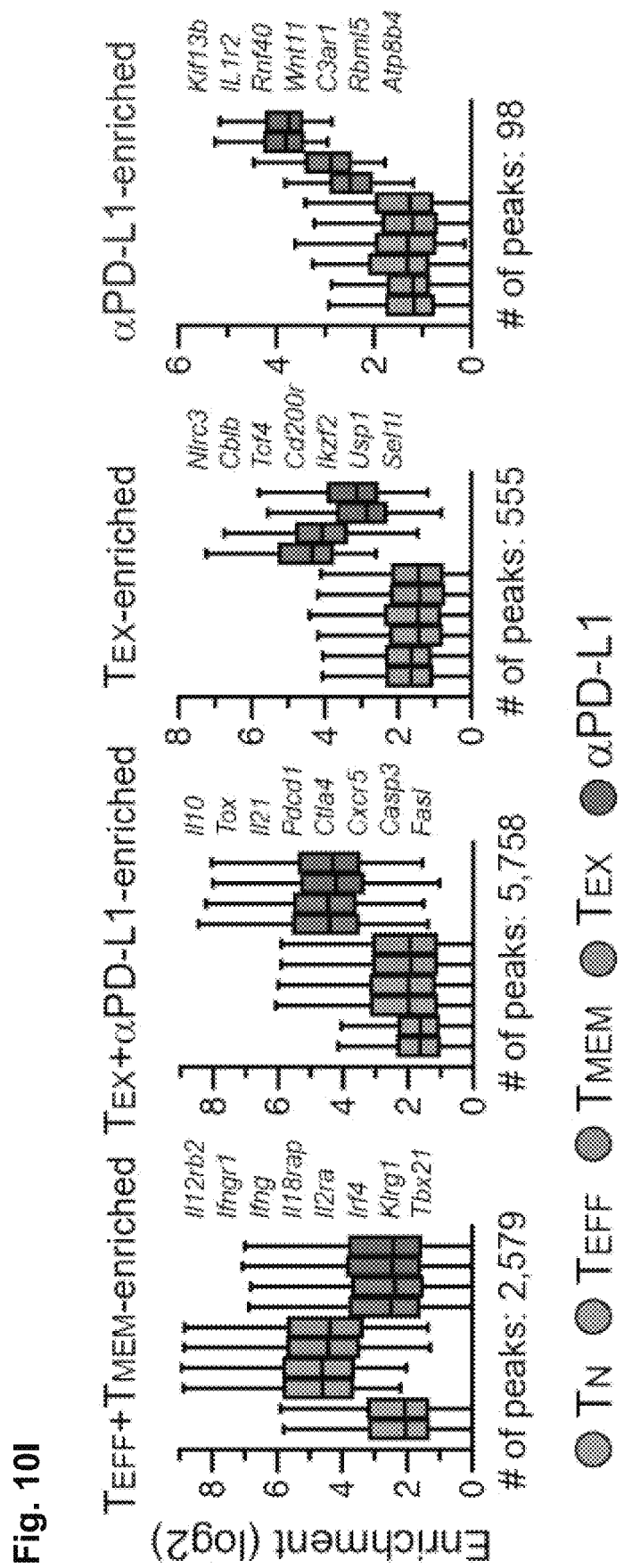
Figure 10J:
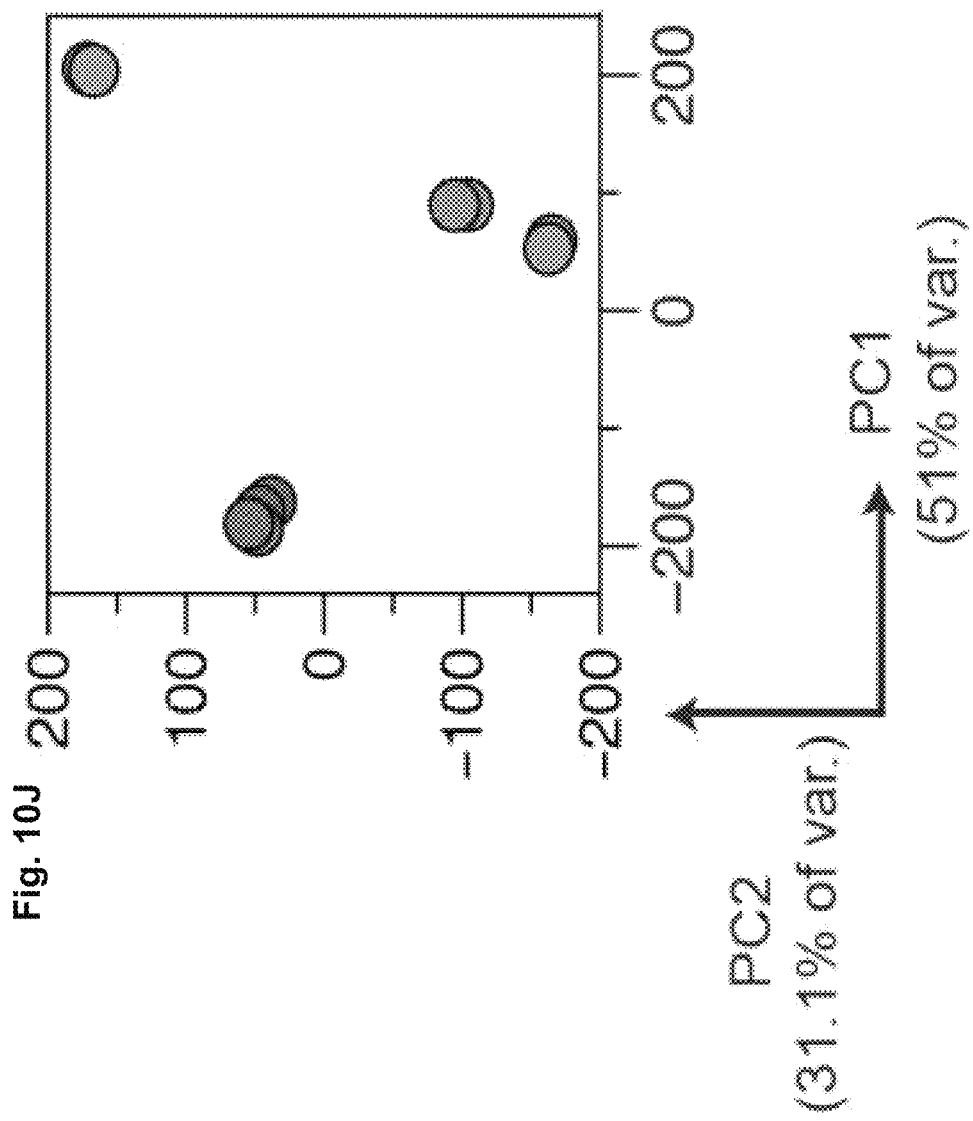

Example 2. PD-1 Pathway Blockade Moderately Improves Antigen-Independent Persistence and IL-7 Signaling in $T_{EX}$ One possible reason the effects of PD-L1 blockade were not sustained was the infection persisted. To test the idea that if the infection was cured, then anti-PD-L1 might induce differentiation into $T_{MEM}$, equal numbers of control $T_{EX}$, anti-PD-L1-treated $T_{EX}$, or $T_{MEM}$ were transferred into antigen-free mice and persistence was monitored (FIG. 8A). Consistent with previous studies (Shin, et al. J. Exp. Med. 2007, 204: 941-949; Wherry, et al. Proc. Natl. Acad. Sci. U.S.A. 2004, 101:16004-16009), $T_{EX}$ survived poorly in antigen-free recipients compared to functional $T_{MEM}$ (FIGS. 9A-9B). There was a trend toward anti-PD-L1-treated $T_{EX}$ persisting moderately better, though poorly compared to $T_{MEM}$ (FIGS. 9A-9B). Next, potential mechanisms for this trend were interrogated. Following PD-1 pathway blockade, interleukin (IL)-7 receptor transcripts (Il7r; CD127) increased significantly (FIG. 1D and Pauken et al. Table S1 (Pauken et al. Science 2016, 354(6316):1160-1165)). There was also a modest increase in CD127 protein on a subset of $T_{EX}$ following anti-PD-L1 (FIGS. 9C-9E). Upon stimulation with IL-7, anti-PD-L1-treated $T_{EX}$ also showed more phospho-STAT5 compared to control-treated $T_{EX}$ (FIG. 9F and FIG. 8B). In contrast, expression of the IL-15 receptor subunit CD122 and responsiveness to IL-15 in vitro were not substantially altered (FIGS. 9C and 9F, and FIG. 8B). These data suggest that anti-PD-L1 treatment may augment activity of the memory-biased IL-7R pathway.

Figure 8C:
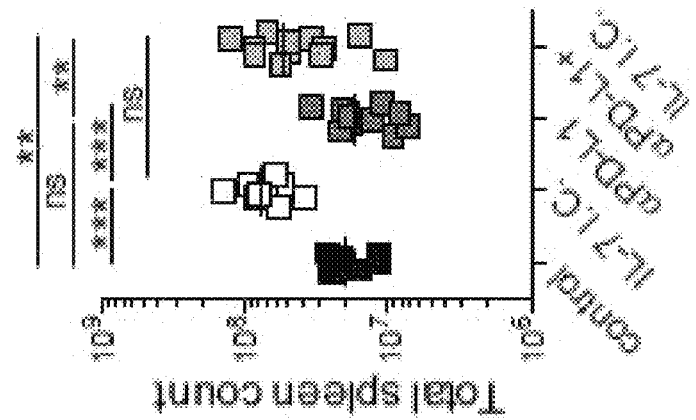
Figure 8D:
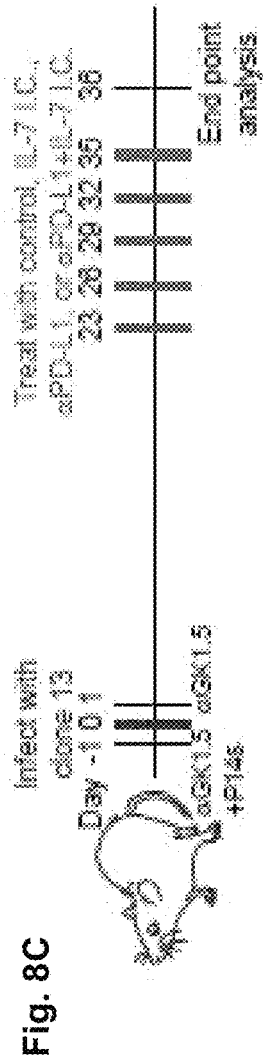
Figure 8E:
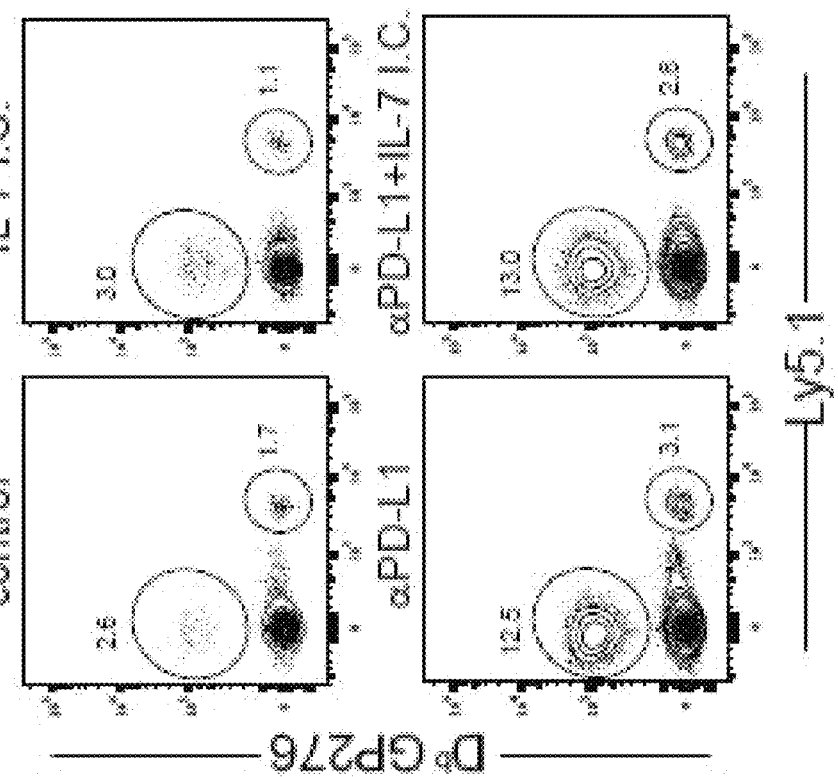
Figure 8H:
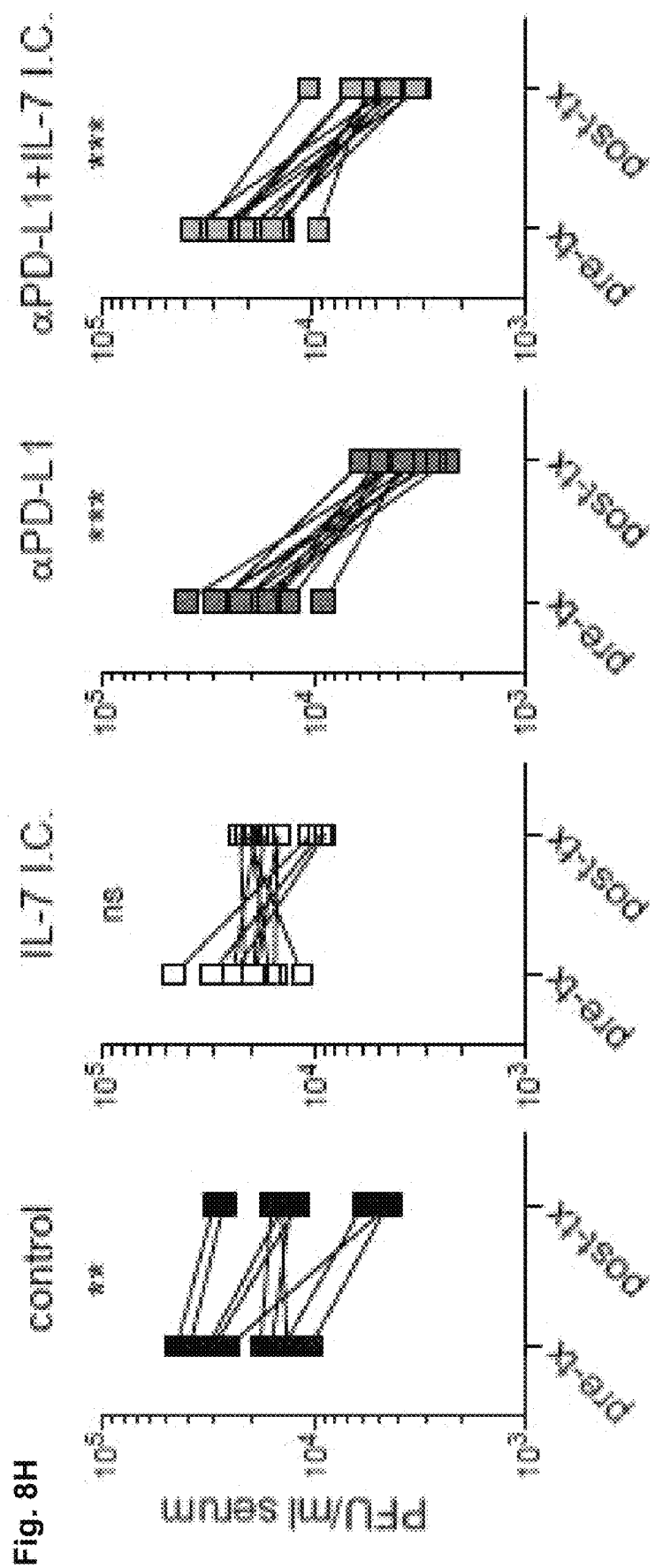

Treating with IL-7 starting in the effector phase can prevent development of exhaustion (Pellegrini, et al. Cell 2011, 144:601-613; Nanjappa, et al. Blood 2011, 117:5123-5132). However, later in chronic infection $T_{EX}$ respond poorly to IL-7 (Shin, et al. J. Exp. Med. 2007, 204: 941-949; Wherry, et al. Proc. Natl. Acad. Sci. U.S.A. 2004, 101: 16004-16009). Anti-PD-L1 improved IL-7R signaling, hence it was tested whether combined treatment had additional benefit (FIG. 8C). Indeed, while other aspects of the response were less affected, treatment with IL-7 and anti-PD-L1, but not IL-7 alone, resulted in more antigen-specific CD8 T cells and improved co-production of IFNγ and TNFα (FIGS. 9G to 9H, and FIGS. 8D to 8H). Thus, it may be possible to exploit pathways upregulated by PD-L1 blockade including IL-7R to improve checkpoint blockade.

Example 3. PD-1 Pathway Blockade Fails to Restore Memory-Like Recall Capacity or Reprogram the Epigenetic Landscape of $T_{EX}$ into $T_{EFF}$ or $T_{MEM}$ Cells It was next tested whether PD-1 pathway blockade could restore robust recall potential upon re-infection, a defining property of $T_{MEM}$. Equal numbers of $D^bGP33^+$ CD8 $T_{EX}$, anti-PD-L1-treated $T_{EX}$, or $T_{MEM}$ were transferred into antigen-free mice, rested, and then re-challenged with Listeria monocytogenes expressing GP33-41. $T_{MEM}$ robustly expanded, and efficiently produced IFNγ (FIGS. 10A-10D). In contrast, both control- and anti-PD-L1-treated $T_{EX}$ mounted poor responses to Listeria-GP33 challenge and re-invigorated $T_{EX}$ were as defective as control $T_{EX}$ in these key properties (FIGS. 10A-10D).

Figure 3B:
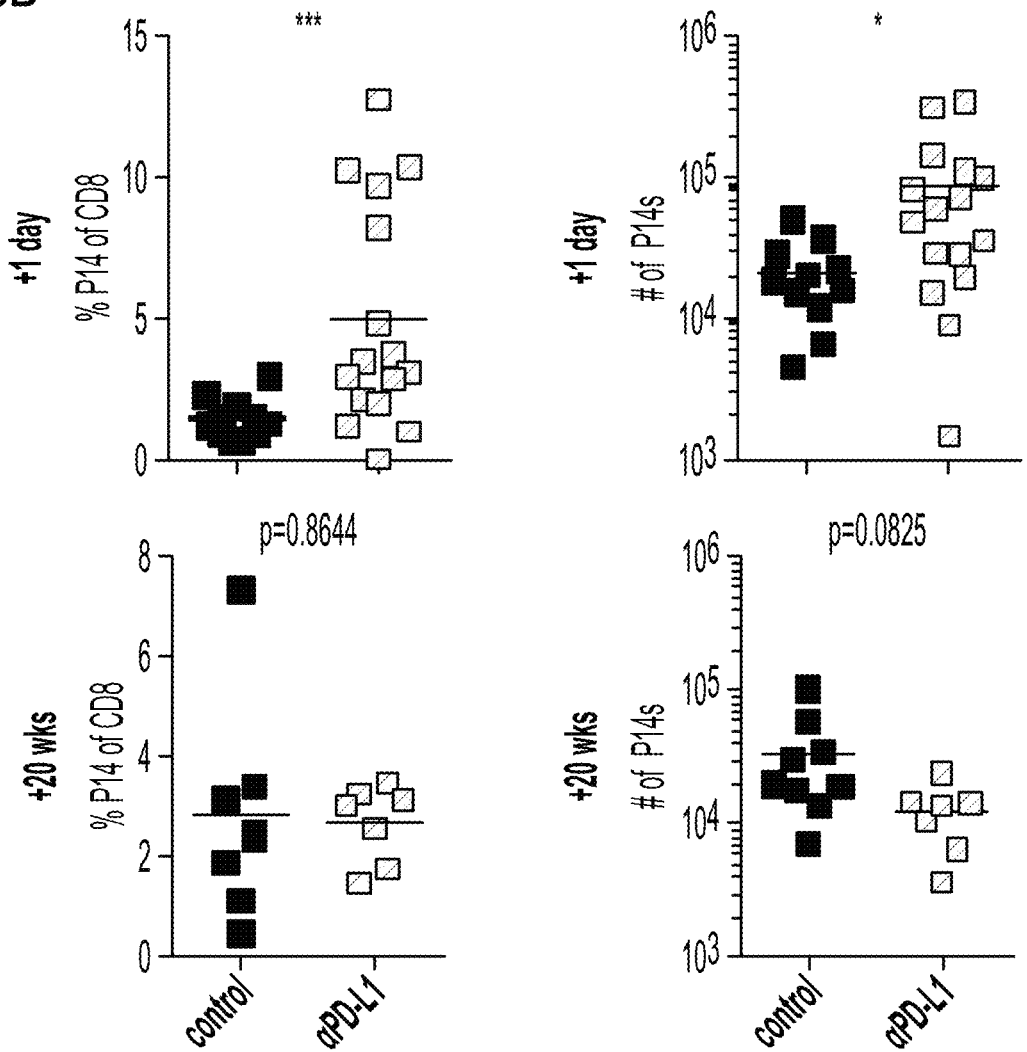
Figure 4B:
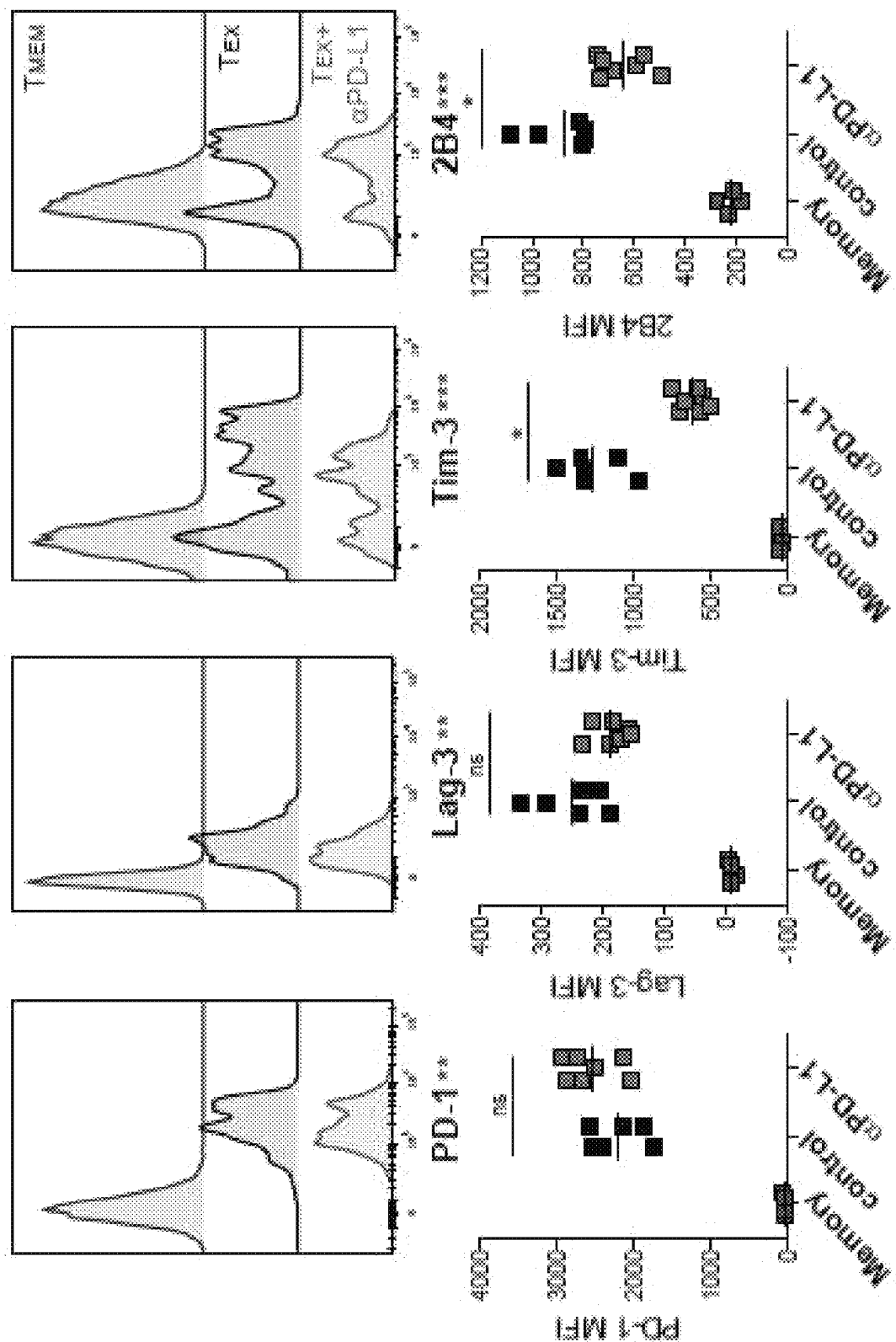
Figure 4C:
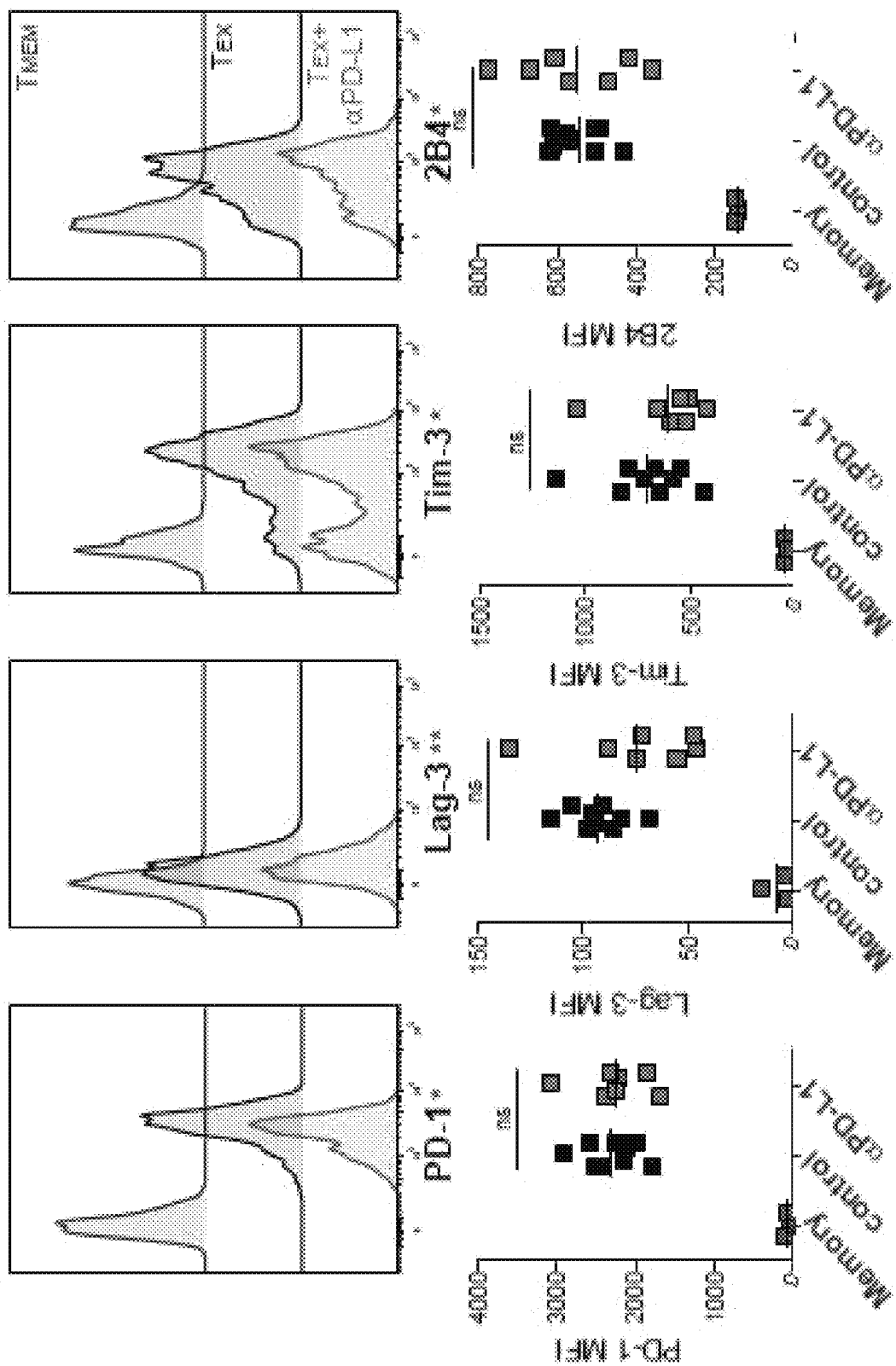
Figure 5B:
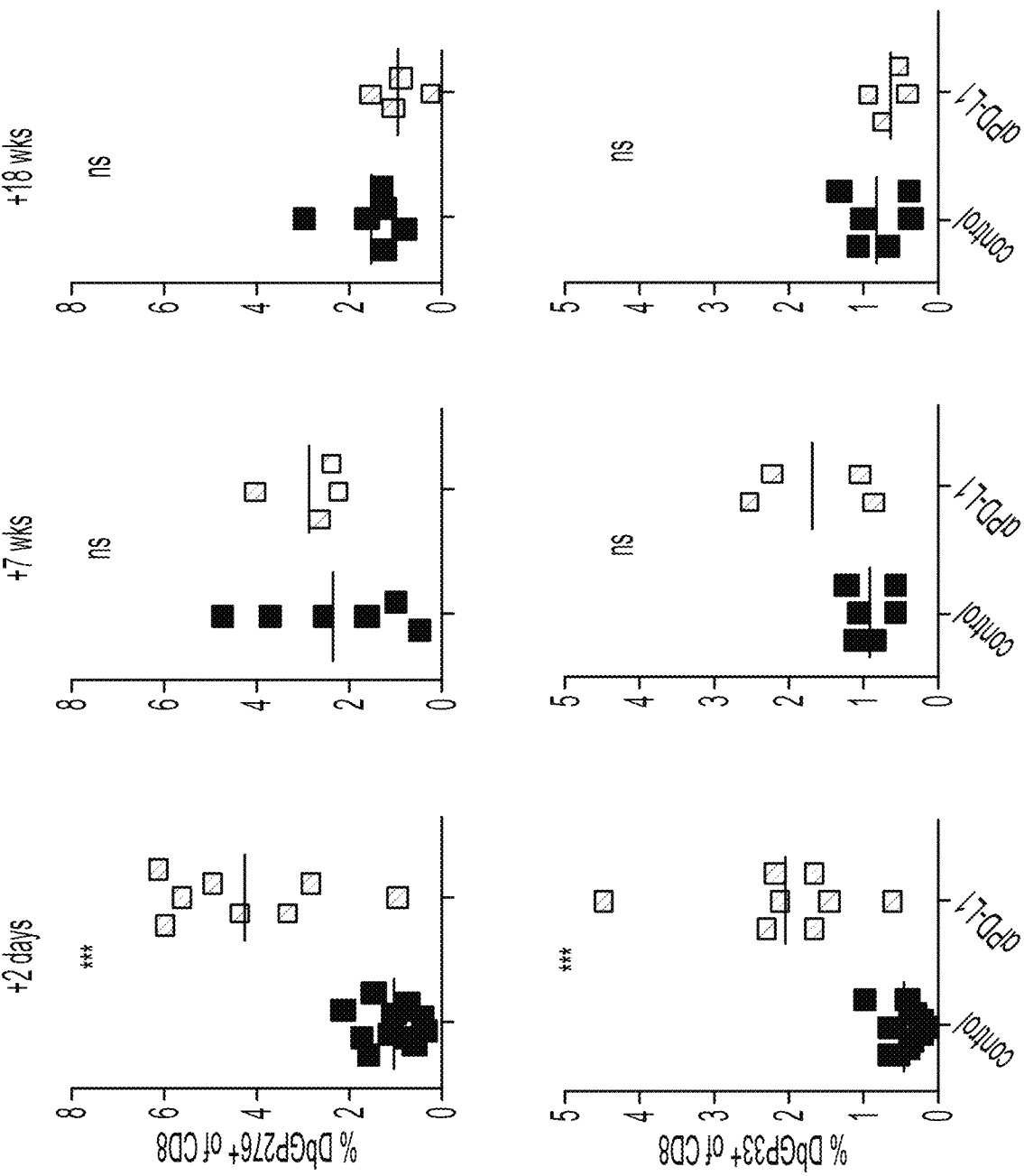
Figure 5E:
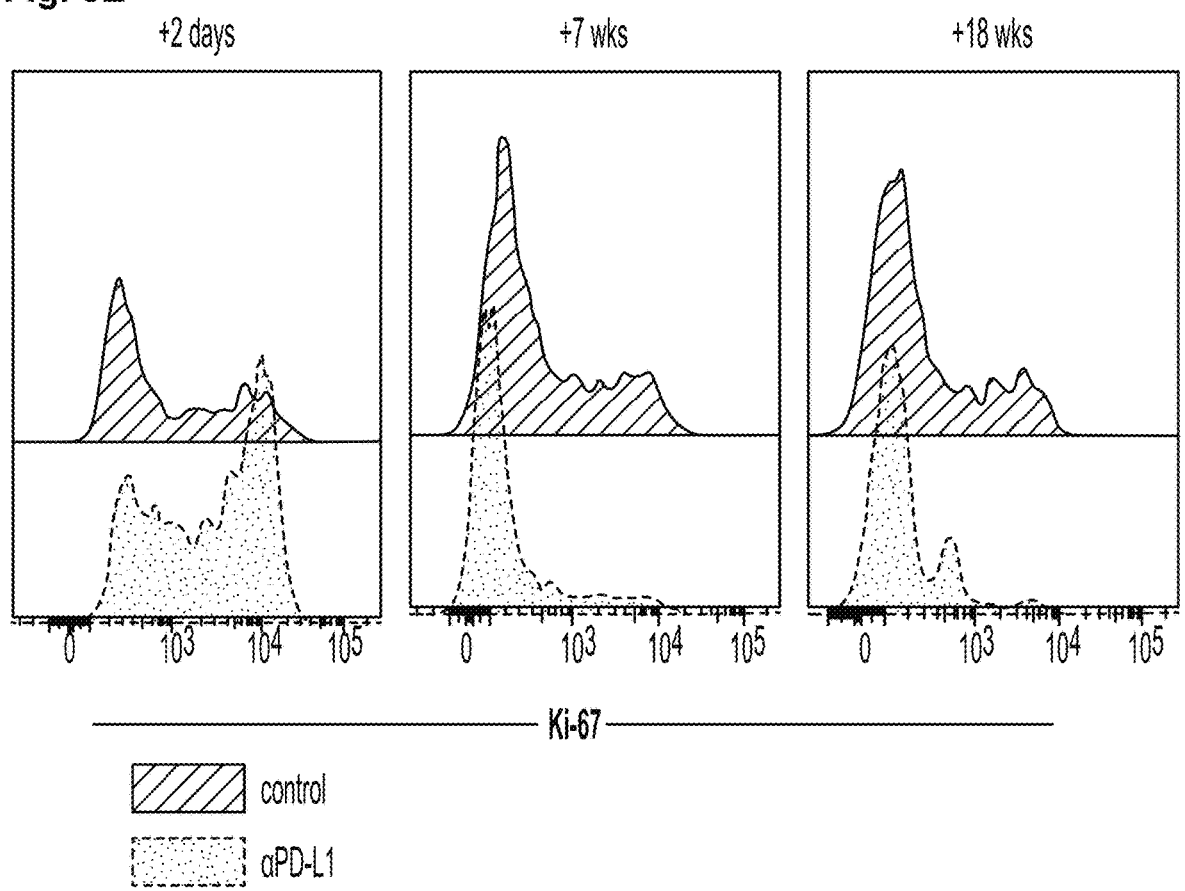
Figure 5F:
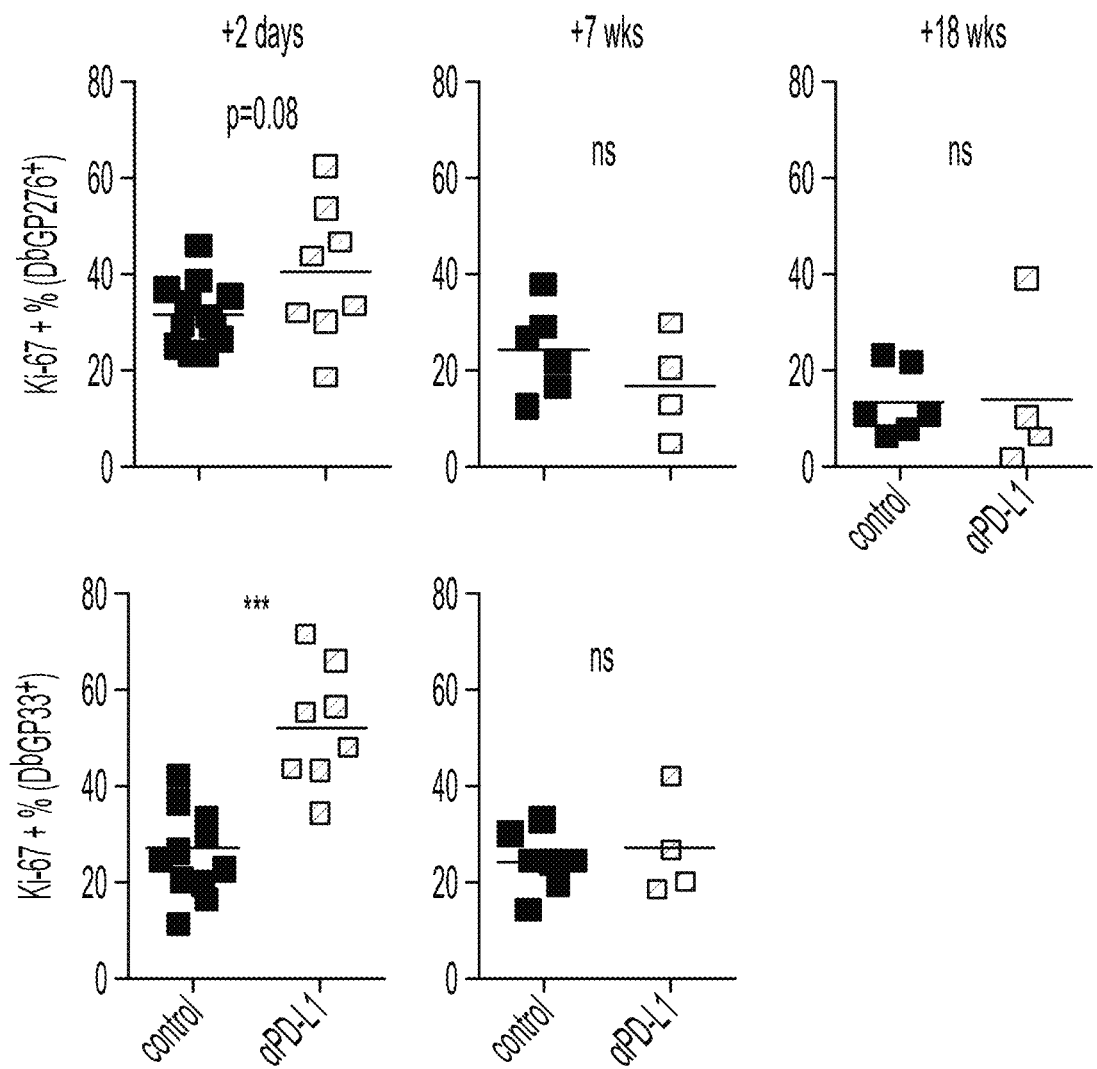
Figure 12A:
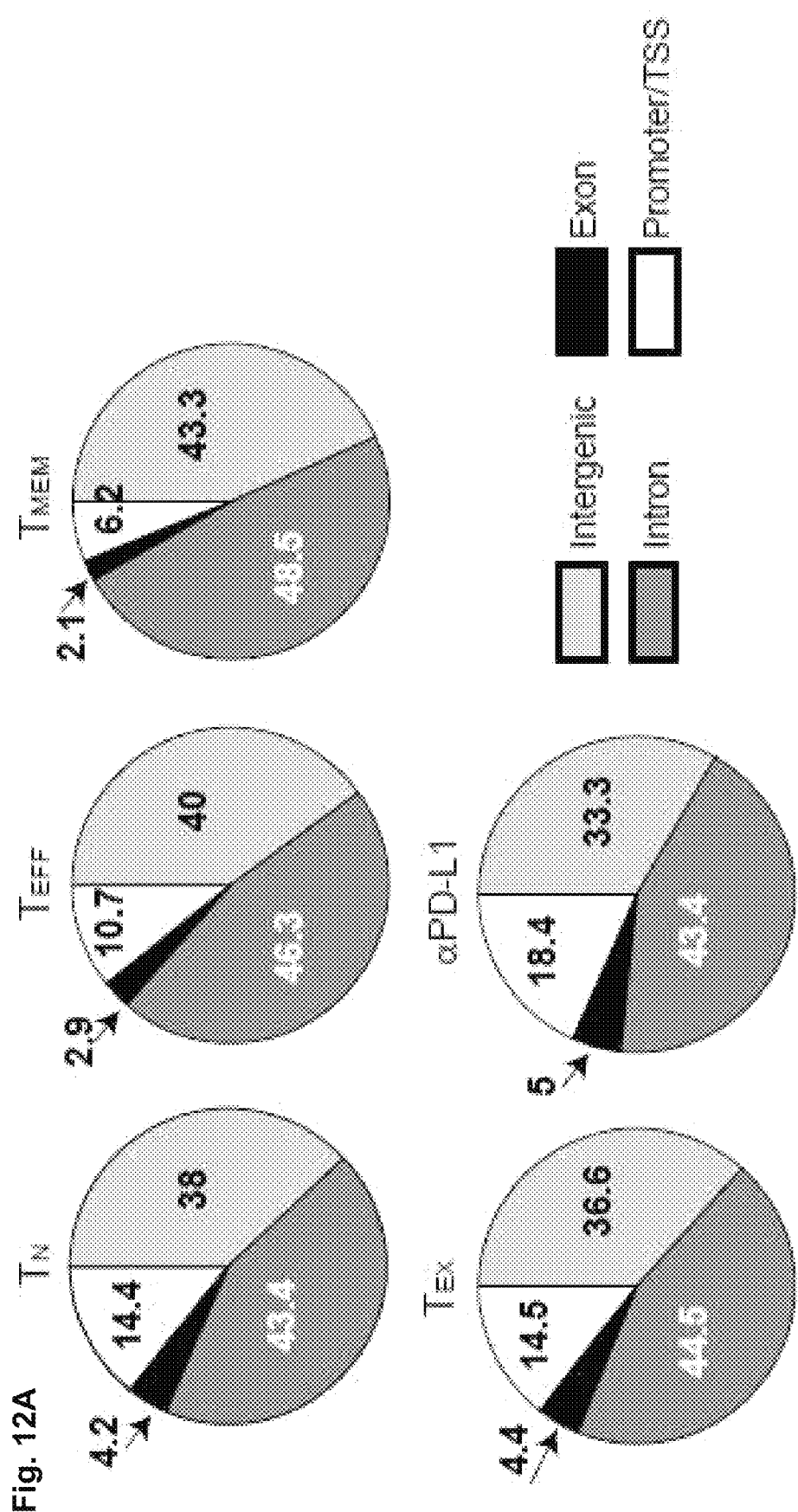
FIGS. 12A-12C are a series of images depicting region distribution of ATAC-seq data.
Figure 12B:
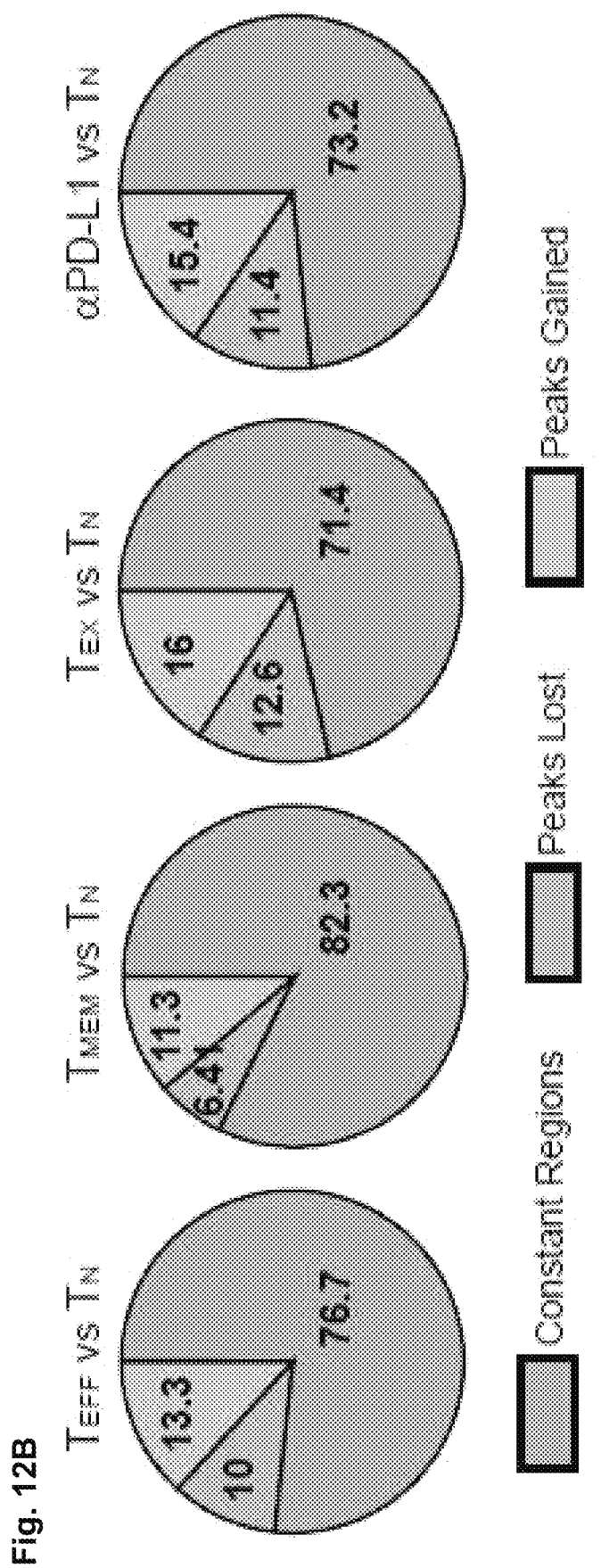
Figure 12C:
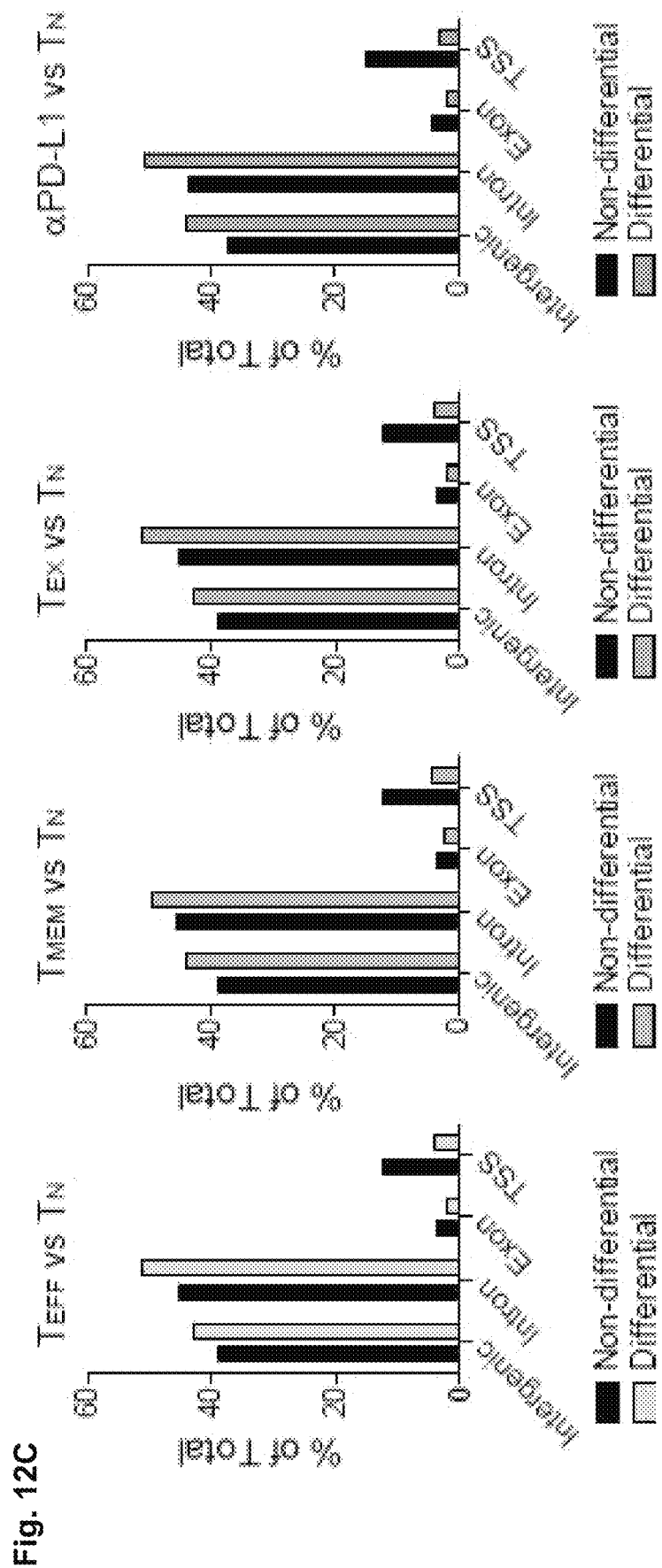

After antigen withdrawal, $T_{EX}$ and anti-PD-L1-treated $T_{EX}$ failed to down-regulate PD-1 (FIG. 10E), consistent with Pdcd1 locus DNA methylation and long-term expression of PD-1 (Youngblood et al. Immunity 2011, 35:400-412; Utzschneider et al. Nat. Immunol. 2013, 14:603-610; Angelosanto et al. J. Virol. 2012, 86:8161-8170). $T_{EX}$ also have lower global di-acetylated histone H3 (Zhang et al. Mol. Ther. 2014, 22:1698-1706), but how this relates to differentiation is unclear. To test whether the genome-wide epigenetic landscape of $T_{EX}$ may contribute to the lack of durable improvements following PD-1 pathway blockade, global chromatin landscape mapping was performed using ATAC-seq (Buenrostro, et al. Nat. Methods 2013, 10:1213-1218) (FIG. 11). The majority of open chromatin regions (OCRs) identified were in intergenic regions (33.3-43.3%) or introns (43.4-48.5%) (FIG. 12A), as expected (Winter et al. J. Immunol. 2008, 181:4832-4839). $T_{EFF}$, $T_{MEM}$, and $T_{EX}$ showed substantial chromatin remodeling compared to $T_N$ (FIG. 3F and FIGS. 12B and 12C) and genes with transcriptional start sites (TSS) within 20 kb of OCRs tended to be more highly expressed (FIG. 13). OCRs at specific genes illustrated distinct patterns for $T_{EFF}$, $T_{MEM}$ and $T_{EX}$. For example, $T_{EX}$ lacked several OCRs present in the Ifng locus in $T_{EFF}$ and $T_{MEM}$ (FIG. 3G, blue boxes). Similarly, for Pdcd1, $T_{EX}$-specific OCRs were identified in the "B" and "C" regions (FIG. 3G, black box) (Staron et al. 2014, Immunity 41:802-814; Oestreich, et al. J. Immunol. 2008, 181:4832-4839; Kao et al. Nat. Immunol. 2011, 12:663-671) and a previously unidentified OCR ~23 kb from the TSS (FIG. 3G, red box). Global hierarchical clustering and co-cluster analysis showed that $T_{EFF}$ and $T_{MEM}$ were more similar to each other than to $T_{EX}$ and that $T_{EX}$ had a distinct global epigenetic landscape (FIG. 3, H to J, and FIGS. 14 to 16). These data suggest that $T_{EX}$ may represent a distinct lineage of CD8 T cells.

Figure 17B:
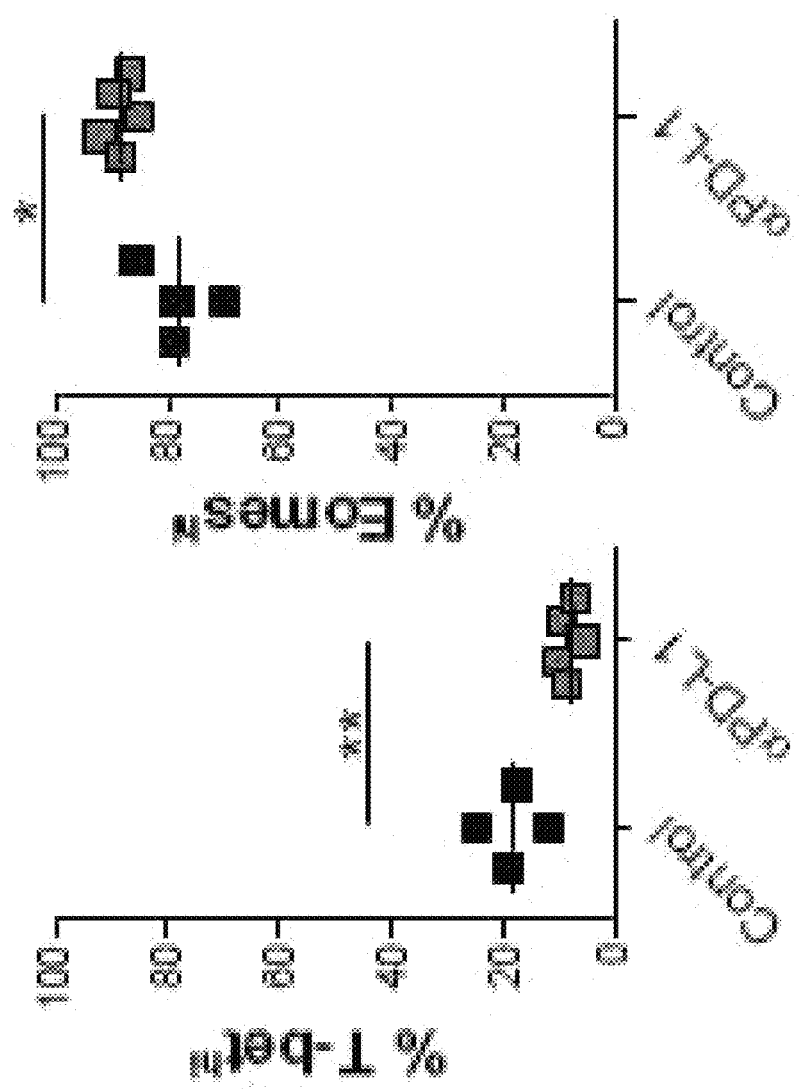
Figure 17A:
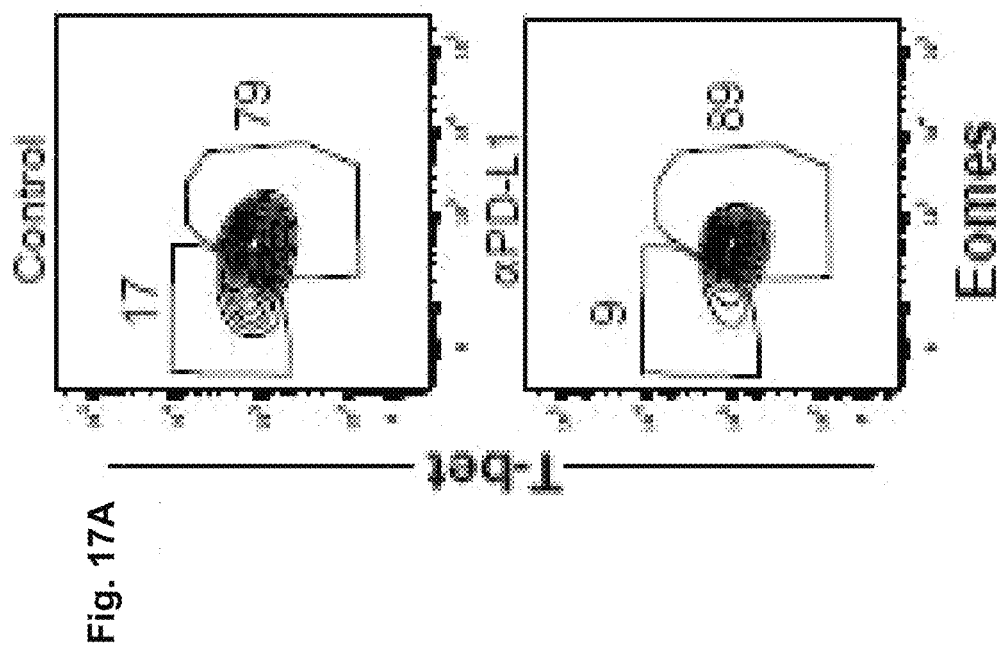
Figure 17C:
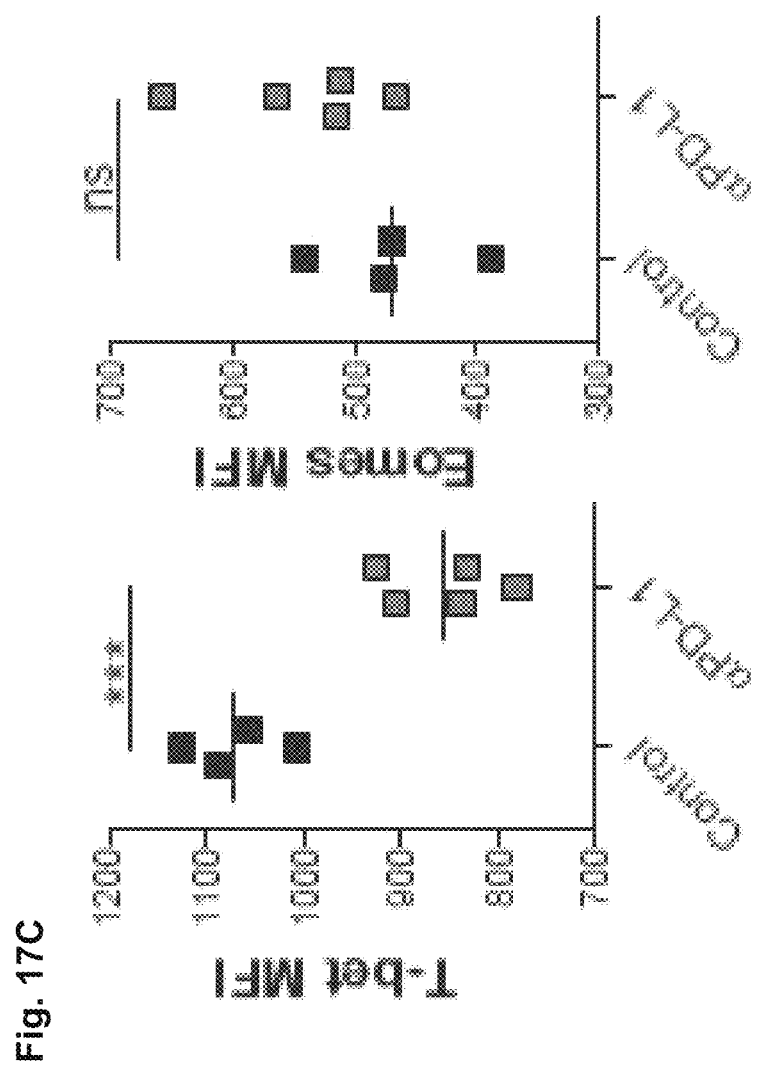
Figure 17E:
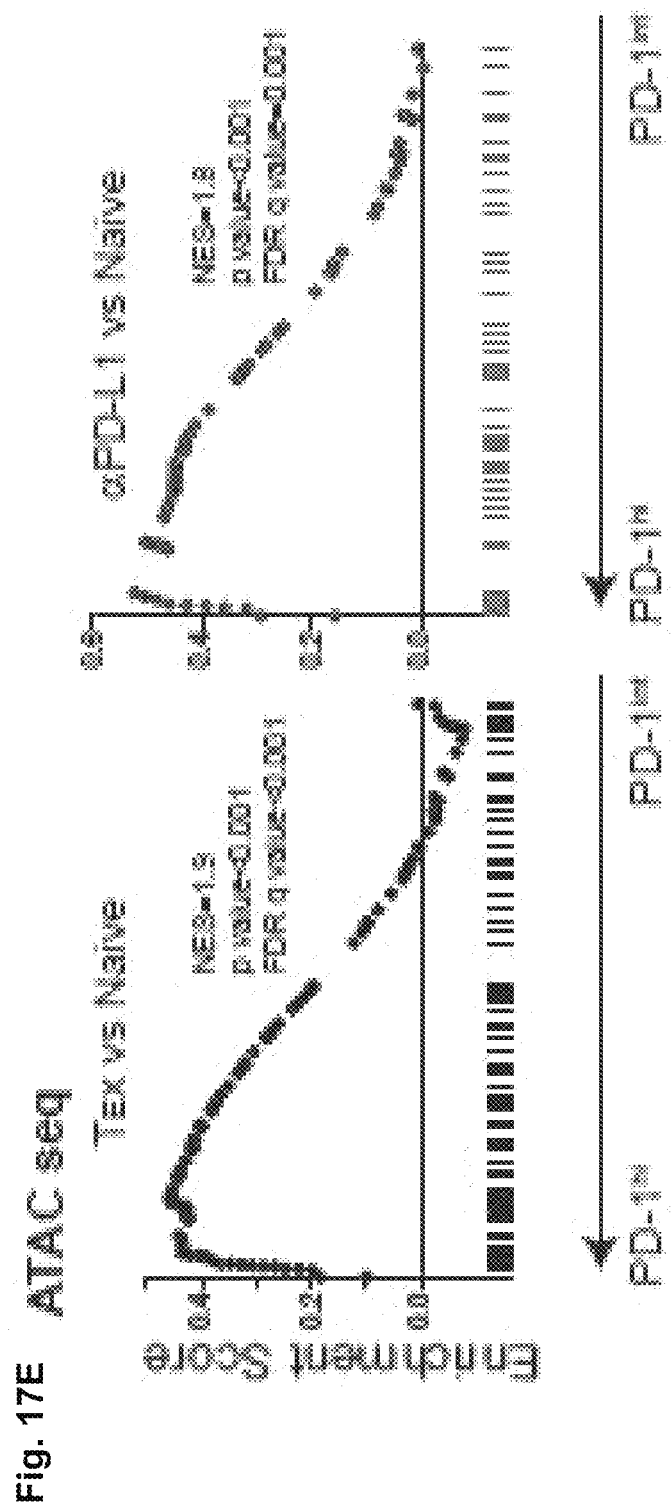
Figure 17G:
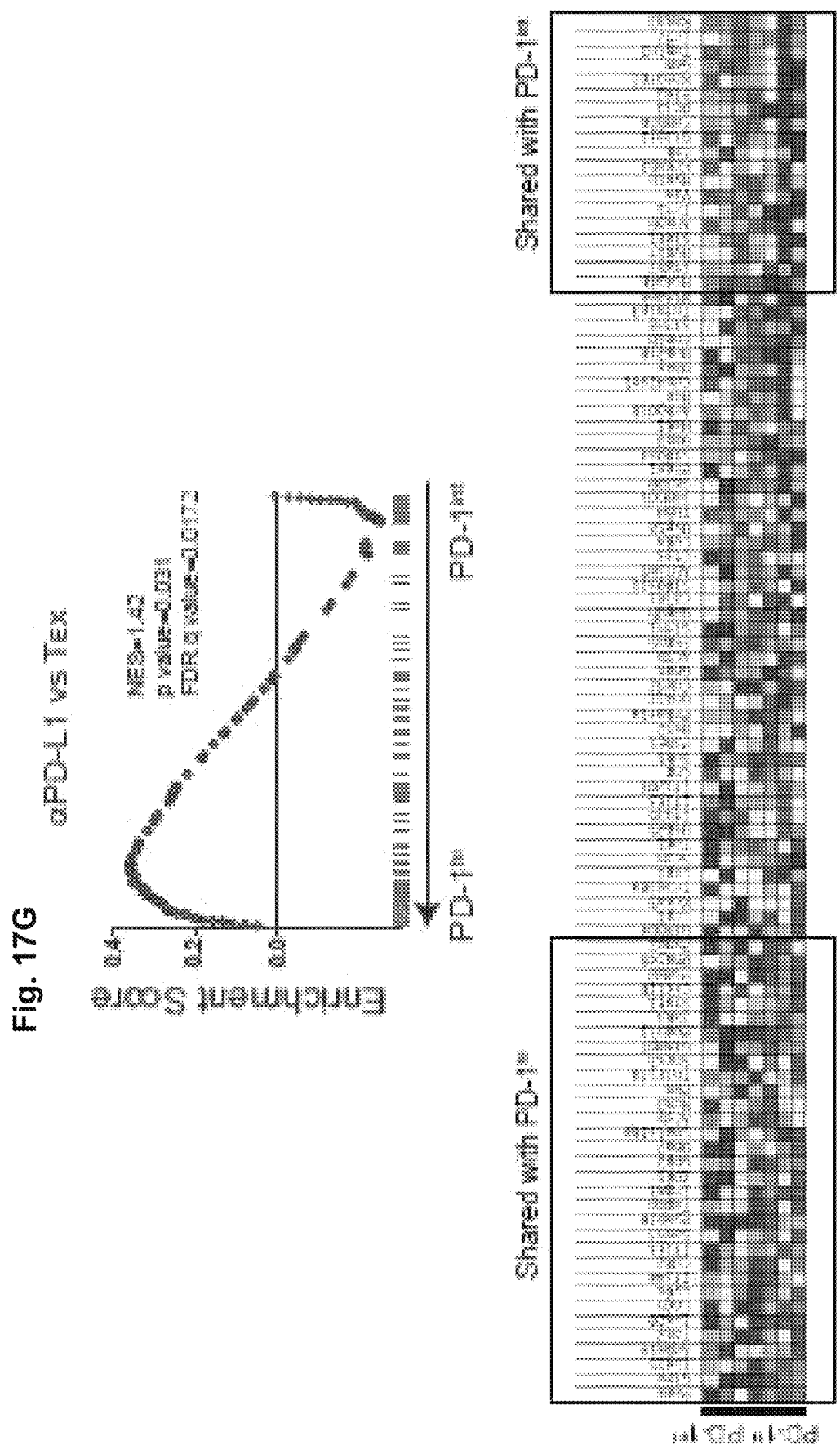

Two subsets of $T_{EX}$ have been defined based on expression of Eomes, T-bet and PD-1 (Paley et al. Science 2012, 338:1220-1225; Blackburn, et al. Proc. Natl. Acad. Sci. U.S.A. 2008, 105:15016-15021) and additional heterogeneity has recently been described (He, et al. Nature 2016, 537:412-428; Im, et al. Nature 2016, 537:417-421; Utzschneider, et al. Immunity 2016, 45:415-427). The T-bet$^{hi}$Eomes$^{lo}$ PD-1$^{int}$ subset can be re-invigorated by PD-1 pathway blockade while the Eomes$^{hi}$PD-1$^{hi}$ subset is more terminal and responds poorly to blocking PD-1 (Paley et al. Science 2012, 338:1220-1225; Blackburn, et al. Proc. Natl. Acad. Sci. U.S.A. 2008, 105:15016-15021). Here, $T_{EX}$ were ~80% Eomes$^{hi}$ and ~20% T-bet$^{hi}$, and this distribution changed minimally upon anti-PD-L1 treatment (FIG. 17A to 17C). The transcriptional and epigenetic profiles of $T_{EX}$ and anti-PD-L1-treated $T_{EX}$ were significantly enriched for genes from the Eomes$^{hi}$ subset (FIGS. 17D and 17E) (Doering, et al. Immunity 2012, 37:1130-1144). However, there was also a trend toward enrichment of genes from the PD-1$^{int}$Tbet$^{hi}$ $T_{EX}$ subset in the anti-PD-L1-treated group (FIGS. 17F and 17G), perhaps reflecting recent conversion of Tbet$^{hi}$ cells into Eomes$^{hi}$ cells or additional heterogeneity.

Figure 13A:
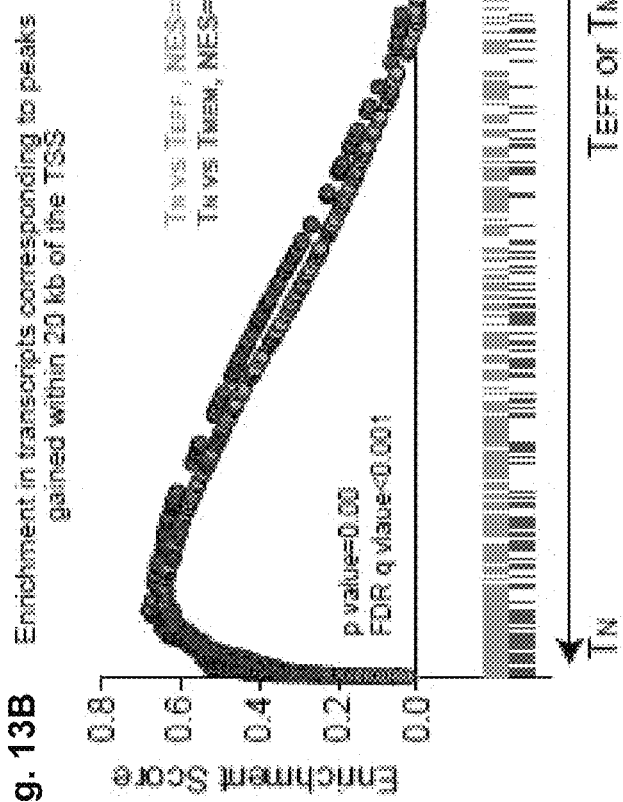
Figure 13B:
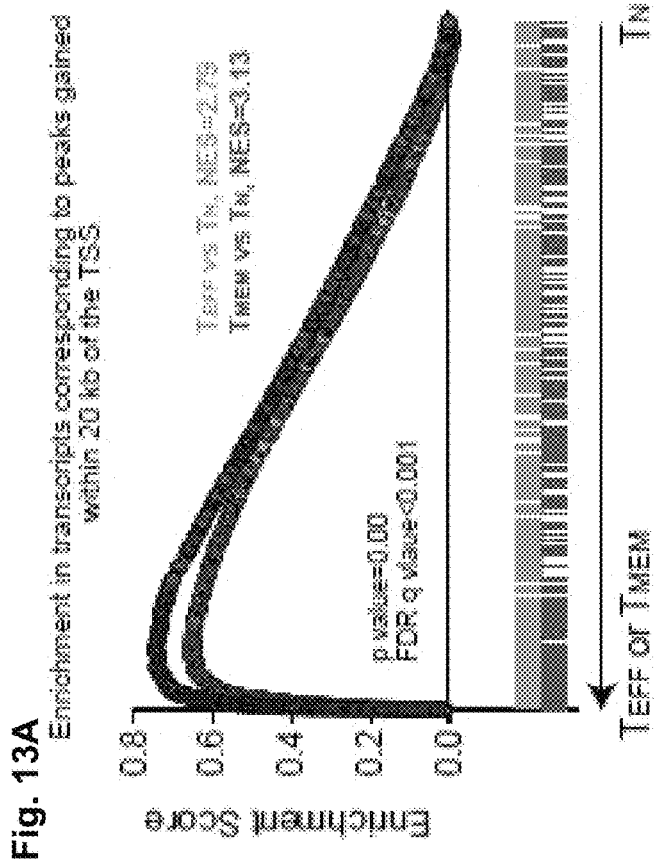
Figure 13C:
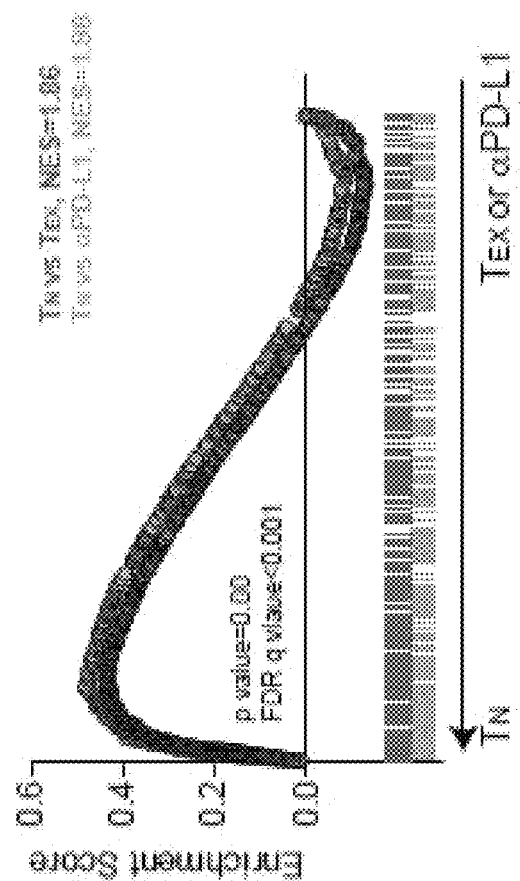
Figure 13D:
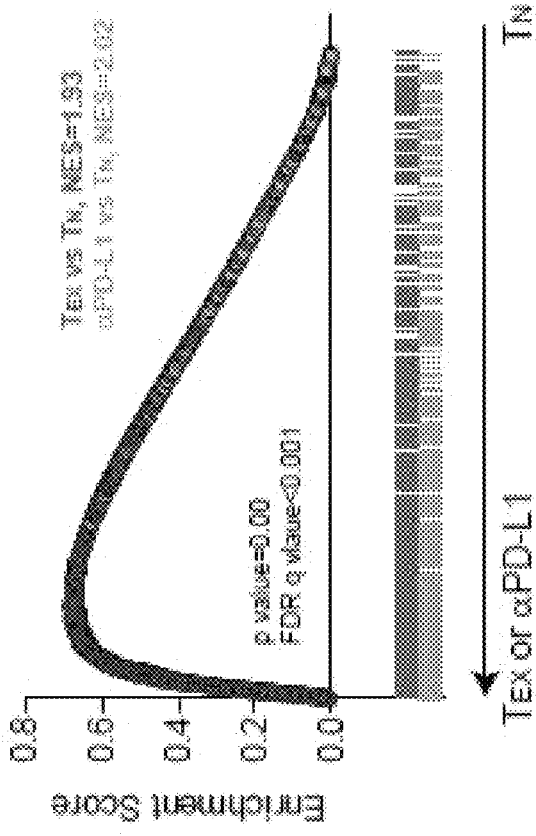
Figure 14:
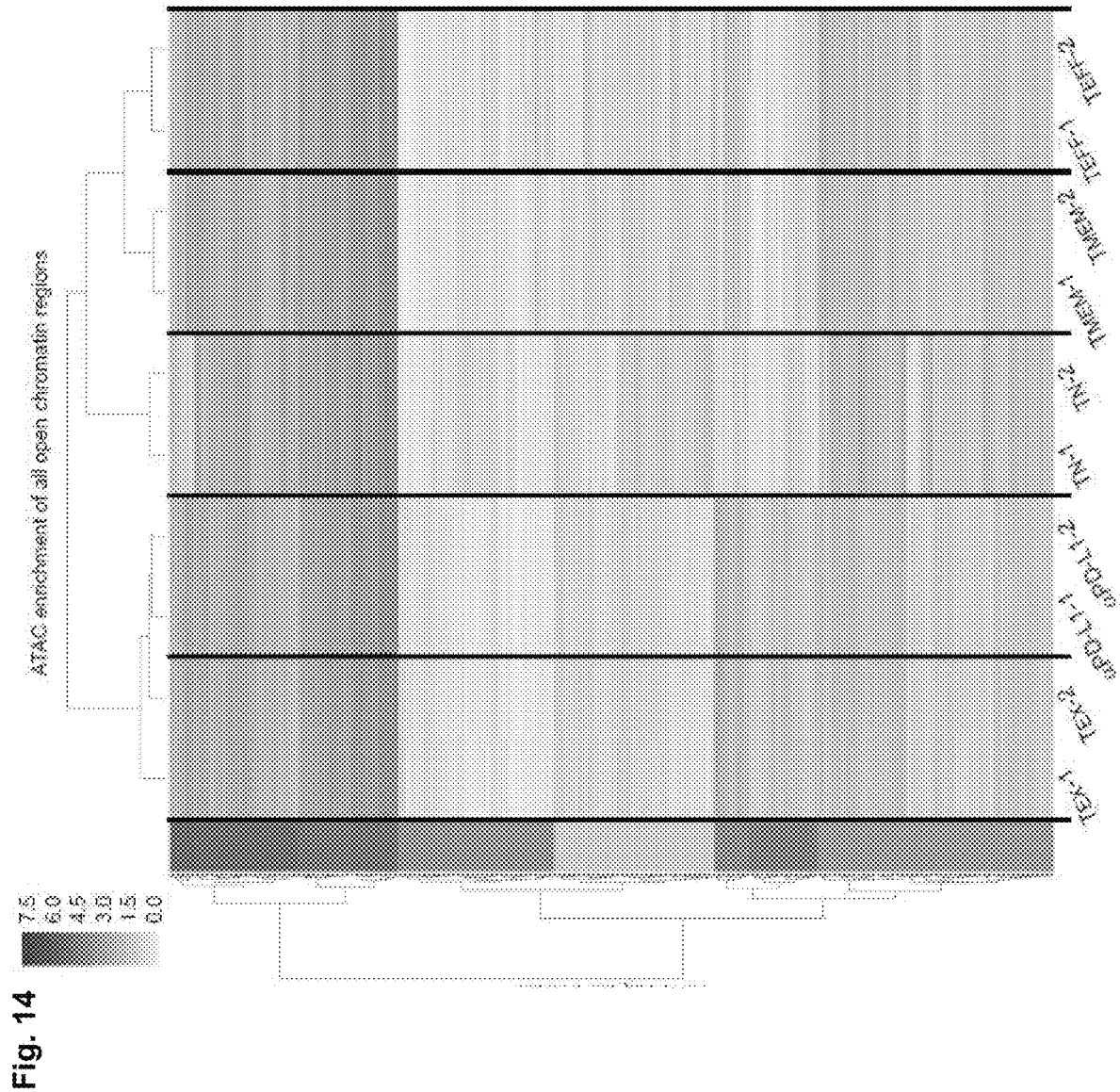
FIG. 14 depicts hierarchical clustering of all ATAC-seq open chromatin regions. Solid lines indicate separation between cell types, showing two replicates side-by-side. Row/clusters determined by flattening threshold of 90 ward clustering of Euclidean distance of input data.
Figure 15A:
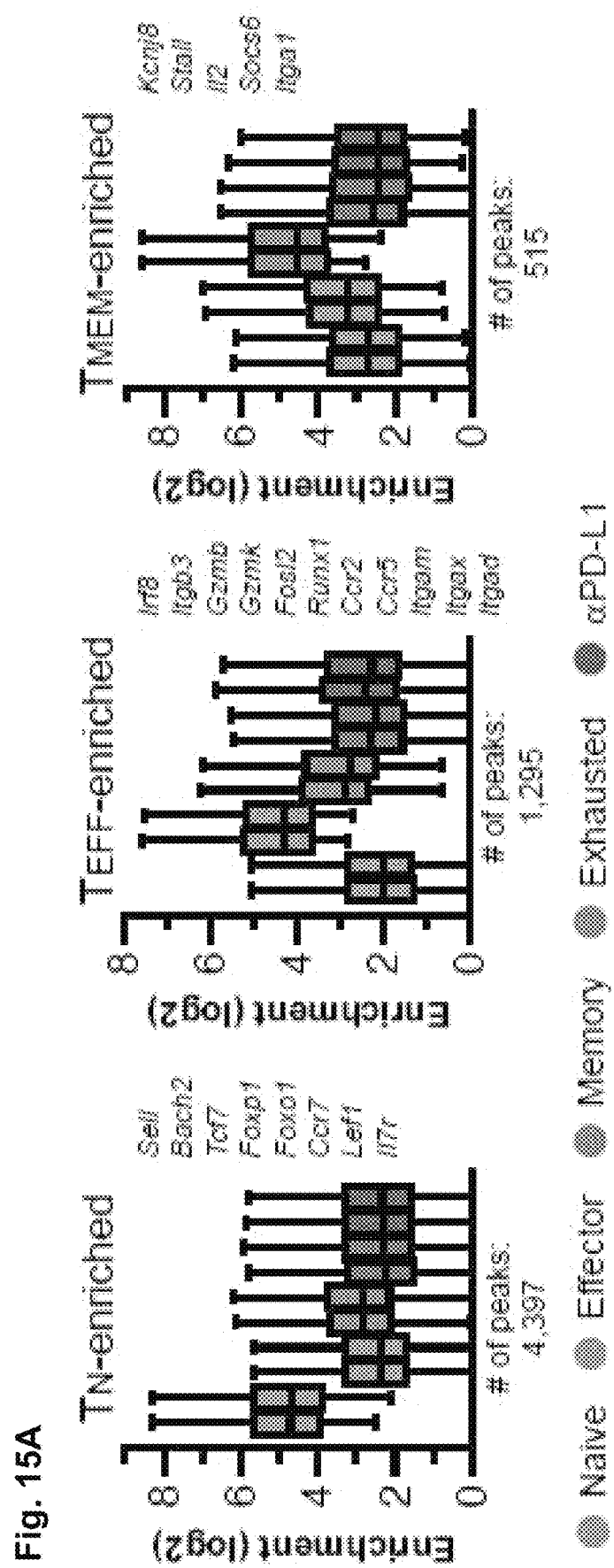
Figure 15D:
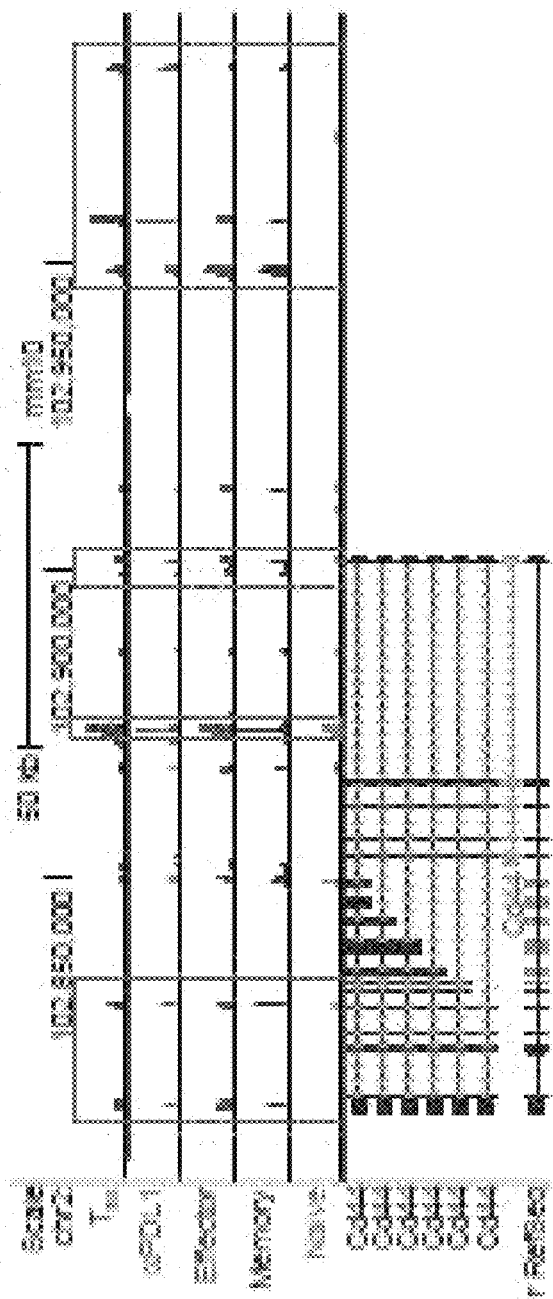
Figure 15E:
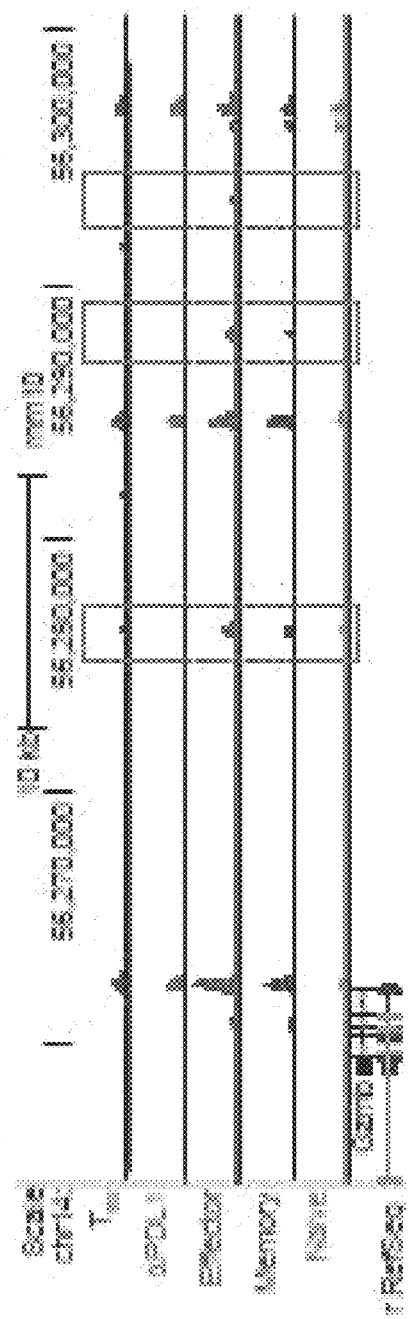
Figure 15F:
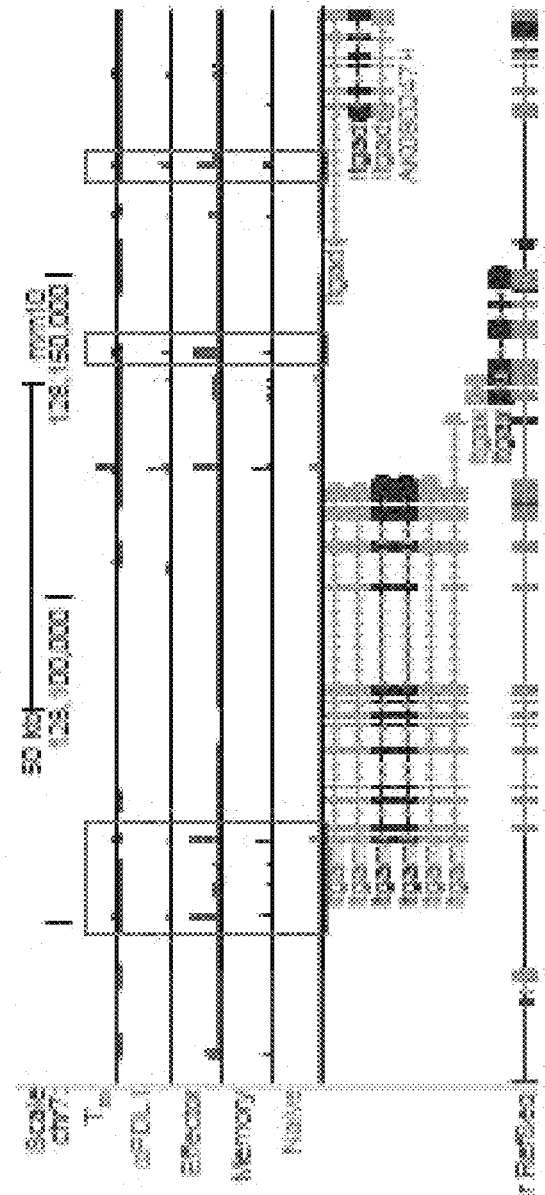
Figure 15G:
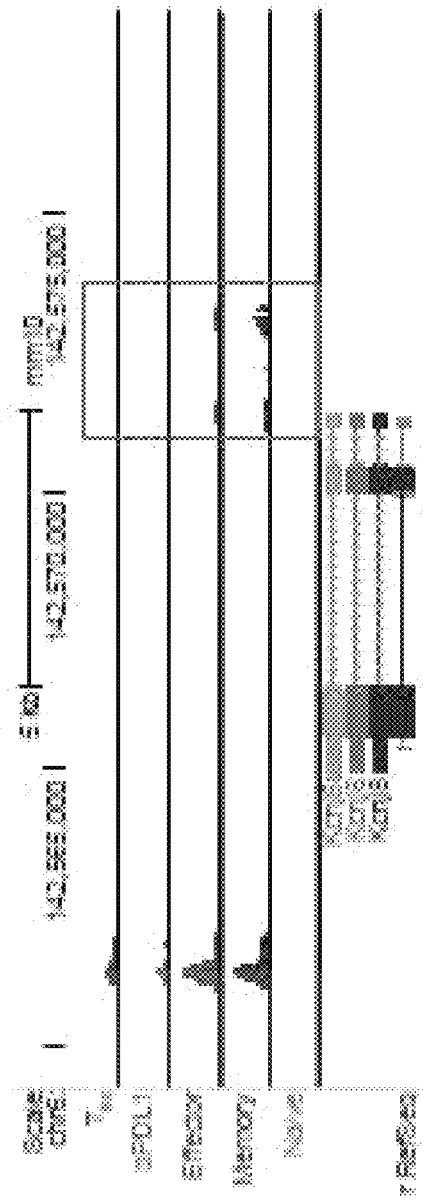
Figure 16E:
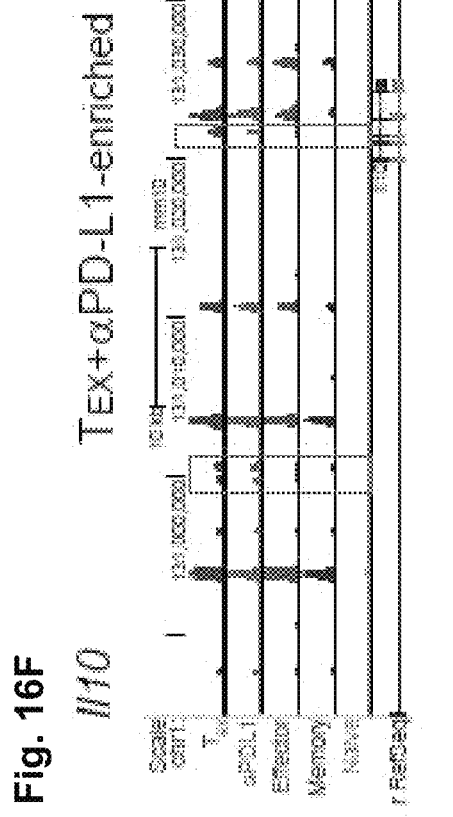
Figure 16F:
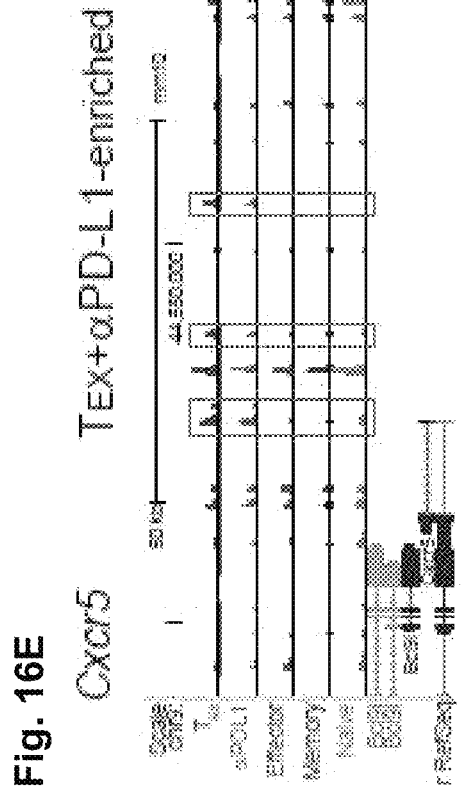
Figure 16H:
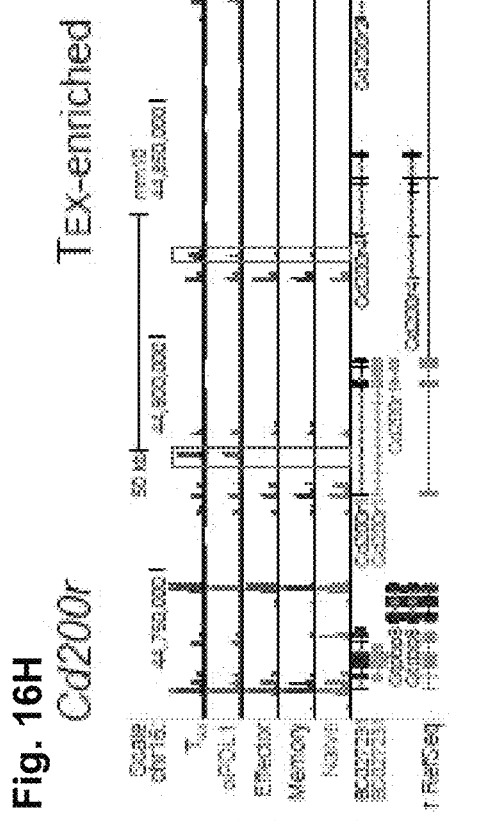
Figure 16G:
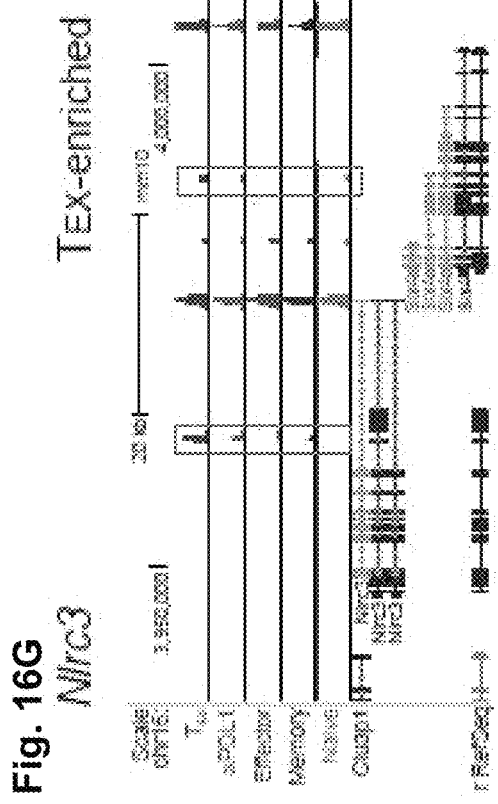
Figure 16I:
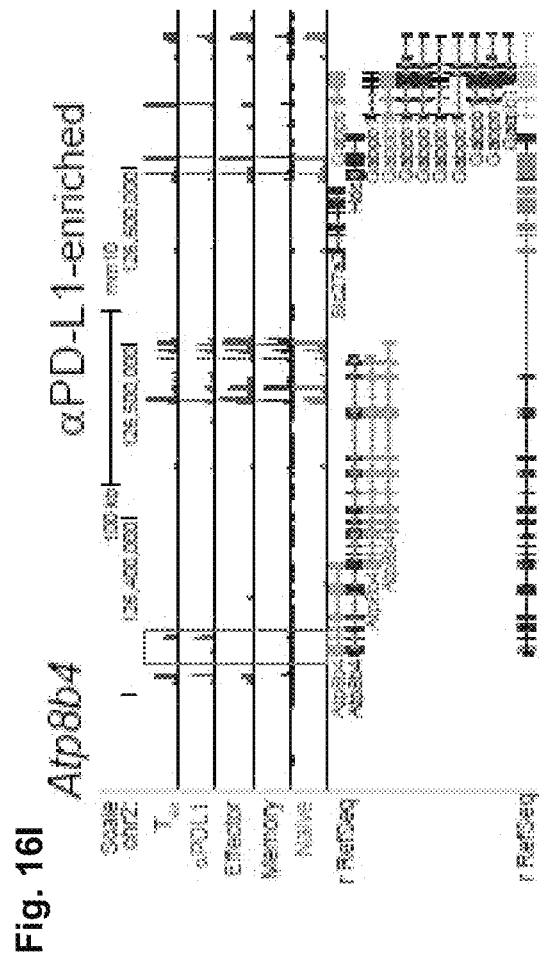
Figure 18A:
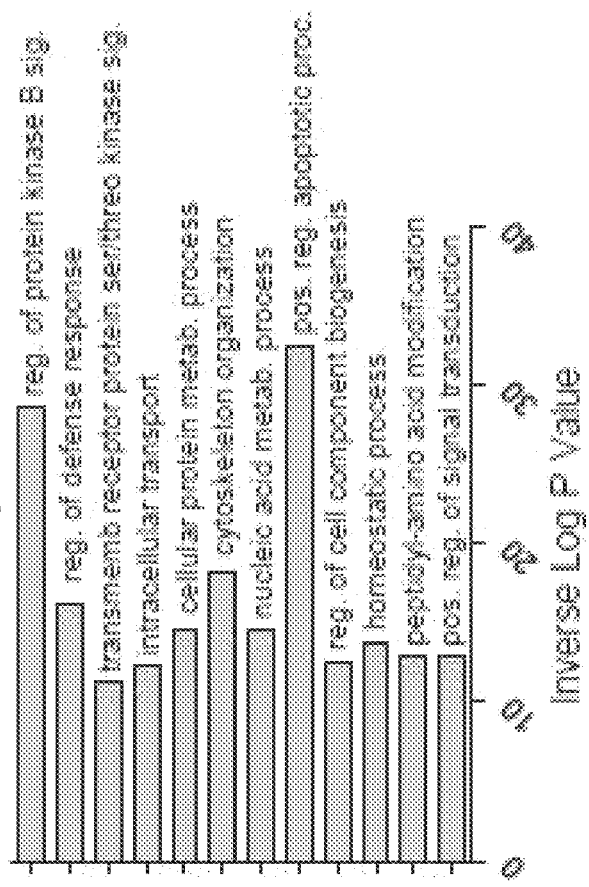
Figure 18C:
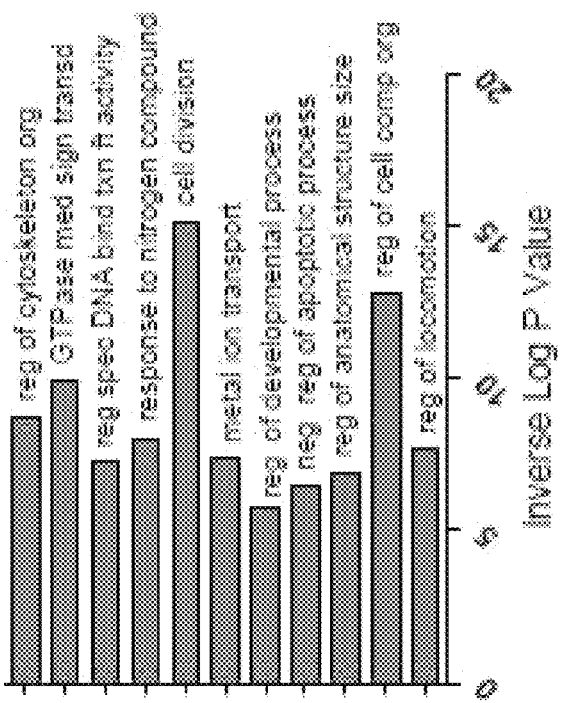
Figure 18B:
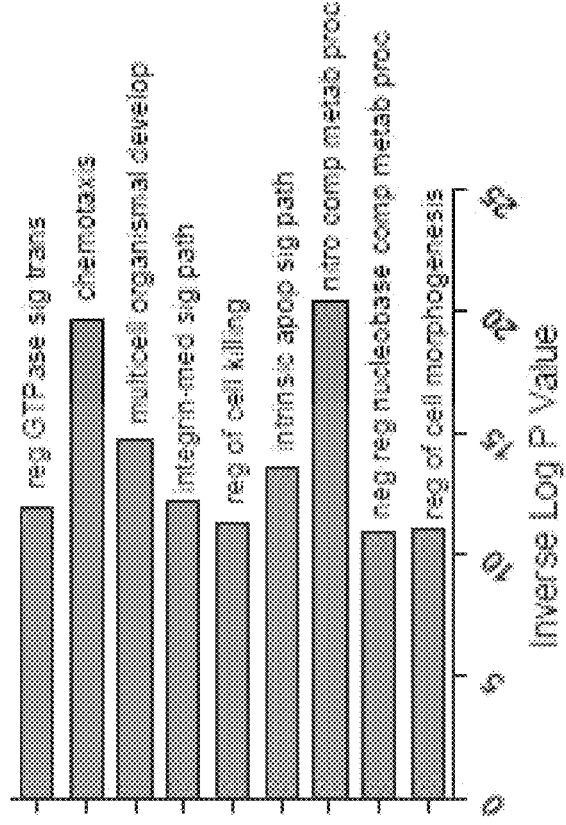

Next, the ability of PD-1 pathway blockade to reprogram the epigenetic landscape of $T_{EX}$ was examined. Hierarchical clustering, co-clustering, and principle component analysis showed considerable similarity between control and anti-PD-L1-treated $T_{EX}$ (FIGS. 10H to 10J, and FIG. 14). OCRs preferentially found in both $T_{EX}$ and anti-PD-L1-treated $T_{EX}$ were located near Pdcd1, Il10, Ctla4, Cxcr5 and elsewhere suggesting state-specific regulation that was not substantially altered following PD-L1 blockade (FIG. 16). While globally the epigenetic changes were modest, co-cluster analysis identified a small subset of OCRs uniquely enriched in $T_{EX}$ (555 peaks) or anti-PD-L1-treated $T_{EX}$ (98 peaks) (FIGS. 10H to 10I; FIG. 16; and Pauken et al. Table S7 (Pauken et al. Science 2016, 354(6316):1160-1165)). Some of these genes showed the same trend epigenetically and transcriptionally (e.g., CD200r; FIG. 13E) and specific biological pathways were enriched in sets of genes near OCRs that changed (FIG. 18).

Figure 19F:
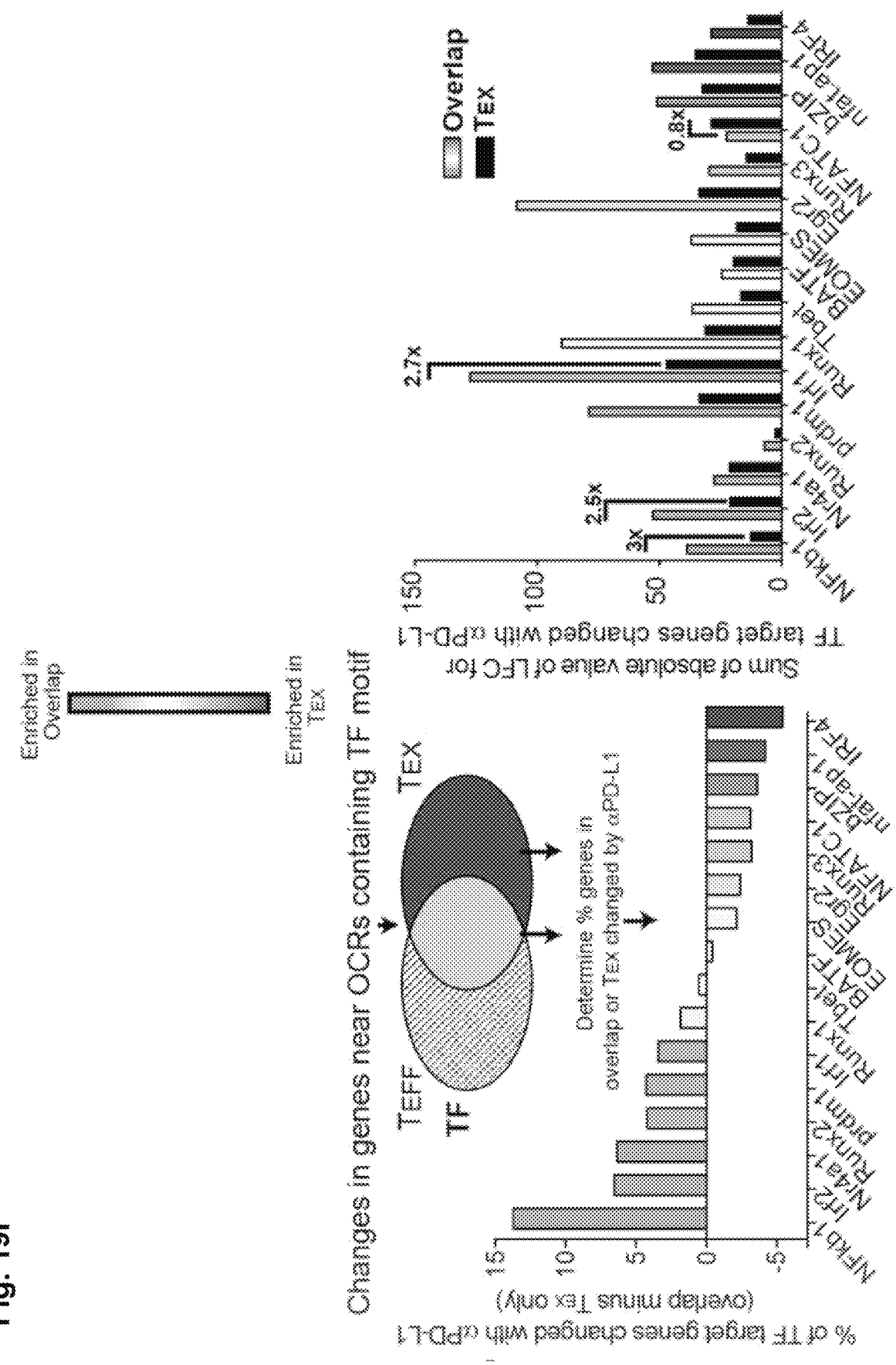
Figure 20:
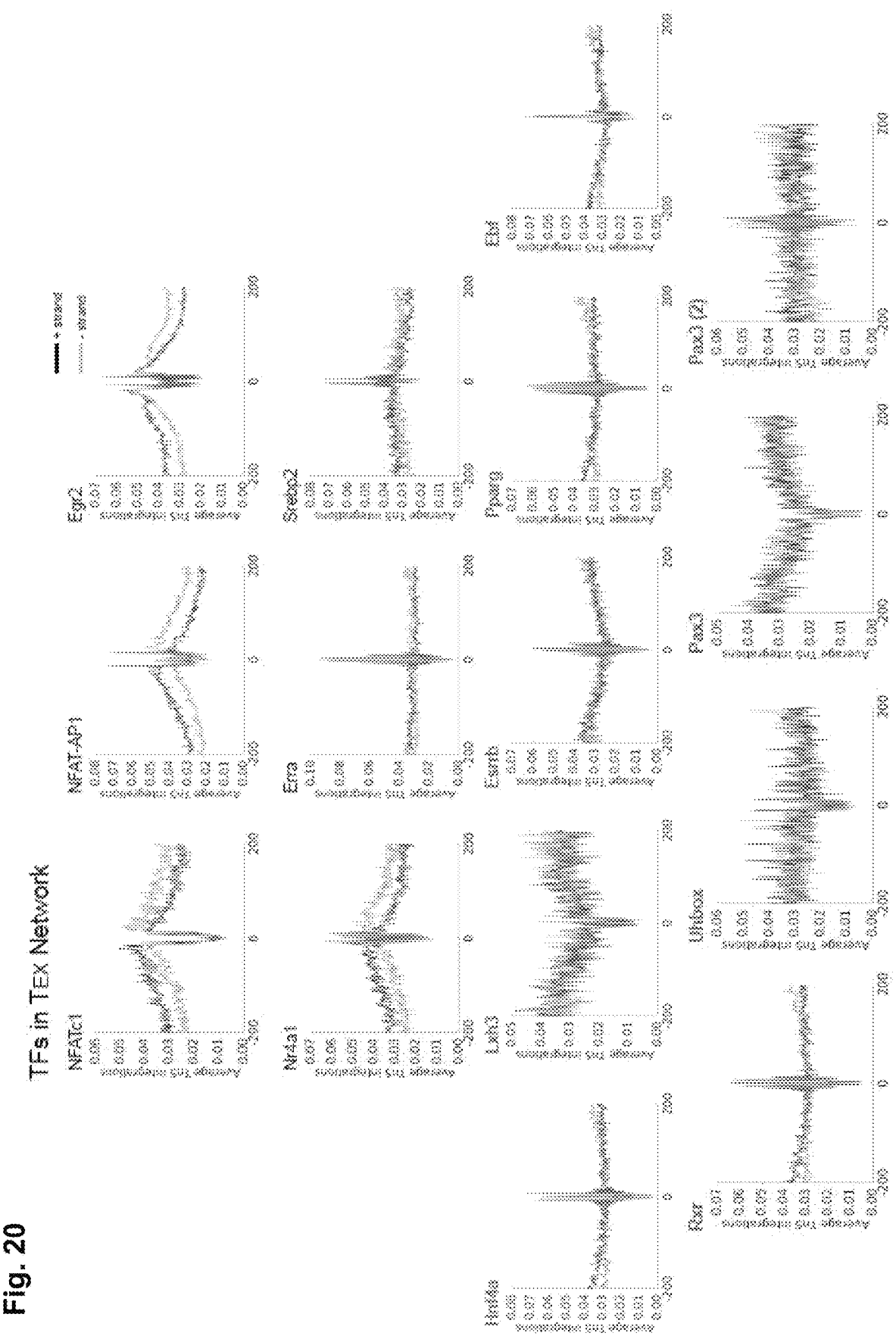
FIG. 20 depicts transcription factor footprinting in control-treated $T_{EX}$ cells. Transcription factor footprinting was performed on merged replicates (see materials & methods under Experimental Examples) for the indicated transcription factors using the ATAC-seq data from control treated $T_{EX}$. Transcription factors shown were identified using Wellington bootstrap analysis in FIG. 19B. Red lettering indicates transcription factors that were excluded from downstream network analysis due to lack of evidence of binding in the footprinting analysis and based on selection criteria described in Materials and Methods.
Figure 21:
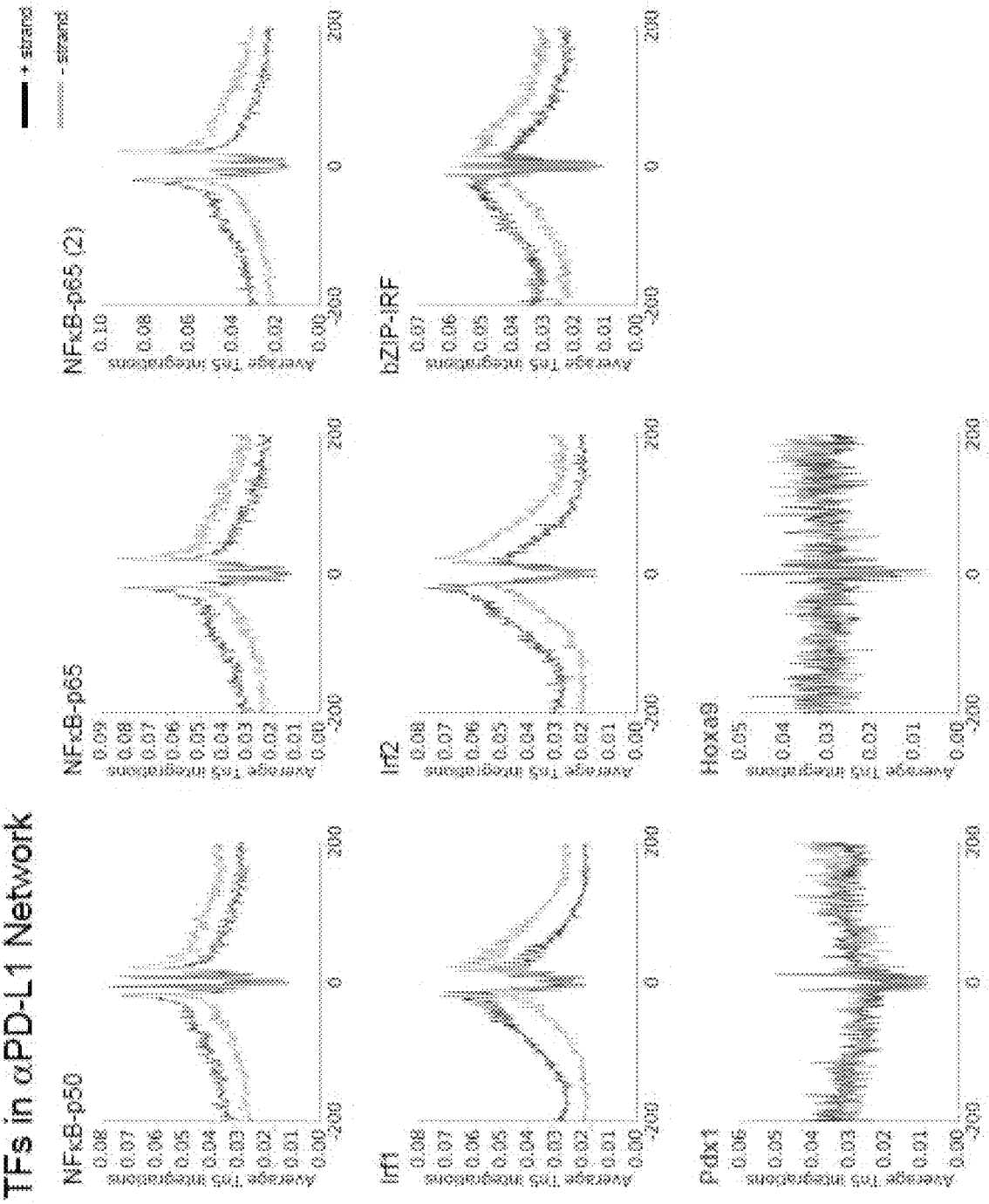
FIG. 21 depicts transcription factor footprinting in anti-PD-L1-treated $T_{EX}$ cells. Transcription factor footprinting was performed on merged replicates (see materials & methods under Experimental Examples) for the indicated transcription factors using the ATAC-seq data from anti-PD-L1 treated $T_{EX}$. Transcription factors shown were identified using Wellington bootstrap analysis in FIG. 19B. Red lettering indicates transcription factors that were excluded from downstream network analysis due to lack of evidence of binding in the footprinting analysis and based on selection criteria described elsewhere herein.

Example 4. Differential Transcription Factor Binding Following PD-1 Pathway Blockade Contributes to an Altered Transcriptional Network During $T_{EX}$ Re-Invigoration $T_{EX}$ displayed ~6000 unique OCR changes compared to $T_{EFF}$ and $T_{MEM}$ (FIGS. 10F to 10I). Thus, the ~650 OCR changes induced by PD-L1 blockade was modest by comparison. To determine whether these changes impacted specific transcriptional circuits, transcription factor (TF) motifs enriched in peaks gained (e.g., NFκB, Jun:AP1, and CTCF) or lost were identified (e.g., NFATc1, NFAT:AP1, Nur77, Eomes and Egr2) (FIG. 19A). To test whether re-invigoration resulted from rewired transcriptional control within the existing $T_{EX}$ epigenetic landscape, Wellington bootstrap analysis was performed to predict TF binding activity (FIG. 19B and Pauken et al. Table S10 (Pauken et al. Science 2016, 354(6316):1160-1165)). $T_{EX}$ and anti-PD-L1-treated $T_{EX}$ were more similar to each other than to $T_N$, $T_{EFF}$ or $T_{MEM}$. However, TF motifs biased toward $T_{EX}$ or anti-PD-L1-treated $T_{EX}$ were identified (FIG. 19B and Pauken et al. Table S10 (Pauken et al. Science 2016, 354(6316):1160-1165)). TF footprinting was then performed to identify TFs with evidence of likely binding (FIG. 19C and FIGS. 20 and 21). An integrated network was then constructed for transcriptional circuitry based on predicted TF activity (FIG. 19D and Pauken et al. Table S11 (Pauken et al. Science 2016, 354(6316):1160-1165)). This network identified augmented activity of NFκB, IRFs, and bZip factors (AP-1 family) and decreased activity of NFAT, Egr2, and Nur77 upon PD-L1 blockade. Major features of this transcriptional network were recapitulated using a second network approach where additional TF families were identified (e.g., Runx, Nr2%, Prdm1, Rarb, Pparg.Rxra and homeobox TFs; FIG. 22 and Pauken et al. Table S12 (Pauken et al. Science 2016, 354(6316):1160-1165)). To further interrogate how these changes might affect a specific TF, we examined NFAT. NFAT working with AP-1 transactivates many effector-phase genes. In contrast, "partnerless" NFAT that fails to bind AP-1 induces a subset of $T_{EX}$ genes (Martinez, et al. Immunity 2015, 42:265-278). Here, upon anti-PD-L1 treatment, there was significantly reduced expression of targets of partnerless NFAT in re-invigorated $T_{EX}$ (FIG. 19E), suggesting a rewiring of this transcriptional circuit following blockade.

Together these data suggested that, while PD-1 pathway blockade did not fully reprogram $T_{EX}$ into $T_{MEM}$ or $T_{EFF}$, these cells may (re)acquire some features of $T_{EFF}$ biology. One hypothesis is that upon PD-L1 blockade the rewired transcriptional network allows $T_{EX}$ to preferentially re engage features of their epigenomic program that overlap with $T_{EFF}$. To test this idea, we separated TF target genes into those containing OCRs that were: a) unique to $T_{EFF}$; b) unique to $T_{EX}$; or c) shared between $T_{EFF}$ and $T_{EX}$ (FIG. 19F). We then examined the change in genes expressed in each category following PD-L1 blockade. For several TFs including T-bet and Eomes there was no redistribution of the pattern of target gene expression (FIG. 19F). However, for many TFs identified above that have a key role in effector biology such as NFκB, IRF1, IRF2, Nur77 and Blimp-1 (encoded by Prdm1), there was an increase in the number of target genes expressed in the $T_{EFF}$ and $T_{EX}$ overlap group compared to the $T_{EX}$-only group upon PD-L1 blockade (FIG. 19F). Moreover, genes in the shared $T_{EFF}$ and $T_{EX}$ epigenetic module displayed a substantially greater magnitude of change in expression than genes in the $T_{EX}$ only group (FIG. 19F). These data indicate that PD-1 pathway blockade induces rewired transcriptional activity allowing $T_{EX}$ to more effectively re-engage modules of effector genes contained within the epigenetic landscape of $T_{EX}$. Specific TF circuits altered such as NFκB may have implications for co-targeting PD-1 and TNFR family pathways (Wherry et al. Nat. Rev. Immunol. 2015, 15:486-499; Sharma et al. Science 2015, 348:56-61; Ward-Kavanagh, et al. Immunity 2016, 44:1005-1019) and may be relevant for design of future therapeutics.

The data above demonstrates that in settings of severe T cell exhaustion, re-acquiring durable immune memory may be challenging, especially if tumor or viral antigen persists. However, the data also indicates that PD-1 pathway blockade may reveal opportunities to further augment T cell quality or effector activity (e.g., NFκB, IL-7R). Additional strategies such as priming new T cell responses (Sharma et al. Science 2015, 348:56-61), selectively expanding less exhausted subsets (Blackburn, et al. Proc. Natl. Acad. Sci. U.S.A. 2008, 105:15016-15021), or targeting multiple immunoregulatory or homeostatic pathways (e.g., IL-7, IL-2) simultaneously (Wherry et al. Nat. Rev. Immunol. 2015, 15:486-499; Sharma et al. Science 2015, 348:56-61) may also augment acquisition of durable immunity. These studies provide the impetus for extending epigenetic landscape mapping to human $T_{EX}$, future evaluation of checkpoint blockade combined with epigenetic modifiers, or epigenomic engineering for T cells. Thus, integrated cellular, transcriptional and epigenetic profiling of $T_{EX}$ not only reveals mechanistic insights into PD-1 pathway blockade mediated re-invigoration, but also points to key opportunities to improve long-term durability of these effects.

Figure 23B:
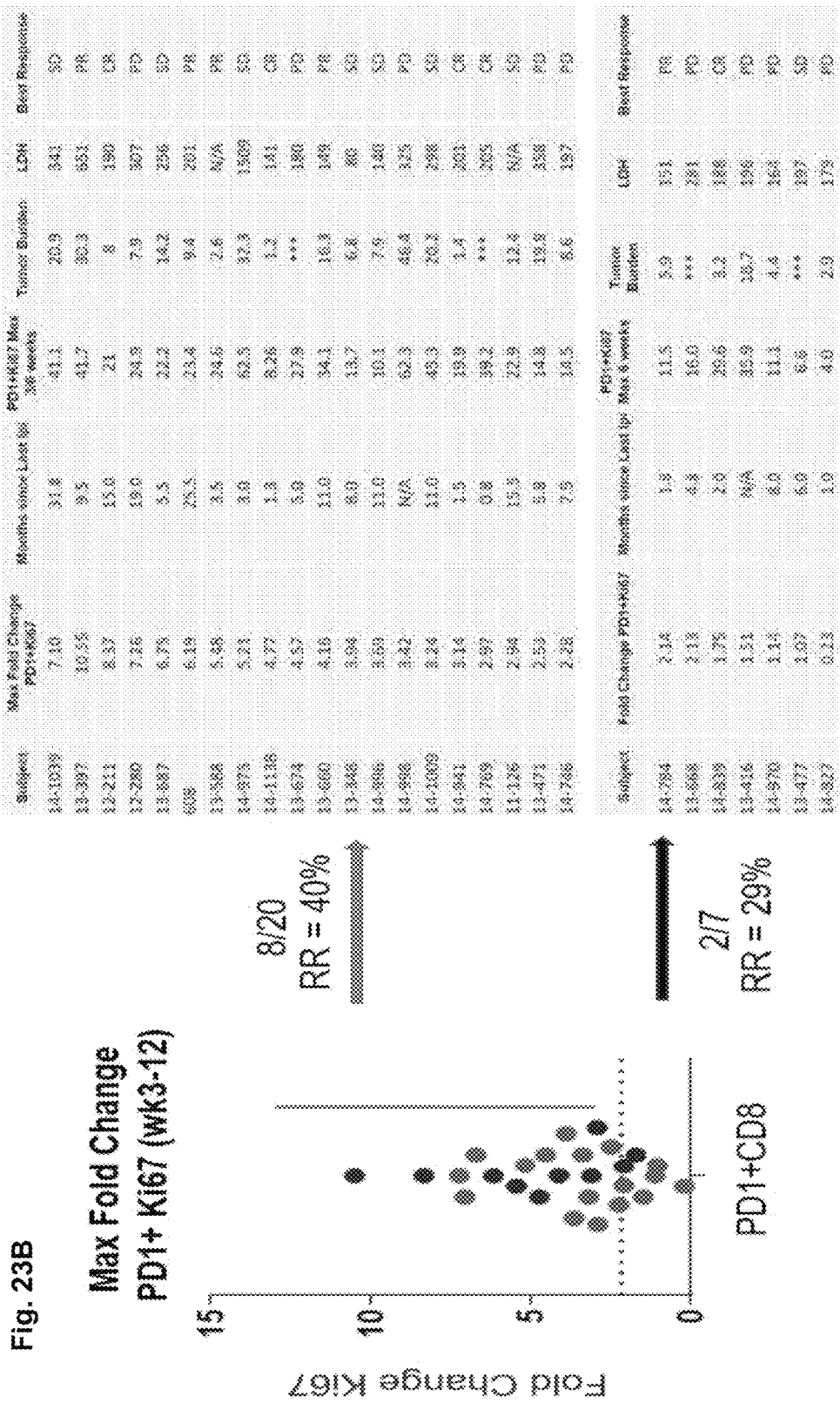
Figures 24A, 24B:
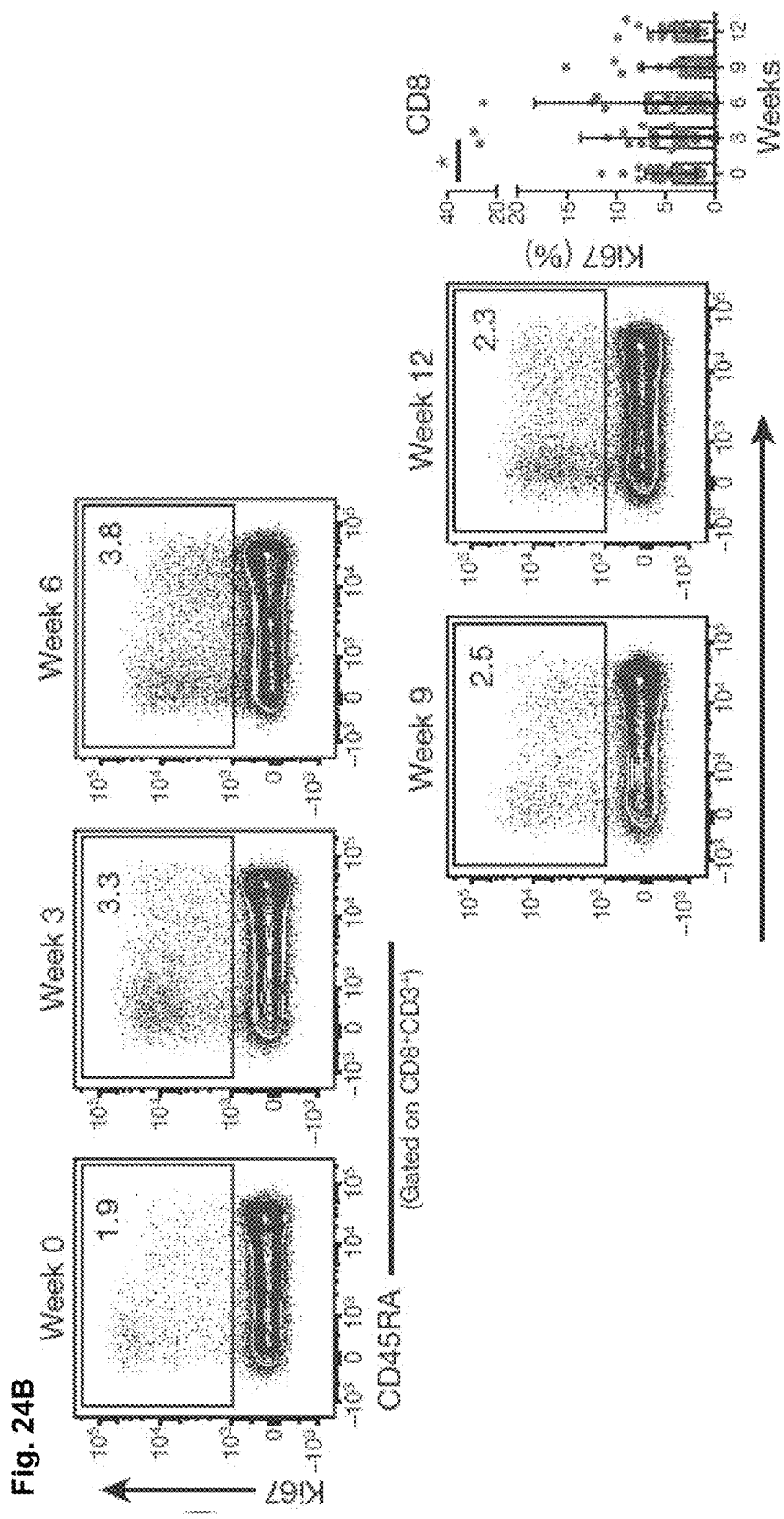
Figure 24C:
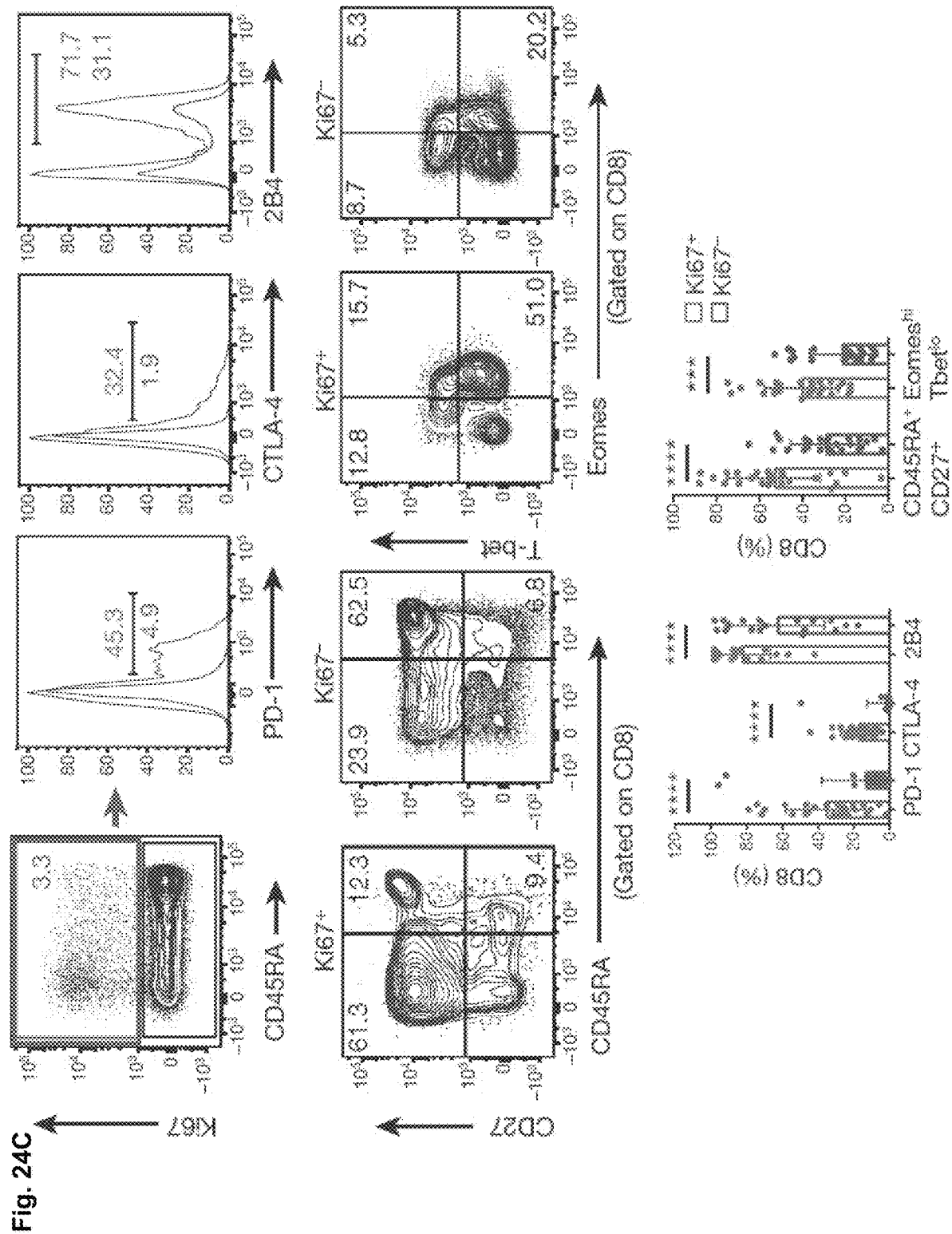

Example 5. CD8 T Cells Responding to Anti-PD-1 Therapy Display an Exhausted Phenotype Healthy donor versus melanoma patients were compared. Twenty-nine patients with stage IV melanoma treated with the anti-PD-1 antibody pembrolizumab (pembro) were enrolled the clinical trial described herein. All patients had previously received anti-CTLA-4 therapy (FIG. 23). Patients were treated with pembro, and blood was obtained before therapy and every 3 weeks during therapy for a total of 12 weeks. 62% of patients did not have an objective clinical response, determined on the basis of immune RECIST (response evaluation criteria in solid tumors) criteria, consistent with published trials (Robert et al. N. Engl. J. Med. 2015, 372:2521-2532; Ribas et al. Lancet Oncol. 2015, 16:908-918) (FIG. 24a, FIG. 23).

Peripheral blood T cells from patients with melanoma were first compared to those from age-matched healthy donors using high-dimensional flow cytometry. The frequencies of CD4 and CD8 T cells, memory T-cell subsets, and CD4 and CD8 T-cell co-expression of inhibitory receptors (PD-1, CTLA-4, 2B4, and TIM-3) were similar (data not shown). However, patients with melanoma had a higher frequency of CD4$^+$FOXP3$^+$ T cells and Ki67 expression by FOXP3$^+$ cells (FIG. 25a). Ki67 expression was also increased in CD8 T cells from patients with melanoma (P<0.0001, FIG. 25b), predominantly in the PD-1$^+$ CD8 T-cell subset (P<0.0001, FIG. 25C), suggesting a pre-existing immune response.

Figure 25D:
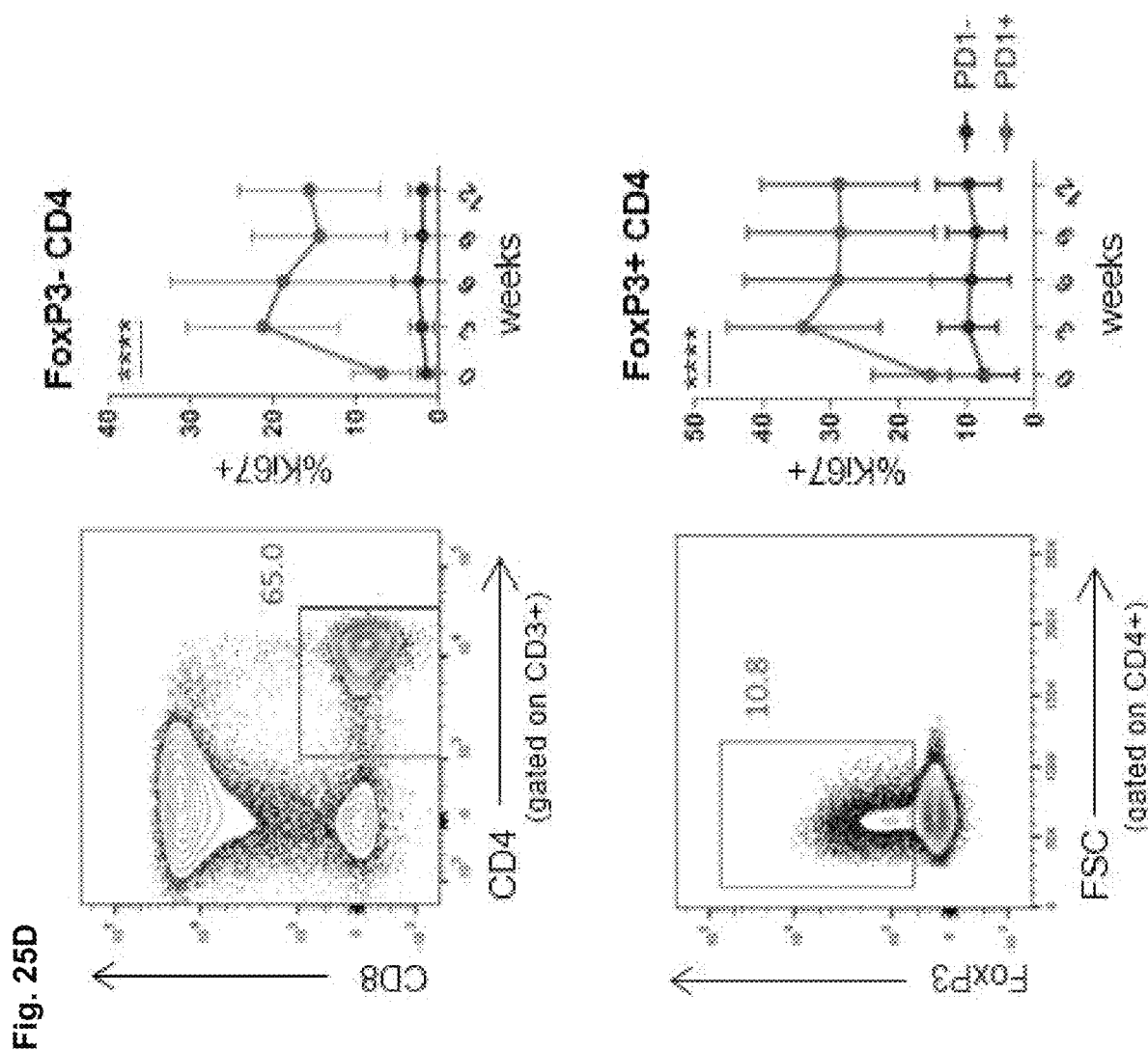
Figure 25E:
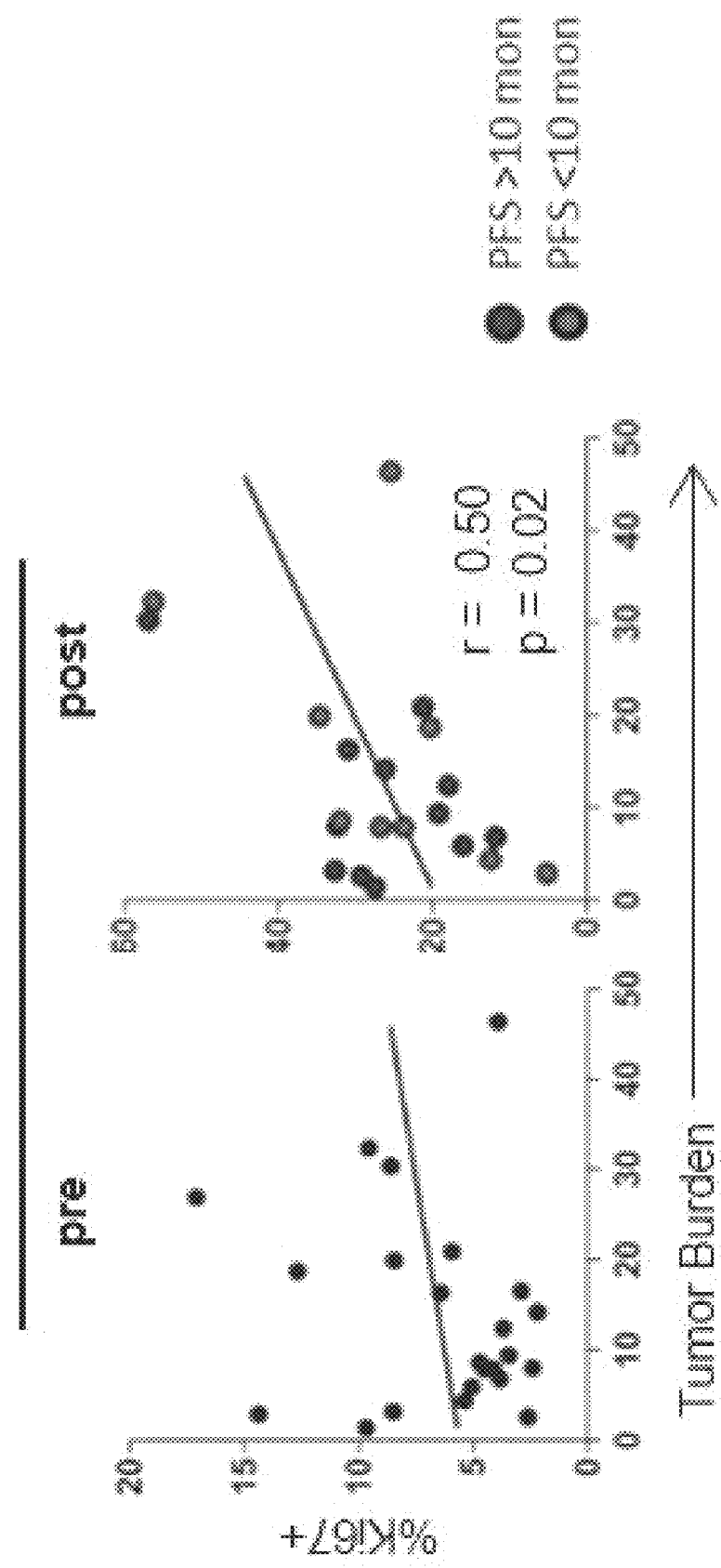
Figure 25F:
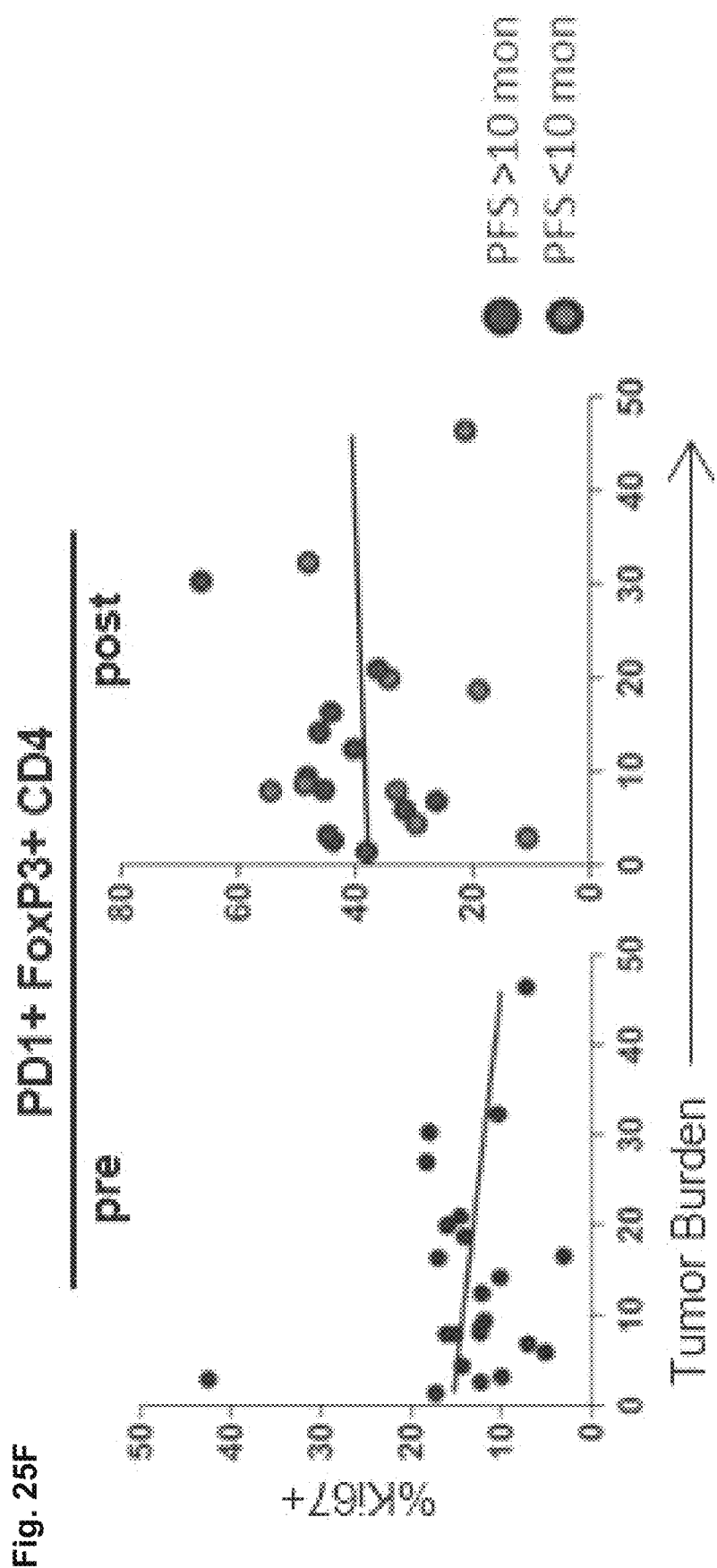
Figure 26C:
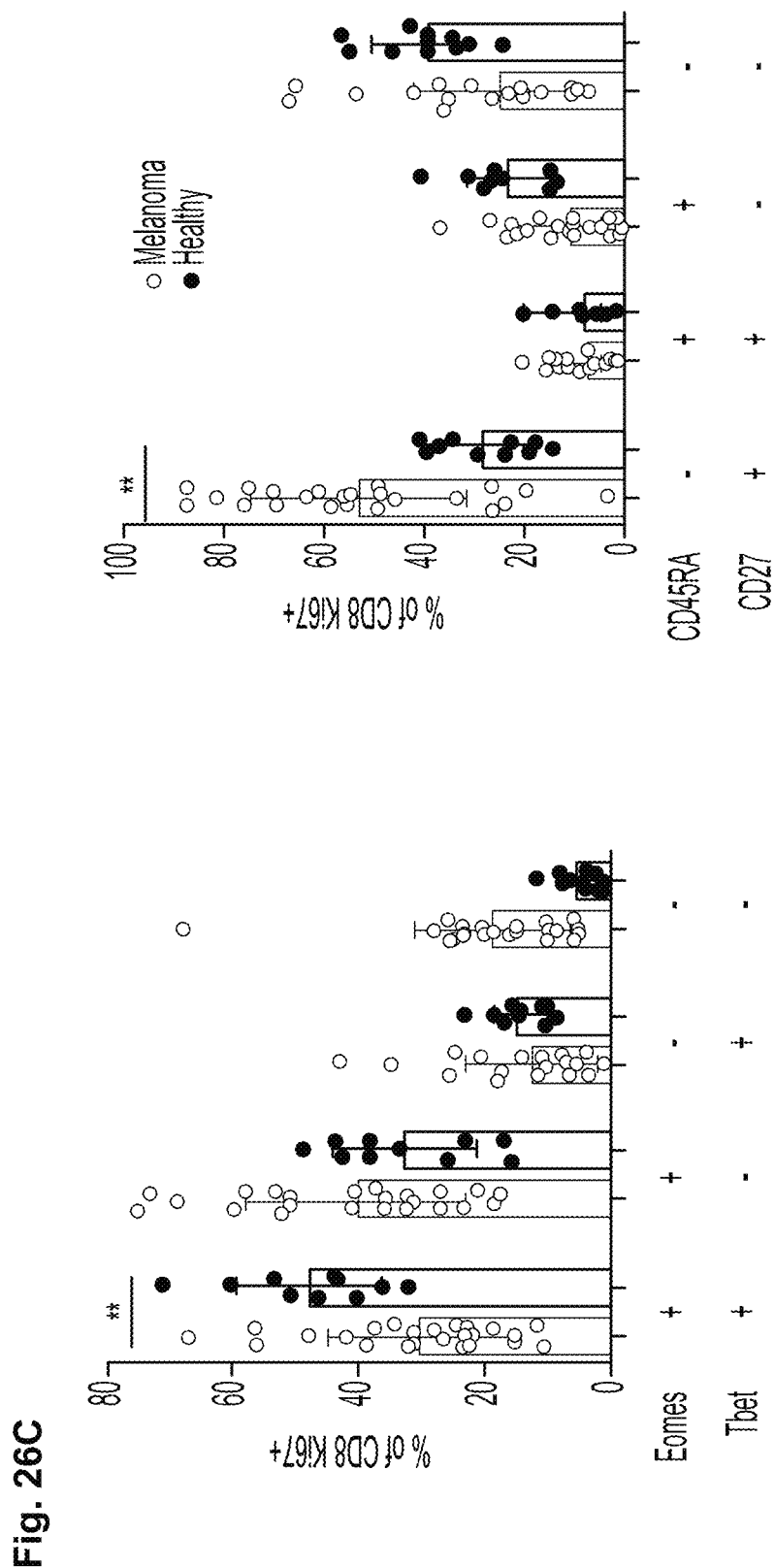

A pharmacodynamic immune response to anti-PD-1 was observed. Ki67 is a marker of cellular proliferation and T-cell reinvigoration in mouse models upon checkpoint blockade (Blackburn et al. Nat. Immunol. 2009, 10:29-37), as well as in humans receiving anti-CTLA-4 treatment plus radiation (Twyman-Saint Victor et al. Nature 2015, 520:373-377). Thus, changes in Ki67 expression were examined in more detail. Indeed, the frequency of Ki67$^+$ CD8 T cells was increased at 3 weeks after pembro treatment and then declined in most patients (FIG. 24B). The responding Ki67$^+$ CD8 T-cell population was largely CD45RA$^{lo}$CD27$^{hi}$ and contained cells with high expression of CTLA-4, 2B4, and PD-1 (FIG. 24C) (using an anti-IgG4 detection approach (Brahmer et al. J. Clin. Oncol. 2010, 28:3167-3175, see materials & methods under Experimental Examples and FIG. 26A). Moreover, the responding Ki67$^+$ cells were Eomes$^{hi}$ and T-bet$^{lo}$ (P<0.0001, FIG. 24C), consistent with the phenotype of T$_{EX}$ cells (Blackburn, et al. Nat. Immunol. 2009, 10:29-37; Paley, et al. Science 2012, 338:1220-1225). In contrast, the Ki67+ population in healthy donors was largely Eomes$^{hi}$T-bet$^{hi}$ and CD27$^{lo}$, consistent with an effector phenotype (FIGS. 26B, 26C). In addition to CD8 T cells, Ki67 increased in FOXP3$^-$ CD4 T cells and FOXP3$^+$ CD4 T cells following pembro treatment, mainly in the PD-1$^+$ subset of each population (FIG. 25D). Neither FOXP3$^-$ nor FOXP3$^+$ CD4 T-cell responses correlated with clinical outcome (FIGS. 25E, 25F).

Figure 24F:
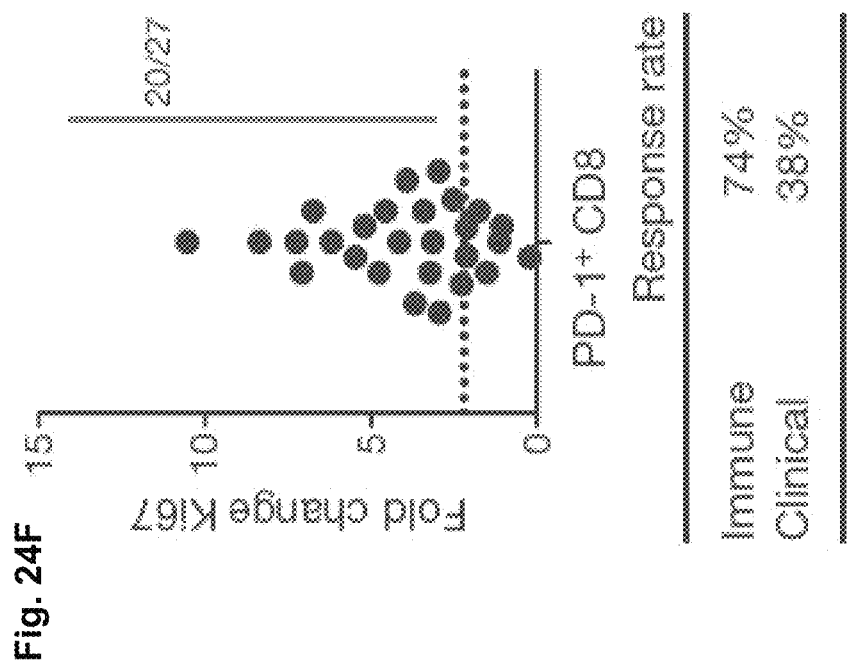
Figure 24E:
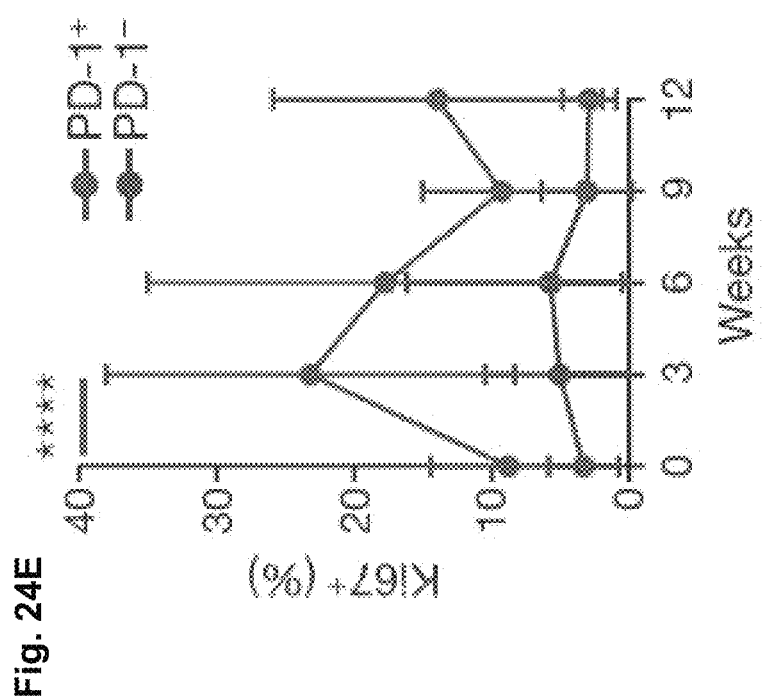
Figure 26D:
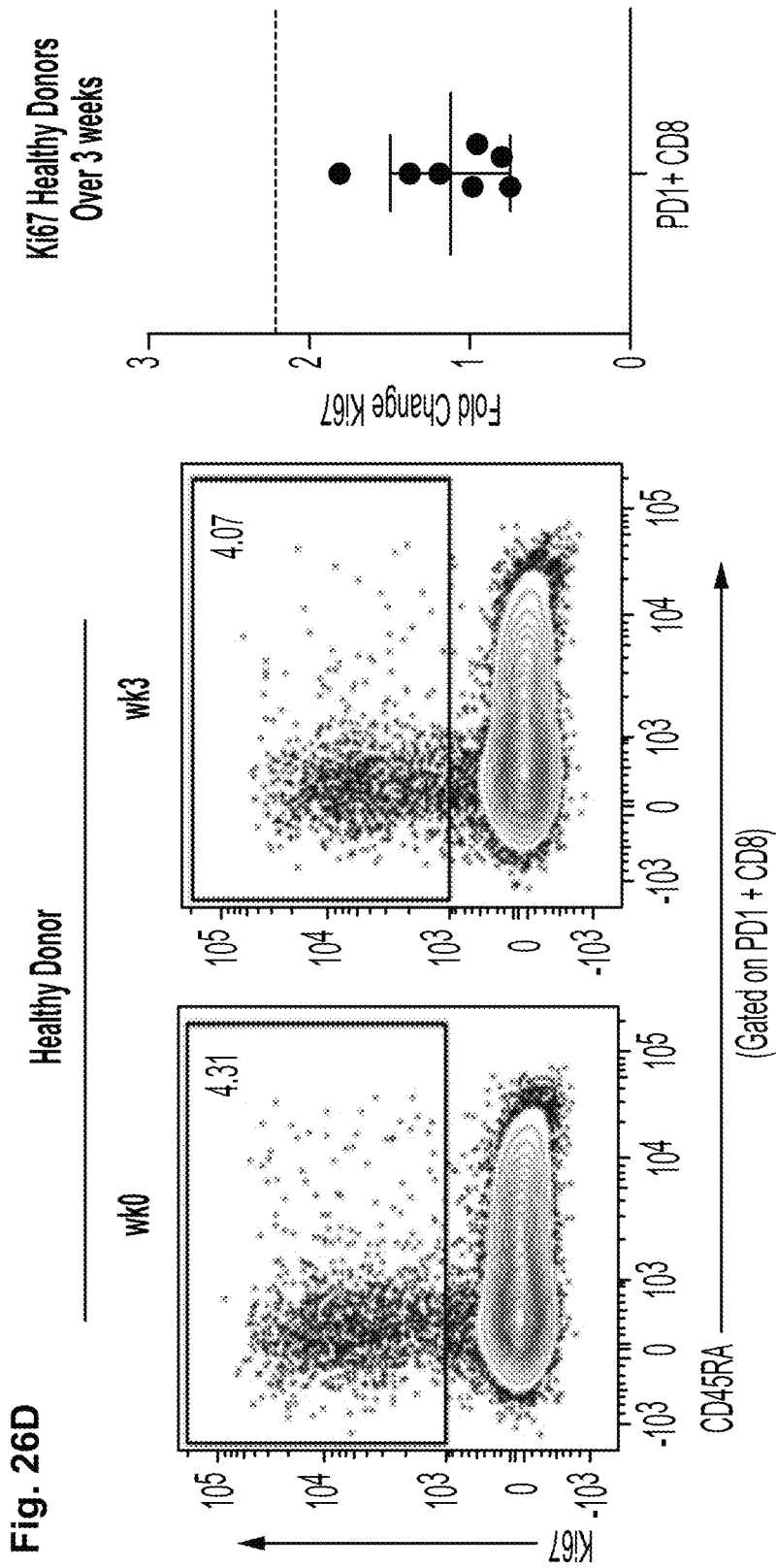

The increase in Ki67 expression was most prominent in the PD-1$^+$ versus PD-1$^-$ CD8 T cells (P<0.0001; FIG. 24D). Moreover, this Ki67 response in the PD-1$^+$ subset peaked at 3 weeks after treatment compared to the PD-1$^-$ subset (P<0.0001, FIG. 24E). The time since last dose of anti-CTLA-4 therapy did not correlate with subsequent post-pembro Ki67 levels or treatment response (FIGS. 27A-27C), suggesting that the immunologic response observed in this instance was mainly due to anti-PD-1 therapy. In healthy donors, Ki67 expression by PD-1$^+$ CD8 T cells varied little over 3 weeks, changing 1.1-fold±0.37 (FIG. 26d). In contrast, the majority of patients with melanoma (20 out of 27) had a biologically meaningful increase in Ki67 in their PD-1$^+$ CD8 T cells after treatment (FIG. 24F, FIG. 23). Despite this 74% immunologic response rate, only 38% achieved a clinical response, indicating that not all patients with an immunologic response to pembro have clinical benefit.

Figures 28A, 28B:
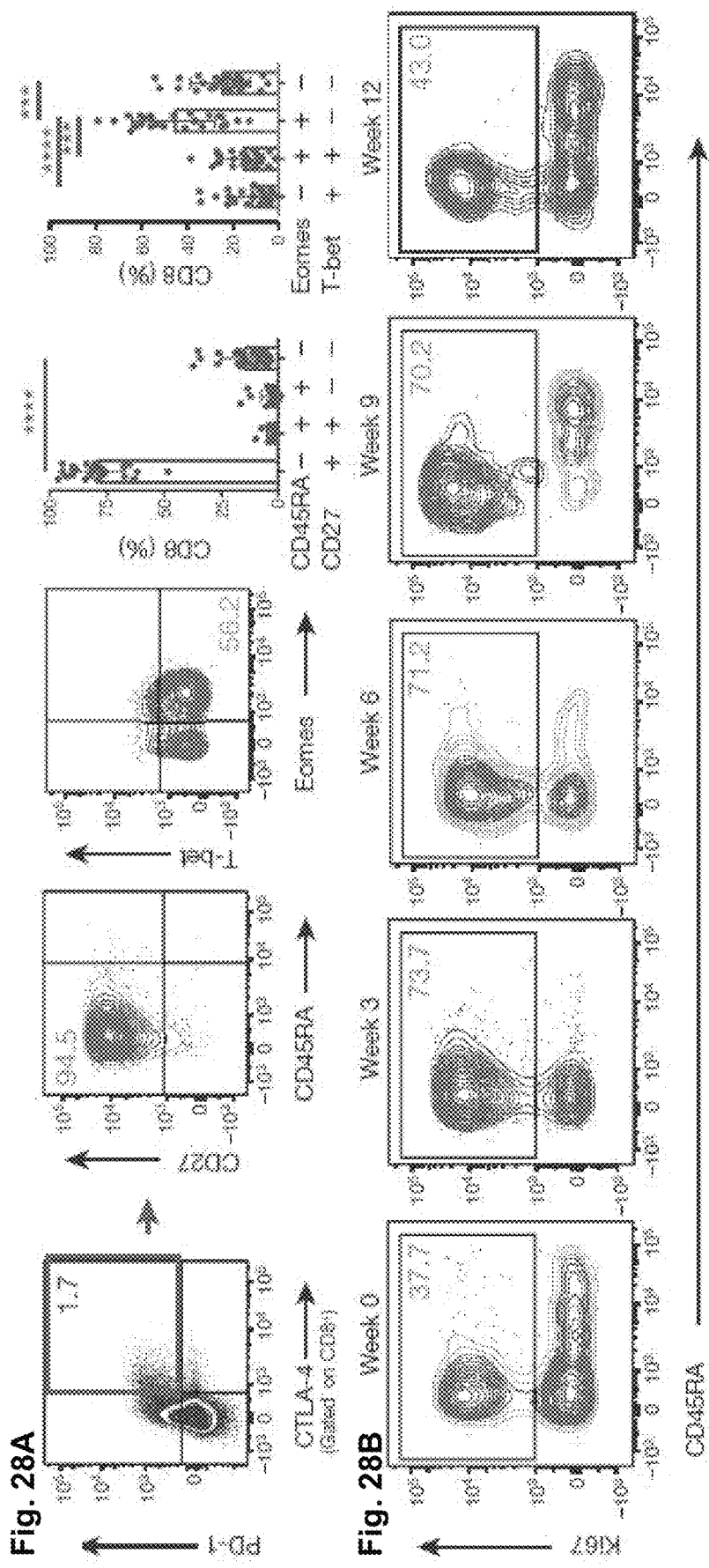
FIGS. 28A-28H are a series of images depicting that exhausted-phenotype CD8 T cells are preferentially reinvigorated by anti-PD-1 therapy.
Figure 28C:
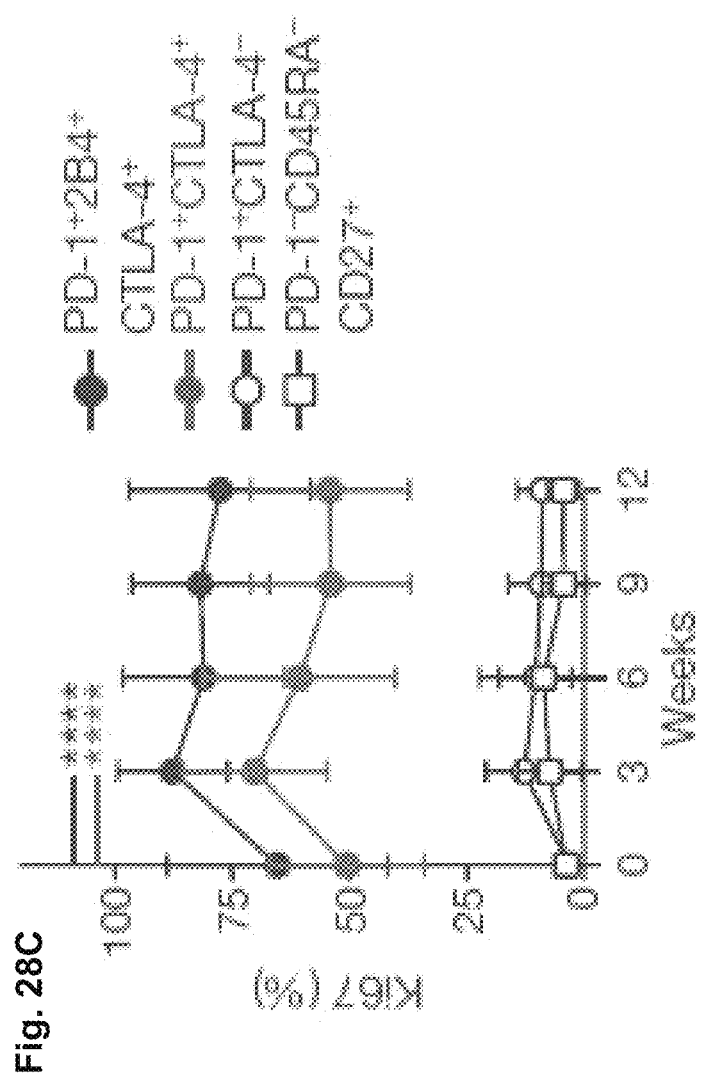
Figure 29D:
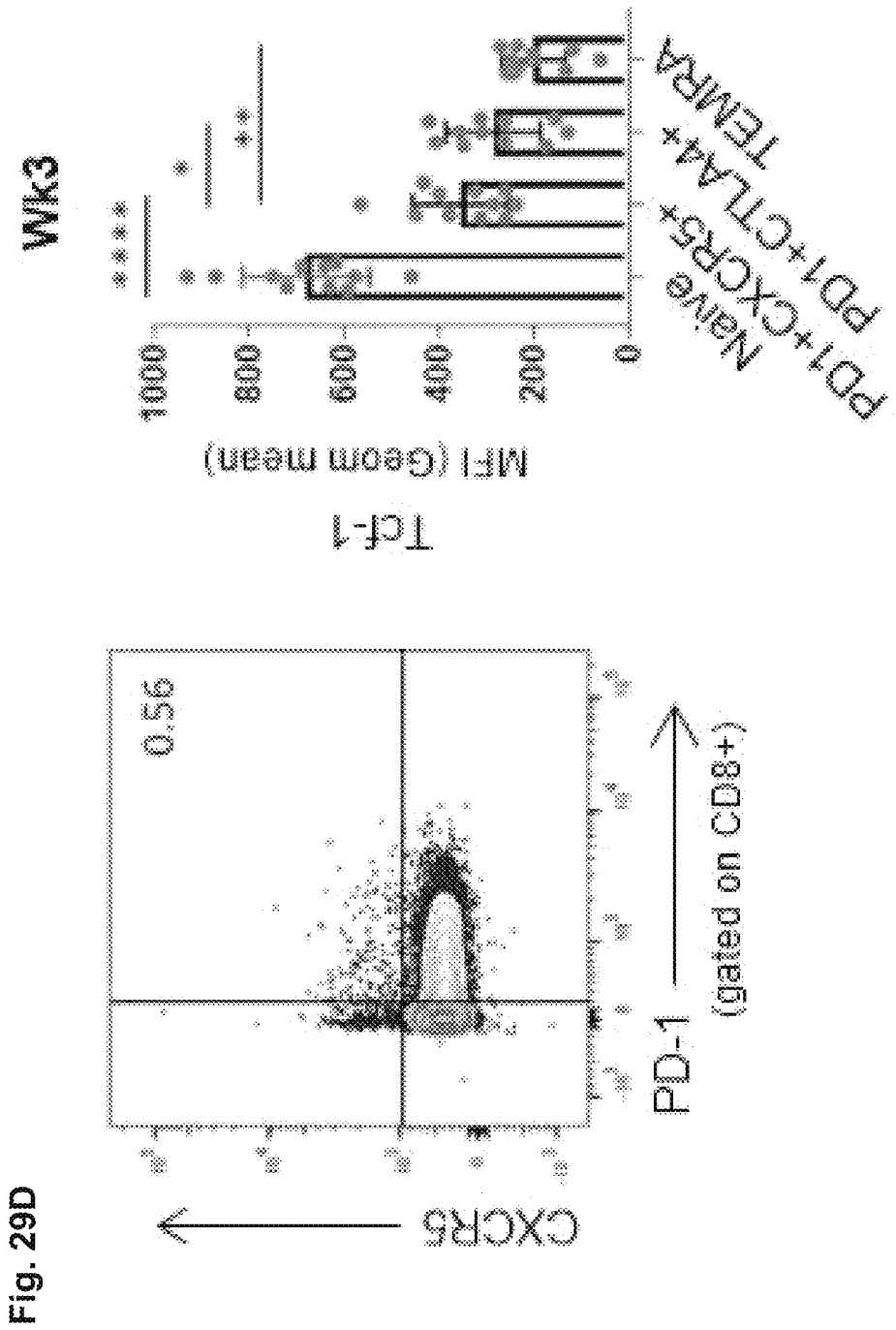
Figure 29E:
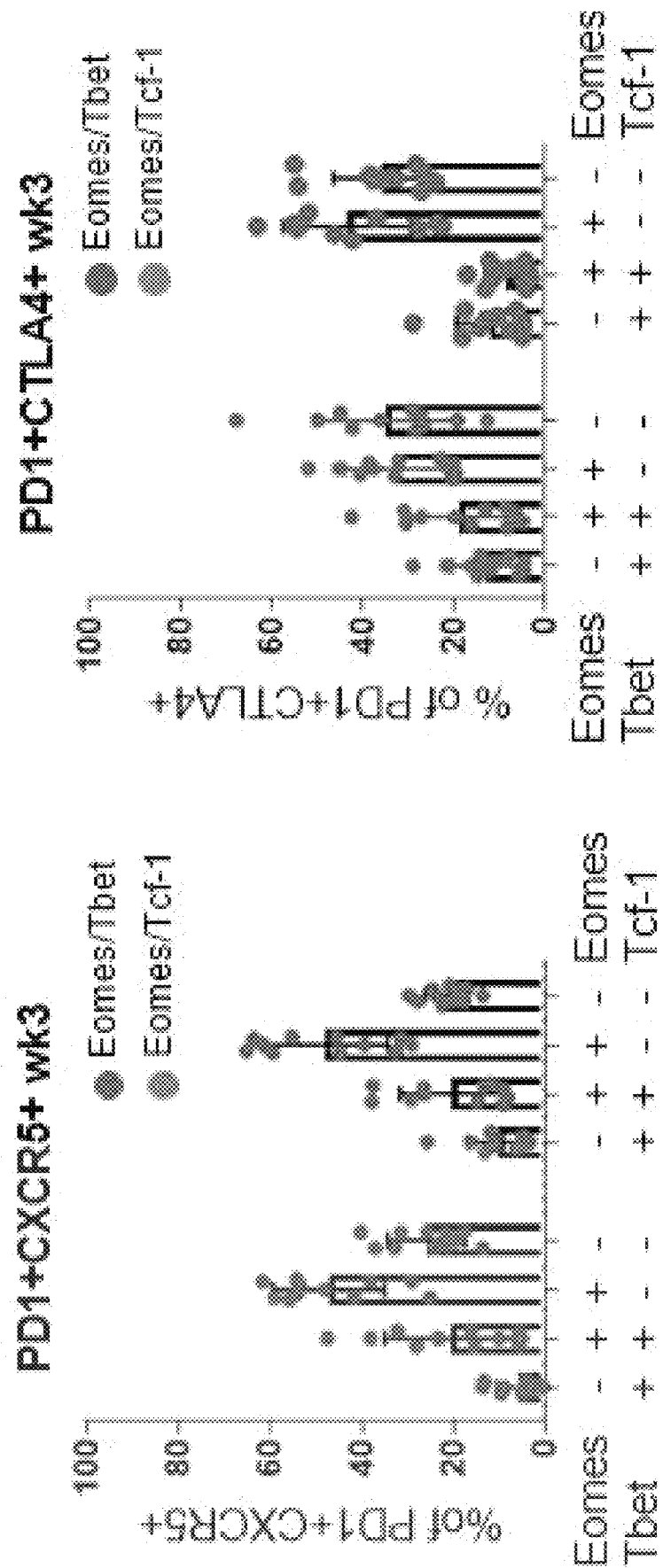
Figure 29G:
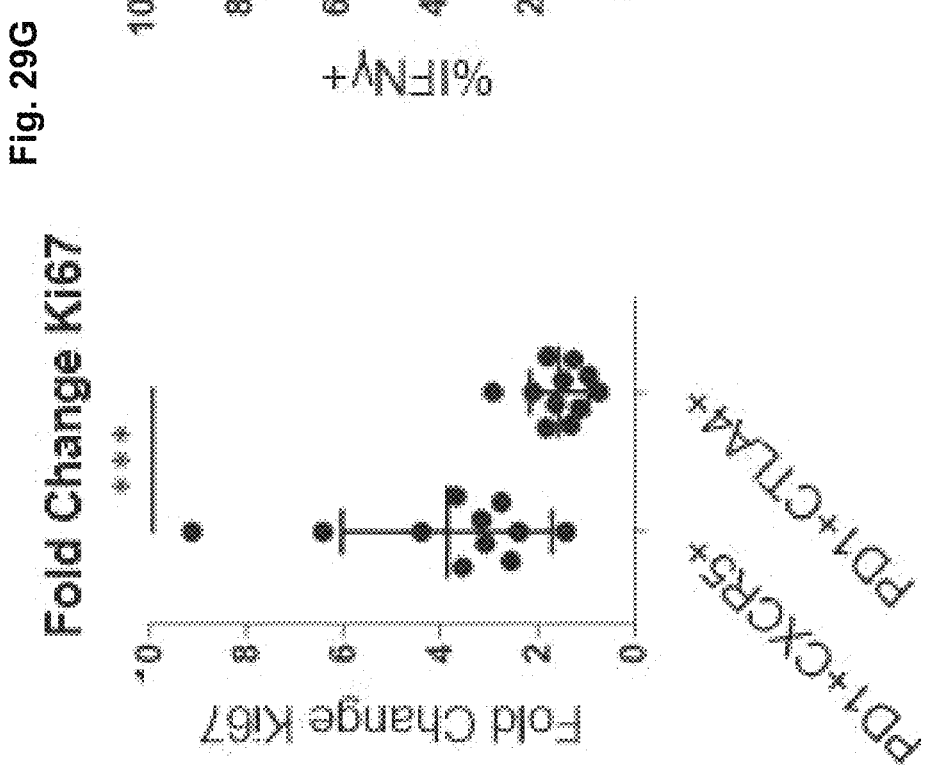
Figure 29F:
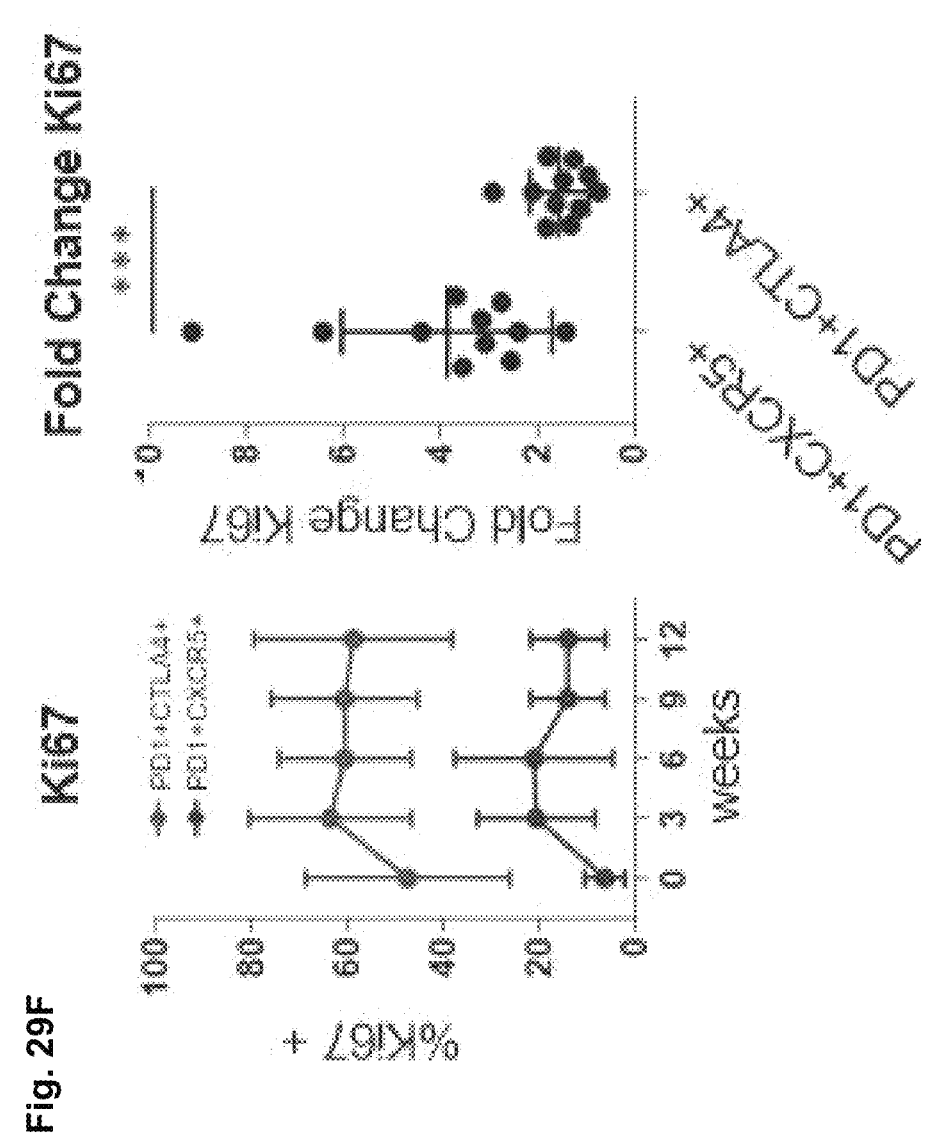

Example 6. Exhausted-Phenotype CD8 T Cells are Preferentially Reinvigorated by Anti-PD-1 Therapy Reinvigorated T$_{EX}$ cells were detected in peripheral blood. Next, it was assessed whether CD8 T cells that co-expressed PD-1 and other inhibitory receptors provided greater precision in tracking the pharmacodynamic effects of PD-1 blockade. Circulating populations of PD-1$^+$CTLA-4$^+$ CD8 T cells were largely Eomes$^{hi}$T-bet$^{lo}$ and CD45RA$^{lo}$CD27$^{hi}$ (FIG. 28A). Furthermore, around 50% of PD-1$^+$CTLA-4$^+$ cells expressed Ki67 before treatment, consistent with data on T$_{EX}$ cells in mice (Paley et al. Science 2012, 338:1220-1225), and this increased to around 75% after treatment (FIGS. 28B, 28C). There was substantially lower Ki67 expression in the PD-1$^+$CTLA-4$^-$ T cells (FIG. 28C). Addition of a third inhibitory receptor (for example, 2B4) or focusing on the recently described PD-1$^+$CXCR5$^+$ TCF-1$^+$ subset (Im et al. Nature 2016, 537:417-421; He et al. Nature 2016, 537:412-416) further enriched for cells responding to anti-PD-1 therapy (FIG. 28C, FIG. 29). Moreover, IFNγ-producing PD-1$^+$CTLA-4$^+$ and PD-1$^+$CXCR5$^+$ subsets increased after anti-PD-1 therapy, consistent with reinvigoration of T$_{EX}$ cells (FIG. 29G).

Figure 28D:
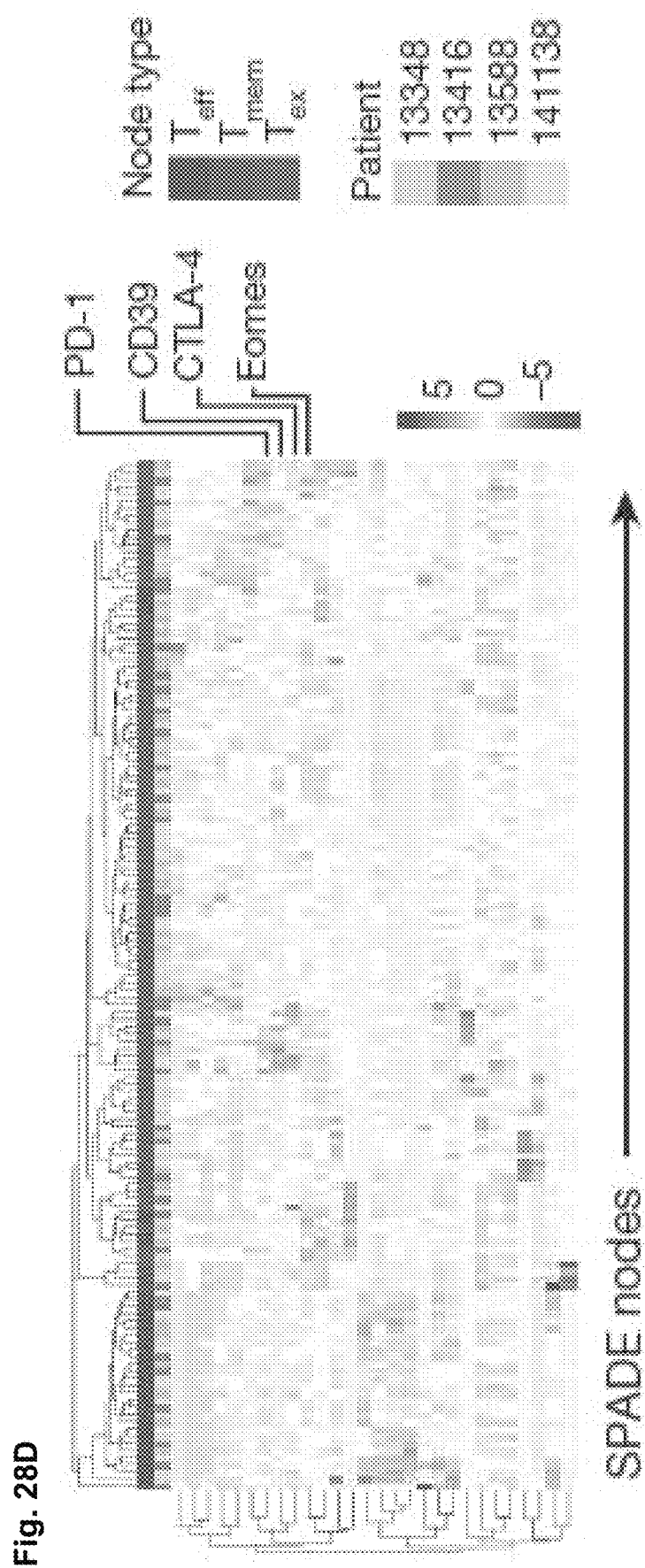
Figure 28E:
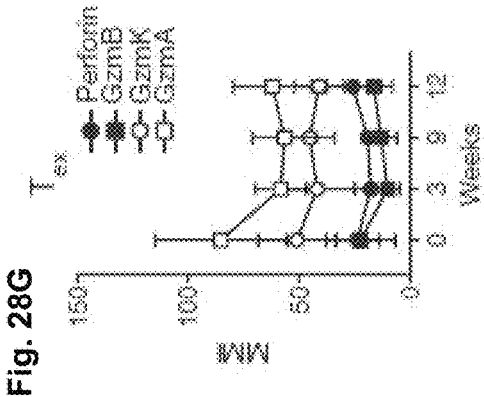
Figure 28F:
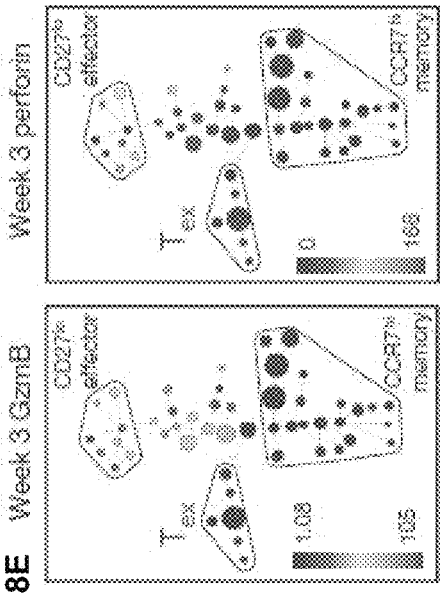
Figure 28G:
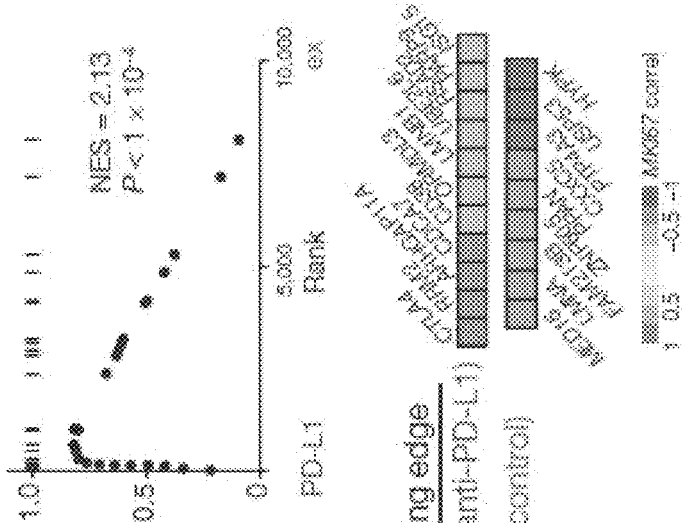
Figure 30E:
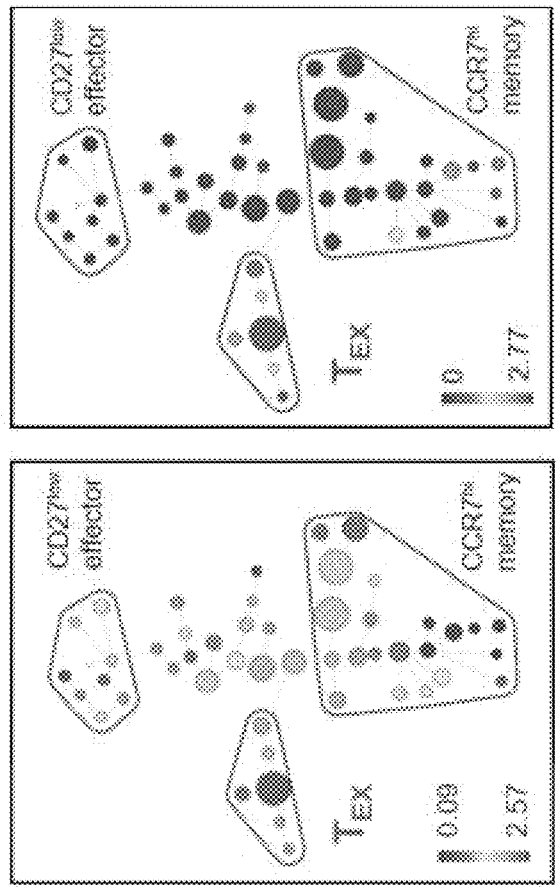
Figure 30F:
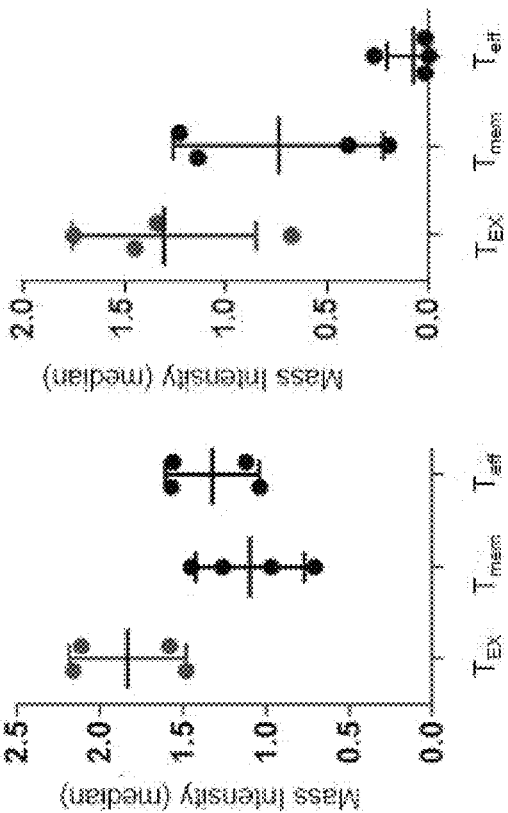

To characterize further the pembro-reactive T cells, we used mass cytometry (CyTOF) and RNA sequencing (RNA-seq). For CyTOF, we used high-dimensional visualization and unsupervised clustering. PD-1 is known to be expressed not only by T$_{EX}$ cells, but also effector, effector memory and central memory CD8 T cells (Bengsch, et al. PLoS Pathog. 2010, 6:e1000947; Duraiswamy, et al. J. Immunol. 2011, 186:4200-4212). Indeed, memory (CCR7$^{hi}$) and effector (CD27$^{lo}$) populations were among PD-1-expressing CD8 T cells (FIG. 30A). However, a third population, expressing markers of exhaustion (for example, Eomes, CD39 (Gupta et al. PLoS Pathog. 2015, 11:e1005177); FIG. 28D, FIGS. 30E, 30F) was also identified that increased in frequency and Ki67 expression after anti-PD-1 therapy (FIGS. 30B-30D). This population of circulating T$_{EX}$ cells had low expression of granzyme B and perforin but high granzyme A and K, before and after anti-PD-1 therapy (FIGS. 28E-28G). RNA-seq from total CD8 T cells identified few transcripts that robustly changed following treatment (FIGS. 31A, 31B).

Figure 28H:
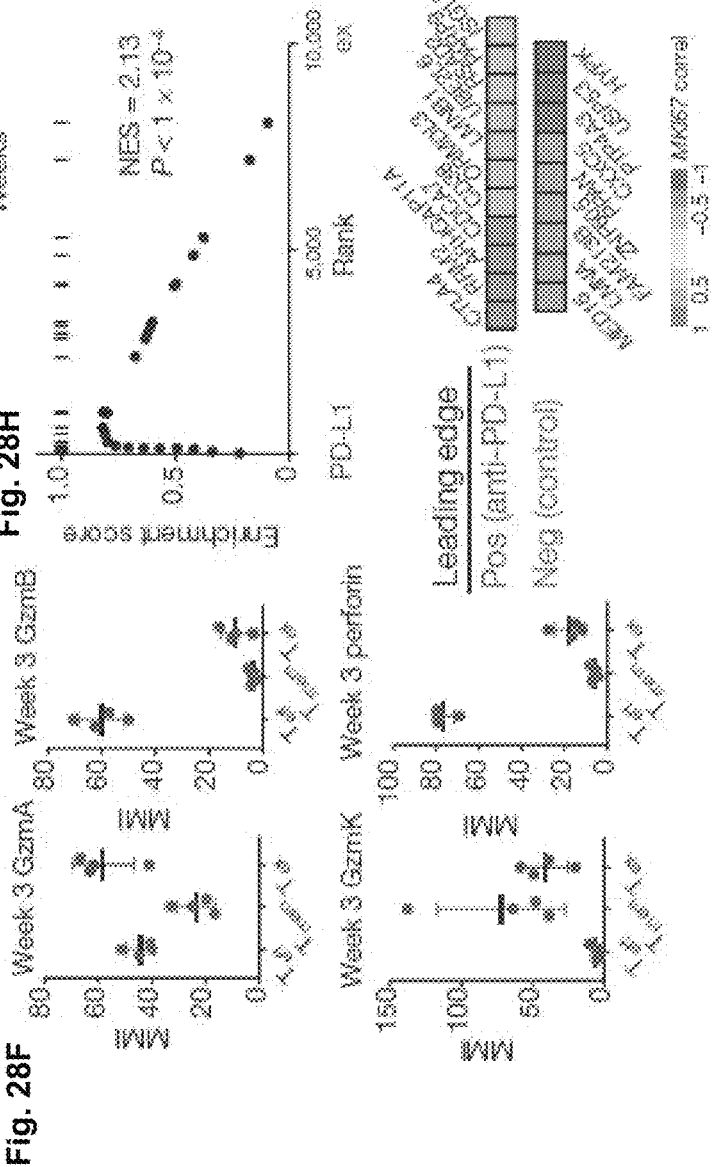
Figure 31C:
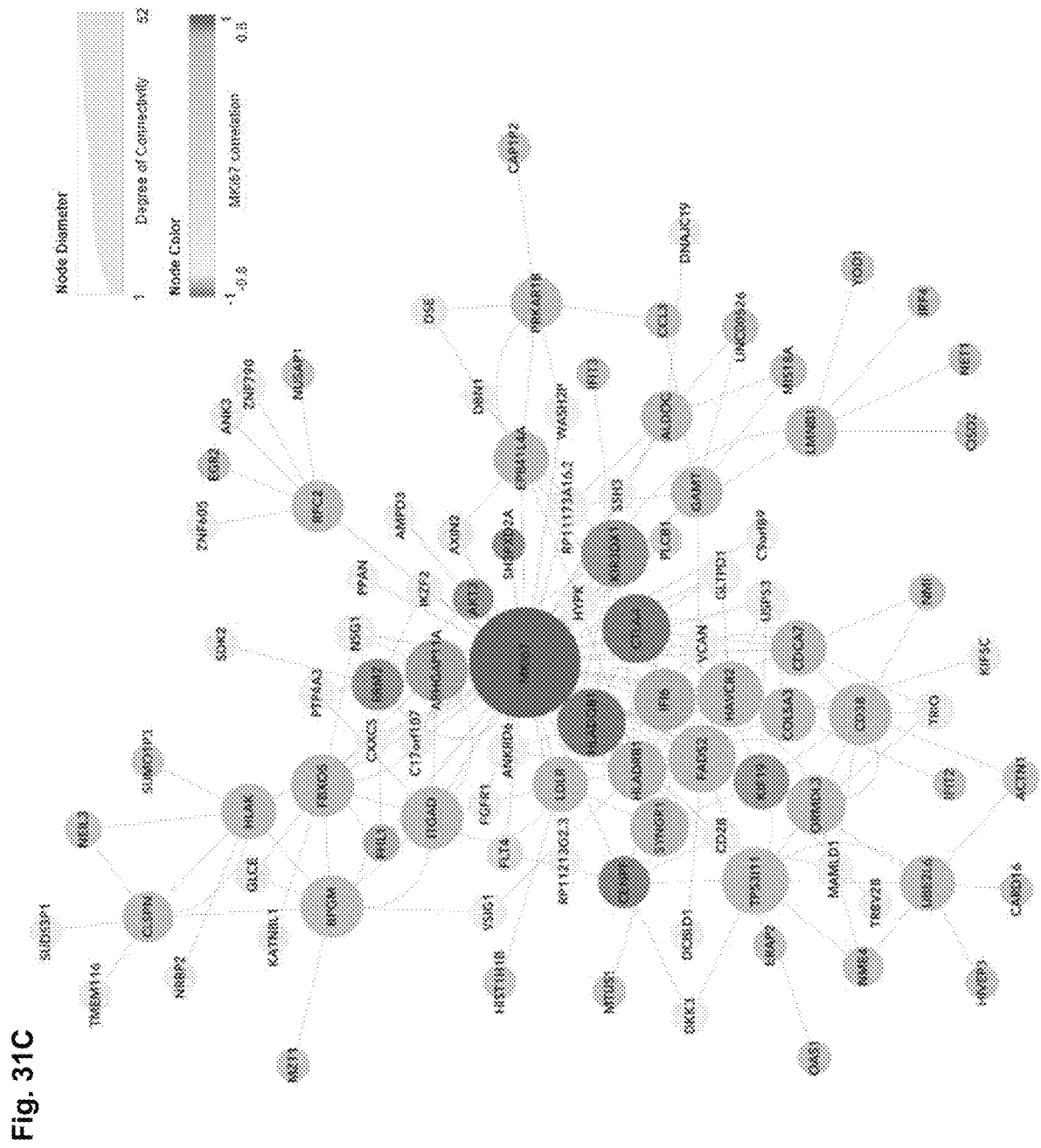
Figure 31D:
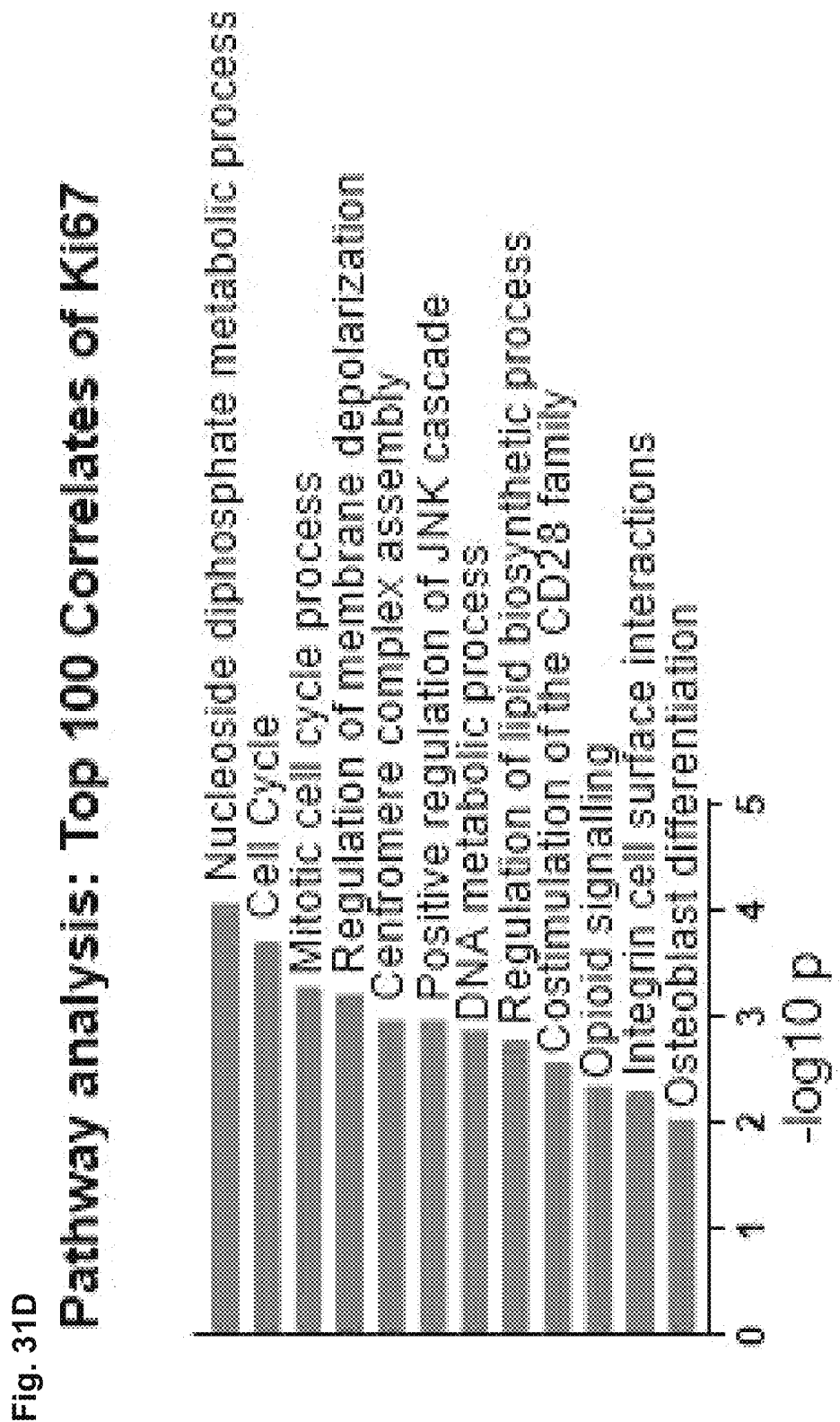

However, focusing on genes with altered expression following the same pattern as Ki67 in bulk CD8 T cells revealed transcriptional changes consistent with T$_{EX}$ cells (FIGS. 31C, 31D, Table 1). These analyses identified increased expression of CTLA4, HAVCR2 (encoding TIM-3), HLA DRB1 and CD38, and changes in pathways including proliferation, metabolism, CD28 co-stimulation, and JNK signaling. Moreover, the set of top 50 positive gene correlates of Ki67 was highly enriched for a signature of T$_{EX}$ cells reinvigorated by PD-1 blockade previously obtained in the LCMV system in mice (Pauken, et al. Science 2016, 354:1160-1165, incorporated herein by reference in its entirety) (FIG. 28H). Together, these data identified a circulating population with a T$_{EX}$-cell phenotype in the blood and revealed changes in this population following anti-PD-1 therapy, consistent with reinvigoration of T$_{EX}$ cells.

Example 7. Mass Cytometry (CyTOF) and RNA Sequencing (RNA-Seq) for Further Characterization of the Pembro-Reactive T Cells For CyTOF, high-dimensional visualization and unsupervised clustering was used. PD-1 is known to be expressed not only by T$_{EX}$ cells, but also effector, effector memory and central memory CD8 T cells (Bengsch et al. PLoS Pathog. 2010, 6:e1000947; Duraiswamy et al. J. Immunol. 2011, 186:4200-4212. Indeed, memory (CCR7$^{hi}$) and effector (CD27$^{lo}$) populations were among PD-1-expressing CD8 T cells (FIG. 30A). However, a third population, expressing markers of exhaustion (for example, Eomes, CD39 (Gupta et al. PLoS Pathog. 2015, 11:e1005177); FIG. 28D, FIGS. 30E, 30F) was also identified that increased in frequency and Ki67 expression after anti-PD-1 therapy (FIGS. 30B-30D). This population of circulating T$_{EX}$ cells had low expression of granzyme B and perforin but high granzyme A and K, before and after anti-PD-1 therapy (FIGS. 28E-28G). RNA-seq from total CD8 T cells identified few transcripts that robustly changed following treatment (FIG. 31A, 31B).

However, focusing on genes with altered expression following the same pattern as Ki67 in bulk CD8 T cells revealed transcriptional changes consistent with $T_{EX}$ cells (FIG. 31C, 31D, Table 1). These analyses identified increased expression of CTLA4, HAVCR2 (encoding TIM-3), HLA DRB1 and CD38, and changes in pathways including proliferation, metabolism, CD28 co-stimulation, and JNK signaling. Moreover, the set of top 50 positive gene correlates of Ki67 was highly enriched for a signature of $T_{EX}$ cells reinvigorated by PD-1 blockade previously obtained in the LCMV system in mice (Pauken, et al. Science 2016, 354:1160-1165) (FIG. 28H). Together, these data identified a circulating population with a $T_{EX}$-cell phenotype in the blood and revealed changes in this population following anti-PD-1 therapy, consistent with reinvigoration of $T_{EX}$ cells.

Figure 32C:
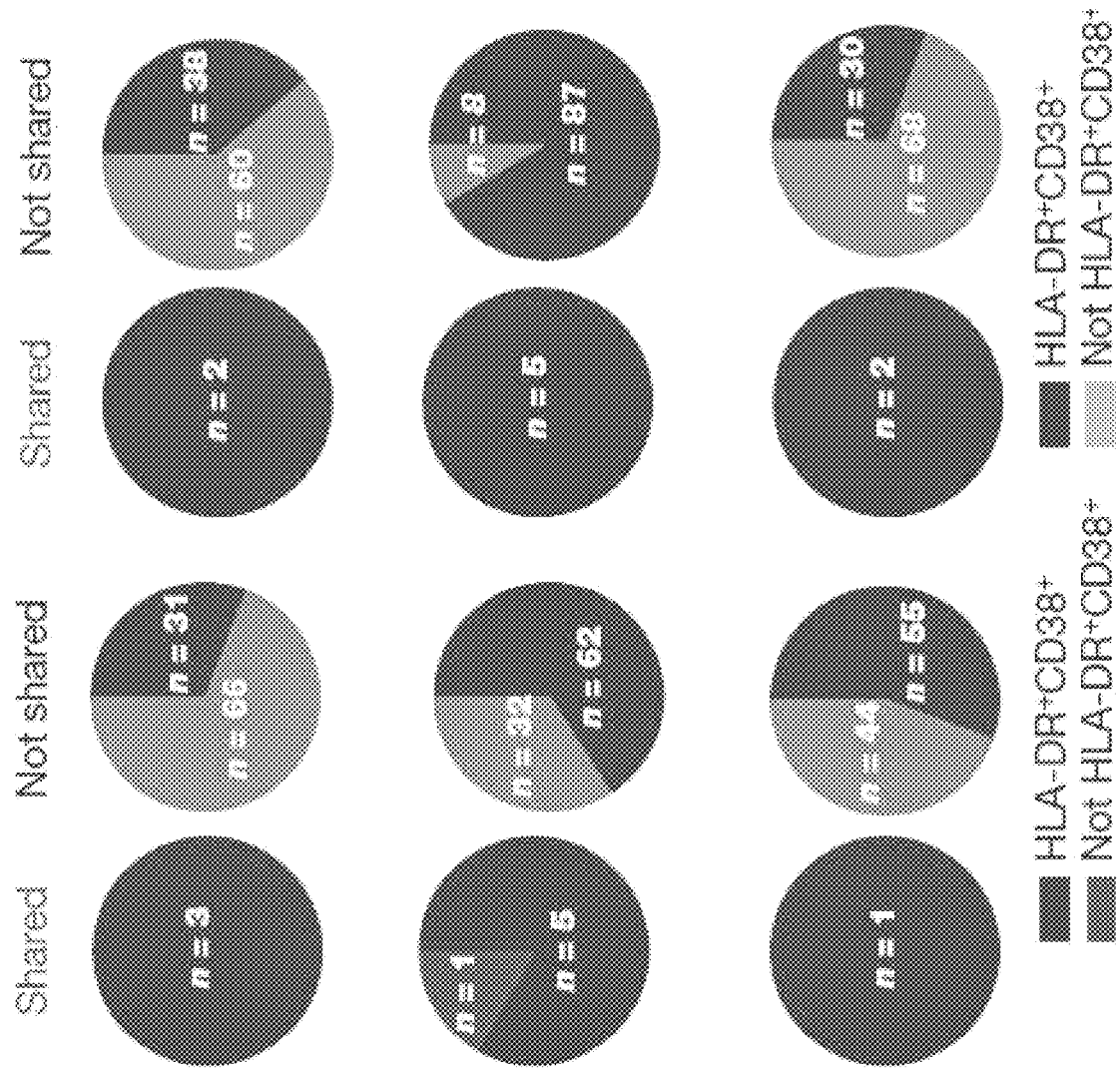
Figure 33A:
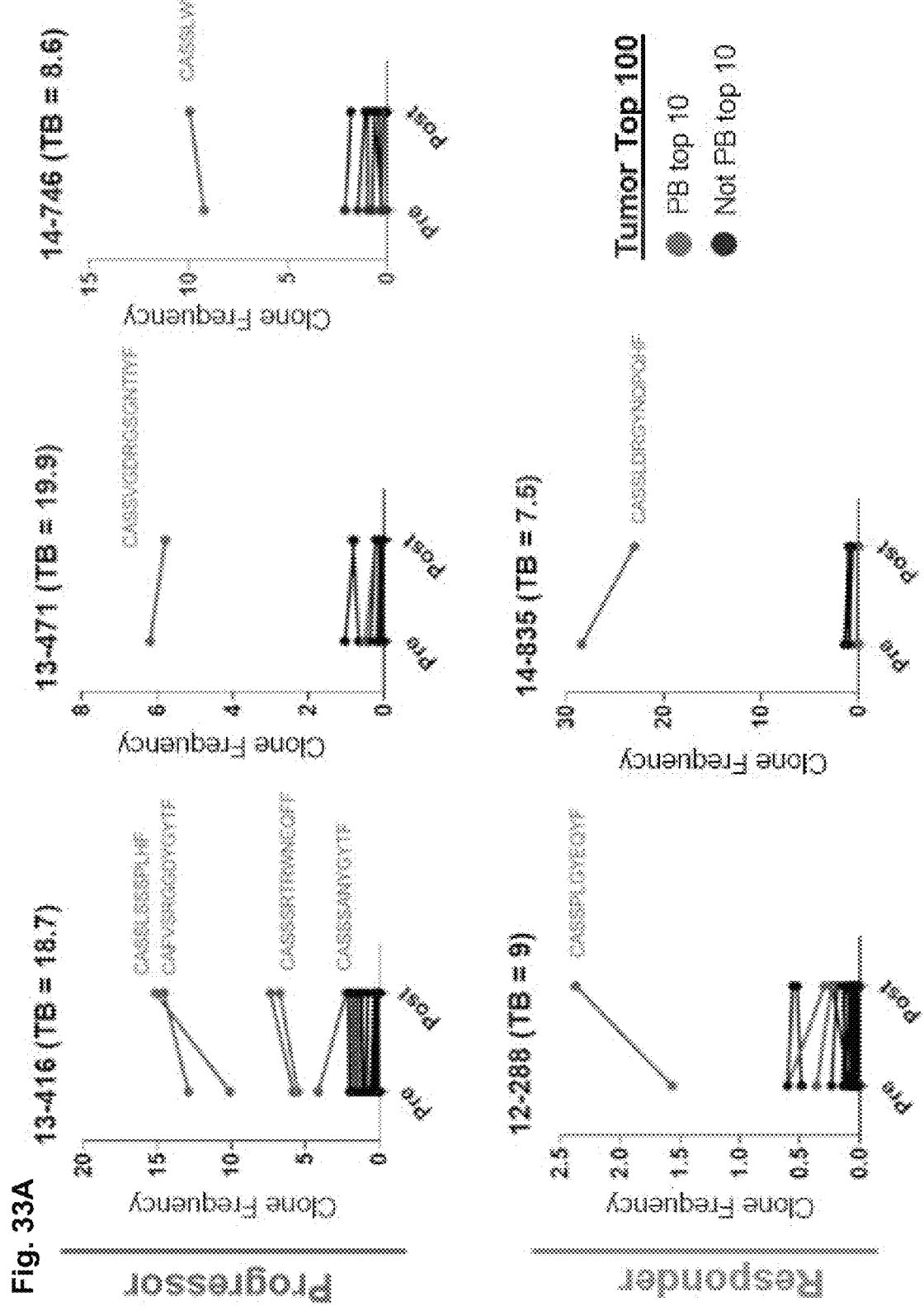
FIGS. 33A-33F are a series of images depicting that HLA-DR and CD38 expression enriches for responding Ki67+ cells and TCR clones found in top 100 clones in tumor identified in blood.

Example 8. Tumor-Infiltrating T-Cell Clones in Responding Peripheral Blood CD8 T-Cell Population and Blood Ki67$^+$ CD8 T-Cell Response Correlates with Tumor Burden Responding T-cell clones from blood were found in tumor. Both neoantigen- and shared-antigen-specific T cells have been identified in the circulating PD-1$^+$ CD8 T-cell population (Gros et al. Nat. Med. 2016, 22:433-438). Moreover, there is clonal overlap between these cells in the blood and tumor-infiltrating T cells (Gros et al. Nat. Med. 2016, 22:433-438). To explore these relationships following anti-PD-1 therapy, CD8 T cells from the blood were sorted at the peak of Ki67 expression after treatment from three responders and three non-responders, and the T-cell receptor (TCR) repertoire was compared to pretreatment tumor-infiltrating T cells. Many of the top 10 tumor-infiltrating T-cell clones were readily identifiable in the blood and after therapy, including the two most abundant clones by frequency in all cases, regardless of clinical response (FIGS. 32A, 32B, FIG. 33A, Table 2).

Figure 33B:
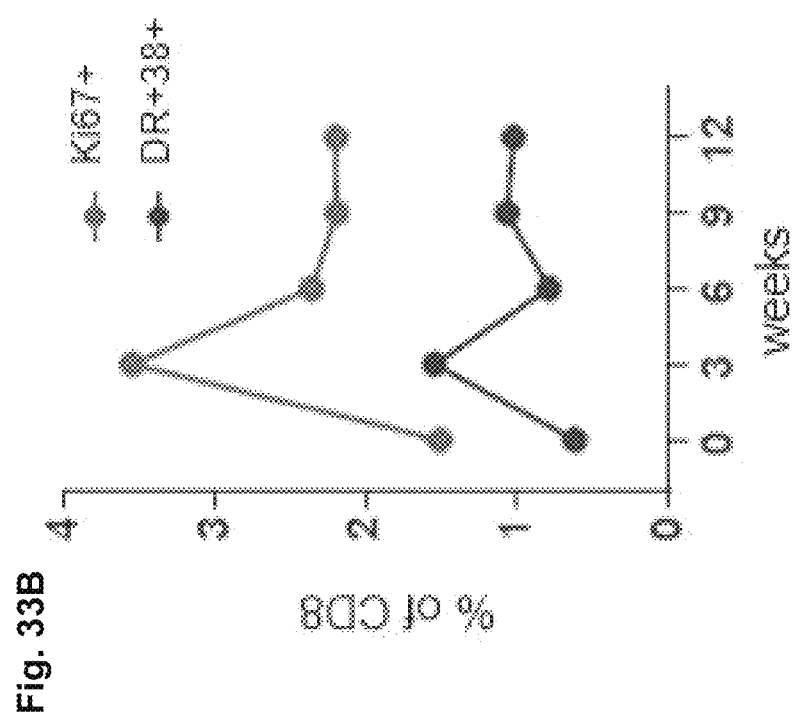
Figure 33C:
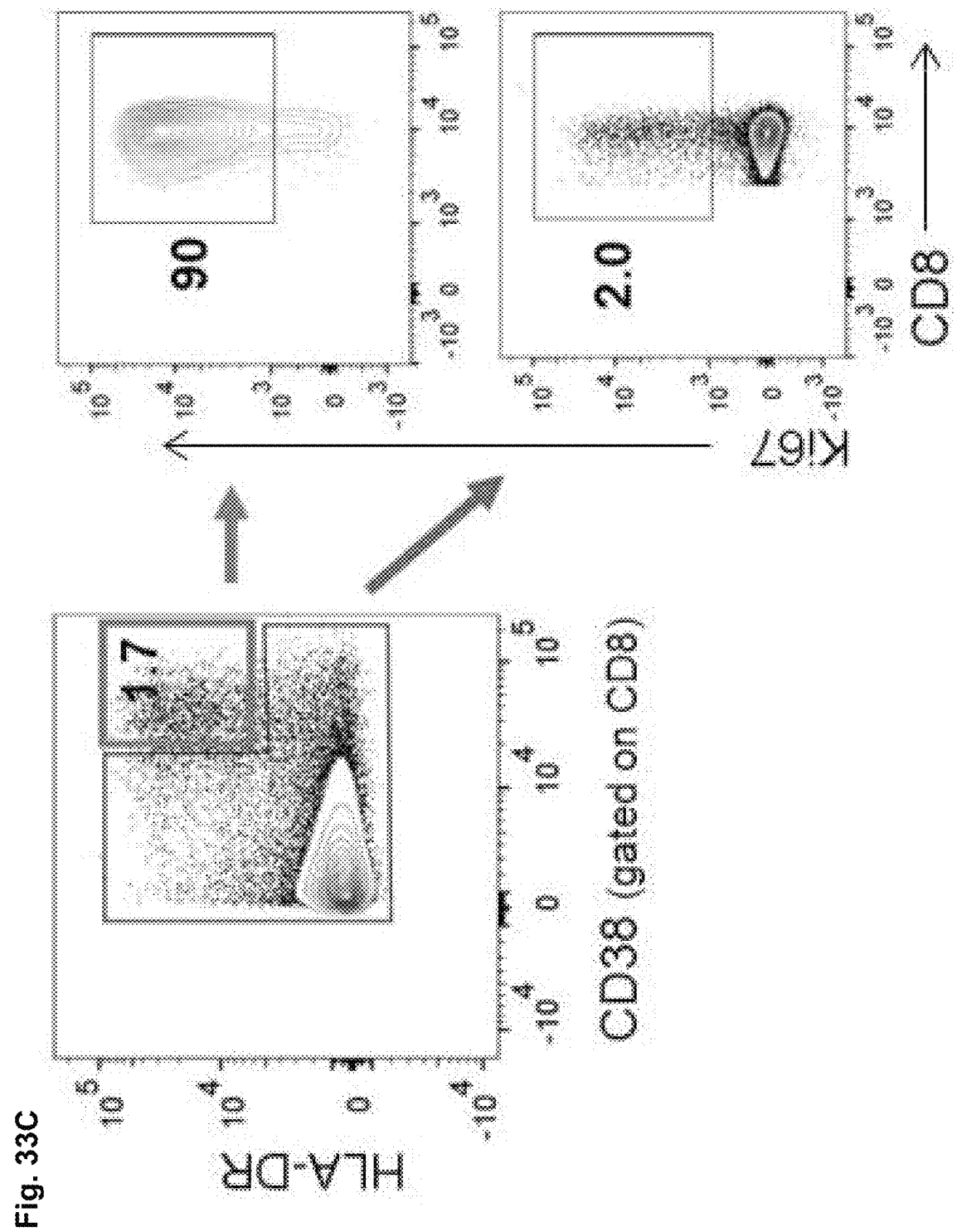
Figure 33D:
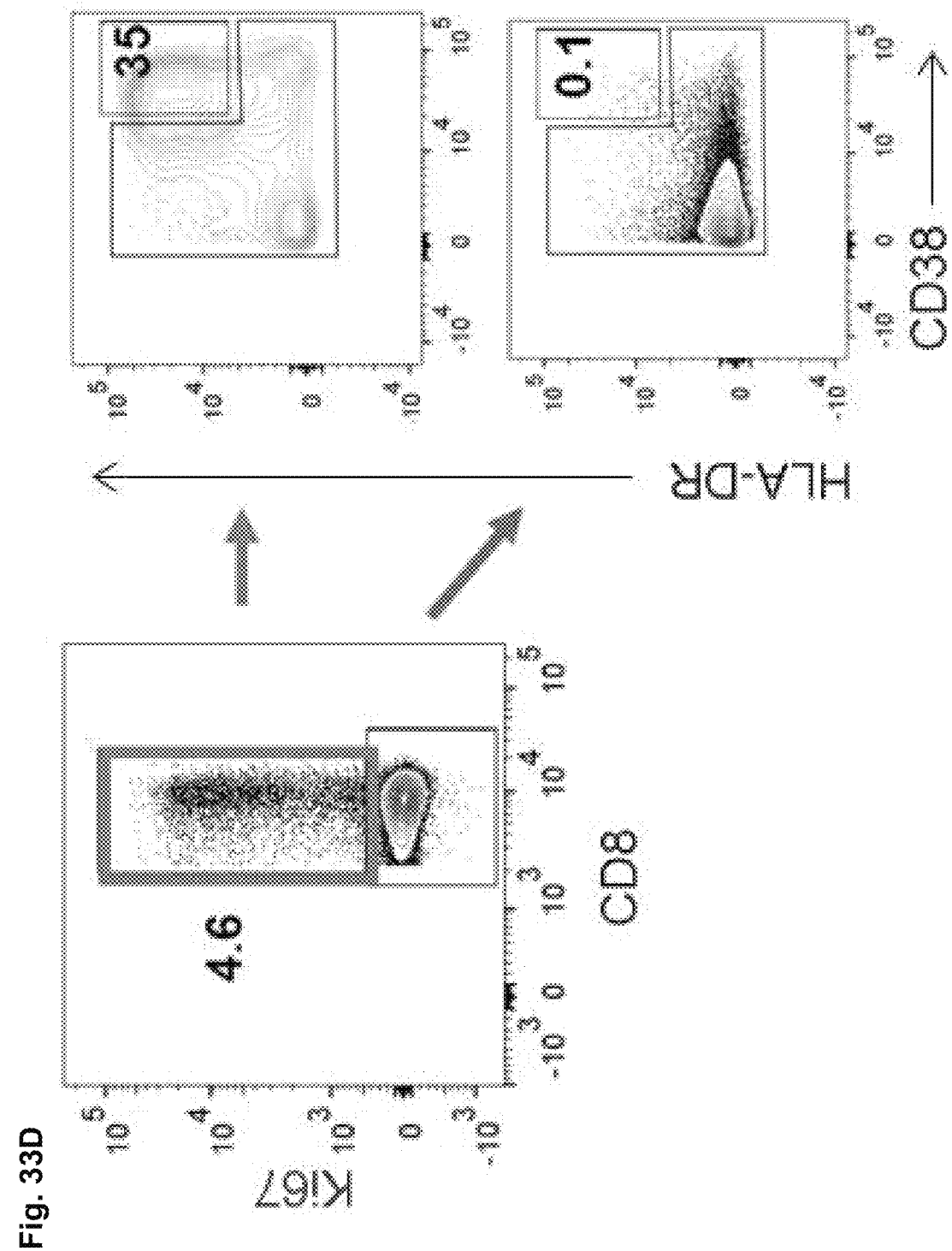
Figure 33E:
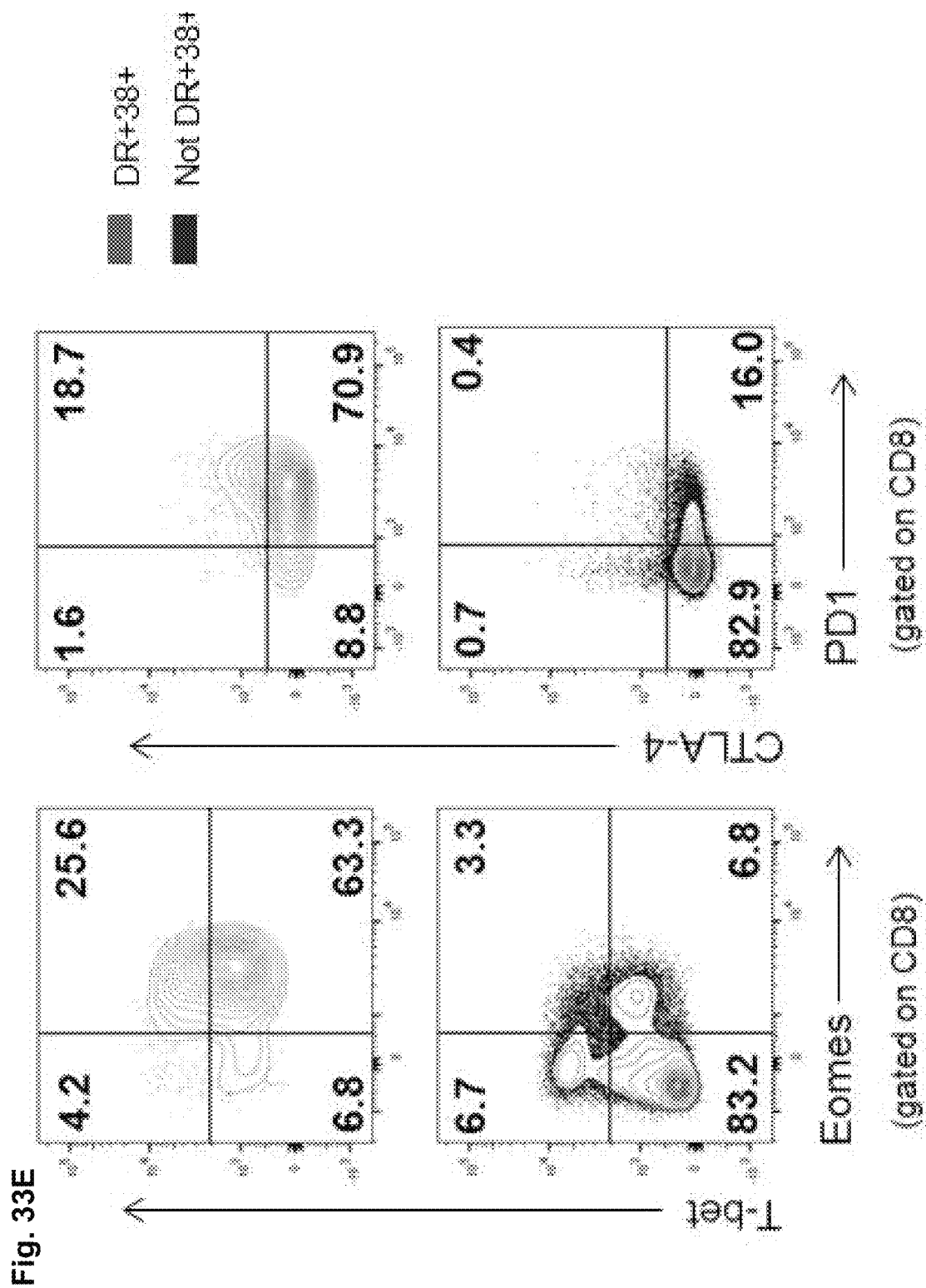
Figure 33F:
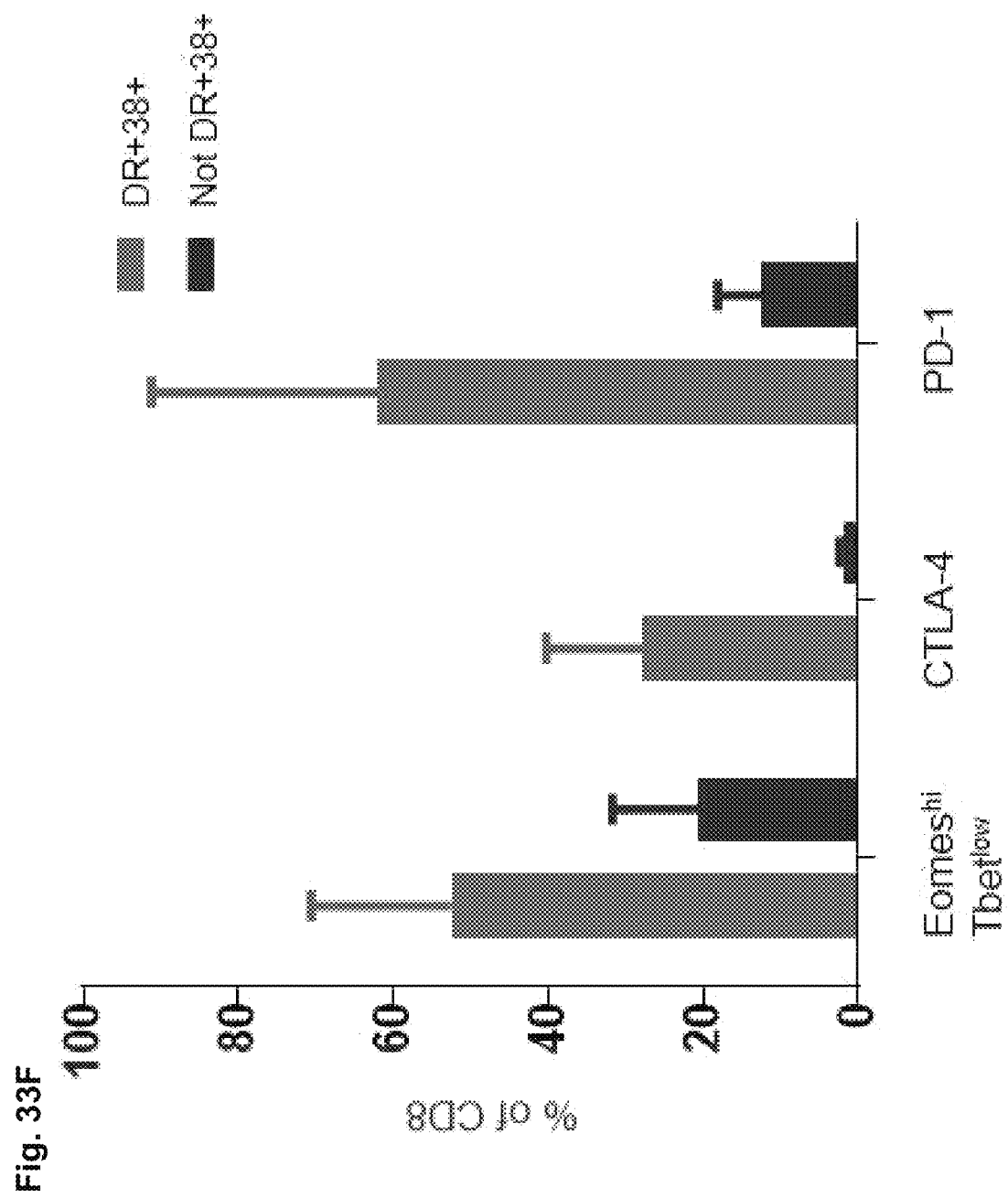

It was then determined whether these shared clones were present in the population responding to anti-PD-1 therapy. To avoid permeabilization, responding cells were sorted using expression of HLA-DR and CD38 (Miller et al. Immunity 2008, 28:710-722), rather than Ki67. Approximately 80% (mean, 80.1%) of the HLA-DR$^+$CD38$^+$ CD8 T cells expressed Ki67, and these HLA-DR$^+$CD38$^+$ cells responded with similar kinetics as Ki67$^+$ CD8 T cells (FIGS. 33B-33D). RNA-seq identified HLA DRB1 and CD38 among the top 50 correlates of Ki67 (Table 1) and these HLA-DR$^+$CD38$^+$ cells were enriched for markers of $T_{EX}$ cells (FIGS. 33E, 33F). Across six patients, 14 clones were present among the top 10 clones in both the tumor and blood (FIG. 32B). All of these (14 out of 14) were HLA-DR$^+$CD38$^+$ in the blood (FIG. 32B). Extending to the top 100 clones, 18 out of 19 clones shared between blood and tumor were HLA-DR$^+$CD38$^+$, whereas a mixture of activated and resting phenotype was found for clones that were only found in the blood and not tumor (FIG. 32C). These observations support the notion that Ki67$^+$ (HLA-DR$^+$CD38$^+$) $T_{EX}$ cells in the blood are reinvigorated by anti-PD-1 therapy and contain T-cell clones that are also present in the tumor.

Figure 32D:
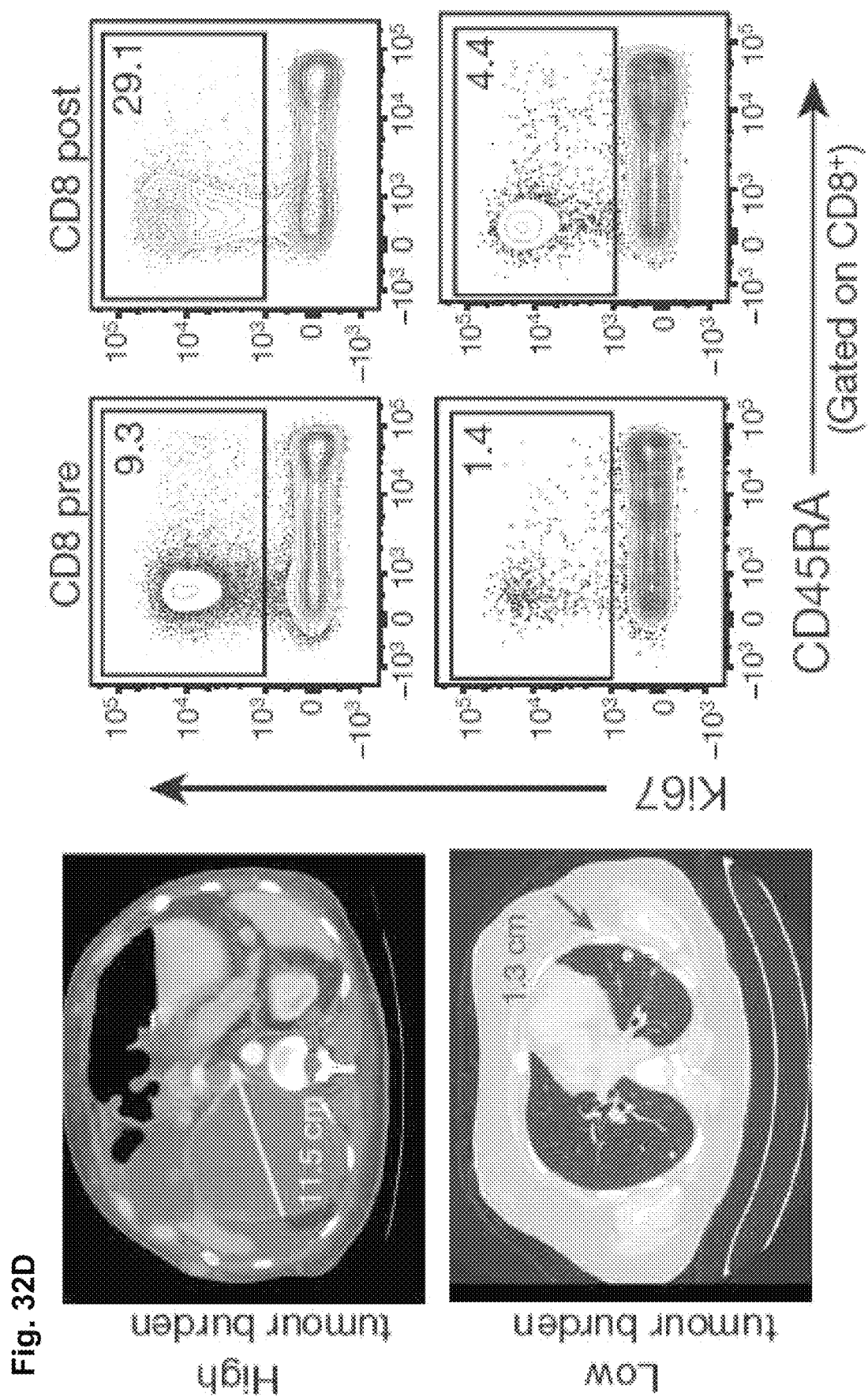
Figure 32F:
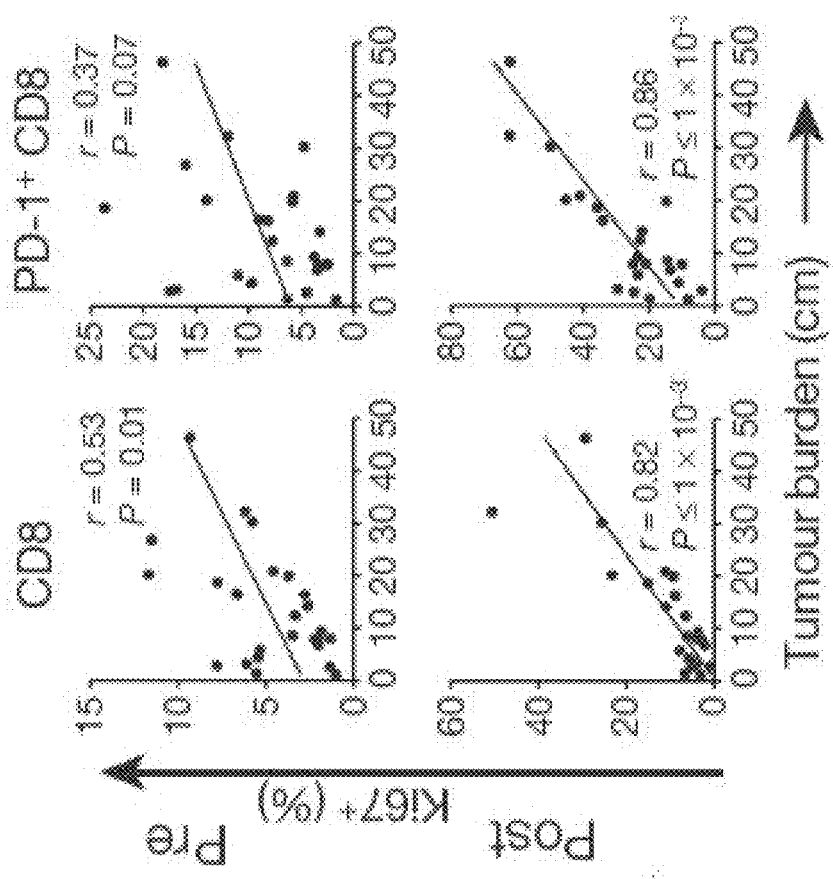
Figure 32E:
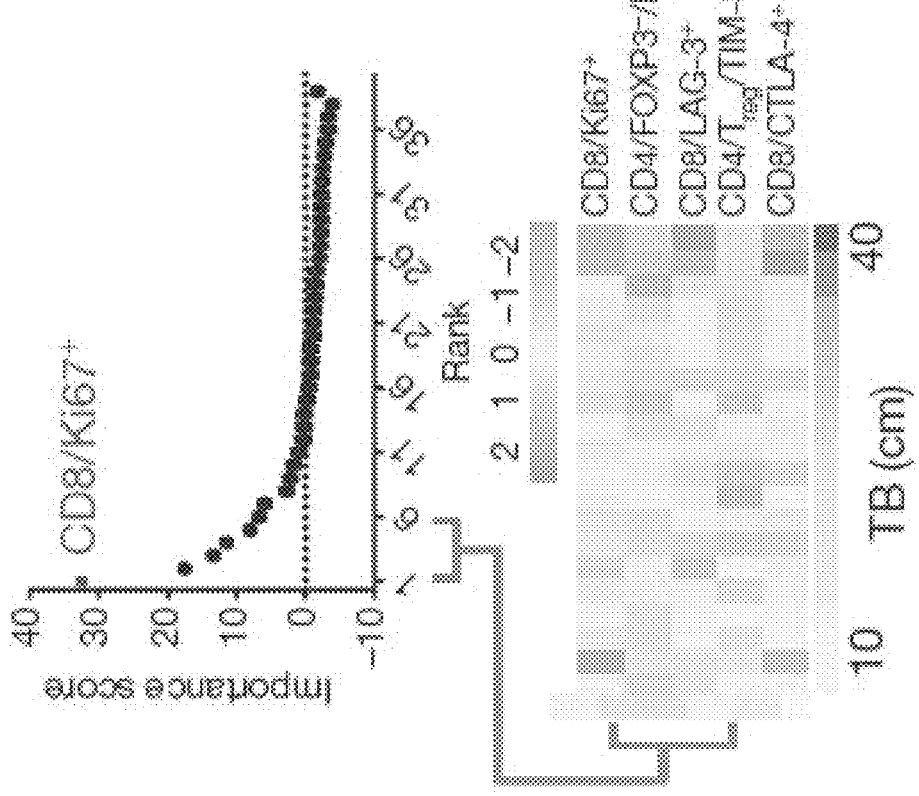

It was demonstrated that T-cell reinvigoration correlates with tumor burden. Antigen burden is a key determinant of the severity of exhaustion and reinvigoration of $T_{EX}$ cells by PD-1 therapy in preclinical models (Blackburn et al. Nat. Immunol. 2009, 10:29-37; Wherry et al. J. Virol. 2003, 77:4911-4927). To test this idea in patients with melanoma, we developed a practical approach to estimate antigen burden using all measurable tumor lesions on the pretreatment imaging scan (tumor burden, see materials & methods under Experimental Examples). Indeed, higher tumor burden was associated with more Ki67$^+$ CD8 T cells both before and after therapy (FIG. 32D). Random forest modelling of 39 immune parameters at 3 weeks showed that Ki67$^+$ CD8 T cells were the strongest correlate of tumor burden (FIG. 32E, Table 3). This correlation was also detectable before treatment, but became stronger after treatment (FIG. 32F), suggesting a pre-existing CD8 T-cell response related to tumor burden, augmented by anti-PD-1 therapy.

Figure 35B:
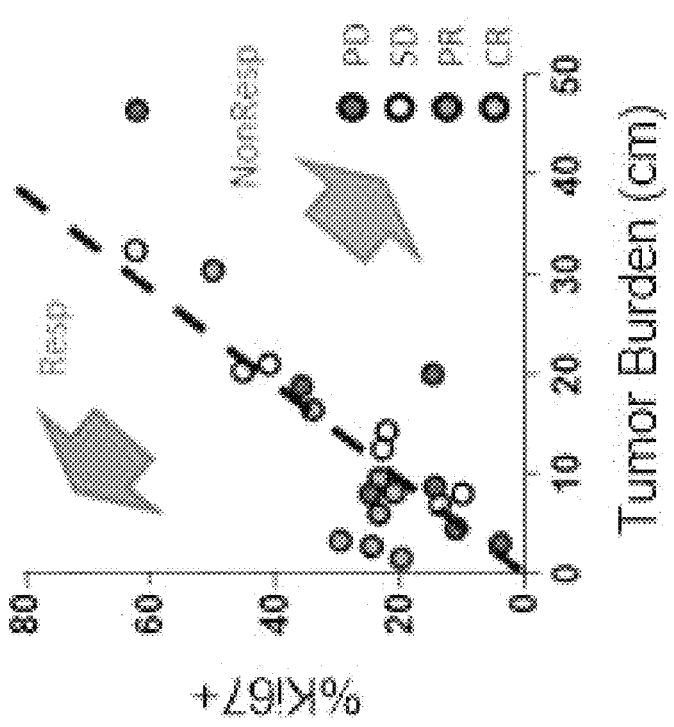
Figure 35A:
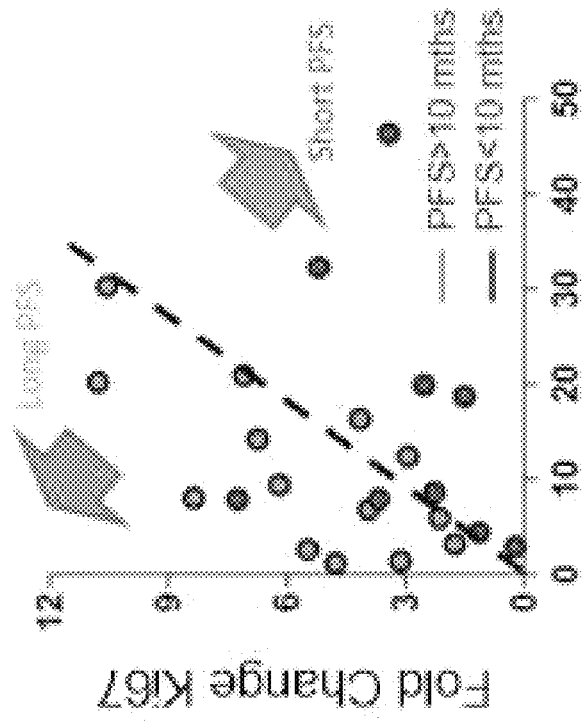
Figure 35C:
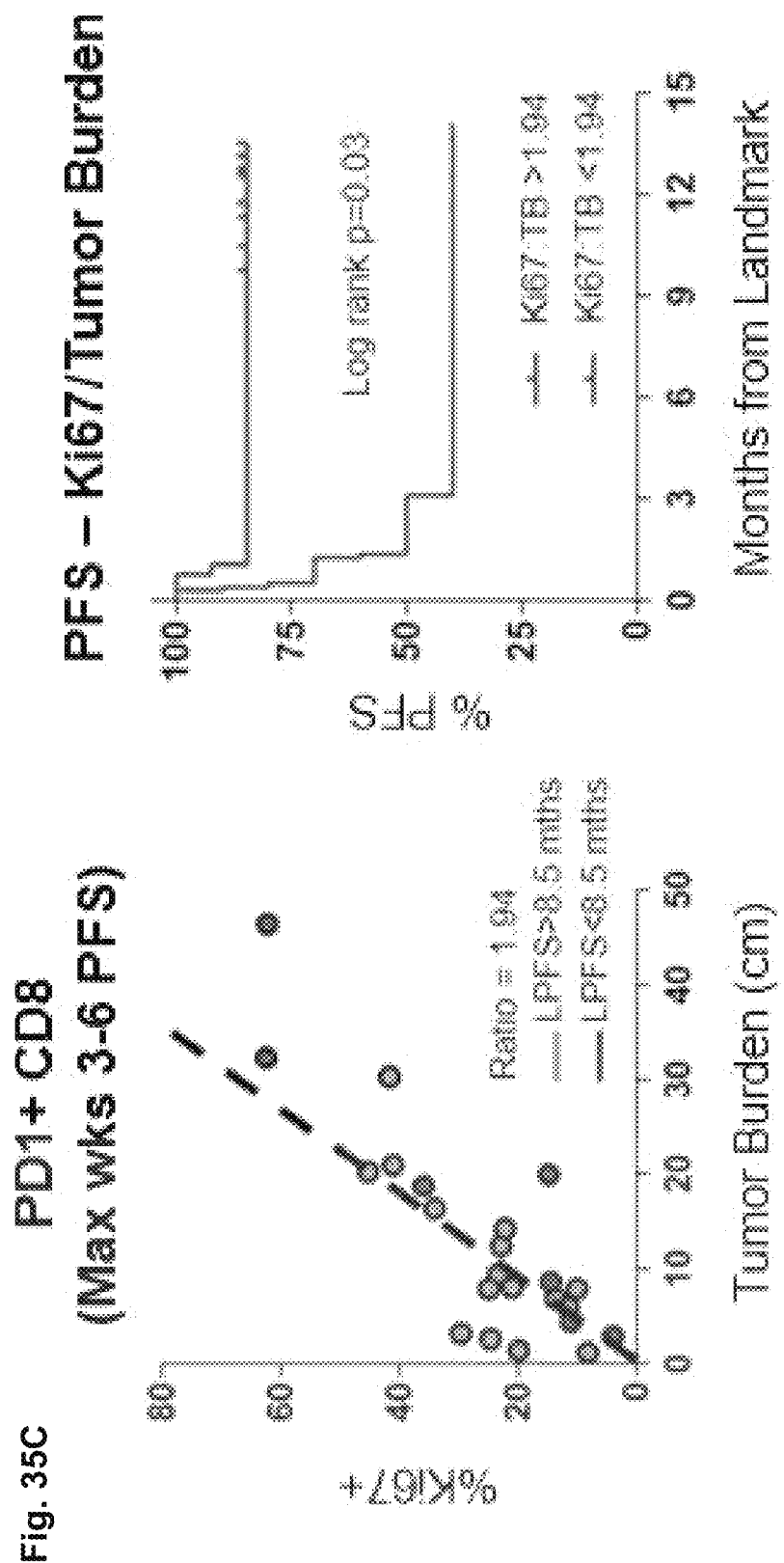
Figure 35D:
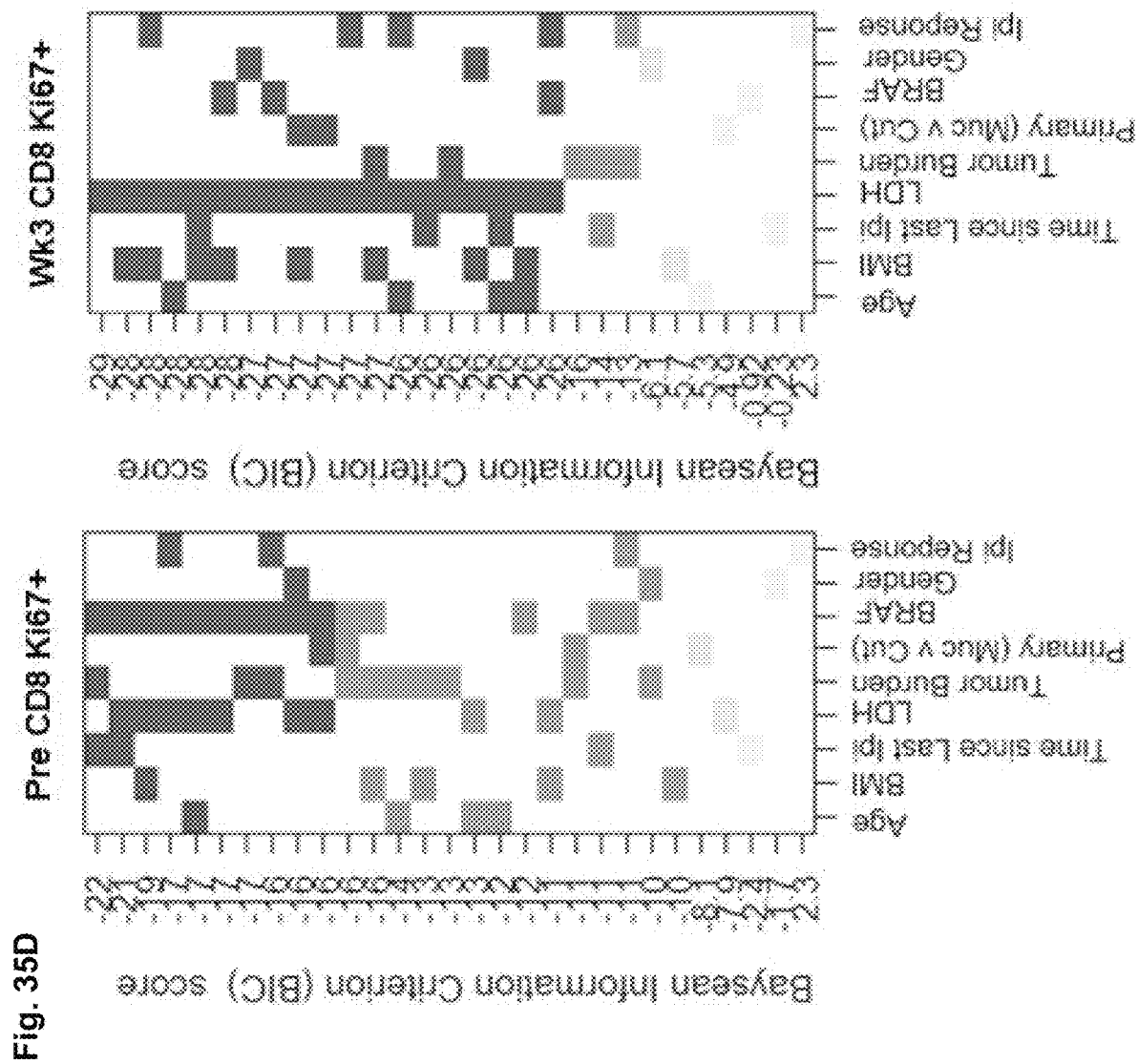
Figure 35E:
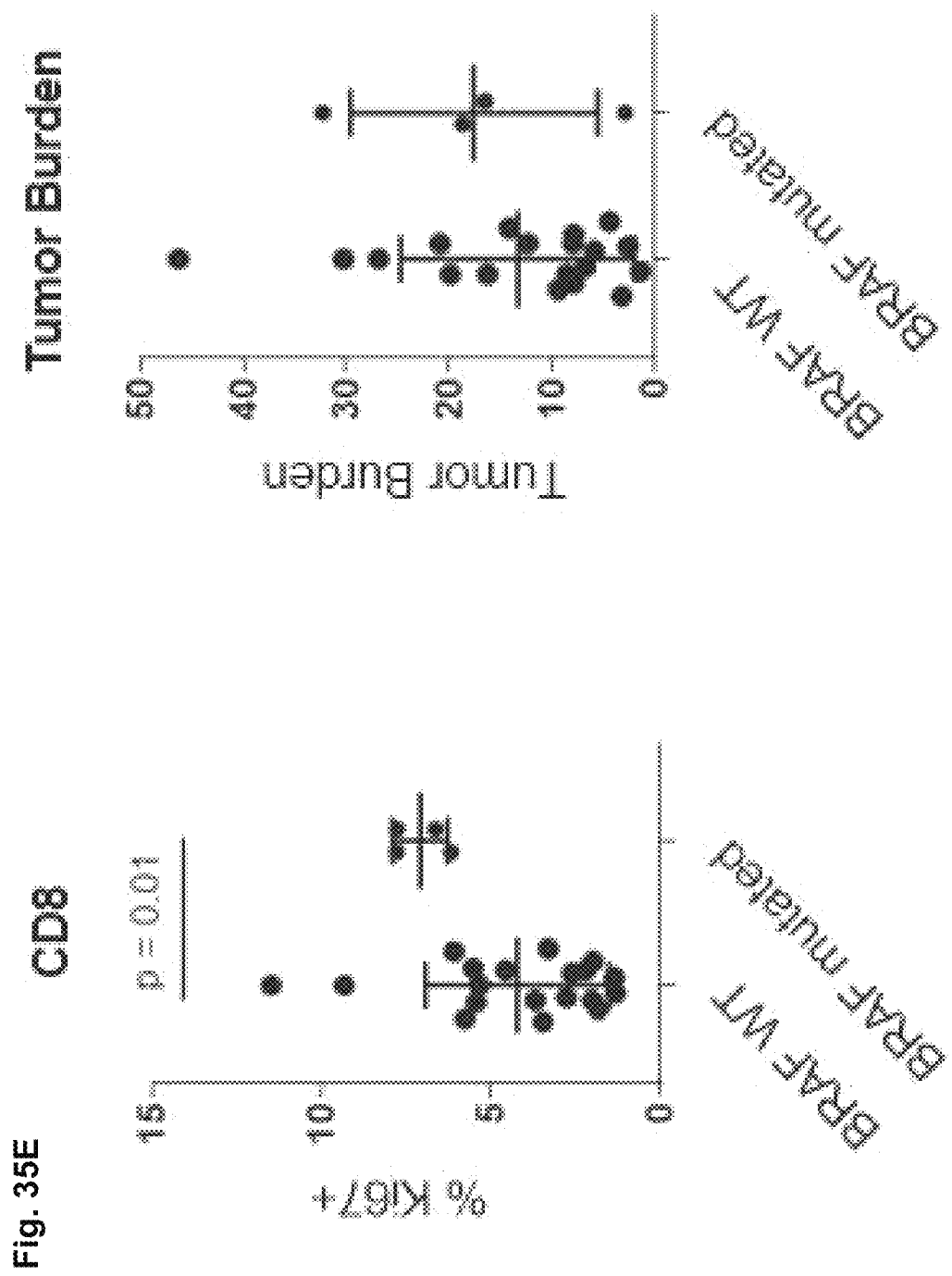
Figure 35F:
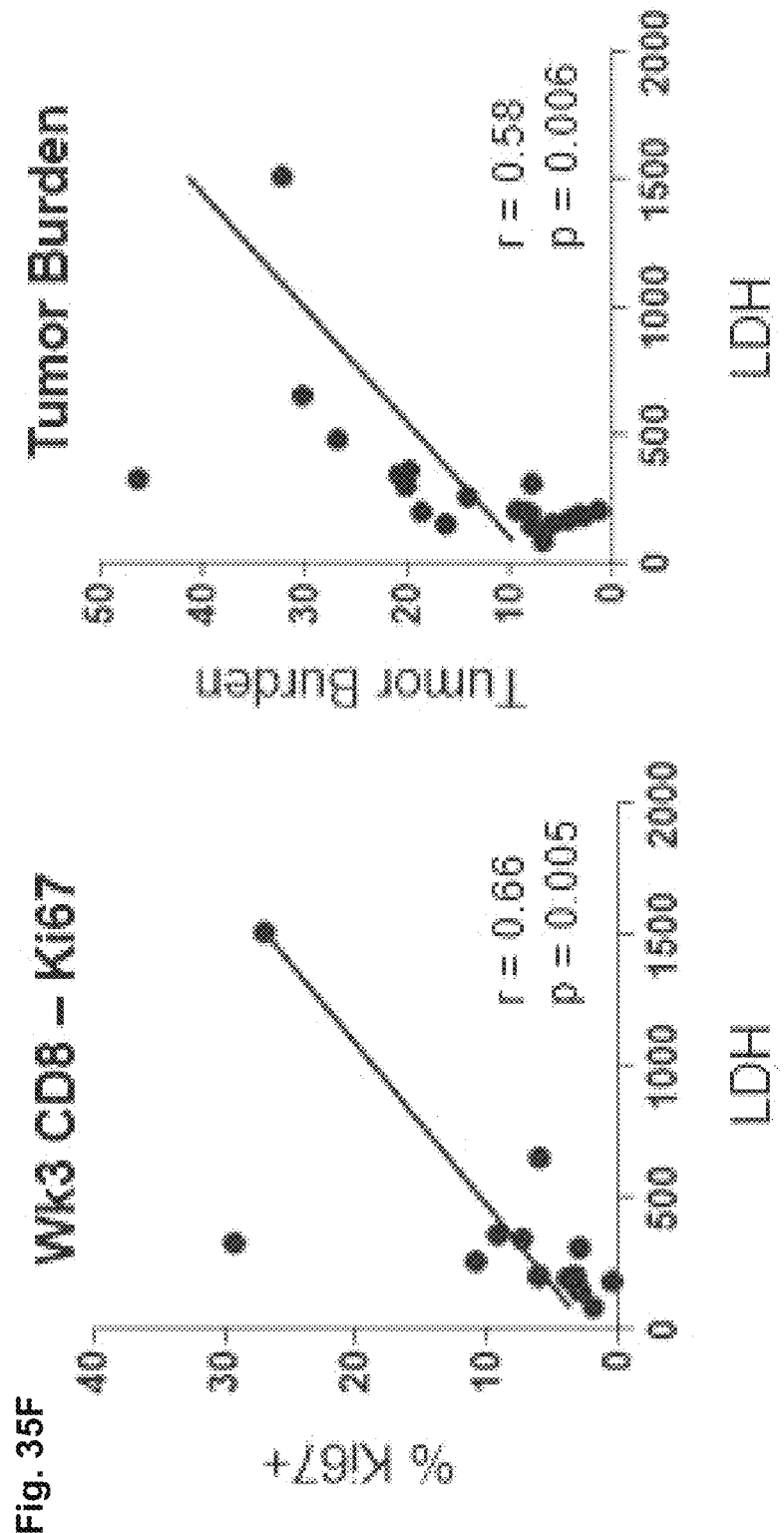

Example 9. Tracking CD8 T-Cell Reinvigoration in Context of Tumor Burden Predicts Response to Anti-PD-1 Therapy It is demonstrated herein that reinvigoration/tumor ratio affects clinical outcome. It was possible that larger baseline immune responses would correlate with clinical response. However, higher pretreatment Ki67 levels in PD-1$^+$ CD8 T cells were in fact an indicator of poor prognosis (FIG. 34A, top). A larger immune response before treatment may reflect higher tumor burden that itself is a poor prognostic indicator (FIG. 34A, bottom). Indeed patients who progressed on anti-PD-1 therapy had evidence of systemic inflammation at baseline (FIGS. 34B, 34C). Random forest analysis showed that Ki67 alone did not correlate with clinical outcome (data not shown). We therefore hypothesized that it was not the absolute magnitude of reinvigoration that mattered, but rather that the ratio of $T_{EX}$-cell reinvigoration to tumor burden might better predict clinical response. To test this, we examined clinical responses in relation to the fold change of PD-1$^+$Ki67$^+$ CD8 T cells after anti-PD-1 therapy, adjusted for baseline tumor burden. Patients with longer progression-free survival (PFS) generally had a low tumor burden and clustered above the fold change of PD-1$^+$Ki67$^+$ CD8 T cells to tumor-burden regression line, suggesting that the ratio of $T_{EX}$-cell reinvigoration to tumor burden may be associated with clinical outcome (FIG. 35A). Moreover, instead of fold change that required measurements both before and after treatment, a higher ratio of Ki67$^+$ CD8 T cells to tumor burden at the post-treatment peak T-cell-response time point was associated with better clinical outcomes. Responders clustered above the PD-1$^+$Ki67$^+$ cell to tumor-burden regression line, whereas non-responders largely fell below (FIG. 35B). Classification and regression tree (CART) analysis identified a Ki67 to tumor burden ratio of 1.94 that segregated patients by clinical outcomes as early as 6 weeks into therapy. A Ki67 to tumor burden ratio greater than 1.94 at 6 weeks was associated with better outcome by objective response rate, PFS and overall survival (FIG. 34D, FIG. 35C). Moreover, by CyTOF, the three patients with clinical benefit (complete response, partial response, and stable disease) showed expansion of $T_{EX}$ cells, whereas the patient who progressed showed an expansion of Ti cells (FIGS. 30G, 30H), supporting the idea that reinvigoration of $T_{EX}$ cells is important.

Other variables were examined by multivariate regression modelling (FIG. 35D), implicating additional roles for BRAF status that may be related to tumor-infiltrating lymphocytes upon BRAF inhibition (Wilmott et al. Clin. Cancer Res. 2012, 18:1386-1394; Knight et al. J. Clin. Invest. 2013, 123:1371-1381) and lactate dehydrogenase, a potential circulating proxy for tumor burden (FIGS. 35E-35G) and known negative-prognostic indicator in stage IV melanoma (Balch et al. J. Clin. Oncol. 2009, 27:6199-6206). Moreover, data from a subset of patients also suggested a role for PD-L1 expression in the tumor and mutational burden, consistent with published observations (Herbst et al. Nature 2014, 515:563-567; Tumeh et al. Nature 2014, 515:568-571; Rizvi et al. Science 2015, 348:124-128). Thus, extending this modelling to include other variables will be important in the future.

A second independent cohort of patients with advanced melanoma that was treated with pembro was analyzed. Flow cytometry was performed on the CD8 T cells from a subset of patients involved in clinical trial NCT01295827 (FIG. 23). Data from this cohort confirmed preferential reinvigoration of PD-1$^+$ and PD-1$^+$CTLA-4$^+$ CD8 T cells after pembro treatment (FIGS. 34E, 34F). These analyses also demonstrated that a Ki67 to tumor burden ratio of 1.94 was associated with overall survival by 6 weeks after treatment (FIG. 34G). These key observations in an independently recruited and analyzed cohort support the idea that the relationship between reinvigorated CD8 T cells in the blood and overall tumor burden correlates with clinical outcome.

Figure 36:
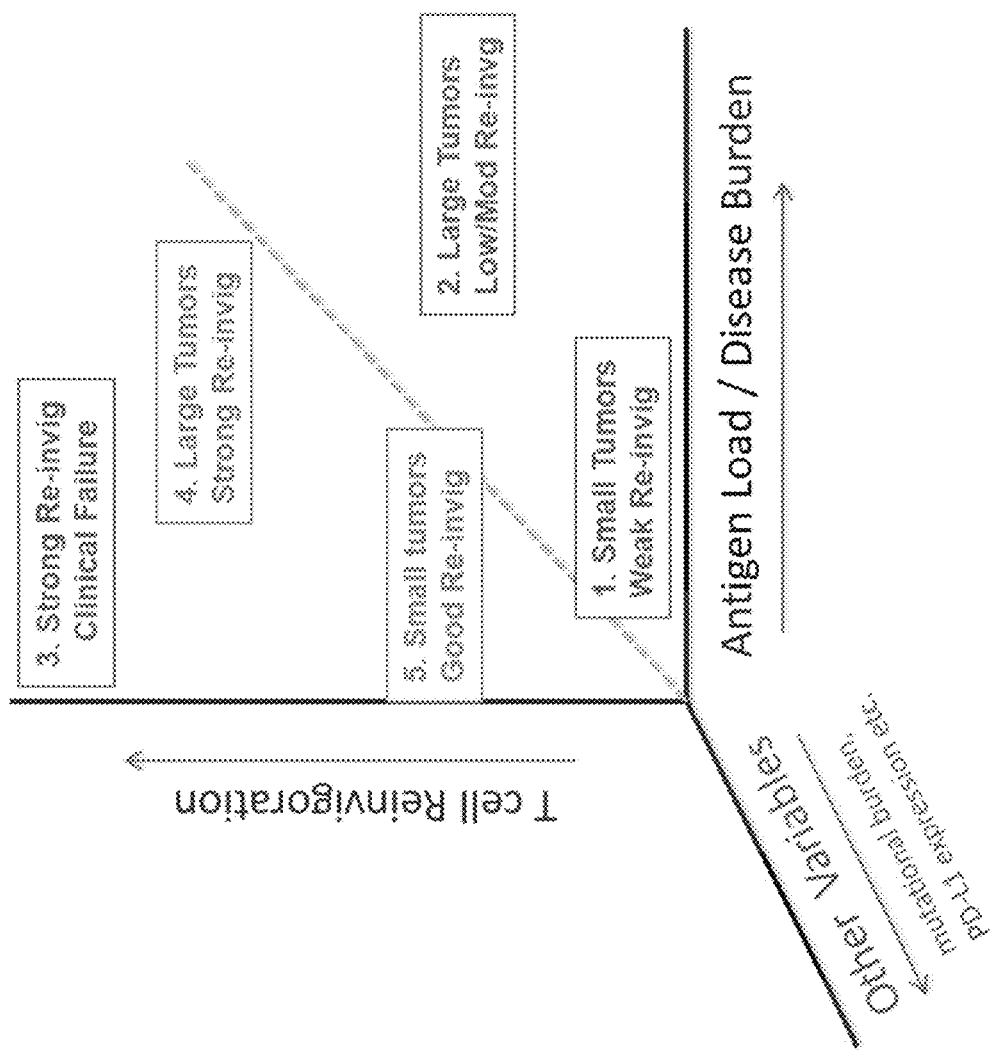
FIG. 36 depicts that T-cell reinvigoration in the context of tumor burden may more accurately reflect the immunobiology of anti-PD-1 patterns of resistance (red) and response (green).

Demonstrated herein are several findings relevant to the understanding of response to PD-1 blockade in patients with advanced melanoma. First, most patients have an on-target immunological effect of PD-1 blockade on CD8 T cells and this effect can be detected, longitudinally monitored and mechanistically interrogated in the peripheral blood. Second, $T_{EX}$ cells were identified as a major target of PD-1 blockade in most patients with melanoma, allowing us to develop a reinvigoration score by relating changes in circulating $T_{EX}$ cells to tumor burden. Third, most patients have a single peak of PD-1-blockade-induced immune reinvigoration, despite ongoing treatment. Fourth, these responding $T_{EX}$ cells in the blood contain TCR clonotypes shared with tumor-infiltrating T cells. Finally, we identify that the ratio of $T_{EX}$-cell reinvigoration to tumor burden can distinguish clinical outcomes and predict response. The relationship between $T_{EX}$-cell reinvigoration and tumor burden suggests a calibration of immune responses to antigen burden and raises the possibility that even robust reinvigoration by anti-PD-1 therapy may be clinically ineffective if the tumor burden is high. On the basis of these observations, it may be possible to delineate classes of predicted therapeutic failures (FIG. 36). Tumor burden alone is not a perfect predictor of response to anti-PD-1 therapy and it has been challenging to define on-treatment predictive markers. An on-treatment biomarker is not only valuable in helping to define clinical responses as early as possible, but also in informing the type of immunological failure and tailor subsequent therapies. It is likely that other parameters such as anatomical location of metastases, PD-L1 expression and mutational phenotype will add further resolution to this relationship between T-cell reinvigoration and tumor burden. Recognizing, on the basis of tumor burden, that the amount of reinvigoration induced by PD-1 blockade in a given patient may be inadequate allows for early clinical intervention, for example with additional immune or targeted therapies (Sharma et al. Cell 2015, 161:205-214; Smyth et al. Nat. Rev. Clin. Oncol. 2016, 13:143-158). It will be important to test if the approaches reported here can be extended to other, especially less immunogenic, tumor types. However, the current study not only illustrates the on-target pharmacodynamic immune effect of PD-1 blockade and utility of blood-based immune monitoring, but also identifies a potential novel predictive biomarker and a framework for future mechanistic dissection by revealing the relationship between overall tumor burden and magnitude of immune reinvigoration by PD-1 blockade.

Tables

TABLE 1

| Gene | Corr |
|---|---|
| MKI67 | 1 |
| CTLA4 | 0.884615 |
| HLA.DQB1 | 0.884615 |
| CENPF | 0.873626 |
| RRM2 | 0.855572 |
| KIR3DX1 | 0.851243 |
| KIF19 | 0.846154 |
| ARHGAP11A | 0.82967 |
| IFI6 | 0.813187 |
| SYNGR1 | 0.802198 |
| HLA.DRB1 | 0.802198 |
| EPB41L4A | 0.801117 |
| FADS2 | 0.79952 |
| CDCA7 | 0.785127 |
| HAVCR2 | 0.78022 |
| LDLR | 0.769231 |
| FBXO5 | 0.763736 |
| ITGAD | 0.760519 |
| ALDOC | 0.758242 |
| GAMT | 0.751393 |
| CD38 | 0.747253 |
| RFC2 | 0.74553 |
| ORMDL3 | 0.741758 |
| COL5A3 | 0.740343 |
| TP53I11 | 0.737277 |
| HLA.K | 0.737277 |
| LMNB1 | 0.730769 |
| PRKAR1B | 0.724521 |
| CLSPN | 0.71978 |
| UBE2L6 | 0.714286 |
| BPGM | 0.714286 |
| ANKS6 | −0.70426 |
| FAM213B | −0.70621 |
| TRIO | −0.70702 |
| ZNF823 | −0.70799 |
| DKK3 | −0.71626 |
| ZNF605 | −0.72527 |
| VSIG1 | −0.72902 |
| MAMLD1 | −0.72988 |
| DBN1 | −0.73077 |
| TRBV28 | −0.73077 |
| PPAN | −0.73453 |
| PCDH1 | −0.73453 |
| C9orf89 | −0.73829 |
| RP11.173A16.2 | −0.74003 |
| CXXC5 | −0.74102 |
| RP11.213G2.3 | −0.74176 |
| GLTPD1 | −0.74176 |
| IKZF2 | −0.74725 |
| VCAN | −0.75929 |

TABLE 2

| Nucleotide | AA | PBMC Freq (%) | TIL Freq (%) |
|---|---|---|---|
| 14784 | | | |
| 1 CCCCTGATCCTGGAGTCGCCCAG CCCCAACCAGACCTCTCTGTACT TCTGTGCCAGCAGTTCCTATTAC GAGCAGTACTTCGGGCCG (SEQ ID NO: 35) | CASSSYYEQYF (SEQ ID NO: 65) | 8.04 | 0.31 |

TABLE 2-continued

|  | Nucleotide | AA | PBMC Freq (%) | TIL Freq (%) |
|---|---|---|---|---|
| 2 | AGTGCCCATCCTGAAGACAGCAG CTTCTACATCTGCAGTGCTAGGA GCACCGGGACTATGATTCGGGCT GAGCAGTTCTTCGGGCCA (SEQ ID NO: 36) | CSARSTGTMIRAEQFF (SEQ ID NO: 66) | 1.45 | 0.27 |
| 3 | CTGACTGTGAGCAACATGAGCCC TGAAGACAGCAGCATATATCTCT GCAGCGTCCAAGGGGGATCTCCT GAAGCTTTCTTTGGACAA (SEQ ID NO: 37) | CSVQGGSPEAFF (SEQ ID NO: 67) | 1.38 | 0.22 |
| 4 | CTAAACCTGAGCTCTCTGGAGCT GGGGGACTCAGCTTTGTATTTCT GTGCCAGCAGCGTGTTAGGGGAT GAGCAGTTCTTCGGGCCA (SEQ ID NO: 38) | CASSVLGDEQFF (SEQ ID NO: 68) | 0.8 | 0.64 |
| 5 | CTGAATGTGAACGCCTTGTTGCT GGGGGACTCGGCCCTCTATCTCT GTGCCAGCAGCTTTAGGTCCGGG GAGCTGTTTTTTGGAGAA (SEQ ID NO: 39) | CASSFRSGELFF (SEQ ID NO: 69) | 0.43 | 0.25 |
| 6 | CTGCTGGGGTTGGAGTCGGCTGC TCCCTCCCAAACATCTGTGTACTT CTGTGCCAGCCGGCAGGGTTTTG GCTACACCTTCGGTTCG (SEQ ID NO: 40) | CASRQGFGYTF (SEQ ID NO: 70) | 0.14 | 1.35 |
| 7 | ACTCTGACGATCCAGCGCACACA GCAGGAGGACTCGGCCGTGTATC TCTGTGCCAGCAGCTTAGGGTAC ACCATATATTTTGGAGAG (SEQ ID NO: 41) | CASSLGYTIYF (SEQ ID NO: 71) | 0.03 | 1.56 |
| 8 | CACGCCCTGCAGCCAGAAGACTC AGCCCTGTATCTCTGCGCCAGCA GCCAAGTGCCTAGCGGCCCCTAC GAGCAGTACTTCGGGCCG (SEQ ID NO: 42) | CASSQVPSGPYEQYF (SEQ ID NO: 72) | 0.03 | 0.82 |
| 9 | ACCAGTGCCCATCCTGAAGACAG CAGCTTCTACATCTGCAGTGCTC CGGGGATCGGGCGACGGGGGAC TGAAGCTTTCTTTGGACAA (SEQ ID NO: 43) | CSAPGIGRRGTEAFF (SEQ ID NO: 73) | 0 | 0.27 |
| 10 | GCTGCTCCCTCCCAGACATCTGT GTACTTCTGTGCCAGCAGTCTAA CAGGGGTGGTCATATACACCGGG GAGCTGTTTTTTGGAGAA (SEQ ID NO: 44) | CASSLTGVVIYTGELFF (SEQ ID NO: 74) | 0 | 0.27 |
| 12288 | | | | |
| 1 | CTGAAGATCCAGCCCTCAGAACC CAGGGACTCAGCTGTGTACTTCT GTGCCAGCAGTCCCTTGGGCTAC GAGCAGTACTTCGGGCCG (SEQ ID NO: 45) | CASSPLGYEQYF (SEQ ID NO: 75) | 2.37 | 0.42 |
| 2 | AGCACCTTGGAGCTGGGGGACTC GGCCCTTTATCTTTGCGCCAGCA GCGGGGGACAGGCCAGCTCCTAC GAGCAGTACTTCGGGCCG (SEQ ID NO: 46) | CASSGGQASSYEQYF (SEQ ID NO: 76) | 0.3 | 0.58 |
| 3 | ATCCGGTCCACAAAGCTGGAGGA CTCAGCCATGTACTTCTGTGCCA GCAGAGGACAAGACCAGAACAC TGAAGCTTTCTTTGGACAA (SEQ ID NO: 47) | CASRGQDQNTEAFF (SEQ ID NO: 77) | 0.24 | 0.89 |

TABLE 2-continued

| | Nucleotide | AA | PBMC Freq (%) | TIL Freq (%) |
|---|---|---|---|---|
| 4 | CTCAGGCTGGAGTCGGCTGCTCC CTCCCAGACATCTGTGTACTTCTG TGCCAGCAGTGAAACAGACACTG AAGCTTTCTTTGGACAA (SEQ ID NO: 48) | CASSETDTEAFF (SEQ ID NO: 78) | 0.04 | 0.51 |
| 5 | CACCTACACACCCTGCAGCCAGA AGACTCGGCCCTGTATCTCTGCG CCAGCAGCCAAATCGGGGATAA GACGGCTTTCTTTGGACAA (SEQ ID NO: 49) | CASSQIGDKTAFF (SEQ ID NO: 79) | 0.02 | |
| 6 | AAGATCCAGCCTGCAGAGCTTGG GGACTCGGCCGTGTATCTCTGTG CCAGCAGCCATACAAACACCGGG GAGCTGTTTTTTGGAGAA (SEQ ID NO: 50) | CASSHTNTGELFF (SEQ ID NO: 80) | 0.01 | 0.57 |
| 7 | TTGGAGTCGGCTGCTCCCTCCCA AACATCTGTGTACTTCTGTGCCA GCAGTTACGGGGACAGGGGCCT GAAGCTTTCTTTGGACAA (SEQ ID NO: 51) | CASSYGGQGPEAFF (SEQ ID NO: 81) | 0.01 | 0.44 |
| 8 | GAGATCCAGCGCACAGAGCAGG GGGACTCGGCCATGTATCTCTGT GCCAGCAGTCTAGTCGGGGGGAG GGAAGCTTTCTTTGGACAA (SEQ ID NO: 52) | CASSLVGGREAFF (SEQ ID NO: 82) | 0 | 1.3 |

14835

| | Nucleotide | AA | PBMC Freq (%) | TIL Freq (%) |
|---|---|---|---|---|
| 1 | CACGCCCTGCAGCCAGAAGACTC AGCCCTGTATCTCTGCGCCAGCA GCCTGGACAGGGGGTATAATCAG CCCCAGCATTTTGGTGAT (SEQ ID NO: 53) | CASSLDRGYNQPQHF (SEQ ID NO: 83) | 23.03 | 1.09 |
| 2 | CAACCTGCAAAGCTTGAGGACTC GGCCGTGTATCTCTGTGCCAGCA GCTTCAATGGGAGATGAACACT GAAGCTTTCTTTGGACAA (SEQ ID NO: 54) | CASSFNGEMNTEAFF (SEQ ID NO: 84) | 0.01 | 1.36 |

13416

| | Nucleotide | AA | PBMC Freq (%) | TIL Freq (%) |
|---|---|---|---|---|
| 1 | TTGGAGATCCAGCGCACAGAGCA GGGGGACTCGGCCATGTATCTCT GTGCCAGCAGCCTTTCCTCTTCAC CCCTCCACTTTGGGAAC (SEQ ID NO: 55) | CASSLSSSPLHF (SEQ ID NO: 85) | 15.16 | 1.42 |
| 2 | TCTAAGAAGCTCCTCCTCAGTGA CTCTGGCTTCTATCTCTGTGCCTT CGTCAGCAGGGGAGGCGACTATG GCTACACCTTCGGTTCG (SEQ ID NO: 56) | CAFVSRGGDYGYTF (SEQ ID NO: 86) | 14.59 | 0.65 |
| 3 | CTGAGCTCTCTGGAGCTGGGGGA CTCAGCTTTGTATTTCTGTGCCAG CAGCGCCTCCGCGTGGGCCGCTG AAGCTTTCTTTGGACAA (SEQ ID NO: 57) | CASSASAWAAEAFF (SEQ ID NO: 87) | 7.38 | 1.34 |
| 4 | ATGAGCTCCTTGGAGCTGGGGGA CTCAGCCCTGTACTTCTGTGCCA GCAGCTCGAGGACTAGGTGGAAT GAGCAGTTCTTCGGGCCA (SEQ ID NO: 58) | CASSSRTRWNEQFF (SEQ ID NO: 88) | 6.73 | 0.78 |
| 5 | CTGAAGATCCAGCCCTCAGAACC CAGGGACTCAGCTGTGTACTTCT GTGCCAGCAGCAGTGCTAACTAT GGCTACACCTTCGGTTCG (SEQ ID NO: 59) | CASSSANYGYTF (SEQ ID NO: 89) | 2.26 | 1.94 |

TABLE 2-continued

|   | Nucleotide | AA | PBMC Freq (%) | TIL Freq (%) |
|---|---|---|---|---|
| 6 | GAACTGAACATGAGCTCCTTGGA GCTGGGGGACTCAGCCCTGTACT TCTGTGCCAGCAGTTCATCTGAT ACGCAGTATTTTGGCCCA (SEQ ID NO: 60) | CASSSSDTQYF (SEQ ID NO: 90) | 0 | 0.82 |

13471

|   | Nucleotide | AA | PBMC Freq (%) | TIL Freq (%) |
|---|---|---|---|---|
| 1 | TCTCTGGAGCTGGGGGACTCAGC TTTGTATTTCTGTGCCAGCAGCGT AGGGGACAGGGGGTCTGGAAAC ACCATATATTTTGGAGAG (SEQ ID NO: 61) | CASSVGDRGSGNTIYF (SEQ ID NO: 91) | 5.8 | 0.6 |
| 2 | TCCGCTACCAGCTCCCAGACATC TGTGTACTTCTGTGCCATCAGTG ACCTCGGCGGCCCGGCCGCAGAT ACGCAGTATTTTGGCCCA (SEQ ID NO: 62) | CAISDLGGPAADTQYF (SEQ ID NO: 92) | 0.84 | 0.29 |

14746

|   | Nucleotide | AA | PBMC Freq (%) | TIL Freq (%) |
|---|---|---|---|---|
| 1 | CCCAGCCCCAACCAGACCTCTCT GTACTTCTGTGCCAGCAGTTTAT GGGGCGGCGGGAGCTCCTACAAT GAGCAGTTCTTCGGGCCA (SEQ ID NO: 63) | CASSLWGGGSSYNEQFF (SEQ ID NO: 93) | 9.96 | 3.54 |
| 2 | CAGCCTGCAGAACTGGAGGATTC TGGAGTTTATTTCTGTGCCAGCA GCCAACTGACAGGGGCTGACACT GAAGCTTTCTTTGGACAA (SEQ ID NO: 64) | CASSQLTGADTEAFF (SEQ ID NO: 94) | 0.4 | 0.59 |

TABLE 3

| Pre-Tumor Burden | | | Wk3-Tumor Burden | | |
|---|---|---|---|---|---|
| Rank | Immune Subset | IS | Rank | Immune Subset | IS |
| 1 | CD8/Lag3+ | Freq. of Parent (%) | 9.55 | 1 | CD8/Ki67+ | Freq. of Parent (%) | 32.47 |
| 2 | CD8/Ki67+ | Freq. of Parent (%) | 9.46 | 2 | CD4/Non-Tregs/PD1+ | Freq. of Parent (%) | 17.58 |
| 3 | CD4 | Freq. of Parent (%) | 5.66 | 3 | CD8/Lag3+ | Freq. of Parent (%) | 13.41 |
| 4 | CD4/Non-Tregs/Q4: CD45RA−, CD27− | Freq. of Parent (%) | 4.74 | 4 | CD4/Tregs/Tim3+ | Freq. of Parent (%) | 11.47 |
| 5 | CD4/Tregs/Tim3+ | Freq. of Parent (%) | 3.05 | 5 | CD8/CTLA4+ | Freq. of Parent (%) | 8.04 |
| 6 | CD8 | Freq. of Parent (%) | 2.96 | 6 | CD4/Non-Tregs/Lag3+ | Freq. of Parent (%) | 6.75 |
| 7 | CD4/Non-Tregs/Tim3+ | Freq. of Parent (%) | 2.57 | 7 | CD4/Non-Tregs/Ki67+ | Freq. of Parent (%) | 5.92 |
| 8 | CD4/Non-Tregs/Q1: CD45RA−, CD27+ | Freq. of Parent (%) | 0.76 | 8 | CD4/Non-Tregs/CTLA4+ | Freq. of Parent (%) | 2.74 |
| 9 | CD8/Eomes+ | Freq. of Parent (%) | 0.51 | 9 | CD8/PD1+ | Freq. of Parent (%) | 2.24 |
| 10 | CD8/Tim3+ | Freq. of Parent (%) | 0.44 | 10 | CD8/Tim3+ | Freq. of Parent (%) | 1.79 |
| 11 | CD8/naïve | Freq. of Parent (%) | 0.22 | 11 | CD8/Eomes+ | Freq. of Parent (%) | 0.95 |
| 12 | CD4/Non-Treg/Q3: CD45RA+, CD27− | Freq. of Parent (%) | 0.19 | 12 | CD4/Tregs/Tbet+ | Freq. of Parent (%) | 0.42 |
| 13 | CD4/Non-Tregs/Q2: CD45RA+, CD27+ | Freq. of Parent (%) | −0.04 | 13 | CD8/naïve | Freq. of Parent (%) | 0.24 |
| 14 | CD8/Q23: CD45RA+, CD27− | Freq. of Parent (%) | −0.23 | 14 | CD4/Tregs/PD1+ | Freq. of Parent (%) | 0.23 |
| 15 | CD4/Tregs/PD1+ | Freq. of Parent (%) | −0.54 | 15 | CD4 | Freq. of Parent (%) | −0.23 |
| 16 | CD8/PD1+ | Freq. of Parent (%) | −0.61 | 16 | CD8/Q21: CD45RA−, CD27+ | Freq. of Parent (%) | −0.51 |
| 17 | CD8/Q24: CD45RA−, CD27− | Freq. of Parent (%) | −0.66 | 17 | CD8/Q22: CD45RA+, CD27+ | Freq. of Parent (%) | −0.67 |
| 18 | CD4/Non-Tregs/Lag3+ | Freq. of Parent (%) | −1.24 | 18 | CD4/Tregs/GzmB+ | Freq. of Parent (%) | −0.71 |
| 19 | CD8/Q21: CD45RA−, CD27+ | Freq. of Parent (%) | −1.39 | 19 | CD8/Q24: CD45RA−, CD27− | Freq. of Parent (%) | −0.74 |
| 20 | CD8/Q22: CD45RA+, CD27+ | Freq. of Parent (%) | −1.81 | 20 | CD4/Tregs/naïve | Freq. of Parent (%) | −1.01 |
| 21 | CD4/Non-Tregs/CTLA4+ | Freq. of Parent (%) | −1.83 | 21 | CD4/Non-Tregs/Tim3+ | Freq. of Parent (%) | −1.10 |
| 22 | CD8/CD160+ | Freq. of Parent (%) | −2.09 | 22 | CD4/Non-Treg/Q3: CD45RA+, CD27− | Freq. of Parent (%) | −1.15 |

TABLE 3-continued

| Rank | Immune Subset | IS | Rank | Immune Subset | IS |
|---|---|---|---|---|---|
| 23 | CD4/Non-Tregs/PD1+ \| Freq. of Parent (%) | −2.15 | 23 | CD4/Tregs/Eomes+ \| Freq. of Parent (%) | −1.35 |
| 24 | CD4/Tregs/naïve \| Freq. of Parent (%) | −2.16 | 24 | CD4/Non-Tregs/Q2: CD45RA+, CD27+ \| Freq. of Parent (%) | −1.38 |
| 25 | CD4/Non-Tregs/Eomes+ \| Freq. of Parent (%) | −2.19 | 25 | CD8/CD160+ \| Freq. of Parent (%) | −1.53 |
| 26 | CD4/Non-Tregs/Ki67+ \| Freq. of Parent (%) | −2.93 | 26 | CD4/Non-Tregs/GzmB+ \| Freq. of Parent (%) | −1.99 |
| 27 | CD4/Tregs \| Freq. of Parent (%) | −3.09 | 27 | CD8/GzmB+ \| Freq. of Parent (%) | −2.06 |
| 28 | CD8/CTLA4+ \| Freq. of Parent (%) | −3.30 | 28 | CD8 \| Freq. of Parent (%) | −2.19 |
| 29 | CD4/Tregs/Ki67+ \| Freq. of Parent (%) | −3.73 | 29 | CD4/Non-Tregs/Q4: CD45RA−, CD27− \| Freq. of Parent (%) | −2.19 |
| 30 | CD4/Tregs/Eomes+ \| Freq. of Parent (%) | −3.96 | 30 | CD4/Non-Tregs \| Freq. of Parent (%) | −2.25 |
| 31 | CD4/Tregs/Tbet+ \| Freq. of Parent (%) | −4.01 | 31 | CD4/Tregs \| Freq. of Parent (%) | −2.28 |
| 32 | CD4/Tregs/Lag3+ \| Freq. of Parent (%) | −4.08 | 32 | CD8/Q23: CD45RA+, CD27− \| Freq. of Parent (%) | −2.35 |
| 33 | CD8/Tbet+ \| Freq. of Parent (%) | −4.78 | 33 | CD4/Non-Tregs/Eomes+ \| Freq. of Parent (%) | −2.43 |
| 34 | CD8/GzmB+ \| Freq. of Parent (%) | −4.82 | 34 | CD4/Non-Tregs/Q1: CD45RA−, CD27+ \| Freq. of Parent (%) | −2.72 |
| 35 | CD4/Tregs/GzmB+ \| Freq. of Parent (%) | −4.82 | 35 | CD4/Tregs/Ki67+ \| Freq. of Parent (%) | −2.94 |
| 36 | CD4/Non-Tregs/Tbet+ \| Freq. of Parent (%) | −7.01 | 36 | CD4/Non-Tregs/Tbet+ \| Freq. of Parent (%) | −3.27 |
| 37 | CD4/Non-Tregs/GzmB+ \| Freq. of Parent (%) | −7.48 | 37 | CD4/Tregs/Lag3+ \| Freq. of Parent (%) | −3.36 |
| 38 | CD4/Tregs/CTLA4+ \| Freq. of Parent (%) | −7.61 | 38 | CD8/Tbet+ \| Freq. of Parent (%) | −3.83 |
| 39 | CD4/Non-Tregs \| Freq. of Parent (%) | −7.85 | 39 | CD4/Tregs/CTLA4+ \| Freq. of Parent (%) | −5.76 |

| Pre-PFS | | | Wk3-PFS | | |
|---|---|---|---|---|---|
| Rank | Immune Subset | IS | Rank | Immune Subset | IS |
| 1 | CD8/CD160+ \| Freq. of Parent (%) | 30.75 | 1 | CD4/Non-Tregs/Tbet+ \| Freq. of Parent (%) | 18.02 |
| 2 | CD8/Ki67+ \| Freq. of Parent (%) | 14.48 | 2 | CD4/Tregs/Tbet+ \| Freq. of Parent (%) | 16.01 |
| 3 | CD4/Non-Treg/Q3: CD45RA+, CD27− \| Freq. of Parent (%) | 11.54 | 3 | CD4/Non-Treg/Q3: CD45RA+, CD27− \| Freq. of Parent (%) | 12.41 |
| 4 | CD8/Lag3+ \| Freq. of Parent (%) | 7.30 | 4 | CD8/CTLA4+ \| Freq. of Parent (%) | 10.32 |
| 5 | CD4/Non-Tregs/Q4: CD45RA−, CD27− \| Freq. of Parent (%) | 3.66 | 5 | CD4/Non-Tregs/Eomes+ \| Freq. of Parent (%) | 6.45 |
| 6 | CD4/Tregs/Lag3+ \| Freq. of Parent (%) | 3.53 | 6 | CD4/Tregs \| Freq. of Parent (%) | 3.49 |
| 7 | CD4/Non-Tregs/Ki67+ \| Freq. of Parent (%) | 3.15 | 7 | CD8/GzmB+ \| Freq. of Parent (%) | 2.84 |
| 8 | CD8/Tbet+ \| Freq. of Parent (%) | 2.71 | 8 | CD8 \| Freq. of Parent (%) | 2.36 |
| 9 | CD8/GzmB+ \| Freq. of Parent (%) | 2.04 | 9 | CD8/PD1+ \| Freq. of Parent (%) | 1.54 |
| 10 | CD4/Non-Tregs/CTLA4+ \| Freq. of Parent (%) | 1.63 | 10 | CD4/Non-Tregs \| Freq. of Parent (%) | 1.51 |
| 11 | CD4/Non-Tregs/Tbet+ \| Freq. of Parent (%) | 1.23 | 11 | CD8/Q24: CD45RA−, CD27− \| Freq. of Parent (%) | 1.34 |
| 12 | CD8/Q22: CD45RA+, CD27+ \| Freq. of Parent (%) | 0.70 | 12 | CD8/Tim3+ \| Freq. of Parent (%) | 1.16 |
| 13 | CD4/Tregs/PD1+ \| Freq. of Parent (%) | 0.47 | 13 | CD4/Non-Tregs/Ki67+ \| Freq. of Parent (%) | 0.88 |
| 14 | CD8/CTLA4+ \| Freq. of Parent (%) | 0.22 | 14 | CD8/Eomes+ \| Freq. of Parent (%) | 0.66 |
| 15 | CD8/Eomes+ \| Freq. of Parent (%) | −0.39 | 15 | CD4 \| Freq. of Parent (%) | 0.58 |
| 16 | CD4/Non-Tregs/Eomes+ \| Freq. of Parent (%) | −0.49 | 16 | CD4/Tregs/PD1+ \| Freq. of Parent (%) | 0.39 |
| 17 | CD4 \| Freq. of Parent (%) | −0.66 | 17 | CD4/Tregs/Ki67+ \| Freq. of Parent (%) | −0.38 |
| 18 | CD4/Non-Tregs/Lag3+ \| Freq. of Parent (%) | −1.02 | 18 | CD4/Tregs/Eomes+ \| Freq. of Parent (%) | −0.46 |
| 19 | CD4/Non-Tregs/Tim3+ \| Freq. of Parent (%) | −1.58 | 19 | CD8/Q22: CD45RA+, CD27+ \| Freq. of Parent (%) | −0.83 |
| 20 | CD8 \| Freq. of Parent (%) | −1.61 | 20 | CD4/Tregs/Lag3+ \| Freq. of Parent (%) | −0.91 |
| 21 | CD4/Non-Tregs/PD1+ \| Freq. of Parent (%) | −1.81 | 21 | CD4/Non-Tregs/PD1+ \| Freq. of Parent (%) | −0.92 |
| 22 | CD4/Tregs/Tim3+ \| Freq. of Parent (%) | −1.82 | 22 | CD4/Non-Tregs/GzmB+ \| Freq. of Parent (%) | −1.06 |
| 23 | CD8/Q23: CD45RA+, CD27− \| Freq. of Parent (%) | −2.14 | 23 | CD8/CD160+ \| Freq. of Parent (%) | −1.58 |
| 24 | CD4/Tregs/Ki67+ \| Freq. of Parent (%) | −2.90 | 24 | CD4/Tregs/Tim3+ \| Freq. of Parent (%) | −1.74 |
| 25 | CD4/Non-Tregs \| Freq. of Parent (%) | −2.98 | 25 | CD4/Non-Tregs/CTLA4+ \| Freq. of Parent (%) | −2.05 |
| 26 | CD4/Tregs/Tbet+ \| Freq. of Parent (%) | −3.09 | 26 | CD4/Non-Tregs/Tim3+ \| Freq. of Parent (%) | −2.28 |
| 27 | CD8/naïve \| Freq. of Parent (%) | −3.28 | 27 | CD4/Tregs/naïve \| Freq. of Parent (%) | −2.42 |
| 28 | CD8/Tim3+ \| Freq. of Parent (%) | −3.60 | 28 | CD4/Non-Tregs/Lag3+ \| Freq. of Parent (%) | −2.67 |
| 29 | CD8/Q24: CD45RA−, CD27− \| Freq. of Parent (%) | −3.61 | 29 | CD8/Tbet+ \| Freq. of Parent (%) | −2.68 |
| 30 | CD4/Tregs/naïve \| Freq. of Parent (%) | −3.81 | 30 | CD4/Non-Tregs/Q2: CD45RA+, CD27+ \| Freq. of Parent (%) | −2.75 |
| 31 | CD8/Q21: CD45RA−, CD27+ \| Freq. of Parent (%) | −3.95 | 31 | CD4/Non-Tregs/Q1: CD45RA−, CD27+ \| Freq. of Parent (%) | −2.86 |
| 32 | CD4/Tregs/CTLA4+ \| Freq. of Parent (%) | −3.99 | 32 | CD4/Tregs/CTLA4+ \| Freq. of Parent (%) | −2.96 |
| 33 | CD4/Non-Tregs/Q1: CD45RA−, CD27+ \| Freq. of Parent (%) | −4.00 | 33 | CD4/Non-Tregs/Q4: CD45RA−, CD27− \| Freq. of Parent (%) | −3.02 |
| 34 | CD8/PD1+ \| Freq. of Parent (%) | −4.20 | 34 | CD4/Tregs/GzmB+ \| Freq. of Parent (%) | −3.12 |
| 35 | CD4/Tregs/GzmB+ \| Freq. of Parent (%) | −4.65 | 35 | CD8/Q23: CD45RA+, CD2− \| Freq. of Parent (%) | −3.12 |
| 36 | CD4/Tregs \| Freq. of Parent (%) | −5.03 | 36 | CD8/Q21: CD45RA−, CD27+ \| Freq. of Parent (%) | −4.06 |
| 37 | CD4/Non-Tregs/GzmB+ \| Freq. of Parent (%) | −5.20 | 37 | CD8/naïve \| Freq. of Parent (%) | −4.57 |
| 38 | CD4/Tregs/Eomes+ \| Freq. of Parent (%) | −5.83 | 38 | CD8/Ki67+ \| Freq. of Parent (%) | −5.08 |
| 39 | CD4/Non-Tregs/Q2: CD45RA+, CD27+ \| Freq. of Parent (%) | −6.61 | 39 | CD8/Lag3+ \| Freq. of Parent (%) | −5.30 |

Example 10. Identification of Genes with Unique Expression Patterns in $T_{EX}$

Exhausted CD8 T cells ($T_{EX}$) undergo major transcriptional changes that distinguish them from naïve ($T_N$), effector ($T_{EFF}$) and memory ($T_{MEM}$) T cells (FIG. 37A) (Wherry and Kurachi. *Nat Rev Immunol.* 2015, 15(8):486-499). Functional and transcriptional features of exhaustion arise during chronic LCMV infection after ~2 weeks of chronic infection (Angelosanto et al. (2012) *J Virol* 86:8161-8170; Doering et al. (2012) *Immunity* 37:1130-1144) with a similar onset in cancer models (Philip et al. (2017) *Nature* 545:452-456; Schietinger et al. (2016) *Immunity* 45:389-401). In the present study, a core signature of genes specifically regulated in $T_{EX}$ during chronic LCMV infection was identified that could be used to identify and monitor $T_{EX}$ in other settings. Although we and others (Doering et al. (2012) *Immunity* 37:1130-1144; Singer et al. (2016) *Cell* 166:1500-1511, e1509; Wherry et al. (2007) *Immunity* 27:670-684) have previously reported transcriptional signatures of exhaustion, here our goal and approach was distinct. We aimed to identify a focused set of highly $T_{EX}$-biased genes, to validate this signature against a wide range of signatures from other settings of exhaustion and then to use epigenetic information for individual genes to further refine the signature, enabling the development of a mass cytometry platform that converts these signatures from bulk RNA and epigenetic data to a single-cell method for interrogating the biology of human $T_{EX}$.

Figure 37A:
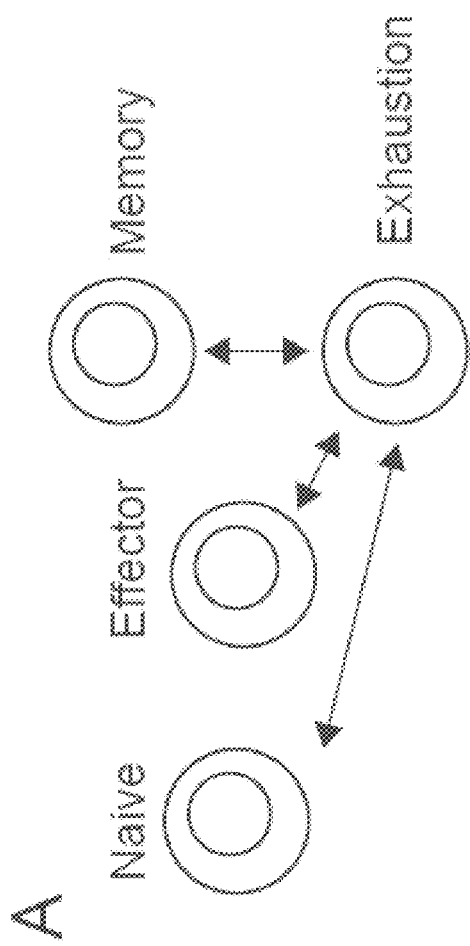
FIGS. 37A-37H illustrate how a mouse-derived transcriptomic exhaustion signature translates to human exhaustion.
Figure 37B:
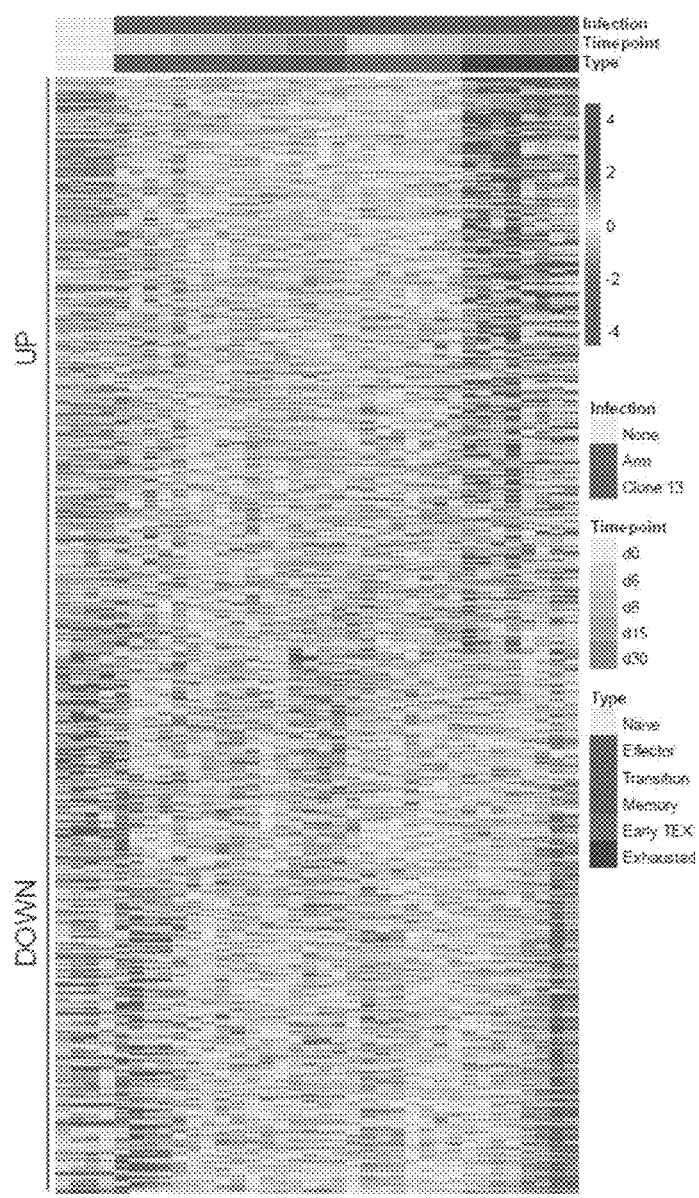
Figure 37C:
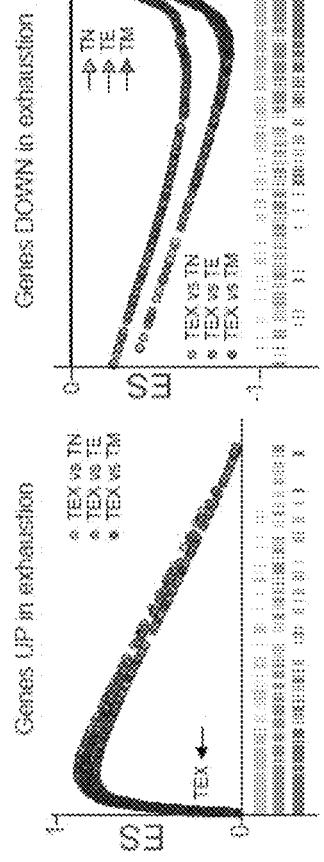
Figure 37D:
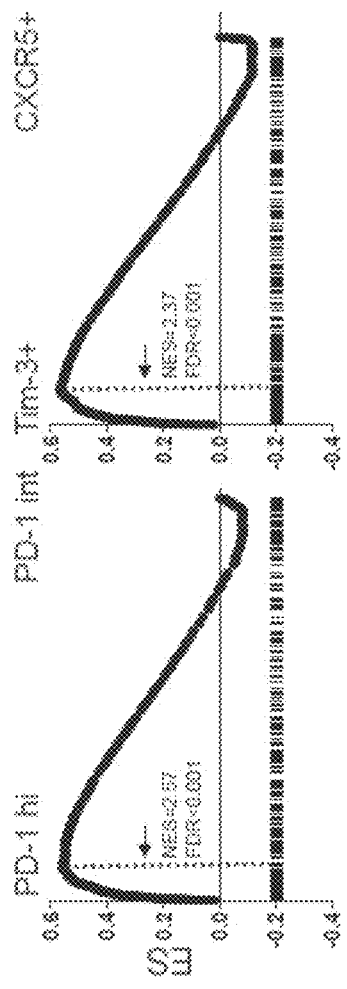
Figure 37E:
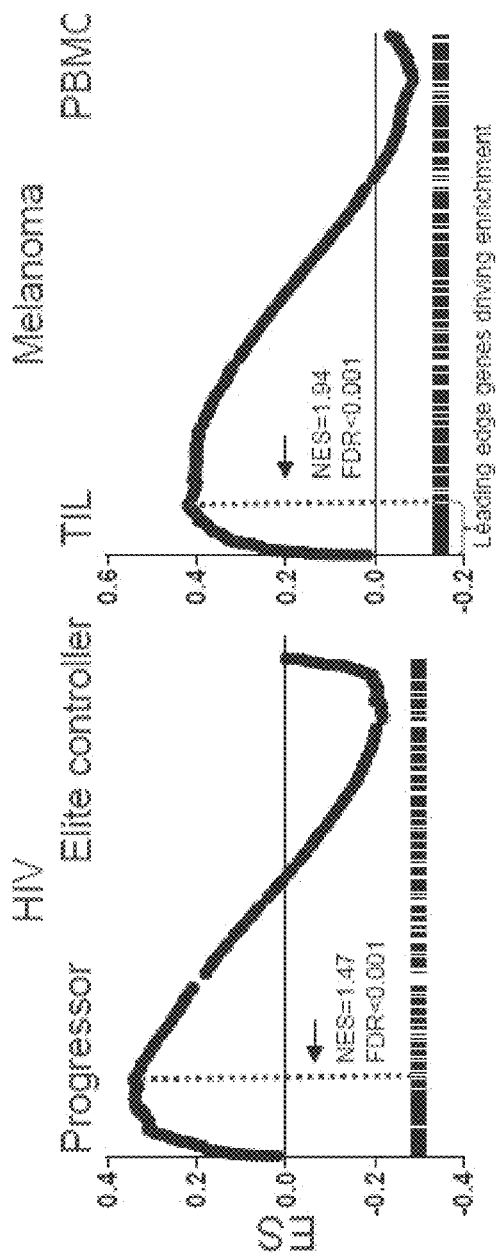
Figure 37F:
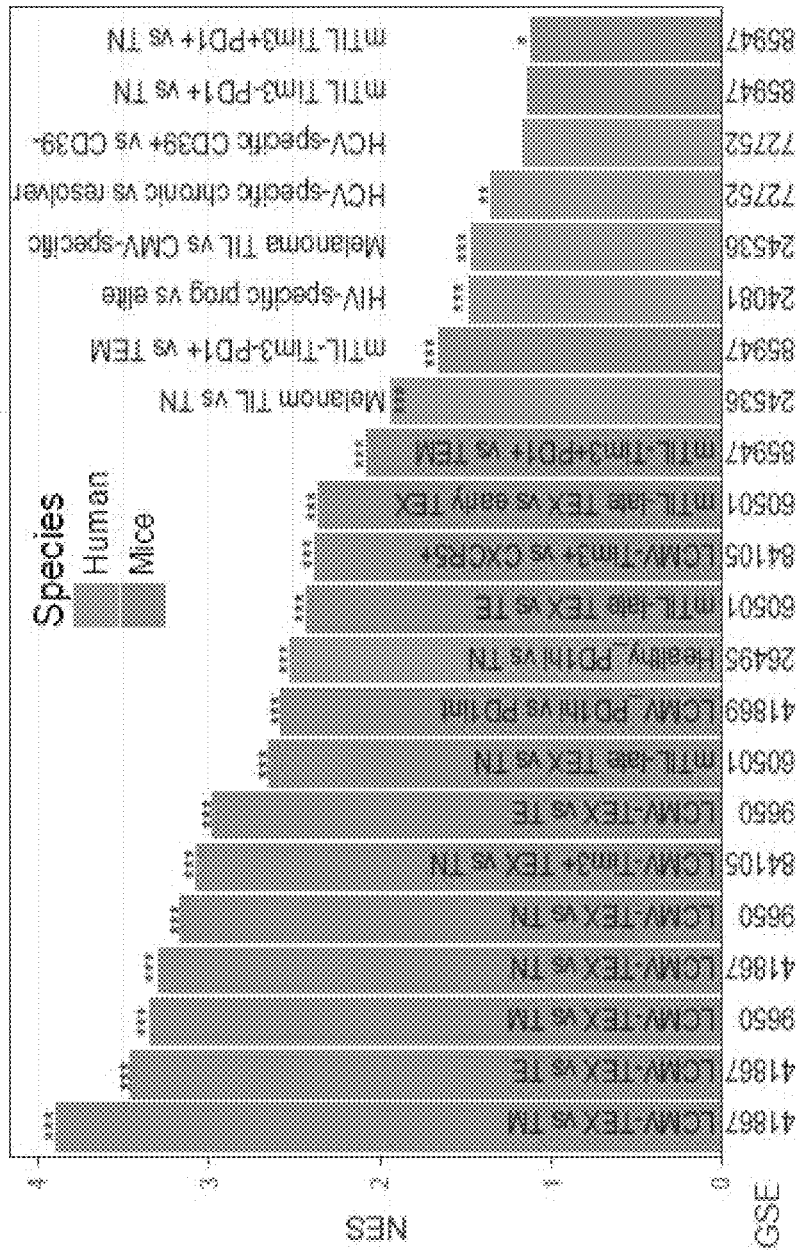
Figure 37H:
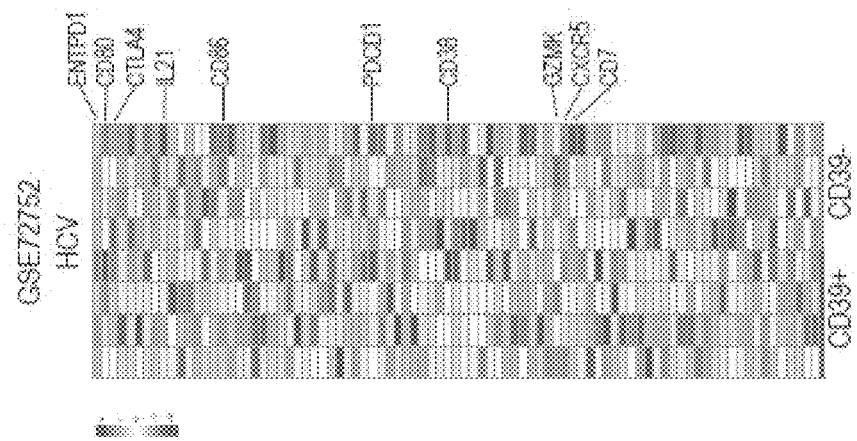
Figure 37G:
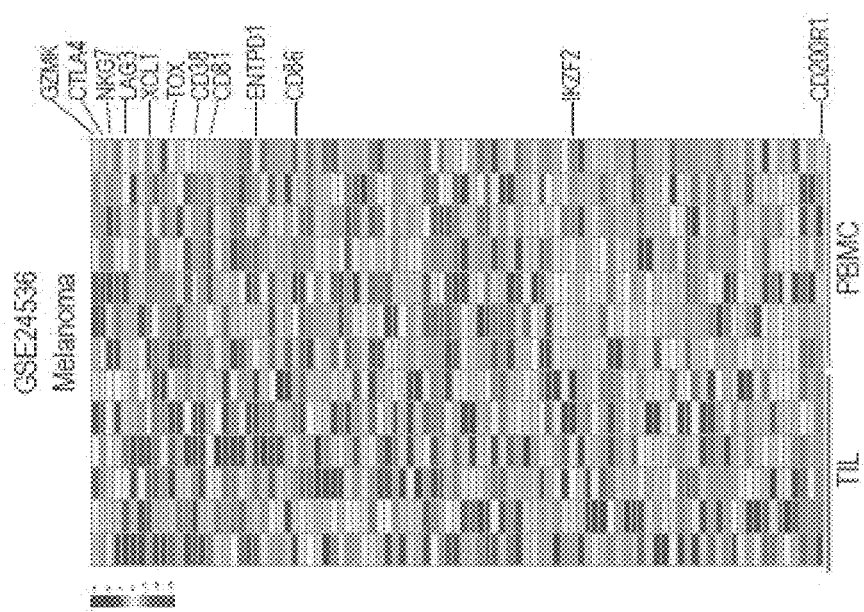

Thus, genes were identified that are specifically up- or down-regulated in virus-specific $T_{EX}$ during chronic LCMV infection compared to $T_N$, $T_{EFF}$, and $T_{MEM}$ in acute resolving LCMV Armstrong infection (FIGS. 37A, 37B). The focus was placed on genes highly biased to $T_{EX}$ compared to activation-related genes found in T. For example, Havcr1 encoding Tim-3 was more highly expressed in $T_{EFF}$ compared to $T_{EX}$ and, thus, was not included, in contrast to CD38 that was higher in $T_{EX}$ compared to T. The selection of genes was validated by Gene Set Enrichment Analysis (GSEA) (Subramanian et al. (2005) *Proc Natl Acad Sci USA* 102: 15545-15550) comparing $T_{EX}$ isolated after 30d of clone 13 infection to $T_{MEM}$, $T_{EFF}$ and $T_N$ (FIG. 37C). It was also investigated whether this signature would enrich in subsets of $T_{EX}$ (Blackburn et al. (2008) *Proc Natl Acad Sci USA* 105:15016-15021; Im et al. (2016) *Nature* 537:417-421; Paley et al. (2012) *Science* 338:1220-1225). GSEA showed strong enrichment in signatures of the more terminally exhausted $T_{EX}$ subset expressing high levels of PD-1 compared to the progenitor subset of $T_{EX}$ expressing lower levels of PD-1 (FIG. 37D). Analysis of Tim-3+ compared to CXCR5+ $T_{EX}$ revealed a similar enrichment in the more terminal Tim-3+ subset (FIG. 37D), in line with reports of more severe exhaustion in PD-1$^{hi}$ and Tim-3+ subsets of $T_{EX}$ ((Blackburn et al. (2008) *Proc Natl Acad Sci USA* 105: 15016-15021; Im et al. (2016) *Nature* 537:417-421). However, the genes selected also enriched in the less terminal subsets of $T_{EX}$ if these cells were compared to $T_{EFF}$ rather than terminal $T_{EX}$ suggesting high sensitivity of this signature. Moreover, this $T_{EX}$ signature strongly enriched in tumor infiltrating lymphocytes (TIL) from melanoma patients versus peripheral blood and in HIV-specific T cells from HIV progressor patients versus elite controllers (FIG. 37E), in agreement with previous reports (Baitsch et al. (2011) *J Clin Invest* 121:2350-2360). A number of exhaustion genes were enriched in elite controllers indicating that the signature also includes genes that might be useful for discriminating less dysfunctional exhaustion states (FIG. 37E). Extending these analyses to other transcriptomic datasets also identified more exhausted human T cell populations in silico such as CD39+ HCV-specific CD8 T cells (Gupta et al., 2015) (FIG. 37F). Leading edge analysis identified genes strongly contributing to the enrichment, including ENTPD1 (encoding CD39), CTLA4, PDCD1 and CD38 that were common to enrichment for TILs from melanoma and chronic HCV infection (FIGS. 37G, 37H). In sum, these analyses identified a transcriptomic signature of $T_{EX}$ in chronic LCMV infection that was shared across species and disease types. Moreover, the patterns of enrichment suggested that elements of this signature might be capable of distinguishing different features of exhaustion in distinct human diseases.

Example 11. Uniquely Regulated $T_{EX}$ Genes Identified by Epigenetic Changes

Remodeling of the epigenome underlies cellular fate decisions and controls stability of gene expression often in a lineage specific manner (Nashun et al. (2015) *EMBO J* 34:1296-1308). Thus, epigenetic patterns may be more faithful indicators of cell identity than gene expression. For example, in Th1 and Th2 cells, T-bet or GATA3 can be genetically removed but these CD4 T cells retain major epigenetic features of Th1 and Th2 identity (Vahedi et al. (2012) *Cell* 151:981-993). To date, signatures of $T_{EX}$ that co-integrate transcriptomic and epigenetic changes have not been developed. Without wishing to be bound by theory, one hypothesis is that genes uniquely up- or downregulated in $T_{EX}$ that also displayed $T_{EX}$-specific epigenetic changes (i.e. at open chromatin regions (OCR: e.g. enhancers)) may provide a more robust and stable signature of exhaustion. To test this hypothesis, enhancers were identified in $T_{EX}$ from chronic LCMV infection compared to $T_N$, Ti and $T_{MEM}$ using epigenomic profiling by Assay for Transposase-Accessible Chromatin with high throughput sequencing (ATAC-Seq) in GSE86797 and GSE87646 datasets (Pauken et al. *Science* 2016, 354(6316):1160-1165; Sen et al. *Science* 2016, 354(6316):1165-1169).

Figure 38A:
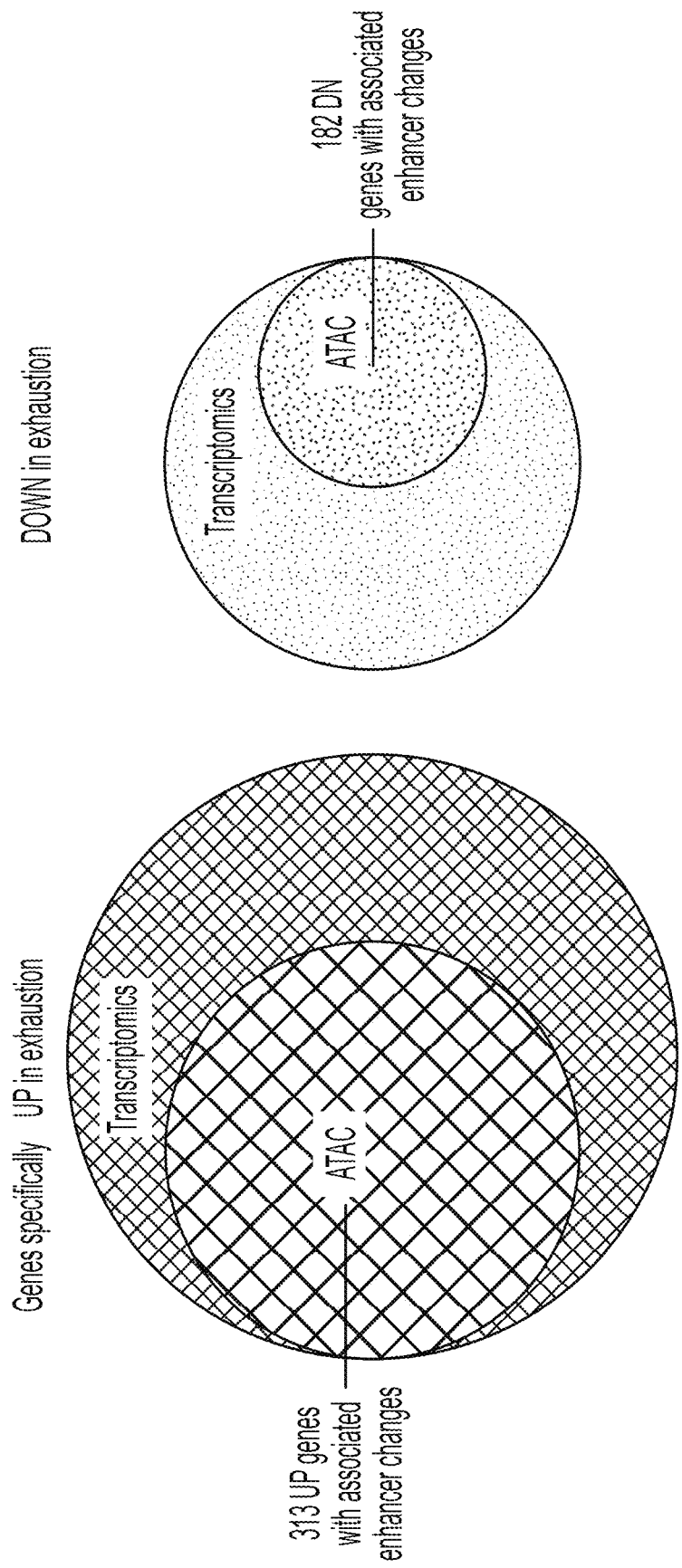
FIGS. 38A-38F illustrate uniquely regulated genes in exhaustion identified by specific epigenetic accessibility. Genes specifically regulated in $T_{EX}$ identified in FIG. 37, were analyzed for the presence of associated epigenetic changes in ATAC-seq datasets of $T_{EX}$, $T_N$, $T_{EFF}$, and $T_{MEM}$ in LCMV infection (GSE86797, GSE87646).
Figure 38B:
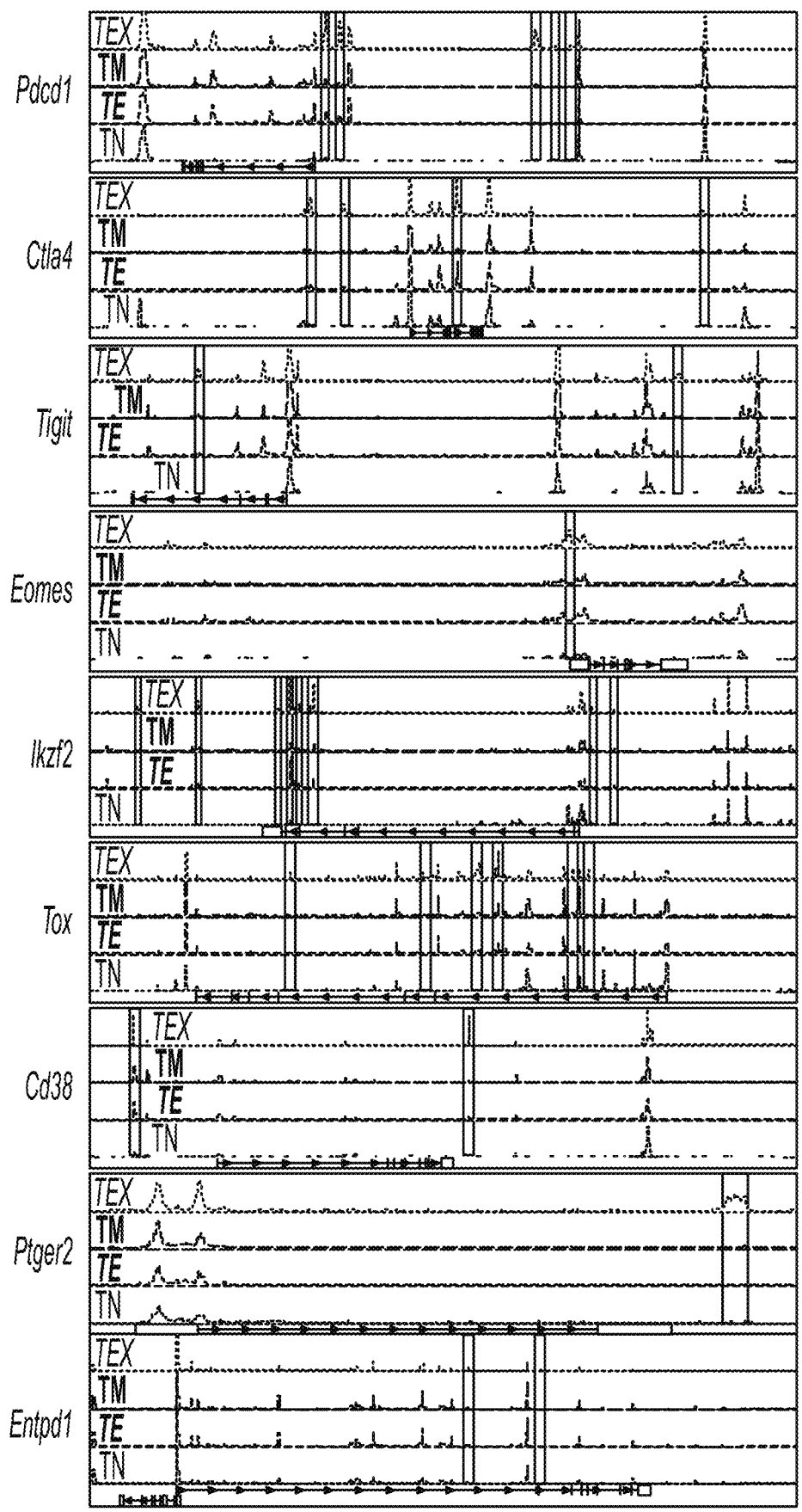
Figure 38C:
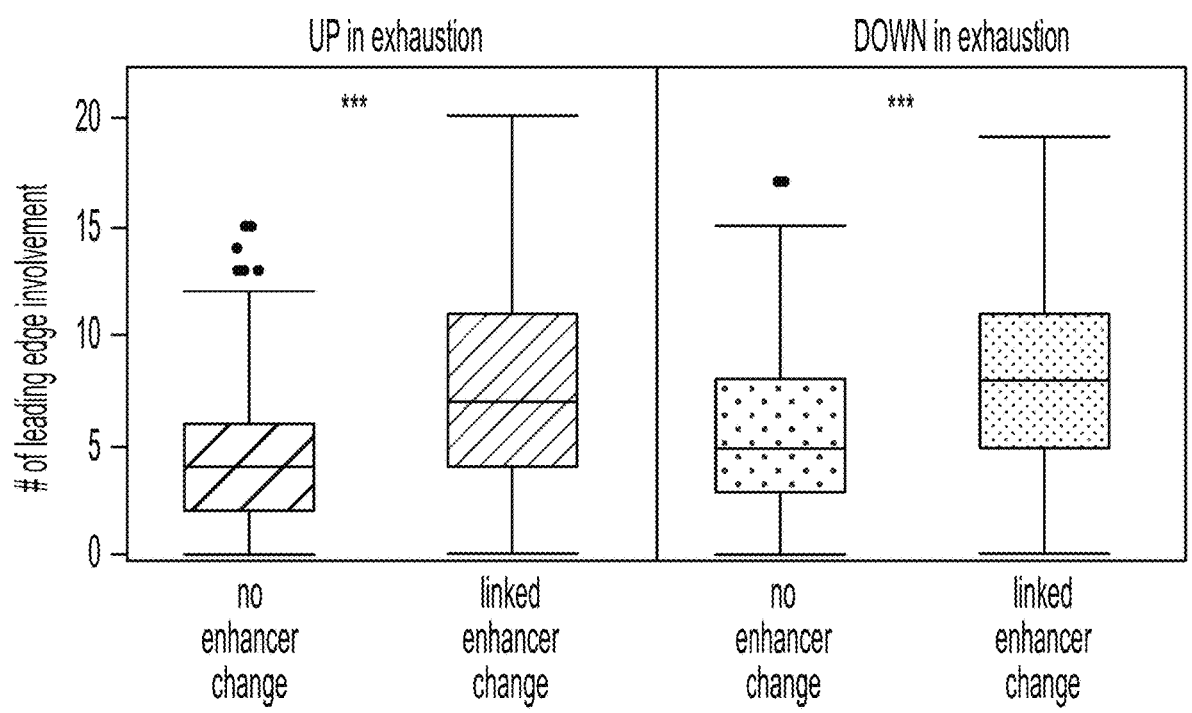
Figure 38D:
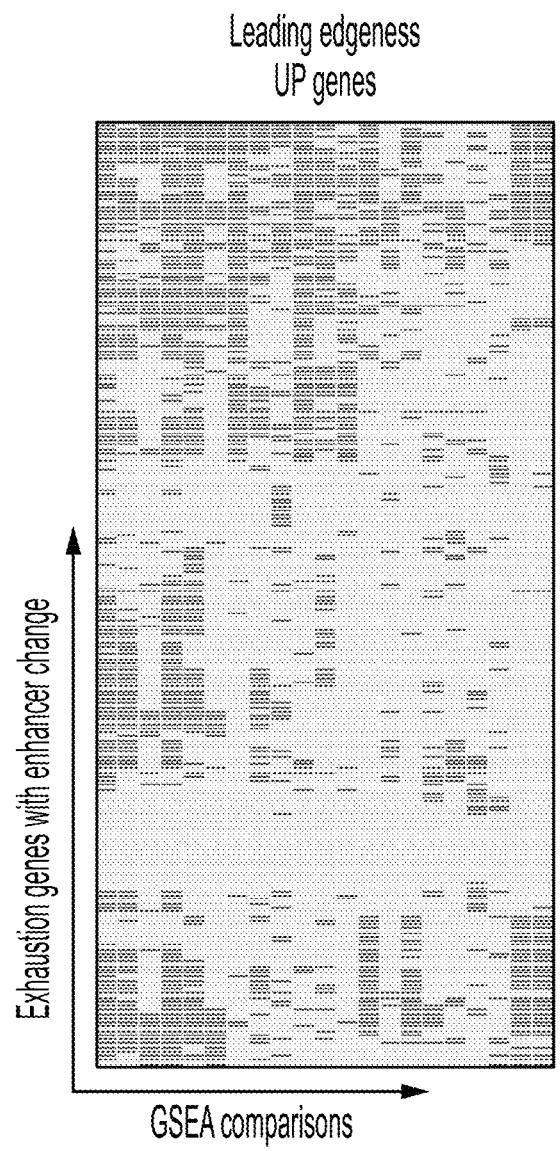
Figure 38E:
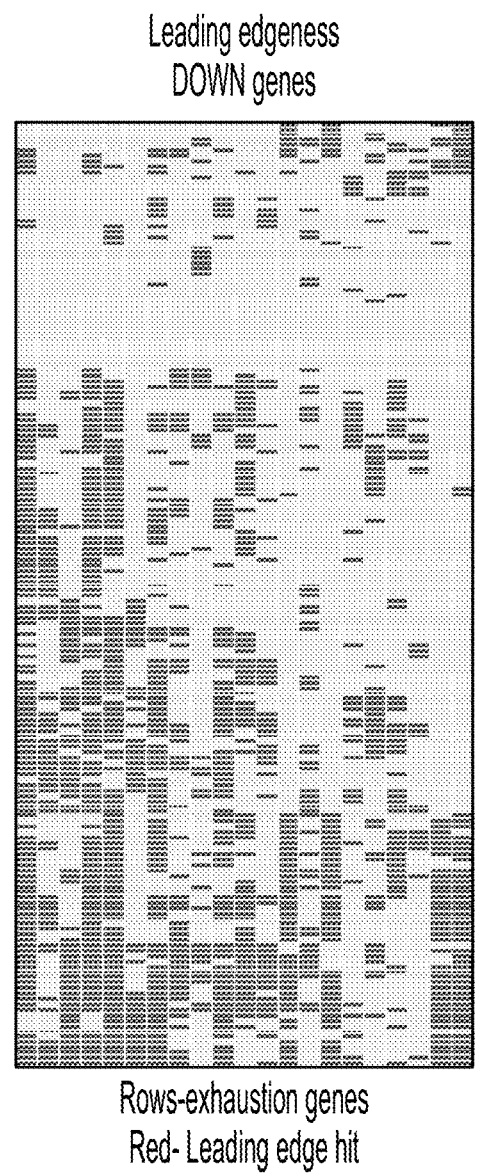
Figure 38F:
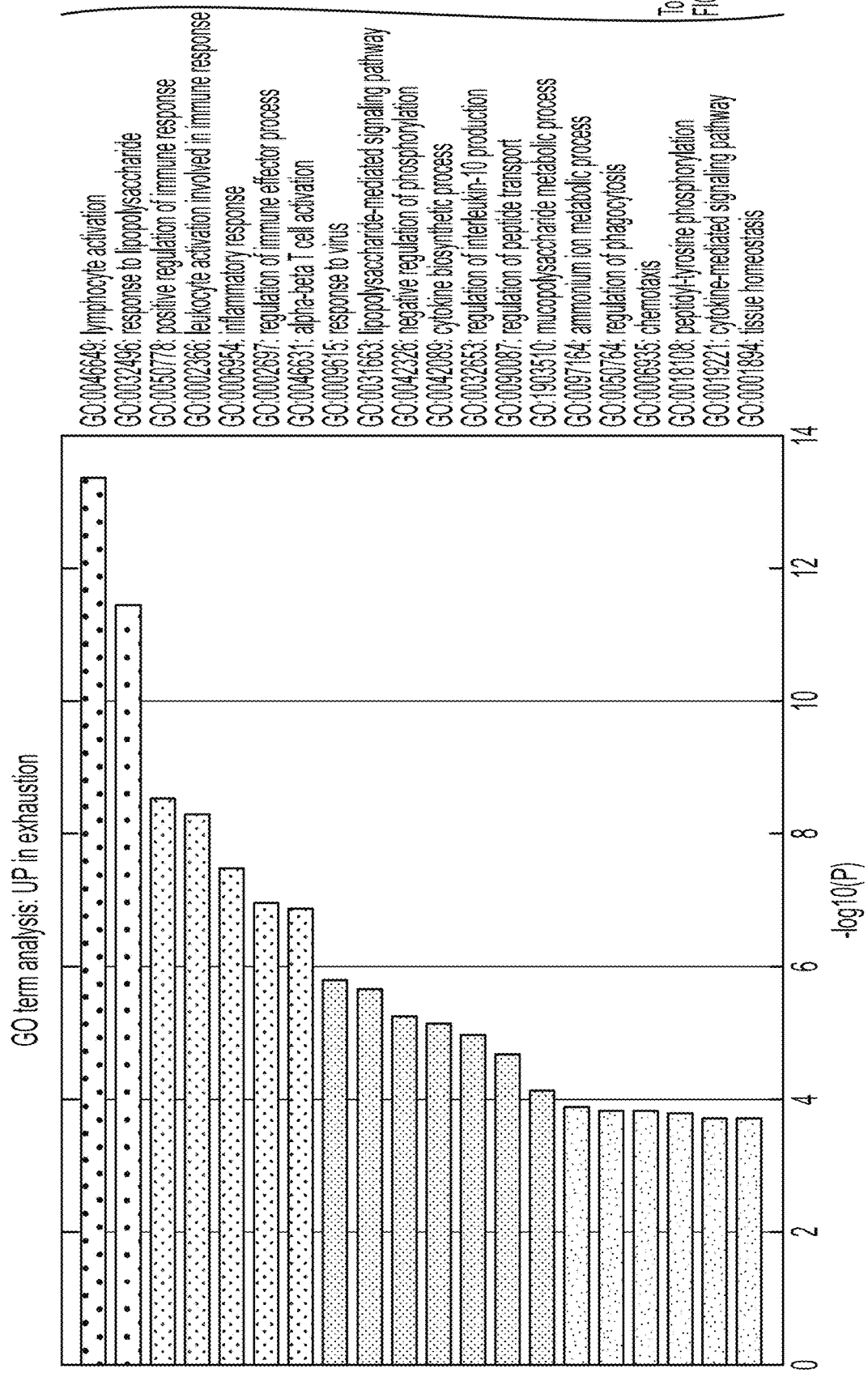
Figures 1, 38F:
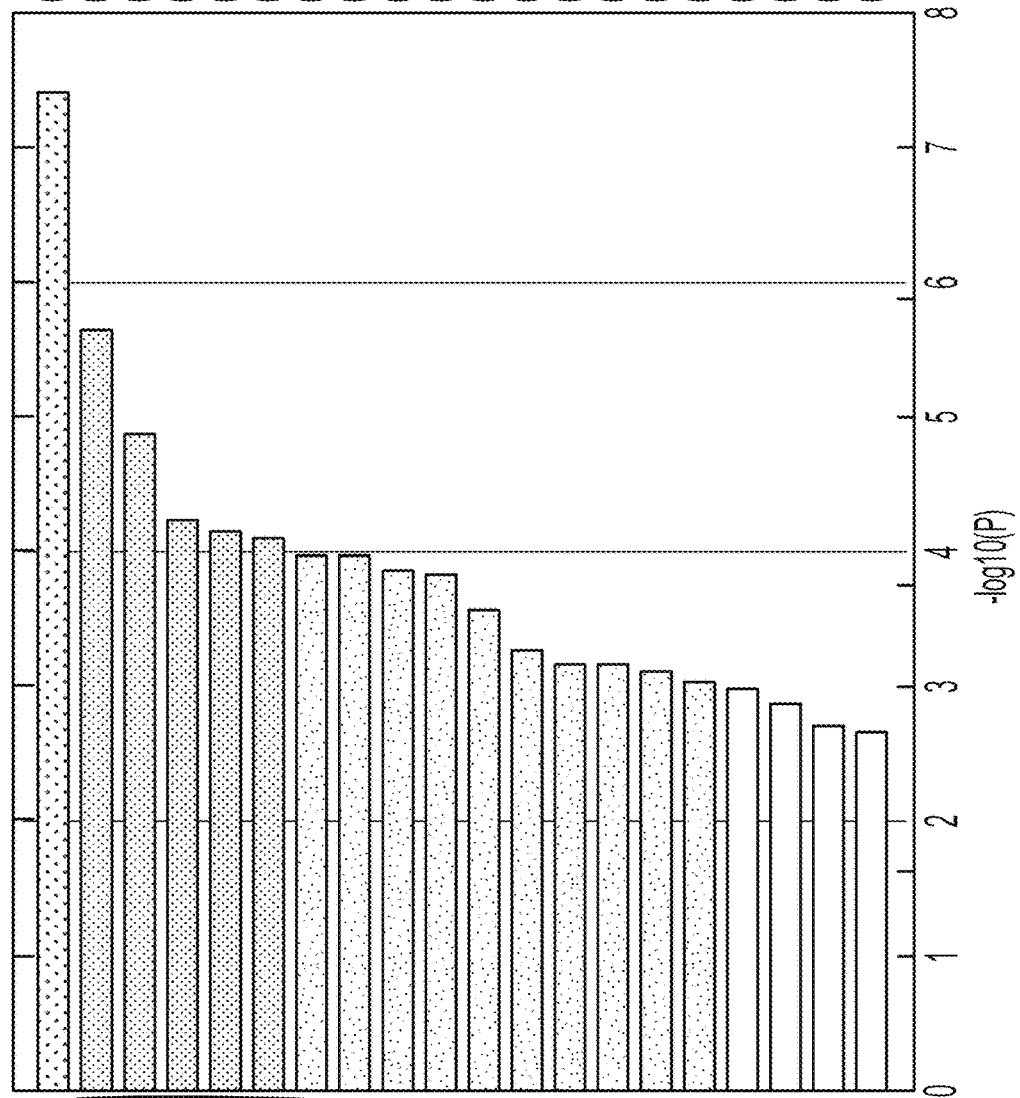

Starting with the differentially expressed genes identified in FIG. 37, 313 up-regulated and 182 down-regulated exhaustion specific genes also contained associated $T_{EX}$-related epigenetic (e.g. enhancer) changes (FIGS. 38A, 38B). These genes included those with more accessible OCR close to genes encoding IRs (e.g., Pdcd1, Tigit, Ctla4), ectoenzymes implicated in metabolic regulation (e.g. Cd38, Empd1), chemokines and cytokines (e.g. Xcl1) and transcription factors (e.g. Eomes, Ikzf2, Tox) (FIG. 38B). Genes with reduced accessibility of OCR linked to down-regulated expression in $T_{EX}$ (e.g., Ccr7, Il7r, Nt5e, Tcf7, Lef1) were also identified. $T_{EX}$ genes with associated OCR changes contributed significantly more frequently to the enrichments observed in the comparisons of $T_{EX}$ populations across diseases in FIG. 37 compared to genes without a $T_{EX}$-related epigenetic change. This feature was manifest by significantly higher GSEA leading edge contributions (FIGS. 38C, 38D, 38E). GO term analysis indicated that these "epigenomically selected" up-regulated exhaustion genes were enriched in immune activation and regulation of phosphorylation pathways, whereas down-regulated genes enriched for metabolic processes (FIG. 38F), in line with known biology of $T_{EX}$. These data indicate that key genes distinguishing $T_{EX}$ from canonical T cell subsets are revealed by a combination of unique transcriptomic expression patterns and associated epigenetic changes. Thus, these uniquely regulated genes are strong candidates for biomarkers of exhaustion across diverse disease types.

Figure 39B:
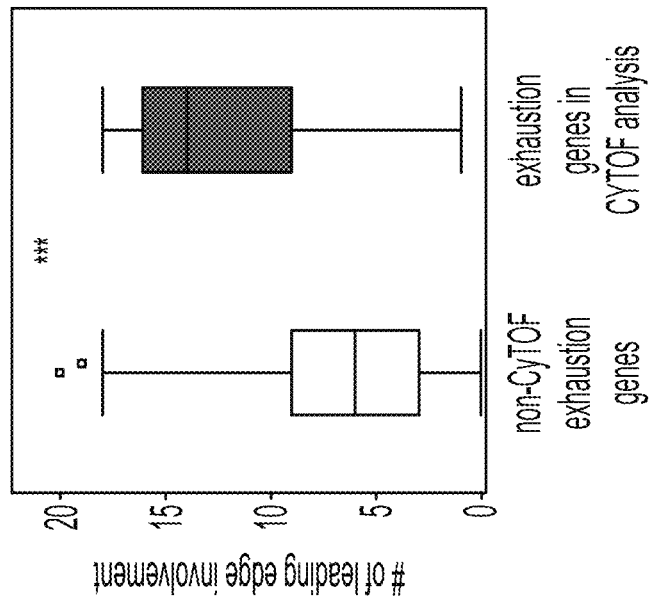
FIGS. 39A-39F illustrate mass cytometry analysis of exhaustion molecule expression.
Figure 39A:
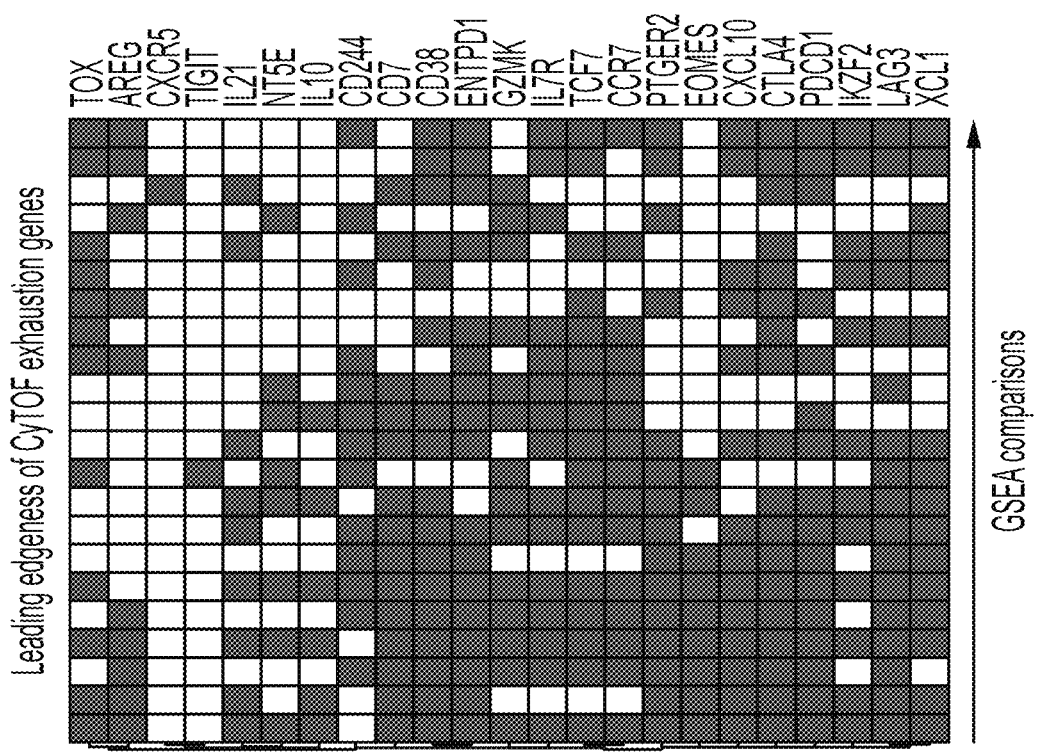
Figure 44:
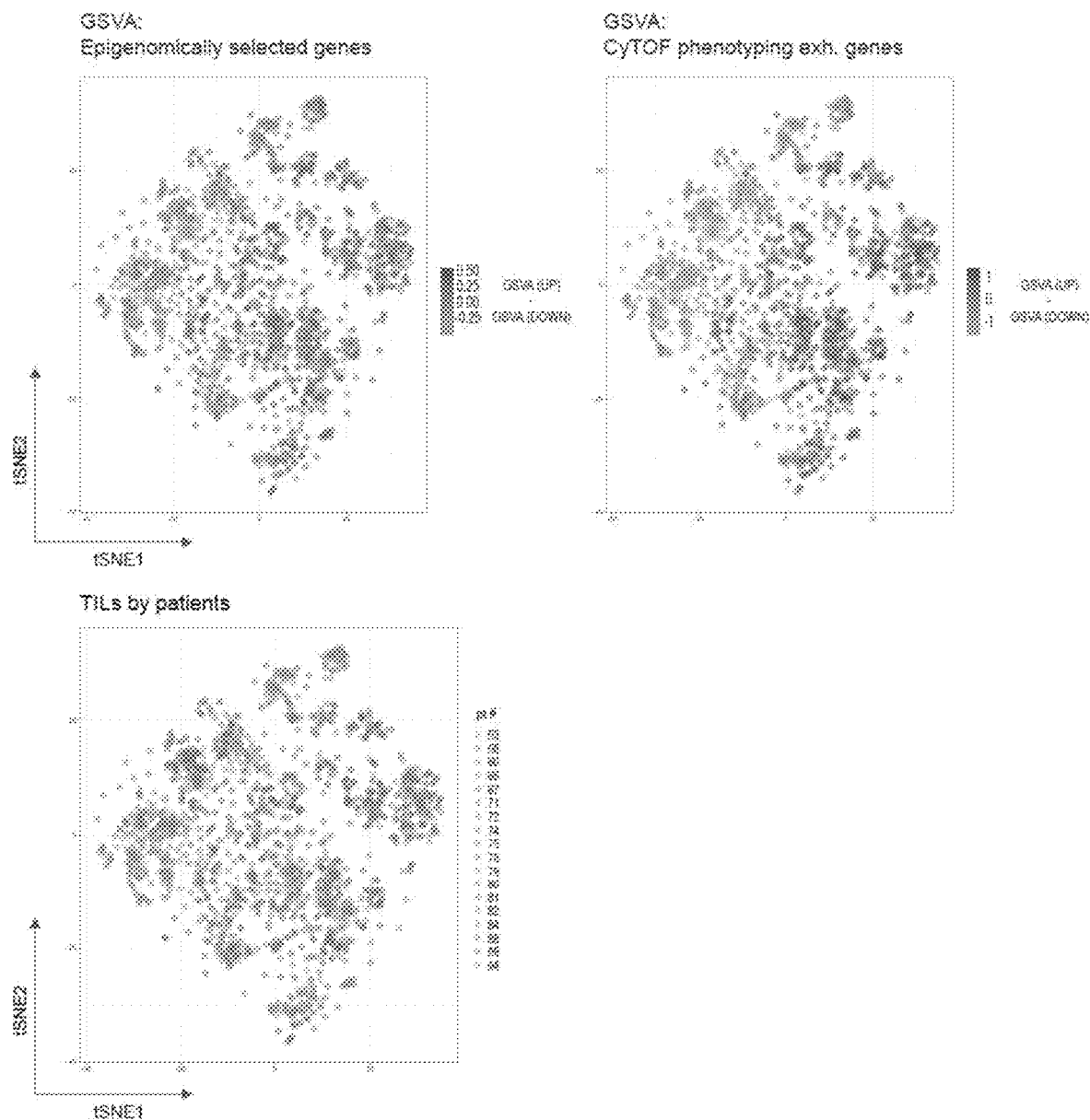
FIG. 44 illustrates evaluating epigenomically-selected and CyTOF-panel subset of $T_{EX}$ genes in single-cell (sc) transcriptome data from tumor microenvironment (TME). CD8 single-cell RNA-seq data from human melanoma were extracted from GSE72056 (www.ncbi.nlm.nih.gov/geo/query/acc.cgi?acc=GSE72056) and arranged in 2D by tSNE analysis. Next, Gene-set variation analysis (GSVA) of single-cell data was performed using the full epigenomically—and transcriptomically defined exhaustion gene list or a subset of genes later analyzed by CyTOF. The results of the GSVA analysis using the UP- and DOWN-regulated gene lists were then subtracted (GSVA_score_UP−GSVA_score_DN) for each cell and displayed in heatmap fashion on the tSNE representation, resulting in a relative estimate of the strength of the exhaustion signatures in the single-cell TIL data (Left and middle panel). In the right panel, CD8 TIL single-cell data is displayed for individual patients as reported by Tirosh et al. (2016) Science 352:189-196.

Example 12. CD8 T Cells Expressing Exhaustion Genes are Biomarkers of HIV Disease Progression $T_{EX}$ are a hallmark of chronic HIV infection and severe exhaustion has been reported in advanced HIV disease when the CD4/CD8 ratio declines and viral load is elevated (Buggert et al. (2014)*J Immunol* 192:2099-2108; Hoffmann et al. (2016) *PLoS Pathog* 12, e1005661; Serrano-Villar et al. (2014) *PLoS Pathog* 10, e1004078). Without wishing to be bound by theory, a hypothesis is that converting the population-based epigenomic exhaustion signature defined above to a single-cell profiling approach could provide insights into the diversity of $T_{EX}$ in HIV disease. A mass cytometry panel was thus constructed that integrated 16+ epigenomically-selected exhaustion-related genes together with other T cell markers for defining lineage and other differentiation states. The genes selected for further analysis by CyTOF were chosen, in part, based on the availability of high quality antibodies for cytometry analysis. Many other potentially interesting epigenomically-selected genes are also available for future analyses including ADAM19, BHLHE41, DUSP4, GLP1R, GPR65, GPR155, 1E127, IFI44, PRDM1, PTPN13, RGS16, SLC22A15, among others. The exhaustion genes encoding proteins selected for this CyTOF panel had a high leading edge contribution to the enrichment of the exhaustion signature in different diseases indicating that even this subset of genes was emblematic of key features of exhaustion (FIGS. 39A, 39B). To interrogate whether these selected genes/proteins had discriminatory potential in single-cell datasets and to test how the 16 $T_{EX}$ targets selected for the CyTOF panel compared to the larger epigenomically selected list, Gene Set Variation Analysis (GSVA) of a recently published CD8 T cell single-cell transcriptomic dataset from human melanoma tumor infiltrating lymphocytes (TTh) (Tirosh et al. (2016) *Science* 352:189-196) was used. These analyses indicated that: a) both the total epigenomically selected genes, and the CyTOF selected gene set discriminated considerable variation in the scRNA-seq data that corresponded to samples from different patients, and b) the genes selected for CyTOF analysis had similar discriminating potential to the larger epigenomically selected gene list (FIG. 44).

Figure 39C:
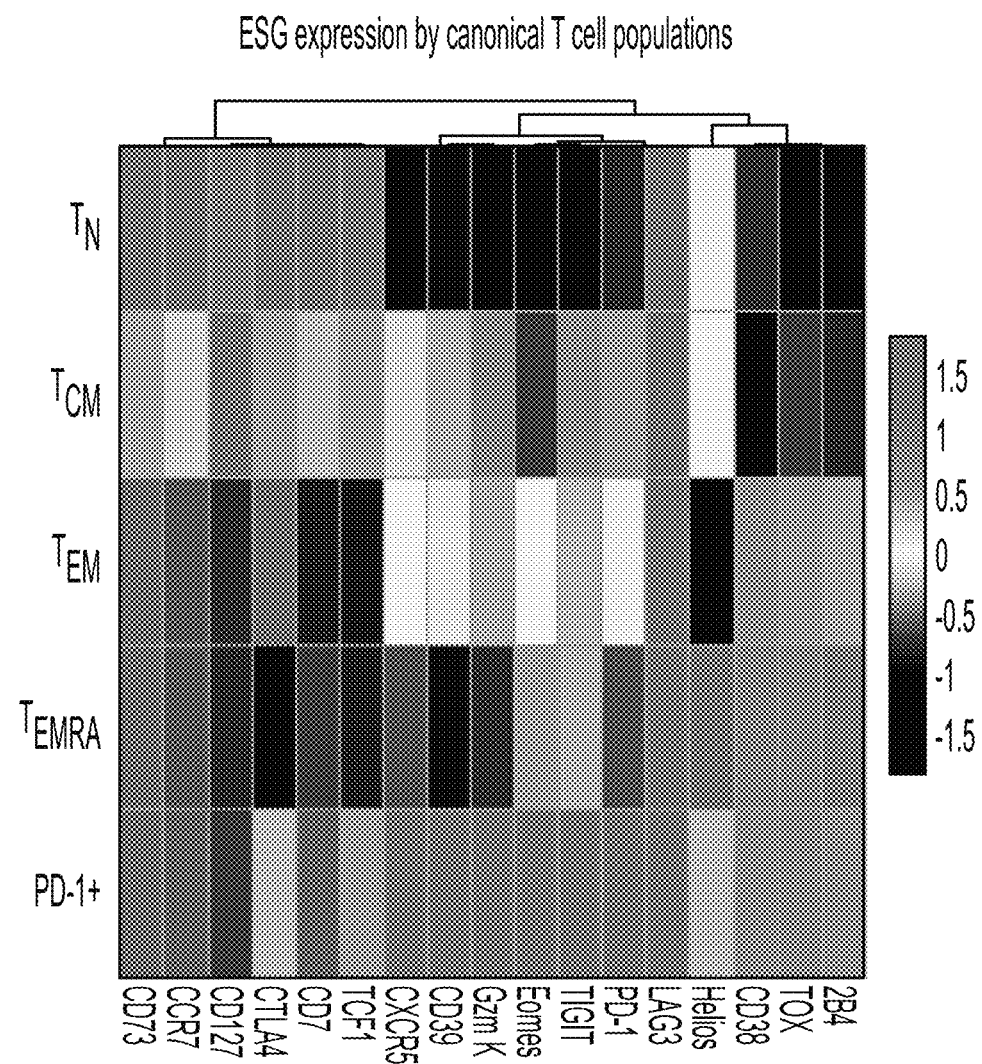
Figure 39D:
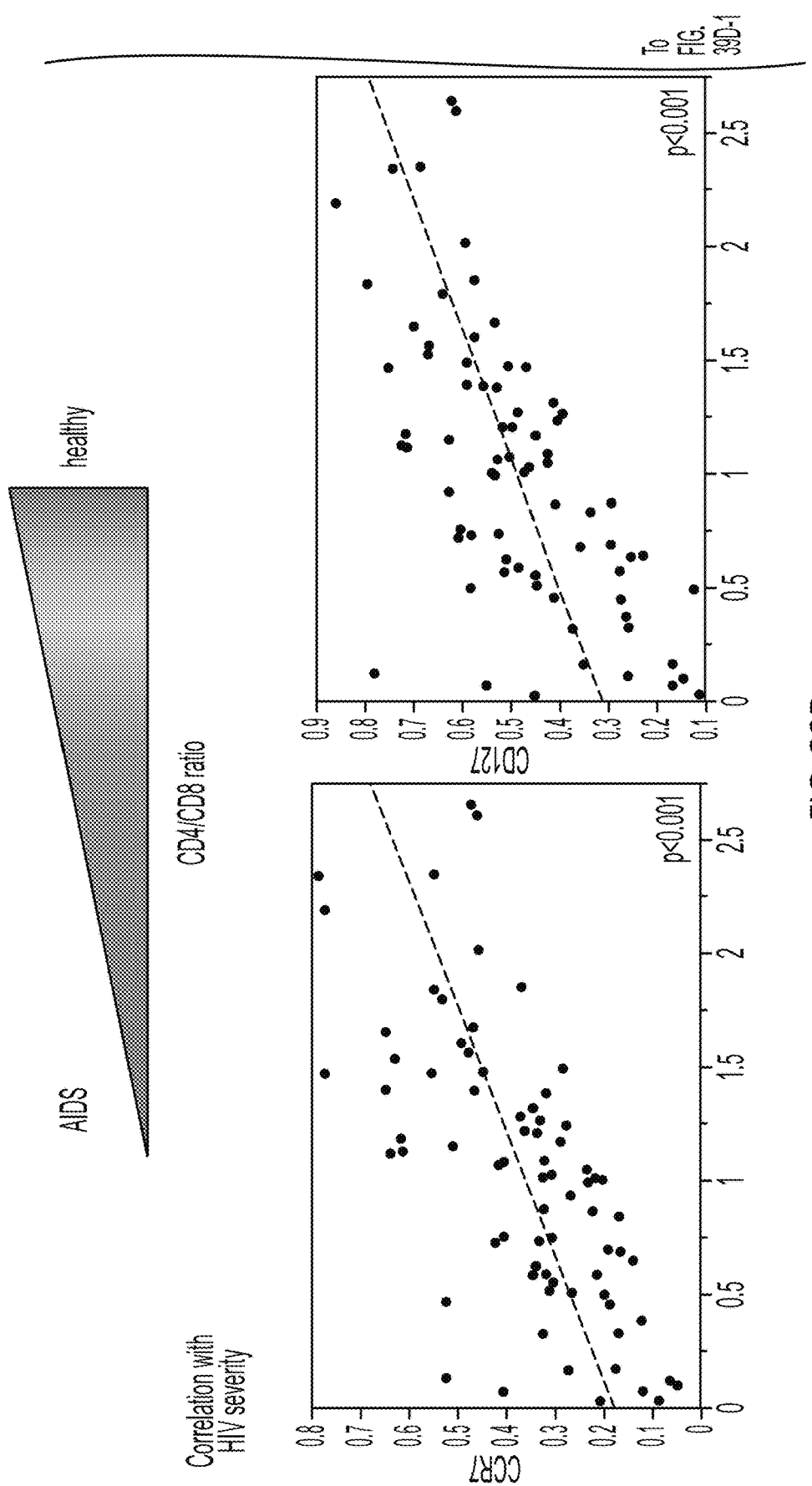
Figures 1, 39D:
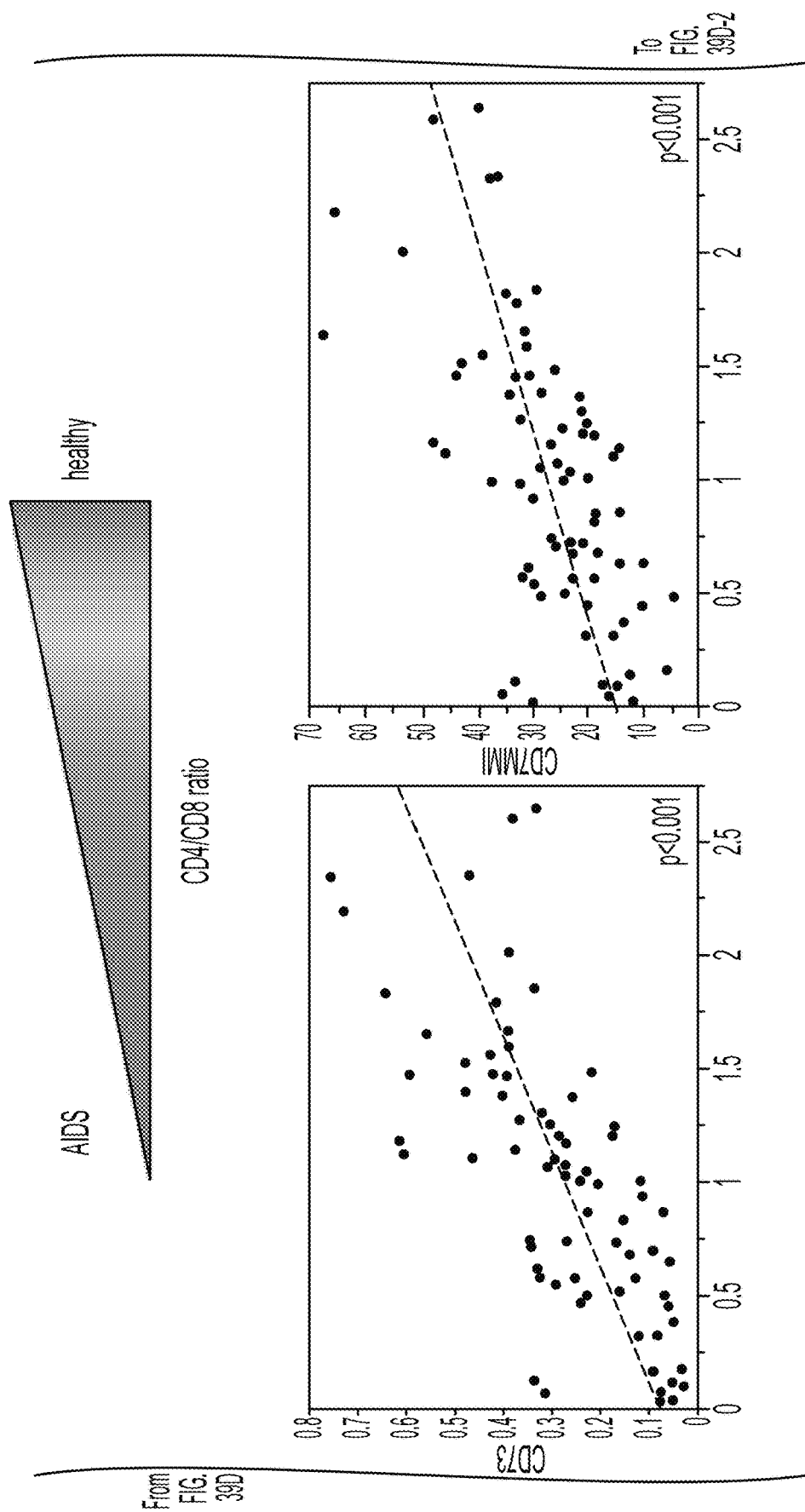
Figures 2, 39D:
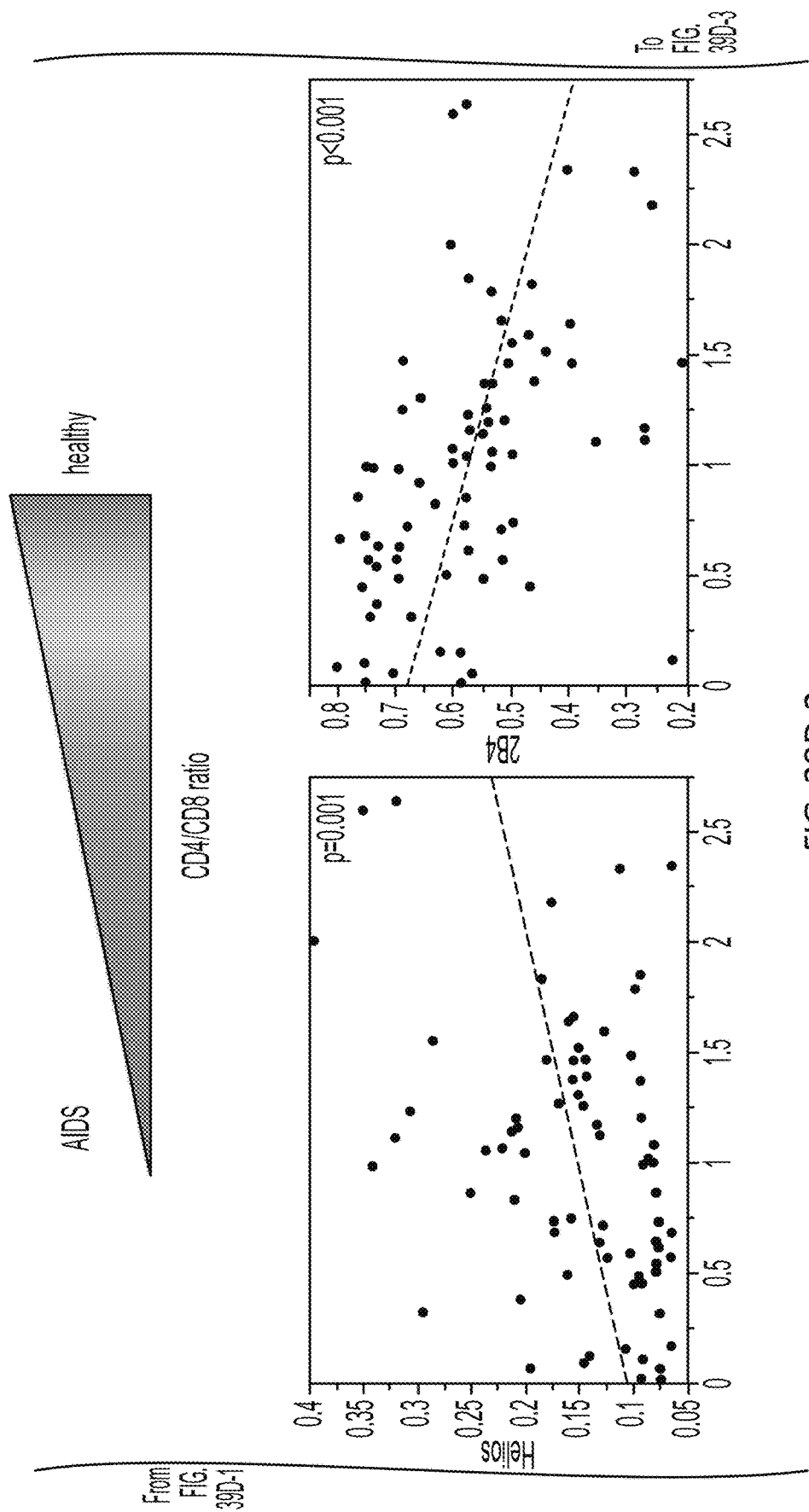
Figures 3, 39D:
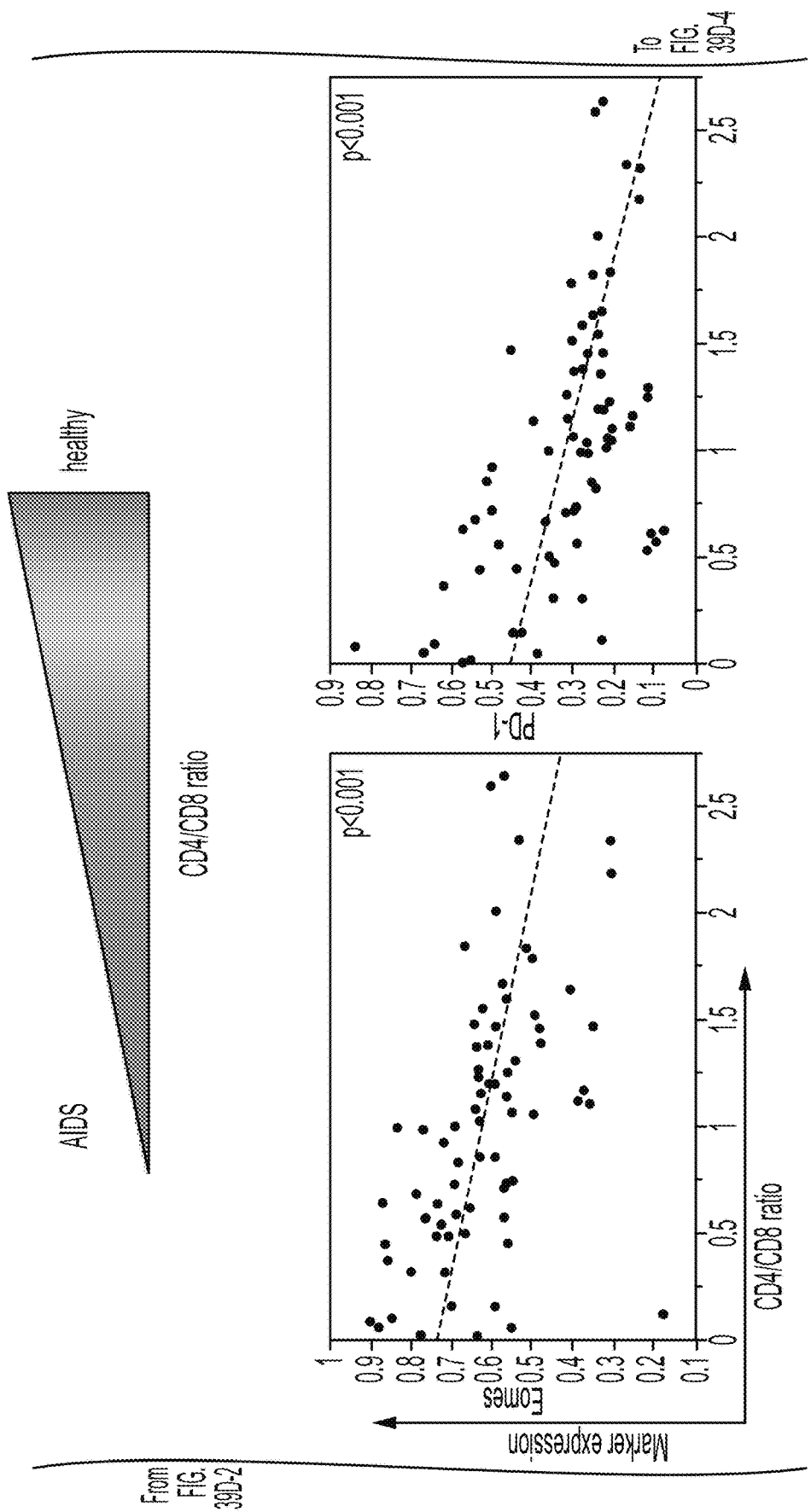
Figures 4, 39D:
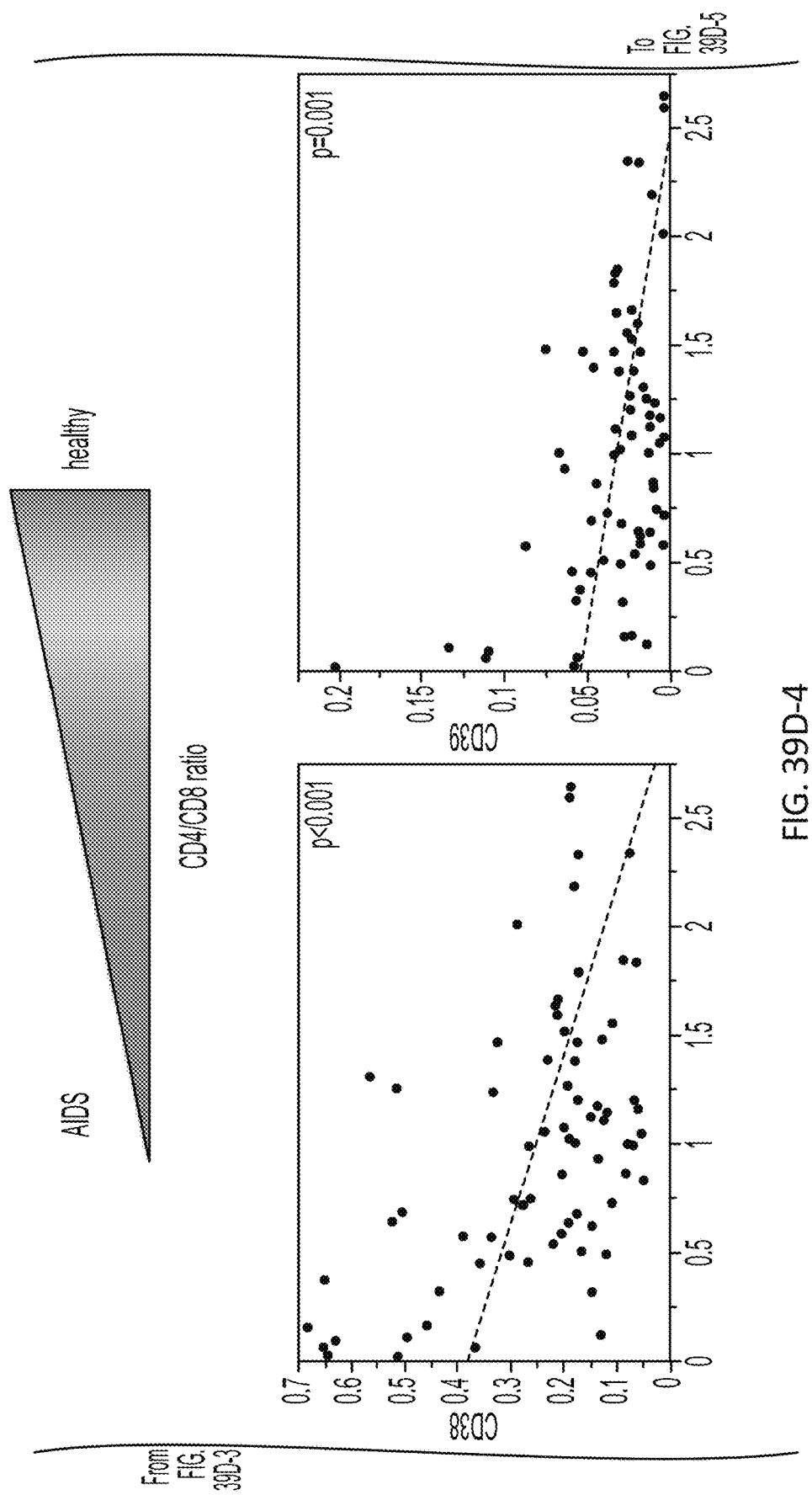
Figures 5, 39D:
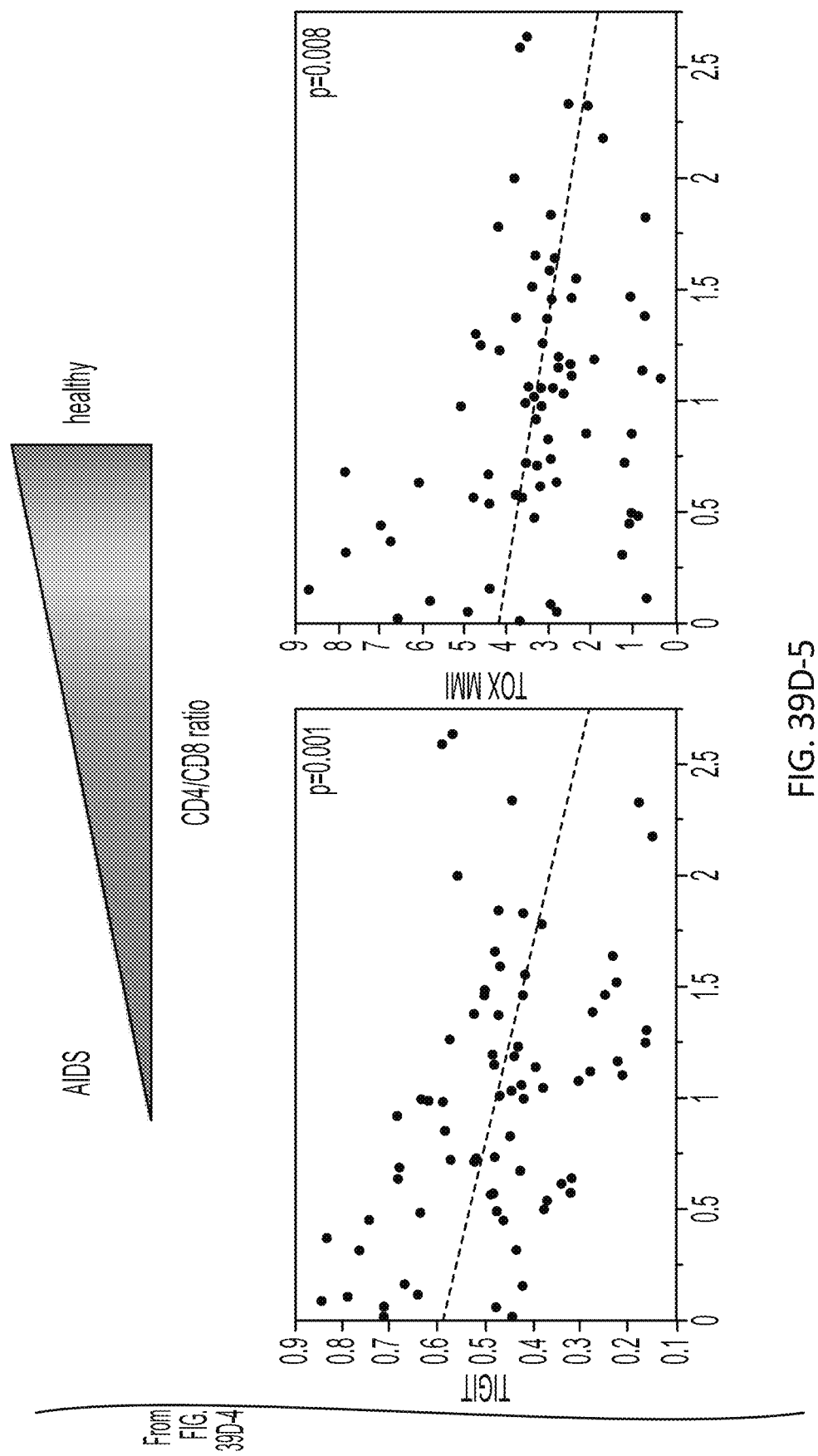

This CyTOF panel was then applied to analysis of PBMC from a cohort of healthy control subjects and patients with active HIV infection as well as HIV patients on anti-retroviral therapy (ART). In later analyses, samples from lung cancer patients were included, including PBMC cells from macroscopically uninvolved lung tissue and TIL from the lung tumors. Classically defined $T_N$, $T_{EFF}$, effector memory ($T_{EM}$), central memory ($T_{CM}$) and terminally differentiated effector memory RA ($T_{EMRA}$) CD8 T cell populations were examined as well as PD-1+ CD8 T cells for the expression of epigenomically-selected exhaustion markers in this CyTOF panel (FIGS. 39C, 39D). PD-1+ cells expressed many more of the $T_{EX}$ markers than any of the other phenotypically defined CD8 T cell populations, whereas $T_N$ and $T_{CM}$ expressed molecules downregulated by $T_{EX}$ (FIG. 39C).

Figure 39E:
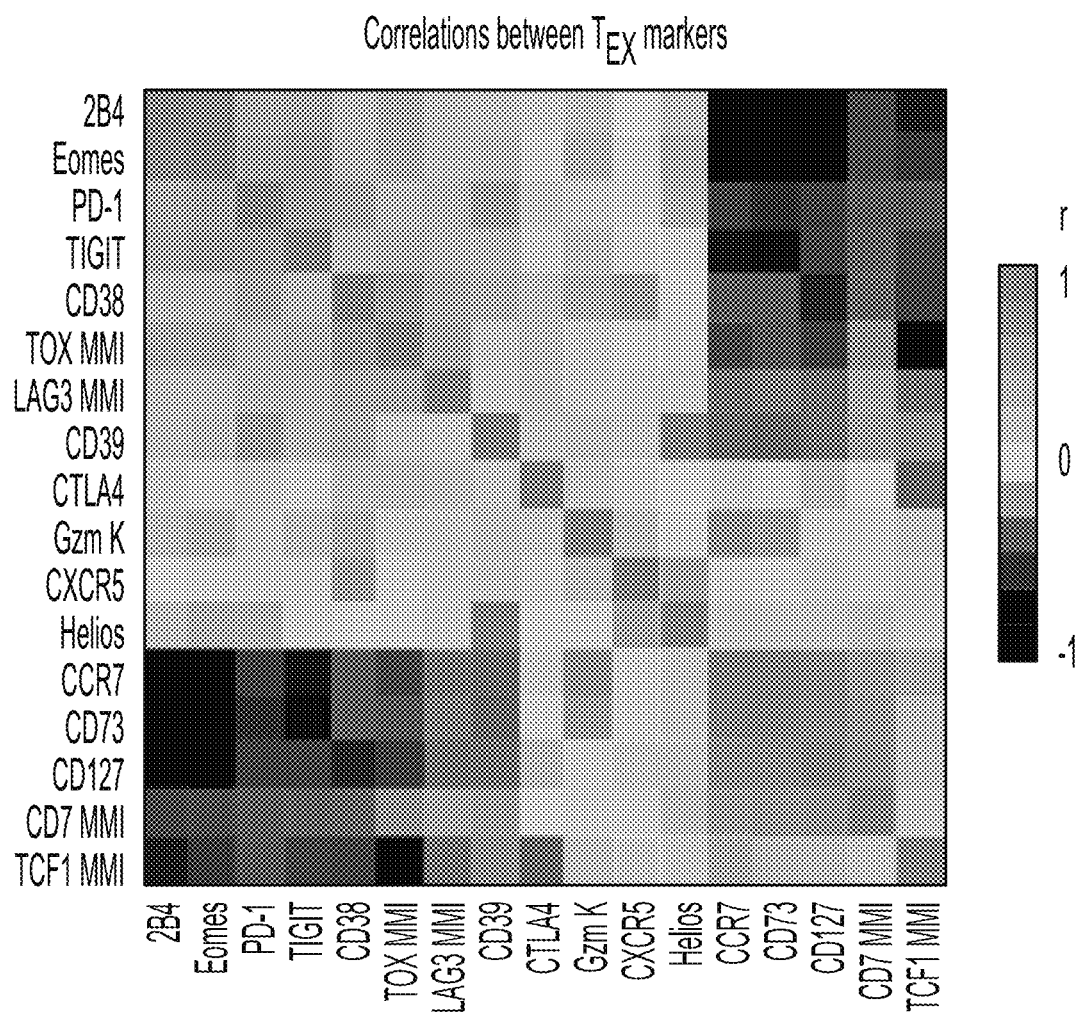
Figure 39F:
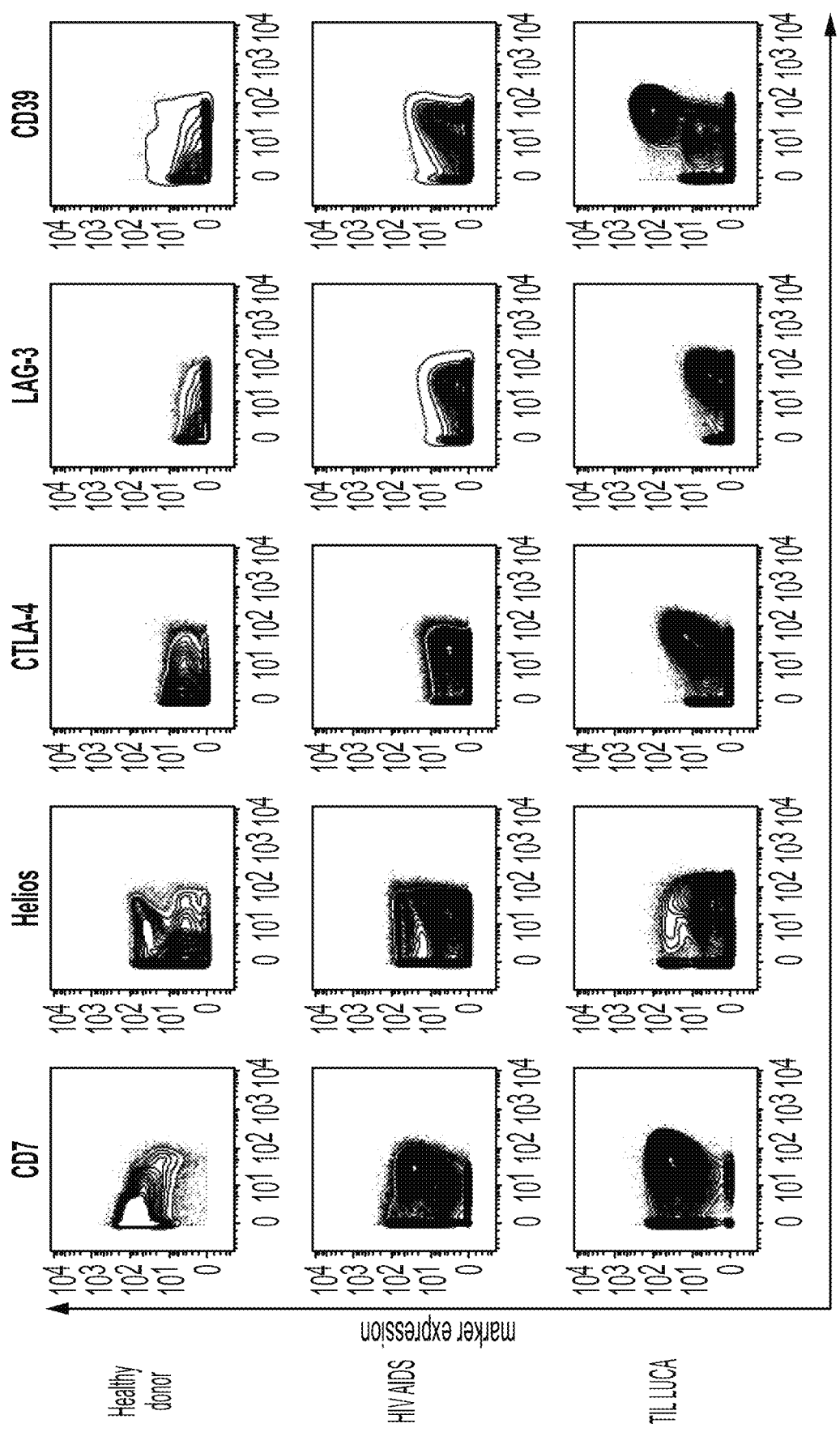
Figure 46A:
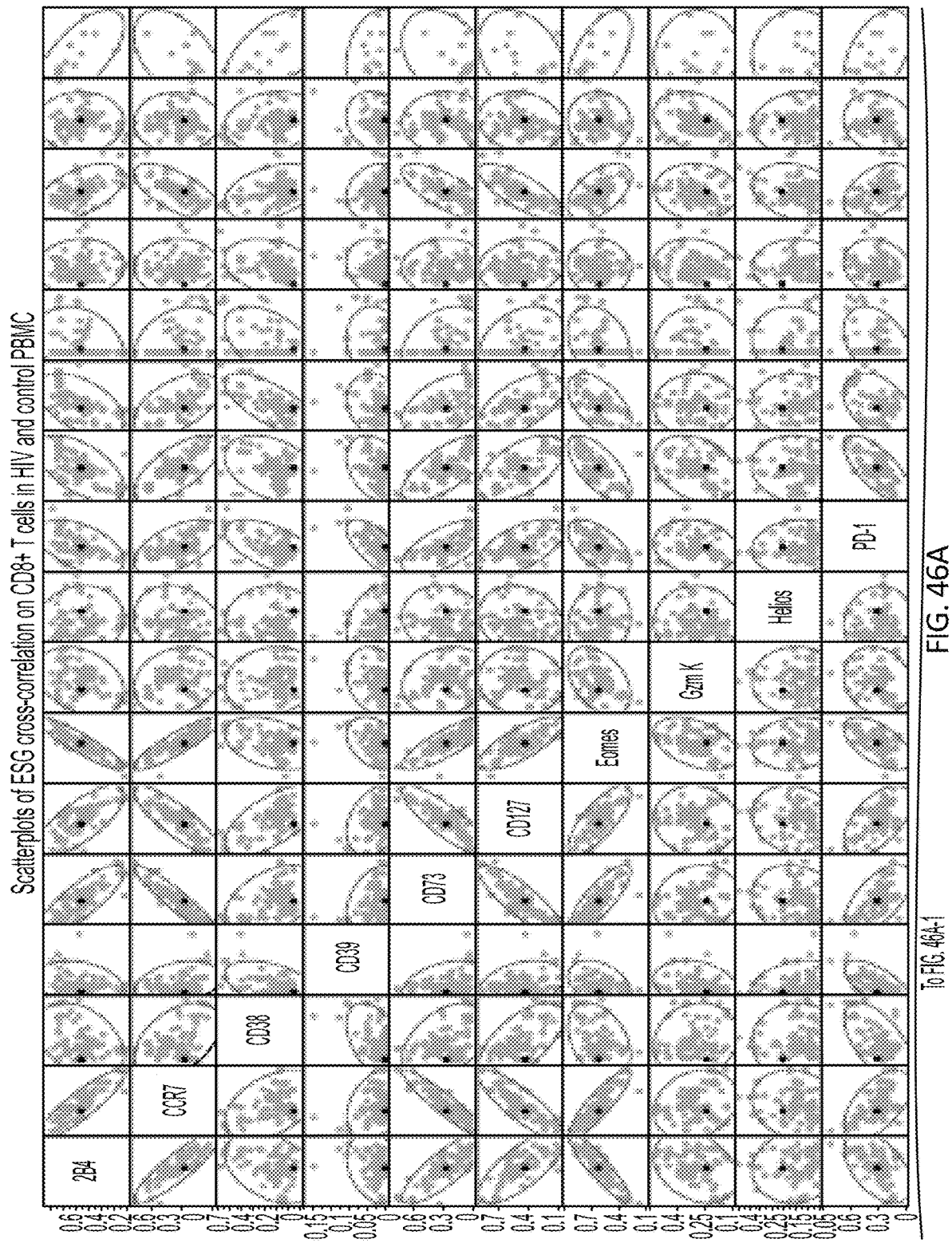
FIGS. 46A-46B illustrate that exhaustion marker expression for peripheral CD8 T cells which was analyzed in FIG. 39 was further analyzed for cross-correlation of marker expression estimated by pairwise method as shown in heatmap FIG. 39E.
Figures 1, 46A:
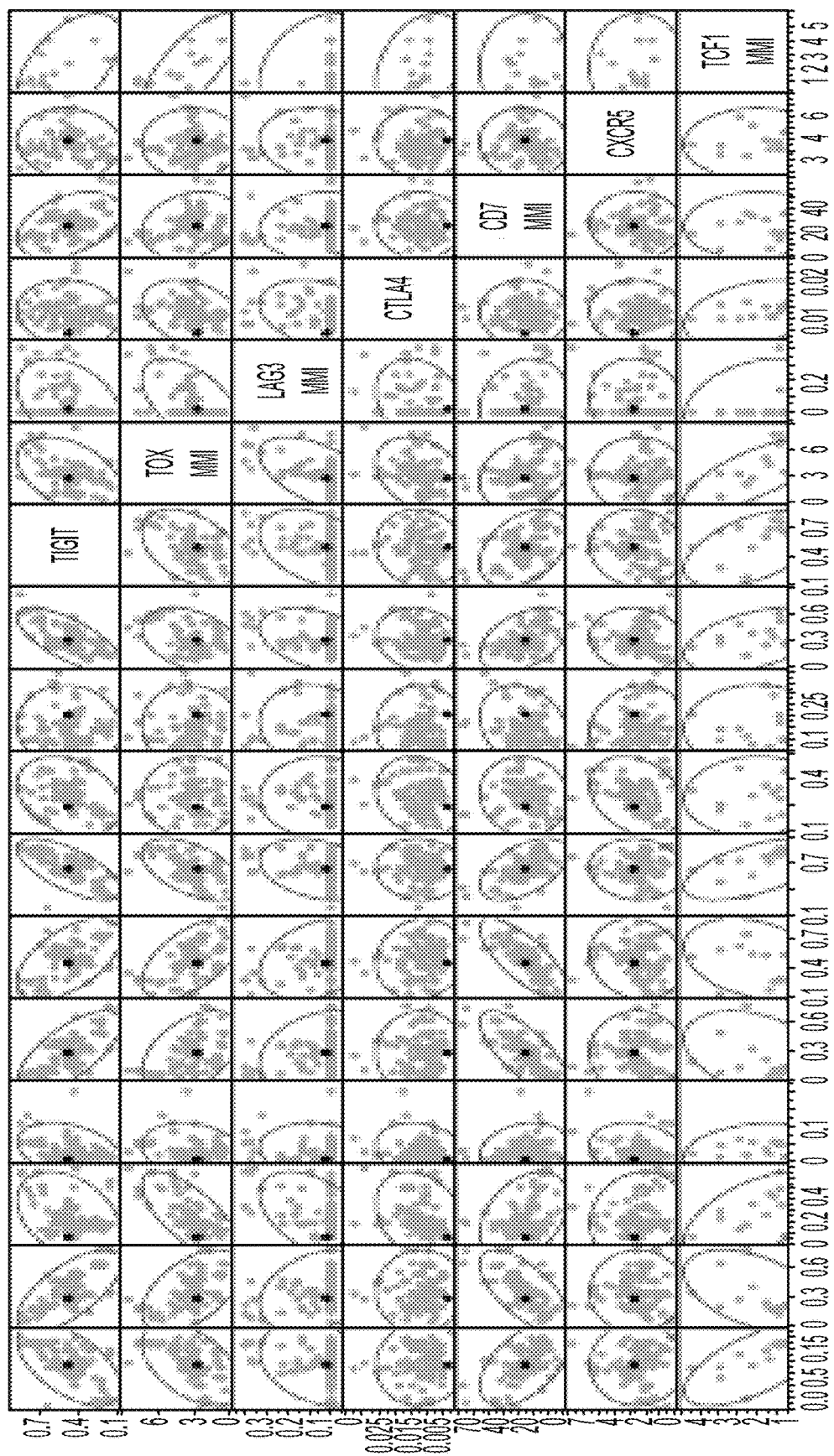
Figure 46B:
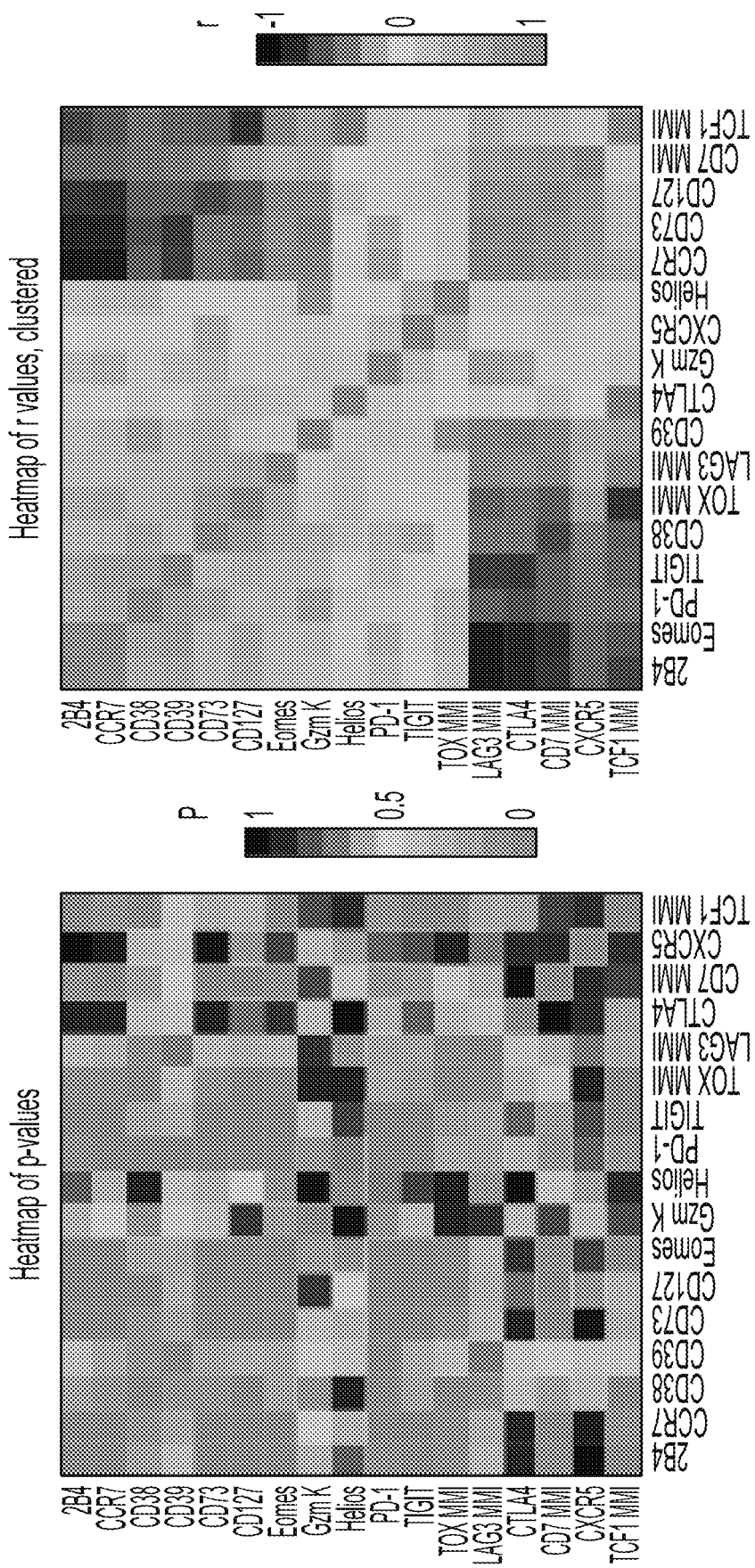

The correlation between expression of individual exhaustion molecules with the CD4/CD8 ratio was examined, as an established metric of immune dysregulation and progressive HIV disease (FIG. 39D). Molecules predicted to be down in $T_{EX}$ correlated with health, mild disease, and a higher CD4/CD8 ratio (e.g. CCR7, CD73, CD127), whereas molecules predicted to be up in $T_{EX}$ were correlated with low CD4/CD8 ratios indicating advanced disease (e.g. 2B4, CD38, CD39, Eomes, PD-1, TIGIT, TOX) (FIG. 39D; FIG. 45). Correlation matrix analysis identified sets of highly co-regulated exhaustion-related molecules in HIV, such as PD-1, Eomes, 2B4, TIGIT and CD38 (FIG. 39E, FIG. 46). Several of these molecules, (i.e. CD38 and PD-1) are known indicators of immune activation and/or exhaustion in progressive HIV infection (Cockerham et al. (2014) *AIDS* 28:1749-1758). Some markers predicted to be up-regulated in exhaustion did, however, only display trends towards enrichment in severe HIV (LAG-3, CTLA-4), or were even associated with less severe disease (CD7, Helios), suggesting that exhaustion in severe HIV infection involves more complex single-cell phenotypes poorly captured by the analysis of single markers. Indeed, for individual patients with HIV-AIDS or lung cancer more extreme $T_{EX}$ phenotypes existed that were identified, for example, by co-expression of CD7 and PD-1 (FIG. 39F). Moreover, other molecules that displayed no obvious, negative (CTLA-4, LAG-3, CD39) or a complex (Helios) co-expression pattern with PD-1 in healthy subjects became positively associated with PD-1 in disease pointing towards the need for high-dimensional analysis of $T_{EX}$.

Figure 40A:
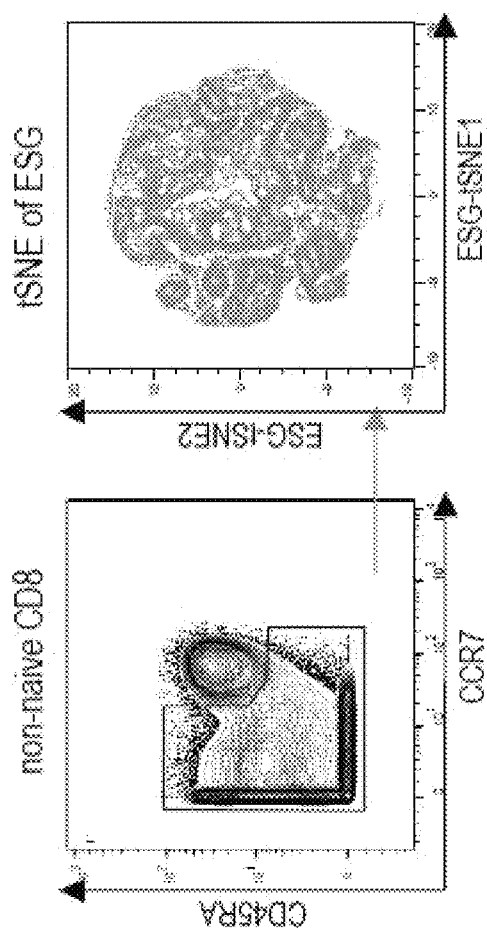
FIGS. 40A-40G show that an exhaustion map allows comparison of $T_{EX}$ states across HIV and lung cancer.
Figure 40B:
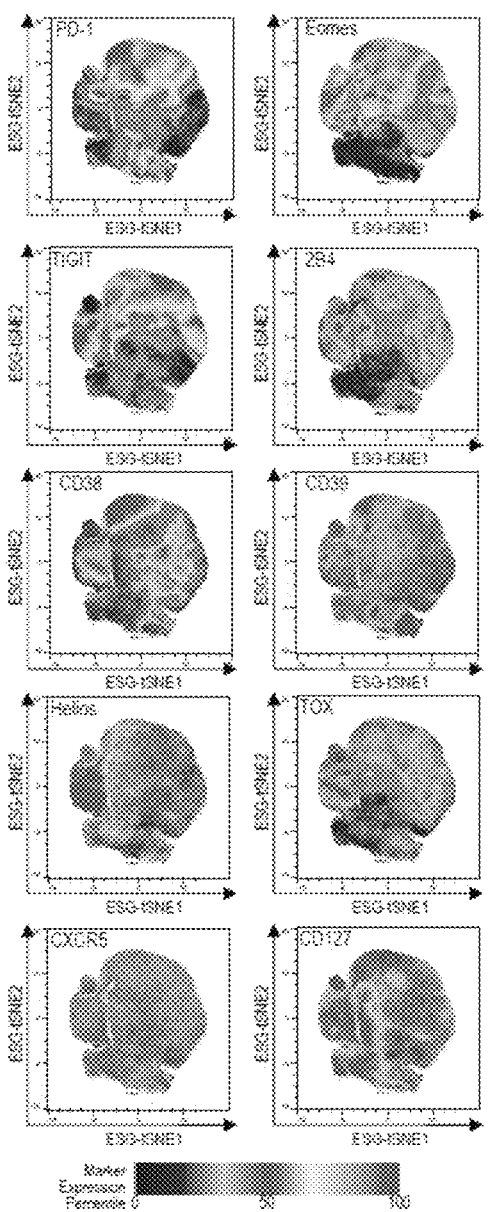
Figure 40C:
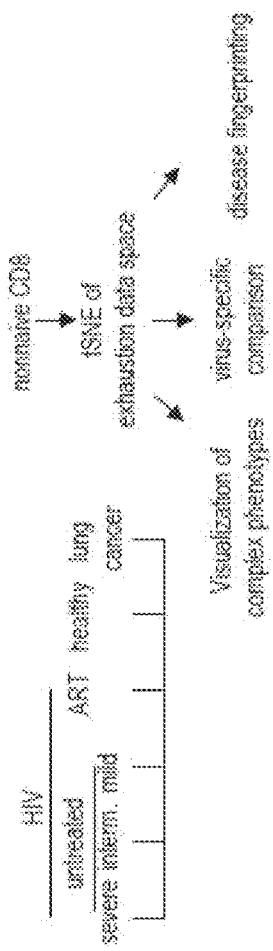
Figure 40D:
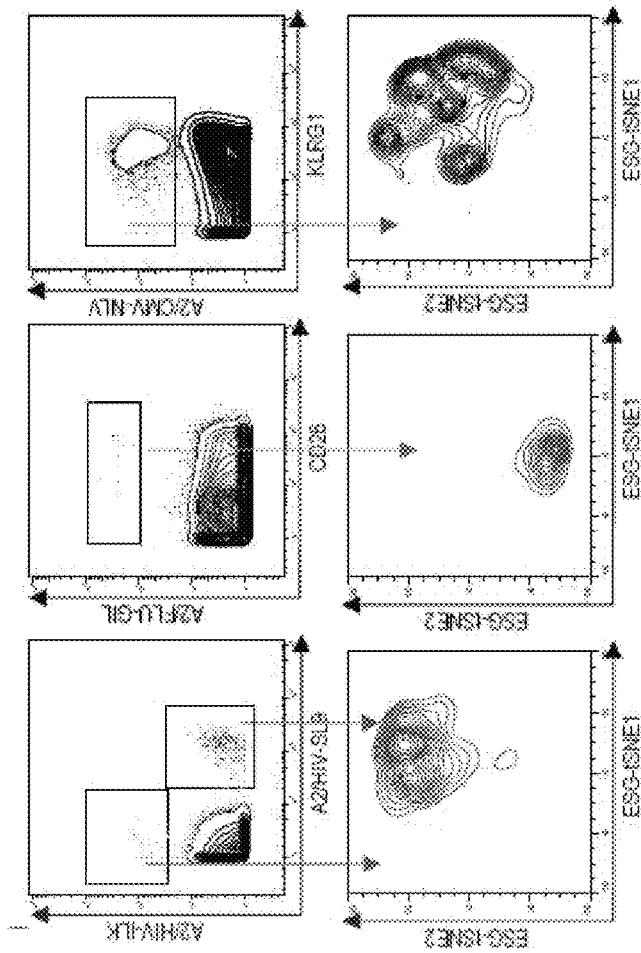
Figure 40E:
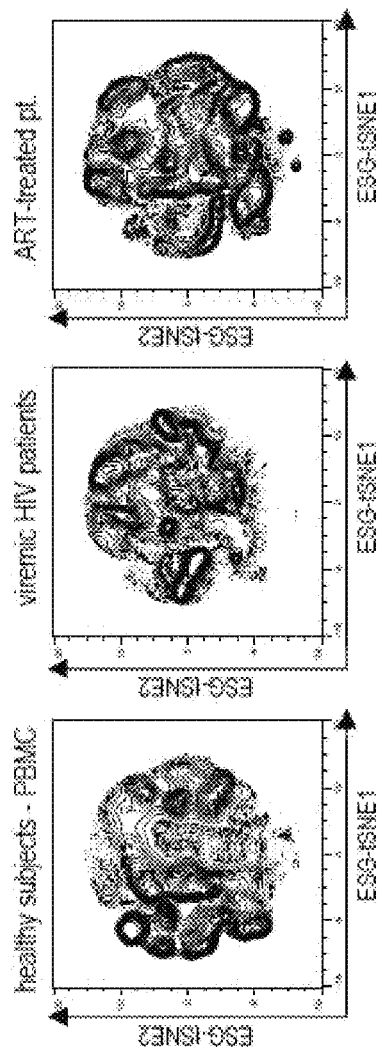

Example 13. A High-Dimensional Single-Cell Map of Exhaustion Reveals Distinct Locations of Virus-Specific T Cells and TILs in the $T_{EX}$ Landscape To visualize the complex $T_{EX}$ phenotypes defined by this CyTOF panel, a tSNE-based dimensionality reduction approach was first used integrating the information from the exhaustion markers analyzed by CyTOF. We displayed the high-dimensional exhaustion data of non-naïve CD8 T cells on an "exhaustion map" (FIG. 40A). Cells with closely related high-dimensional phenotypes localized in neighboring areas of the map (FIG. 40B). For example, PD-1 expression largely overlapped with Eomes, multiple other IRs and a paucity of CD127 expression (FIG. 40B). Smaller regions of PD-1+ cells that lacked Eomes and other IRs were also apparent, perhaps reflecting activation-dependent PD-1 expression. Other regions displayed expression of other $T_{EX}$ genes (e.g. CD38, CD39, Helios and TOX) with different patterns of co-expression (FIG. 40B). This exhaustion map was used to interrogate differences in exhaustion states across patients and diseases (FIG. 40C). Where bona fide virus-specific CD8 T cell populations mapped in this landscape was interrogated first. Virus-specific CD8 T cells targeting CMV- and influenza virus (FLU) epitopes localized to distinct areas of the exhaustion map compared to HIV-specific CD8 T cells, confirming the ability of this approach to distinguish known differentiation patterns of virus-specific CD8 T cells (FIG. 40D) (Appay et al. (2008) *Cytometry A* 73:975-983). Moreover, the HIV-specific CD8 T cells, but not FLU-specific and few CMV-specific populations overlapped with the PD-1+ part of the exhaustion map (FIGS. 40B, 40D). Thus, examination of virus-specific CD8 T cells validated the exhaustion map in the ability distinguish HIV-, CMV- and FLU-specific populations.

Figure 40F:
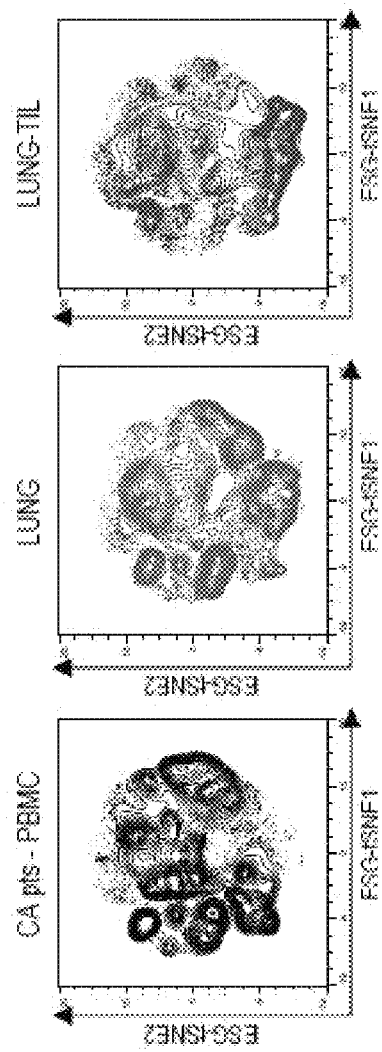
Figure 40G:
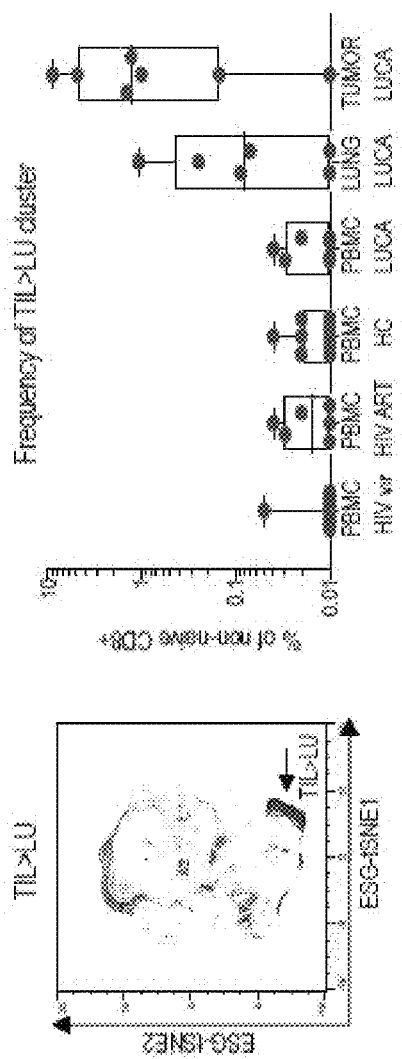

All non-naïve CD8 T cells from healthy subjects and HIV patients on and off therapy were examined. Concatenated data shown in FIG. 40E, revealed distinct distributions of T cell populations in these cohorts, pointing to the possibility of using "exhaustion fingerprints" for dissecting disease states. Although $T_{EX}$ have been reported in viral infections as well as cancer, it remains unclear whether there are common versus distinct features of $T_{EX}$ in different diseases. To address this question, TIL isolated from lung cancer patients and T cells isolated from macroscopically unaffected adjacent tissue from the same lung were examined (FIG. 40F). TIL mapped to regions with some overlap with HIV-specific T cells, but also displayed features distinct from HIV $T_{EX}$ (FIG. 40F). However, the lung tissue microenvironment might contribute to the signature of lung cancer TIL. Indeed, after removal of the phenotypic signature of cells from the uninvolved lung tissue, some features of TIL partially overlapped with HIV-specific CD8 T cells where there was strong co-expression of PD-1, other IRs and Eomes (e.g. top of the exhaustion map (FIGS. 40B, 40F, 40G)) whereas other features highly enriched in TIL such as strong PD-1 and CD39 co-expression localized to other regions of the $T_{EX}$ landscape (FIGS. 40F, 40G). In sum, high-dimensional profiling of $T_{EX}$ identified distinct features of the differentiation landscape for HIV-specific CD8 T cells and TILs.

Example 14. High-Dimensional $T_{EX}$ Cluster Dynamics in HIV Infection

Figure 41A:
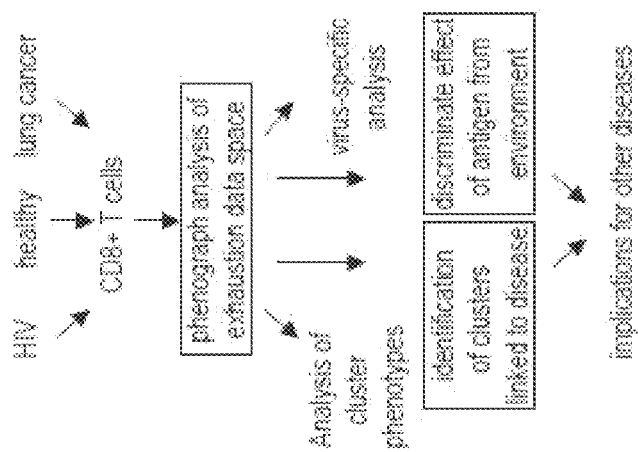
FIGS. 41A-41G show that high-dimensional clustering identifies $T_{EX}$ phenotypes and links to HIV disease progression.
Figure 41B:
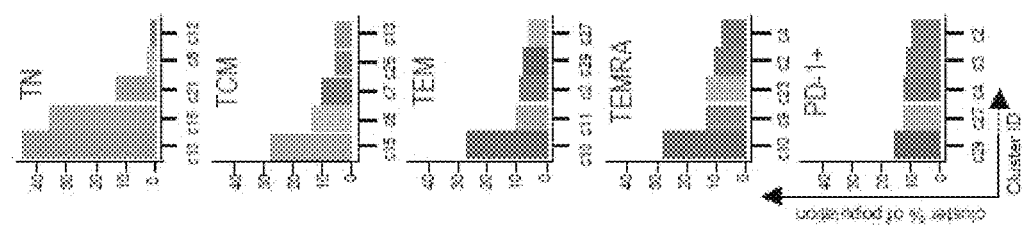
Figure 41C:
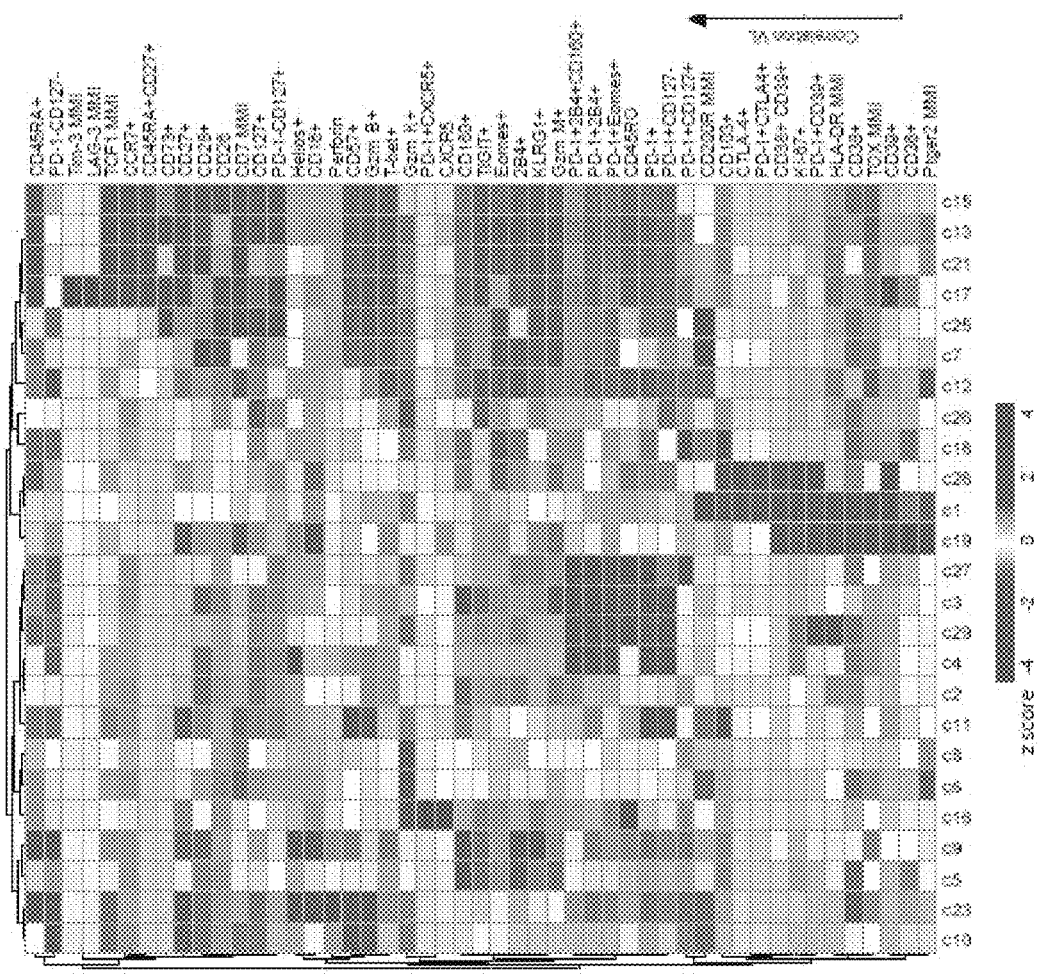

The tSNE approach applied above provides a useful visualization of some relationships in high-dimensional space, but requires considerable downsampling of the data and, in some cases, the loss of high-dimensional information can render interpretation of the topology of the data structure challenging. Additional insights into these $T_{EX}$ data and disease relevance were achieved by a non-redundant high-dimensional analytical approach using Phenograph (FIG. 41A) (Levine et al. (2015) Cell 162:184-197). This approach enables high stability of cluster identification and does not employ downsampling or dimensionality-reduction (Melchiotti et al. (2017) Cytometry A 91:73-84). In these analyses, a graph was constructed based on the high dimensional phenotypic similarities of exhaustion marker expression patterns. Phenotypically defined cellular neighborhoods were then partitioned into clusters of closely interconnected cells. This analysis identified 25 clusters based on expression of exhaustion markers (30 clusters were computed, but clusters c14, c20, c22, c24, c30 contained very few events and were excluded from further analyses; see STAR Methods). Whether this analysis identified clusters representing classically defined $T_N$, $T_{CM}$, $T_{EM}$, and $T_{EMRA}$ was tested (FIG. 39C). Indeed, some phenograph clusters were clearly associated with phenotypically defined $T_N$ and $T_{CM}$ (clusters such as c13, c15 or c21) or populations with features of $T_{EM}$ (e.g. clusters c10, and c11) or $T_{EMRA}$-like cells (e.g., clusters c10, c9, c23) (FIGS. 41B, 41C). In contrast, the cluster contribution to PD-1+CD8 T cells showed more diversity and no single cluster contributed to more than 15% of the population (FIG. 41B). Approximately 9-12 clusters in this analysis contain putative $T_{EX}$ based on co-expression of 3 or more (up to 9) IRs (c1, c2, c3, c4, c9, c16, c18, c19, c27, c28, c29), whereas 9 clusters were associated with $T_N$ and/or $T_{CM}$ phenotypes and contained cells with <3 IRs. $T_{EM}$ and $T_{EMRA}$ phenotype cells were contained in 3-8 distinct clusters. Notably, 3 of these clusters contained cells with <3 IRs, but the other clusters containing classically defined $T_{EM}$ and $T_{EMRA}$ also contained clusters expressing IRs (FIG. 41C). This observation likely reflects the fact that $T_{EX}$ phenotype cells are mostly CD27+CD45RA− (Bengsch et al. (2010) PLoS Pathog 6, e1000947; Huang et al. (2017) Nature 545:60-65) and fall into the CD8 T cell subset defined by the classic definition of $T_{EM}$ (CCR7−CD45RA−), with additional $T_{EX}$ acquiring a CD27-CD45RA+ phenotype. Thus, this high dimensional approach is necessary to parse these different CD8 T cell populations.

Figure 41D:
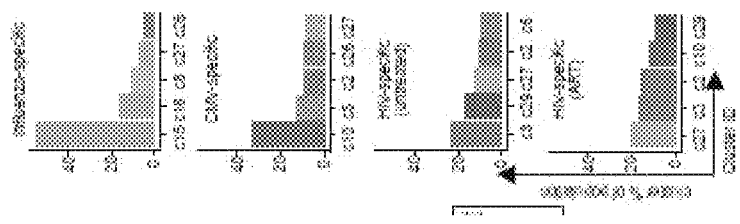

Applying this approach to virus-specific CD8 T cells revealed distinct cluster distribution patterns for HIV-, FLU-, and CMV-specific CD8 T cells (FIG. 41D). Cluster c10 that contained cells with high expression of T-bet, Granzyme B, Perforin and CD57, a phenotype often associated with $T_{EMRA}$ and/or T cell senescence was strongly enriched in CMV-specific CD8 T cells (FIG. 41D). In contrast, cluster c15 with hallmarks of $T_{CM}$ was enriched in FLU-specific CD8 T cells isolated from the blood (FIGS. 41B, 41C, 41D). However, FLU-specific CD8 T cells from lungs were enriched in clusters c18 and c28 that expressed CD103, a molecule used to home to tissues and often expressed by resident memory T cells ($T_{RM}$) (FIG. 47) (Gordon et al. (2017) J Exp Med 214:651-667; Hombrink et al. (2016) Nat Immunol 17:1467-1478; Schenkel and Masopust (2014) Immunity 45:389-401). HIV-specific CD8 T cells enriched in clusters expressing high levels of exhaustion markers (FIGS. 41C, 41D), and the distribution of these $T_{EX}$ clusters was altered in ART-treated HIV patients (FIG. 41D).

Figure 41E:
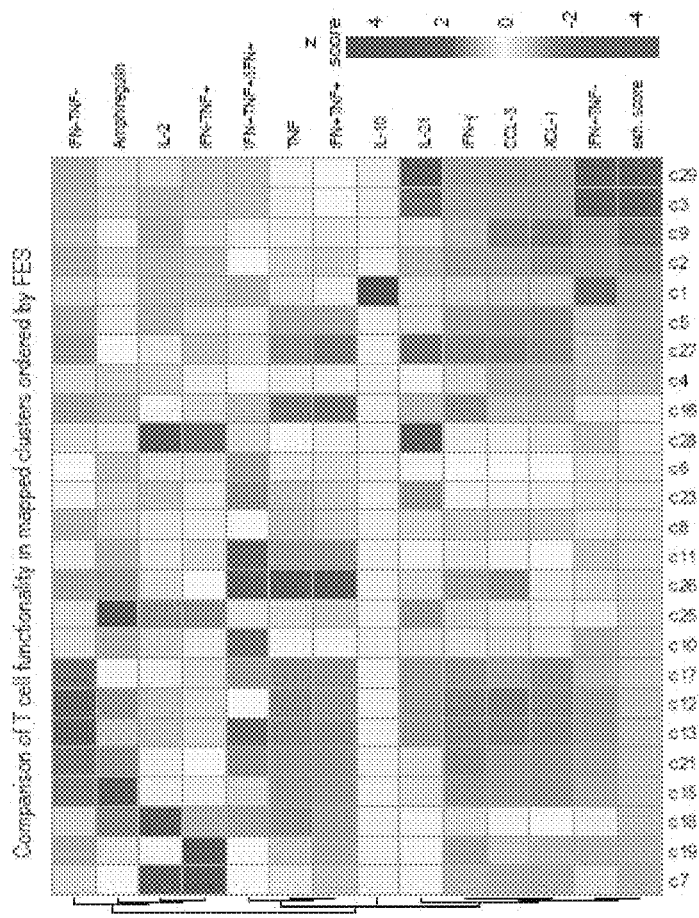
Figure 41F:
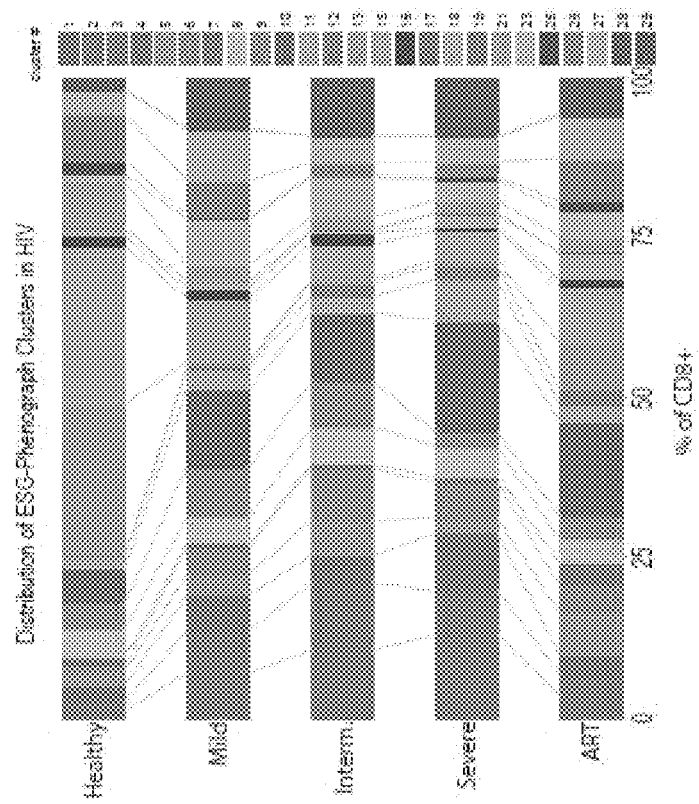

T cell exhaustion was originally defined by altered and often poor function (Zajac et al. (1998) J Exp Med 188: 2205-2213). However, $T_{EX}$ are not functionally inert. Rather, exhaustion is defined, in some cases by reduced IFN-γ production, but more often by a poor ability to simultaneously produce IFN-γ and TNF (i.e. low polyfunctionality), lack of IL-2 and reduced cytotoxicity despite expression of cytotoxic molecules such as granzymes (Badr et al. (2008) J Virol 82: 10017-10031; Betts et al. (2006) Blood 107: 4781-4789; Blackburn et al. (2010) J Virol 84:2078-2089; Brooks et al. (2008) Proc Natl Acad Sci USA 105:20428-20433; Buggert et al. (2014) PLoS Pathog 10, e1004251; Wherry et al. (2003) J Virol 77:4911-4927; Wherry et al. (2007) Immunity 27:670-684). Nevertheless, $T_{EX}$ often retain the ability to make some IFN-γ and also robustly produce chemokines (Betts et al. (2006) Blood 107:4781-4789; Blackburn et al. (2010) J Virol 84:2078-2089; Crawford et al. (2014) Immunity 40(2):289-302). Our transcriptomic and epigenomic profiling also indicated up-regulation of functional chemokines and cytokines, i.e chemokines CCL3, XCL1 and immunoregulatory cytokines 1L10, IL-21 and amphiregulin in $T_{EX}$. Thus, $T_{EX}$ have function that, although unable to mediate complete pathogen or tumor eradication, may enable a critical host-pathogen or host-tumor equilibrium while limiting tissue damage (Wherry and Kurachi, 2015). It remained unclear whether the high dimensional $T_{EX}$ clusters identified by phenotype also reflected functional characteristics of exhaustion. Functional features of exhaustion and their relationship to the clusters determined above were thus interrogated. CD8 T cells from viremic HIV patients were stimulated and expression of IFN-γ, TNF, IL-2, IL-10, IL-21, CCL3, XCL1 and Amphiregulin was examined (FIG. 39A) using a cytokine panel built on the framework of 13 phenotypic exhaustion markers analyzed above, with an emphasis on molecules that had stable expression before and after in vitro stimulation. Mapping chemokine and cytokine production to phenotypic clusters identified distinct cluster functionality (FIG. 41E). In agreement with our epigenomic analyses, expression of CCL3, XCL1, IL-10 and IL-21 was identified in clusters such as c2, c16 and c29 with other features of exhaustion. In contrast, amphiregulin that was identified epigenomically, stained primarily in clusters with naïve or memory phenotypes (e.g. c13, c15, c17, c21; FIG. 41E) rather than $T_{EX}$ clusters, though the reasons for this disparity between the mouse genomic and human protein data are currently unclear. Cells that retained IFN-γ production but lost TNF production (i.e. reduced polyfunctionality) were prominently associated with the clusters c3, c16, c29 that also co-expressed many IRs (FIGS. 41C, 41E) consistent with the definition of exhaustion. To enable comparisons, a functional "exhaustion score" (FES) was developed for every cluster that increased for functional hallmarks of exhaustion (e.g. loss of TNF or IL-2 production, upregulation of chemokines) and decreased with the presence of effector or memory functionality (e.g. IL-2 production or IFN-γ and TNF coproduction) (see Materials and Methods). The highest FES was observed for cluster c29 that phenotypically resembled highly exhausted T cells based on the co-expression of 6-7 IRs and other features of $T_{EX}$ (FIGS. 41C, 41E). This analysis identified 9 clusters with high FES that also mapped to clusters with high IR co-expression. However, 3 clusters (c18, c19, c28) that co-expressed 3-4 IRs had intermediate to low FES. As expected, $T_{CM}$, $T_{EM}$, $T_{EMRA}$ enriched for clusters with low FES (FIG. 41E). Notably, however, even healthy subjects have detectable frequencies of $T_{EX}$ clusters including especially those with lower FES such as c5, c9, c16 and c27 (FIGS. 41F, 41D).

Figure 41G:
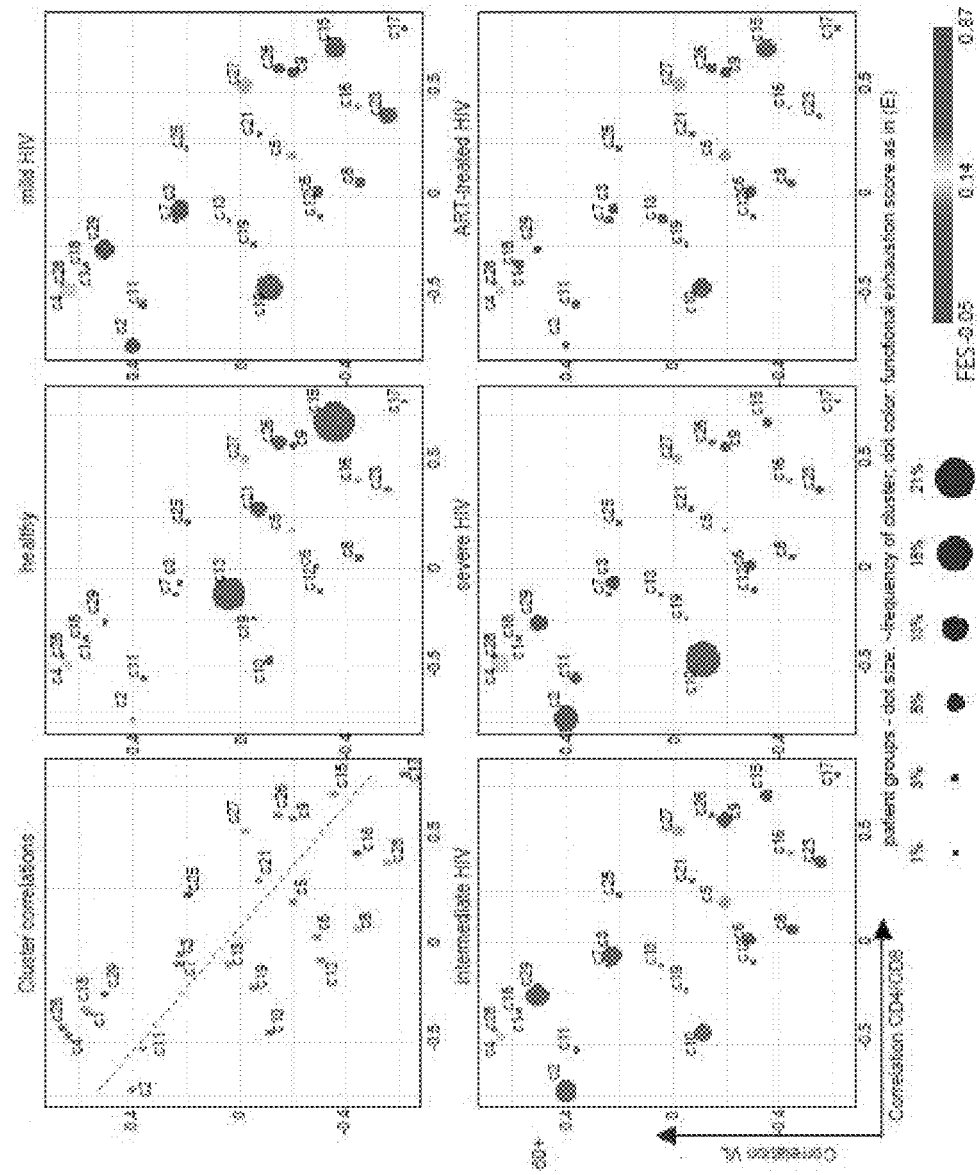

How these $T_{EX}$ clusters changed with HIV disease severity and after control of viral replication by ART was next examined. $T_{EX}$ clusters such as c2 and c29 were expanded in advanced HIV infection, but were decreased in ART therapy (FIG. 41F). Clusters such as c1, c2, c4, c11, c18, c28 and c29 were positively associated with both high viral load and low CD4/CD8 ratio (FIG. 41G, left upper panel). Other clusters including the $T_{EX}$ clusters c5, c9 and c27 as well as $T_N/T_{CM}$ clusters including c15 and c17 were associated with low viral load and higher CD4/CD8 ratio. In contrast, clusters such as c10, a cluster with characteristics of $T_{EM}$ and $T_{EMRA}$ and low FES, were more strongly associated with low CD4/CD8 ratio than changes in viral load, and c10, in particular, was expanded in HIV infection suggesting a bystander effect (FIG. 41G). Many $T_{EX}$ clusters were linked to severe HIV disease (e.g., c29, c2, c3, c4), displayed co-expression of IRs (e.g. PD-1, 2B4, CD160, and TIGIT), and had high Eomes, a phenotype consistent with severe exhaustion (Paley et al., 2012) (FIGS. 41C, 41G). Some of these clusters also included markers of activation and metabolic regulation (e.g., CD38+CD39+ expression, c1 and c29). In contrast, other clusters were enriched in mild HIV (e.g., c16, c27, c9) and one of these, c16, included CXCR5+ cells with expression of TCF1 and CD127 (FIGS. 41C, 41G), resembling a phenotype implicated in homing to germinal centers (He et al. (2016) Nature 537:412-428; Petrovas et al. (2017) Sci Transl Med 9). A separate cluster, c27 also expressed molecules consistent with progenitor $T_{EX}$ (e.g., CD127, some TCF1) in addition to IRs and other exhaustion markers. A link to mild disease was also observed for a cluster with low PD-1, but high 2B4, CD160 and TIGIT and high expression of cytotoxic molecules (c9), suggesting possible preserved cytotoxicity potential as well as exhaustion in the absence of PD-1. Together, these results point to multiple subtypes of $T_{EX}$ differentially linked to HIV disease progression or therapy and identified features of $T_{EX}$ and other T cell subsets that are preferentially associated with changes in viral load, overall decline in immune dysregulation captured by CD4/CD8 ratio and response to ART.

Figure 42B:
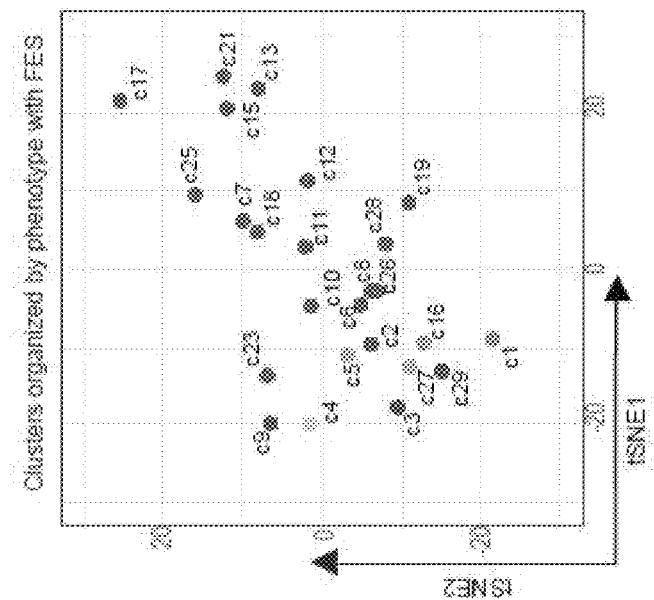
FIGS. 42A-42F illustrate that phenotypically and transcriptionally distinct functionally exhausted high dimensional clusters are enriched in HIV patients and are differentially linked to HIV progression.
Figure 42A:
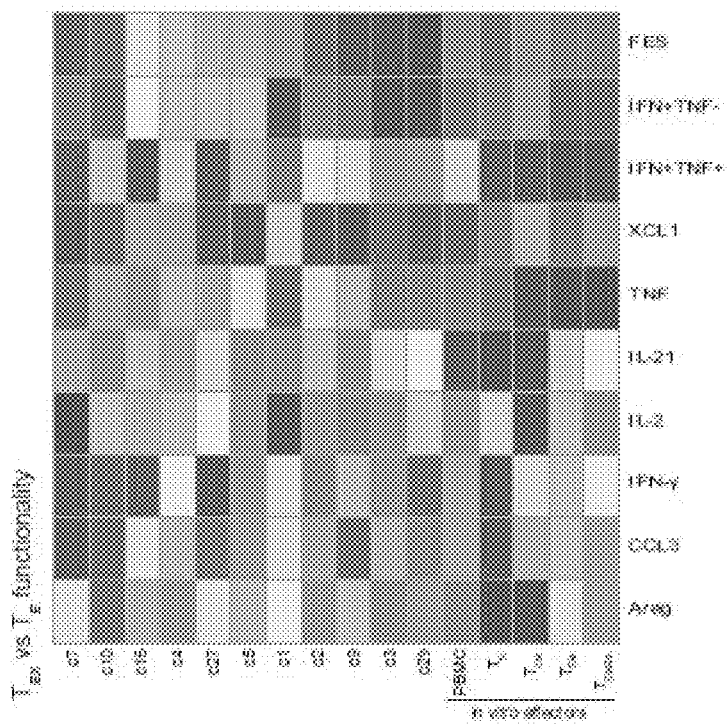
Figure 42C:
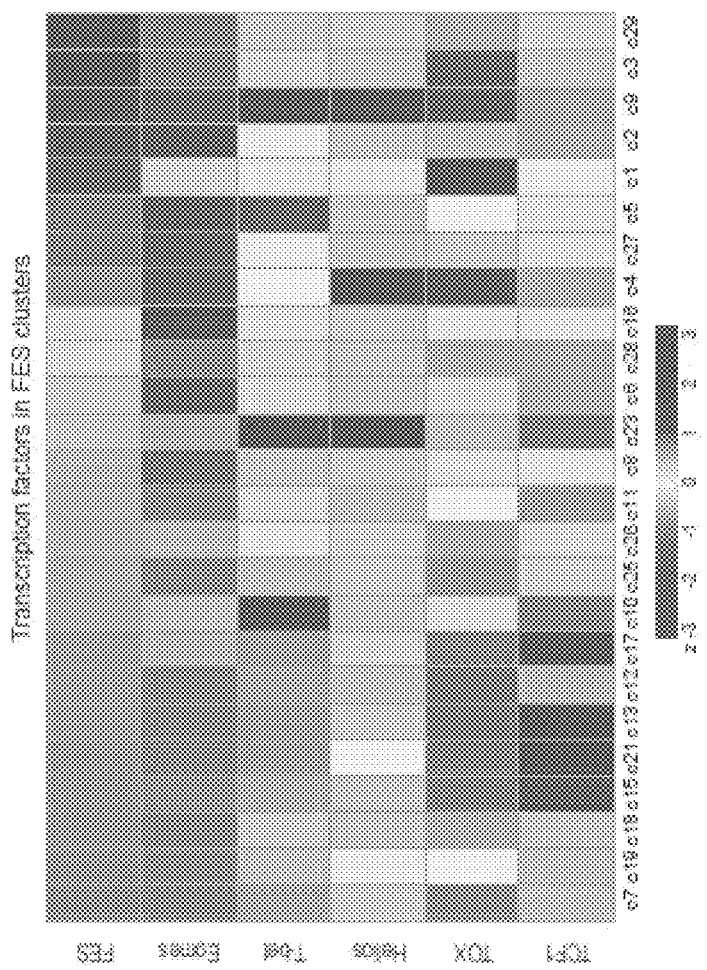

Example 15. Distinct Functional, Phenotypic and Transcriptional Features of $T_{EX}$ Clusters To test whether these analyses could distinguish $T_{EX}$ from $T_{EFF}$, $T_{EFF}$ were generated in vitro starting with total PBMC or sorted $T_N$, $T_{CM}$, $T_{EM}$, or $T_{EMRA}$ and then examined the functional and phenotypic profile of the resulting T. $T_{EFF}$ had high polyfunctionality, IFN-γ and TNF coproduction, and a low FES score, distinguishing $T_{EX}$ from T. To test how the FES related to the high-dimensional phenotypes, the phenograph-derived clusters of $T_{EX}$ were plotted using tSNE (FIG. 48), and the FES was projected onto this simplified cluster map of exhaustion space (FIG. 42B). Clusters with positive exhaustion scores fell in close proximity on this map (FIG. 42B). Analysis of the transcription factor expression patterns in $T_{EX}$ clusters revealed high Eomes and TOX in clusters with a high FES (FIG. 42C). In contrast, high T-bet and Helios were present in $T_{EX}$ cluster c9 that expresses many cytotoxic molecules. Finally, TCF1 was expressed by a subset of $T_{EX}$, including clusters c1 and c16, but this transcription factor was highest in non-$T_{EX}$ (FIG. 42C) consistent with the major role for TCF1 in $T_N$ and $T_{MEM}$. These results indicated that high dimensional $T_{EX}$ clusters display distinct phenotypic, transcriptional and functional properties.

Example 16. Use of $T_{EX}$ Clusters to Interrogate Disease Associations

Figure 42D:
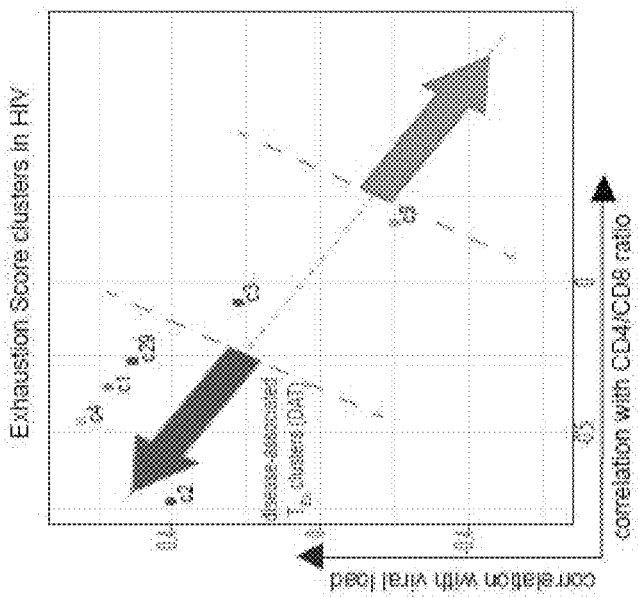
Figure 42E:
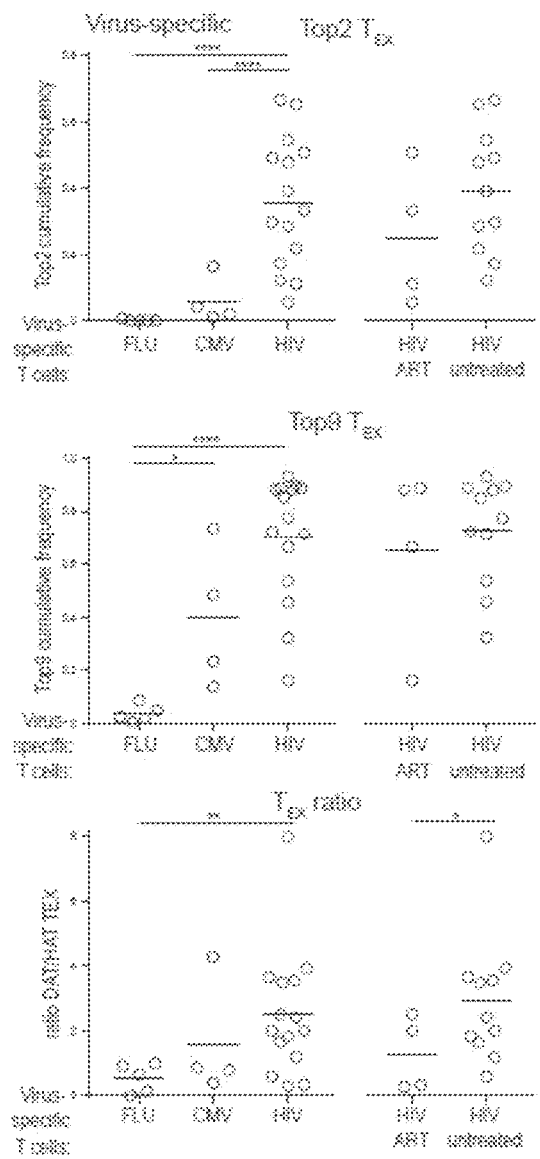
Figure 42F:
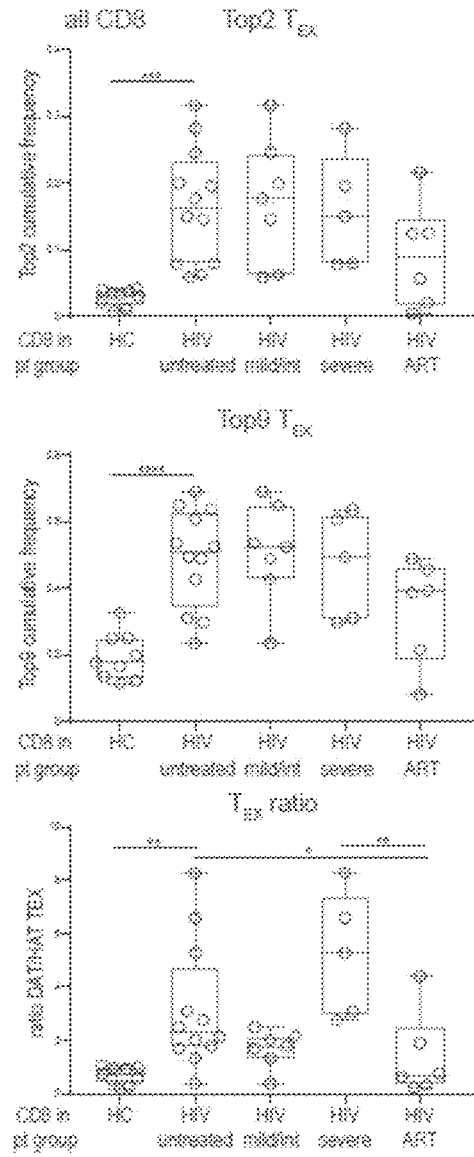
Figure 49A:
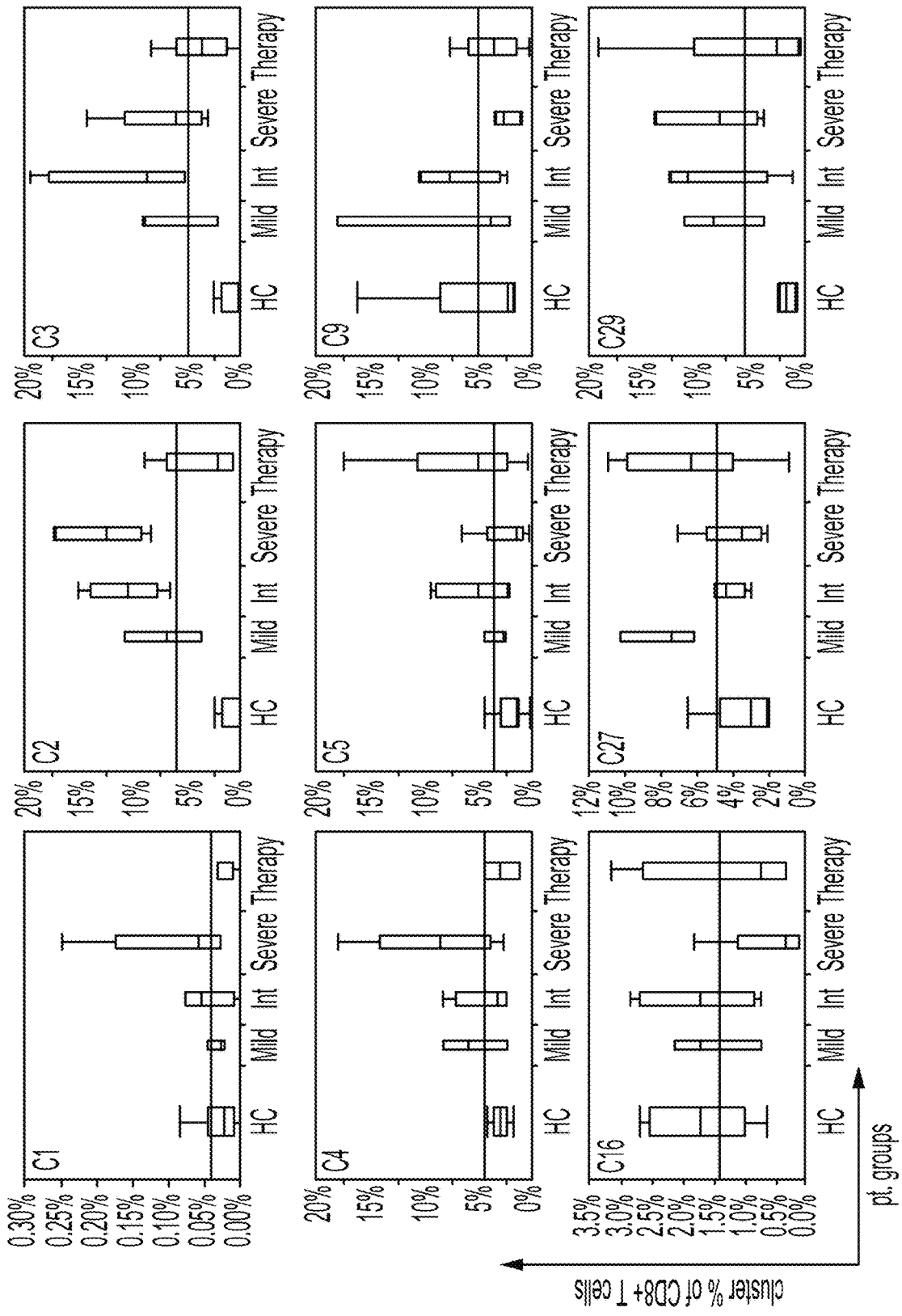
FIGS. 49A-49B illustrate that CD8+ T cells from HIV patients and healthy subjects were analyzed for the abundance of clusters with a high FES according to FIG. 41.
Figure 49B:
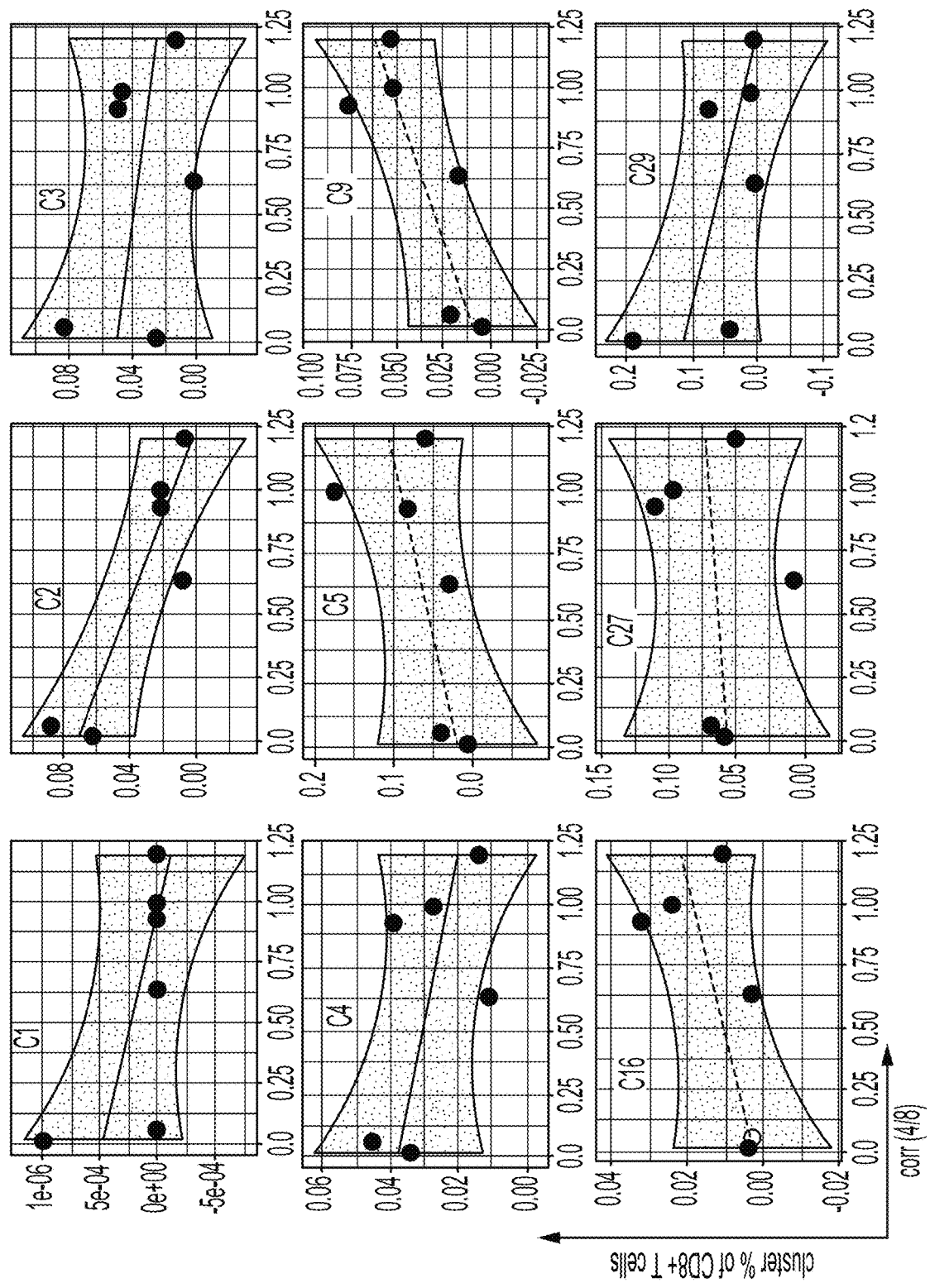

A hypothesis is that the distribution of $T_{EX}$ clusters linked to severe HIV ("Disease Associated $T_{EX}$", (DAT)) compared to those associated with mild disease ("Health Associated $T_{EX}$", (HAT)) might be an indicator of disease state based on $T_{EX}$ biology (FIG. 42D). To test this hypothesis, FLU, CMV or HIV-specific T cells were analyzed for the sum of the frequency of the top 2 or top 9 $T_{EX}$ clusters with the highest FES and for the ratio of clusters linked to severe versus mild HIV disease ($T_{EX}$ ratio). HIV-specific T cells had higher frequencies of $T_{EX}$ clusters and also a higher ratio of Disease Associated to Health Associated $T_{EX}$ clusters compared to FLU- and CMV-specific T cells (FIG. 42E). The $T_{EX}$ ratio also revealed changes during ART therapy, with increased Health Associated $T_{EX}$ clusters (FIG. 42E). These findings observed on HIV-specific CD8+ T cells could be extended to profiling of total CD8 T cells that showed an enrichment of the Top2 and Top9 $T_{EX}$ clusters and a higher $T_{EX}$ ratio in viremic HIV patients compared to healthy individuals and some reduction upon therapy (FIG. 42F). Although the correlations associating clusters with severe or mild HIV were derived from viremic untreated patients (FIG. 41), the correlations of $T_{EX}$ clusters with the CD4/CD8 ratio remained stable in ART-treated patients (FIG. 49). Thus, detailed analysis of $T_{EX}$ biology was able to provide insight into changes in HIV disease and may provide a framework to understand specific features of exhaustion involved in different stages of disease or to identify how alterations in $T_{EX}$ biology are associated with novel therapeutic approaches.

Example 17. Organ- and Disease-Specific Changes in $T_{EX}$ in Lung Cancer

Figure 43B:
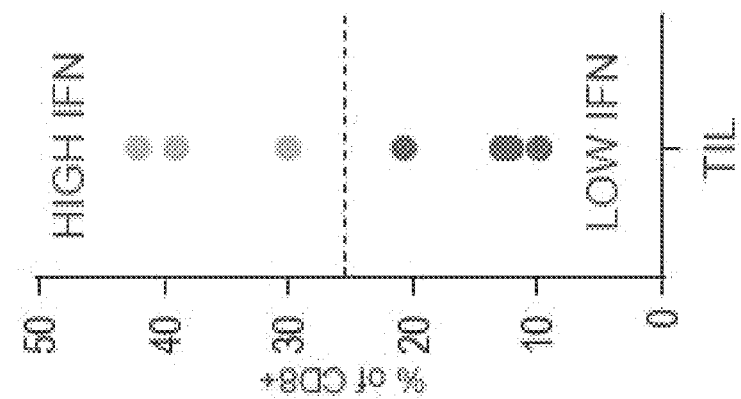
FIGS. 43A-43G illustrate that TIL dysfunction in lung cancer is linked to $T_{EX}$ phenotypes shared with severe HIV and tissue-associated features.
Figure 43A:
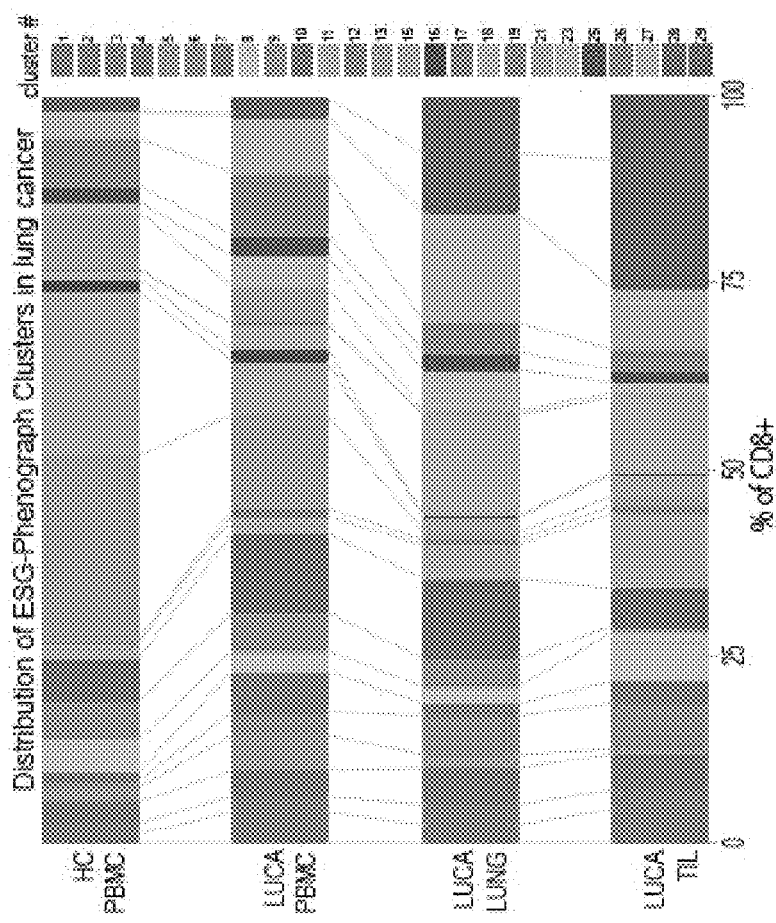
Figures 47A, 47B:
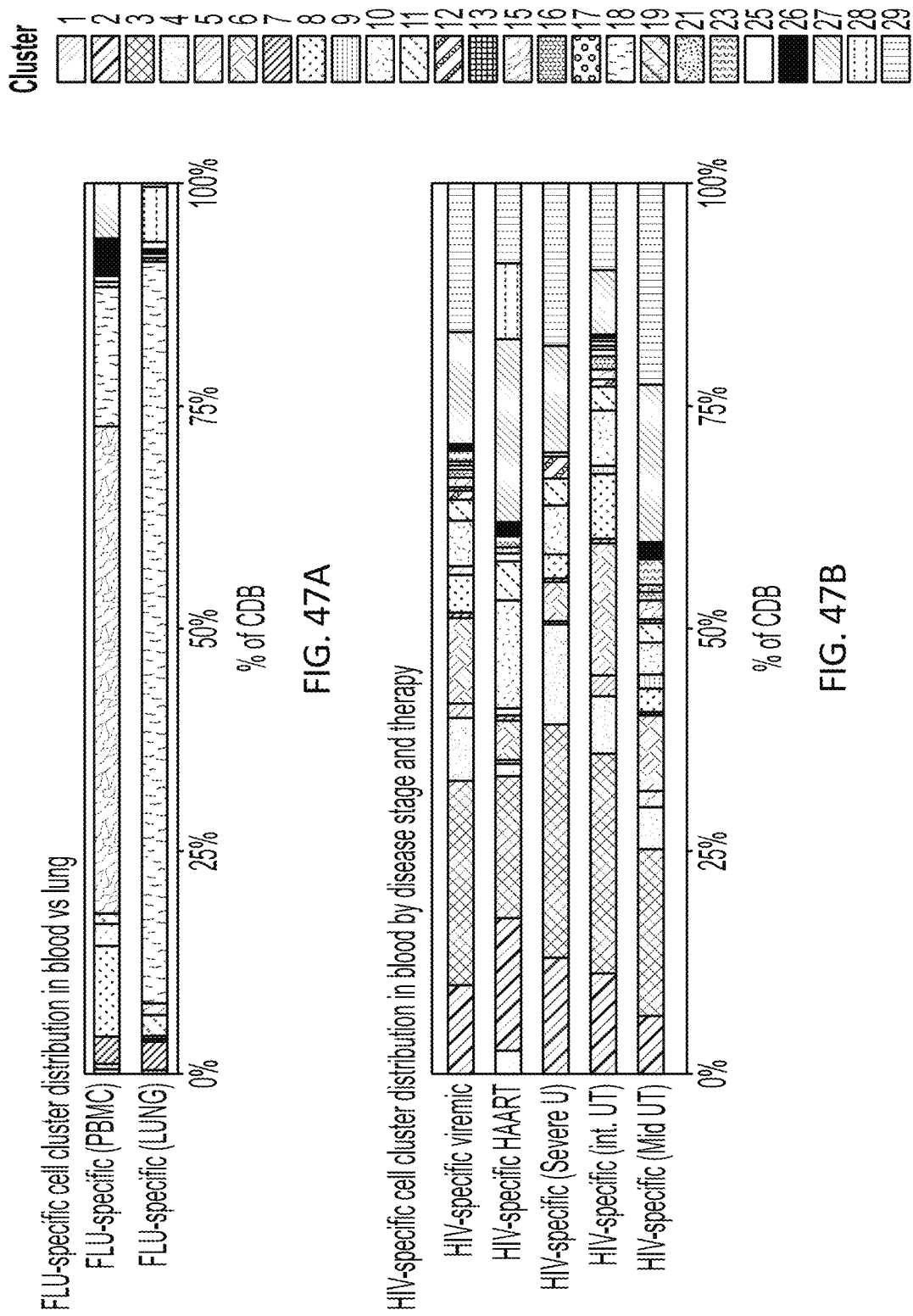
FIGS. 47A-47D illustrate distribution of high dimensional phenograph clusters for virus-specific T cells and TILs. The cluster distribution per group analyzed is shown as fraction of virus-specific or TIL CD8 T cells, as in FIG. 41-43.
Figures 47C, 47D:
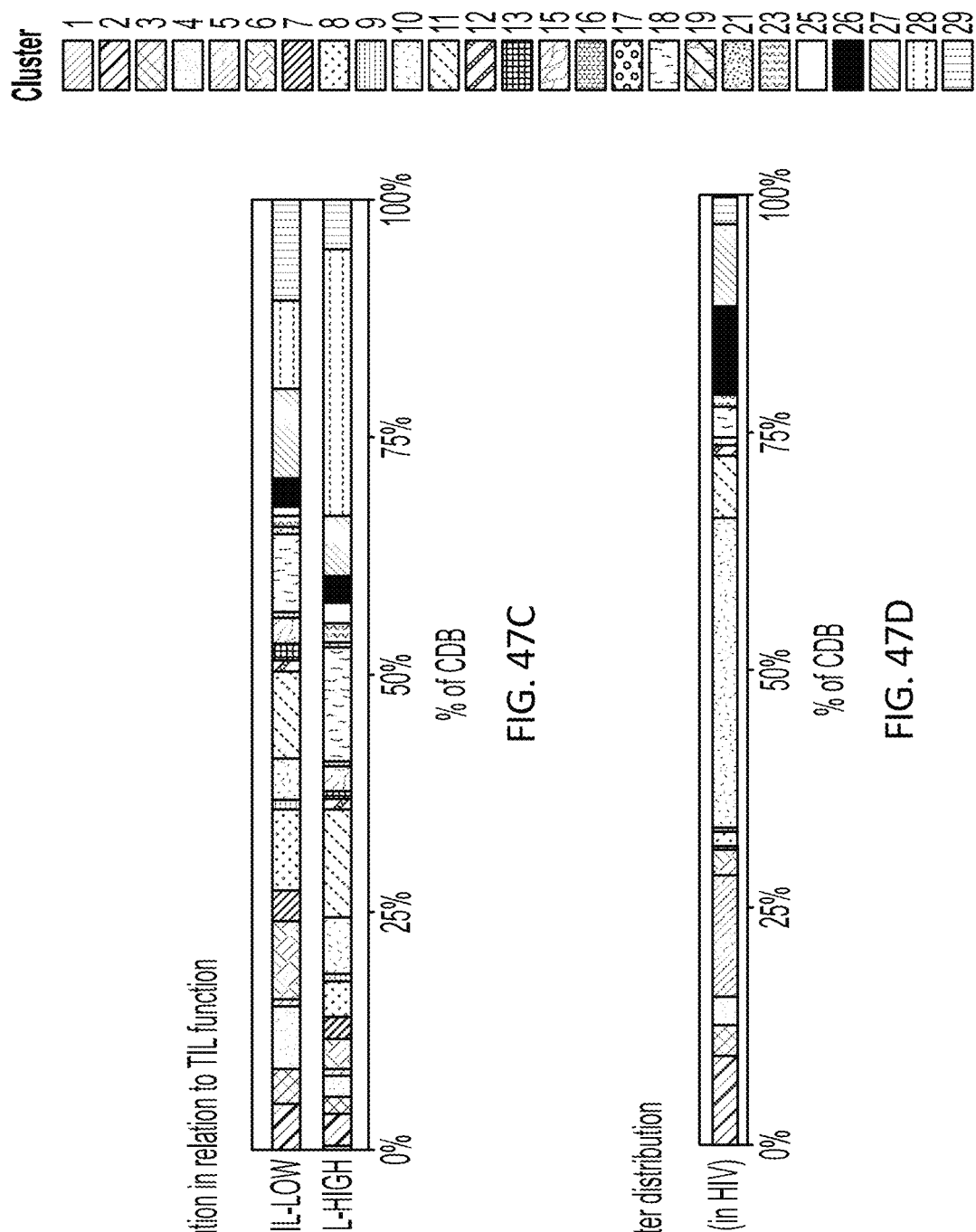

One unresolved question is whether key features of exhaustion are shared across different diseases and/or tissue sites. To interrogate this issue, CD8 T cells from patients with newly diagnosed lung cancer were examined, using samples from peripheral blood, lung tumors and macroscopically unaffected lung tissue using the approach outlined above. Clusters with $T_N$ and $T_{CM}$-like features (c13, c15, c21) were reduced in lung cancer patient PBMC compared to healthy subjects (FIG. 43A). Larger changes in cluster distribution were observed between the blood, the lung tissue and TIL including an enrichment in $T_{EX}$ clusters c2 and c29, as well as the $T_{EM}/T_{EMRA}$ cluster c10 in TTh (FIG. 43A). Clusters expressing CD103 a molecule often involved in tissue residency were enriched in the uninvolved lung tissue and TIL samples (e.g., c11, c18, c28) suggesting a lung tissue imprint on the both $T_{EX}$ and non-$T_{EX}$ populations even in the tumor microenvironment (FIG. 43A). The $T_{RM}$-like populations also included FLU-specific cells (FIG. 47). Thus, cells with general features of $T_{EX}$ in the respiratory tract of lung cancer patients overlap with those observed in blood, but this anatomical location is also associated with alterations in $T_{EX}$ and non-$T_{EX}$ populations that may relate to tissue-specific programming.

Figure 43C:
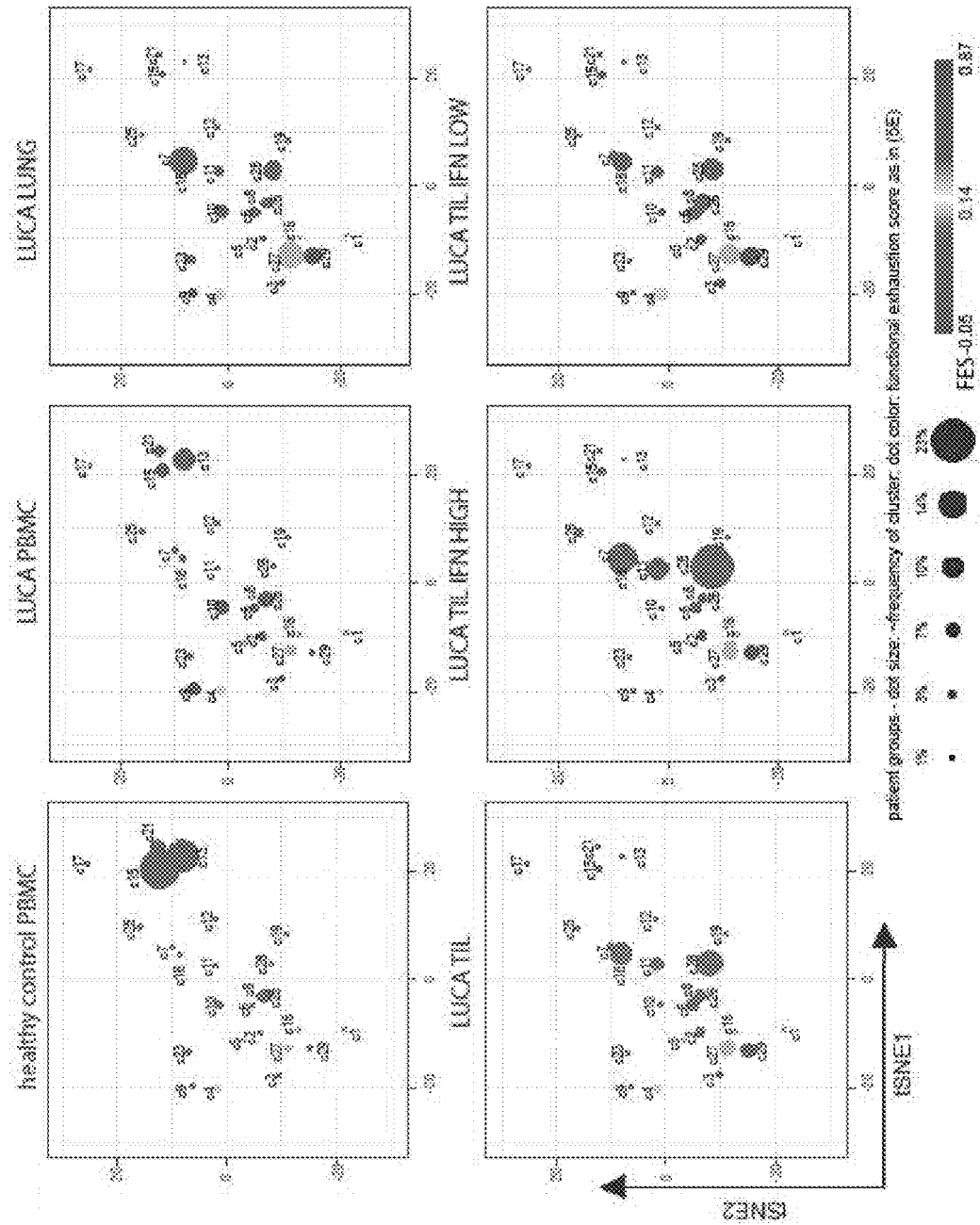
Figure 43D:
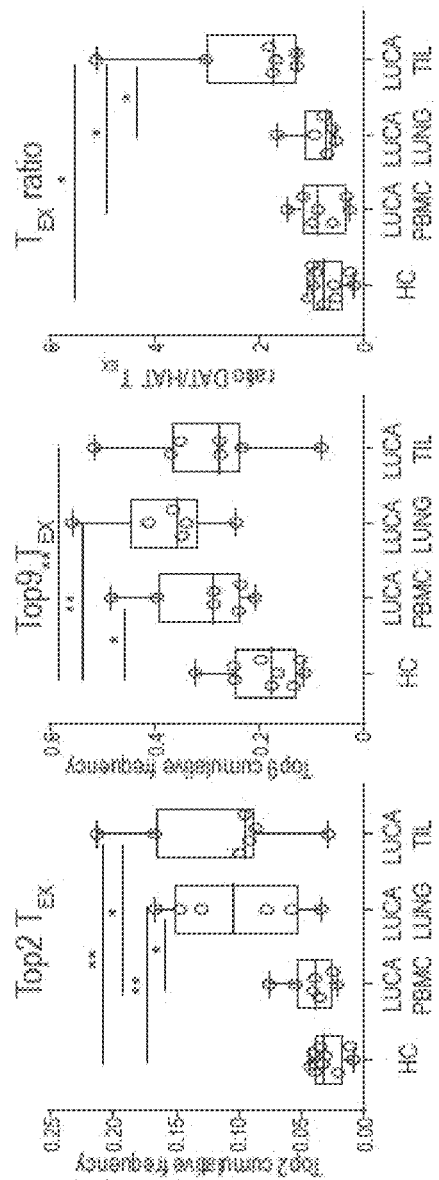
Figure 43E:
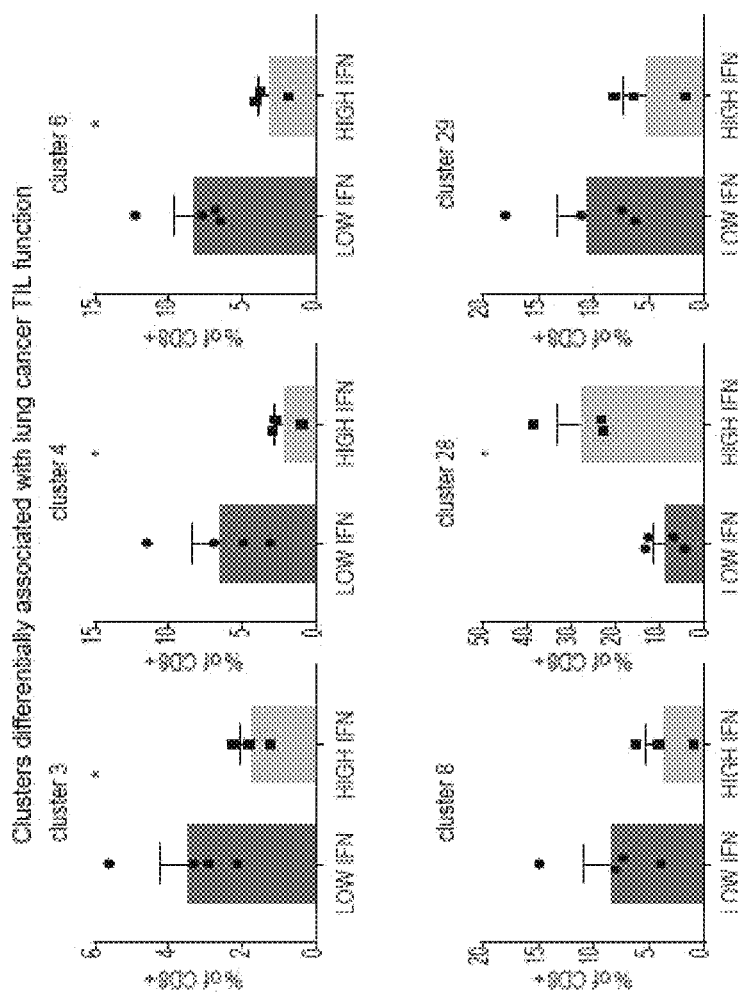
Figures 43F, 43G:
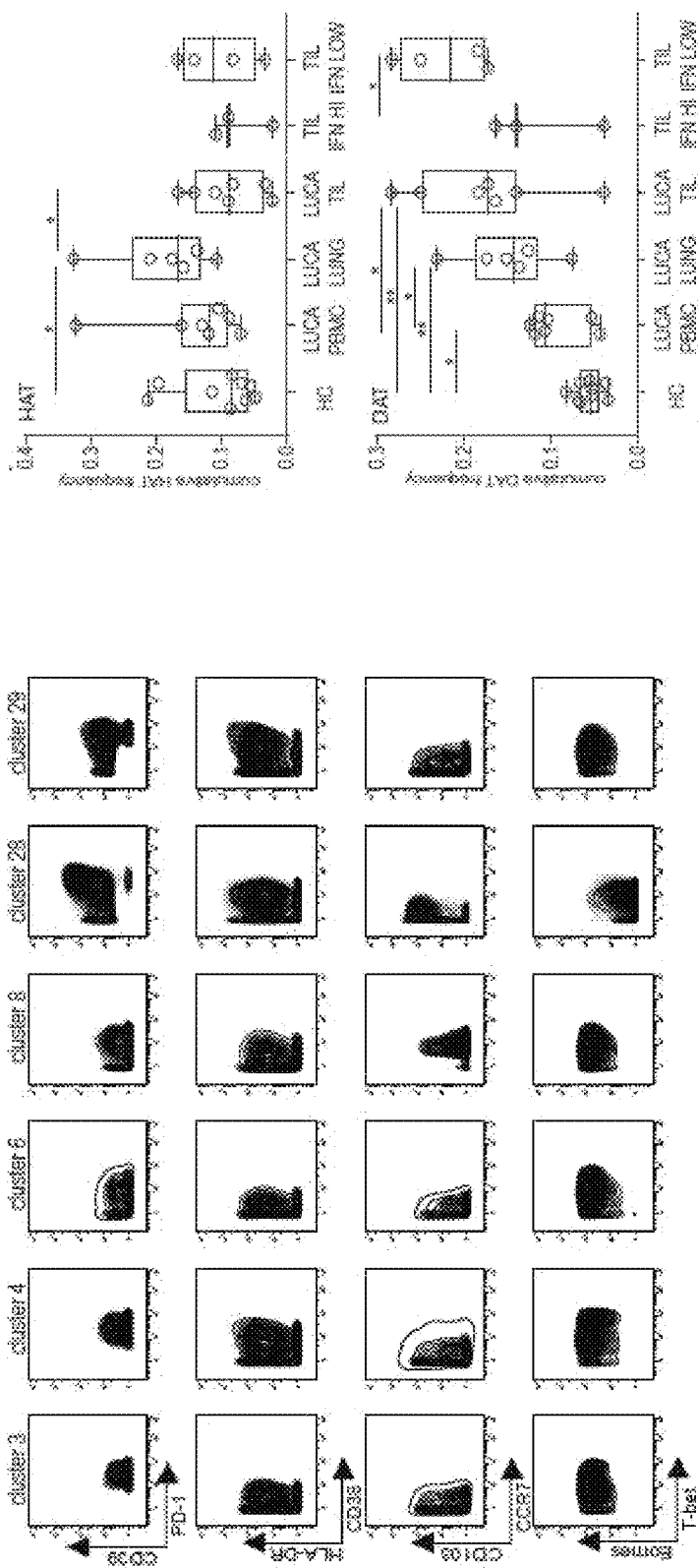

Example 18. Enrichment of $T_{EX}$ Signatures in Poorly Functional Lung Cancer TIL Populations To interrogate how these TIL clusters related to function, IFN-γ production was examined after short-term in vitro stimulation (FIG. 43B). Samples were then grouped into high and low IFN-γ producers. Using the FES clustering approach developed above (FIG. 41) we plotted the change in cluster enrichment comparing PBMC from healthy control versus PBMC from lung cancer patients, CD8 T cells from lung tissue and TTh (FIG. 43C). TTh were also compared with high versus low IFN-γ functionality (FIG. 43C). Blood from lung cancer patients had a notable loss of $T_N$ and $T_{CM}$ clusters (c13, c15) and enrichment of $T_{EX}$ clusters c4 and c9. Lung tissue was enriched for clusters such as c11, c18 and c28 that expressed CD103 (FIG. 43C). In more functional TIL populations the non-$T_{EX}$ clusters c11 and c18 as well as cluster c28 were enriched whereas in TTh with low functionality $T_{EX}$ clusters c4, c27 and c29 were overrepresented (FIG. 43C). Having calibrated our assessment of $T_{EX}$ heterogeneity and role in HIV infection, we sought to investigate whether these results could be used to inform the examination of exhaustion and disease in the tumor context. Compared to PBMC, CD8 T cells from lung and TIL enriched in the sum of the top 2 or top 9 $T_{EX}$ clusters identified above (FIG. 43D). Moreover, the $T_{EX}$ FES cluster ratio strongly increased in the TTh samples compared to the adjacent lung (FIG. 43D). Examining specific clusters, c3, c4, and c6 were enriched in TIL with low IFN-γ production, with similar trends for c8 and c29 (FIG. 43E). These clusters co-expressed PD-1 and Eomes, and many also had high co-expression of multiple IRs (FIGS. 41C, 43F). In contrast, c28 was overrepresented in tumors with higher IFN-γ production (FIG. 43C, 43E). This cluster expressed CD103 as well as some PD-1 and other exhaustion-associated molecules (e.g., CD39, CTLA4, TOX), but lacked expression of other features of severe exhaustion, such as Eomes and the highest expression of other IRs (e.g., 2B4, CD160, TIGIT) and also did not have high FES in the HIV data. Although high and low function TIL contained "Health Associated" $T_{EX}$ clusters (as defined above), low function TTh were substantially enriched in "Disease Associated" $T_{EX}$ clusters (FIG. 43G). These results indicate that the dysfunctional tumor microenvironment is defined by a shift from functional Tim-like populations and mild exhaustion characteristics to more severely dysfunctional $T_{EX}$. Moreover, these analyses revealed conserved $T_{EX}$ biology across HIV and cancer, with additional insights into disease specific enrichments (such as a prominence of CD103+ clusters in lung tissue and lung TIL). These results demonstrate the ability to use an epigenomically-guided CyTOF approach to connect the differentiation landscape of $T_{EX}$ across tissues, disease type and disease severity. Moreover, this approach reveals common $T_{EX}$ biology and disease specific features.

Materials and Methods for Examples 19-22

Overview of Enhancer qPCR Method
1. Target Cell Enrichment
    A. Relevant cells for the disease to be tested were enriched from total blood or PBMCs by magnetic bead separation using appropriated surface antigens (e.g. PD1 and/or CD39 for cancer patients).
2. Membrane Lysis and Chromatin Release
    A. Sample Washing
        (i) Target cells were transferred to 1.5 ml Eppendorf DNA Lo-Bind tubes and spun down at 650×g for 7 min at 4° C. Celsius. (ii) Medium was aspirated and replaced with 500 ul of cold phosphate-buffered saline (PBS). Cells were then spun down again at 650×g for 7 min at 4° C. (iii) PBS was then aspirated and replaced with another 500 ul of cold PBS. Cells were again spun down at 650×g for 7 min at 4° C.
    B. Outer and Nuclear Membrane Lysis
        (i) PBS was aspirated and replaced with an appropriate amount of cell lysis medium (10 mM Tris-HCl pH8.0, 10 mM NaCl, 3 mM $MgCl_2$, 0.1% Tween20). The volume of cell lysis medium was scaled to the number of target cells in the reaction (50 ul for fewer than 50,000 cells; 50 ul for 50,000 cells; added 1 ul of lysis medium per additional 1,000 target cells). (ii) Cells were mixed in lysis medium 10 times with a P200 pipette and incubated on ice for 5 min. (iii) Cells were then spun down at 650×g for 10 minutes at 4° C. Celsius.
3. Transposition Reaction
    A. Transposition Reaction
        (i) Lysis solution and cell debris were aspirated and replaced with an appropriate amount of transposition reaction solution. The volume of transposition reaction solution was scaled to the number of target cells in the reaction (25 ul for fewer than 25,000 cells; 25 ul for 25,000 cells; added 1 ul of reaction solution per additional 1,000 target cells). For a 50 ul reaction, the transposition reaction solution contains: 25 ul of 2×ATAC TD Buffer (20 mM Tris pH 7.5, 10 mM $MgCl_2$, 20% DMF), 22.5 ul Nuclease-free UltraPure Water, 2.5 ul of Tn5 adapter-loaded transposase mixture (Illumina, FC-121-1031). (ii) Cells were mixed in the transposition solution 10 times with a P200 pipette and incubated at 37° C. Celsius for 45 minutes.
    B. Sample Cleanup
        (i) Purification of transposed genetic material was performed using a MinElute Reaction Cleanup Kit, following manufacturer instructions (Qiagen, 28204). (ii) Samples were eluted from columns with 11 ul of elution buffer (EB; 10 mM Tris, pH 8.0).
4. Library Amplification
    A. Library Amplification
        (i) 10ul of transposed DNA samples were amplified in Amplification Solution (10 ul nuclease-free water, 25 ul of NEBNext High-Fidelity 2×PCR Master Mix (New England Biolabs, M0541), 2.5 ul of N501 Primer, 2.5 ul of N701 Primer (Illumina, FC-121-1012). Samples were mixed thoroughly and transferred to polymerase chain reaction (PCR) 8-strip 100 ul reaction tubes. Library amplification was performed in a thermocycler with a heated lid using the following protocol: 1. 72° C.—5 minutes, 2. 98° C.—30 seconds, 3. 98° C.—10 seconds, 4. 63° C.—30 seconds, 5. 72° C.—60 seconds. Steps 3-5 were repeated an additional 11 times.
  B. Sample Cleanup
    (i) Purification of transposed genetic material was performed using a MinElute PCR Purification Kit, following manufacturer instructions (Qiagen, 28004). (ii) Samples were eluted from columns with 20 ul of elution buffer (EB; 10 mM Tris, pH 8.0).
5. Compilation of Health and Disease-Specific OCR Library
  A. Disease-Specific OCRs
    (i) Disease-specific OCRs are identified with a variety of methods comparing patient samples with normal donors using 1) DESeq2, 2) spectral or bi-clustering, 3) random forest. A list of human exhaustion, effector, and memory OCRs have been generated using cross-species mapping and the defined CD8 T cell subsets in mice (documents). These are likely to be relevant in a large number of diseases. OCRs have been defined that are different in blood non-naïve CD8 T cells and Tregs in melanoma patients compared to normal donors that can be used as biomarkers of disease (documents).
  B. Positive Control OCRs
    (i) Positive control OCRs are identified as genomic regions that are open in all CD8 T cells subsets in normal donors and disease patients. Specifically, the candidate positive OCRs are chosen as not significant between normal donors and disease patients. This list is the filtered on the top quartile of mean, lowest quartile of variance of counts across all samples, and a minimum peak length of 160—then, sorted by variance (low to high).
  C. Negative Control OCRs
    (i) Negative control OCRs are identified as regions that are open in an irrelevant cell type but not open in any CD8 T cell subset as determined by bedtools intersect. This list of candidate negative control OCRs is used to calculate the number of reads in each relevant patient ATAC-seq sample (bedtools coverage), then is sorted (low to high) on the mean of counts across patient samples.
6. Generation of OCR-Specific qPCR Primers
  A. NCBI Primer-BLAST was used to generate 2 primer pairs with the following parameters: amplicon size 80-120 base-pairs; optimal primer melting temperature 60° C. Celsius; specificity testing on the most recent Human or Mouse reference genome assemblies. The top 2 primer sets closest to the peak center were chosen for each OCR region. For each positive control OCR locus and disease-associated OCR, the center 50% of the region is used for the sequence input; for the negative control region, the entire peak length is used.
  B. Primers are validated by testing with the appropriate genomic DNA (mouse or human) and calculate $R^2$ and PCR efficiency values. Specifically, the delta ct is calculated by subtracting the mean ct of the highest standard from raw ct values of individual standard points; fold change accessibility is subsequently quantified by calculating $2^{-delta\ ct}$. These values are plotted against DNA concentration and linear regression was performed to calculate the $R^2$ value. PCR efficiency for representative primer pairs is calculated with the following formula:

$$Efficiency = -1 + 10^{(-1/slope)}$$

using the slope of the line calculated from plotting raw ct values against DNA concentration. qPCR analysis will only be considered valid for primers with an $R^2$ value above 0.95 and an efficiency between 90-110%.

7. Multi-Locus qPCR-Based Testing (Medium Throughput, 20-50 Targets)
  A. Transposed and amplified cDNA samples were diluted in PCR-grade water to a concentration of 33.3 ng/ml. A "standard" curve was generated by pooling all amplified DNA and creating a 5-step 5-fold serial dilution. 100 µg (3 ul) of transposed and amplified DNA samples (or "standard" or PCR-grade water blank) were added to 5 ul iTaq Universal SYBR Green Supermix (BioRad) and 1 ul each of forward and reverse primers (for a final primer concentration of 500 nM). Samples were plated in triplicate in a 384-well plate and then quantitatively amplified in a thermal cycler at the following conditions: 1. 95° C.—30 seconds, 2. 95° C.—1 second, 3. 60° C.—20 seconds. Steps 2-3 were repeated an additional 39 times. 4. Gradient from 65-95° C., in 0.5° C. increments at 2 seconds/step (for melt curve analysis)
8. Array-Based Testing (High Throughput, >1000 Targets)
  A. Array Construction
    (i) Customized 8×15,000 microarrays were printed by Agilent Technologies. The arrays included 1,500 exhausted or disease-specific OCR probes, 500 positive control probes, 500 negative control probes, and 500 probes for hybridization and printing quality controls. Each probe was represented 5 times on each array. Eight identical microarrays were printed on each customized slide, allowing for 8 samples to be processed simultaneously.
  B. Probe Design
    (i) Probes were designed by isolating the 80 base-pairs upstream and 80 base pairs downstream of each OCR peak center. Each 160-mer was split into unique 60-mers at 30 bp intervals and checked for sequence specificity via NCBI BLAST. All 60-mers with greater than 1 matches to the mouse or human RefSeq databases were discarded. Of the remaining 60-mers, the 2 with the lowest E-Value were selected for probe synthesis.
  C. Sample Preparation for Microarray Analysis
    (i) OCR libraries from patients or mice were prepared as per the protocols above. For microarray analysis, labeled cRNA was generated using a Low Input Quick Amp Labeling Kit (Cy5, Agilent Technologies 5190-2307). Samples were loaded onto custom chips and scanned as per the protocol described in the One-Color Microarray-Based Gene Expression Analysis technical manual (Agilent Technologies).
9. Data Analysis
  A. Quantification of enhancer accessibility is calculated using two approaches. 1) Internal normalization: the relative accessibility of disease-associated OCRs is compared to positive and negative OCRs within the patient sample. 2) External normalization: the accessibility of disease-associated OCRs is compared to synthetic standards. This analysis provides an absolute value of accessibility for each disease-associated OCR and allow for comparisons across patients.
Enhancer qPCR Development and Optimization Experiments Generate Naïve and Effector CD8 T cells. To isolate naïve murine CD8 T cells, spleens were harvested from C57/B16 mice and dissociated on a 70 um filter with a syringe. Cells were washed through the filter with 3 washes of PBS. Dissociated cells were spun down at 1650 RPM for 7 min at 4 degrees Celsius. PBS was aspirated and replaced with 1 ml of Ack Lysis Buffer (Invitrogen). Cells were incubated in Ack at room temperature for 5 min. Lysis buffer was quenched with 10 ml of PBS with 10% fetal calf serum (FCS). Cell mixture was then passed through another 70 um filter to remove cellular debris and fat tissue. Cells were spun down at 1500 RPM for 5 min are room temperature and resuspended in 1 ml magnetic separation buffer (MSB, PBS with 10% FCS and 4 mM EDTA) per 100 million cells. 50 ul of normal rat serum was added per ml of MSB to block non-specific antibody interactions. Subsequently, the following biotinylated antibodies were added at a 1:200 dilution: anti-CD4, anti-NK1.1, anti-CD19, anti-B220, anti-CD11c, anti-CD11a, anti-Ter119, anti-CD44. Antibody-cell mixture was incubated at room temperature for 15 min, prior to the addition of 125 ul of streptavidin magnetic beads (Miltenyi) per 1 ml of MSB. Mixture was incubated for another 15 min at room temperature after which, total volume was brought up to 3 ml with MSB. Sample was then mixed gently and placed in a magnetic separator (StemCell) for 10 min at room temperature. Unbound fraction was decanted into a 15 ml conical tube. Sample was washed twice with 10 ml PBS and placed on ice until next step.

To generate in vitro differentiated effector cells, purified naïve CD8 T cells from the steps above were counted and resuspended at 1×10^6 cells per 1 ml of RPMI medium supplemented with 10% FCS, 500 uM beta-mercaptoethanol, 20 mM HEPES, non-essential amino acids (1:100, Invitrogen) sodium pyruvate (1:100, Invitrogen), penicillin, and streptomycin. 3 ml of cell mixture was placed in a well of 12 well cluster dish. Cells were activated for 24 hours with anti-mouse CD3e (1:1000, BioLegend), anti-mouse CD28 (1:2000, BioLegend), and 100 U/ml recombinant human IL-2 (rhIL-2, Peprotech). Cells were then harvested from each well, counted, and washed 1 time in warm PBS. To differentiated activated CD8 T cells into effector cells, they were resuspended at 1×10^6 Per 1 ml of supplemented RPMI and 100 U/ml of rhIL-2 and 3 ml of cells were plated per well of a 6 well cluster dish. This was repeated for an additional 4 days, until a total of 6 days post-activation.

Membrane Lysis and Chromatin Release. Cells were transferred to 1.5 ml Eppendorf DNA Lo-Bind tubes and spun down at 650×g for 7 min at 4 degrees Celsius. Medium was aspirated and replaced with 500 ul of cold phosphate-buffered saline (PBS). Cells were then spun down again at 650×g for 7 min at 4 degrees. PBS was then aspirated and replaced with another 500 ul of cold PBS. Cells were again spun down at 650×g for 7 min at 4 degrees. PBS was aspirated and replaced with an appropriate amount of cell lysis medium (10 mM Tris-HCl pH8.0, 10 mM NaCl, 3 mM $MgCl_2$, 0.1% IGEPAL). The volume of cell lysis medium was scaled to the number of target cells in the reaction (<50 ul for fewer than 50,000 cells; 50 ul for 50,000 cells; added 1 ul of lysis medium per additional 1,000 target cells). Cells were mixed in lysis medium 10 times with a P200 pipette and incubated on ice for 5 min. Cells were then spun down at 650×g for 10 min at 4 degrees Celsius.

Transposition Reaction and Sample Cleanup. Lysis solution and cell debris were aspirated and replaced with an appropriate amount of transposition reaction solution. The volume of transposition reaction solution was scaled to the number of target cells in the reaction (5 ul for fewer than 5,000 cells; 5 ul for 5,000 cells; added 1 ul of reaction solution per additional 1,000 target cells). For a 50 ul reaction, the transposition reaction solution contains: 25 ul of 2×ATAC TD Buffer (20 mM Tris pH 7.5, 10 mM $MgCl_2$, 20% DMF), 22.5 ul Nuclease-free UltraPure Water, 2.5 ul of Tn5 adapter-loaded transposase mixture (Illumina, FC-121-1031). (ii) Cells were mixed in the transposition solution 10 times with a P200 pipette and incubated at 37 degrees Celsius for 45 min.

Purification of transposed genetic material was performed using a MinElute Reaction Cleanup Kit, following manufacturer instructions (Qiagen, 28204). (ii) Samples were eluted from columns with 11 ul of elution buffer (EB; 10 mM Tris, pH 8.0).

Library Amplification and Sample Cleanup. 10 ul of transposed DNA samples were amplified in Amplification Solution (10 ul nuclease-free water, 25 ul of NEBNext High-Fidelity 2×PCR Master Mix (New England Biolabs, M0541), 2.5 ul of N501 Primer, 2.5 ul of N701 Primer (Illumina, FC-121-1012). Samples were mixed thoroughly and transferred to polymerase chain reaction (PCR) 8-strip 100 ul reaction tubes. Library amplification was performed in a thermocycler with a heated lid using the following protocol: 1. 72 degrees—5 min, 2.98 degrees—30 seconds, 3. 98 degrees—10 seconds, 4. 63 degrees—30 seconds, 5. 72 degrees—60 seconds. Steps 3-5 were repeated an additional 11 times.

Purification of transposed genetic material was performed using a MinElute PCR Purification Kit, following manufacturer instructions (Qiagen, 28004). (ii) Samples were eluted from columns with 20 ul of elution buffer (EB; 10 mM Tris, pH 8.0).

Identification of positive control OCRs, negative control OCRs, and OCRs of interest. CD8 T cell ATAC-seq libraries from Pauken, et al. were processed using the attached script. Naïve, effector, memory, and exhaustion-specific OCRs were defined as being statistically increased in one subset compared to all others (DESeq2). Positive control loci were defined as regions that are open in all CD8 T cell subsets (naïve, effector, memory, and exhaustion) and are not being statistically different in any pairwise comparison (DESeq2): OCRs associated with CD8, CD3e, CD3g, TCF1. Negative control loci were defined as regions that are open in the 3T3 cell line but not in any of the 4 mouse primary CD8 T cell subsets (naïve, effector, memory, or exhausted: OCRs associated with the genes Col1a2 and Tinagl1. OCRs of interest were chosen from the effector- and exhaustion-specific OCR lists: OCRs associated with the genes IFNγ, IL-2RA, PD-1.

Validation of Control and Disease Associated OCR Library via qPCR. For each OCR locus, 2 primer pairs with non-overlapping amplicons were generated. OCR sequences were entered into NCBI Primer-BLAST and primer pairs were generated with the following parameters: amplicon size 80-120 base-pairs; optimal primer melting temperature 60 degrees Celsius; specificity testing on the most recent Human or Mouse reference genome assemblies. Of the returned primers, only those with amplicons closest to the center of the OCR sequence were selected. Lastly, the top two "centered" pairs with non-overlapping amplicons were selected for use in subsequent assays.

Primer Validation via qPCR. For each primer, melt curve analysis was performed after qPCR amplification. Additionally, cDNA "standards" were created by pooling amplified cDNA from all samples and diluting serially. Delta ct was calculated by subtracting the mean ct of the highest standard from raw ct values; fold change accessibility was subsequently quantified by calculating $2^{-delta\ ct}$. These values were plotted against DNA concentration and linear regression was performed to calculate the $R^2$ value. PCR efficiency for representative primer pairs was calculated with the following formula:

$$\text{Efficiency} = -1 + 10^{(-1/slope)}$$

using the slope of the line calculated from plotting raw ct values against DNA concentration. qPCR analysis was only considered valid for primers with an $R^2$ value above 0.95 and an efficiency between 90-110%.

To quantify accessibility for individual samples, delta Ct was first calculated by subtracting the mean Ct across all positive control primers from the individual Ct value for the experimental primer with the following equation:

$$\text{Delta Ct} = \text{Ct}^{experimental\ primer} - (\text{Ct}^{CD3g\ Pr\ 1} + \text{Ct}^{CD3g\ Pr\ 2} + \text{Ct}^{CD3e\ UTR\ 1} + \text{Ct}^{CD3e\ UTR\ 2})/4$$

Fold change accessibility was subsequently quantified by calculating 2'.

Figure 50:
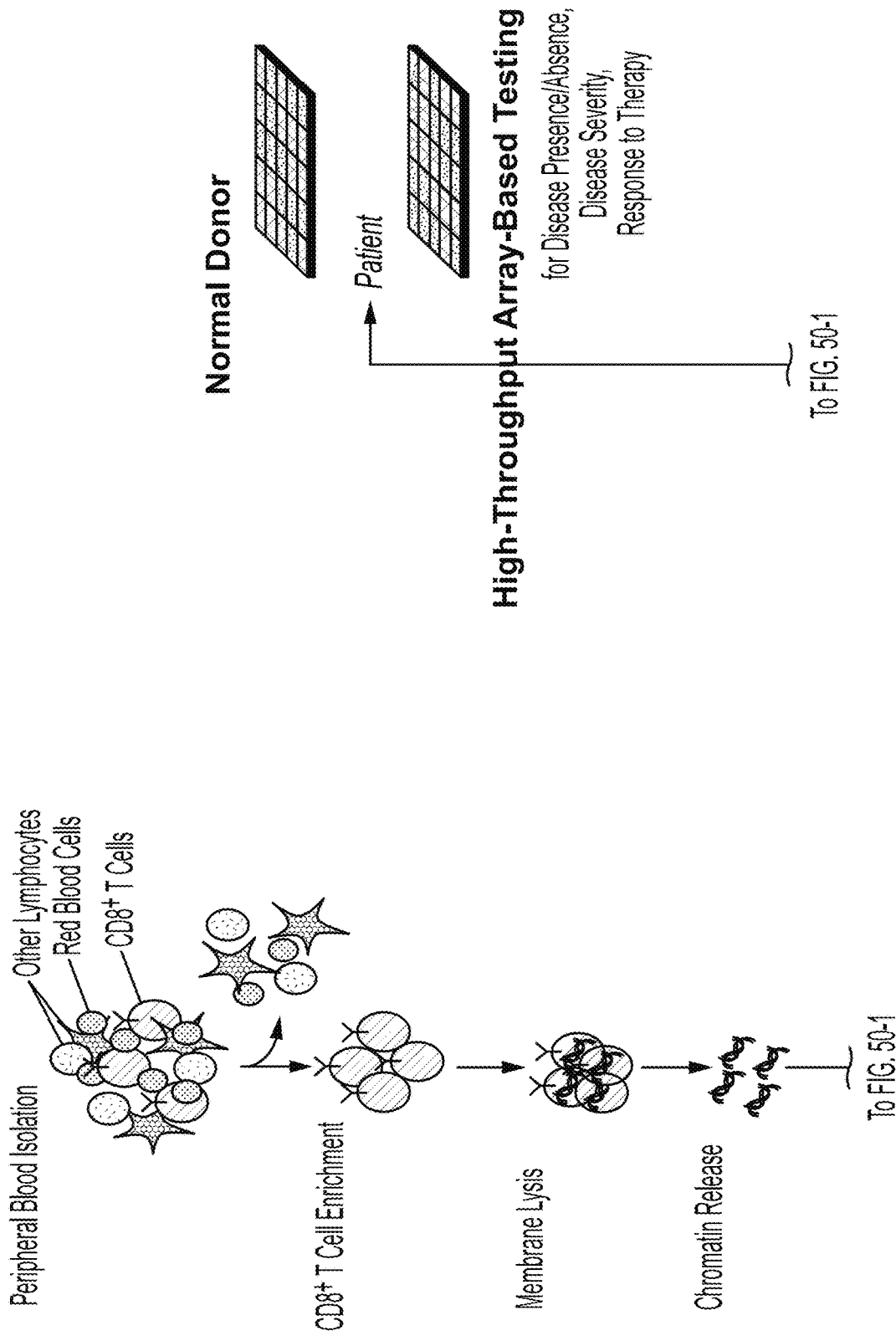
FIG. 50 depicts a series of images illustrating an enhancer qPCR experiment schematic, from sample preparation to OCR library generation and accessibility assay to assay scale-up for high-throughput analysis of samples to evaluate the presence or absence of epigenetic states of different cell types associated with disease, health or predicted clinical outcomes of treatments.
Figures 1, 50:
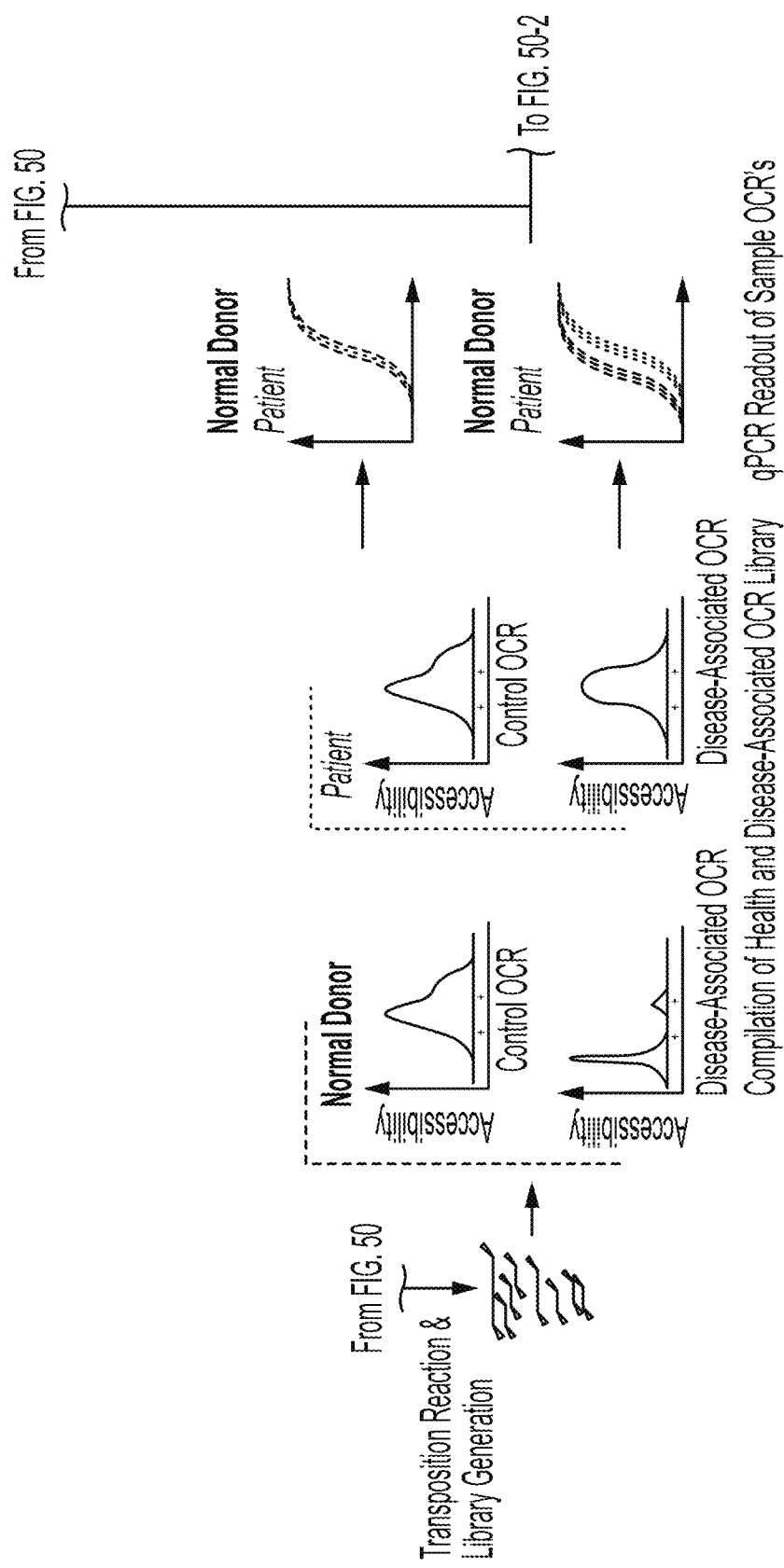
Figures 2, 50:
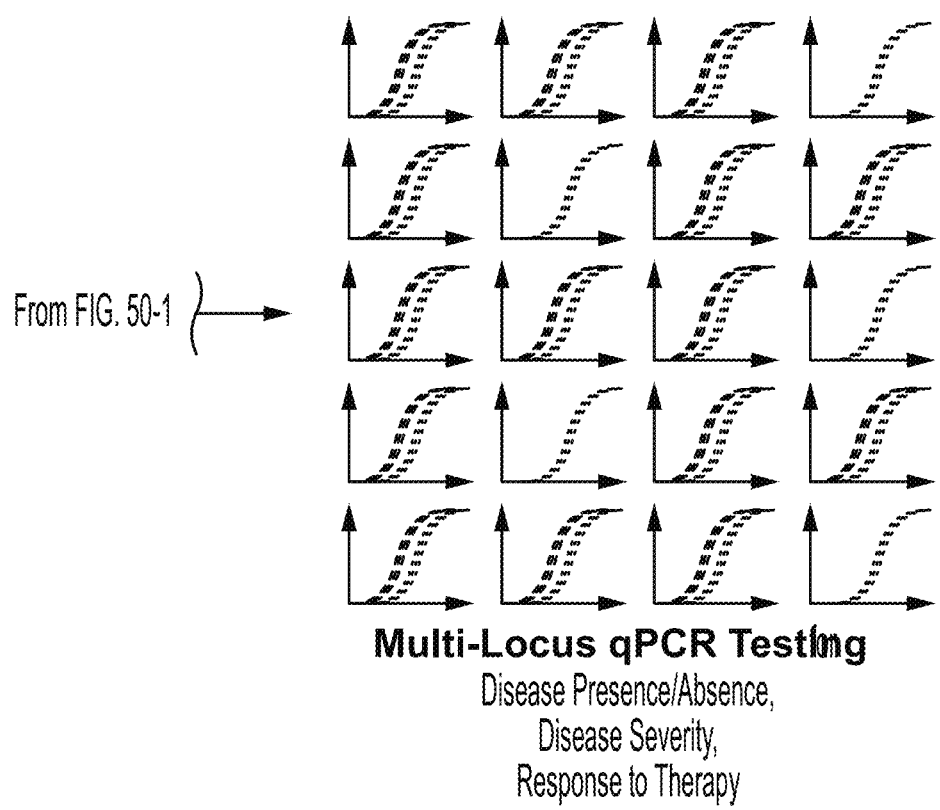

Example 19. Enhancer Openness PCR Assay to Interrogate Epigenetic State and Therapeutic Modulation An overview and schematic of the assay is provided in FIG. 50. Target cells are first enriched and then lysed to collect chromatin, which is then treated with Tn5 adaptor-loaded transposase, which can only transpose and integrate into open chromatin regions (OCRs). This DNA library is subjected to a first round of amplification, in which only adaptor-tagged transposed DNA is amplified. Subsequently, qPCR is run on these transposed and amplified DNA libraries with primers against disease-specific OCRs as well as positive and negative control OCRs. While both normal donors and patients should have similar accessibility at control open chromatin regions, disease-specific OCRs should only have quantifiable accessibility in patients and not normal donors. Eventually, this assay can be scaled up for multi-locus testing via high-throughput arrays.

Example 20. qPCR Efficiency of Representative Primers

FIG. 51 illustrates the assay performance and demonstrates that the PCR readout scales linearly. DNA "standards" were created by pooling amplified DNA from all samples and diluting serially. Delta ct was calculated by subtracting the mean ct (or cycle threshold) of the highest standard from raw ct values; fold change accessibility was subsequently quantified by calculating $2^{-delta\ ct}$. These values were plotted against DNA concentration and linear regression was performed to calculate the $R^2$ value for representative primer pairs (FIG. 51, top row). PCR efficiency for representative primer pairs was calculated with the following formula:

$$\text{Efficiency} = -1 + 10^{(-1/slope)}$$

using the slope of the line calculated from plotting raw ct values against DNA concentration (FIG. 51, bottom row). In these representative primer sets (Tcf7, CD8, and PD1), the qPCR efficiency is relatively high and close to 100%, indicating assay performance and reliability of qPCR on DNA generated from ATAC transposition and amplification.

Figure 52A:
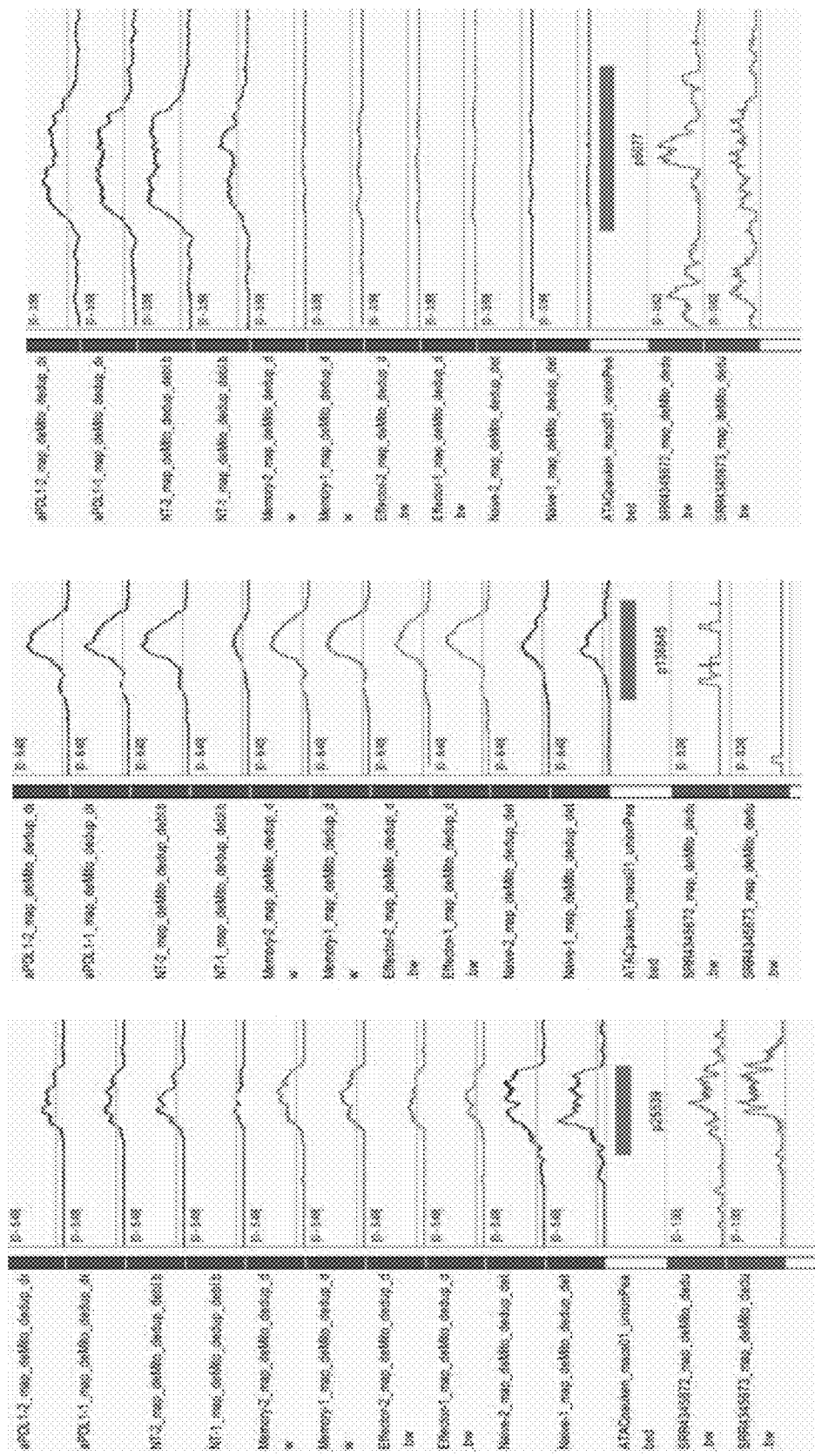
FIG. 52A-52B depicts a series of graphs showing differential chromatin accessibility at various representative loci across different cell types.
Figure 52B:
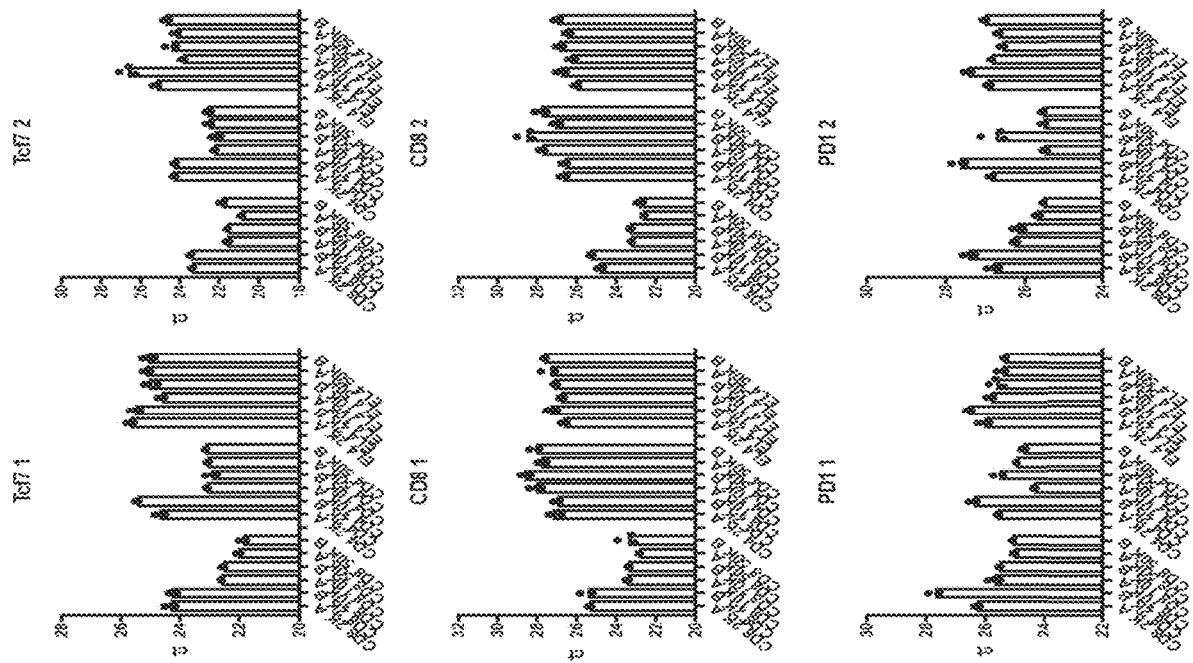

Example 21. Enhancers of Known Accessibility Demonstrate Appropriate Relative Openness Across Various Cell Types Naïve CD8 and CD4 T cells were isolated from mice and compared to EL4 cells, a murine lymphoma cell line. Multiple cell concentrations were tested in duplicate to assess assay sensitivity. Representative loci of known accessibility across various cell types (FIG. 52A) were assayed for relative openness. Because quantitative normalization requires a cell-type-specific reference locus, raw ct values were used to evaluate relative openness between these cell types, with low ct values indicating amplification and thus relative locus accessibility and high ct values indicating a lack of amplification and thus relative locus inaccessibility. Tcf7, a known chromatin locus open in naïve T cells but not EL4 cells, showed lower ct values in CD4 and CD8 T cells, indicating relative openness, and higher ct values in EL4 cells, indicating inaccessibility in this cell type (FIG. 52B, top). The enhancer at the CD8 locus showed low ct values in CD8 T cells and high ct values in CD4 T cells and EL4s, indicating appropriate cell type-specific chromatin accessibility (FIG. 52B, middle). Lastly, the exhaustion-specific PD1 enhancer, which is known to be open in EL4 cells, a subset of CD4 T cells (Tregs), and exhausted but not naïve CD8 T cells (Sen et al. Science. 2016, 354(6316):1165-1169), showed amplification in CD4 T cells but not naïve CD8 T cells (FIG. 52B, bottom). With many primer sets, differential cell concentrations demonstrated differential signal strength: lower ct values with 10K and 50K cells indicate stronger assay signal.

Example 22. Optimization of Cycle Number

Figure 53:
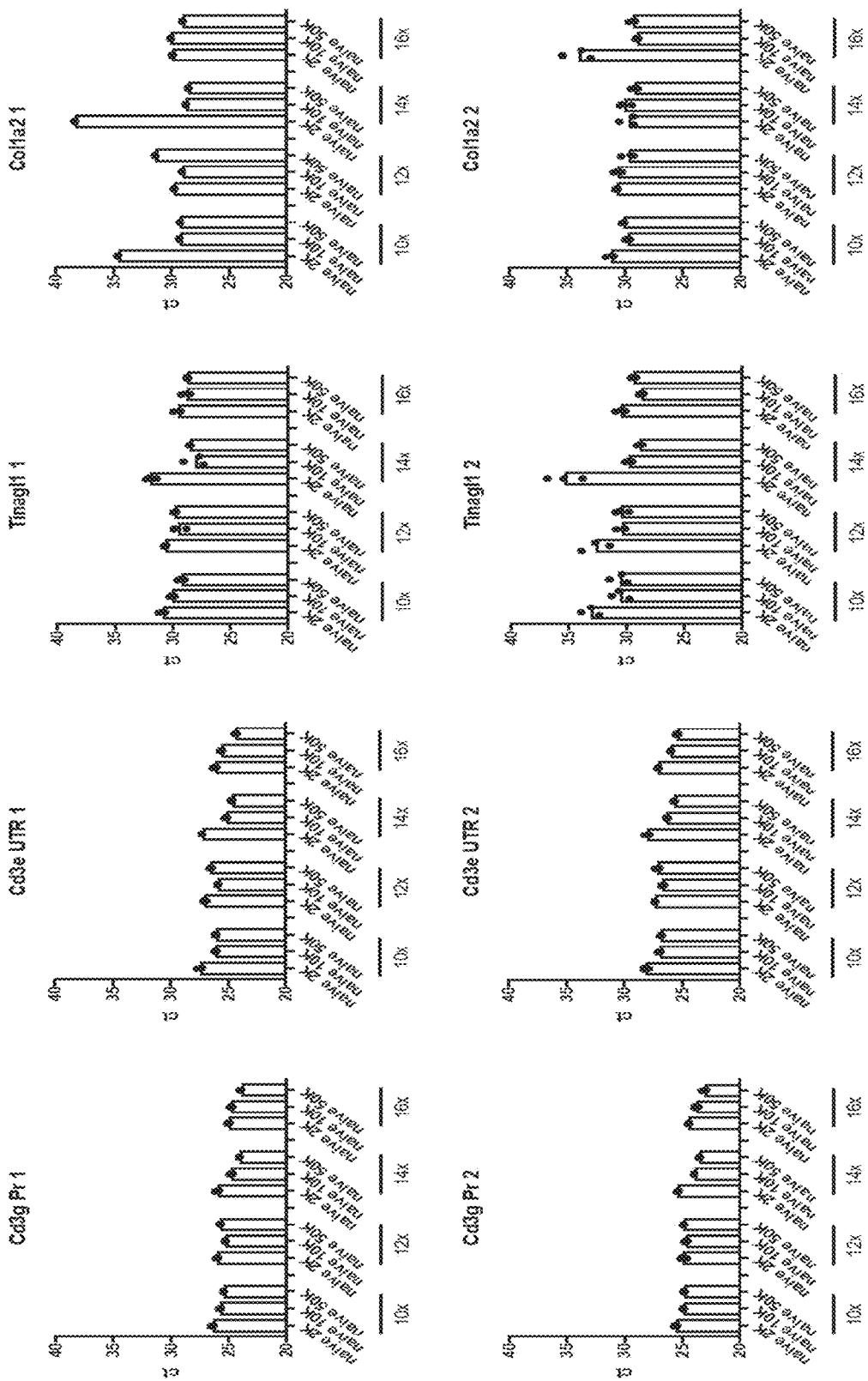
FIG. 53 depicts a series of graphs showing summary data of raw $C_t$ values indicating relative chromatin accessibility in naïve CD8 T cells at two positive control loci (Cd3gamma Promoter and Cd3epsilon 3' untranslated region (UTR)) and two negative control loci (Tinagl1 and Col1alpha2). Varying cell concentrations and number of amplification cycles were tested to optimize assay performance.

Naïve CD8 T cells were isolated and assayed for chromatin accessibility at multiple positive and negative control loci. Multiple cell concentrations and amplification cycles were tested to optimize assay sensitivity (FIG. 53). Open chromatin regions in various CD3 loci were selected as positive controls due to the role of CD3 as a T cell-specific surface and identity marker. Two representative negative control loci were identified by comparing ATACseq analyses between NIH3T3 fibroblasts and CD8 T cell subsets and selecting peaks enriched only in NIH3T3s and not T cells. Across varying cell concentrations and number of amplification cycles, naïve CD8 T cells generated similar raw ct values (~25) at positive control loci (CD3gamma Pr and CD3epsilon UTR), indicating uniform relative chromatin accessibility at these open chromatin regions. At negative control loci (Tinagl1 and Col1a2), raw Ct values demonstrated more variability depending on cell concentration and number of amplification cycles; however, these raw ct values were high (>30 in most samples), indicating lack of amplification and accessibility at these loci. In both positive and negative control loci, the condition with the least amount of variability observed was at 12 cycles of amplification and 50K cells.

Figure 54A:
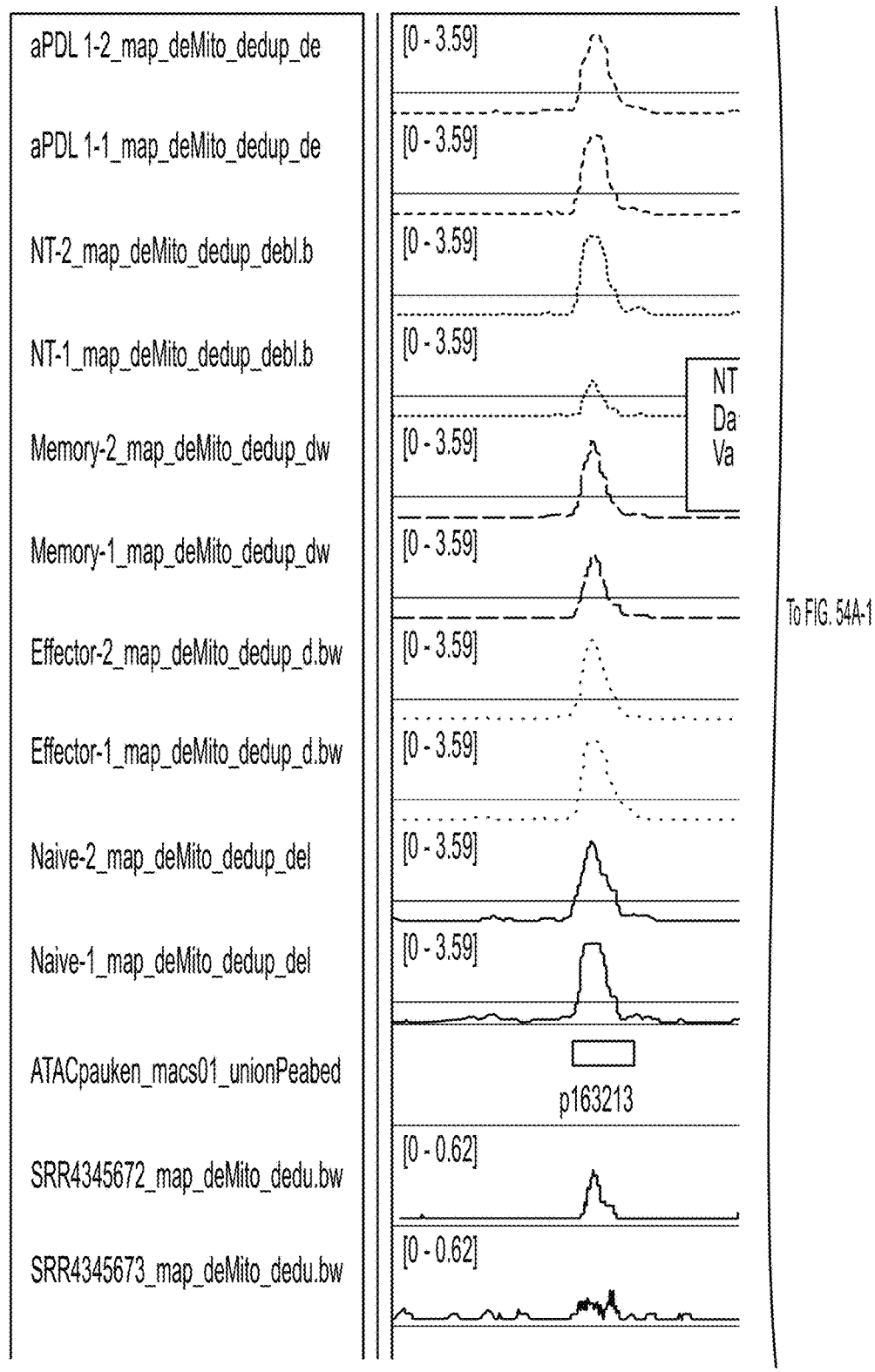
FIG. 54A-54B depicts a series of graphs showing differential chromatin accessibility at various representative control loci between naïve and effector CD8 T cells.
Figures 1, 54A:
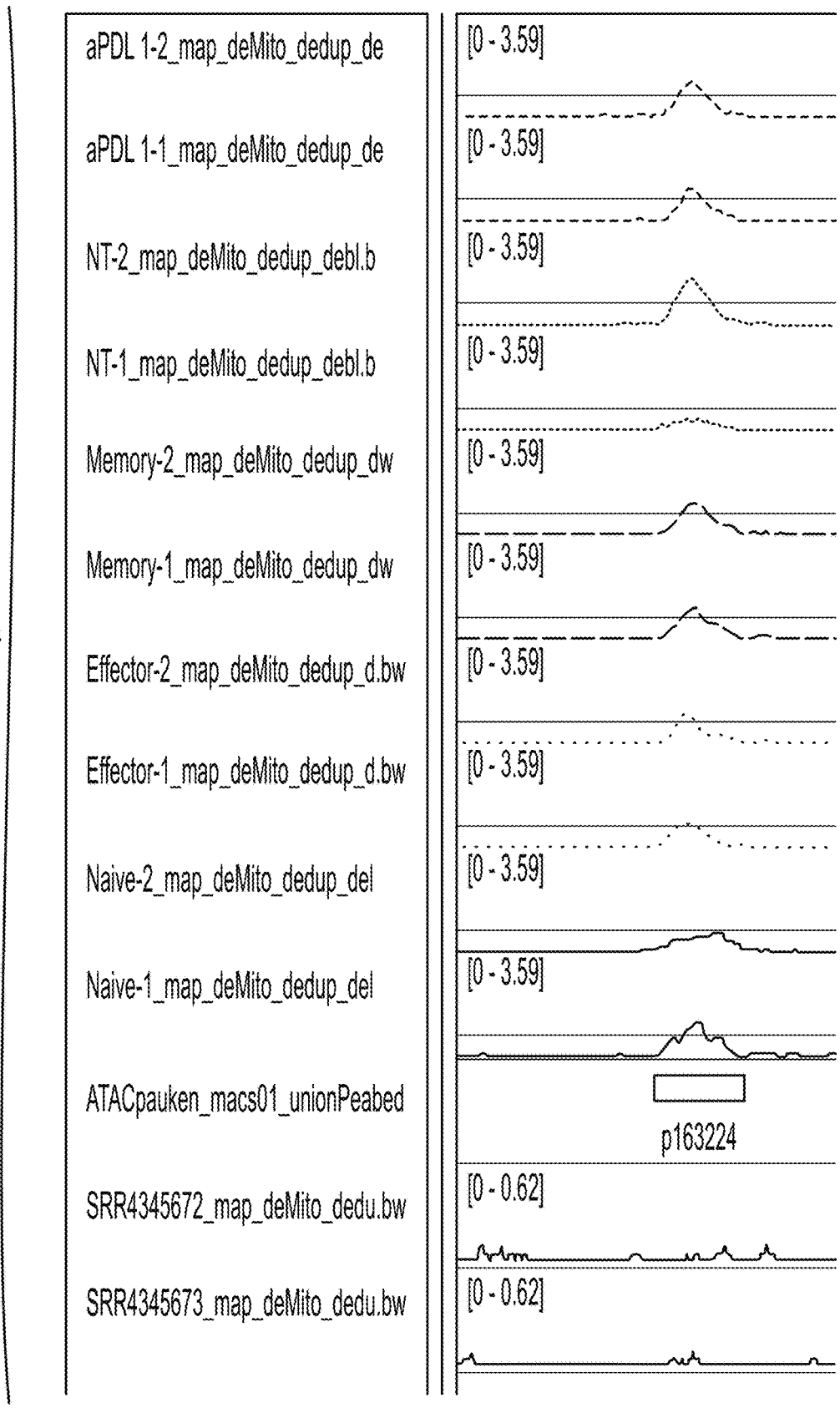
Figure 54B:
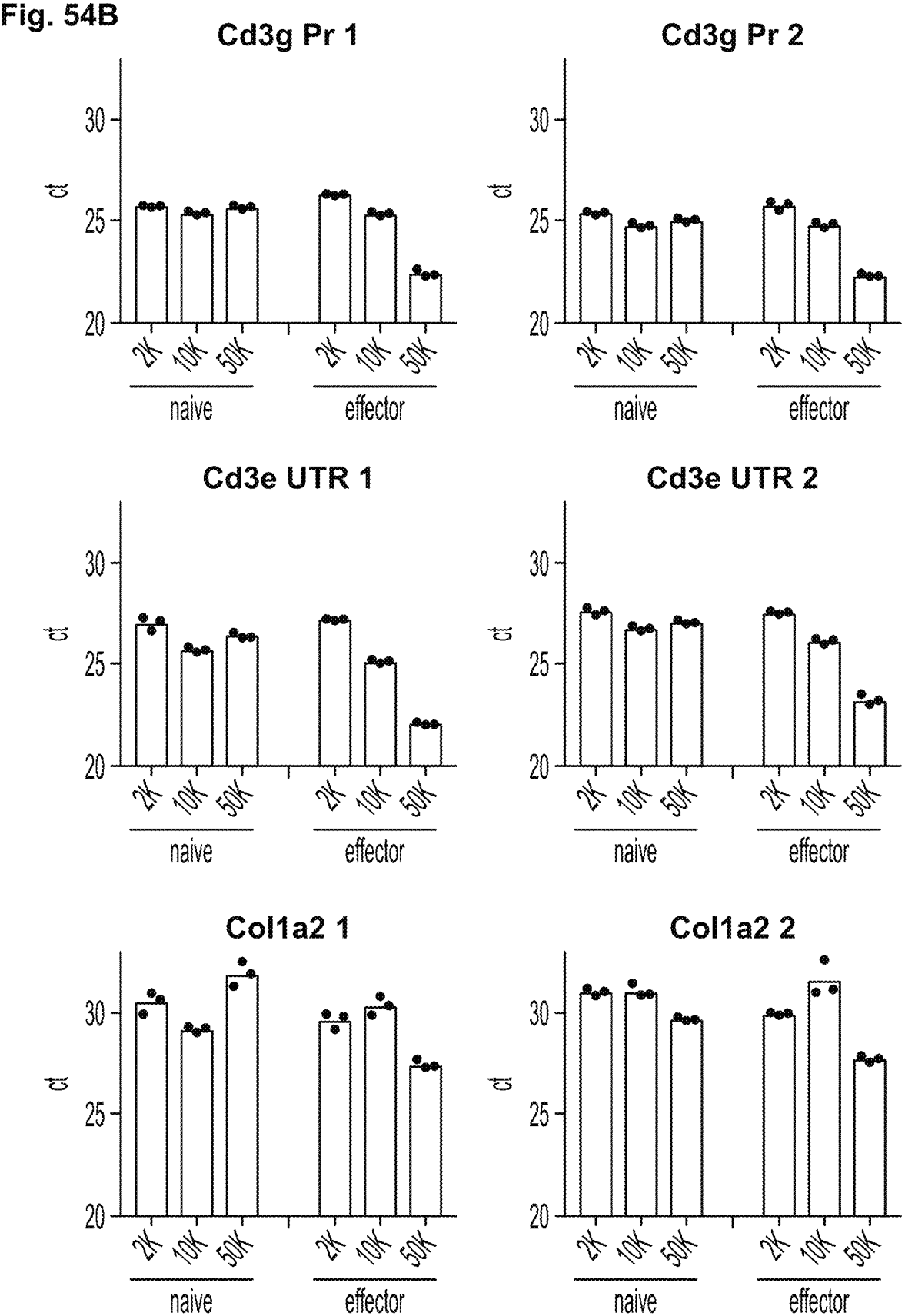

Example 23. Positive and Negative Control Loci Demonstrate Appropriate Relative Chromatin Accessibility Between Naïve and Effector CD8 T Cells Effector CD8 T cells were generated in vitro (Pipkin et al. Immunity. 2010, 32(1):79-90) and compared to naïve CD8 T cells isolated from littermate mice. Multiple cell concentrations were tested to assess assay sensitivity. Open chromatin regions in various CD3 loci were selected as positive controls due to the role of CD3 as a T cell-specific surface and identity marker and known accessibility at these regions (FIG. 54A). A representative negative control locus was identified by comparing ATACseq analyses between NIH3T3 fibroblasts and CD8 T cell subsets and selecting peaks enriched only in NIH3T3s and not T cells. Low ct values (~25) were generated for both naïve and effector CD8 T cells in the positive control loci, Cd3g Pr and CD3e UTR, indicating accessibility across all conditions (FIG. 54B, top and middle). High ct values (>30) were generated for both naïve and effector CD8 T cells at all cell concentrations in the negative control locus Col1a2, indicating that this locus is uniformly closed (FIG. 54B, bottom).

Figure 55A:
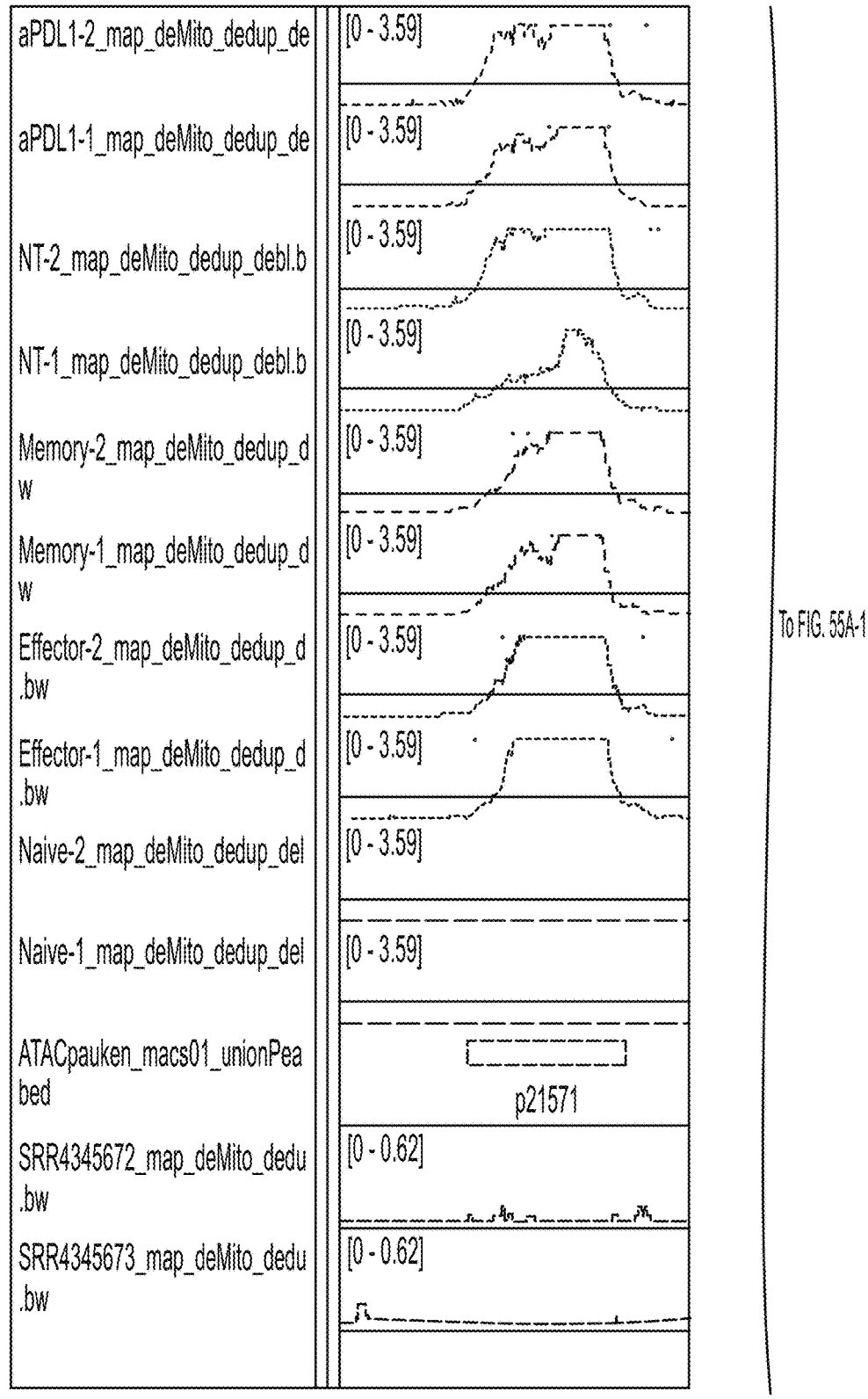
FIG. 55A-55B, depicts a series of graphs showing differential chromatin accessibility at various effector-specific loci between naïve and effector CD8 T cells.
Figures 1, 55A:
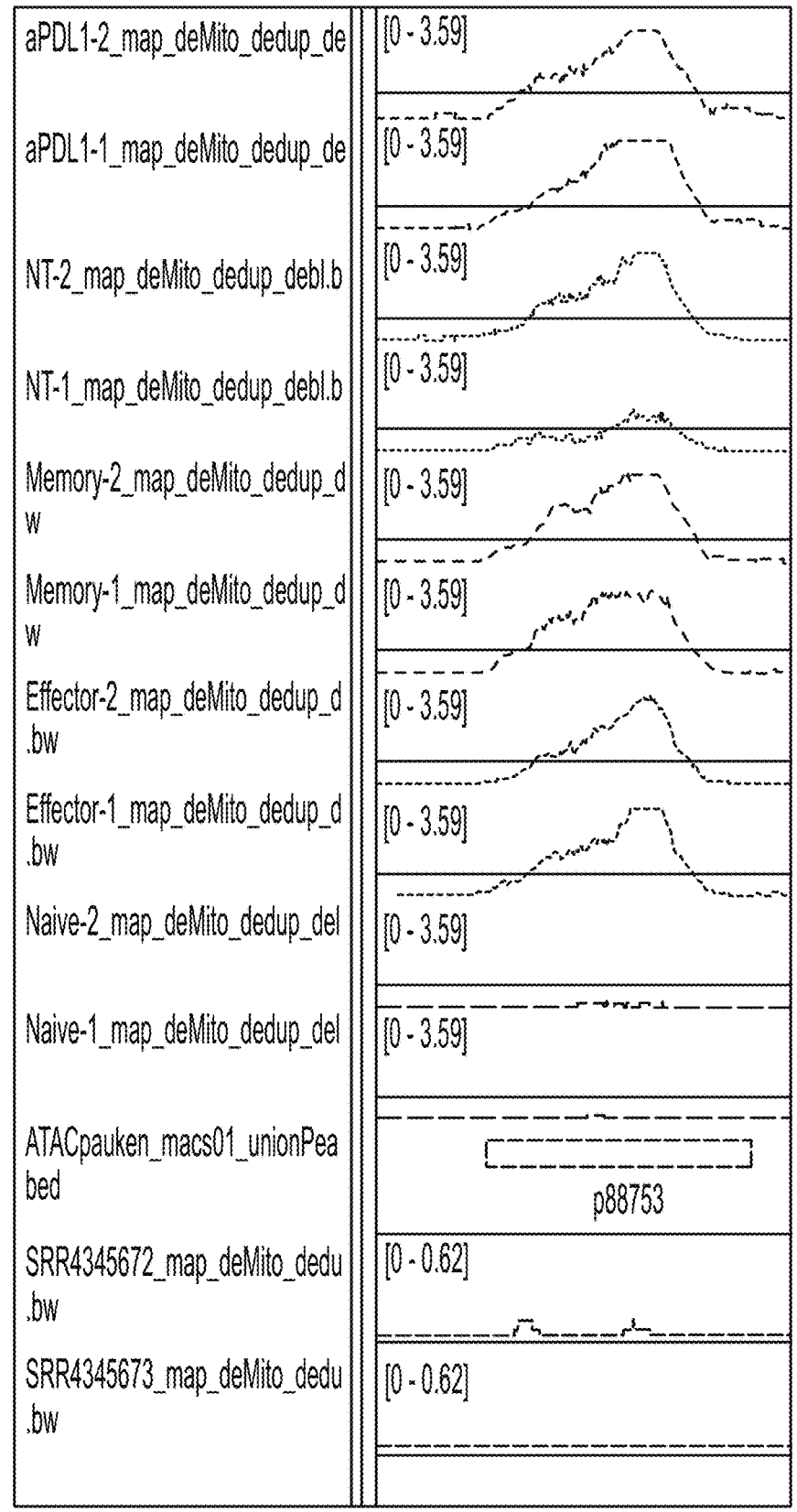
Figure 55B:
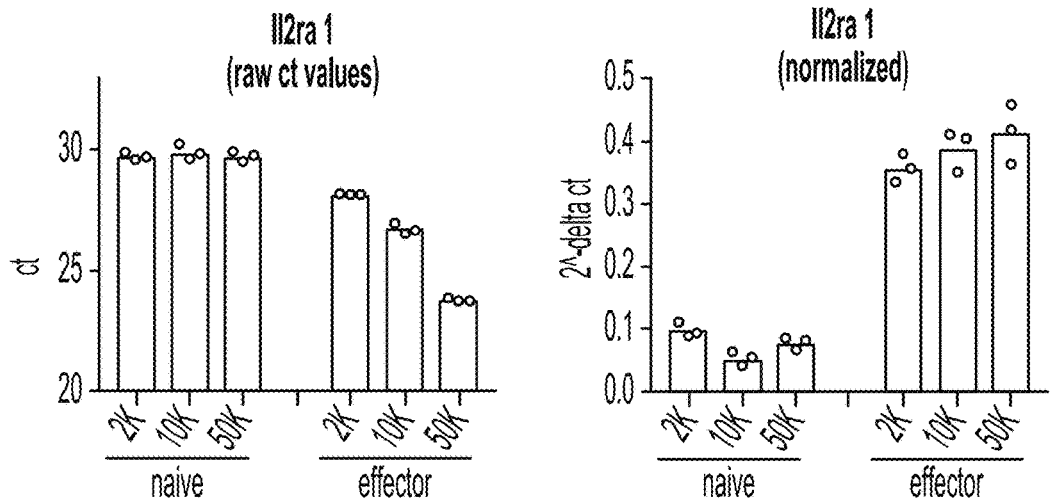
Figure 1:
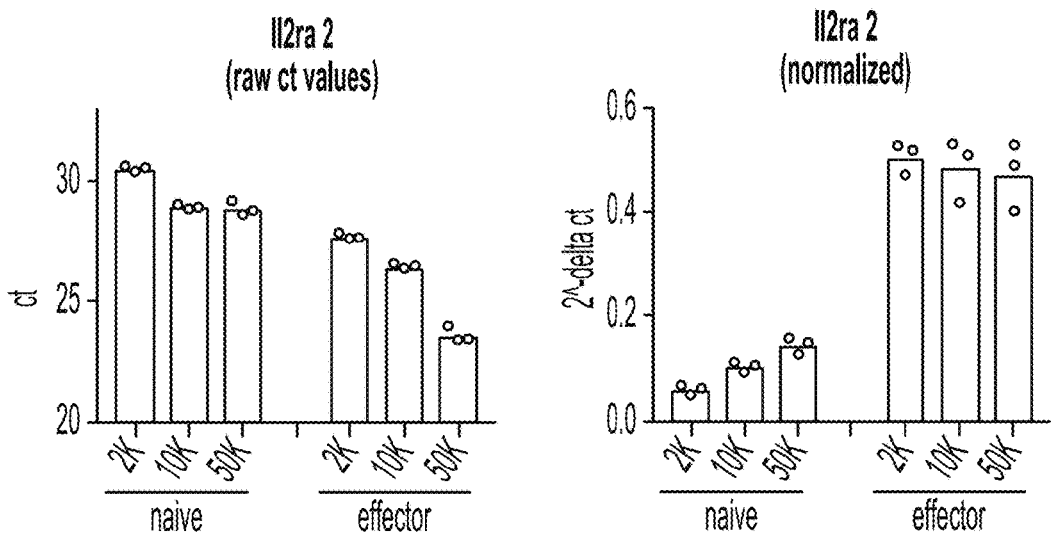

Example 24. Effector-Specific Loci Demonstrate Appropriate Accessibility Fold Change Between Naïve and Effector CD8 T Cells Effector CD8 T cells were generated in vitro (Pipkin et al. Immunity. 2010, 32(1):79-90) and compared to naïve CD8 T cells isolated from littermate mice. Multiple cell concentrations were tested to assess assay sensitivity. Ifng and Il2ra were selected as loci with known differential accessibility at effector-specific genes (FIG. 55A) and compared for accessibility between naïve and effector CD8 T cells. Naïve CD8 T cells showed high raw ct values (between 25-30 in the Ifng locus and ~30 in the Il2ra locus), demonstrating low amplification and thus low accessibility at these loci (FIG. 55B, left panels). Effector CD8 T cells showed wide variation in raw ct values at different cell concentrations, indicating differential assay sensitivity with varying amounts of input material. At a concentration of 2K cells, the raw ct values were similar between naïve and effector CD8 T cells. However, accessibility fold change, quantified by normalizing raw ct values to mean ct values across positive control loci (Cd3g Pr and Cd3e UTR) for respective individual samples and calculating $2^{-\Delta ct}$ from these values, was significantly increased in effector cells compared to naïve cells at both the Ifng and Il2ra loci. Furthermore, after normalization, accessibility fold change values were similar between different cell concentrations (FIG. 42B, right panels).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

| Cluster | | Cluster distinguishing markers | | | | | | | | |
|---|---|---|---|---|---|---|---|---|---|---|
| c1 | Exhausted (IL-10+) | PD-1+ CD39+ | CD38+ CD39+ | GzmK+ | TIGIT+ | TCF+ | 2B4+ | TIGIT+ | CD160 | CD7 |
| c10 | Effector Memory (EM)/EM CD45RA+ (EMRA) | PD-1− CD127− | Perf+ | CD57+ | GzmB+ | Tbet+ | KLRG1+ | GzmM+ | PD-1− | |
| c11 | Effector/ Tissue Resident Memory | PD-1+ Eomes+ | CD160+ TIGIT+ | GzmB+ | CD103+ | KLRG1+ | CD38+ | TIGIT− | 2B4− | CD160− |
| c12 | Unclear | PD-1− CD127− | CCR7+ | CD45RA+ CD2 | | | | | | |
| c13 | Naïve | PD-1− CD127+ | CD127+ | CD7+ | CD26+ | CD28+ | CD27+ | CD73+ | CD45RA+ CD2 | CCR7+ |
| c15 | Central Memory (CM) or Naïve | PD-1− CD127+ | CD127+ | CD7+ | CD26++ | CD28+ | CD27+ | CD73+ | CD45RA+ CD2 | CCR7+ |
| c16 | Mild Exhaustion | PD-1+ | CD160+ | TIGIT+ | 2B4+ | CXCR5+ | GzmK+ | CD27+ | TCF1+ | |
| c17 | Early Activated? | PD-1− CD127+ | CD127+ | CD7+ | CD26+ | CD28+ | CD27+ | CD73+ | CD45RA+ CD2 | CCR7+ |
| c18 | Tissue Resident Memory | PD-1+ CD127+ | Tbet+ | CD28+ | CD103+ | CD200R+ | | | | |
| c19 | Activated/ Exhausted | CD38+ CD39+ | CD16+ | CXCR5+ | Helios+ | PD-1+ CD39+ | CTLA4− | 2B4− | TIGIT− | CD160− |
| c2 | Exhausted | PD-1+ Eomes+ | 2B4+ CD160+ TIGIT+ | GzmB+ | CD16+ | Perf+ | CD57+ | CD38+ CD39− | Tbet+ | GzmK− |
| c21 | Central Memory (CM) or Naïve | PD-1− CD127+ | CD127+ | CD7+ | CD26+ | CD28+ | CD27+ | CD73+/− | CD45RA+ CD2 | CCR7+ |
| c23 | Effector Memory (EM)/EM CD45RA+ (EMRA) | Helios+ | CD45RA+ | CD16+ | CD38+ | Tox+ | PD-1− | | | |
| c25 | EM | PD-1− CD127+ | CD127+ | CD7+ | CD26+ | CD28+ | CD73+ | CD27+ | CD200R+ | CD103 Int |
| c26 | Early Activated? | PD-1+ CD127+ | Eomes+ | 2B4+ | KLRG1+ | GzmM+ | GzmK+ | Tbet+ | CD127+ | CD26 Int |
| c27 | Exhausted | PD-1+ Eomes+ | 2B4+ CD160+ TIGIT+ | GzmB+ | Tox+ | GzmK+ | | | | |

-continued

| | | | | | | | | | | |
|---|---|---|---|---|---|---|---|---|---|---|
| c28 | Mild Exhaustion | PD-1+ | PD-1+ CD39+ | Cd39+ | Ki67+ | CD38+ CD39+ | CTLA4+ | CD103+ | CD200R+ | TIM3+ |
| c29 | Severe Exhaustion | PD-1+ Eomes+ | 2B4+ CD160+ TIGIT+ | GzmB+ | Tox+ | CD38+ | GzmK+ | Ki67+ | HLA-DR+ | CXCR5+ |
| c3 | Severe Exhaustion | PD-1+ Eomes+ | 2B4+ CD160+ TIGIT+ | GzmB+ | Tox+ | GzmK- | | | | |
| c4 | Exhausted | PD-1+ Eomes+ | 2B4+ CD160+ TIGIT+ | GzmB+ | Helios+ | CD16+ | Perf+ | CD57+ | PD-1++ | Ki67 |
| c5 | Exhausted | TIGIT | Eomes | GzmB- | CD160 | 2B4+ | Tbet+ | Tox- Int | | |
| c7 | Early Activated? | PD-1- CD127+ | CD127+ | CD7 Int | CD26+ | CD28+ | CD27+ | TIGIT+ | CD200R+ | CD39+ |
| c9 | Severe Exhaustion | TIGIT | Eomes | GzmB+ | CD160 | 2B4+ | Tbet+ | Tox+ | CD16+ | CD57+ |
| c6 | Effector/EM | GzmK+ | GzmB Int | Tbet Int | Eomes Int | GzmM Int | PD-1 Int | | | |
| c8 | Effector/EM | GzmK+ | Tbet Int | Eomes Int | GzmM Int | PD-1 Int | PD-1+ CD127+ | CD27+ | CD28+ | CCR7+ |

| Cluster | Cluster distinguishing markers | | | | | | | | |
|---|---|---|---|---|---|---|---|---|---|
| c1 | Helios | CD103 | Ptger2 | CTLA4+ | Tim3+ | LAG3+ | | | |
| c10 | | | | | | | | | |
| e11 | CD57+ | | | | | | | | |
| c12 | | | | | | | | | |
| c13 | TCF1 + | CD5RA+ | | | | | | | |
| c15 | TCF1 + | CD45RA+ | | | | | | | |
| c16 | | | | | | | | | |
| c17 | TCF1+ | CD45RA+ | Tim3+ | LAG3+ | Eomes+ | CD200R+ | CD39+ | CD36+ | Ptger2 Int |
| c18 | | | | | | | | | |
| c19 | CD7+ | Ptger2+ | | | | | | | |
| c2 | | | | | | | | | |
| c21 | TCF1+ | CD45RA+ | Helios Int | CD38 Int | CD36 Int | | | | |
| c23 | | | | | | | | | |
| c25 | | | | | | | | | |
| c26 | CD28 Int | | | | | | | | |
| c27 | | | | | | | | | |
| c28 | LAG3+ | CD28+ | | | | | | | |
| c29 | PD-1+ CD39+ | | | | | | | | |
| c3 | | | | | | | | | |
| c4 | | | | | | | | | |
| c5 | | | | | | | | | |
| c7 | Ptger2 Int | | | | | | | | |
| c9 | Perf+ | GzmB+ | | | | | | | |
| c6 | | | | | | | | | |
| c8 | TCF1+ | | | | | | | | |

| | | Exhaustion | | Abundance (-, +, ++, +++) | | | |
|---|---|---|---|---|---|---|---|
| Cluster | | Score (0, 1, 2, 3) | Features Corr Viral Load | Corr CD4 counts | Recover w ART | HIV | Lung Ca |
| c1 | Exhausted (IL-10+) | 2 | Y | N | ND | - | - |
| c10 | Effector Memory (EM)/ EM CD45RA+ (EMRA) | 0 | N | Y | - | - | + |
| e11 | Effector/Tissue Resident Memory | 1 | Y | Y | + | - | ++ |
| c12 | Unclear | 0 | N | Y | - | - | - |
| c13 | Naïve | 0 | N | N | + | - | - |
| c15 | Central Memory (CM) or Naïve | 0 | Y | N | + | ++ | - |
| c16 | Mild Exhaustion | 2 | N | Y | - | +/- | - |
| c17 | Early Activated? | 0 | Y | N | - | - | - |
| c18 | Tissue Resident Memory | 0 | Y | N | + | + | +++ |
| c19 | Activated/Exhausted | 0 | N | Y | + | +/- | - |
| c2 | Exhausted | 3 | Y | N | + | +++ | + |
| c21 | Central Memory (CM) or Naïve | 0 | | | | | |
| c23 | Effector Memory (EM)/ EM CD45RA+ (EMRA) | 1 | N | Y | - | - | + |
| c25 | EM | 0 | N | Y | - | - | - |
| c26 | Early Activated? | 0 | Y | N | + | - | + |
| c27 | Exhausted | 2 | Y | N | - | + | ++ |
| c28 | Mild Exhaustion | 1 | Y | N | ND | - | +++ |
| c29 | Severe Exhaustion | 3 | Y | N | +/- | ++ | ++ |
| c3 | Severe Exhaustion | 3 | Y | Y | + | ++ | + |
| c4 | Exhausted | 2 | Y | N | + | ++ | + |

-continued

| | | | | | | | |
|---|---|---|---|---|---|---|---|
| c5 | Exhausted | 2 | N | Y | − | ++ | +/− |
| c7 | Early Activated? | 0 | N | N | + | − | + |
| c9 | Severe Exhaustion | 3 | N | Y | + | ++ | +/− |
| c6 | Effector/GM | 1 | N | Y | − | + | + |
| c8 | Effector/GM | 1 | N | Y | − | + | + |

TABLE 5

Mass cytometry reagents used

| Channel/Isotope | Reagent/Target | Clone | Source |
|---|---|---|---|
| 89Y | CD45 | HI30 | Fluidigm |
| 113 In | CD45RO | UCHL1 | BD |
| 115 In | CD57 | TB01 | Ebioscience |
| 139 La | MM-DOTA L/D | | In-house |
| 140 etc | Beads | | Fluidigm |
| 141 Pr | CD3 | UCHT1 | Biolegend |
| 142 Nd | CD26 | BA5b | Biolegend |
| 142 Nd | IFN-g | B27 | Biolegend |
| 143 Nd | CD4 | RPA-T4 | Biolegend |
| 144 Nd | CTLA-4 | BNI3 | BD |
| 145 Nd | CD19 | HIB19 | Biolegend |
| 145 Nd | TNF | MAb11 | Ebioscience |
| 146 Nd | CD8 | RPA-T8 | Biolegend |
| 147 Sm | CD45RA | H100 | BD |
| 148 Nd | CD7 | eBio124-1D1 | Ebioscience |
| 149 Sm | CD73 | AD2 | Biolegend |
| 149 Sm | CCL3 | MAB2701 | R&D |
| 150 Nd | CD127 | HIL-7R-M21 | BD |
| 151 Eu | CD39 | A1 | Biolegend |
| 152 Sm | Granzyme B | CLB-GB11 | Novus |
| 152 Sm | IL-2 | MQ1-17H12 | Ebioscience |
| 153 Eu | Tim-3 | F38-2E2 | DVS |
| 154 Sm | Granzyme K | GM6C3 | Santa Cruz |
| 154 Sm | XCL1 | MAB6951 | R&D |
| 155 Gd | CD27 | L128 | Fluidigm |
| 156 Gd | Helios | 22F6 | Biolegend |
| 157 Gd | Ki-67 | B56 | BD |
| 158 Gd | PD-1 | EH12.2H7 | Fluidigm |
| 159 Tb | CCR7 | G043H7 | Fluidigm |
| 160 Gd | Tbet | 4B10 | Fluidigm |
| 161 Dy | CD28 | CD28.2 | Biolegend |
| 162 Dy | FoxP3 | PCH101 | Fluidigm |
| 162 Dy | IL-21 | 3A3-N2 | Biolegend |
| 162 Dy | Gzm M | 4B2G4 | Bovenschen lab |
| 163 Dy | tetramer - Streptavidin | | NIH core/ Newell lab |
| 163 Dy | ICOS | C398.4A | Biolegend |
| 163 Dy | TCF1 | 7F11A10 | Biolegend |
| 164 Dy | tetramer - Streptavidin | | NIH core/ Newell lab |
| 164 Dy | CXCL10 | J034D6 | Biolegend |
| 165 Ho | Eomes | WD1928 | Ebioscience |
| 166 Er | CD200R2 | OX-108 | Ebioscience |
| 166 Er | Perforin | B-D48 | Abcam |
| 166 Er | Areg | pAB-1 | ThermoFisher |
| 167 Er | CD38 | HIT2 | Fluidigm |
| 168 Er | TOX | Rea473 | Miltenyi |
| 169 Tm | TIGIT | MBSA43 | Ebioscience |
| 170 Er | CXCR5 | RF8B2 | BD |
| 171 Yb | 2B4 | C1.7 | Biolegend |
| 172 Yb | CD160 | BY55 | Biolegend |
| 173 Yb | KLRG1 | 13F12F2 | Pircher lab |
| 173 Yb | HLA-DR | L243 | Biolegend |
| 174 Yb | tetramer - Streptavidin | | NIH core/ Newell lab |
| 174 Yb | CD 103 | Ber-ACT8 | Biolegend |
| 174 Yb | IL-10 | JES3-9D7 | Biolegend |
| 175 Lu | LAG-3 | 17B4 | Enzo |
| 176 Yb | Ptger2 | AB9472 | EMD |
| 176 Yb | CD36* | 5-271 | Biolegend |
| 191/193 | Iridium | | Fluidigm |
| 195 Pt | Cisplatin | | Fluidigm |
| 209 Bi | CD16 | 3G8 | Fluidigm |

TABLE 6

Primers

| Primer Name | SEQ ID NO | Sequence |
|---|---|---|
| TCF Primer Pair 1 Forward | 1 | AGCAGACCCGAGACGTAGTA |
| TCF Primer Pair 1 Reverse | 2 | AGCATCAAAGCCCACTTGAA |
| TCF Primer Pair 2 Forward | 3 | AACCCCAGCAAGAAATAGCG |
| TCF Primer Pair 2 Reverse | 4 | TGGGAATACTACGTCTCGGGT |
| CD8 Primer Pair 1 Forward | 5 | GGCGGATGTCACTGTGGTTA |
| CD8 Primer Pair 1 Reverse | 6 | GAGGTGAGGGGAATGCCAAA |
| CD8 Primer Pair 2 Forward | 7 | TGGGCTACAGAAAGCAAGCA |
| CD8 Primer Pair 2 Reverse | 8 | AGGTGAGGGGAATGCCAAAG |
| PD1 Primer Pair Forward | 9 | ACCTGTTTTGTTCTGTACGCTC |
| PD1 Primer Pair Reverse | 10 | TGCATGTTCTGTTATCTCAATGTTCT |

TABLE 6-continued

Primers

| Primer Name | SEQ ID NO | Sequence |
|---|---|---|
| Cd3g Pr Primer Pair 1 For. | 11 | CTCCACCCAGCATGCATTGA |
| Cd3g Pr Primer Pair 1 Rev. | 12 | GGCGGAGACACCTGGTATTG |
| Cd3g Pr Primer Pair 2 For. | 13 | TGGGACTCTGAGTAGAGGCA |
| Cd3g Pr Primer Pair 2 Rev. | 14 | CCTGCTGCCCACACTCTAC |
| Cd3e UTR Primer Pair 1 For | 15 | TCTCATCCTCACTCCCAGCA |
| Cd3e UTR Primer Pair 1 Rev | 16 | GTCTGAAGCCCCAAGCAGTA |
| Cd3d UTR Primer Pair 2 For | 17 | GCTCTGGGTTCCTCTCTCCT |
| Cd3d UTR Primer Pair 2 Rev | 18 | CCAGACACTGGAGGCTATCG |
| Ifng Primer Pair 1 Forward | 19 | CCCCCACCTATCTGTCACCA |
| Ifng Primer Pair 1 Reverse | 20 | GAAGGCTCCTCGGGATTACG |
| Ifng Primer Pair 2 Forward | 21 | CGTAATCCCGAGGAGCCTTC |
| Ifng Primer Pair 2 Reverse | 22 | GTGTCTTCTCTAGGTCAGCCG |
| Il2ra Primer Pair 1 Forward | 23 | GCTCTGAACACAGAGGTGTGA |
| Il2ra Primer Pair 1 Reverse | 24 | CTCTTCAAGGCACAGCCCAG |
| Il2ra Primer Pair 2 Forward | 25 | CTCCCAAGCTAATGGTGTTTGC |
| Il2ra Primer Pair 2 Reverse | 26 | AGCTTAACCACATGCCCACA |
| Col1a2 Primer Pair 1 For. | 27 | GCCCTCCCCTTCCAAAAGA |
| Col1a2 Primer Pair 1 Rev. | 28 | GGTCCTAGGATGGAGGCTGA |
| Col1a2 Primer Pair 2 For. | 29 | GCTGCGCTTCCTGAAGACTA |
| Col1a2 Primer Pair 2 Rev. | 30 | CAAAGACAGCCGCTTTTGGG |
| Tinagl1 Primer Pair 1 For. | 31 | TGGTGACTCTCCTCCCTCAG |
| Tinagl1 Primer Pair 1 Rev. | 32 | AAAACAAGGCCCAGAGAGGG |
| Tinagl1 Primer Pair 2 For. | 33 | ACATGTTAGCACAGCCTCCC |
| Tinagl1 Primer Pair 2 Rev. | 34 | GCTTCGTCTCACCTGCAGAA |

The invention claimed is:

1. A method for detecting exhausted T cells in a subject, wherein the method comprises
detecting an OCR footprint in T cells from the subject, wherein the OCR footprint is correlated with exhausted T cells, and wherein said OCR footprint in said T cells from the subject is determined by a method comprising conducting quantitative PCR (qPCR) on a chromatin library from said population of T cells from the subject, and conducting high-throughput array-based testing on amplification products of said qPCR.

2. A method for detecting exhausted T cells in a subject, wherein the method comprises detecting an OCR footprint in T cells from the subject, wherein the OCR footprint is correlated with exhausted T cells, and wherein said OCR footprint in said T cells from the subject is determined by a method comprising conducting quantitative PCR (qPCR) on a chromatin library from said population of T cells from the subject, and conducting multi-locus qPCR testing.

* * * * *

SEQUENCE LISTING

<160> NUMBER OF SEQ ID NOS: 94

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
agcagacccg agacgtagta                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

```
<400> SEQUENCE: 2
agcatcaaag cccacttgaa                                              20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
aaccccagca agaaatagcg                                              20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
tgggaatact acgtctcggg t                                            21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggcggatgtc actgtggtta                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gaggtgaggg gaatgccaaa                                              20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tgggctacag aaagcaagca                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aggtgagggg aatgccaaag                                              20

<210> SEQ ID NO 9
```

```
<211> LENGTH: 22
<212> TYPE: DNA
<213> ORGANISM: Artificial Sequence
<220> FEATURE:
<223> OTHER INFORMATION: Primer

<400> SEQUENCE: 9
acctgttttg ttctgtacgc tc                                            22

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
tgcatgttct gttatctcaa tgttct                                        26

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctccacccag catgcattga                                               20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ggcggagaca cctggtattg                                               20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tgggactctg agtagaggca                                               20

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
cctgctgccc acactctac                                                19

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
```
tctcatcctc actcccagca                                                   20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gtctgaagcc ccaagcagta                                                   20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gctctgggtt cctctctcct                                                   20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ccagacactg gaggctatcg                                                   20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cccccaccta tctgtcacca                                                   20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gaaggctcct cgggattacg                                                   20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cgtaatcccg aggagccttc                                                   20

<210> SEQ ID NO 22
<211> LENGTH: 21
<212> TYPE: DNA

```
<213> ORGANISM: Artificial Sequence
<220> FEATURE:
<223> OTHER INFORMATION: Primer

<400> SEQUENCE: 22
gtgtcttctc taggtcagcc g                                              21

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
gctctgaaca cagaggtgtg a                                              21

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ctcttcaagg cacagcccag                                                20

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
ctcccaagct aatggtgttt gc                                             22

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
agcttaacca catgcccaca                                                20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
gccctcccct tccaaaaaga                                                20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ggtcctagga tggaggctga                                                20
```

```
<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gctgcgcttc ctgaagacta                                               20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
caaagacagc cgcttttggg                                               20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tggtgactct cctccctcag                                               20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
aaaacaaggc ccagagaggg                                               20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
acatgttagc acagcctccc                                               20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gcttcgtctc acctgcagaa                                               20

<210> SEQ ID NO 35
<211> LENGTH: 87
<212> TYPE: DNA
<213> ORGANISM: Homo Sapiens
```

```
<400> SEQUENCE: 35
cccctgatcc tggagtcgcc cagccccaac cagacctctc tgtacttctg tgccagcagt        60
tcctattacg agcagtactt cgggccg                                            87

<210> SEQ ID NO 36
<211> LENGTH: 87
<212> TYPE: DNA
<213> ORGANISM: Homo Sapiens

<400> SEQUENCE: 36
agtgcccatc ctgaagacag cagcttctac atctgcagtg ctaggagcac cgggactatg        60
attcgggctg agcagttctt cgggcca                                            87

<210> SEQ ID NO 37
<211> LENGTH: 87
<212> TYPE: DNA
<213> ORGANISM: Homo Sapiens

<400> SEQUENCE: 37
ctgactgtga gcaacatgag ccctgaagac agcagcatat atctctgcag cgtccaaggg        60
ggatctcctg aagctttctt tggacaa                                            87

<210> SEQ ID NO 38
<211> LENGTH: 87
<212> TYPE: DNA
<213> ORGANISM: Homo Sapiens

<400> SEQUENCE: 38
ctaaacctga gctctctgga gctgggggac tcagctttgt atttctgtgc cagcagcgtg        60
ttaggggatg agcagttctt cgggcca                                            87

<210> SEQ ID NO 39
<211> LENGTH: 87
<212> TYPE: DNA
<213> ORGANISM: Homo Sapiens

<400> SEQUENCE: 39
ctgaatgtga acgccttgtt gctgggggac tcggccctct atctctgtgc cagcagcttt        60
aggtccgggg agctgttttt tggagaa                                            87

<210> SEQ ID NO 40
<211> LENGTH: 87
<212> TYPE: DNA
<213> ORGANISM: Homo Sapiens

<400> SEQUENCE: 40
ctgctggggt tggagtcggc tgctccctcc caaacatctg tgtacttctg tgccagccgg        60
cagggttttg gctacacctt cggttcg                                            87

<210> SEQ ID NO 41
<211> LENGTH: 87
<212> TYPE: DNA
<213> ORGANISM: Homo Sapiens

<400> SEQUENCE: 41
actctgacga tccagcgcac acagcaggag gactcggccg tgtatctctg tgccagcagc        60
ttagggtaca ccatatattt tggagag                                            87
```

```
<210> SEQ ID NO 42
<211> LENGTH: 87
<212> TYPE: DNA
<213> ORGANISM: Homo Sapiens

<400> SEQUENCE: 42
cacgccctgc agccagaaga ctcagccctg tatctctgcg ccagcagcca agtgcctagc      60
ggcccctacg agcagtactt cgggccg                                         87

<210> SEQ ID NO 43
<211> LENGTH: 87
<212> TYPE: DNA
<213> ORGANISM: Homo Sapiens

<400> SEQUENCE: 43
accagtgccc atcctgaaga cagcagcttc tacatctgca gtgctccggg gatcgggcga      60 cggggactg aagctttctt tggacaa                                          87

<210> SEQ ID NO 44
<211> LENGTH: 87
<212> TYPE: DNA
<213> ORGANISM: Homo Sapiens

<400> SEQUENCE: 44
gctgctccct cccagacatc tgtgtacttc tgtgccagca gtctaacagg ggtggtcata     60
tacaccgggg agctgttttt tggagaa                                         87

<210> SEQ ID NO 45
<211> LENGTH: 87
<212> TYPE: DNA
<213> ORGANISM: Homo Sapiens

<400> SEQUENCE: 45
ctgaagatcc agccctcaga acccagggac tcagctgtgt acttctgtgc cagcagtccc      60
ttgggctacg agcagtactt cgggccg                                         87

<210> SEQ ID NO 46
<211> LENGTH: 87
<212> TYPE: DNA
<213> ORGANISM: Homo Sapiens

<400> SEQUENCE: 46
agcaccttgg agctggggga ctcggccctt tatctttgcg ccagcagcgg gggacaggcc      60
agctcctacg agcagtactt cgggccg                                         87

<210> SEQ ID NO 47
<211> LENGTH: 87
<212> TYPE: DNA
<213> ORGANISM: Homo Sapiens

<400> SEQUENCE: 47
atccggtcca caaagctgga ggactcagcc atgtacttct gtgccagcag aggacaagac      60
cagaacactg aagctttctt tggacaa                                         87

<210> SEQ ID NO 48
<211> LENGTH: 87
<212> TYPE: DNA
<213> ORGANISM: Homo Sapiens

<400> SEQUENCE: 48
```

```
ctcaggctgg agtcggctgc tccctcccag acatctgtgt acttctgtgc cagcagtgaa    60
acagacactg aagctttctt tggacaa                                        87

<210> SEQ ID NO 49
<211> LENGTH: 87
<212> TYPE: DNA
<213> ORGANISM: Homo Sapiens

<400> SEQUENCE: 49
cacctacaca ccctgcagcc agaagactcg ccctgtatc tctgcgccag cagccaaatc    60
ggggataaga cggctttctt tggacaa                                        87

<210> SEQ ID NO 50
<211> LENGTH: 87
<212> TYPE: DNA
<213> ORGANISM: Homo Sapiens

<400> SEQUENCE: 50
aagatccagc ctgcagagct tggggactcg gccgtgtatc tctgtgccag cagccataca    60
aacaccgggg agctgttttt tggagaa                                        87

<210> SEQ ID NO 51
<211> LENGTH: 87
<212> TYPE: DNA
<213> ORGANISM: Homo Sapiens

<400> SEQUENCE: 51
ttggagtcgg ctgctccctc ccaaacatct gtgtacttct gtgccagcag ttacggggga    60
caggggcctg aagctttctt tggacaa                                        87

<210> SEQ ID NO 52
<211> LENGTH: 87
<212> TYPE: DNA
<213> ORGANISM: Homo Sapiens

<400> SEQUENCE: 52
gagatccagc gcacagagca gggggactcg gccatgtatc tctgtgccag cagtctagtc    60
gggggagggg aagctttctt tggacaa                                        87

<210> SEQ ID NO 53
<211> LENGTH: 87
<212> TYPE: DNA
<213> ORGANISM: Homo Sapiens

<400> SEQUENCE: 53
cacgccctgc agccagaaga ctcagccctg tatctctgcg ccagcagcct ggacaggggg    60
tataatcagc cccagcattt tggtgat                                        87

<210> SEQ ID NO 54
<211> LENGTH: 87
<212> TYPE: DNA
<213> ORGANISM: Homo Sapiens

<400> SEQUENCE: 54
caacctgcaa agcttgagga ctcggccgtg tatctctgtg ccagcagctt caatggggag    60
atgaacactg aagctttctt tggacaa                                        87

<210> SEQ ID NO 55
<211> LENGTH: 87
```

```
<212> TYPE: DNA
<213> ORGANISM: Homo Sapiens

<400> SEQUENCE: 55
ttggagatcc agcgcacaga gcaggggac tcggccatgt atctctgtgc cagcagcctt      60
tcctcttcac ccctccactt tgggaac                                         87

<210> SEQ ID NO 56
<211> LENGTH: 87
<212> TYPE: DNA
<213> ORGANISM: Homo Sapiens

<400> SEQUENCE: 56
tctaagaagc tcctcctcag tgactctggc ttctatctct gtgccttcgt cagcagggga      60
ggcgactatg gctacaccct cggttcg                                         87

<210> SEQ ID NO 57
<211> LENGTH: 87
<212> TYPE: DNA
<213> ORGANISM: Homo Sapiens

<400> SEQUENCE: 57
ctgagctctc tggagctggg ggactcagct ttgtatttct gtgccagcag cgcctccgcg      60
tgggccgctg aagctttctt tggacaa                                         87

<210> SEQ ID NO 58
<211> LENGTH: 87
<212> TYPE: DNA
<213> ORGANISM: Homo Sapiens

<400> SEQUENCE: 58
atgagctcct tggagctggg ggactcagcc ctgtacttct gtgccagcag ctcgaggact      60
aggtggaatg agcagttctt cgggcca                                         87

<210> SEQ ID NO 59
<211> LENGTH: 87
<212> TYPE: DNA
<213> ORGANISM: Homo Sapiens

<400> SEQUENCE: 59
ctgaagatcc agccctcaga acccagggac tcagctgtgt acttctgtgc cagcagcagt      60
gctaactatg gctacaccct cggttcg                                         87

<210> SEQ ID NO 60
<211> LENGTH: 87
<212> TYPE: DNA
<213> ORGANISM: Homo Sapiens

<400> SEQUENCE: 60
gaactgaaca tgagctcctt ggagctgggg gactcagccc tgtacttctg tgccagcagt      60
tcatctgata cgcagtattt tggccca                                         87

<210> SEQ ID NO 61
<211> LENGTH: 87
<212> TYPE: DNA
<213> ORGANISM: Homo Sapiens

<400> SEQUENCE: 61
tctctggagc tgggggactc agctttgtat ttctgtgcca gcagcgtagg ggacaggggg      60
```

-continued

```
tctggaaaca ccatatattt tggagag                                             87

<210> SEQ ID NO 62
<211> LENGTH: 87
<212> TYPE: DNA
<213> ORGANISM: Homo Sapiens

<400> SEQUENCE: 62
tccgctacca gctcccagac atctgtgtac ttctgtgcca tcagtgacct cggcggcccg        60
gccgcagata cgcagtattt tggccca                                             87

<210> SEQ ID NO 63
<211> LENGTH: 87
<212> TYPE: DNA
<213> ORGANISM: Homo Sapiens

<400> SEQUENCE: 63
cccagcccca accagacctc tctgtacttc tgtgccagca gtttatgggg cggcgggagc        60
tcctacaatg agcagttctt cgggcca                                             87

<210> SEQ ID NO 64
<211> LENGTH: 87
<212> TYPE: DNA
<213> ORGANISM: Homo Sapiens

<400> SEQUENCE: 64
cagcctgcag aactggagga ttctggagtt tatttctgtg ccagcagcca actgacaggg        60
gctgacactg aagctttctt tggacaa                                             87

<210> SEQ ID NO 65
<211> LENGTH: 11
<212> TYPE: PRT
<213> ORGANISM: Homo Sapiens

<400> SEQUENCE: 65

Cys Ala Ser Ser Ser Tyr Tyr Glu Gln Tyr Phe
1               5                   10

<210> SEQ ID NO 66
<211> LENGTH: 16
<212> TYPE: PRT
<213> ORGANISM: Homo Sapiens

<400> SEQUENCE: 66

Cys Ser Ala Arg Ser Thr Gly Thr Met Ile Arg Ala Glu Gln Phe Phe
1               5                   10                  15

<210> SEQ ID NO 67
<211> LENGTH: 12
<212> TYPE: PRT
<213> ORGANISM: Homo Sapiens

<400> SEQUENCE: 67

Cys Ser Val Gln Gly Gly Ser Pro Glu Ala Phe Phe
1               5                   10

<210> SEQ ID NO 68
<211> LENGTH: 12
<212> TYPE: PRT
<213> ORGANISM: Homo Sapiens

<400> SEQUENCE: 68
```

Cys Ala Ser Ser Val Leu Gly Asp Glu Gln Phe Phe
1               5                   10

<210> SEQ ID NO 69
<211> LENGTH: 12
<212> TYPE: PRT
<213> ORGANISM: Homo Sapiens

<400> SEQUENCE: 69

Cys Ala Ser Ser Phe Arg Ser Gly Glu Leu Phe Phe
1               5                   10

<210> SEQ ID NO 70
<211> LENGTH: 11
<212> TYPE: PRT
<213> ORGANISM: Homo Sapiens

<400> SEQUENCE: 70

Cys Ala Ser Arg Gln Gly Phe Gly Tyr Thr Phe
1               5                   10

<210> SEQ ID NO 71
<211> LENGTH: 11
<212> TYPE: PRT
<213> ORGANISM: Homo Sapiens

<400> SEQUENCE: 71

Cys Ala Ser Ser Leu Gly Tyr Thr Ile Tyr Phe
1               5                   10

<210> SEQ ID NO 72
<211> LENGTH: 15
<212> TYPE: PRT
<213> ORGANISM: Homo Sapiens

<400> SEQUENCE: 72

Cys Ala Ser Ser Gln Val Pro Ser Gly Pro Tyr Glu Gln Tyr Phe
1               5                   10                  15

<210> SEQ ID NO 73
<211> LENGTH: 15
<212> TYPE: PRT
<213> ORGANISM: Homo Sapiens

<400> SEQUENCE: 73

Cys Ser Ala Pro Gly Ile Gly Arg Arg Gly Thr Glu Ala Phe Phe
1               5                   10                  15

<210> SEQ ID NO 74
<211> LENGTH: 17
<212> TYPE: PRT
<213> ORGANISM: Homo Sapiens

<400> SEQUENCE: 74

Cys Ala Ser Ser Leu Thr Gly Val Val Ile Tyr Thr Gly Glu Leu Phe
1               5                   10                  15

Phe

<210> SEQ ID NO 75
<211> LENGTH: 12
<212> TYPE: PRT
<213> ORGANISM: Homo Sapiens

<400> SEQUENCE: 75

```
Cys Ala Ser Ser Pro Leu Gly Tyr Glu Gln Tyr Phe
1               5                   10
```

<210> SEQ ID NO 76
<211> LENGTH: 15
<212> TYPE: PRT
<213> ORGANISM: Homo Sapiens

<400> SEQUENCE: 76

```
Cys Ala Ser Ser Gly Gly Gln Ala Ser Ser Tyr Glu Gln Tyr Phe
1               5                   10                  15
```

<210> SEQ ID NO 77
<211> LENGTH: 14
<212> TYPE: PRT
<213> ORGANISM: Homo Sapiens

<400> SEQUENCE: 77

```
Cys Ala Ser Arg Gly Gln Asp Gln Asn Thr Glu Ala Phe Phe
1               5                   10
```

<210> SEQ ID NO 78
<211> LENGTH: 12
<212> TYPE: PRT
<213> ORGANISM: Homo Sapiens

<400> SEQUENCE: 78

```
Cys Ala Ser Ser Glu Thr Asp Thr Glu Ala Phe Phe
1               5                   10
```

<210> SEQ ID NO 79
<211> LENGTH: 13
<212> TYPE: PRT
<213> ORGANISM: Homo Sapiens

<400> SEQUENCE: 79

```
Cys Ala Ser Ser Gln Ile Gly Asp Lys Thr Ala Phe Phe
1               5                   10
```

<210> SEQ ID NO 80
<211> LENGTH: 13
<212> TYPE: PRT
<213> ORGANISM: Homo Sapiens

<400> SEQUENCE: 80

```
Cys Ala Ser Ser His Thr Asn Thr Gly Glu Leu Phe Phe
1               5                   10
```

<210> SEQ ID NO 81
<211> LENGTH: 14
<212> TYPE: PRT
<213> ORGANISM: Homo Sapiens

<400> SEQUENCE: 81

```
Cys Ala Ser Ser Tyr Gly Gly Gln Gly Pro Glu Ala Phe Phe
1               5                   10
```

<210> SEQ ID NO 82
<211> LENGTH: 13
<212> TYPE: PRT
<213> ORGANISM: Homo Sapiens

<400> SEQUENCE: 82

```
Cys Ala Ser Ser Leu Val Gly Gly Arg Glu Ala Phe Phe
1               5                   10
```

```
<210> SEQ ID NO 83
<211> LENGTH: 15
<212> TYPE: PRT
<213> ORGANISM: Homo Sapiens

<400> SEQUENCE: 83

Cys Ala Ser Ser Leu Asp Arg Gly Tyr Asn Gln Pro Gln His Phe
1               5                   10                  15

<210> SEQ ID NO 84
<211> LENGTH: 15
<212> TYPE: PRT
<213> ORGANISM: Homo Sapiens

<400> SEQUENCE: 84

Cys Ala Ser Ser Phe Asn Gly Glu Met Asn Thr Glu Ala Phe Phe
1               5                   10                  15

<210> SEQ ID NO 85
<211> LENGTH: 12
<212> TYPE: PRT
<213> ORGANISM: Homo Sapiens

<400> SEQUENCE: 85

Cys Ala Ser Ser Leu Ser Ser Ser Pro Leu His Phe
1               5                   10

<210> SEQ ID NO 86
<211> LENGTH: 14
<212> TYPE: PRT
<213> ORGANISM: Homo Sapiens

<400> SEQUENCE: 86

Cys Ala Phe Val Ser Arg Gly Gly Asp Tyr Gly Tyr Thr Phe
1               5                   10

<210> SEQ ID NO 87
<211> LENGTH: 14
<212> TYPE: PRT
<213> ORGANISM: Homo Sapiens

<400> SEQUENCE: 87

Cys Ala Ser Ser Ala Ser Ala Trp Ala Ala Glu Ala Phe Phe
1               5                   10

<210> SEQ ID NO 88
<211> LENGTH: 14
<212> TYPE: PRT
<213> ORGANISM: Homo Sapiens

<400> SEQUENCE: 88

Cys Ala Ser Ser Ser Arg Thr Arg Trp Asn Glu Gln Phe Phe
1               5                   10

<210> SEQ ID NO 89
<211> LENGTH: 12
<212> TYPE: PRT
<213> ORGANISM: Homo Sapiens

<400> SEQUENCE: 89

Cys Ala Ser Ser Ser Ala Asn Tyr Gly Tyr Thr Phe
1               5                   10
```

```
<210> SEQ ID NO 90
<211> LENGTH: 11
<212> TYPE: PRT
<213> ORGANISM: Homo Sapiens

<400> SEQUENCE: 90

Cys Ala Ser Ser Ser Ser Asp Thr Gln Tyr Phe
1               5                   10

<210> SEQ ID NO 91
<211> LENGTH: 16
<212> TYPE: PRT
<213> ORGANISM: Homo Sapiens

<400> SEQUENCE: 91

Cys Ala Ser Ser Val Gly Asp Arg Gly Ser Gly Asn Thr Ile Tyr Phe
1               5                   10                  15

<210> SEQ ID NO 92
<211> LENGTH: 16
<212> TYPE: PRT
<213> ORGANISM: Homo Sapiens

<400> SEQUENCE: 92

Cys Ala Ile Ser Asp Leu Gly Gly Pro Ala Ala Asp Thr Gln Tyr Phe
1               5                   10                  15

<210> SEQ ID NO 93
<211> LENGTH: 17
<212> TYPE: PRT
<213> ORGANISM: Homo Sapiens

<400> SEQUENCE: 93

Cys Ala Ser Ser Leu Trp Gly Gly Gly Ser Ser Tyr Asn Glu Gln Phe
1               5                   10                  15

Phe

<210> SEQ ID NO 94
<211> LENGTH: 15
<212> TYPE: PRT
<213> ORGANISM: Homo Sapiens

<400> SEQUENCE: 94

Cys Ala Ser Ser Gln Leu Thr Gly Ala Asp Thr Glu Ala Phe Phe
1               5                   10                  15
```

UNITED STATES PATENT AND TRADEMARK OFFICE
CERTIFICATE OF CORRECTION

PATENT NO. : 11,906,511 B2
APPLICATION NO. : 16/759676
DATED : February 20, 2024
INVENTOR(S) : E. John Wherry et al.

It is certified that error appears in the above-identified patent and that said Letters Patent is hereby corrected as shown below:

In the Specification

In Column 1, after the heading "STATEMENT REGARDING FEDERALLY SPONSORED RESEARCH OR DEVELOPMENT," please replace the paragraph at Lines 23-26 with the following paragraph:
--This invention was made with government support under AI082630, and AI105343 awarded by the National Institutes of Health. The government has certain rights in the invention.--

Signed and Sealed this
Ninth Day of April, 2024

Katherine Kelly Vidal
*Director of the United States Patent and Trademark Office*